(12) United States Patent
Inze et al.

(10) Patent No.: US 8,193,414 B2
(45) Date of Patent: Jun. 5, 2012

(54) METHOD FOR MODULATING PLANT GROWTH, NUCLEIC ACID MOLECULES AND POLYPEPTIDES ENCODED THEREOF USEFUL AS MODULATING AGENT

(75) Inventors: Dirk Inze, Aalst (BE); Veronique Boudolf, Ghent (BE); Lieven De Veylder, Ghent (BE); Juan Antonio Torres Acosta, Ghent (BE); Zoltan Magyar, Ghent (BE)

(73) Assignee: CropDesign N.V. (BE)

( * ) Notice: Subject to any disclaimer, the term of this patent is extended or adjusted under 35 U.S.C. 154(b) by 2332 days.

(21) Appl. No.: 10/276,032

(22) PCT Filed: May 14, 2001

(86) PCT No.: PCT/IB01/01307
§ 371 (c)(1),
(2), (4) Date: Dec. 16, 2002

(87) PCT Pub. No.: WO01/85946
PCT Pub. Date: Nov. 15, 2001

(65) Prior Publication Data
US 2008/0207449 A1 Aug. 28, 2008

Related U.S. Application Data

(60) Provisional application No. 60/204,045, filed on May 12, 2000.

(51) Int. Cl.
*C12N 15/82* (2006.01)
*A01H 5/00* (2006.01)

(52) U.S. Cl. .................. 800/290; 800/298

(58) Field of Classification Search .......... None
See application file for complete search history.

(56) References Cited

U.S. PATENT DOCUMENTS
6,284,947 B1 * 9/2001 Gordon-Kamm et al. .... 800/290

FOREIGN PATENT DOCUMENTS
| WO | WO 92/09685 | * | 6/1992 |
| WO | WO 99/13083 | * | 3/1999 |
| WO | WO 99/14331 |   | 3/1999 |
| WO | WO 99/22002 | * | 5/1999 |
| WO | WO 99/64599 | * | 12/1999 |

OTHER PUBLICATIONS

Luban J. et al. The yeast two-hybrid system for studying protein-protein interactions. Curr Opin Biotechnol. Feb. 1995;6(1):59-64. Review.*

Caponigro G. et al. Functional analysis of expressed peptides that bind yeast STE proteins. J Biotechnol. Aug. 15, 2003;103(3):213-25.*
GenBank Accession AY138520, Wheat dwarf virus replication-associated protein (RepA) gene, complete cds, Sep. 15, 2002.*
Hill M.A. et al. Functional analysis of conserved histidines in ADP-glucose pyrophosphorylase from *Escherichia coli*. Biochem Biophys Res Commun. Mar. 17, 1998;244(2):573-7.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
Zhou et al. The plant cyclin-dependent kinase inhibitor ICK1 has distinct functional domains for in vivo kinase inhibition, protein instability and nuclear localization. Plant J. Aug. 2003;35(4):476-89.*
Sandler S.J. et al. Inhibition of gene expression in transformed plants by antisense RNA. Plant Molecular Biology, 1988, vol. 11, No. 3, pp. 301-310.*
van der Krol A.R. et al. Inhibition of flower pigmentation by antisense CHS genes: promoter and minimal sequence requirements for the antisense effect. Plant Mol Biol. Apr. 1990;14(4):457-66.*
Waterhouse et al. Virus resistance and gene silencing: killing the messenger. Trends Plant Sci. Nov. 1999;4(11):452-457.*
Temple S.J. et al. Down-regulation of specific members of the glutamine synthetase gene family in alfalfa by antisense RNA technology. Plant Mol Biol. Jun. 1998;37(3):535-47.*
Carey A.T. at et al. Down-regulation of a ripening-related beta-galactosidase gene (TBG1) in transgenic tomato fruits. J Exp Bot. Apr. 2001;52(357):663-8.*
Federspiel et al. (1999) "*Arabidopsis thaliana* chromosome I BAC T16N11 genomic sequence, complete sequence", *EMBL*, Accession No. AC013453.
Kouchi et al. (1995) "Distinct Classes of Mitotic Cyclins are Differentially Expressed in the Soybean Shoot Apex during the Cell Cycle", *The Plant Cell*, 7:1143-1155.
Kouchi et al. (1995) "Glycin max mRNA for mitotic cyclin a2-type, complete cds.", *EMBL*, Accession No. D50869.
Lu et al. (1994) "*Arabidopsis thaliana* cyclin 3c mRNA partial cds." *EMBL*, Accession No. U17890.
Mironov et al. (1999) "Cyclin-Dependent Kinases and Cell Division in Plants—The Nexus", *The Plant Cell*,11:509-521.
Szarka et al. (1994) "*Brassica napus* cyclin mRNA, complete cds." *EMBL*, Accession No. L25405.

* cited by examiner

*Primary Examiner* — Cynthia Collins
(74) *Attorney, Agent, or Firm* — Connolly Bove Lodge & Hutz LLP

(57) ABSTRACT

The present invention relates to the field of molecular biology. The invention provides a method for modulating growth of a plant comprising introducing into a plant a CCP (cell cycle protein) modulator. Further provided are nucleic acid molecules and the polypeptides encoded thereof useful as modulating agents for performing such methods.

14 Claims, 65 Drawing Sheets

A.
CCP molecule: CCP1 nucleotide sequence (CDC2bDN-IC19):
cttttaagttgggggatgtttcgattttgaaatttgatttcttcaagagaagagatttaatgaaa
ataaataacttccgcagataacgaagaagaagaaaatggttagatcagatgaaaatagccttgga
ttaatcggatcaatgagtctccaaggtaccctaaatcgatcgattttgttattaaaaatcaaaac
tttcgttctctttgattttccccccaaattgattttgaatttacttgatgtagggggaggagtag
taggaaagatcaagacgacggcaacaacaggaccgacaagaagagcactaagtactattaacaag
aacatcactgaagcgccgtcttacccttatgctgtcaacaagagatcagtttctgaaagagatgg
catttgtaataaaccacctgtgcatcgaccagttactaggaagtttgctgctcagttagcagatc
ataagccacatatccgtgatgaggaaactaagaaaccagactcagtttcaagtgaagaaccagag
acgattatcattgatgtggatgaaagtgataaagaaggaggtgactctaatgagccaatgtttgt
acaacatactgaagcaatgctggaggagattgaacagatggagaaggagattgaaatggaagatg
cagacaaagaagaagagcctgtgatcgatattgatgcctgtgataagaataatcctttggctgcg
gttgaatatatccatgatatgcataccttctacaagaattttgagaaacttagttgcgtgcctcc
taactatatggacaatcaacaagatcttaatgagagaatgagaggaatcctcattgactggttaa
ttgaggtgcactacaagtttgaactgatggaggaaactctttatctcacaatcaatgtcatcgac
agattccttgcggttcatcaaatcgtgaggaaaaagcttcagcttgttggtgttactgctttgtt
gcttgcatgtaaatatgaagaagtttcagttccagtggtagatgatctcatcttgatctctgaca
aagcttactctagaagagaagtgctagatatggagaagctaatggccaacaccttgcaattcaat
ttctctctaccaactccatatgttttcatgaaacgatttctcaaagctgcccaatctgacaagaa
gcttgagattttatcattctttatgatcgagctttgccttgtggagtatgagatgctagagtatc
ttccatctaagctggcggcctcagcaatctacactgctcagtgtacacttaagggatttgaagaa
tggagcaaaacctgtgagtttcacacaggctacaacgaaaaacagctactggcatgtgcgagaaa
gatggttgctttccatcacaaggcaggaacagggaagctcacaggagttcacagaaagtacaaca
catctaagttctgtcatgctgcaagaactgaaccagctggttttctgattaaatattaataagaa
tctaatatgacttaactcgagttttctttagaacaaaaagagtgtgagagaaagagagatagta
gagcaagttgcccaaaatggagaagaatggatctttagatatcatggcaagtagcccaaaaaga
gtgtattcttctctttctaaggtctttagatctttcttcacttgagagagaataaaaagaatctt
ctgaaaaaaaaaaaaaaaaaaaaaa B.
CCP molecule: CCP1 amino acid sequence (CDC2bDN-IC19):
MVRSDENSLGLIGSMSLQGTLNRSILLLKIKTFVLFDFSPKLILNLLDVGGGVVGKIKTTATTGP
TRRALSTINKNITEAPSYPYAVNKRSVSERDGICNKPPVHRPVTRKFAAQLADHKPHIRDEETKK
PDSVSSEEPETIIIDVDESDKEGGDSNEPMFVQHTEAMLEEIEQMEKEIEMEDADKEEEPVIDID
ACDKNNPLAAVEYIHDMHTFYKNFEKLSCVPPNYMDNQQDLNERMRGILIDWLIEVHYKFELMEE
TLYLTINVIDRFLAVHQIVRKKLQLVGVTALLLACKYEEVSVPVVDDLILISDKAYSRREVLDME
KLMANTLQFNFSLPTPYVFMKRFLKAAQSDKKLEILSFFMIELCLVEYEMLEYLPSKLAASAIYT
AQCTLKGFEEWSKTCEFHTGYNEKQLLACARKMVAFHHKAGTGKLTGVHRKYNTSKFCHAARTEP
AGFLI

FIGURE 1

CCP molecule: CCP2 nucleotide sequence (CDC2bDN-IC20):
aacccacgtcaattcttttcaaaggcatatattctctctgtttcaaactttgtgtctcttcttc
tccttctctgatcgttcgttttctggacgagagagatggtaaatccgggtcacggaagaggaccc
gattcgggtactgctgctggtgggtcaaactccgacccgtttcctgcgaatcttcgagttcttgt
cgttgatgatgatccaacttgtctcatgatcttagagaggatgcttatgacttgtctctacagag
taactaaatgtaacagagcagagagcgcattgtctctgcttcggaagaacaagaatggttttgat
attgtcattagtgatgttcatatgcctgacatggatggtttcaagctccttgaacacgttggttt
agagatggatttacctgttatcatgatgtctgcggatgattcgaagagcgttgtgttgaaggag
tgactcacggtgcagttgattacctcatcaaaccggtacgtattgaggctttgaagaatatatgg
caacatgtggtgcggaagaagcgtaac-gagtggaatgtttctgaacattctggaggaagtattg
in CDC2bDN-IC20: c        g
aagatactggcggtgacagggacaggcagcagcagcataggaggatgctgataacaactcgtct
tcagttaatgaagggaacggaggagctcgaggaagcggaaggaagaggaagtagatgatcaagg
ggatgataaggaagactcatcgagtttaaagaaaccacgcgtggtttggtctgttgaattgcatc
agcagtttgttgctgctgtgaatcagctaggcgttgacaaagctgttcctaagaagatcttagag
atgatgaatgtacccgggctaacgcgagaaaacgtagccagtcacctccagaagtatcggatata
tctgagacggcttggaggagtatcgcaacaccaaggaaatatgaaccattcgtttatgactggtc
aagatcagagttttggacctcttcttcgttgaatggatttgatcttcaatctttagctgttact
ggtcagctccctcctcagagccttgcacagcttcaagcagctggtcttggccggcctacactcgc
taaaccagggatgtcggtttctcccttgtagatcagagaagcatcttcaactttgaaaacccaa
aaataagatttggagacggacatggtcagacgatgaacaatggaaatttgcttcatggtgtccca
acgggtagtcacatgcgtctgcgtcctggacagaatgttcagagcagcggaatgatgttccagt
agcagaccagctacctcgaggaggaccatcgatgctaccatccctcgggcaacagccgatattgt
caagcagcgtttcaagaagaagcgatctcactggtgcgctggcggttagaaacagtatccccgag
accaacagcagagtgttaccaactactcactcggtcttcaataacttccccgcggatctacctcg
cagcagcttcccgttggcaagtgccccagggatttcagttccagtatcagtttcttaccaagaag
aggtcaacagctcggatgcaaaaggaggttcatcagctgctactgctggatttggtaacccaagc
tacgacatatttaacgattttccgcagcaccaacagcacaacaagaacatcagcaataaactaaa
cgattgggatctgcggaatatgggattggtcttcagttccaatcaggacgcagcaactgcaaccg
caaccgcagcattttccacttcggaagcatactcttcgtcttctacgcagagaaaaagacgggaa
acggacgcaacagttgtgggtgagcatgggcagaacctgcagtcaccgagccggaatctgtatca
tctgaaccacgtttttatggacggtggttcagtcagagtgaagtcagaaagagtggcggagacag
tgacttgtcctccagcaaatacattgtttcacgagcagtataatcaagaagatctgatgagcgca
tttctcaaacaggaaggcatcccatccgtagataacgagttcgaatttgacggatactccatcga
taatatccaggtctgactacagaaactcagactagactgcaagattctttgttttcttctccct
ccttcgaggtacaaagctcaaaacatggcaataaccgaagggaaagataga

FIGURE 2

CCP molecule: CCP2 amino acid sequence (CDC2bDN-IC20):
MVNPGHGRGPDSGTAAGGSNSDPFPANLRVLVVDDDPTCLMILERMLMTCLYRVTKCNRAESALS
LLRKNKNGFDIVISDVHMPDMDGFKLLEHVGLEMDLPVIMMSADDSKSVVLKGVTHGAVDYLIKP
VRIEALKNIWQHVVRKKRNEWNVSEHSGGSIEDTGGDRDRQQQHREDADNNSSSVNEGNGRSSRK
RKEEEVDDQGDDKEDSSSLKKPRVVWSVELHQQFVAAVNQLGVDKAVPKKILEMMNVPGLTRENV
ASHLQKYRIYLRRLGGVSQHQGNMNHSFMTGQDQSFGPLSSLNGFDLQSLAVTGQLPPQSLAQLQ
AAGLGRPTLAKPGMSVSPLVDQRSIFNFENPKIRFGDGHGQTMNNGNLLHGVPTGSHMRLRPGQN
VQSSGMMLPVADQLPRGGPSMLPSLGQQPILSSSVSRRSDLTGALAVRNSIPETNSRVLPTTHSV
FNNFPADLPRSSFPLASAPGISVPVSVSYQEEVNSSDAKGGSSAATAGFGNPSYDIFNDFPQHQQ
HNKNISNKLNDWDLRNMGLVFSSNQDAATATATAAFSTSEAYSSSSTQRKRRETDATVVGEHGQN
LQSPSRNLYHLNHVFMDGGSVRVKSERVAETVTCPPANTLFHEQYNQEDLMSAFLKQEGIPSVDN
EFEFDGYSIDNIQV

FIGURE 3

A.
CCP molecule: CCP3 nucleotide sequence (CDC2bDN-IC21):
aggctgtgttttatcgtgggattttaaacatggggaaggaaaatgctgtgtctcggccattcac
tcgttcccttgcctctgctttgcgcgcttcagaagtgacttctactacacagaatcaacagagag
taaacacaaaagaccagccttggaggatacaagagccactggacccaacaagaggaagaagcga
gcggttctaggggagatcacaaatgttaactccaatacagctatacttgaggccaaaaacagcaa
gcagataaagaaaggacgcggtcatggattggcgagtacatcccagttggcaacttctgttactt
cagaagtcacagatcttcagtccaggaccgatgcaaaagttgaagttgcatcaaatacagcagga
aacctttctgtttctaaaggcacagataacacagctgataactgtattgagatatggaattctag
attgcctccaagacctcttgggagatcagcttctacagctgagaaaagtgctgttattggtagtt
caactgtaccggatatcccaaaatttgtagacatcgattcagatgacaaggatcctttactgtgc
tgcctctatgcccctgaaatccactacaatttgcgtgtttcagagcttaaacgcagaccacttcc
ggactttatggagagaatacagaaggatgtcacccagtccatgcggggaattctggttgattggc
ttgtggaggtctctgaagaatacacacttgcatctgacactctctacctcacagtgtatctcata
gactggttcctccatggaaactacgtgcaaagacagcaacttcaactgctcggcatcacttgcat
gctaattgcctcgaagtatgaggaaatctctgctccacgcattgaggagttttgcttcattacgg
ataacacctacacaagagatcaggtcctggaaatggagaaccaagtacttaagcattttagcttt
caaatatacactcccactccaaaaacgttccttaggagatttctcagagcagctcaagcctctcg
cctgagcccaagccttgaagtcgagtttctagccagctatctaacagagttgacattaatagact
accatttcttaaagtttcttccttccgttgttgctgcttcagcggttttctcgccaagtggaca
                                               g (in CDC2bDN-IC21)
atggaccaatcaaaccacccatggaatccaacacttgagcattacacaacgtacaaagcatcgga
tctgaaagcatctgttcatgccttacaagatctgcagcttaacaccaaaggttgccccttgagcg
ctatacgcatgaagtataggcaagagaaatacaaatctgtggcggttctcacgtctccaaagcta
cttgacacgctattcttcgaggtttcaactcctaaccgataatagtttt B.
CCP molecule: CCP3 amino acid sequence (CDC2bDN-IC21):
MGKENAVSRPFTRSLASALRASEVTSTTQNQQRVNTKRPALEDTRATGPNKRKKRAVLGEITNVN
SNTAILEAKNSKQIKKGRGHGLASTSQLATSVTSEVTDLQSRTDAKVEVASNTAGNLSVSKGTDN
TADNCIEIWNSRLPPRPLGRSASTAEKSAVIGSSTVPDIPKFVDIDSDDKDPLLCCLYAPEIHYN
LRVSELKRRPLPDFMERIQKDVTQSMRGILVDWLVEVSEEYTLASDTLYLTVYLIDWFLHGNYVQ
RQQLQLLGITCMLIASKYEEISAPRIEEFCFITDNTYTRDQVLEMENQVLKHFSFQIYTPTPKTF
LRRFLRAAQASRLSPSLEVEFLASYLTELTLIDYHFLKFLPSVVAASAVFLAKWTMDQSNHPWNP
TLEHYTTYKASDLKASVHALQDLQLNTKGCPLSAIRMKYRQEKYKSVAVLTSPKLLDTLF

FIGURE 4

A.
CCP molecule: CCP4 nucleotide sequence (CDC2bDN-IC26M):
atgggaagaagtgtgatttatgtaacggtgttgcaagaatgtattgcgagtcagatcaagctag
tttatgttgggattgcgacggtaaagttcacggcgctaatttcttggtagctaaacacacgcgtt
gtcttctctgtagcgcttgtcagtctcttacgccgtggaaagctactgggcttcgtcttggccca
actttctccgtctgcgagtcatgcgtcgctcttaaaaacgccggcggtggccgtggaaacagagt
tttatcggagaatcgtggtcaggaggaggttaatagtttcgagtccgaagaagatcggattagag
aagatcacggtgacggtgacgacgcggagtcttacgatgatgatgaggaagaagatgaggatgaa
gagtacagcgacgatgaggatgaggatgatgatgaggatggtgatgatgaggaagcggagaatca
agttgtgccgtggtctgcggcggcgcaagttcctccggtgatgagttcttcatcttctgacggag
gaagcggaggttcagtgacgaagaggacgagggctagagagaattcagatcttctctgctccgat
gatgagatcggaagctcttcagctcaagggtcaaactattctcggccgttgaagcgatcggcgtt
taaatcaacggttgttgttaactcacactctaccgtatcgtcagaatgaacggcgccgatacat
cgtcttctccgatctttgcgatctccaaaacaagaagagatctcagccgttgattcc B.
CCP molecule: CCP4 amino acid sequence (CDC2bDN-IC26M):
MGKKCDLCNGVARMYCESDQASLCWDCDGKVHGANFLVAKHTRCLLCSACQSLTPWKATGLRLGP
TFSVCESCVALKNAGGGRGNRVLSENRGQEEVNSFESEEDRIREDHGDGDDAESYDDDEEEDEDE
EYSDDEDEDDDEDGDDEEAENQVVPWSAAAQVPPVMSSSSSDGGSGGSVTKRTRARENSDLLCSD
DEIGSSAQGSNYSRPLKRSAFKSTVVV

FIGURE 5

A.
CCP molecule: CCP5 nucleotide sequence (CDC2bDN-IC39):
ggcacgagaaaaaaaaatggttaactcatgcgagaacaaaatcttcgttaaacccacttcaacga
cgattcttcaagatgaaacaagaagtagaaaattcggacaagagatgaagagggagaagagaaga
gtgttgcgtgtgattaaccagaatctcgctggtgcaagagtttatccttgtgttgtcaacaagaa
aggaagcttattgtctaataagcaagaacaagaagaaggatgtcaaaagaagaagtttgattctt
tgcgtccttcagttacaagatctggagttgaggaagagactaacaagaagctgaagccctcagtt
ccaagtgctaacgacttcggtgattgtatatttattgatgaggaggaagctacattggaccttcc
aatgccaatgtcgcttgagaaaccatacattgaagctgatccaatggaagaagttgagatggagg
atgtaacagtggaagaaccgatcgtggatatcgatgtcttagactcgaagaactcgcttgcggct
gttgaatatgttcaagatctttacgcattttacagaacaatggagagatttagttgtgttccagt
agactatatgatgcaacaaatcgacttaaacgagaagatgagagcaatactaatcgactggttaa
tcgaggtacatgacaagtttgatctgatgaacgagacactgtttctgacagtgaatctgatagat
agattcttgtccaagcaaaatgttatgagaaagaagcttcagcttgtagggttagtagctttgct
gttagcttgtaagtatgaggaggtttcggttcctgttgtcgaagatttagtactcatttcggaca
aagcgtatacgaggaacgatgttctagagatggagaaaacaatgttgagtactttgcaattcaat
atctcgttaccgacacaatacccgttcttgaaaagattcctcaaggcagctcaagcagacaagaa
gtgtgaggtcttggcgtcgttcttgatccagcttgcccttgtggagtacgagatgcttcggtttc
caccatcattactagctgccacatctgtctacactgctcaatgtacacttgatggttccaggaaa
tggaacagtacatgtgaattccattgtcattactctgaagaccagctcatggaatgttcacggaa
gctggtgagtctgcatcagagggcggcgacaggaaacttaacaggagtatataggaagtacagca
caagcaaatttggttacatagcaaaatgtgaagctgcacactttctagtgtctgagtctcatcat
tcttaatccaaaaggacagtagtaagtagtttgtacagcttcctgacatagttccctcattcact
ctgtagcacaaataagaagaaacaaaaaaaaagccaattaaatttgtcttatgattgattctgt
tttttgttgttactctttgttcacttcacttgtcagtattaaactctacaatgaatgataaatg
attgaatcatttcattctttgttcagaatgaaatgtattttgtatcttatttgagctaaaaaaa
aaaaaaaaaaaaaactcgagggggcccggtaccc B.
CCP molecule: CCP5 amino acid sequence (CDC2bDN-IC39):
MVNSCENKIFVKPTSTTILQDETRSRKFGQEMKREKRRVLRVINQNLAGARVYPCVVNKKGSLLS
NKQEEEEGCQKKKFDSLRPSVTRSGVEETNKKLKPSVPSANDFGDCIFIDEEEATLDLPMPMSL
EKPYIEADPMEEVEMEDVTVEEPIVDIDVLDSKNSLAAVEYVQDLYAFYRTMERFSCVPVDYMMQ
QIDLNEKMRAILIDWLIEVHDKFDLMNETLFLTVNLIDRFLSKQNVMRKKLQLVGLVALLLACKY
EEVSVEVVEDLVLISDKAYTRNDVLEMEKTMLSTLQFNISLPTQYPFLKRFLKAAQADKKCEVLA
SFLIELALVEYEMLRFPPSLLAATSVYTAQCTLDGSRKWNSTCEFHCHYSEDQLMECSRKLVSLH
QRAATGNLTGVYRKYSTSKFGYIAKCEAAHFLVSESHHS

FIGURE 6

CCP molecule: CCP6 nucleotide sequence (CDC2bDN-IC57):
atttgagaggaagctttattttgtgtgtagatggcgaataatcctccgcagtcttctggtacccagggtca
gcattttgttcctgcagcttcacaaccttttcacccttatggacatgtacctccaaatgttcaaagtcagc
ctccacagtattctcagccgatacagcagcagcagctctttccagtgagaccaggtcagcctgtgcatatt
acatcatcctcacaggctgtatcagttccgtatattcaaacgaacaagattctcacttctggatctactca
accacagccaaatgcacctccaatgacgggctttgctacatctggacctccattttcttctccatatactt
ttgtaccatcatcttatcctcagcaacaaccaacatccttggtccaaccaaattctcagatgcatgtagct
ggcgtccctccagcagcaaacacttggcctgttcctgttaatcaaagcacatcacttgtttccctgtgca
gcagactgggcaacaaacaccggtcgcagtttccacagacccaggaaacttgactccgcaatctgcatctg
actggcaggagcatacatctgctgatgggagaaaggctgatgcatccactgtatggaaggaatttacaaca
cctgaaggaaagaaatattattataacaaggttacaaaggagtctaagtggacaattccggaagatttaaa
gttagctcgggaacaagcccaactagctagtgaaaaaacgtccctttcggaagctggatctacccctctat
cccaccatgctgcatcctcgtctgatctagcagttagcactgtgacttctgttgttcccagcacatcttca
gcacttactggacattcttcaagccctattcaagcgggtttggctgtacctgtcacccgtcctccctctgt
tgctcctgttactccaacatctggtgcaattagtgacactgaggctactacaatgtactattttccttgg
gaagttttgctgagaataaggaaatgtctgtgaatggaaaagccaatttgtcacctgctggtgacaaagca
aatgtcgaggaacctatggtatatgctactaagcaggaggccaaagctgctttcaagtctcttttggaatc
tgtaaatgttcattccgactggacatgggaacagacattgaaagagattgttcacgataaaagatatggtg
ctttgaggacactcggcgagcggaaacaagcgtttaacgagtatcttggccaaaggaaaaaagtggaagct
gaggaaagacgaaggaggcagaagaaagctcgggaagaatttgtcaagatgctagaggagtgtgaagaact
ttcatcatccctgaaatggagcaaagcaatgagtttgttcgaaaatgatcagcgtttaaagctgttgacc
gtcctagggatcgtgaagatctttttgacaattacattgtggaacttgagaggaaggaagagaaaaggca
gcggaggaacatcggcagtatatggcagactatcggaagtttcttgaaacctgtgactatatcaaagctgg
tacacaatggcgcaaaattcaagatagactggaggatgatgacagatgctcatgtcttgaaaagatagatc
gtctgattggttttgaggaatacattcttgacctagagaaggaagaagaagagctgaagagagtagagaaa
gaacatgtaaggcgggccgagagaaaaaaccgtgatgcatttcgtacactattggaagaacatgttgctgc
aggcatccttacagccaagacgtactggttggattattgcattgagttaaaagacttgccccaataccaag
ctgttgcatctaatacatctggttcaactccgaaagacttgtttgaagatgtcacagaagaattagagaag
cagtatcatgaggataagagctatgtgaaggatgctgaagtcaagaaag- - - - - - - - - - - - - - -
 in CDC2bDN-IC57: atttccatggtctcctcgtg
- - - - - - -gcaaattttaaatctgctatttcagaagatctcagtactcaacagatatcagacataaatttaa
gctgtttgaag in CDC2bDN-IC57
agcttatatatgatgacttggttgggagagtgaaggaaaaagaagaaaaagaggccagaaagcttcagcgt
ctggctgaagaatttaccaatctgttgcacactttcaaggaaatcaccgtagcttcaaattgggaagatag
caaacaactagtagaagaaagtcaagagtacagatcgattggagatgaaagtgttagccaagggttatttg
aggaatacataacgagtttacaagaaaggcaaaggagaaggagcgtaagcgtgacgaggaaaaggttaga
aaagagaaggaaagggacgagaaagagaaacggaaagacaaggataaggagagaagggaaaaggaaagaga
acgtgaaaaagagaagggaaagagaggagtaaacgggaagaatcagatggtgagactgctatggatgtga
gcgaaggtcataaagacgagaaaagaagggaaaagatcgtgacagaaacatcgaagacggcatcacaac
aattctgatgaagatgttagttctgatagggatgacagagatgagtcgaagaaatcatcccgtaaacatgg
taatgatcgcaaagaatcaagaaagcacgcaaactcgcctgaatcggagagtgaaaaccggcataaaagac
agaaaaaagagagtagtcgccgaagtggtaatgacgagctagaggatggagaagttggggagtgatagtga
aattcgacattaatctgaaacctt

FIGURE 7

CCP molecule: CCP6 amino acid sequence (CDC2bDN-IC57):
MANNPPQSSGTQGQHFVPAASQPFHPYGHVPPNVQSQPPQYSQPIQQQQLFPVRPGQPVHITSSS
QAVSVPYIQTNKILTSGSTQPQPNAPPMTGFATSGPPFSSPYTFVPSSYPQQQPTSLVQPNSQMH
VAGVPPAANTWPVPVNQSTSLVSPVQQTGQQTPVAVSTDPGNLTPQSASDWQEHTSADGRKADAS
TVWKEFTTPEGKKYYYNKVTKESKWTIPEDLKLAREQAQLASEKTSLSEAGSTPLSHHAASSSDL
AVSTVTSVVPSTSSALTGHSSSPIQAGLAVPVTRPPSVAPVTPTSGAISDTEATTMYYFSLGSFA
ENKEMSVNGKANLSPAGDKANVEEPMVYAT<u>KQEAKAAFKSLLESVNVHSDWTWEQTLKEIVHDKR
YGALRTLGERKQAFNEYLGQRKKVEAEERRRQKKAREEFVKMLEECEELSSSLKWSKAMSLFEN
DQRFKAVDRPRDREDLFDNYIVELERKEREKAAEEHRQYMADYRKFLETCDYIKAGTQWRKIQDR
LEDDDRCSCLEKIDRLIGFEEYILDLEKEEEELKRVEKEHVRRAERKNRDAFRTLLEEHVAAGIL
TAKTYWLDYCIELKDLPQYQAVASNTSGSTPKDLFEDVTEELEKQYHEDKSYVKDAMKSRK
AN---------FKSAISEDLSTQQISDINLKLIYDDLVGRVKEKEEKEARKLQRLAEEFTNLLHT
ISMVSSWLFED in CDC2bDN-IC57</u>
FKEITVASNWEDSKQLVEESQEYRSIGDESVSQGLFEEYITSLQEKAKEKERKRDEEKVRKEKER
DEKEKRKDKDKERREKEREREKEKGKERSKREESDGETAMDVSEGHKDEKRKGKDRDRKHRRRHH
NNSDEDVSSDRDDRDESKKSSRKHGNDRKKSRKHANSPESESENRHKRQKKESSRRSGNDELEDG
EVGE

CCP molecule: CCP7/CCP8 nucleotide sequence (CDC2bDN-IC62/E2F3ca55):

tgaaacctagatttctgcaactgaattcctaattcgaaaaagaatggagggttcgtcgtcgacga
tagcaaggaagacatgggaactagagaacagcattctaacagtagactcacctgattcaacctcc
gacaacatcttctactacgacgatacttcacagactaggttccagcaagagaaaccgtgggagaa
tgatcctcactactttaaacgagtcaagatctcagcgctcgctcttcttaagatggtggttcacg
ctcgctctggtggtacaattgaaataatgggtcttatgcaaggtaagaccgatggtgatactatc
attgttatggatgcttttgctttaccagtggaaggtactgagacaagggttaatgctcaggatga
tgcttatgagtacatggttgagtattcacagaccaacaagctcgcggggc-ggctggagaatgtt
          in CDC2bDN-IC62:  c
                 - in E2F3ca55
gttggatggtatcactctcaccctggatatggatgctggctctccggtattgatgtttctacgca
gaggcttaaccaacagcatcaggagccatttttagctgttgttattgatcccacaaggactgttt
cagctggtaaggttgagattggtgctttcagaacatactctaaaggatataag--cctccagatg
         in CDC2bDN-IC62: agc
         in E2F3ca55: g--
aacctgtttctgagtatcaaa-ctattcctttaaataagattgaggactttggtgttcactgcaa
      a  in CDC2bDN-IC62
      -  in E2F3ca55
acagtactattcattagatgtcacttatttcaagtcatctcttgattctcaccttctggatctac
tatggaacaagtactgggtgaacactctttcttcttctccactgctgggtaatggagactatgtt
gctggacaaatatcagacttagctgagaagcttgagcaagccgagagtcatctggttcagtctcg
ctttggaggagttgtgccatcatcccttcataagaaaaagaagatgagtctcaactaactaaga
                 g in E2F3ca55
taactcgggatagcgcaaagataactgtggaacaggtccatggactaatgtcgcaggtcataaaa
gatgaattattcaactcaatgcgtcagtccaacaacaaatctcccactgactcgtcggatccaga
ccctatgattacatatggaagttgctcttctttttggtttctanttttggattgacccatcatttg
         in E2F3ca55:  g
ttgtcctttcatttatttttctgttgtgtaaagaattataatgctaatcagaataatacagaagaa
gattttggttaaaaaaaaaaaaaaaaaaa

B.

CCP molecule: CCP7/CCP8 amino acid sequence (CDC2bDN-IC62/E2F3ca55):
MEGSSSTIARKTWELENSILT VDSPDSTSDNIFYYDDTSQTRFQQEKPWENDPHYFKRVKISALALLKMV
VHARSGGTIEIMGLMQGKTDGDTIIVMDAFALPVEGTETRVNAQDDAYEYMVEYSQTNKLAGRLENVVGW
YHSHPGYGCWLSGIDVSTQTLNQQHQEPFLAVVIDPTRTVSAGKVEIGAFRTYSKGYKPPDEPVSEYQTI
PLNKIEDFGVHCKQYYSLDVTYFKSSLDSHLLDLLWNKYWVNTLSSSPLLGNGDYVAGQISDLAEKLEQA
ESHLVQSRFGGVVPSSLHKKKEDESQLTKITRDSAKITVEQVHGLMSQVIKDELFNSMRQSNNKSPTDSS
DPDPMITY

FIGURE 9

A.
CCP molecule: CCP9 nucleotide sequence (CDC2bDN-IC9):
ggcacgagtctctctctctctggagcgttctcttctctccttgagcttctcttaccgccattaga
gctccttcacaaactcataaacctatttgttgagccaggcttggcttaaccactggccttttcc
agactaaattatgtattgctcttcttcgatgcatccaaatgcaaacaaagaaaatatctctactt
cagatgtacaggagagttttgtacgaataacgagatcacgagctaaaaagccatgggaagagga
gtatcaatacctccaacaaaaccttcttttaaacagcaaaagagacgtgcagtacttaaggatgt
gagtaatacctctgcagatattatttattcagaacttcgaaagggaggcaacatcaaggcaaaca
gaaaatgtctaaaagagcctaaaaaagcagcaaaggaaggtgctaacagtgccatggatattctg
gtagatatgcatacagaaaaatcaaaattagcagaagatttgtccaagatcaggatggctgaagc
ccaagatgtctctctttcaaactttaaagatgaagaattactgagcaacaagaagatggatcag
gtgtcatggagttacttcaagttgtagatattgattccaacgtcgaagatccacagtgttgcagc
ttgtatgctgctgatatatatgacaacatacatgttgcagagcttcaacaacgacccttggctaa
ttatatggagcttgtgcagcgagatatcgacccagacatgagaaagattctgattgactggcttg
tagaagtttctgacgactacaagctggttccagatacgctttaccttacagtgaatcttatcgac
cggtttctgtccaacagttacattgaaaggcaaagactccagctccttggtgtctcttgcatgct
tatagcttcaaaatatgaagagctttccgcaccaggggtggaggagttttgcttcattacggcca
acacatacacaagacgagaagtgctgagcatggagattcaaattctaaattttgtgcactttaga
ttatcggttcctaccaccaaaacatttctgaggcggttcattaaagcagctcaagcttcgtacaa
ggtgcctttcattgaactggagtatttagcaaactatctcgccgaattgacactggtggaatata
gtttcctaaggttcctgccatcactaattgctgcttcagctgttttcctagcccgatggacactc
gaccaaactgaccatccttggaacccctactctgcaacactacaccagatatgaggtagctgagct
gaagaacacagttctcgccatggaggacttgcagctcaacaccagtggctgtactctcgctgcca
cccgtgagaaatacaaccaaccaaagtttaagagcgtggcaaagctgacatctcccaaacgagtc
acattactattctcaagatgacaccaagaacatcgaaaacagagcccaagtcaggtgatcaaaa
tacctatttcagacattggatgttatgtcgtctctttgccagttttgtctgtctgtaattctgt
agctattgtgtggcgccttaattgtaggccattacttgtcacaccacttagctttaaataaatgt
tatggaattttctaatcgcattgctacaactatttactatcctgcgggattttgtacctaggag
cacttggaaaacgaatacaaaagtgttaattaatataaatttcactgttcatggcaaaaaaa B.
CCP molecule: CCP9 amino acid sequence (CDC2bDN-IC9):
MYCSSSMHPNANKENISTSDVQESFVRITRSRAKKAMGRGVSIPPTKPSFKQQKRRAVLKDVSNT
SADIIYSELRKGGNIKANRKCLKEPKKAAKEGANSAMDILVDMHTEKSKLAEDLSKIRMAEAQDV
SLSNFKDEEITEQQEDGSGVMELLQVVDIDSNVEDPQCCSLYAADIYDNIHVAELQQRPLANYME
LVQRDIDPDMRKILIDWLVEVSDDYKLVPDTLYLTVNLIDRFLSNSYIERQRLQLLGVSCMLIAS
KYEELSAPGVEEFCFITANTYTRREVLSMEIQILNFVHFRLSVPTTKTFLRRFIKAAQASYKVPF
IELEYLANYLAELTLVEYSFLRFLPSLIAASAVFLARWTLDQTDHPWNPTLQHYTRYEVAELKNT
VLAMEDLQLNTSGCTLAATREKYNQPKFKSVAKLTSPKRVTLLFSR

FIGURE 10

A.
CCP molecule: CCP10 nucleotide sequence (CKSBC001):
cgacatcttctaagaaagaaacaaagaaagacttcacattttaccattatttgctctgagctcag
taggagagttcaagaaacaatggcaaagatgcaattatcaatctttatcgctgtcgttgcgctta
tcgtctgctctgcatctgctaaaaccgcaagccctccagctccagtgctgccaccgacaccagct
ccagcaccagccccggaaaatgtgaatctcaccgagcttttaagtgtagctggtccgttccacac
attcctcgactaccttctctcgactggagtcattgagactttccaaaaccaagctaacaacactg
aggaaggcatcacaatctttgtccctaaagatgatgctttcaaagctcagaagaatcctcctttg
tcaaatctcacaaaggatcagcttaagcagcttgttctcttccatgctctgcctcattactattc
gctttcggaattcaagaacttgagccaatctggtccagtgagcacctttgctggtggtcaatact
ccttgaaattcactgatgtttctggcacggttaggattgattctttatggaccaggactaaagtc
agcagcagtgttttctccactgaccctgttgcggtttaccaagtgaaccgcgtgcttctacccga
agcaatctttggtactgatgtccctccaatgcctgctccagctcctgctcctatcgttagtgctc
cttcggattctccttcagttgctgattctgaaggagcttcttcaccaaagtcctcacacaagaac
tccggacaaaagctgctacttgcaccaatctccatggttatttccggtttggtggcattgttctt
gtgatcagatggttttgcagattgagttatgttttaagttacaatgtgaaagattgtattacat
catttgaattgtcttttgattttgaaacccattttttattatacatttttatcattattattg
tttgtcattacgattgttgtgaattgaaattgttcctccaaaaaaaaaaaaaaaaaaaa B.
CCP molecule: CCP10 amino acid sequence (CKSBC001):
MAKMQLSIFIAVVALIVCSASAKTASPPAPVLPPTPAPAPAPENVNLTELLSVAGPFHTFLDYLL
STGVIETFQNQANNTEEGITIFVPKDDAFKAQKNPPLSNLTKDQLKQLVLFHALPHYYSLSEFKN·
LSQSGPVSTFAGGQYSLKFTDVSGTVRIDSLWTRTKVSSSVFSTDPVAVYQVNRVLLPEAIFGTD
VPPMPAPAPAPIVSAPSDSPSVADSEGASSPKSSHKNSGQKLLLAPISMVISGLVALFL

FIGURE 11

A.
CCP molecule: CCP11 nucleotide sequence (CKSBC011):
cttaaactacatttatcattacagtctgatttgagctaagttctctcatcataaactctccttgg
agaatcatggctatttcaaaagctcttatcgcttctcttctcatatctcttcttgttctccaact
cgtccaggctgatgtcgaaaactcacagaagaaaaatggttacgcaaagaagatcgattgtggga
gtgcgtgtgtagcacggtgcaggctttcgaggaggccgaggctgtgtcacagagcgtgcgggac
ttgctgctacaggtgcaactgtgtgcctccgggtacgtacggaaactacgacaagtgccagtgct
acgctagcctcaccacccacggtggacgccgcaagtgcccataagaagaaacaaagctcttaatt
gctgcggataatgggacgatgtcgtttgttagtatttactttggcgtatatatgtggatcgaat
aataaacgagaacgtacgttgtcgttgtgagtgtgagtactgtattattaatggttctatttgtt
tttacttgcaagttttcttgtttgaatttgttttttcatatttgtatatcgattcgtgcatta
ttgtattatttcaatttgtaataagattatgttacctttgagtggttgtttaaaaaaaaaaaaa
aaaa B.
CCP molecule: CCP11 amino acid sequence (CKSBC011): SEQ ID NO:77
MAISKALIASFLISLLVLQLVQADVENSQKKNGYAKKIDCGSACVARLQAFEEAEAVSQSVRDLL
LQVQLCASGYVRKLRQVPVLR C.
CCP molecule: CCP11 amino acid sequence (CKSBC011): SEQ ID NO:110
MAISKALIASLLISLLVLQLVQADVENSQKKNGYAKKIDCGSACVARCRLSRRPRLCHRACGTCC
YRCNCVPPGTYGNYDKCQCYASLTTHGGRRKCP

FIGURE 12

A.
CCP molecule: CCP12 and CCP13 nucleotide sequence (CKSBC98-7 C-term and N-term, respectively):
agatggggaagaagaacaagagaagtcaagacgagtctgagctcgaattggagccagagctaacg
aaaataatcgatggagactctaaaaagaagaaaaataagaataagaagaagagaagccatgaaga
tacggagatagaaccggagcaaaagatgagtctcgacggagactcgagggaggagaagataaaga
agaagaggaagaacaagaaccaagaggaggagccagagcttgtgacggagaaaacgaaagtccaa
gaggaggaaaagggaaatgtagaagagggtagagccactgttagcatagccatagctggttcaat
catccacaacactcaatcacttgagctcgccacacgcgtaatctctctttctctctatctctccc
ttcgtttctctgttttccattcccagataatttaaagtccccttcttccatttctaacatttct
cagctcgccggccaaattgctcgtgcagctacaattttccgaatcgacgagatcgtagtgttcga
caataagagcagctcagaaatcgaatcagctgctacgaatgcttctgatagcaatgaaagtggtg
cctcctttctcgttcgtatcttgaagtatctagagacaccacaatatttgaggaaatctctcttc
cccaagcaaaatgatcttagatatgtgggtatgttgccgggtatgttgccacctcttgatgctcc
tcaccatctgcgtaagcacgagtgggaacaataccgtgaagnnnnnattgttccaccctctaagc
caagggaagaagcaggaatgtattgggatacaaagtacgatatgcatcacaattaa
= in CKSBC98-7 C-term
gttcagtattcaaggaatgcccttcgagggtggttacgattatttgattggtacctcggagcac
ggcctggtaattagttcatctgagctgaaaataccaacatttaggcacctattgattgcatttgg
tggacttgctgggcttgaagaaagtattgaagatgataatcagtataaggggaaaaacgttcgag
atgtgtttaatgtatacttgaatacttgtccacatcaaggtagccgaaccattcgagcagaggaa
gcgatgtttatatcacttcagtacttccaggaacccatcagcaggcagtgagaagactttaagc
ttcgataaaagagtcaaagaagctattttgttctcatagatctgaggtttgtctgaaaagagt
gatgtaatgtaactgttttagaaaaaaaaaaaaaaaaa B.
CCP molecule: CCP12 and CCP13 amino acid sequence (CKSBC98-7 C-term and N-term, respectively):
MGKKNKRSQDESELELEPELTKIIDGDSKKKKNKNKKKRSHEDTEIEPEQKMSLDGDSREEKIKK
KRKNKNQEEEPELVTEKTKVQEEEKGNVEEGRATVSIAIAGSIIHNTQSLELATRVISLSLYLSL
RFSVFPFPDNLKSPSSISNISQLAGQIARAATIFRIDEIVVFDNKSSSEIESAATNASDSNESGA
SFLVRILKYLETPQYLRKSLFPKQNDLRYVGMLPGMLPPLDAPHHLRKHEWEQYREXXIVPPSKP
REEAGMYWGYKVRYASQLSSVFKECPFEGGYDYLIGTSEHGLVISSSELKIPTFRHLLIAFGGLA
GLEESIEDDNQYKGKNVRDVFNVYLNTCPHQGSRTIRAEEAMFISLQYFQEPISRAVRRL

FIGURE 13

A.
CCP molecule: CCP14 nucleotide sequence (CKSBC103-19):
atggaattgcttgacatgaactcaatggctgcctcaatcggcgtctccgtcgccgttctccgttt
cctcctctgtttcgtcgcaacgataccaatctcattttttatggcgattcatcccgagtcgactcg
gtaaacacatatactcagctgcttctggagctttcctctcttatctctcctttggcttctcctca
aatcttcacttccttgtcccaatgacgattggttacgcttcaatggcgatttatcgacccttgtc
tggattcattactttcttcctaggcttcgcttatctcattggctgtcatgtgttttatatgagtg
gtgatgcttggaaagaaggaggaattgattctactggagctttgatggtattaacactgaaagtg
atttcgtgttcgataaactacaacgatggaatgttgaaagaagaaggtctacgtgaggctcagaa
gaagaaccgtttgattcagatgccttctcttattgagtactttggttattgcctctgttgtggaa
gccatttcgctggcccggttttcgaaatgaaagattatctcgaatggactgaagagaaaggaatt
tgggctgtttctgaaaaaggaaagagaccatcgccttatggagcaatgattcgagctgtgtttca
agctgcgatttgtatggctctctatctctatttagtacctcagtttccgttaactcggttcactg
aaccagtgtaccaagaatggggattcttgaagagatttggttaccaatacatggcgggtttcacg
gctcgttggaagtattactttatatggtctatctcagaggcttctattattatctctggtttggg
tttcagtggttggactgatgaaactcagacaaaggctaaatgggaccgcgctaagaatgtcgata
ttttgggggttgagcttgccaagagtgcggttcagattccgcttttctggaacatacaagtcagc
acatggctccgtcactacgtatatgagagaattgtgaagcccgggaagaaagcgggtttcttcca
attgctagctacgcaaaccgtcagtgctgtctggcatggactgtatcctggatacattatattct
ttgtgcaatcagcattgatgatcgatggttcgaaagctatttaccggtggcaacaagcaatacct
ccgaaaatggcaatgctgagaaatgttttggttctcatcaatttcctctacacagtagtggttct
caattactcatccgtcggtttcatggttttaagcttgcacgaaacactagtcgccttcaagagtg
tatattacattggaacagttatacctatcgctgtgcttcttctcagctacttagttcctgtgaag
cctgttagaccaaagaccagaaaagaagaataatgttgtcttttttaaaaaatcaacaacattttg
gttcttttctttttttccacttggnccgttttatgtaaaacaagagaaatcaagatttgaggttt
tattcttaaaaaaaaaaaaaaaaaa B.
CCP molecule: CCP14 amino acid sequence (CKSBC103-19):
MELLDMNSMAASIGVSVAVLRFLLCFVATIPISFLWRFIPSRLGKHIYSAASGAFLSYLSFGFSS
NLHFLVPMTIGYASMAIYRPLSGFITFFLGFAYLIGCHVFYMSGDAWKEGGIDSTGALMVLTLKV
ISCSINYNDGMLKEEGLREAQKKNRLIQMPSLIEYFGYCLCCGSHFAGPVFEMKDYLEWTEEKGI
WAVSEKGKRPSPYGAMIRAVFQAAICMALYLYLVPQFPLTRFTEPVYQEWGFLKRFGYQYMAGFT
ARWKYYFIWSISEASIIISGLGFSGWTDETQTKAKWDRAKNVDILGVELAKSAVQIPLFWNIQVS
TWLRHYVYERIVKPGKKAGFFQLLATQTVSAVWHGLYPGYIIFFVQSALMIDGSKAIYRWQQAIP
PKMAMLRNVLVLINFLYTVVVLNYSSVGFMVLSLHETLVAFKSVYYIGTVIPIAVLLLSYLVPVK
PVRPKTRKEE

FIGURE 14

A.
CCP molecule: CCP15 nucleotide sequence (CKSBC199-20):
ttatataacctatctacactttgatctccgacaattcactttcccaataagaaccaactgagaga
gagagagcgccggagaagaagaattttagagagcg<span style="background:black;color:white">atg</span>gacgagggagttatagcagtttccgcc
atggatgctttcgagaagcttgagaaagttggtgagggacatacgggaaagtttacagagccag
agagaaagctaccgggaaaatcgtcgctctaaagaagacgcgtctccatgaggacgaagaaggcg
ttccttccaccactctccgcgagatctccattttgcgaatgctcgctcgtgatcctcacgtcgtc
aggttaatggatgttaagcaaggactaagcaaagaaggcaaaactgtactgtacctggttttga
atacatggacactgatgtcaagaaattcatcagaagtttccgtagcactggcaagaacattccaa
cccaaactatcaagagcttgatgtatcaactatgcaaaggtatggcattctgccatggtcacggg
atattgcacagagatctcaagcctcacaatctcttgatggatcccaagacaatgaggctcaaaat
agcagatcttggtttagccagagccttcactctgccaatgaagaagtatacccatgagatattaa
ctctttggtatagagctccagaggtt-cttcttggtgccacccattactctacagctg
    in CKSBC199.20:  ngntt
tggatatgtggtctgttggctgcatatttgctgaacttgtgaccaaccaagcaatcttt
        n in CKSBC199.20
cagggagactctgagctccaacagctcctccatattttcaagttgtttgggacacccaa
                        in CKSBC199.20: -
tgaagaaatgtggccaggagtgagcacactcaagaactggcatgaatacccacagtggaaaccat
cgactctatcctctgctgttccaaacctcgacgaggctggagttgatcttcta
      - in CKSBC199.20
tctaaaatgctgcagtacgagccagcgaaacgaatctcagcaaagatggctatggagca
                                         a in CKSBC199.20
tccttactttgatgatctgccagaaaagtcctctctc<span style="background:black;color:white">taag</span>gatttaaaatcttcagttagtatc
tttccaagttttatggttttttctagttttgcttctttcaagcatatctctagtgtgctgcttccc
cctctatgaa B.
CCP molecule: CCP15 amino acid sequence (CKSBC199-20):
MDEGVIAVSAMDAFEKLEKV<span style="background:black;color:white">GEGTYGKVY</span>RAREKATGKIVALKKTRLHEDEEGV|PSTTLRE|ISIL
RMLARDPHVVRLMDVKQGLSKEGKTVLYLVFEYMDTDVKKFIRSFRSTGKNIPTQTIKSLMYQLC KGMAFCHGHGIL<u>HRDLKPHNLL</u>MDPKTMRLKIADLGLARAFTLPMKKYTHEILTLWYRAPEVLLG
                                                                                    *** ****
ATHYSTAV<u>DMWSVGCIFAEL</u>VTNQAIFQGDSELQQLLHIFKLFGTPNEEMWPGVSTLKNWHEYPQ
   *  ** * *****++    + ++++ ++ ++   +++ + ++++       +
                                                          11111    1
WKPSTLSSAVPNLDEAGVDLLSKMLQYEPAKRISAKMAMEHPYFDDLPEKSSL
+      -   -  -   -  -- ----   - --    - --   -
1     11   1  1     1111  1 1   11 1  1  1 111 1

FIGURE 15

A.
CCP molecule: CCP16 nucleotide sequence (E2F5BBC1):
tagtcaacgatggatttgagacatgaacaactaattgatttgatttcgtgtagctaactttgtta
attggtaaattgtgtagagaaggatgagtatggagatggagttgtttgtcactccagagaagcag
aggcaacatccttcagtgagcgttgagaaaactccagtgagaaggaaattgattgttgatgatga
ttctgaaattggatcagagaagaaagggcaatcaagaacttctggaggcgggcttcgtcaattca
gtgttatggtttgtcagaagttggaagccaagaagataactacttacaaggaggttgcagacgaa
attatttcgattttgccacaattaagcaaaacgcagagaagcctttgaatgaaaatgagtacaa
tgagaagaacataaggcggagagtctacgatgcgctcaatgtgttcatggcgttggatattattg
caagggataaaaaggaaatccggtggaaaggacttcctattacctgcaaaaaggatgtggaagaa
gtcaagatggatcgtaataaagttatgagcagtgtgcaaaagaaggctgcttttcttaaagagtt
gagagaaaaggtctcaagtcttgagagtcttatgtcgagaaatcaagagatggttgtgaagactc
aaggcccagcagaaggatttaccttaccattcattctacttgagacaaaccctcacgcagtagtc
gaaatcgagatttctgaagatatgcaacttgtacacctcgacttcaatagcacacctttctcggt
ccatgatgatgcttacattttgaaactgatgcaagaacagaagcaa
                                             in E2F5BBC1:  g
gaacagaacagagtatcttcttcttcatctacacatcaccaatctcaacatagctccgctcattc
ttcatccagttcttgcattgcttctggaacctcaggcccggtttgctggaactcgggatccattg
atactcgctgaccgagcttctattcccaaattcttcaagaagaagaagtaatgatctaattggta
tactaaaaaattatacatctggtttagtgttcaattgagagagactgtaaaatcaattcataggc
caacaaatgtttgtttatccaattttcctttttattcgaacttgatgcgatatttcaacggaaac
agaaactattgttttaaaccaaaaaaaaaaaaaaaaaa B.
CCP molecule: CCP16 amino acid sequence (E2F5BBC1):
MSMEMELFVTPEKQRQHPSVSVEKTPVRRKLIVDDDSEIGSEKKGQSRTSGGGLRQFSVMVCQKL
EAKKITTYKEVADEIISDEATIKQNAEKPLNENEYNEKNIRRRVYDALNVFMALDIIARDKKEIR
WKGLPITCKKDVEEVKMDRNKVMSSVQKKAAFLKELREKVSSLESLMSRNQEMVVKTQGPAEGFT
LPFILLETNPHAVVEIEISEDMQLVHLDFNSTPFSVHDDAYILKLMQEQKQEQNRVSSSSSTHHQ
SQHSSAHSSSSSCIASGTSGPVCWNSGSIDTR

CCP molecule: CCP17 nucleotide sequence (FL67BC4-2):
caaattctctggaagaagaagaagacgaagatgcaaccgacagagacgtcgcagccggcgccgtc
ggatcaaggccgccggcttaaggatcagttatcggagagtatgagcttcagtagccaaatgaaga
aggaagacgatgagttgtcgatgaaagctttgtcggcgttcaaggccaaagaagaggagatcgag
aagaagaagatggagatcagagaaagagttcaagctcagcttggtcgtgttgaagatgagtccaa
gcgtctcgctatgattcgcgaggaacttgaaggttttgctgatcccatgaggaaggaagttacta
tggtgaggaagaagattgattctctcgacaaagaattaaagccattggggaatacagttcagaaa
aaggaaacagagtacaaggatgctcttgaagcattcaatgaaaagaacaaggagaaggtggagct
gatcaccaagctacaggagttggaggagaaagcgagaaattcaggttcaagaagctggaggagc
taagcaagaacattgatctaaccaaacctagtgttggacgagagagtcgctgggatttggcta
ttcaaagttctaaaaagtcacttttttagagtatttcattgttcttttatgattctagtaatat
atataatttataaaataaaagtaagaagatatgtgtttgaactagatgttgcaaagaaaatgta
acaaagttacgatggcactacattatcgacgtgattggcagaattgtaatagtaatgtaaagaaa
ctatgtttgttccggaaaaaaaaaaaaaaaaaaaaaaaaa

B.

CCP molecule: CCP17 amino acid sequence (FL67BC4-2):
MQPTETSQPAPSDQGRRLKDQLSESMSFSSQMKKEDDELSMKALSAFKAKEEEIEKKKMEIRERV
QAQLGRVEDESKRLAMIREELEGFADPMRKEVTMVRKKIDSLDKELKPLGNTVQKKETEYKDALE
AFNEKNKEKVELITKLQELEGESEKFRFKKLEELSKNIDLTKP

FIGURE 17

A.
CCP molecule: CCP18 nucleotide sequence (FL67BC12-17):
atgaatagggaaaagttgatgaagatggctaacactgtccgcactggcggaaaggggacagtaag
aagaaagaagaaggctgttcacaagaccactacaaccgatgacaagaggctccagagcactctta
agagagttggagtcaattccattcccgccattgaagaagttaacattttttaaggatgatgtagtc
attcagttcattaaccctaaagttcaagcttcaattgctgctaacacatgggttgtgagtggtac
accacagacgaaaaaattgcaagacattcttcctcagattatcagccaacttggaccagataact
tggacaacctgaagaagctagcagagcaattccagaaacaagctccaggtgcaggtgatgtccca
gcaacaatccaagaagaggacgatgatgatgatgtcccagatcttgtagtgggagagactttcga
gaccctgctactgaagaggctcccaaagctgctgcttcttagaggaggaggaagaagaaggaga
agagctcacctgcaaaacccatcataaaaatgtttgtcgctcgacctcttctgagcactgtcaga
ttcttgttttctctaatgcttgcgaacagaaagacttggttttattatcacttgatgcttttgg
tccgaacagcaattttcctttattaaggttagatcgcttttgtttaccacctgttcaaatgag
tactactatgtcctgtcgcttcatacacttcttgcaacacagtcctttgttttgagtcaaaaaaa
aaaaaaaaaaaaaaaaaaaaaaa B.
CCP molecule: CCP18 amino acid sequence (FL67BC12-17):
MNREKLMKMANTVRTGGKGTVRRKKKAVHKTTTTDDKRLQSTLKRVGVNSIPAIEEVNIFKDDVV
IQFINPKVQASIAANTWVVSGTPQTKKLQDILPQIISQLGPDNLDNLKKLAEQFQKQAPGAGDVP
ATIQEEDDDDDVPDLVVGETFETPATEEAPKAAAS

FIGURE 18

A.
CCP molecule: CCP19 nucleotide sequence (JUT1):
tatccggtgaccttatccctcgccggtgagcgaatctcagatccaaaattttgcaaaatcctca
gatcgtcttaccttctccgaatcgatcgattttcatggaggacgacgacgagattcagtcaatt
ccatctccgggagattcttccctttcaccacaagctcctccttctccgccgattttgccaacaaa
cgacgtgacggtggccgtcgtgaagaaaccacaaccggggctttcttctcaatctccgtccatga
acgctttagcgttagtggttcatactccttctgtaaccggtggtggtggtagcggaaacagaaac
ggacgaggaggaggaggaggaagcggtggtggtggaggaggaagagatgattgttggagcgaaga
agctacaaaggttctaatcgaagcttggggagatcgattctctgaaccaggtaaggaactttga
agcaacaacattggaagaagtagctgagattgtgaacaagagtcgtcaatgcaaatacccttaaa
actgatattcagtgtaagaacagaattgatacggtgaagaagaagtataagcaagagaaagctaa
gattgcttctggtgatggacctagtaaatgggttttcttcaagaagcttgagagtttgattggtg
gtactacaacattcattgcttcttcaaaagcttcagagaaggctcctatgggaggagctcttggg
aatagccgttcgagtatgtttaaacggcaaactaaaggtaatcagattgtgcagcaacaacaaga
gaagagaggctctgattcgatgcggtggcatttaggaaacgtagtgcttctgagactgagtctg
agtctgatcctgaacctgaggcttctcctgaggaatctgctgagagtctcccaccttttgcaaccg
attcaaccgctttcgtttcatatgccaaagcggttgaaggtggataagagtggaggtggagggag
tggagttggagatgtggcgagggcgatacttggatttacggaagcttatgagaaggcggaaactg
ctaagcttaagttaatggcggaactggaaaaggagaggatgaaatttgctaaagagatggagttg
cagagaatgcagttcttgaaaactcaattggagataacacagaacaatcaagaagaggaagagag
gagcaggcagcgaggagaaaggaggatcgttgatgatgatgatgatcgcaatggcaagaataacg
gcaatgtaagtagctgacaattgaacacacaaatgttcctatgatatttgctatgataagctgga
ttttaggttttgatgttgttgttgttattgttactgccttgtgggatgt B.
CCP molecule: CCP19 amino acid sequence (JUT1):
MEDDDEIQSIPSPGDSSLSPQAPPSPPILPTNDVTVAVVKKPQPGLSSQSPSMNALALVVHTPSV
TGGGGSGNRNGRGGGGGSGGGGGGRDDCWSEEATKVLIEAWGDRFSEPGKGTLKQQHWKEVAEIV
NKSRQCKYPKTDIQCKNRIDTVKKKYKQEKAKIASGDGPSKWVFFKKLESLIGGTTTFIASSKAS
EKAPMGGALGNSRSSMFKRQTKGNQIVQQQQEKRGSDSMRWHFRKRSASETESESDPEPEASPEE
SAESLPPLQPIQPLSFHMPKRLKVDKSGGGGSGVGDVARAILGFTEAYEKAETAKLKLMAELEKE
RMKFAKEMELQRMQFLKTQLEITQNNQEEEERSRQRGERRIVDDDDDRNGKNNGNVSS

FIGURE 19

CCP molecule: CCP20 and CCP21 nucleotide sequence (JUT2 and JUT3, respectively):
aagctttactacttatactcttttgttcctatggccacogtatcttcttcctcctggccaaaccc
caacoctaatcccgattccacgtctgcctcagattccgattctacttttccctctcaccgcgatc
gcgtagacgaacccgactctctcgattccttctcctccatgagtctt
     in JUT2 (N-term): n
aactccgacgaacctaatcagacttctaatcaatcgcctctttctccccctacgcccaatttacc
ggtgatgcctcctccgtccgtgcttcatctttcctttaaccaagatcatgctt
in JUT2 (N-term):t   t
gcttcgc-tgtcggcactgaccgtggcttc-cggatccttaattgcgatccctttcgcg
   c n     a n n in JUT2 (N-term)
agatttccggcgtgatttcgatcgtggcggtggtgttgcagtcgtggagatgcttttc
    g in JUT2 (N-term)
agatgcaatatattagccctagttggtggcggacctgatcctcaatatcctcctaataaggttat
gatttgggatgatcaccagggccgatgtatcggagaactctctttcaggtccgatgttagatccg
tccggcttaggagggatcggattattgtcgttcttgagcagaagattttttgtctacaatttctct
gacctcaagctgatgcatcagattgaaaccattgccaaccctaagggtttgtgtgctgtttctca
gggtgttggttctatggttttggtatgtccaggtttgcagaaaggtcaagttcggatcgagcact
acgcttctaaacggaccaaattcgtcatg
     in JUT3: -
gctcatgattccagaatagcttgcttcgctctcacgcaggatggccatttgttggccactgctag
ctctaagggtactctggttcggatcttcaatactgttgatggtaccttgcgtcaagagtctggca
                      in JUT3: -------
cttctgaggatgaaataggtaaggaggg-tgcggatagagcagagat
----------------- g in JUT3
ctacagtttggccttctcttcaaatgctcagtggttagctgtctcaagtgacaaaggaacggtcc
atgtctttggtctcaaagtcaactccggatctcaagtgaaagactcatcccgaattgcacctgat
gctactccctcatcccatcgtcgtctctgtctttattcaa---agt
     in JUT3: agg
gttaccgaggtatttcagctcggagtggtcggtggctcagttcaggttggttgaaggaactcagt
acatagccgcctttggccatcaaaagaacaccgttgttattcttggcatggatgggagcttctac
agatgccagtttgatccggtgaacggcggtgaaatgtctcagcttgagtaccacaactgtctgaa
accgccttcagttttcGaaaagctttactacttatactcttttgttccttctctctctttatatc
tctctgcaacttaagcggtgagatatggtgtatagttttgtgtataataatgatgggtcgtcc
tataatttgtaaaaccttttatcgctaccgggtcgactctagagccctatagtgagtcgtatta
ctgcagagatctatgaatcgtagatactgaaaaa

FIGURE 20

CCP molecule: CCP20 and CCP21 amino acid sequence (JUT2 and JUT3, respectively):

MATVSSSSWPNPNPNPDSTSASDSDSTFPSHRDRVDEPDSLDSFSSMSLNSDEPNQTSNQSPLSP
PTPNLPVMPPPSVLHLSFNQDHACFAVGTDRGFRILNCDPFREIFRRDFDRGGGVAVVEMLFRCN
ILALVGGGPDPQYPPNKVMIWDDHQGRCIGELSFRSDVRSVRLRRDRIIVVLEQKIFVYNFSDLK
LMHQIETIANPKGLCAVSQGVGSMVLVCPGLQKGQVRIEHYASKRTKFVMAHDSRIACFALTQDG
HLLATASSKGTLVRIFNTVDGTLRQESGTSEDEIGKEGADRAEIYSLAFSSNAQWLAVSSDKGTV
                              VRR-------- in JUT3
HVFGLKVNSGSQVKDSSRIAPDATPSSPSSSLSLFK-VLPRYFSSEWSVAQFRLVEGTQYIAAFG
                                    G in JUT3
HQKNTVVILGMDGSFYRCQFDPVNGGEMSQLEYHNCLKPPSVF

FIGURE 21

CCP molecule: CCP22 nucleotide sequence (JUT6):

agagcttcctctctctatatctggctttctatcgatgtaggagttactacggcgaagtctatact
tgagaagcctctgaagcttctcactgaagaagacatttctcagcttactcgcgaagattgccgca
aattcctcaaagagaaaggtttcttcttcttcctttctccatttttttccggtcttattgtcttc
gacgaatggcggctgacacgtgtcgaaacaggaatgcgcaggccttcgtggaataaatctcaggc
gatccagcaagttttatctcttaaagctctctatgaacctggagatgattccggcgccggaatcc
tccgcaagatccttgtttctcagccgccaaatccgcctcgcgttacaacaacgttgattgagcca
aggaacgagctcgaagcttgtggaaggattcctttacaggaagatgatggtgcgtgccatagaag
ggattctccaagatcagctgagttttctggtagttctggtcagtttgttgcggataaagatagcc
acaagactgtttctgtttcccccagaagcccagctgaaacaaatgcggtggttgggcaaatgacg
atatttatagtggcaaagtgaatgtatatgatggagtaccacctgaaaaggcccggtctatcat
gcattttgcagccaatccaattgatttgcctgaaaatggtattttgcttctagtagaatgattt
cgaaacccatgagtaaagagaagatggtggagcttccccaatatggacttgaaaaggcacctgct
tctcgtgattctgatgttgagggtcaggcgaacagaaagtatcgttgcaaagatatcttgaaaa
gcggaaagacagattttctaagaccaagaaggctccaggagttgcgtcctctagcttggagatgt
ttctgaatcgtcagccacggatgaacgctgcatattcacaaaaccttagtggcacagggcattgc
gagtcacctgaaaatcaaacaaaaagtcccaatatctcagttgatctaaacagtgatctaaacag
cgaaggtgccaaaagaactggagatggtactacgggtcaaaaggcgggaagaacaatttcatgtt
cttataacatgactaagacatcacgaggaacacgatgggtgaagcggtcaagagaagaagtgatt
caagcttggtatatggatgatagtgaagaggatcagagacttcctcaccacaaggatcctaaaga
gtttgtatcgttggacaaacttgcagagctgggagtacttagctggagacttgatgctgataact
atgaaaccgatgaggatttgaaaaagatccgtgaatctcgtggttactctta<u>catggacttttgt</u>
<u>gaggtatgcccggaaaagcttccaaactatgaagtgaaagtgaagagcttttcgaagaacattt</u>
<u>acacactgatgaggagatccgttactgcgttgcaggaactggttactttgatgtgagagatcgta</u>
<u>atgaagcttggattagggtattggtaaagaagggaggtatgatagtcttacctgctgggatctat</u>
<u>catcgcttcactgtggactctgacaactatatcaaggcaatgcggctattcgtgggtgaaccggt</u>
<u>atggacaccatacaatcgcccacgaccatcttcctgcaaggaaagaatatgtcgataacttca</u>
<u>tgatcaatgcctcggcttag</u>agagcttcctctctctatatctggctttctgaaacaaggatctat
aaacaaggcctacaataaagaaagctttcctgtcaagtattggatatttatatgtattcctgtgt
agaatgatggcttttggtatgcttgagttgttgtaaacttagttacactctctgatatgtctctc
tttaccatctttgtcgtatcccatatacgaaaagattacattgggattcatattgtcttacgttc
gttcctatgtgcaatatgttgagtttt

FIGURE 22

CCP molecule: CCP22 amino acid sequence (JUT6):
MDVGVTTAKSILEKPLKLLTEEDISQLTREDCRKFLKEKGFFFFLSPFFSGLIVFDEWRLTRVET
GMRRPSWNKSQAIQQVLSLKALYEPGDDSGAGILRKILVSQPPNPPRVTTTLIEPRNELEACGRI
PLQEDDGACHRRDSPRSAEFSGSSGQFVADKDSHKTVSVSPRSPAETNAVVGQMTIFYSGKVNVY
DGVPPEKARSIMHFAANPIDLPENGIFASSRMISKPMSKEKMVELPQYGLEKAPASRDSDVEGQA
NRKVSLQRYLEKRKDRFSKTKKAPGVASSSLEMFLNRQPRMNAAYSQNLSGTGHCESPENQTKSP
NISVDLNSDLNSEGAKRTGDGTTGQKAGRTISCSYNMTKTSRGTRWVKRSREEVIQAWYMDDSEE
DQRLPHHKDPKEFVSLDKLAELGVLSWRLDADNYETDEDLKKIRESRGYSYMDFCEVCPEKLPNY
EVKVKSFFEEHLHTDEEIRYCVAGTGYFDVRDRNEAWIRVLVKKGGMIVLPAGIYHRFTVDSDNY
IKAMRLFVGEPVWTPYNRPHDHLPARKEYVDNFMINASA

FIGURE 23

A.
CCP molecule: CCP23 nucleotide sequence (kbp1):
catcgcttttcgctgaaatcaaaatttctccagttttccgatcagtcgcaagaaaaccc
c in KBP1
taaaaatggatggtcatgattctaaggatactaagcagagcactgctgatatgactgct
g in KBP1
tttgtccaaaatcttctccagcagatgcaaaccaggttccagacaatgtcggactccatcatcac
aaagattgatgacatgggaggcagaatcaatgagctggagcaaagcatcaatgatctaagagccg
agatgggagtagaaggcactcctcctccagcctccaaatcaggcgatgaacccaaaacacggct
agttcctcttaaaaaggaatgtggtgttcattgacatgtccgaaggaaaaagaaaaactatgaaa
tatgttaagagcagtattacttttaaaattcctgttttaagaaacgagtttgttgtttattaaag
- in KBP1
ttcatcaaatagattgatgatgtggtgcattacattattctccacctatgaattgcatttctatt
ttggtctaaaaaaaaaa B.
CCP molecule: CCP23 amino acid sequence (kbp1): SEQ ID NO:89
TSFPITRKKTLKMDGHDSEDTKQSTADMTAFVQNLLQQMQTRFQTMSDSIITKIDDMGGRINELE
QSINDLRAEMGVEGTPPPASKSGDEPKTPASSS C.
CCP molecule: CCP23 amino acid sequence (kbp1): SEQ ID NO:118
MDGHDSKDTKQSTADMTAFVQNLLQQMQTRFQTMSDSIITKIDDMGGRINELEQSINDLRAEMGV
EGTPPPASKSGDEPKTPASSS

FIGURE 24

CCP molecule: CCP24 nucleotide sequence (kbp3):

agaacaattgagattcttggttgtgttaagatggaaatctacaccatgaaaacgaatttcttgt
actggctttgtctttgtgtatccttctttcaagcttccatgaggtttcttgtcaggatgatggta
gtggtttgagtaatttggatctaatagaacgtgattatcaagatagtgtcaatgctcttcaaggc
aaggacgatgaagatcagtctgcaaagatacagagtgaaaaccagaataacactacagtgactga
taagaacactatttctctatctctatcagatgaatctgaggttggatctgttagtgatgaaagcg
ttggacgttcgagtctgttggatcaaatcaaacttgaattcgaagctcatcacaatagtattaac
caagctggatctgatggtgtcaaggctgaatccaaggatgatgatgaagaattatctgctcatag
acagaaaatgttggaagaaatcgaacatgagtttgaagctgcttcagatagtctgaaacaactaa
agactgatgatgtaaacgaaggaaatgatgaagaacattctgcaaagaggcaaagtttgttggaa
gagatcgaacgtgagtttgaagctgctacaaaagaacttgaacaactaaaggttaatgacttcac
cggggacaaagatgacgaagaacactctgcaaagagaaaaagtatgcttgaagctattgaacgcg
agtttgaagctgctatggaaggcattgaagcacttaaggtttctgattccacaggaagcggagat
gatgaagaacaatctgcaaagagactaagtatgcttgaagagatcgaacgggaatttgaagctgc
ttcaaaaggtcttgaacaactaagggctagcgattcaaccgcggacaataacgaagaagaacacg
ctgcaaagggacaaagtttgttagaagagatcgaacgagagttcgaagctgctacagagagcctt
aagcaacttcaagttgatgattctactgaagacaaagaacactgtaaagcactcttcttcttatt
atctgctattctttctctatggttatctgaatcaggctttgaatgtattgtagttacagctgcaa
agaggcaaagtctgctggaagagattgaacgtgaatttgaagctgcaacaaaagatcttaaacaa
ctaaatgatttcactgaaggcagtgctgatgatgaacaatctgcaaagagaaacaaatgttgga
agatatcgaacgcgaatttgaagctgctacaataggtcttgaacaactaaaggctaatgatttct
ctgaaggcaataataatgaagaacaatctgcaaagagaaagagtatgcttgaagagatcgaacgc
gagttcgaagctgctattggaggtcttaaacagatcaaagttgatgattccagaaatcttgaaga
agaatctgctaagagaaagataattttggaagagatggaacgtgaatttgaagaagcacacagtg
gtattaatgcaaaggctgacaaagaagaatctgcaaagaaacagagtggctctgctataccagag
gttcttggactaggacagtcaggtggttgtagctgttctaaacaagacgaagattcctcgattgt
tataccaacaaaatatagcatagaagatatcctctctgaagaatctgcagtccagggaacagaga
cttctagtctcaccgcgtctttgactcaactcgttgagaatcacaggaaagaaaaggaatctcta
ctcggacacagagttctcacttctccttctatagcttcttccacaagcgaatcatctgctacatc
agagactgtagaaaccctaaggctaaactgaatgagcttcgcggcttaaccgctcgtgagcttg
tgacacgtaaagatttcggtcagattctcattacggctgcgagttttgaagagctaagttcagct
ccaatcagttacatttctaggttagctaaatacagaaacgtcatcaaagaaggacttgaagcttc
tgagagagttcacatcgcgcaggtacgagcaaaaatgctcaaagaagttgccacggagaagcaaa
ccgccgtggacactcatttcgcaaccgctaaaaagcttgctcaagaaggagacgcgttgttcgtt
aaaatcttcgcaatcaagaaactgttggcgaaacttgaagcagagaagaatctgttgatggaaa
gtttaaggagactgtgaaagaactttctcatcttctggctgatgcttctgaggcttacgaagagt
atcatggcgcggtgaggaaggcgaaagacgagcaagcggctgaggaatttgcgaaagaggcgacg
caaagtgcagagatcatttgggttaagtttcttagttctctttagagaacaattgagattcttgg
ttgtgttaagagcaaatctagagctcttgttggttcttgttatgtatttgtgatgatgttctgt
ttcagagtttgtgtgttggttgtatcaggagaagaggctgggagatagagagaagagagtctc
tgcgaaaactaataatgttttttcagatatctaaataataagcttttacaaaaaaaaaaaaaaaa
aaaaaaaaa

FIGURE 25

CCP molecule: CCP24 amino acid sequence (kbp3):
MEIYTMKTNFLVLALSLCILLSSFHEVSCQDDGSGLSNLDLIERDYQDSVNALQGKDDEDQSAKI
QSENQNNTTVTDKNTISLSLSDESEVGSVSDESVGRSSLLDQIKLEFEAHHNSINQAGSDGVKAE
SKDDDEELSAHRQKMLEEIEHEFEAASDSLKQLKTDDVNEGNDEEHSAKRQSLLEEIEREFEAAT
KELEQLKVNDFTGDKDDEEHSAKRKSMLEAIEREFEAAMEGIEALKVSDSTGSGDDEEQSAKRLS
MLEEIEREFEAASKGLEQLRASDSTADNNEEEHAAKGQSLLEEIEREFEAATESLKQLQVDDSTE
DKEHCKALFFLLSAILSLWLSESGFECIVVTAAKRQSLLEEIEREFEAATKDLKQLNDFTEGSAD
DEQSAKRNKMLEDIEREFEAATIGLEQLKANDFSEGNNNEEQSAKRKSMLEEIEREFEAAIGGLK
QIKVDDSRNLEEESAKRKIILEEMEREFEEAHSGINAKADKEESAKKQSGSAIPEVLGLGQSGGC
SCSKQDEDSSIVIPTKYSIEDILSEESAVQGTETSSLTASLTQLVENHRKEKESLLGHRVLTSPS
IASSTSESSATSETVETLRAKLNELRGLTARELVTRKDFGQILITAASFEELSSAPISYISRLAK
YRNVIKEGLEASERVHI<u>AQVRAKMLKEVATEKQTAVDTHFATAKKLAQEGDALFVKIFAIKKLLA
KLEAEKESVDGKFKETVKELSHLLADASEAYEEYHGAVRKAKDEQAAEEFAKEATQSAEIIWVKF
LSSL</u>

FIGURE 26

CCP molecule: CCP25 nucleotide sequence (kbp6):

aatttgaatccaatccccaaattatctcatatggagtttggatcttttcttgtgtccttagggac
atctttttgttatcttcgtcattctcatgcttctcttcacctggctttctcgcaaatctggaaatg
ctcccatttattacccgaatcggatccttaaagggctggagccatgggaaggcacctccttgact
cgaaacccttttgcttggatgcgtgaagctttgacttcctctgaacaagatgtcgttaacttatc
cggcgtcgatactgctgtccactttgtcttcttgagcactgttctggggatatttgcttgttcca
gtcttcttctcctaccaactctactgcctctagccgctacagacaacaacataaagaacacaaag
aatgcgacagataccacaagcaaaggaacttttagccaacttgataatctatcaatggctaacat
cacaaaaaaagttcgaggctgtgggcgttcctaggagctgtttactggatatctttggtcacat
atttcttcttgtggaaagcttataagcatgtctcttcattgagagctcaagctctgatgtctgct
gatgtaaaacccgagcaattcgctattcttgttagggatatgcctgcaccacctgacgggcagac
acagaaagagtttattgattcttatttcagagaaatatacctgagacattctacagatcgcttg
tcgcaacagaaaacagcaaggttaataaaatatgggaaaaattggaaggttacaagaagaagctt
gcgcgagcagaagcaatattagcagcaactaataaccgtcccacgaacaaaaccggcttctgtgg
gctagtcggtaaacaagtagacagcattgagtattcactgagctaatcaacgagtctgtagcca
aactggaaacagagcagaaagcggttcttgctgagaagcagcaaaccgcagcagtggttttcttc
acaaccagggttgctgctgcatcagcagctcagtctctgcactgccagatggttgataaatggac
tgtgaccgaagctcctgagccacggcagctcctatggcagaatctcaacatcaagctcttcagca
gaataatccggcaatacttcatctacttctttgttgcagtgaccattctgttttacatgatacca
atcgcgttcgtctctgccatcaccactcttaagaatcttcagaggattattccgttcataaagcc
ggttgtggagataaccgccataagaaccgttttggagtcttttccttcctcagattgcgctcattg
tttttcttggccatgttgccgaagcttctcttgtttctctccaaagccgaggggattccttcacag
agccatgccattagggctgcttcagggaagtacttttacttctcggtctttaatgtcttcattgg
tgttacccttgctgggactttgttcaacacagtgaaggatatcgcgaaaaatcccaaactcgaca
tgattattaaccttttggctactagcctccctaagagcgcaactttcttcctgacctacgttgct
ctcaagttctttatcggttatggccttgagctgtctcggatcatacctttgataatcttccacct
gaaaaagaagtatctctgcaaaaccgaagcggaggtcaaagaagcttggtacccgggagacttaa
gctatgcgactagggttcccggagacatgctcatcctcacaatcacgttctgctattcagtcatt
gctcctcttatcctcatattcggcatcacctactttggtttaggctggctagtcctcaggaatca
ggcgttgaaagtgtacgttccatcatacgagagctatggaagaatgtggccgcatattcaccagc
gcatactagcagcgttgtttctattccaagtggtaatgtttggctacttaggagccaagacattc
ttctacacggcccttgtgatccctctcattatcacctctctcatcttcggatatgtgtgccgcca
gaaattctacgagaggttcgaacacacagctctcgaggtagcttgccgtgagctgaagcagagtc
cagacctagaggagattttcagagcatacattccgcatagcttgagctctcacaaaccagaagaa
cacgagttcaaaggcgcaatgtctcgttatcaagatttcaacgcaatagcaggcgtttaaagctt
gagagattcctctggctaaacccag

FIGURE 27

CCP molecule: CCP25 amino acid sequence (kbp6):
MEFGSFLVSLGTSFVIFVILMLLFTWLSRKSGNAPIYYPNRILKGLEPWEGTSLTRNPFAWMREA
LTSSEQDVVNLSGVDTAVHFVFLSTVLGIFACSSLLLLPTLLPLAATDNNIKNTKNATDTTSKGT
FSQLDNLSMANITKKSSRLWAFLGAVYWISLVTYFFLWKAYKHVSSLRAQALMSADVKPEQFAIL
VRDMPAPPDGQTQKEFIDSYFREIYPETFYRSLVATENSKVNKIWEKLEGYKKKLARAEAILAAT
NNRPTNKTGFCGLVGKQVDSIEYYTELINESVAKLETEQKAVLAEKQQTAAVVFFTTRVAAASAA
QSLHCQMVDKWTVTEAPEPRQLLWQNLNIKLFSRIIRQYFIYFFVAVTILFYMIPIAFVSAITTL
KNLQRIIPFIKPVVEITAIRTVLESFLPQIALIVFLAMLPKLLLFLSKAEGIPSQSHAIRAASGK
YFYFSVFNVFIGVTLAGTLFNTVKDIAKNPKLDMIINLLATSLPKSATFFLTYVALKFFIGYGLE
LSRIIPLIIFHLKKKYLCKTEAEVKEAWYPGDLSYATRVPGDMLILTITFCYSVIAPLILIFGIT
YFGLGWLVLRNQALKVYVPSYESYGRMWPHIHQRILAALFLFQVVMFGYLGAKTFFYTALVIPLI
ITSLIFGYVCRQKFYGGFEHTALEVACRELKQSPDLEEIFRAYIPHSLSSHKPEEHEFKGAMSRY
QDFNAIAGV

FIGURE 28

CCP molecule: CCP26 nucleotide sequence (kbp9):

```
aacaataagaagaaaaagtttcattttctgatggcggagcagaagagtaccaatatgtggaactg
ggaggtgactgggttcgaatcgaagaagtcgccttctagtgaggaaggcgttcatcggacaccgt
cttctatgcttcgacggtactcgatcccgaagaactcgcttccaccgcactcgtcggagcttgcg
tctaaggttcagagtttgaaggataaagttcagcttgcaaaggacgattatgtgggattgagaca
ggaagctactgatcttcaagagtactccaatgcgaagcttgaaagggttacacgttatttaggtg
ttctggctgataaaagtcgtaaactggatcaatatgcacttgagactgaggctaggatatctcca
cttatcaatgagaagaagagactgttcaatgacttactgacgaccaaaggtgcacatcttccatt
tccgacgtcattctctatccttacttctattgatattgatcacaccagacccttatttgaagacg
agggtcctctatcattgaatttcctgataactgcactatacgcgtaaacactagtgatgatact
ctgtccaatcccaagaaggaatttgaatttgatagagtttatgggcctcaagttggacaagcttc
actgttcagtgatgtccaaccttttgtgcaatccgctctggatggatcgaacgtttctatattg
cgtatggccaaactcacgcggggaagacatacaccatggttgccctccttcccttcctctct
gaaattagatataggtcttgtttggatttaaatatgataggcaagttcatggacgttcatagtaa
gttcatggacgaaggatctaatcaggaccgtggtttatatgctcgttgttttgaggaacttatgg
acttggccaattctgattcaacttccgcatctcagttcagtttctctgtttcagtgtttgagctt
tataacgaacaggtcagggatttactctcgggttgtcagagcaatttgccaaagatcaatatggg
tttacgcgaatcggttatagaactttcacaggaaaagttgataatccatcagagttcatgagag
tcctgaactctgcatttcagaatagagggaatgataaatcaaagtctactgtgacccatctgatt
gtctcgatacacatttgttatagcaacacaattacgagagaaaatgtaattagcaagctttcttt
agttgacctggctggaagtgaaggtttaactgtggaggatgacaatggagatcatgtaactgatc
tgctccatgtaacaaattcaatttccgcgctgggagatgttttatcatctttgacgtcaaaaaga
gataccattccttacgagaactcatttcttacaagaatacttgcagattcactaggagggagctc
caaaacattgatgatcgtcaacatttgtccaagtgcacggaacttgtctgaaataatgtcgtgtc
tcaactatgctgctagagctcgaaatactgtaccaagccttgggaatcgagacacaattaagaaa
tggagagacgtggcaaatgatgctcggaaggaggtattggagaaagagagggaaaatcagcgtct
aaaacaagaggttacgggtttaaaacaagcacttaaagaagcaaatgaccaatgtgtactgctct
ataatgaagtacagagagcgtggagagtttcattcacactgcaatcagatttaaagtcagagaat
gcgatggttgtagacaaacataaaatagaaaggagcagaattttcagttaagaaatcaaatagc
tcaacttttacagttagaacaggaacaaaagctgcaggcgcaacaacaagattccaccattcaaa
atctccagtctaaagtgaaagacttagaatcacaactaagtaaagctctgaagtctgacatgaca
agatcgagagatcccttggaacctcagcccagagcagctgagaacacactcgattcttctgcagt
taccaagaaacttgaggaagaattgaaaaaacgtgatgcactgattgagaggttgcatgaagaaa
atgaaaaattgttcgacagattaacagaaaagtcagtggctagctcgactcaggtatctagcccc
tcatcaaaagcttcaccaacagtgcagcctgcagatgttgacaggaaaaatagcgcgggcactt
accgtcttcagtggataaaaatgagggcacgattacattagtaaaatccagctctgaattagtaa
aaaccactccagctggagaatacttaacagctgcattgaatgatttgatcccgaacaatatgaa
ggtcttgcagccatagctgatggcgcaaacaagcttctgatgctggtcttagcagctgtcataaa
ggctggtgcttccagagagcatgaaatccttgctgagatcagagattctgtcttttcatttatcc
ggaaaatggaaccaaggagagtaatggatacaatgcttgtttctcgagtcaggatattgtacata
aggtccttacttgcacgatcacctgagcttcagtcgatcaaggtttctcctgttgaacgctttt
ggagaagccatatactggtcgaactagaagctccagcgggagtagcagcccaggtagatcaccag
```

FIGURE 29

```
ttcgatattatgatgagcagatttatggctttaaagttaatttaaagccagaaaagaaaagtaag
ttggtatctgtagtttcaagaatccgtggacatgaccaggatactgggaggcagcaagtgactgg
aggaaagctgagggagatacaagatgaagccaaaagttttgccattggaaacaaacccttagctg
ctttatttgttcacactccggctggtgaactgcaaagacagattaggtcatggcttgcagaaagt
tttgagtttctctctgttacagcagatgatgtttcaggagtaaccactggccaattagagcttct
ttccacagcaattatggatggctggatggctggagtaggagctgcggtgccacctcacacagacg
ctttaggacagct
                            c         t    in KBP9
tttgtctgagtatgcaaaacgagtctacacttctcagatgcagcatctaaaggatattg
  g                   g    in KBP9
ccggtactttggcttcggaagaggcagaagatgctggtcaagtcgcgaagcttcgatcagctctc
gagtctgttgaccacaaaagaagaaagatttgcaacaaatgagaagtgatgcagctttgtttac
cttggaagaaggcagttcccctgttcaaaatccatctacagcagccgaagactcgagattagcct
ccctcatttctctggatgccatactgaagcaagtcaaggaaataacaagacaagcctctgtccac
gttttgagtaaaagcaagaaaaaggcattgcttgagtctcttgatgaacttaacgaacgaatgcc
ttctctgcttgatgttgatcatccatgtgcacagagagaaattgatacggctcaccagttggtcg
agacaattccagaacaagaggacaatcttcaagacgaaaagagaccttcaatagattcaatatct
tcgactgaaaccgatgtgtctcaatggaatgttttgcaattcaacacaggaggctcttcagctcc
attcatcataaaatgcggagctaactccaactcagagctcgtgatcaaagcggatgcccgtattc
aagaacctaaaggaggcgaaatagtgagagttgtgccaagaccttcggttttagaaaacatgagc
ttagaggaaatgaaacaagtgtttggtcagttgcccgaagctctaagttcactggccttagctag
aacagctgatggcacacgggctcgatactctagactctacagaactctagccatgaaggttccct
ctcttagggacctcgttggagagcttgagaaggaggagtcttaaaagatacaaaatcgacatga
taggattagggttttttcgtgaatttgaaa
```

FIGURE 29 (continued)

CCP molecule: CCP26 amino acid sequence (kbp9):

MAEQKSTNMWNWEVTGFESKKSPSSEEGVHRTPSSMLRRYSIPKNSLPPHSSELASKVQSLKDKV
QLAKDDYVGLRQEATDLQEYSNAKLERVTRYLGVLADKSRKLDQYALETEARISPLINEKKRLFN
DLLTTKGAHLPFPTSFSILTSIDIDHTRPLFEDEGPSIIEFPDNCTIRVNTSDDTLSNPKKEFEF
DRVYGPQVGQASLFSDVQPFVQSALDGSNVSIFAYGQTHAGKTYTMVAPPFPFLSEIRYRSCLDL
NMIGKFMDVHSKFMDEGSNQDRGLYARCFEELMDLANSDSTSASQFSFSVSVFELYNEQVRDLLS
GCQSNLPKINMGLRESVIELSQEKVDNPSEFMRVLNSAFQNRGNDKSKSTVTHLIVSIHICYSNT
ITRENVISKLSLVDLAGSEGLTVEDDNGDHVTDLLHVTNSISALGDVLSSLTSKRDTIPYENSFL
TRILADSLGGSSKTLMIVNICPSARNLSEIMSCLNYAARARNTVPSLGNRDTIKKWRDVANDARK
EVLEKERENQRLKQEVTGLKQALKEANDQCVLLYNEVQRAWRVSFTLQSDLKSENAMVVDKHKIE
KEQNFQLRNQIAQLLQLEQEQKLQAQQQDSTIQNLQSKVKDLESQLSKALKSDMTRSRDPLEPQP
RAAENTLDSSAVTKKLEEELKKRDALIERLHEENEKLFDRLTEKSVASSTQVSSPSSKASPTVQP
ADVDRKNSAGTLPSSVDKNEGTITLVKSSSELVKTTPAGEYLTAALNDFDPEQYEGLAAIADGAN
KLLMLVLAAVIKAGASREHEILAEIRDSVFSFIRKMEPRRVMDTMLVSRVRILYIRSLLARSPEL
QSIKVSPVERFLEKPYTGRTRSSSGSSSPGRSPVRYYDEQIYGFKVNLKPEKKSKLVSVVSRIRG
HDQDTGRQQVTGGKLREIQDEAKSFAIGNKPLAALFVHTPAGELQRQIRSWLAESFEFLSVTADD
VSGVTTGQLELLSTAIMDGWMAGVGAAVPPHTDALGQLLSEYAKRVYTSQMQHLKDIAGTLASEE
<u>P in KBP9</u>
<u>AEDAGQVAKLRSALESVDHKRRKILQQMRSDAALFTLEEGSSPVQNPSTAAEDSRLASLISLDAI</u>
<u>LKQVKEITRQASVHVLSKSKKKALLESLDELNERMPSLLDVDHPCAQREIDTAHQLVETIPEQED</u>
<u>NLQDEKRPSIDSISSTETDVSQWNVLQFNTGGSSAPFIIKCGANSNSELVIKADARIQEPKGGEI</u>
<u>VRVVPRPSVLENMSLEEMKQVFGQLPEALSSLALARTADGTRARYSRLYRTLAMKVPSLRDLVGE</u>
<u>LEKGGVLKDTKST</u>

FIGURE 30

A.
CCP molecule: CCP27 nucleotide sequence (kbp11):
ttagttagataggcggtggttggtgcgttcatggcgaatccttggtgggtagggaatgttgcgat
cggtggagttgagagtccagtgacgtcatcagctccttctttgcaccacagaaacagtaacaaca
acaacccaccgactatgactcgttcggatccaagattggaccatgacttcaccaccaacaacagt
ggaagccctaatacccagactcagagccaagaagaacagaacagcagagacgagcaaccagctgt
tgaaccggatccggatccgggtctacgggtcgtcgtcctagaggtagacctcctggttccaaga
acaaaccaaagagtccagttgttgttaccaaagaaagccctaactctctccagagccatgttctt
gagattgctacgggagctgacgtggcggaaagcttaaacgcctttgctcgtagacgcggccgggg
cgtttcggtgctgagcggtagtggtttggttactaatgttactctgcgtcagcctgctgcatccg
gtggagttgttagtttacgtggtcagtttgagatcttgtctatgtgtgggcttttcttcctacg
tctggctctcctgctgcagccgctggtttaaccatttacttagctggagctcaaggtcaagttgt
gggaggtggagttgctggcccgcttattgcctctggacccgttattgtgatagctgctacgtttt
gcaatgccacttatgagaggttaccgattgaggaagaacaacagcaagagcagccgcttcaacta
gaagatgggaagaagcagaaagaagagaatgatgataacgagagtgggaataacggaaacgaagg
atcgatgcagccgccgatgtataatatgcctcctaatttatcccaaatggtcatcaaatggctc
aacacgacgtgtattggggtggtcctccgcctcgtgctcctccttcgtattcgatta-gttagata
                                                            in KBP11 a
ggcggtggttggtgcgttctttttactggaatgattatattttccattaggatggttaggctttt
gtttattaaagctatcaagtttcttttttttacggataattcggatgacaattagctagtgtt
    - in KBP11             - in KBP11
tgtttgtttgttttgtggc-ggcttttctgacttgactatttttgatcgcggatagctttgtatga
                  c        -in KBP11
aagtgaattgattgtagaatcgtcttttgaattttgatgttggaaaaaaccaagcaatggtgtgt
ggcctttgcaatggaagc
 n  in KBP11

B.
CCP molecule: CCP27 amino acid sequence (kbp11):
MANPWWVGNVAIGGVESPVTSSAPSLHHRNSNNNNPPTMTRSDPRLDHDFTTNNSGSPNTQTQSQ
EEQNSRDEQPAVEPGSGSGSTGRRPRGRPPGSKNKPKSPVVVTKESPNSLQSHVLEIATGADVAE
SLNAFARRRGRGVSVLSGSGLVTNVTLRQPAASGGVVSLRGQFEILSMCGAFLPTSGSPAAAAGL
TIYLAGAQGQVVGGGVAGPLIASGPVIVIAATFCNATYERLPIEEEQQQEQPLQLEDGKKQKEEN
DDNESGNNGNEGSMQPPMYNMPPNFIPNGHQMAQHDVYWGGPPPRAPPSY

FIGURE 31

CCP molecule: CCP28 nucleotide sequence (kbp12):
aatttgctttatctttgcattgttgttggcatggctctaatctccgtdagaaacagactgaatg
tgtaatccggatgttgaatctgaaccaacctttgaatccaagtggaactgcgaacgaagaagttt
acaagatcttgatttacgataggttttgtcagaacattctatctccattgacccatgtcaggat
ctgcgtaagcatggagttacactcttctttctcatagacaaagatcgacaacctgttcatgatgt
tcccgctgtctactttgttcaaccaactgaatccaacctccagaggatcatagccgatgcttcta
gatctctctacgataccttcatctgaatttctcgtcttcgatccctcgtaagtttcttgaagag
ctagcttctgggactcttaaatctggttctgttgagaaagtctcgaaagtgcatgatcagtatct
ggagtttgtgactttggaagataacttgttctcgctggctcagcaatctacctatgttcaaatga
atgacccatcagcaggggagaaagagattaatgagattatcgaaagggtcgctagtggtttgttt
tgtgtgttggtaacgcttggtgtggttcctgttatccgatgccctagtggtggacctgcagagat
ggtggcgtctttgttggatcagaaactgagggatcatcttttgtccaagaacaatctgtttactg
aaggtggcggtttcatgagctcgtttcagcgtcccctcttgtgcatatttgataggaactttgag
ctctcggttgggattcagcatgatttcagataccggcctctcgttcacgatgttctcgggttaaa
gctcaaccaattgaaagtgcagggagagaaaggaccaccgaaatcgtttgagctggacagttcgg
acccattctggtcagcaaacagtactctggagtttccagatgtcgctgtggagatcgaaacacag
ttgaacaagtacaagagagacgttgaagaggttaacaagaaaaccggaggtgggagcggcgctga
gtttgatgggacagatctgattggaaacatccacaccgagcatctcatgaacactgtgaaatcgc
tcccggagttaactgagcgaaagaaagtgattgacaaacacaccaatatcgcaacagcgctctta
ggacagatcaaggagagatctattgacgctttcactaagaaagaaagcgacatgatgatgagggg
cggaatcgacagaactgaacttatggctgctctgaaaggcaaagggacaaagatggacaagctcc
ggtttgcaatcatgtacctgatctccacagaaaccataaaccaatcggaagttgaagcagtggag
gcagcattgaatgaagctgaggctgatacaagtgcgtttcagtatgtaaagaaaatcaaatcgtt
aaacgcatcttttgcagctacatcagcgaattcagctagcagaagcaacattgtagactgggccg
agaagctttacggacagtctataagcgcagtgactgcaggagtcaagaatctgttatctagtgat
caacaattggcagtgactcgaacagtcgaagctttaacagaaggaaaaccaaacccggagatcga
ttcttaccgcttcctggacccaagagctccaaagtcgtctagctccggtggtagccatgtaaaag
gaccgttcagagaagctatagtgttcatgatcggtggaggtaactatgttgagtatggaagtttg
caggagttgactcagagacagttaaccgttaaaaacgttatttatggagccactgagattcttaa
cggaggtgagttggtggagcagcttggactttgggaagaagatgggattaggaggtccggtcg
cttcaacgctgaagaggctgggaatggctggtaaagaggagactgatgtatctgcacaagggtct
taaccagggaggccactgagatatggaggagtgagttggaatctcgccggtttcaggtagatag

FIGURE 32

```
tttagaagctgaacttgtggatgtcaaggcttaccttgagtttggctcagaagaagatgccagaa
aggagttaggagttctttcgggtagggtcagatcgactgcaactatgttgcgttatttgagatca
aaagctagagtcttggccattcctgatgatctagcaaatgtgtcatgcggtgtggaacagattga
agaactgaaaggattgaaccttgttgagaaagatggtggttcatcttcttctgacggggctagga
acactaatcctgaaactagaaggtacagtggttccttgggtgtagaggatggagcctatactaat
gagatgctccagtccatagagatggttactgatgtgctggactctcttgtgaggagggttacagt
agcagaatctgagtctgctgttcaaaaggagagggcacttttgggagaggaa-gaaatcagtagg
                         -   in KBP12                   a   in KBP12
aa-gactatccaaatcgaaaatttgtccgtgaagttagaagagatggaacgatttgcttatggga
  a   in KBP12
ctaatagtgttctaaacgaaatgcgggaaaggattgaggaattagttgaagagacgatgaggcag
agggaaaaagctgtggaaaacgaagaggagttgtgtcgtgtgaagagagagttcgagtcgcttaa
           in KBP12       n         nn                             n
aagctacgtcagtacttttaccaatgttcgagaaacacttctttcgtccgagagacaattcaaaa
ccattgaggagctctttgaacggttggtcactaagacgacacaattagaaggggagaaggcacaa
aaggaggttgaagtacagaaactgatggaggagaatgtgaaattgacagcacttctcgacaagaa
agaggctcagcttctagctttgaatgaacaatgcaaagttatggctttgagtgcatcaaacata
gactctctaatccaaccgaatctcaagcttcc
```

FIGURE 32 (continued)

CCP molecule: CCP28 amino acid sequence (kbp12):
MALNLRQKQTECVIRMLNLNQPLNPSGTANEEVYKILIYDRFCQNILSPLTHVKDLRKHGVTLFF
LIDKDRQPVHDVPAVYFVQPTESNLQRIIADASRSLYDTFHLNFSSSIPRKFLEELASGTLKSGS
VEKVSKVHDQYLEFVTLEDNLFSLAQQSTYVQMNDPSAGEKEINEIIERVASGLFCVLVTLGVVP
VIRCPSGGPAEMVASLLDQKLRDHLLSKNNLFTEGGGFMSSFQRPLLCIFDRNFELSVGIQHDFR
YRPLVHDVLGLKLNQLKVQGEKGPPKSFELDSSDPFWSANSTLEFPDVAVEIETQLNKYKRDVEE
VNKKTGGGSGAEFDGTDLIGNIHTEHLMNTVKSLPELTERKKVIDKHTNIATALLGQIKERSIDA
FTKKESDMMMRGGIDRTELMAALKGKGTKMDKLRFAIMYLISTETINQSEVEAVEAALNEAEADT
SAFQYVKKIKSLNASFAATSANSASRSNIVDWAEKLYGQSISAVTAGVKNLLSSDQQLAVTRTVE
ALTEGKPNPEIDSYRFLDPRAPKSSSSGGSHVKGPFREAIVFMIGGGNYVEYGSLQELTQRQLTV
KNVIYGATEILNGGELVEQLGLLGKKMGLGGPVASTLKRLGMAGKEETDVSAQGSLTREATEIWR
SELESRRFQVDSLEAELVDVKAYLEFGSEEDARKELGVLSGRVRSTATMLRYLRSKARVLAIPDD
LANVSCGVEQIEELKGLNLVEKDGGSSSDGARNTNPETRRYSGSLGVEDGAYTNEMLQSIEMVT
DVLDSLVRRVTVAESESAVQKERALLGEEEISRKTIQIENLSVKLEEMERFAYGTNSVLNEMRER
IEELVEETMRQREKAVENEEELCRVKREFESLKSYVSTFTNVRETLLSSERQFKTIEELFERLVT
KTTQLEGEKAQKEVEVQKLMEENVKLTALLDKKEAQLLALNEQCKVMALSASNI

FIGURE 33

A.
CCP molecule: CCP29 nucleotide sequence (kbp13):
ATGACCAATATCGCCATGGCTGATGCTCTCAAATCTCTTGAGATTGTTGATGGTCTTGATGAATA
CATGAATCAATCTGAATCCAGTGCTCCGCATTCTCCAACCAGTGTAGCAAAGCTGCCACCAAGCA
CTGCAACTAGAACAACTCGACGGAAGACCACAACAAAAGCTGAGCCTCAGCCATCATCTCAGTTG
GTGTCCCGTTCTTGTCGTTCGACGAGCAAGTCTCTTGCTGGAGATATGGACCAGGAAAACATAAA
CAAGAATGTTGCTCAAGAAATGAAGACTAGCAATGTCAAGTTTGAAGCCAATGTGCTCAAAACTC
CAGCAGCAGGAAGCACAAGGAAAACTTCAGCAGCAACTTCTTGCACTAAGAAGGATGAATTGGTC
CAGTCGGTCTACAGCACTAGGAGATCAACCAGGCTGTTAGAGAAATGTATGGCCGATCTGAGTTT
GAAGACTAAAGAAACTGTGGATAATAAACCTGCCAAGAATGAAGATACAGAACAGAAAGTATCTG
CACAGGAGAAGAATCTAACTGGTTAG B.
CCP molecule: CCP29 amino acid sequence (kbp13):
MTNIAMADALKSLEIVDGLDEYMNQSESSAPHSPTSVAKLPPSTATRTTRRKTTTKAEPQPSSQL
VSRSCRSTSKSLAGDMDQENINKNVAQEMKTSNVKFEANVLKTPAAGSTRKTSAATSCTKKDELV
QSVYSTRRSTRLLEKCMADLSLKTKETVDNKPAKNEDTEQKVSAQEKNLTG

FIGURE 34

A.
CCP molecule: CCP30 nucleotide sequence (kbp15):
atgctgatgctgtgtgggttcacggtcttggatatgctaaagcaccacgaccttgggaagatccg
agcacccttgcatcctctcagaaagaagatgcagattcagcacgcttaccagcagatacatcagg
ggtcaaaactgttgaagatggaccggatgatgttgagagggaccaaaagaaggatacgcgtgag
gaaaggaaacctgcaaagagagagaaggaagaaagacatgataggcgtgaaaaacgcgaaaggca
tgagaagcgaagcgctcgtgattcagatgatagaaagaagcacaagaaagagaagaaggagaaaa
aagaaggcatgactctgattctgattgaagcgaattgtcccaggatggaacatttgctcttca
gaggaagagtggtcggctaggtaccaaaatccagctaccacttctgcaagatttaaatctgttgc
ttatttcatttacgaatcgtggagtaaagtgttgtga

B.
CCP molecule: CCP30 nucleotide sequence (kbp15):
ggctgataaatatagggagaactatttgggtcacagtatcaaagcccctgttggaagatggcaaa
aaggtaaagatcttcattggtatgctagagataaaaagcaaaaggggttccgagatggatgctatg
aaagaagagattcaaagagttaaggaacaagaggagcaggccatgagggaggctcttggcttggc
accaaagtcctctacaaggccacaaggaaatcgccttgataagcaagagtttactgaacttgtga
agaggggttcgacagcagaggacttaggtgcagggaatgctgatgctgtgtgggttcacggtctt
ggatatgctaaagcaccacgaccttggaagatccgagcacccttgcatcctctcagaaagaaga
tgcagattcagcacgcttaccagcagatacatcagggtcaaaactgttgaagatggaccggatg
atgttgagagggaccaaagaaggataggcgtgaggaaaggaaacctgcaaagagagagaaggaag
aaagacatgataggcgtgaaaaacgcgaaaggcatgagaagcgaagcgctcgtgattcagatgat
agaaagaagcacaagaaagagaagaaggagaaaaaagaaggcatgactctgattctgattgaag
cgaattgtcccaggatggaacatttgctcttcagaggaagagtggtcggctaggtaccaaaatc
cagctaccacttctgcaagatttaaatctgttgcttatttcatttacgaatcgtggagtaaagtg
ttgttgtgaacattgttgaaaatgtttgttaaaacacatgaaaaatgtggtttgatattataacaaa
ccgagacgctcgttttagct

C.
CCP molecule: CCP30 amino acid sequence (kbp15):
MLMLCGFTVLDMLKHHDLGKIRAPLHPLRKKMQIQHAYQQIHQGSKLLKMDRMMLRGTRRRIGVR
IGNLHRESRKEDMIGVKNAKGMRSEALVIQMIERSTRKRRRRKKEGMTLILIEANCPRMEHFALQ
RKSGRLGTKIQLPLLQDLNLLLISFTNRGVKCC

D.
CCP molecule: CCP30 amino acid sequence (kbp15):
MDAMKEEIQRVKEQEEQAMREALGLAPKSSTRPQGNRLDKQEFTELVKRGSTAEDLGAGNADAVW
VHGLGYAKAPRPWEDPSTLASSQKEDADSARLPADTSGVKTVEDGPDDVERDQRRIGVRKGNLQR
ERRKKDMIGVKNAKGMRSEALVIQMIERSTRKRRRRKKEGMTLILIEANCPRMEHFALQRKSGRL
GTKIQLPLLQDLNLLLISFTNRGVKCC

FIGURE 35

CCP molecule: CCP31 nucleotide sequence (kbp20):
GCAAAAGAGAGAAACATCTGACCCGGAATCTGACCTGAAAACCCGGAAGAATCGAAAAATGGGGA
AAGATGGTCTGAGCGACGATCAGGTCTCGTCGATGAAGGAAGCCTTCATGCTCTTCGACACCGAT
GGCGACGGCAAAATCGCACCGTCAGAGCTCGGGATCCTCATGCGATCTCTCGGCGGAAACCCGAC
CCAAGCCCAGCTGAAATCCATAATCGCATCCGAGAATCTCTCTTCACCGTTTGATTTCAACAGAT
TCCTCGATCTCATGGCGAAACATCTGAAGACGGAACCTTTCGATCGCCAGCTCCGTGACGCATTC
AAAGTGCTCGATAAGGAAGGTACCGGGTTCGTTGCTGTGGCGGATCTGAGGCATATTCTGACCAG
TATCGGAGAGAAGCTGGAGCCTAATGAGTTCGATGAGTGGATCAAGGAGGTGGATGTTGGATCCG
ATGGAAAGATCCGGTATGAAGATTTCATAGCAAGGATGGTTGCTAAGTGAGATCTAATCTTTTAT
GTTTTGAAAGTTGAAATTTTTAAGAAGAGATTCTTTTGNGGTTTTTTCACTTGGTTGGTTTGATT
TCGAGCGAATCCTAACTAGGGGTTGGTTTATCATTGNGGAATTTGCTTACTAACTTTGGCTTCTT
CATGGTTGGGTTTCAATTTTTAATGGNAAATGGTGGCTGGGGGAATTCCTAAAAAAAAAAAAAAA
AAAAAAAA

FIGURE 36

CCP molecule: CCP31 amino acid sequence (kbp20):
MGKDGLSDDQVSSMKEAFMLFDTDGDGKIAPSELGILMRSLGGNPTQAQLKSIIASENLSSPFDF
NRFLDLMAKHLKTEPFDRQLRDAFKVLDKEGTGFVAVADLRHILTSIGEKLEPNEFDEWIKEVDV
GSDGKIRYEDFIARMVAK

FIGURE 37

A.
CCP molecule: CCP32 nucleotide sequence (E2F5BBC16):
caaaaaaagagatcgcttcaatggagaaacagagtactcaadcaatttgcggccaagaggctctc
caacttctcaattgcgtcgcggagtctcctttcgatcaagagaaatgcgtccgatttttgcaatc
tctcagagaatgcgttctatcaaagaaagtaaagaagttctcgataccgagtcaagatcacgact
ctgagggagcagcttcagctacaaagagaccttcataacgttctttgttccgatttctttatc
gtttgagttgtaatcatgtaattgatttaatgtcatgccttggattcataagctgggtcatgcc
ttgtttccccttgttgtcttgtatgttgaatattgcaaactctaaagagcatatttataagaag
aaataaaagtttctacaaaaaaaaaaaaaaaaaaaa B.
CCP molecule: CCP32 amino acid sequence (E2F5BBC16): SEQ ID NO:126
MEKQSTQPICGQEALQLLNCVAESPFDQEKCVRFLQSLRECVLSKKVKKFSIPSQDHDSEGAASA
TKRPS C.
CCP molecule: CCP32 amino acid sequence (E2F5BBC16): SEQ ID NO:98
RGVSFRSREMRPIFAISQRMRSIKESKEVLDTESRSRL

FIGURE 38

A.
CCP molecule: CCP33 nucleotide sequence (DP):
atgacaactactgggtctaattctaatcacaaccaccatgaaagcaataataacaacaataaccc
tagtactaggtcttggggcacggcggtttcaggtcaatctgtgtctactagcggcagtatgggct
ctccgtcgagccggagtgagcaaaccatcaccgttgttacatctactagcgacactactttcaa
cgcctgaataatttggacattcaaggtgatgatgctggttctcaaggagcttctggtgttaagaa
gaagaagaggggacagcgtgcggctggtccagataagactggaagaggactacgtcaatttagta
tgaaagtttgtgaaaaggtggaaagcaaaggaaggacaacttacaatgaggttgcagacgagctt
gttgctgaatttgcacttccaaataacgatggaacatcccctgatcagcaacagtatgatgagaa
aaacataagacgaagagtatatgatgctttaaacgtcctcatggctatggatataatatccaagg
ataaaaagaaattcaatggagaggtcttcctcggacaagcttaagcgacattgaagaattaaag
aacgaacgactctcacttaggaacagaattgagaagaaaactgcatattcccaagaactggaaga
acaatatgtaggccttcagaatctgatacagagaaatgagcacttatatagctcaggaaatgctc
ccagtggcggtgttgctcttccttttatccttgtccagactcgtcctcacgcaacagtagaagtg
gagatatcagaagatatgcagctcgtgcattttgatttcaacagcactccatttgagctccacga
cgacaattttgtcctcaagactatgaagttttgtgatcaaccgccgcaacaaccaaacggtcgga
acaacagccagctggtttgtcacaatttcacgccagaaaacctaacaaaggccccagcacaggt
ccaacaccgcagctggatatgtacgagactcatcttcaatcgcaacaacatcagcagcattctca
gctacaaatcattcctatgcctgagactaacaacgttacttccagcgctgatactgctccagtga
aatccccgtctcttccagggataatgaactccagcatgaagccggagaattga B.
CCP molecule: CCP33 amino acid sequence (DP):
MTTTGSNSNHNHHESNNNNNNPSTRSWGTAVSGQSVSTSGSMGSPSSRSEQTITVVTSTSDTTFQ
RLNNLDIQGDDAGSQGASGVKKKKRGQRAAGPDKTGRGLRQFSMKVCEKVESKGRTTYNEVADEL
VAEFALPNNDGTSPDQQQYDEKNIRRRVYDALNVLMAMDIISKDKKEIQWRGLPRTSLSDIEELK
NERLSLRNRIEKKTAYSQELEEQYVGLQNLIQRNEHLYSSGNAPSGGVALPFILVQTRPHATVEV
EISEDMQLVHFDFNSTPFELHDDNFVLKTMKFCDQPPQQPNGRNNSQLVCHNFTPENPNKGPSTG
PTPQLDMYETHLQSQQHQQHSQLQIIPMPETNNVTSSADTAPVKSPSLPGIMNSSMKPEN

FIGURE 39

A.
CCP molecule: CCP35 nucleotide sequence
atggcgctgcagaacattggtgcttccaaccgtaacgatgccttctacaggtacaagatgcctaa
gatggttaccaaaaccgaaggcaaaggtaatggcattaagaccaacattatcaacaatgttgaga
ttgccaaagccttggctagaccgccttcttatacgaccaagtactttggttgtgagcttggagcg
cagtctaagtttgatgagaagactgggacgtcgcttgtgaatggagctcacaacacgtctaagct
tgctggcttttggagaatttattaagaagtttgttcagtgttatggatgtggtaacccggaga
ctgagattattacgaagacgcagatggtgaatctcaagtgtgctgcttgtgggtttatctct
gaggtcgacatgagggataagttgactaatttcattctcaagaacccacctgagcagaagaaggt
gtcaaaggataagaaagcaatgaggaaagctgagaaggagaggcttaaagaaggcgagctagctg
atgaggagcagagaaagctgaaagctaagaagaaagcattgtctaacggcaaggattctaagacg
tctaagaaccattcttctgatgaggatataagcccgaagcatgatgagaatgctctagaggtgga
tgaggatgaagatgatgatgatggtgtcgagtggcaaactgatacttcccgagaagctgctgaga
aaagaatgatggaacagttgagtgctaaaactgccgaaatggtgatgctctctgcaatggaagta
gaagagaaaaaggcgcccaaaagcaaatctaacgggaacgttgtgaaaactgagaatcctcctcc
gcaagagaagaatctcgtgcaggatatgaaagagtatctgaagaagggtcaccaataagcgcgc
tcaaaagtttcatctcgtctctctctgaacctcctcaagacatcatggacgcactcttcaatgct
ctctttgatggtgtgggaaagggattcgccaaagaagtgactaagaagaagaattacttagcggc
tgctgcaacaatgcaagaggatggatcacagatgcatctgctcaattcgattgggacattctgtg
gaaagaatggaaacgaagaagctttgaaagaggtggctctggttcttaaagcattgtacgaccaa
gacatcattgaggaagaggtagtgttggattggtacgaaaagggtctcaccggagctgacaaaag
ctcgccggtttggaagaatgttaagccttttgtggagtggcttcagagcgctgagtctgagtccg
aagaggaggatgagtcacttttttcttccctcctaactttctttgcggcatttcttataatac
ttcgtcagttttcagaattcttaaatctttttgctgtgttcttataaagaaacatcatctattaa
agttgtcttcgtttggatttggttttgacgactttgggaaatatttatgtttaagaaaaaaaaaa
aaaaaaaaaa B.
CCP molecule: CCP35 amino acid sequence
MALQNIGASNRNDAFYRYKMPKMVTKTEGKGNGIKTNIINNVEIAKALARPPSYTTKYFGCELGA
QSKFDEKTGTSLVNGAHNTSKLAGLLENFIKKFVQCYGCGNPETEIIITKTQMVNLKCAACGFIS
EVDMRDKLTNFILKNPPEQKKVSKDKKAMRKAEKERLKEGELADEEQRKLKAKKKALSNGKDSKT
SKNHSSDEDISPKHDENALEVDEDEDDDGVEWQTDTSREAAEKRMMEQLSAKTAEMVMLSAMEV
EEKKAPKSKSNGNVVKTENPPPQEKNLVQDMKEYLKKGSPISALKSFISSLSEPPQDIMDALFNA
LFDGVGKGFAKEVTKKKNYLAAAATMQEDGSQMHLLNSIGTFCGKNGNEEALKEVALVLKALYDQ
DIIEEEVVLDWYEKGLTGADKSSPVWKNVKPFVEWLQSAESESEEED

FIGURE 40

CCP molecule: CCP36 nucleotide sequence atggcggctaacaaattcgcgactctgattcatcggaaaacaaaccgaatcactttaatcctcgt
atacgcttttctcgaatggtcactcatttcttcattttgctcaactctctcttttcttatttca
tactcagattcgctgattatttcggtcttaaacgtccttgtctcttctgctctagactcgatcgt
ttcttcgatgcttctggtaaatctccttctcatcgagatcttctctgcgatgatcatgctctcca
attacattcaaaacctgttgaagaatctaattgtggtttcggagaatttcacaatgatttggttc
atcgtggttgttgcgtagagaagataagttcgtcactatgtgctccgattgagtctgactttggg
aatttagattatccaattggagatgaaggtcagatttacaatggtcttaagtttcctcgatcgat
cttcgtctttgaagaagagaaagtaggatctgtaaatttgaatgattctcaggaagaaacagagg
agaagaaagttccccaatctcatgagaaacttgaagatgatgatgttgatgaggagttttcatgc
tatgtatcaagcttcgattgtaagaacaaagaaattgcaacagagaaggaagaagaaaacagagt
ggatctacctatagaggtggaaactgcagaatcagctccgaaaaacctcgagttctatattgatg
aagaagactgtcatttgattccagttgaattctataaaccgagtgaagaagttcgagagatttcc
gacattaacggagatttttatcctcgatttcggcgttgagcatgatttcacggcggcggcggagac
ggaggaaatctccgactttgcttcgccgggtgaatcgaaaccggaggatgcagagacgaatctag
ttgcttcggaaatggaaaacgacgacgaagaaacagacgcagaggtttctataggtacagagatt
cctgatcatgagcaaatcggagatattccttctcaccagctcattcctcaccacgatgacgatga
tcatgaggaggaaacgttggagttcaaaacagtaacgattgaaaccaagatgccagtcttaaaca
tcaacgaagagcggattttagaagctcaaggctcgatggaaagctcgcatagtagtctacataac
gctatgtttcacttagagcaaagagtatctgttgatggtattgaatgtcctgaaggagtactcac
tgttgataagttgaagtttgagttacaagaagagagaaaagcacttcacgcgttatacgaggagc
tggaggtagagaggaatgcgtctgctgttgctgccagtgaaacaatggcgatgatcaataggttg
catgaggagaaagctgcgatgcagatggaagcgttgcagtatcagagaatgatggaggagcaagc
tgagtttgatcaagaagctttgcagttgttgaatgagcttatggtgaatagagagaaggagaatg
ctgagcttgagaaggagctagaggtgtatagaagagaatggaggagtatgaagctaaagagaaa
atggggatgttgaggaggagattgagagattcctctgttgattcgtatagaaataatggcgattc
tgatgagaatagcaatggagagttacagtttaagaacgttgaaggggttacggattggaaatata
gagagaatgagatggagaatacgccggtggatgttgtacttcgtcttgatgagtgtttagatgat
tatgatggagagaggctttcgattcttgggagattgaagtttcttgaagagaaactcacagatct
taataacgaagaggacgacgaggaggaggctaaaacgtttgagagtaatggtagcatcaatggaa
atgagcatattcatggcaaagaaacaaacgggaagcacagagttatcaagtcaaagagatta
                             in E2F3ca2:   c        a
cttcccctgtttgatgcggtcgatggagagatggaaaacgggttaagtaacggaaaccatcacga
aaacgggtttgatgattcggagaagggtgagaatgtgacgatagaagaagaagtggatgagcttt
acgagaggttagaagctctagaggcagatagagagttcttaagacattgtgttggttcattgaaa
aaaggagacaaaggtgtacatctcctccatgagattctgcaacatcttcgtgatctaaggaatat
cgatcttactcgcgtcagagaaaacggagacatgagtttatgagtttgattttgagttttgggtt
tgagtccactctttgcatagtgacccaaagaacaagaaaaatcatacaggtatggaagtgacatg
ttgcttgtgaggcaaggaacaacgacaaggtttcagatgaagaagaaacgttctcagaataaaa
gtatttaagtatatactctgaggaaaagtgtcagatcagaatgttcgtcttcttcgttcattt
tcattattataagttttgtttttatattgaagatttatttagagagagggaagtgtcagtataa
tttcacttttatattttatatttgggagttgtctttatgagtggtggtaatagaaaaggtagaa
tgatgagtgaagaaaaaaaaaaaaaaaaaaaa

CCP molecule: CCP36 amino acid sequence

MAANKFATLIHRKTNRITLILVYAFLEWSLIFFILLNSLFSYFILRFADYFGLKRPCLFCSRLDRFFDASG
KSPSHRDLLCDDHALQLHSKPVEESNCGFGEFHNDLVHRGCCVEKISSSLCAPIESDFGNLDYPIGDEGQI
YNGLKFPRSIFVFEEEKVGSVNLNDSQEETEEKKVPQSHEKLEDDDVDEEFSCYVSSFDCKNKEIATEKEE
ENRVDLPIEVETAESAPKNLEFYIDEEDCHLIPVEFYKPSEEVREISDINGDFILDFGVEHDFTAAAETEE
ISDFASPGESKPEDAETNLVASEMENDDEETDAEVSIGTEIPDHEQIGDIPSHQLIPHHDDDDHEEETLEF
KTVTIETKMPVLNINEERILEAQGSMESSHSSLHNAMFHLEQRVSVDGIECPEGVLTVDKLKFELQEERKA
LHALYEELEVERNASAVAASETMAMINRLHEEKAAMQMEALQYQRMMEEQAEFDQEALQLLNELMVNREKE
NAELEKELEVYRKRMEEYEAKEKMGMLRRRLRDSSVDSYRNNGDSDENSNGELQFKNVEGVTDWKYRENEM
ENTPVDVVLRLDECLDDYDGERLSILGRLKFLEEKLTDLNNEEDDEEEAKTFESNGSINGNEHIHGKETNG
KHRVIKSKRLLPLFDAVDGEMENGLSNGNHHENGFDDSEKGENVTIEEEVDELYERLEALEADREFLRHCV
GSLKKGDKGVHLLHEILQHLRDLRNIDLTRVRENGDMSL

FIGURE 42

CCP molecule: CCP36 nucleotide sequence

```
atgtcagacgctctttctgcgattccggccgcagttcatcgcaatctctccgataaactctatga
gaagcgcaaaaatgctgcgcttgagcttgagaatattgtgaagaatctaacttcttcgggtgatc
atgacaagatctcgaaagtcattgagatgttgattaaggaatttgccaaatctcctcaagctaat
catcggaagggtggtctaattggcttagctgctgtaactgttggtttgtctacagaagctgctca
atatcttgagcaaatagtgccacctgtgattaattccttttctgatcaagatagccgagttcggt
actatgcatgtgaagctctctataacattgcaaaggttgtgcgaggcgatttcattatttcttc
aataagatatttgatgccttatgcaaactctcagcagattctgatgccaatgtccaaagtgctgc
tcatctttggatcgccttgttaaggatattgtgacggaaagtgatcagttcagtattgaggaat
tcatacctcttttaaaagagcgaatgaacgttctcaaccctttacgtccggcaatttctggttgga
tggatcactgttcttgatagtgttccagacattgacatgcttgggtttctgccagactttctcga
tgggttattcaatatgttgagcgactctagtcatgaaatacgacagcaagctgattcagctcttt
cagagtttcttcaagagataaaaaattcaccatctgtagattatggtcgcatggctgaaatactg
gtgcagagggctgcttctcctgatgaattcactcgattaacagccatcacgtggataaacgagtt
cgtaaaacttgggggagaccagctcgtgcgttattatgctgacattcttggggctatcttgcctt
gcatatctgacaaagaagagaaaatcagggtggttgctcgtgaaaccaatgaagaacttcgttca
atccatgttgaaccctcagatggttttgatgttggcgcaattctctctgttgcaaggaggcagct
atcaagtgagtttgaggctactcggattgaagcattgaattggatatcaacactttaaacaagc
atcgtactgaggtcttgtgcttcctcaatgacatatttgacacccttctaaaagcactatctgat
                                                              - in E2F3ca9
tcttctgatgacgtggtgctcttggttctggaggttcatgctggtgtagcaaaagatccacaaca
ctttcgccagctcatcgtatttcttgtccacaatttccgagctgataattctctttggaaaggc
gcggtgcccttattgtccgaagaatgtgtgtacttttggatgccgaaagagtctaccgagagctc
tctacaattcttgagggagaagataatcttgactttgcttctaccatggttcaggcattgaattt
gattttgcttacttccccggagttatcgaaactgagagaactattaaaaggttcactcgtcaatc
gcgaagggaaagaacttttcgttgccttgtatacttcatggtgccattcacccatgg-caattat
                                                                in E2F3ca9 g aagcctctgcttattagctcaggcttacca-gcatgcgagtgtcgtgattcaatcattggtagaa
          in E2F3ca9    a        a   c   c        a gaagacattaacgtc-aaatttct-agtacagcttgataaa-ttgatccggcttctggaaactcc
              c         t  gc           a      in E2F3ca9
aatctttacttaccttagattgcagcttctggaaccaggaaggtacacatggttgctgaaaacac
tttatggtcttcttatgttacttcctcagcaaagtgcggcgttcaagatacttaggacaagactc
aaaactgtgccaacgtactcattcagtactggaaaccaaataggcagagcaacttcaggagttcc
tttctctcagtataagcatcaaaacgaggacggtgacttagaagacgataacatcaacagttctc
accaaggaatcaatttgctgtgcggctacaacagttcgaaaacgtacagaatctacatcgtggc
caggcaaggactagagtgaactactatatcactcttcctcttcttctacatcaaaggaggtgag
gagatctgaagaacaacaacagcagcagcagcaacaacaacagcaacaacaacaacaacaacgac
caccaccttcttcgacatcatcatcagttgcagataacaatagacctccatcaagaacttcaaga
aaaggccctggtcaattacagcttaacctacctggtaatcataaataataaataatattccatc
```

FIGURE 43

```
cccgacaatcatcatcttcatcttctttgtgtggacaccaccgatccctttgtctcctgtaaaa
ttgtatatctctctttttagtaactcttcaagtttcgacggaacttgtggaaaagctacggtcg
tgtccatcatctctttctctctgtcgggtttttttatttacgagagattcttcttcagtccctc
agtctacctttatattgttttttggggtttctcgtttctttgaatttgtttcattgtttggag
ctttttatattttaccttatgtggagatgtaagaaaaagaagtgatcatgtggttttgtgttgt
tttttataactggaaaaccacatgagtttgtagaggtcacttattggatattttatgtcaaatg
atgctccttttttacaaaaaaaaaaaaaaaaaa
```

FIGURE 43 (continued)

CCP molecule: CCP36 amino acid sequence
MSDALSAIPAAVHRNLSDKLYEKRKNAALELENIVKNLTSSGDHDKISKVIEMLIKEFAKSPQAN
HRKGGLIGLAAVTVGLSTEAAQYLEQIVPPVINSFSDQDSRVRYYACEALYNIAKVVRGDFIIFF
NKIFDALCKLSADSDANVQSAAHLLDRLVKDIVTESDQFSIEEFIPLLKERMNVLNPYVRQFLVG
WITVLDSVPDIDMLGFLPDFLDGLFNMLSDSSHEIRQQADSALSEFLQEIKNSPSVDYGRMAEIL
VQRAASPDEFTRLTAITWINEFVKLGGDQLVRYYADILGAILPCISDKEEKIRVVARETNEELRS
IHVEPSDGFDVGAILSVARRQLSSEFEATRIEALNWISTLLNKHRTEVLCFLNDIFDTLLKALSD
SSDDVVLLVLEVHAGVAKDPQHFRQLIVFLVHNFRADNSLLERGALIVRRMCVLLDAERVYRELS
TILEGEDNLDFASTMVQALNLILLTSPELSKLRELLKGSLVNREGKELFVALYTSWCHSPMAIIS
LCLLAQAYQHASVVIQSLVEEDINVKFLVQLDKLIRLLETPIFTYLRLQLLEPGRYTWLLKTLYG
LLMLLPQQSAAFKILRTRLKTVPTYSFSTGNQIGRATSGVPFSQYKHQNEDGDLEDDNINSSHQG
INFAVRLQQFENVQNLHRGQARTRVNYSYHSSSSSTSKEVRRSEEQQQQQQQQQQQQQQQQRPPP
SSTSSSVADNNRPPSRTSRKGPGQLQL

FIGURE 44

CCP molecule: CCP37 nucleotide sequence atgtcactcttgttcctcaatcatccgtttccctccaattcaatccacccaattcctcgtcgtgc
cgccggaatatcctccattcgatgctcaatttctgcaccggagaagaaaccgaggaggaggaga
agcagaagcgcggcgacggagctgagaatgacgactctttgtctttcggaagtggtgaagctgtc
tccgctctggagaggagtctccgcctcacttttatggacgagcttatggaacgagctagaaatcg
agatacttcaggtgtttctgaggttatctatgacatgattgctgctgggcttagccctggacctc
gttctttccatggtttggttgtagctcacgcgcttaacggcgacgaacaaggcgcgatgcactcg
ctgagaaaggagctaggtgcaggccaacgtccgcttcctgagactatgattgctttggttcgtct
ctctggttcgaaagggaatgctacgagaggcctagaaatcctcgccgctatggaaaagcttaagt
atgacattcgtcaagcttggctcattcttgttgaggagctcatgaggatcaatcacttggaagat
gcgaataaagttttcttgaagggtgcaagaggtgggatgagagcaacagatcagctttatgattt
gatgattgaagaagattgcaaagctggagatcattctaatgccttagacatctcttacgaaatgg
aggcagctggtagaatggccacaacatttcatttcaactgtcttcttagtgtgcaggctacatgt
gggattcccgaggtagcttatgctacattcgaaaatatggagtacggtgaaggtttatttatgaa
gcctgacactgagacatataactgggtgattcaagcctacactagagccgagtcatatgataggg
ttcaggatgttgctgaattacttggaatgatggttgaggaccacaaacgtgtgcagccaaatgtg
aagacttatgcgctcttagttgagtgcttcaccaaatattgtgtcgtgaaggaagcgattagaca
ttttcgtgctcttaaaaactttgaaggaggaacagtaattttacacaatgcagggaattttgagg
atcctctctctttgtatctcagggctttgtgtcgagaaggaagaattgttgagcttattgatgct
tagatgcaatgcgcaaagataaccaacctatacctccaagagccatgattatgagcagaaagta
tcgaacactagtcagctcatggattgaaccattgcaagaagaagctgaacttggctatgagattg
attatttagcgaggtacatagaggaaggggggacttactggtgaacgcaagcgttgggtacctcga
agagggaaaactcctttagatcccgatgcttctggttttatatactcaaaccctattgaaacatc
ctttaaacagagatgccttgaagattggaaagttcaccataggaagctcttgagaaccttacaga
gtgaaggtcttccagttctaggagatgcatcagaatctgattacatgagagtggtggagagatta
cggaacataataaaaggtcctgcactgaatcttttgaagccgaaagcagcaagcaagatggttgt
atcagagttaaaggaagaactcgaagctcagggtttgccaattgatggaacaagaaatgtgcttt
accagcgtgtccaaaaagcaaggagaataaacaaatctcgaggtcgacctctttgggttcctcca
attgaagaagaagaggaggaggtcgatgaagaagtagacgatttaatatgtcgaatcaagctaca
tgaaggagacacagagttctggaaacgtcggtttcttggagaaggcttgattgaaacttcagttg
aatccaaggaaacgactgaatcagtggttacaggtgaatcggagaaagcgattgaagatatttca
aaagaagctgacaatgaggaggatgatgatgaggaggaacaagaaggagatgaggatgatgatga
aaatgaagaggaagaagtggttgttccagaaactgagaatcgagcagaaggagaagatttagtga
agaataaggcagctgacgcgaagaagcatcttcaaatgattggagtccaactcttgaaagaatcc
gatgaagcaaacagaacaaagaaacgtgggaagagggcatctcgtatgacacttgaggatgatgc
agatgaggattggttccctgaggaaccatttgaagcattcaaagaaatgagggaaagaaaagtgt
tcgatgtggctgacatgtatacaatagcagacgtttggggttggacatgggagaaggattttaag
aacaaaactccaaggaaatggtcacaagagtgggaagtcgagttggcaattgtgctcatgacaaa
ggtgattgaattgggtggaattccaacgattggtgattgtgcagtgatattacgagctgctttaa
gagctccc

FIGURE 45

```
atgccttcagccttcttgaagatcttgcagacgacacacagtcttggctactcatttggcagccc
gttgtacgatgagatcatcacattgtgtttggaccttggagaacttgatgcagccatcgccatag
ttgcagatatggaaaccacagggatcactgtccctgatcaaacccttgacaaggtcatatctgct
agacaatctaatgagagtccgcggtctgagcctgaagagccagcatcaacagtaagctcttagtt
atcatatcctcttctgcttgttgtgaagtctctataagaaacagaaatcggtagaaggagctgaa
tctgtcttagttatgaaagttttgttcattataagtacaagtcatgtagttccgagtgtagaaca
gtttttactagtgttgcaccaggtccctccagtctgatacttaattctttagtgttggatctttc
tatataagaaaaaaaaaaaaaaaa
```

FIGURE 45 (continued)

CCP molecule: CCP37 amino acid sequence
MSLLFLNPPFPSNSIHPIPRRAAGISSIRCSISAPEKKPRRRRKQKRGDGAENDDSLSFGSGEAVSALERS
LRLTFMDELMERARNRDTSGVSEVIYDMIAAGLSPGPRSFHGLVVAHALNGDEQGAMHSLRKELGAGQRPL
PETMIALVRLSGSKGNATRGLEILAAMEKLKYDIRQAWLILVEELMRINHLEDANKVFLKGARGGMRATDQ
LYDLMIEEDCKAGDHSNALDISYEMEAAGRMATTFHFNCLLSVQATCGIPEVAYATFENMEYGEGLFMKPD
TETYNWVIQAYTRAESYDRVQDVAELLGMMVEDHKRVQPNVKTYALLVECFTKYCVVKEAIRHFRALKNFE
GGTVILHNAGNFEDPLSLYLRALCREGRIVELIDALDAMRKDNQPIPPRAMIMSRKYRTLVSSWIEPLQEE
AELGYEIDYLARYIEEGGLTGERKRWVPRRGKTPLDPDASGFIYSNPIETSFKQRCLEDWKVHHRKLLRTL
QSEGLPVLGDASESDYMRVVERLRNIIKGPALNLLKPKAASKMVVSELKEELEAQGLPIDGTRNVLYQRVQ
KARRINKSRGRPLWVPPIEEEEEEVDEEVDDLICRIKLHEGDTEFWKRRFLGEGLIETSVESKETTESVVT
GESEKAIEDISKEADNEEDDDEEEQEGDEDDDENEEEEVVVPETENRAEGEDLVKNKAADAKKHLQMIGVQ
LLKESDEANRTKKRGKRASRMTLEDDADEDWFPEEPFEAFKEMRERKVFDVADMYTIADVWGWTWEKDFKN
KTPRKWSQEWEVELAIVLMTKVIELGGIPTIGDCAVILRAALRAPMPSAFLKILQTTHSLGYSFGSPLYDE
IITLCLDLGELDAAIAIVADMETTGITVPDQTLDKVISARQSNESPRSEPEEPASTVSS

FIGURE 46

A.
CCP molecule: CCP38 amino acid sequence
aagcttcgaagtcgatttcaatggaaggttcctcgtcagccatcgcgaggaagacatgggagcta
gagaacaacattctcccagtggaaccaaccgattcagcctccgacagtatattccactacgacga
cgcttcacaagccaaaatccagcaggagaagccatgggcctccgatcctaactacttcaagcgcg
ttcacatctcagcccttgctcttctcaagatggtggttcacgctcgctccggtggcacaatcgag
atcatgggtcttatgcagggtaaaaccgagggtgatacaatcatcgttatggatgcttttgcttt
gcctgttgaaggtactgagactaggggttaatgctcagtctgatgcctatgagtatatggttgaat
actctcagaccagcaagctggctgggaggttggagaacgttgttggatggtatcactctcaccct
gggtatggatgttggctctcgggtattgatgtttcgacacagatgcttaaccaacagtatcagga
gccattcttagctgttgttattgatccaacaaggactgtttcggctggtaaggttgagattgggg
cattcagaacatatccagagggacataagatctcggatgatcatgtttctgagtatcagactatc
cctcttaacaagattgaggactttggtgtacattgcaaacagtactactcattggacatcactta
tttcaagtcatctctcgatagtcaccttctggatctcctttggaacaagtactgggtgaacactc
tttcttcttcccactgttgggcaatggagactatgttgccgggcaaatatcagacttggctgag
aagctcgagcaagcggagagtcagctcgctaactcccggtatggaggaattgcgccagccggtca
ccaaaggaggaaagaggatgagcctcaactcgcgaagataactcgggatagtgcaaagataactg
tcgagcaggtccatggactaatgtcacaggttatcaaagacatcttgttcaattccgctcgtcag
tccaagaagtctgctgacgactcatcagatccagagcccatgattacatcggaagttggtctat
tctttgtttttggctgcggaaattgactatcggtttgacccggtttatgaggcaatgcccatt
gttccctatatctctagtgtagtatctgcttcagacaaagatctttgggttattaaatgacatta
acataaatcgatcattatgttttttgcgttaaaaaaaaaaaaaaaaaaaaaaaaaaaaaaa B.
CCP molecule: CCP38 amino acid sequence
MEGSSSAIARKTWELENNILPVEPTDSASDSIFHYDDASQAKIQQEKPWASDPNYFKRVHISALALLKMVV
HARSGGTIEIMGLMQGKTEGDTIIVMDAFALPVEGTETRVNAQSDAYEYMVEYSQTSKLAGRLENVVGWYH
SHPGYGCWLSGIDVSTQMLNQQYQEPFLAVVIDPTRTVSAGKVEIGAFRTYPEGHKISDDHVSEYQTIPLN
KIEDFGVHCKQYYSLDITYFKSSLDSHLLDLLWNKYWVNTLSSSPLLGNGDYVAGQISDLAEKLEQAESQL
ANSRYGGIAPAGHQRRKEDEPQLAKITRDSAKITVEQVHGLMSQVIKDILFNSARQSKKSADDSSDPEPMI
TS

FIGURE 47

| description of molecule | amino acid sequence SEQ ID NO: | nucleic acid sequence SEQ ID NO: |
|---|---|---|
| Tag•100 epitope | 199 | |
| c-myc epitope | 200 | |
| FLAG®-epitope | 201 | |
| HA epitope | 202 | |
| protein C epitope | 203 | |
| VSV epitope | 204 | |
| DP conserved DNA binding | 240 | |
| DP conserved heterodim domain | 241 | |
| DP conserved heterodim domain | 242 | |
| primer A | | 243 |
| primer B | | 244 |
| primer C | | 245 |
| attB1 site | | 246 |
| Kozak consensus | | 247 |
| attB2 site | | 248 |
| sense E2Fa primer | | 249 |
| antisense E2Fa primer | | 250 |
| sense DPa primer | | 251 |
| antisense DPa primer | | 252 |
| sense CDKA primer | | 253 |
| antisense CDKA primer | | 254 |
| sense CDKB primer | | 255 |
| antisense CDKB primer | | 256 |
| sense histone H4 primer | | 257 |
| antisense histone H4 primer | | 258 |
| sense roc5 primer | | 259 |
| antisense roc5 primer | | 260 |
| sense actin primer | | 261 |
| antisense actin primer | | 262 |
| CDK phosphorylation motif CDC2bDN-IC26M | 263 | |

FIGURE 60

| description of molecule | amino acid sequence SEQ ID NO: | nucleic acid sequence SEQ ID NO: |
|---|---|---|
| ICK4 | 264 | |
| forward sequencing primer prm1024 | | 265 |
| reverse sequencing primer prm1025 | | 266 |
| cyclin destruction box | 267 | |
| cyclin box consensus motif 1 | 268 | |
| cyclin box consensus motif 2 | 269 | |
| CDC2 consensus motif 1 | 270 | |
| CDC2 consensus motif 2 | 271 | |
| CDC2 consensus motif 3 | 272 | |
| CDK phosphorylation site consensus 1 | 273 | |
| CDK phosphorylation site consensus 2 | 274 | |
| CDK phosphorylation site consensus 3 | 275 | |
| CDK phosphorylation site consensus 4 | 276 | |
| NLS consensus 1 | 277 | |
| NLS consensus 2 | 278 | |
| NLS consensus 3 | 279 | |
| NLS consensus 4 | 280 | |
| Cy-like box consensus | 281 | |
| Rb binding domain consensus 1 | 282 | |
| Rb binding domain consensus 2 | 283 | |
| Rb binding domain consensus 3 | 284 | |
| Rb binding domain consensus 4 | 285 | |
| DEF domain | 286 | |
| DNA binding domain | 287 | |
| DCB1 domain consensus 1 | 288 | |
| DCB1 domain consensus 2 | 289 | |
| DCB2 domain | 290 | |

FIGURE 60 (continued)

METHOD FOR MODULATING PLANT GROWTH, NUCLEIC ACID MOLECULES AND POLYPEPTIDES ENCODED THEREOF USEFUL AS MODULATING AGENT

RELATED APPLICATIONS

This application claims priority to U.S. provisional patent application Ser. No. 60/204,045, filed May 12, 2000. The contents of this provisional patent application are incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file conlaining the Sequence Listing is Revised_Sequence_List_14546_00078_US. The size of the text file is 375 KB, and the text file was created on Apr. 13, 2012.

BACKGROUND OF THE INVENTION

Cell division plays a crucial role during all phases of plant development. The continuation of organogenesis and growth responses to a changing environment require precise spatial, temporal, and developmental regulation of cell division.

The basic mechanisms controlling the progression through the cell cycle appear to be conserved in all higher eukaryotes, although the temporal and spatial control of cell division can differ largely between organisms. Plants have unique developmental features which are not found in either animals or fungi. First, due to the presence of a rigid cell wall, plant cells cannot move and consequently organogenesis is dependent on cell division and cell expansion at the site of formation of new organs. Secondly, cell divisions are confined to specialized regions, called meristems. These meristems continuously produce new cells which, as they move away from the meristem, become differentiated. The meristem identity itself can change from a vegetative to a reproductive phase, resulting in the formation of flowers. Thirdly, plant development is largely post-embryonic. During embryogenesis, the main developmental event is the establishment of the root-shoot axis. Most plant growth occurs after germination, by iterative development at the meristems. Lastly, as a consequence of the sessile life of plants, development and cell division are, to a large extent, influenced by environmental factors such as light, gravity, wounding, nutrients, and stress conditions. All these features are reflected in a plant-specific regulation of the factors controlling cell division.

The unparalleled potential of plants for continuous organogenesis and plastic growth also relies on the competent or active state of the cell division apparatus. The discovery of a common mechanism underlying the regulation of the cell cycle in yeasts and animals has led to efforts to extend these findings to the plant kingdom and is leading to research aimed at converting the gathered knowledge into useful traits introduced in transgenic plants.

When eukaryotic cells and, thus, also plant cells divide they go through a highly ordered sequence of events collectively termed as the "cell cycle." Briefly, DNA replication or synthesis (S) and mitotic segregation of the chromosomes (M) occur with intervening gap phases (G1 and G2) and the phases follow the sequence G1-S-G2-M. Cell division is completed after cytokinesis, the last step of the M-phase. Cells that have exited the cell cycle and have become quiescent are said to be in the G0 phase. Cells at the G0 stage can be stimulated to reenter the cell cycle at the G1 phase. The transition between the different phases of the cell cycle are basically driven by the sequential activation/inactivation of a kinase (called "cyclin-dependent kinase", "CDC" or "CDK") by different agonists.

Proteins called cyclins are required for kinase activation. Cyclins are also important for targeting the kinase activity to a given subset of substrate(s). Other factors regulating CDK activity include CDK inhibitors (CKIs or ICKs, KIPs, CIPs, INKs), CDK activating kinase (CAK) and CDK phosphatase (CDC25) (Mironov et al. (1999) *Plant Cell* 11, 509-522 and Won K. et al. (1996) *EMBO J.* 15, 4182-4193).

SUMMARY OF THE INVENTION

The present invention is based, at least in part, on the discovery of novel plant nucleic acid molecules and polypeptides encoded by such nucleic acid molecules, referred to herein as "cell cycle proteins" or "CCP." The CCP nucleic acid and polypeptide molecules of the present invention are useful as modulating agents in regulating cell cycle progression in, for example, plants. Accordingly, in one aspect, this invention provides isolated nucleic acid molecules encoding CCP polypeptides, as well as nucleic acid fragments suitable as primers or hybridization probes for the detection of CCP-encoding nucleic acids.

In one embodiment, a CCP nucleic acid molecule of the invention is at least 60%, 65%, 70%, 75%, 80%, 85%, 90%, 95%, 98% or more identical to the nucleotide sequence (e.g., to the entire length of the nucleotide sequence) of SEQ ID NO:1-66 or 228-239, or a complement thereof.

In a preferred embodiment, the isolated nucleic acid molecule includes the nucleotide sequence shown in SEQ ID NO:1-66 or 228-239, or a complement thereof. In another preferred embodiment, an isolated nucleic acid molecule of the invention encodes the amino acid sequence of a plant CCP polypeptide.

Another embodiment of the invention features nucleic acid molecules, preferably CCP nucleic acid molecules, which specifically detect CCP nucleic acid molecules relative to nucleic acid molecules encoding non-CCP polypeptides. For example, in one embodiment, such a nucleic acid molecule is at least 15, 20, 25, 30, 40, 50, 100, 150, 200, 250, 300, 350, 400, 450, 500, 550, 600, 650, 700, 750, or 800 nucleotides in length and hybridizes under stringent conditions to a nucleic acid molecule comprising the nucleotide sequence shown in SEQ ID NO:1-66 or 228-239, or a complement thereof.

In other preferred embodiments, the nucleic acid molecule encodes a naturally occurring allelic variant of a plant CCP polypeptide, wherein the nucleic acid molecule hybridizes to the nucleic acid molecule of SEQ ID NO:1-66 or 228-239 under stringent conditions.

Another embodiment of the invention provides an isolated nucleic acid molecule which is antisense to a CCP nucleic acid molecule, e.g., the coding strand of a CCP nucleic acid molecule.

Another aspect of the invention provides a vector comprising a CCP nucleic acid molecule. In certain embodiments, the vector is a recombinant expression vector. In another embodiment, the invention provides a host cell containing a vector of the invention. The invention also provides a method for producing a CCP polypeptide, by culturing in a suitable medium a host cell of the invention, e.g., a plant host cell such as a host monocot plant cell (e.g., rice, wheat or corn) or a dicot host cell (e.g., *Arabidopsis thaliana*, oilseed rape, or soybeans) containing a recombinant expression vector, such that the polypeptide is produced.

Another aspect of this invention features isolated or recombinant CCP polypeptides. In one embodiment, an isolated CCP polypeptides has one or more of the following domains: a "cyclin destruction box", a "cyclin box motif 1", a "cyclin box motif 2", a "CDC2 motif", a "CDK phosphorylation site", a "nuclear localization signal", a "Cy-like box", an "Rb binding domain", a "DEF domain", a "DNA binding domain", a "DCB1 domain", a "DCB2 domain" and/or a "SAP domain".

In a preferred embodiment, a CCP polypeptide includes at least one or more of the following domains: a "cyclin destruction box", a "cyclin box motif 1", a "cyclin box motif 2", a "CDC2 motif", a "CDK phosphorylation site", a "nuclear localization signal", a "Cy-like box", an "Rb binding domain", a "DEF domain", a "DNA binding domain", a "DCB1 domain", a "DCB2 domain" and/or a "SAP domain", and has an amino acid sequence at least about 50%, 55%, 60%, 65%, 70%, 75%, 80%, 85%, 90%, 95%, 98%, 99% or more identical to the amino acid sequence of SEQ ID NO:67-132, 205, 211, 215-216, or 220-227.

In another preferred embodiment, a CCP polypeptide includes at least one or more of the following domains: a "cyclin destruction box", a "cyclin box motif 1", a "cyclin box motif 2", a "CDC2 motif", a "CDK phosphorylation site", a "nuclear localization signal", a "Cy-like box", an "Rb binding domain", a "DEF domain", a "DNA binding domain", a "DCB1 domain", a "DCB2 domain" and/or a SAP domain and has a CCP activity (as described herein).

In yet another preferred embodiment, a CCP polypeptide includes one or more of the following domains: a "cyclin destruction box", a "cyclin box motif 1", a "cyclin box motif 2", a "CDC2 motif", a "CDK phosphorylation site", a "nuclear localization signal", a "Cy-like box", an "Rb binding domain", a "DEF domain", a "DNA binding domain", a "DCB1 domain", a "DCB2 domain" and/or a SAP domain and is encoded by a nucleic acid molecule having a nucleotide sequence which hybridizes under stringent hybridization conditions to a nucleic acid molecule comprising the nucleotide sequence of SEQ ID NO:1-66 or 228-239.

In another embodiment, the invention features fragments of the polypeptide having the amino acid sequence of SEQ ID NO:67-132, 205, 211, 215-216, or 220-227, wherein the fragment comprises at least 15 amino acids (e.g. contiguous amino acids) of the amino acid sequence of SEQ ID NO:67-132, 205, 211, 215-216, or 220-227. In another embodiment, a CCP polypeptide has the amino acid sequence of SEQ ID NO:67-132, 205, 211, 215-216, or 220-227.

In another embodiment, the invention features a CCP protein which is encoded by a nucleic acid molecule consisting of a nucleotide sequence at least about 50%, 55%, 60%, 65%, 70%, 75%, 80%, 85%, 90%, 95%, 98%, 99% or more identical to a nucleotide sequence of SEQ ID NO:1-66 or 228-239, or a complement thereof. This invention further features a CCP polypeptide, which is encoded by a nucleic acid molecule consisting of a nucleotide sequence which hybridizes under stringent hybridization conditions to a nucleic acid molecule comprising the nucleotide sequence of SEQ ID NO:1-66 or 228-239, or a complement thereof.

In another embodiment the invention provides transgenic plants (e.g. monocot or dicot plants) containing an isolated nucleic acid molecule of the present invention. For example, the invention provides transgenic plants containing a recombinant expression cassette including a plant promoter operably linked to an isolated nucleic acid molecule of the present invention. The present invention also provides transgenic seed from the transgenic plants. In another embodiment the invention provides methods of modulating, in a transgenic plant, the expression of the nucleic acids of the invention The proteins of the present invention or portions thereof, e.g., biologically active portions thereof, can be operatively linked to a non-CCP polypeptide (e.g., heterologous amino acid sequences) to form fusion proteins. The invention further features antibodies, such as monoclonal or polyclonal antibodies, that specifically bind polypeptide of the invention, preferably CCP polypeptide. In addition, the CCP polypeptide or biologically active portions thereof can be incorporated into pharmaceutical compositions, which optionally include pharmaceutically acceptable carriers.

In another aspect the present invention provides a method for detecting the presence of a CCP nucleic acid molecule, polypeptide in a biological sample by contacting the biological sample with an agent capable of detecting a CCP nucleic acid molecule, polypeptide such that the presence of a CCP nucleic acid molecule, polypeptide is detected in the biological sample.

In another aspect, the present invention provides a method for detecting the presence of CCP activity in a biological sample by contacting the biological sample with an agent capable of detecting an indicator of CCP activity such that the presence of CCP activity is detected in the biological sample.

In another aspect, the invention provides a method for modulating CCP activity comprising contacting a cell capable of expressing CCP with an agent that modulates CCP activity such that CCP activity in the cell is modulated. In one embodiment, the agent inhibits CCP activity. In another embodiment, the agent stimulates CCP activity. In one embodiment, the agent is an antibody that specifically binds to a CCP polypeptide. In another embodiment, the agent modulates expression of CCP by modulating transcription of a CCP gene or translation of a CCP mRNA. In yet another embodiment, the agent is a nucleic acid molecule having a nucleotide sequence that is antisense to the coding strand of a CCP mRNA or a CCP gene.

In one embodiment, the methods of the present invention are used to increase crop yield, improve the growth characteristics of a plant (such as growth rate or size of specific tissues or organs in the plant), modify the architecture or morphology of a plant, improve tolerance to environmental stress conditions (such as drought, salt, temperature, nutrient or deprivation), or improve tolerance to plant pathogens (e.g., pathogens that abuse the cell cycle) by modulating CCP activity in a cell. In one embodiment, the CCP activity is modulated by modulating the expression of a CCP nucleic acid molecule. In yet another embodiment, the CCP activity is modulated by modulating the activity of a CCP polypeptide. Modulators of CCP activity include, for example, a CCP nucleic acid or polypeptide.

The present invention also provides diagnostic assays for identifying the presence or absence of a genetic alteration characterized by at least one of (i) aberrant modification or mutation of a gene encoding a CCP polypeptide; (ii) misregulation of the gene; and (iii) aberrant post-translational modification of a CCP polypeptide, wherein a wild-type form of the gene encodes a protein with a CCP activity.

In another aspect the invention provides methods for identifying a compound that binds to or modulates the activity of a CCP polypeptide, by providing an indicator composition comprising a CCP polypeptide having CCP activity, contacting the indicator composition with a test compound, and determining the effect of the test compound on CCP activity in the indicator composition to identify a compound that modulates the activity of a CCP polypeptide. The identified compounds may be used as herbicides or plant growth regulators.

Other features and advantages of the invention will be apparent from the following detailed description and claims.

BRIEF DESCRIPTION OF THE DRAWINGS

FIG. 1 depicts the cDNA sequence and predicted amino acid sequence of the *Arabidopsis thaliana* CCP1. The complete nucleotide sequence (FIG. 1A) corresponds to nucleic acids 1 to 1715 of SEQ ID NO:39. The complete amino acid sequence FIG. 1B) corresponds to amino acids 1 to 460 of SEQ ID NO:105. Underlined in FIG. 1A and FIG. 1B are the partially characterized nucleotide (SEQ ID NO:1) and predicted partial amino acid (SEQ ID NO:67) sequence, respectively. Further indicated in FIG. 1A are the stop and start codons (both in black shaded boxes) which are part of the primers (grey shaded boxes) used to amplify the coding region of CCP1 by PCR. The SEQ ID NOs of the primers used can be found in Table III. Indicated in FIG. 1B are the cyclin destruction box (black shaded box) and the cyclin box motifs 1 and 2 (both in gray shaded boxes).

FIG. 2 depicts the cDNA sequence of the *Arabidopsis thaliana* CCP2. The complete nucleotide sequence corresponds to nucleic acids 1 to 2195 of SEQ ID NO:40. Underlined is the partially characterized nucleotide (SEQ ID NO:2) sequence. Nucleotide sequence differences between SEQ ID NO:40 and SEQ ID NO:2 are depicted. Indicated are the stop and start codons (both in black shaded boxes) which are part of the primers (grey shaded boxes) used to amplify the coding region of CCP2 by PCR. SEQ ID NOs of the primers used can be found in Table III.

FIG. 3 depicts the predicted amino acid sequence of the *Arabidopsis thaliana* CCP2. The complete amino acid sequence corresponds to amino acids 1 to 664 of SEQ ID NO:106. Underlined is the predicted partial amino acid (SEQ ID NO:68) sequence.

FIG. 4 depicts the cDNA sequence and predicted amino acid sequence of the *Arabidopsis thaliana* CCP3. The complete nucleotide sequence (FIG. 3A) corresponds to nucleic acids 1 to 1413 of SEQ ID NO:41. The complete amino acid sequence (FIG. 3B) corresponds to amino acids 1 to 450 of SEQ ID NO:69. Underlined in FIG. 3A and FIG. 3B are the partially characterized nucleotide (SEQ ID NO:3) and predicted partial amino acid (SEQ ID NO:69) sequences, respectively. Indicated in FIG. 3A are the stop and start codons (both in black shaded boxes) which are part of the primers (grey shaded boxes) used to amplify the coding region of CCP3 by PCR. SEQ ID NOs of the primers used can be found in Table III. Nucleotide sequence differences between SEQ ID NO:41 and SEQ ID NO:3 are depicted Indicated in FIG. 3B are the cyclin destruction box (black shaded box) and the cyclin box motifs 1 and 2 (both in gray shaded boxes).

FIG. 5 depicts the cDNA sequence and predicted amino acid sequence of the *Arabidopsis thaliana* CCP4. The complete nucleotide sequence (FIG. 5A) corresponds to nucleic acids 1 to 672 of SEQ ID NO:4. The complete amino acid sequence (FIG. 5B) corresponds to amino acids 1 to 223 of SEQ ID NO:70. Indicated in FIG. 5A are stop and start codon (both in black shaded boxes) which are part of the primers (grey shaded boxes) used to amplify the coding region of CCP4 by PCR. SEQ ID NOs of the primers used can be found in Table III. Indicated in FIG. 5B is the CDK phosphorylation site (black shaded box).

FIG. 6 depicts the cDNA sequence and predicted amino acid sequence of the *Arabidopsis thaliana* CCP5. The complete nucleotide sequence (FIG. 6A) corresponds to nucleic acids 1 to 1287 of SEQ ID NO:5. The complete amino acid sequence (FIG. 6B) corresponds to amino acids 1 to 429 of SEQ ID NO:71. Indicated in FIG. 6A are the stop and start codons both in black shaded boxes) which are part of the primers (grey shaded boxes) used to amplify the coding region of CCP5 by PCR. SEQ ID NOs of the primers used can be found in Table III. Indicated in FIG. 6B are the cyclin destruction box (black shaded box) and the cyclin box motifs 1 and 2 (both in gray shaded boxes).

FIG. 7 depicts the cDNA sequence of the *Arabidopsis thaliana* CCP6. The complete nucleotide sequence corresponds to nucleic acids 1 to 2766 of SEQ ID NO:42. Underlined is the partially characterized nucleotide (SEQ ID NO:6) sequence. Indicated are the stop and start codons (both in black shaded boxes) which are part of the primers (grey shaded boxes) used to amplify the coding region of CCP6 by PCR. SEQ ID NOs of the primers used can be found in Table III. Nucleotide sequence differences between SEQ ID NO:42 and SEQ ID NO:6 are depicted.

FIG. 8 depicts the predicted amino acid sequence of the *Arabidopsis thaliana* CCP6. The complete amino acid sequence corresponds to amino acids 1 to 901 of SEQ ID NO:108. Underlined is the predicted partial amino acid (SEQ ID NO:72) sequence.

FIG. 9 depicts the cDNA sequence and predicted amino acid sequence of the *Arabidopsis thaliana* CCP7/CCP8. The complete nucleotide sequence (FIG. 9A) corresponds to nucleic-acids 1 to 1260 of SEQ ID NO:43. The complete amino acid sequence (FIG. 9B) corresponds to amino acids 1 to 358 of SEQ ID NO:109. Underlined in FIG. 9A and FIG. 9B are the partially characterized nucleotide (SEQ ID NO:7) and predicted partial amino acid (SEQ ID NO:73) sequence, respectively. Italic sequences in FIG. 9A and FIG. 9B correspond to the partially characterized nucleotide (SEQ ID NO:8) and amino acid (SEQ ID NO:74) sequence, respectively, of another clone found independently to interact with an AtE2F protein in a yeast two-hybrid screen. Indicated in FIG. 9A are the stop and start codons (both in black shaded boxes) which are part of the primers (grey shaded boxes) used to amplify the coding region of CCP7/8 by PCR. SEQ ID NOs of the primers used can be found in Table III. Nucleotide sequence differences between SEQ ID NO:43 and SEQ ID NO:7-8 are depicted.

FIG. 10 depicts the cDNA sequence and predicted amino acid sequence of the *Arabidopsis thaliana* CCP9. The complete nucleotide sequence (FIG. 10A) corresponds to nucleic acids 1 to 1308 of SEQ ID NO:9. The complete amino acid sequence (FIG. 10B) corresponds to amino acids 1 to 436 of SEQ ID NO:75. Indicated in FIG. 10A are the stop and start codons (both in black shaded boxes) which are part of the primers (grey shaded boxes) used to amplify the coding region of CCP9 by PCR. SEQ ID NOs of the primers used can be found in Table III. Indicated in FIG. 10B are the cyclin destruction box (black shaded box) and the cyclin box motifs 1 and 2 (both in gray shaded boxes).

FIG. 11 depicts the cDNA sequence and predicted amino acid sequence of the *Arabidopsis thaliana* CCP10. The complete nucleotide sequence (FIG. 11A) corresponds to nucleic acids 1 to 1006 of SEQ ID NO:10. The complete amino acid sequence (FIG. 11B) corresponds to amino acids 1 to 254 of SEQ ID NO:76. Indicated in FIG. 11A are the stop and start codons (both in black shaded boxes) which are part of the primers (grey shaded boxes) used to amplify the coding region of CCP10 by PCR. SEQ ID NOs of the primers used can be found in Table III.

FIG. 12 depicts the cDNA sequence and predicted amino acid sequence of the *Arabidopsis thaliana* CCP11. The complete nucleotide sequence (FIG. 12A) corresponds to nucleic acids 1 to 653 of SEQ ID NO:44. Indicated in FIG. 12A are the stop and start codons (both in black shaded boxes) which are part of the primers (grey shaded boxes) used to amplify the coding region of CCP11 by PCR. SEQ ID NOs of the primers used can be found in Table III. However, during prediction of the open reading frame a frame shift was introduced which effected the CCP11 open reading frame. The stop codon indicated in italics in a black shaded box is the putative correct stop codon. The amino acid sequence in FIG. 12B corresponds to amino acids 1 to 86 of SEQ ID NO:77, the protein encoded by the initially identified open reading frame of SEQ ID NO:11. The putative correct complete amino acid sequence in FIG. 12C corresponds to amino acids 1 to 98 of SEQ ID NO:110.

FIG. 13 depicts the cDNA sequence and predicted amino acid sequence of the *Arabidopsis thaliana* CCP12/13. The complete nucleotide sequence (FIG. 13A) corresponds to nucleic acids 1 to 1266 of SEQ ID NO:45. The complete amino acid sequence (FIG. 13B) corresponds to amino acids 1 to 385 of SEQ ID NO:111. Double underlined in FIG. 13A and FIG. 13B are the partially characterized 3' nucleotide (SEQ ID NO:12) and C-terminal predicted partial amino acid (SEQ ID NO:78) sequence, respectively. Single underlined in FIG. 13A and FIG. 13B are the partially characterized 5' nucleotide (SEQ ID NO:13) and N-terminal predicted partial amino acid (SEQ ID NO:79) sequences, respectively. Indicated in FIG. 13A are the stop and start codons (both in black shaded boxes) and the primers (grey shaded boxes) used to amplify the coding region of CCP12/13 by PCR. SEQ ID NOs of the primers used can be found in Table III. Nucleotide sequence differences between SEQ ID NO:45 and SEQ ID NO:12 are depicted.

FIG. 14 depicts the cDNA sequence and predicted amino acid sequence of the *Arabidopsis thaliana* CCP14. The complete nucleotide sequence (FIG. 14A) corresponds to nucleic acids 1 to 1520 of SEQ ID NO:46. The complete amino acid sequence (FIG. 14B) corresponds to amino acids 1 to 465 of SEQ ID NO:112. Underlined in FIG. 14A and FIG. 14B are the partially characterized nucleotide (SEQ ID NO:14) and predicted partial amino acid (SEQ ID NO:80) sequence, respectively. Indicated in FIG. 14A are the stop and start codons (both in black shaded boxes) which are part of the primers (grey shaded boxes) used to amplify the coding region of CCP14 by PCR SEQ ID NOs of the primers used can be found in Table III.

FIG. 15 depicts the cDNA sequence and predicted amino acid sequence of the *Arabidopsis thaliana* CCP15. The complete nucleotide sequence (FIG. 15A) corresponds to nucleic acids 1 to 1142 of SEQ ID NO:47. The complete amino acid sequence (FIG. 1B) corresponds to amino acids 1 to 313 of SEQ ID NO:113. Underlined in FIG. 15A and FIG. 15B are the partially characterized nucleotide (SEQ ID NO:15) and predicted partial amino acid (SEQ ID NO:81) sequence, respectively. Indicated in FIG. 15A are the stop and start codons (both in black shaded boxes) which are part of the primers (grey shaded boxes) used to amplify the coding region of CCP15 by PCR. SEQ ID NOs of the primers used can be found in Table III. Nucleotide sequence differences between SEQ ID NO:47 and SEQ ID NO:15 are depicted. Indicated in FIG. 15B are the PSTTLRE motif (boxed) characteristic for the subclass of plant PSTTLRE CDC2 kinases. Further indicated in FIG. 15B are three CDC2 motifs (black shaded box, grey shaded box and double underlined). Other residues conserved in CDC2s are underscored by '*' (residues in common with ProDom domain PD198850), '+' (residues in common with ProDom domain PD015684), '−' (residues in common with ProDom domain PD063669), and '1' (residues in common with ProDom domain-PD195780).

FIG. 16 depicts the cDNA sequence and predicted amino acid sequence of the *Arabidopsis thaliana* CCP16. The complete nucleotide sequence (FIG. 16A) corresponds to nucleic acids 1 to 1189 of SEQ ID NO:48. The complete amino acid sequence (FIG. 16B) corresponds to amino acids 1 to 292 of SEQ ID NO:114. Indicated in FIG. 16A are the stop and the three possible start codons (all in black shaded boxes) and the primers (grey shaded boxes) used to amplify the coding region of CCP16 by PCR SEQ ID NOs of the primers used can be found in Table III. Nucleotide sequence differences between SEQ ID NO:48 and SEQ ID NO:16 are depicted. Indicated in FIG. 16B are the DNA binding domain (black shaded box), DEF domain (grey shaded box), DCB1 domain (single underlined) and DCB2 domain (double underlined), all domains characteristic for a DP protein.

FIG. 17 depicts the cDNA sequence and predicted amino acid sequence of the *Arabidopsis thaliana* CCP17. The complete nucleotide sequence (FIG. 17A) corresponds to nucleic acids 1 to 794 of SEQ ID NO:17. The complete amino acid sequence (FIG. 17B) corresponds to amino acids 1 to 173 of SEQ ID NO:83. Indicated in FIG. 17A are the stop and start codons (both in black shaded boxes) which are part of the primers (grey shaded boxes) used to amplify the coding region of CCP17 by PCR. SEQ ID NOs of the primers used can be found in Table III.

FIG. 18 depicts the cDNA sequence and predicted amino acid sequence of the *Arabidopsis thaliana* CCP18. The complete nucleotide sequence (FIG. 18A) corresponds to nucleic acids 1 to 805 of SEQ ID NO:49. The complete amino acid sequence (FIG. 18B) corresponds to amino acids 1 to 165 of SEQ ID NO:115. Underlined in FIG. 15A and FIG. 15B are the partially characterized nucleotide (SEQ ID NO:18) and predicted partial amino acid (SEQ ID NO:84) sequence, respectively. Indicated in FIG. 18A are the stop and start codons (both in black shaded boxes) which are part of the primers (grey shaded boxes) used to amplify the coding region of CCP18 by PCR-SEQ ID NOs of the primers used can be found in Table III.

FIG. 19 depicts the cDNA sequence and predicted amino acid sequence of the *Arabidopsis thaliana* CCP19. The complete nucleotide sequence (FIG. 19A) corresponds to nucleic acids 1 to 1152 of SEQ ID NO:19. The complete amino acid sequence (FIG. 1B) corresponds to amino acids 1 to 383 of SEQ ID NO:85. Indicated in FIG. 19A are the stop and start codons (both in black shaded boxes) which are part of the primers (grey shaded boxes) used to amplify the coding region of CCP19 by PCR SEQ ID NOs of the primers used can be found in Table III.

FIG. 20 depicts the cDNA sequence of the *Arabidopsis thaliana* CCP20/21. The complete nucleotide sequence corresponds to nucleic acids 1 to 1539 of SEQ ID NO:50. Underlined are the partially characterized 5' nucleotide (SEQ ID NO:20) sequence and the partially characterized 3' nucleotide (SEQ ID NO:21). Indicated in FIG. 20 are the stop and start codons (both in black shaded boxes) which are part of the primers (grey shaded boxes) used to amplify the coding region of CCP20/21 by PCR. SEQ ID NOs of the primers used can be found in Table III. Nucleotide sequence differences between SEQ ID NOs:20-21 and SEQ ID NO:50 are depicted.

FIG. 21 depicts the predicted amino acid sequence of the *Arabidopsis thaliana* CCP20/21. The complete amino acid sequence corresponds to amino acids 1 to 432 of SEQ ID NO:116. Underlined are the partially characterized N-terminal predicted partial amino acid (SEQ ID NO:50) sequence and the partially characterized C-terminal amino predicted partial acid (SEQ ID NO: 87) sequence. Indicated are further differences in amino acid sequence between SEQ ID NO:87 and SEQ ID NO:116.

FIG. 22 depicts the cDNA sequence of the *Arabidopsis thaliana* CCP22. The complete nucleotide sequence corresponds to nucleic acids 1 to 1977 of SEQ ID NO:51. Underlined is the partially characterized nucleotide (SEQ ID NO:22). Indicated are the stop and start codons (both in black shaded boxes) which are part of the primers (grey shaded boxes) used to amplify the coding region of CCP22 by PCR. SEQ ID NOs of the primers used can be found in Table III.

FIG. 23 depicts the predicted amino acid sequence of the *Arabidopsis thaliana* CCP22. The complete amino acid sequence corresponds to amino acids 1 to 559 of SEQ ID NO:117. Underlined is the predicted partial amino acid (SEQ ID NO:88) sequence.

FIG. 24 depicts the cDNA sequence and predicted amino acid sequence of the *Arabidopsis thaliana* CCP23. The complete nucleotide sequence (FIG. 24A) corresponds to nucleic acids 1 to 525 of SEQ ID NO:52. Indicated in FIG. 24A are the stop and start codons (both in black shaded boxes) which are part of the primers (grey shaded boxes) used to amplify the coding region of CCP23 by PCR. SEQ ID NOs of the primers used can be found in Table M. Nucleotide sequence differences between SEQ ID NOs:23 and SEQ ID NO:52 are depicted. The amino acid sequence in FIG. 24B corresponds to amino acids 1 to 98 of SEQ ID NO:89. The complete amino acid sequence in FIG. 24C corresponds to amino acids 1 to 86 of SEQ ID NO:118.

FIG. 25 depicts the cDNA sequence of the *Arabidopsis thaliana* CCP24. The complete nucleotide sequence corresponds to nucleic acids 1 to 2610 of SEQ ID NO:53. Underlined is the partially characterized nucleotide (SEQ ID NO:24). Indicated are the stop and start codons (both in black shaded boxes) which are part of the primers (grey shaded boxes) used to amplify the coding region of CCP24 by PCR. SEQ ID NOs of the primers used can be found in Table III.

FIG. 26 depicts the predicted amino acid sequence of the *Arabidopsis thaliana* CCP24. The complete amino acid sequence corresponds to amino acids 1 to 784 of SEQ ID NO:119. Underlined is the predicted partial amino acid (SEQ ID NO:90) sequence.

FIG. 27 depicts the cDNA sequence of the *Arabidopsis thaliana* CCP25. The complete nucleotide sequence corresponds to nucleic acids 1 to 2235 of SEQ ID NO:54. Underlined is the partially characterized nucleotide (SEQ ID NO:25) sequence. Indicated are stop and start codon (both in black shaded boxes) which are part of the primers (grey shaded boxes) used to amplify the coding region of CCP25 by PCR. SEQ ID NOs of the primers used can be found in Table III.

FIG. 28 depicts the predicted amino acid sequence of the *Arabidopsis thaliana* CCP25. The complete amino acid sequence corresponds to amino acids 1 to 724 of SEQ ID NO:120. Underlined is the predicted partial amino acid (SEQ ID NO:91) sequence.

FIG. 29 depicts the cDNA sequence of the *Arabidopsis thaliana* CCP26. The complete nucleotide sequence corresponds to nucleic acids 1 to 4002 of SEQ ID NO:55. Underlined is the partially characterized nucleotide (SEQ ID NO:26) sequence. Indicated are stop and start codon (both in black shaded boxes) which are part of the primers (grey shaded boxes) used to amplify the coding region of CCP26 by PCR. SEQ ID NOs of the primers used can be found in Table III. Nucleotide sequence differences between SEQ ID NOs: 26 and SEQ ID NO:55 are depicted.

FIG. 30 depicts the predicted amino acid sequence of the *Arabidopsis thaliana* CCP26. The complete amino acid sequence corresponds to amino acids 1 to 1313 of SEQ ID NO:121. Underlined is the predicted partial amino acid (SEQ ID NO:92) sequence. Amino acid sequence differences between SEQ ID NOs:92 and SEQ ID NO:121 are depicted.

FIG. 31 depicts the cDNA sequence and predicted amino acid sequence of the *Arabidopsis thaliana* CCP27. The complete nucleotide sequence (FIG. 31A) corresponds to nucleic acids 1 to 1251 of SEQ ID NO:56. The complete amino acid sequence (FIG. 31B) corresponds to amino acids 1 to 310 of SEQ ID NO:122. Underlined in FIG. 31A and FIG. 31B are the partially characterized nucleotide (SEQ ID NO:27) and predicted partial amino acid (SEQ ID NO:93) sequence, respectively. Indicated in FIG. 31A are the stop and start codons (both in black shaded boxes) which are part of the primers (grey shaded boxes) used to amplify the coding region of CCP27 by PCR. SEQ ID NOs of the primers used can be found in Table III. Nucleotide sequence differences between SEQ ID NO:27 and SEQ ID NO:56 are depicted in FIG. 31A.

FIG. 32 depicts the cDNA sequence of the *Arabidopsis thaliana* CCP28. The complete nucleotide sequence corresponds to nucleic acids 1 to 2955 of SEQ ID NO:56. Underlined is the partially characterized nucleotide (SEQ ID NO:28) sequence. Indicated are the stop and start codons (both in black shaded boxes) which are part of the primers (grey shaded boxes) used to amplify the coding region of CCP28 by PCR. SEQ ID NOs of the primers used can be found in Table III. Nucleotide sequence differences between SEQ ID NO:28 and SEQ ID NO:57 are depicted.

FIG. 33 depicts the predicted amino acid sequence of the *Arabidopsis thaliana* CCP28. The complete amino acid sequence corresponds to amino acids 1 to 964 of SEQ ID NO:123. Underlined is the predicted partial amino acid (SEQ ID NO:94) sequence.

FIG. 34 depicts the cDNA sequence and predicted amino acid sequence of the *Arabidopsis thaliana* CCP29. The complete nucleotide sequence (FIG. 34A) corresponds to nucleic acids 1 to 546 of SEQ ID NO:29. The complete amino acid sequence (FIG. 34B) corresponds to amino acids 1 to 181 of SEQ ID NO:95. Indicated in FIG. 34A are the stop and start codons (both in black shaded boxes) which are part of the primers (grey shaded boxes) used to amplify the coding region of CCP29 by PCR. SEQ ID NOs of the primers used can be found in Table III.

FIG. 35 depicts the cDNA sequences and predicted amino acid sequences of the *Arabidopsis thaliana* CCP30. The complete nucleotide sequence (FIG. 35A) corresponds to nucleic acids 1 to 492 of SEQ ID NO:30. Indicated in FIG. 35A are the stop and start codons (both in black shaded boxes), the complete sense primer and part of the antisense primer (grey shaded boxes) used to amplify the coding region of CCP30 by PCR. SEQ ID NOs of the primers used can be found in Table II. However, after sequencing of the PCR product a sequence error in SEQ ID NO:30 was detected boxed nucleotide 'a' in FIG. 35A not present) which caused a frame shift effectuating the CCP30 open reading frame. The putative correct cDNA sequence is given in FIG. 35B (nucleic acids 1 to 865 of SEQ ID NO:58) wherein the three putative start codons are marked by a black shaded box. The originally identified start codon is indicated in bold letters. The stop codon is unaltered. The amino acid sequence in FIG. 35C corresponds to amino acids 1 to 163 of SEQ ID NO:96, the protein encoded by the initially identified open reading frame of SEQ ID NO:30. The putative correct complete amino acid sequence in FIG. 35D corresponds to amino acids 1 to 222 of SEQ ID NO:124 which comprises the longest possible open reading frame. The Met residues corresponding to the three possible start codons in SEQ ID NO:58 (FIG. 35B) are bold faced.

FIG. 36 depicts the cDNA sequence of the *Arabidopsis thaliana* CCP31. The complete nucleotide sequence corresponds to nucleic acids 1 to 723 of SEQ ID NO:31. Indicated in FIG. 1A are the stop and start codons (both in black shaded boxes).

FIG. 37 depicts the predicted amino acid sequence of the *Arabidopsis thaliana* CCP31. The complete amino acid sequence corresponds to amino acids 1 to 148 of SEQ ID NO:125.

FIG. 38 depicts the cDNA sequence and predicted amino acid sequence of the *Arabidopsis thaliana* CCP32. The complete nucleotide sequence (FIG. 38A) corresponds to nucleic acids 1 to 426 of SEQ ID NO:60. The complete amino acid sequence (FIG. 38B) corresponds to amino acids 1 to 70 of SEQ ID NO:126. Underlined in FIG. 38A is the partially characterized nucleotide (SEQ ID NO:32) sequence. Indicated in FIG. 38A are the stop and start codons (both in black shaded boxes) which are part of the primers (grey shaded boxes) used to amplify the coding region of CCP32 by PCR. SEQ ID NOs of the primers used can be found in Table III. FIG. 38C gives the originally erroneously predicted amino acid sequence of CCP32 (amino acids 1 to 38 of SEQ ID NO:98).

FIG. 39 depicts the cDNA sequence and predicted amino acid sequence of the *Arabidopsis thaliana* CCP33. The complete nucleotide sequence (FIG. 39A) corresponds to nucleic acids 1 to 1442 of SEQ ID NO:61. The complete amino acid sequence (FIG. 39B) corresponds to amino acids 1 to 385 of SEQ ID NO:127. Indicated in FIG. 39A are the stop and start codons (both in black shaded boxes) which are part of the primers (grey shaded boxes) used to amplify the coding region of CCP33 by P CR. SEQ ID NOs of the primers used can be found in Table III. Indicated in FIG. 39B are the DNA binding domain (black shaded box), DEF domain (grey shaded box), DCB1 domain (single underlined) and DCB2 domain (double underlined), all domains characteristic for a DP protein.

FIG. 40 depicts the cDNA sequence and predicted amino acid sequence of the *Arabidopsis thaliana* CCP34. The complete nucleotide sequence (FIG. 40A) corresponds to nucleic acids 1 to 1506 of SEQ ID NO:62. The complete amino acid sequence (FIG. 40B) corresponds to amino acids 1 to 437 of SEQ ID NO:128. Underlined in FIG. 40A and FIG. 40B are the partially characterized nucleotide (SEQ ID NO:34) and predicted partial amino acid (SEQ ID NO:62) sequence, respectively. Indicated in FIG. 40A are the stop and start codons (both in black shaded boxes) which are part of the primers (grey shaded boxes) used to amplify the coding region of CCP34 by PCR. SEQ ID NOs of the primers used can be found in Table III.

FIG. 41 depicts the cDNA sequence of the *Arabidopsis thaliana* CCP35. The complete nucleotide sequence corresponds to nucleic acids 1 to 2631 of SEQ ID NO:63. Underlined is the partially characterized nucleotide (SEQ ID NO:35) sequence. Indicated are the stop and start codons (both in black shaded boxes) and of the primers (grey shaded boxes) used to amplify the coding region of CCP35 by PCR. SEQ ID NOs of the primers used can be found in Table III. Nucleotide sequence differences between SEQ ID NO:33 and SEQ ID NO:63 are depicted.

FIG. 42 depicts the predicted amino acid sequence of the *Arabidopsis thaliana* CCP35. The complete amino acid sequence corresponds to amino acids 1 to 749 of SEQ ID NO:129. Underlined is the predicted partial amino acid (SEQ ID NO:101) sequence.

FIG. 43 depicts the cDNA sequence of the *Arabidopsis thaliana* CCP36. The complete nucleotide sequence corresponds to nucleic acids 1 to 2743 of SEQ ID NO:64. Underlined is the partially characterized nucleotide (SEQ ID NO:36) sequence. Indicated are the stop and start codons (both in black shaded boxes). Nucleotide sequence differences between SEQ ID NO:36 and SEQ ID NO:64 are depicted.

FIG. 44 depicts the predicted amino acid sequence of the *Arabidopsis thaliana* CCP36. The complete amino acid sequence corresponds to amino acids 1 to 742 of SEQ ID NO:130. Underlined is the predicted partial amino acid (SEQ ID NO:102) sequence.

FIG. 45 depicts the cDNA sequence of the *Arabidopsis thaliana* CCP37. The complete nucleotide sequence corresponds to nucleic acids 1 to 2959 of SEQ ID NO:65. Underlined is the partially characterized nucleotide (SEQ ID NO:37) sequence. Indicated are the stop and start codons (both in black shaded boxes) and primers (grey shaded boxes) used to amplify the coding region of CCP45 by PCR. SEQ ID NOs of the primers used can be found in Table III.

FIG. 46 depicts the predicted amino acid sequence of the *Arabidopsis thaliana* CCP37. The complete amino acid sequence corresponds to amino acids 1 to 911 of SEQ ID NO:131. Underlined is the predicted partial amino acid (SEQ ID NO:103) sequence. Indicated in a black shaded box is a SAP-like domain.

FIG. 47 depicts the cDNA sequence and predicted amino acid sequence of the *Arabidopsis thaliana* CCP38. The complete nucleotide sequence (FIG. 47A) corresponds to nucleic acids 1 to 1295 of SEQ ID NO:66. The complete amino acid sequence (FIG. 47B) corresponds to amino acids 1 to 357.0f SEQ ID NO:132. Underlined in FIG. 47A and FIG. 47B are the partially characterized nucleotide (SEQ ID NO:38) and predicted partial amino acid (SEQ ID NO:104) sequence, respectively. Indicated in FIG. 47A are the stop and start codons (both in black shaded boxes) which are part of the primers (grey shaded boxes) used to amplify the coding region of CCP38 by PCR. SEQ ID NOs of the primers used can be found in Table II.

FIG. 60 describes the molecules defined in SEQ ID NOs: 199-204 and 240-290.

DETAILED DESCRIPTION OF THE INVENTION

Figure 48:
FIG. 48 depicts phosphorylation of the *Arabidopsis thaliana* CCP4 by CDKs. The protein CDC2bDN-IC26M (SEQ ID NO:70) contains a consensus CDK phosphorylation site (TPWK, residues 54-57 of SEQ ID NO:263). The corresponding gene (SEQ ID NO:4) was expressed in *E. coli* and the protein was purified from the crude extracts. The purified protein was subsequently shown to be phosphorylated by CDKs in an in vitro CDK phosphorylation assay.-: no IC26M added; +: IC26M added.
Figure 49:
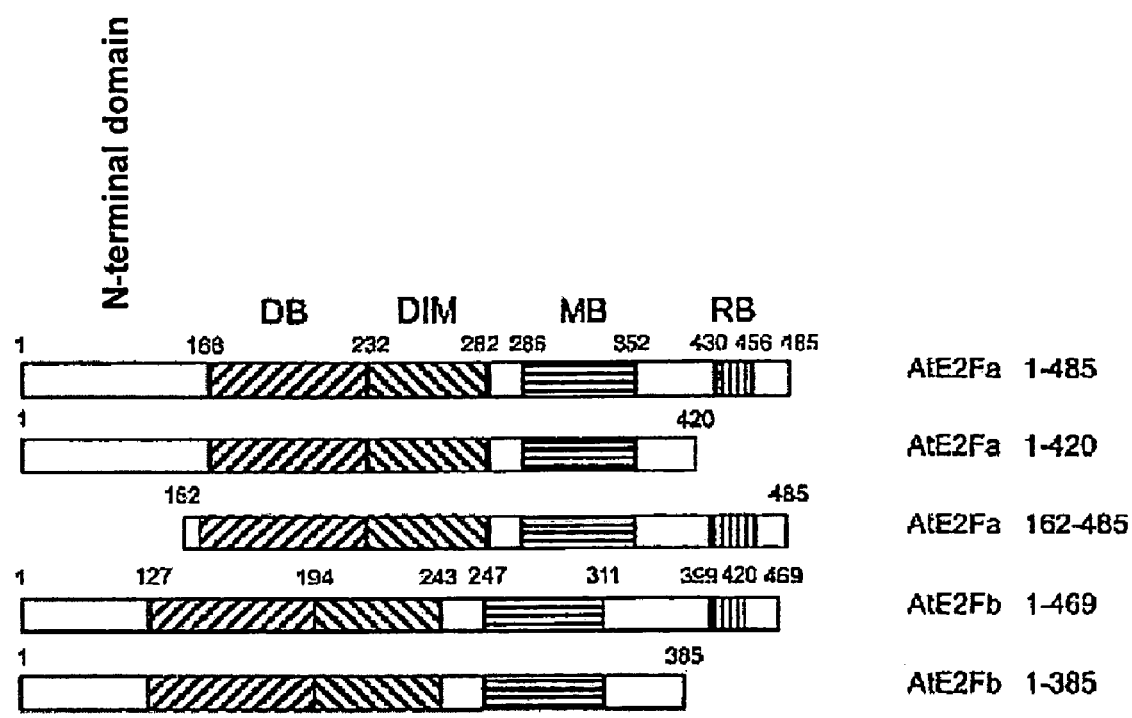
FIG. 49 schematically represents the domain organization of AtE2Fa and AtE2Fb. The DNA-binding domain (DB), the dimerization domain (DIM), the marked box (MB), and the Rb-binding domain (RB) are indicated by marked boxes, the N-terminal domains are indicated by open boxes. Numbering on the right refers to the amino acid sequence contained in the different AtE2F constructs, which were used in the in vitro binding assays.

The present invention is based, at least in part, on the discovery of novel molecules, referred to herein as "cell cycle proteins" or "CCP" nucleic acid and polypeptide molecules. The CCP molecules of the present invention were identified based on their ability, as determined using yeast two-hybrid assays (described in detail in Example 1), to interact with proteins involved in the cell cycle, such as plant cyclin dependent kinases (e.g., a dominant negative form of CDC2b, CDC2bAt.N161), cyclin dependent kinase subunits referred herein as "CKS" (such as CKS1At), cyclin dependent kinase inhibitors referred to herein as "CKI" (such as CKI4), PHO80-like proteins referred to herein as "PLP", E2F, and different domains of kinesin-like proteins referred to herein as "KLPNT.

Because of their ability to interact with (e.g., bind to) the cyclin dependent kinases, the CCP molecules of the present invention may modulate, e.g., upregulate or downregulate, the activity of plant CDKs, such as CDC2 or CDC2b; CKSs, CKIs, PLPs and KLPNTs. Furthermore, because of their ability to interact with (e.g., bind to) the aforementioned proteins which are proteins involved in cell cycle regulation, the CCP molecules of the present invention may also play a role in or function in cell cycle regulation, e.g., plant or animal cell cycle regulation.

As used herein, the term "cell cycle protein" includes a polypeptide which is involved in controlling or regulating the cell cycle, or part thereof, in a cell, tissue, organ or whole organism. Cell cycle proteins may also be capable of binding to, regulating, or being regulated by cyclin dependent kinases, such as plant cyclin dependent kinases, e.g., CDC2a or CDC2b, or their subunits. The term cell cycle protein also includes peptides, polypeptides, fragments, variant, homologs, alleles or precursors (e.g., pre-proteins or pro-proteins) thereof.

As used herein, the term "cell cycle" includes the cyclic biochemical and structural events associated with growth, division and proliferation of cells, and in particular with the regulation of the replication of DNA and mitosis. The cell cycle is divided into periods called: $G_0$, $Gap_1$, $(G_1)$, DNA synthesis (S), $Gap_2$ $(G_2)$, and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

As used herein, the term "plant" includes reference to whole plants, plant organ (e.g., leaves, stems, roots), plant tissue, seeds, and plant cells and progeny thereof. Plant cell, as used herein includes, without limitation, seeds, e.g., seed suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable of transformation techniques, including both monocotyledonous and dicotyledonous plants. Particularly preferred plants are *Arabidopsis thaliana* rice, wheat, maize, tomato, alfalfa, oilseed rape, soybean, cotton, sunflower or canola. The term plant also includes monocotyledonous (monocot) plants and dicotyledonous (dicot) plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea phurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmnodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucaysptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectzum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotomns bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguinezum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

The cell cycle proteins of the present invention are involved in cell cycle regulation which is largely, but not completely, similar in plants and animals. Accordingly, the nucleic acid molecules and polypeptide of the invention, or derivatives thereof, may be used to modulate the cell cycle in a plant or an animal such as by modulating the activity or level or expression of CCP, altering the rate of the cell cycle or phases of the cell cycle, and entry into and out of the various cell cycle phases. In plants, the molecules of the present invention may be used in agriculture to, for example, improve the growth characteristics of plant such as growth rate or size of specific tissues or organs, the architecture or morphology of the plant, increase crop yield, improve tolerance to environmental stress conditions (such as drought, salt, temperature, or nutrient deprivation), improve tolerance to plant pathogens that abuse the cell cycle or as targets to facilitate the identification of inhibitors or activators of CCPs that may be useful as phytopharmaceuticals such as herbicides or plant growth regulators.

As used herein, the term "cell cycle associated disorders" includes a disorder, disease or condition which is caused or characterized by a misregulation (e.g., downregulation or upregulation), abuse, arrest, or modification of the cell cycle. In plants cell cycle associated disorders include endomitosis, acytokinesis, polyploidy, polyteny, and endoreduplication which may be caused by external factors such as pathogens (nematodes, viruses, fungi, or insects), chemicals, environmental stress (e.g., drought, temperature, nutrients, or TV) resulting in for instance neoplastic tissue (e.g., galls, root knots) or inhibition of cell division/proliferation (e.g., stunted growth). Cell cycle associated disorders in animals include proliferative disorders or differentiative disorders, such as cancer, e.g., melanoma, prostate cancer, cervical cancer, breast cancer, colon cancer, or sarcoma.

The present invention is based, at least in part, on the discovery of novel molecules, referred to herein as CCP protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of plant, e.g. *Arabidopsis*, origin, as well as other, distinct proteins of plant, e.g., *Arabidopsis*, origin or alternatively, can contain homologues of other plants, e.g., rice, or of non-plant origin. Members of a family may also have common functional characteristics.

In one embodiment of the invention, a CCP protein of the present invention is identified based on the presence of at least one or more of the following domains:

A. Cyclin Destruction Box

As used herein, the term "Cyclin destruction box" includes a domain of 9-10 amino acid residues in length which typically contains the following consensus pattern:

```
R-X₂-L-X₂-[I/V]-X₁₋₂-N,        (SEQ ID NO: 267)
``` wherein X can be any amino acid, $X_n$ is a stretch of n Xs, $X_{n-m}$ is a stretch of n to m Xs, and wherein [I/V] means that an Ile or Val residue can occur at that position. SEQ ID NO:267 depicts the minimal consensus sequence of the cyclin destruction box and underlies the ubiquitin-mediated proteolytic destruction of the cyclins bearing this motif (Yamano et al. (1998), *EMBO J.* 17: 5670-5678; Renaudin et al. (1998) in Plant Cell Division (Francis, Dudits and Inzé, eds.), Portland Press Research Monograph, Portland Press Ltd. London (1998), pp 67-98).

B. Cyclin Box Motif 1

As used herein, the term "Cyclin box motif 1" includes a domain of 8 amino acid residues in length and which typically contains the following consensus pattern:

```
    MRXIL[I/V]DW,        (SEQ ID NO: 268)
``` wherein X can be any amino acid and wherein [I/V] means that an Ile or Val residue can occur at that position. This motif forms part of the helix H1 of the first cyclin fold and is the best conserved motif in the cyclinA/B family (Renaudin et al. (1998) in Plant Cell Division (Francis, Dudits and Inzé, eds.), Portland Press Research Monograph, Portland Press Ltd. London (1998), pp 67-98).

C. Cyclin Box Motif 2

As used herein, the term "Cyclin box motif 2" includes a domain of 8 amino acid residues in length and which typically contains the following consensus pattern:

```
        KYEE-X₃-P,        (SEQ ID NO: 269)
``` wherein X can be any amino acid and wherein $X_n$ is a stretch of n Xs. This motif forms part of the helix H3 of the first cyclin fold wherein the 2 acidic residues are part of the CDK binding site (Renaudin et al. (1998) in Plant Cell Division (Francis, Dudits and Inzé, eds.), Portland Press Research Monograph, Portland Press Ltd. London (1998), pp 67-98).

D. CDC2 Motifs

As used herein, the term "CDC2 motifs" includes domains of about 9-12 amino acid residues in length and which typically contain one of the following consensus patterns:

```
    GXG-X₂-GXVY             (SEQ ID NO: 270)

HRDXK-X₂-NXL            (SEQ ID NO: 271)

D-X₁₋₂-[W/Y]SXG-X₄-E    (SEQ ID NO: 272)
``` wherein X can be any amino acid, $X_n$ is a stretch of n Xs, $X_{n-m}$ is a stretch of n to m Xs, and wherein [W/Y] means that an Trp or Tyr residue can occur at that position.

E. CDK Phosphorylation Site

As used herein the term "CDK phosphorylation site" includes a domain of about 5-7 amino acids in length and which contains one or more of the following consensus domains:

```
    TPX₁₋₂[R/K]        (SEQ ID NO: 273)

SPX[R/K]           (SEQ ID NO: 274)

SPX(Hu)            (SEQ ID NO: 275)

SP(Hu)X            (SEQ ID NO: 276)
``` with Hu being a hydrophobic uncharged amino acid (M, I, L, V) and X any amino acid. The foregoing are typically found in cyclin-dependent kinase substrates such as histone kinase, transcription factors such as E2F or transcription regulators like Rb. CDK phosphorylation sites are described in, for example, Tamrakar et al. 2000, Frontiers Biosci 5, d121-137.

CCP proteins of the present invention comprising a CDK phosphorylation site can be mutated in said CDK phosphorylation site such that said CCP proteins are no longer able to be phosphorylated on the CDK phosphorylation site. Mutations of a CDK phosphorylation site include all mutations of the ser or thr residue in any of SEQ ID NOs:273-276 into a non-phosphorylatable amino acid residue, e.g., an ala or glu residue. Mutation of one or more CDK phosphorylation site (s) in a CCP protein of the invention is expected to modulate modifications of the CCP protein by CDKs and, thus, to modulate the biological or biochemical function of the CCP protein.

F. E Nuclear Localisation Signal (NLS)

As used herein the term "nuclear localization signal" or "NLS" includes a domain conferring to a protein comprising the NLS domain the ability to be imported into the nucleus and to, for example, accumulate within the nucleus. NLS domains include one or more of the following concensus patterns:

```
    PKKXRKV            (SEQ ID NO: 277)

KRX₁₀KKKK          (SEQ ID NO: 278)

KRPRP              (SEQ ID NO: 279)

PAAKRVKLD          (SEQ ID NO: 280)
```

NLS domains have been found in the SV40 T antigen, in nucleoplasmin (bipartite NLS), in a Adeno EIA, and in c-Myc. NLS domains are described in, for example, Laskey et al. (1998) *Biochem. Soc. Trans.* 26, 561-567.

G. Cy-Like Boxes

As used herein, the term "Cy-like box" includes a domain of 3-6 amino acid residues in length with has the consensus motif R-X-X-F (SEQ ID NO:281) with X being any amino acid and one of two Xs preferably being a hydrophobic residue.

H. Rb Binding Domain

As used herein, the term "Rb binding domain" includes a domain which when present in a protein confers to the protein the ability to bind the Rb protein. Rb binding domains include one or more of the following concensus patterns:

```
    LXCXE              (SEQ ID NO: 282)

LXSXE              (SEQ ID NO: 283)
```

-continued

DYX₇EX₃DLFD (SEQ ID NO: 284)

DYX₆DX₄DMWE (SEQ ID NO: 285)

Rb binding domains have been found in D-cyclins, in protein phosphatase 1, in human E2F-1, and in plant E2F. Rb binding domains are described in, for example, Rubin et al. (1998) *Frontiers Biosci* 3, d1209-1219; Phelps et al. (1992) *J. Virol.* 66, 2418-2427, and Cress et al. (1993) *Mol. Cell. Biol.* 13, 6314-6325.

I. DEF Domain

As used herein the term "DEF domain" includes a protein domain which is required for the formation of heterodimers between DP proteins and E2F proteins. DEF domains comprise the following concensus pattern:

(SEQ ID NO: 286)
[D/N/-][Q/E]KNIR[R/G]RV[Y/D]DALNV[L/F]MA[M/I/L/-]

[N/D][V/I]I[S/A][K/R][D/E]KKEI[K/Q/R/-]W[R/K/I]GLP

J. DNA Binding Domain

As used herein the term "DNA binding domain" includes a domain which is involved in the binding of DP proteins and/or DP-E2F heterodimers to DNA. DNA binding domains include the following concensus pattern:

(SEQ ID NO: 287)
[G/N][K/R]GLR[H/Q]FS[M/V][K/M][I/V]X₍₀₋₁₇₎C[E/Q]K

[V/L][Q/E/-][S/-]XK[G/K]-[R/I/-]TT[S/-]Y[N/K]EVADE

[L/I][V/I][A/S][E/D]F

DNA binding domains are described in, for example, Hao et al. (1995) *J. Cell Sci.* 108, 2945-2954; Bandara et al. (1993) *EMBO J.* 12, 4317-4324; and Girling et al. (1994) *Mol. Biol. Cell* 5, 1081-1092.

K. DCB1 Domain:

As used herein the term "DCB1 domain" includes a protein domain which is conserved among DP proteins and has the following concensus patterns:

(SEQ ID NO: 288)
[R/S][I/V]X[Q/K]KX₃[L/S]XE (SEQ ID NO: 289)
[R/S][I/V]X[Q/K]KX₃[L/S]XE[L/M]X₂₋₃[Q/H]X₄₋₅NL

[V/I/M][Q/E]RN

DCB1 domains are described in, for example, Hao et al. (1995) *J Cell Sci.* 108, 2945-2954; Bandara et al. (1993) *EMBO J.* 12, 4317-4324; and Girling et al. (1994) *Mol. Biol. Cell* 5, 1081-1092.

L. DCB2 Domain:

As used herein the term "DCB2 domain" includes a protein domain which is conserved among DP proteins and has the following concensus pattern:

(SEQ ID NO: 290)
[L/I]PFI[L/I][V/L]XTX₃₋₄[T/V]VX₁₂₋₁₄FX₃₋₄F[E/S]

[Hu]HDDX₂[V/I]L[R/K]XM

DCB2 domains are described in, for example, Hao et al. (1995) *J. Cell. Sci.* 108, 2945-2954; Bandara et al. (1993) *EMBO J.* 12, 4317-4324; and Girling et al. (1994) *Mol. Biol. Cell* 5, 1081-1092.

M. SAP Domain:

As used herein the term SAP motif includes a protein domain of about 35 amino acid residues which is found in a variety of nuclear proteins involved in transcription, DNA repair, DNA processing or apoptotic chromatin degradation. It was named after SAF-A/B, Acinus and PIAS, three proteins known to contain it. The SAP motif reveals a bipartite distribution of strongly conserved hydrophobic, polar and bulky amino acids separated by a region that contains a glycine. The SAP domain has been proposed to be a DNA-binding motif (Aravind and Koonin (2000) *Trends Biochem. Sci.* 25:112-114).

Isolated CCP proteins of the present invention have an amino acid sequence sufficiently identical to the amino acid sequence of SEQ ID NO:67-132, 205, 211, 215-216, or 220-227 or are encoded by a nucleotide sequence sufficiently identical to SEQ ID NO:1-66 or 228-239. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical.

As used interchangeably herein, an "CCP activity", "biological activity of CCP" or "functional activity of CCP", refers to an activity exerted by a CCP protein, polypeptide or nucleic acid molecule on a CCP responsive cell or tissue, or on a CCP protein substrate, as determined in vivo, or in vitro, according to standard techniques. In one embodiment, a CCP activity is a direct activity, such as an association with a CCP-target molecule. As used herein, a "target molecule" or "binding partner" is a molecule with which a CCP protein binds or interacts in nature, such that CCP-mediated function is achieved. A CCP target molecule can be a non-CCP molecule or a CCP protein or polypeptide of the present invention, e.g., a plant cyclin dependent kinase, such as CDC2b. In an exemplary embodiment, a CCP target molecule is a CCP ligand. Alternatively, a CCP activity is an indirect activity, such as a cellular signaling activity mediated by interaction of the CCP protein with a CCP ligand. The biological activities of CCP are described herein. For example, the CCP proteins of the present invention can have one or more of the following activities: (1) they may interact with a non-CCP protein molecule, e.g., a CCP ligand; (2) they may modulate a CCP-dependent signal transduction pathway; (3) they may modulate the activity of a plant cyclin dependent kinase, such as CDC2a, CDC2b, or CDC2c, and (4) they may modulate the cell cycle.

Accordingly, another embodiment of the invention features isolated CCP proteins and polypeptides having a CCP activity. Preferred proteins are CCP proteins having at least one or more of the following domains: a "cyclin destruction box", a "cyclin box motif 1", a "cyclin box motif 2", a "CDC2 motif", a "CDK phosphorylation site", a "nuclear localization signal", a "Cy-like box", an "Rb binding domain", a "DEF domain", a "DNA binding domain", a "DCB1 domain", a "DCB2 domain" and/or a SAP domain, and, preferably, a CCP activity.

Additional preferred proteins have at least one or more of the following domains: a "cyclin destruction box", a "cyclin box motif 1", a "cyclin box motif 2", a "CDC2 motif", a "CDK phosphorylation site", a "nuclear localization signal", a "Cy-like box", an "Rb binding domain", a "DEF domain", a "DNA binding domain", a "DCB1 domain", a "DCB2 domain" and/or a SAP domain and are, preferably, encoded by a nucleic acid molecule having a nucleotide sequence which hybridizes under stringent hybridization conditions to a nucleic acid molecule comprising the nucleotide sequence of SEQ ID NO:1-66 or 228-239.

The sequences of the present invention are summarized below, in Table I.

TABLE I

| CCP Molecule | Clone Name | Bait | Homolog/ function | motif | SEQ ID NO: partial DNA | SEQ ID NO: full-length DNA | SEQ ID NO: partial Protein | SEQ ID NO: full-length Protein |
|---|---|---|---|---|---|---|---|---|
| CCP1 | CDC2bDN-IC19 | CDC2bAt.N161 | Novel CYCB2; 3 | cyclin box motifs 1 and 2; cyclin destruction box | 1 | 39 | 67 | 105 |
| CCP2 | CDC2bDN-IC20 | CDC2bAt.N161 | ARR2 | | 2 | 40 | 68 | 106 |
| CCP3 | CDC2bDN-IC21 | CDC2bAt.N161 | novel A-type cyclin | cyclin box motifs 1 and 2; cyclin destruction box | 3 | 41 | 69 | 107 |
| CCP4 | CDC2bDN-IC26M | CDC2bAt.N161 | | CDK phosphorylation site | 4 | 4 | 70 | 70 |
| CCP5 | CDC2bDN-IC39 | CDC2bAt.N161 | Arath CYCB2; 1 | cyclin box motifs 1 and 2; cyclin destruction box | 5 | 5 | 71 | 71 |
| CCP6 | CDC2bDN-IC57 | CDC2bAt.N161 | | | 6 | 42 | 72 | 108 |
| CCP7 | CDC2bDN-IC62 | CDC2bAt.N161 | AJH2-COP9 | | 7 | 43 | 73 | 109 |
| CCP8 | E2F3ca55 | E2F3 N-terminal | | | 8 | 43 | 74 | 109 |
| CCP9 | CDC2bDN-IC9 | CDC2bAt.N161 | Arath CYCA2; 2 | cyclin box motifs 1 and 2; cyclin destruction box | 9 | 9 | 75 | 75 |
| CCP10 | CKSBC001 | CKS1At | | | 10 | 10 | 76 | 76 |
| CCP11 | CKSBC011 | CKS1At | gibberellin-regulated protein GASA1 precursor | | 11 | 44 | 77 | 110 |
| CCP12 | CKSBC98-7 (Cterm) | CKS1At | | | 12 | 45 | 78 | 111 |
| CCP13 | CKSBC98-7 (Nterm) | CKS1At | | | 13 | 45 | 79 | 111 |
| CCP14 | CKSBC103-19 (Cterm) | CKS1At | | | 14 | 46 | 80 | 112 |
| CCP15 | CKSBC199-20 | CKS1At | PSTTLRE-type CDK | CDC2 motifs | 15 | 47 | 81 | 113 |
| CCP16 | E2F5BBC1 | E2F5 dimerisation domain | DPa | DNA-binding domain; DEF domain; DCB1 and DCB2 domain | 16 | 48 | 82 | 114 |
| CCP17 | FL67BC4-2 | CKI4 | | | 17 | 17 | 83 | 83 |
| CCP18 | FL67BC12-17 | CKI4 | RNA polymerase B transcription factor 3 | | 18 | 49 | 84 | 115 |

TABLE I-continued

| CCP Molecule | Clone Name | Bait | Homolog/ function | motif | SEQ ID NO: partial DNA | SEQ ID NO: full-length DNA | SEQ ID NO: partial Protein | SEQ ID NO: full-length Protein |
|---|---|---|---|---|---|---|---|---|
| CCP19 | JUT1 | PLP1 | | | 19 | 19 | 85 | 85 |
| CCP20 | JUT2 | PLP1 | | | 20 | 50 | 86 | 116 |
| CCP21 | JUT3 | PLP1 | | | 21 | 50 | 87 | 116 |
| CCP22 | JUT6 | PLP1 | Submergence induced protein2 or *Oryza sativa* | | 22 | 51 | 88 | 117 |
| CCP23 | kbp1 | KLPNT1 36-508 aa (motor domain) KLPNT2 (TH65) 73-186 aa (neck domain) | HSF1 | | 23 | 52 | 89 | 118 |
| CCP24 | kbp3 | KLPNT1 (427-86 7aa) stalk domain | | | 24 | 53 | 90 | 119 |
| CCP25 | kbp6 | KLPNT2 (TH65) 73-186 aa neck domain | | | 25 | 54 | 91 | 120 |
| CCP26 | kbp9 | KLPNT2 (TH65) 73-186 aa neck domain | AtKLPNT1 | | 26 | 55 | 92 | 121 |
| CCP27 | kbp11 | KLPNT2 (TH65) 73-186 aa neck domain | | | 27 | 56 | 93 | 122 |
| CCP28 | kbp12 | KLPNT2 (TH65) 73-186 aa neck domain | | | 28 | 57 | 94 | 123 |
| CCP29 | kbp13 | KLPNT2 (TH65) 73-186 aa neck domain | | | 29 | 29 | 95 | 95 |
| CCP30 | kbp15 | KLPNT2 (TH65) 73-186 aa neck domain | Centromere/ microtubule binding protein CBF5 from yeast | | 30 | 58 | 96 | 124 |
| CCP31 | kbp20 | KLPNT2 (TH65) 73-608 aa stalk domain | VU91C calmodulin from yeast | | 31 | 59 | 97 | 125 |
| CCP32 | E2F5BB C16 | E2F5 dimerization | | | 32 | 60 | 98 | 126 |
| CCP33 | DPb | / | | DNA-binding domain; DEF domain; DCB1 and DCB2 domain | 33 | 61 | 99 | 127 |
| CCP34 | E2F3ca1 | E2F3 N-terminal | | | 34 | 62 | 100 | 128 |
| CCP35 | E2F3ca2 | E2F3 N-terminal | | | 35 | 63 | 101 | 129 |
| CCP36 | E2F3ca9 | E2F3 N-terminal | | | 36 | 64 | 102 | 130 |
| CCP37 | E2F3ca12 | E2F3 N-terminal | | SAP domain | 37 | 65 | 103 | 131 |
| CCP38 | E2F3ca50 | E2F3 N-terminal | | | 38 | 66 | 104 | 132 |

Detailed studies of interactions between AtDPs (a and b forms, SEQ ID NO:114 and SEQ ID NO:127, respectively) and AtE2Fs (a and b forms; GenBank accession numbers AJ294534 and AJ294533, respectively) revealed that the regions of AtDPa and AtDPb involved in the binding of AtE2Fb are different.

Binding of AtDPa to AtE2Fb requires at least the AtDPa dimerization domain and the whole (or possibly part of) the C-terminal domain of AtDPa. The N-terminal domain and the DNA-binding domain of AtDPa do not seem to contribute to the interaction of AtDPa with AtE2Fb (Examples 11, 12, Table 5, FIG. 54).

Binding of AtDPb to AtE2Fb, however, only requires an intact AtDPb dimerization domain. Neither the region including the N-terminal and DNA-binding domains of AtDPb, nor the C-terminal region of AtDPb seem to contribute to the interaction of AtDPb with AtE2Fb (Examples 11, 12, Table 5, FIG. 55). These observations indicate that modulating the formation of specific E2F/DP-complexes may be useful in modulating cell cycle traversal and the regulation thereof.

AtDPa and AtDPb, respectively, do not form homodimers but both interact with either AtE2Fa or AtE2Fb (Example 12, Table 5). In reciprocal experiments it was shown that the N-terminal domain of AtE2Fa is not required for binding AtDPa or AtDPb. Likewise, the Rb-binding domains of AtE2Fa and AtE2Fb, respectively, do not seem to contribute to the binding to either AtDPa or AtDPb. The region of AtE2Fa encompassing the dimerization domain and the marked box is sufficient for binding to AtDPa and AtDPb (Examples 11, 12, FIG. 50, FIG. 51, Table 5). The dimerization domain of AtE2Fs appears to be sufficient for binding to AtDPs.

Accordingly, it is shown herein for the first time (for plant DPs and plant E2Fs) that the minimal DP and E2F proteins or corresponding coding DNA sequences that can be used in modifying E2F/DP-related processes, e.g., regulation of gene expression by E2F/DP, include:

(A) Plant DP dimerization domain with or without (art of) the C-terminal DP domain. These domains include the proteins AtDPa143-292 and AtDPa143-213 (numbering indicates the amino acids included in said fragment relative to the full-length AtDPa protein) set forth in SEQ ID NO:221 and SEQ ID NO:222, respectively. The coding sequences corresponding to the foregoing amino acid sequences are set forth in SEQ ID NO:232 and SEQ ID NO:233, respectively. Also included are the corresponding regions of the AtDPb protein characterized by AtDPb182-385 and AtDPb182-263 (parts of the full-length AtDPb protein). The foregoing regions of AtDPb are set forth in SEQ ID NO:216 and SEQ ID NO:215, respectively, and the coding sequences corresponding thereto are set forth in SEQ ID NO:231 and SEQ ID NO:230, respectively. The AtDPb1-263 domain (SEQ ID NO:223) and the corresponding AtDPa1-214 domain (SEQ ID NO:220) encoded by the nucleic acid sequences SEQ ID NO:234 and SEQ ID NO:239, respectively, can also be used. Further included are nucleic acid sequences hybridizing to SEQ ID NOs:229-234 or SEQ ID NO:239 or encoding a protein at least 50%, 55%, 60%, 65%, 70%, 75%, 80%, 85%, 90%, 95%, 98% or more identical to SEQ ID NOs:211, 215-216 and 220-223.

(B) Plant E2F dimerization domain with or without (part of) the marked box. These domains include the proteins AtE2Fa232-282, AtE2Fa232-352 and AtE2Fa226-356 set forth in SEQ ID NO:224, SEQ ID NO:225 and SEQ ID NO:205, respectively. The corresponding coding DNA sequences are set forth in SEQ ID NO:235, SEQ ID NO:236 and SEQ ID NO:228, respectively. Also included are the corresponding regions of the AtE2Fb protein characterized by AtE2Fb194-243 and AtE2Fb194-311 set forth in SEQ ID NO:226 and SEQ ID NO:227, respectively. The corresponding coding DNA sequences are set forth in SEQ ID NO:237 and SEQ ID NO:238, respectively. Further included are nucleic acid sequences hybridizing to SEQ ID NO:228 or SEQ ID NOs:235-238 or encoding a protein at least 70%, 75%, 80%, 85%, 90%, 95%, 98% identical to SEQ ID NO:205 or SEQ ID NOs:224-227.

(C) Full-length plant DP and plant E2F proteins or corresponding DNA sequences may also be used to modify said E2F/DP-related processes. Furthermore, plant DP and plant E2F proteins or corresponding DNA sequences, or parts thereof, can be used either separately or in combination to modify said E2F/DP-related processes. This is underscored by the demonstration that AtDPs and AtE2Fs are co-expressed in actively dividing cells and in at least some plant tissues (Example 13 and FIGS. 57 and 58).

Various aspects of the invention are described in further detail in the following subsections:

I. Isolated Nucleic Acid Molecules

One aspect of the invention pertains to isolated nucleic acid molecules that encode CCP proteins or biologically active portions thereof, as well as nucleic acid fragments sufficient for use as hybridization probes to identify CCP-encoding nucleic acids (e.g., CCP mRNA) and fragments for use as PCR primers for the amplification or mutation of CCP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated CCP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1-66 or 228-239 or a portion thereof, can be isolated using standard molecular biology techniques and the sequence information provided herein. For example, using all or portion of the nucleic acid sequence of SEQ ID NO:1-66 or 228-239, as a hybridization probe, CCP nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1-66 or 228-239 can be isolated by the polymerase chain reaction (PCR) using synthetic oligonucleotide primers designed based upon the sequence of SEQ ID NO:1-66 or 228-239, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CCP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1-66 or 228-239.

In another preferred embodiment, an isolated nucleic acid molecule of the invention comprises a nucleic acid molecule which is a complement of the nucleotide sequence shown in SEQ ID NO:1-66 or 228-239, or a portion of any of these nucleotide sequences. A nucleic acid molecule which is complementary to the nucleotide sequence shown in SEQ ID NO:1-66 or 228-239, is one which is sufficiently complementary to the nucleotide sequence shown in SEQ ID NO:1-66 or 228-239, respectively, such that it can hybridize to the nucleotide sequence shown in SEQ ID NO:1-66 or 228-239, respectively, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1-66 or 228-239, or a portion of any of these nucleotide sequences.

Moreover, the nucleic acid molecule of the invention can comprise only a portion of the nucleic acid sequence of SEQ ID NO:1-66 or 228-239, for example a fragment which can be used as a probe or primer or a fragment encoding a biologically active portion of a CCP protein. The nucleotide sequence determined from the cloning of the CCP gene allows for the generation of probes and primers designed for use in identifying and/or cloning other CCP family members, as well as CCP homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1-66 or 228-239, or of a naturally occurring allelic variant or mutant of SEQ ID NO:1-66 or 228-239. In an exemplary embodiment, a nucleic acid molecule of the present invention comprises a nucleotide sequence which is at least 100, 150, 200, 250, 300, 350, 400, 450, 500, 550, 600, 650, 700, 750, or 800 nucleotides in length and hybridizes under stringent hybridization conditions to a nucleic acid molecule of SEQ ID NO:1-66 or 228-239.

Probes based on the CCP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a CCP protein, such as by measuring a level of a CCP-encoding nucleic acid in a sample of cells from a subject e.g., detecting CCP mRNA levels or determining whether a genomic CCP gene has been mutated or deleted.

A nucleic acid fragment encoding a "biologically active portion of a CCP protein" can be prepared by isolating a portion of the nucleotide sequence of SEQ ID NO:1-66 or 228-239, which encodes a polypeptide having a CCP biological activity (the biological activities of the CCP proteins are described herein), expressing the encoded portion of the CCP protein (e.g., by recombinant expression in vitro) and assessing the activity of the encoded portion of the CCP protein.

The invention further encompasses nucleic acid molecules that differ from the nucleotide sequence shown in SEQ ID NO:1-66 or 228-239, due to the degeneracy of the genetic code and, thus, encode the same CCP proteins as those encoded by the nucleotide sequence shown in SEQ ID NO:1-66 or 228-239. In another embodiment, an isolated nucleic acid molecule of the invention has a nucleotide sequence encoding a CCP protein.

In addition to the CCP nucleotide sequences shown in SEQ ID NO:1-66 or 228-239, it will be appreciated by those skilled in the art that DNA sequence polymorphisms that lead to changes in the amino acid sequences of the CCP proteins may exist within a population (e.g., an *Arabidopsis* or rice plant population). Such genetic polymorphism in the CCP genes may exist among individuals within a population due to natural allelic variation. As used herein, the terms "gene" and "recombinant gene" refer to nucleic acid molecules which include an open reading frame encoding an CCP protein, preferably a plant CCP protein, and can further include non-coding regulatory sequences, and introns. Such natural allelic variations include both functional and non-functional CCP proteins and can typically result in 1-5% variance in the nucleotide sequence of a CCP gene. Any and all such nucleotide variations and resulting amino acid polymorphisms in CCP genes that are the result of natural allelic variation and that do not alter the functional activity of a CCP protein are intended to be within the scope of the invention. Differences in preferred codon usage are illustrated below for *Agrobacterium tumefaciens* (a bacterium), *Arabidopsis thaliana, Medicago sativa* (two dicotyledonous plants) and *Oryza sativa* (a monocotyledonous plant). These examples were extracted from http://Nwv.kazusa.or.jp/codon. For example, the codon GGC (for glycine) is the most frequently used codon in *A. tumefaciens* (36.2‰), is the second most frequently used codon in *O. sativa* but is used at much lower frequencies in *A. thaliana* and *M. sativa* (9‰ and 8.4‰, respectively). Of the four possible codons encoding glycine the GGC codon is most preferably used in *A. tumefaciens* and *O. sativa*. However, in *A. thaliana* the GGA (and GGU) codon is most preferably used, whereas in *M. sativa* the GGU (and GGA) codon is most preferably used.

Moreover, nucleic acid molecules encoding other CCP family members and, thus, which have a nucleotide sequence which differs from the CCP sequences of SEQ ID NO:1-66 or 228-239 are intended to be within the scope of the invention. For example, another CCP cDNA can be identified based on the nucleotide sequence of the plant CCP molecules described herein. Moreover, nucleic acid molecules encoding CCP proteins from different species, and thus which have a nucleotide sequence which differs from the CCP sequences of SEQ ID NO:1-66 or 228-239 are intended to be within the scope of the invention. For example, a human CCP cDNA can be identified based on the nucleotide sequence of a plant CCP.

Nucleic acid molecules corresponding to natural allelic variants and homologues of the CCP cDNAs of the invention can be isolated based on their homology to the CCP nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1-66 or 228-239. In other embodiment, the nucleic acid is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6x sodium chloride/sodium citrate (SSC) at about 45° C., followed by one or more washes in 0.2×SSC, 0.1% SDS at about 45° C., followed by one or more washes in 0.2×SSC, 0.1% SDS at 50° C., preferably at 55° C., more preferably at 60° C., and even more preferably at 65° C. Ranges intermediate to the above-recited values, e.g., at 60-65° C. or at 55-60° C. are also intended to be encompassed by the present invention. Preferably, an isolated nucleic acid molecule of the invention that hybridizes under stringent conditions to the sequence of SEQ ID NO:1-66 or 228-239 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CCP sequences that may exist in nature, the skilled artisan will further appreciate that changes can be introduced by mutation into the nucleotide sequences of SEQ ID NO:1-66 or 228-239, thereby leading to changes in the amino acid sequence of the encoded CCP proteins, without altering the functional ability of the CCP proteins. For example, nucleotide substitutions leading to amino acid substitutions at "non-essential" amino acid residues can be made in the sequence of a CCP protein. A "non-essential" amino acid residue is a residue that can be altered from the wild-type sequence of CCP without altering the biological activity, whereas an "essential" amino acid residue is required for biological activity. For example, amino acid residues that are conserved among the CCP proteins of the present invention, are predicted to be particularly unamenable to alteration. Furthermore, additional amino acid residues that are conserved between the CCP proteins of the present invention and other CCP family members are not likely to be amenable to alteration.

Accordingly, another aspect of the invention pertains to nucleic acid molecules encoding CCP proteins that contain changes in amino acid residues that are not essential for activity.

An isolated nucleic acid molecule encoding a CCP protein homologous to the CCP proteins of the present invention can be created by introducing one or more nucleotide substitutions, additions or deletions into the nucleotide sequence of SEQ ID NO:1-66 or 228-239, such that one or more amino acid substitutions, additions or deletions are introduced into the encoded protein. Mutations can be introduced into SEQ ID NO:1-66 or 228-239 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a CCP protein is preferably replaced with another amino acid residue from the same side chain family. Alternatively, in another embodiment, mutations can be introduced randomly along all or part of a CCP coding sequence, such as by saturation mutagenesis, and the resultant mutants can be screened for CCP biological activity to identify mutants that retain activity. Following mutagenesis of SEQ ID NO:1-66 or 228-239, the encoded protein can be expressed recombinantly and the activity of the protein can be determined. Another alternative embodiment comprises targeted in vivo gene correction or modification which can be achieved by chimeric RNA/DNA oligonucleotides (e.g., Yoon et al. (1996), Proc. Natl. Acad. Sci. USA 93, 2071-2076; Amtzen et al. (1999) WO99/07865).

In a preferred embodiment, a mutant CCP protein can be assayed for the ability to: (1) regulate transmission of signals from cellular receptors, e.g. hormone receptors; (2) control cell cycle checkpoints, e.g. entry of cells into mitosis; (3) modulate the cell cycle; (4) modulate cell death, e.g., apoptosis; (5) modulate cytoskeleton function, e.g. actin bundling; (6) phosphorylate a substrate; (7) create dominant negative or dominant positive effects in transgenic plants; (8) interact with other cell cycle control proteins in, e.g. a yeast two hybrid assay; (9) modulate CDK activity (e.g., cyclin-CDK activity); (10) regulate cyclin-CDK complex assembly; (11) regulate the commitment of cells to divide, e.g., by integrating mitogenic and antimitogenic signals; (12) regulate cell cycle progression; (13) regulate DNA replication and/or DNA repair; (14) modulate gene transcription, e.g., regulate E2F/DP-dependent transcription of genes; (15) regulate cyclin degradation; (16) modulate cell cycle withdrawal and/or cell differentiation; (17) control organ (e.g., plant organ) and/or organism (e.g., plant organism) size; (18) control organ (e.g., plant organ) and/or organism (e.g., plant organism) growth or growth rate; and (19) regulate endoreduplication.

In addition to the nucleic acid molecules encoding CCP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CCP coding strand, or only to a portion thereof. In one embodiment, an antisense nucleic acid molecule is antisense to a "coding region" of the coding strand of a nucleotide sequence encoding CCP. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding CCP. The term "noncoding region" refers to 5' and 3' sequences which flank the coding region that are not translated into amino acids (i.e., also referred to as 5' and 3' untranslated regions).

Given the coding strand sequences encoding CCP disclosed herein, antisense nucleic acids of the invention can be designed according to the rules of Watson and Crick base pairing. The antisense nucleic acid molecule can be complementary to the entire coding region of CCP mRNA, but more preferably is an oligonucleotide which is antisense to only a portion of the coding or noncoding region of CCP mRNA. For example, the antisense oligonucleotide can be complementary to the region surrounding the translation start site of CCP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Preferably, production of antisense nucleic acids in plants occurs by means of a stably integrated transgene comprising a promoter operative in plants, an antisense oligonucleotide, and a terminator.

Other known nucleotide modifications include methylation, cyclization and 'caps' and substitution of one or more of the naturally occurring nucleotides with an analog such as inosine. Modifications of nucleotides include modifications generated by the addition to nucleotides of acridine, amine, biotin, cascade blue, cholesterol, Cy3®, Cy5®, Cy5.5® Dabcyl, digoxigenin, dinitrophenyl, Edans. 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothioate, RNA, 2'-OMeRNA. Base modifications include 2-amino-dA, 2-aminopurine, 3'-(ddA), 3'dA(cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-1-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP(purine analogue), dK(pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-1-dU, $O^4$-triazol dU.

The antisense nucleic acid molecules of the invention are typically introduced into a plant or administered to a subject or generated in situ such that they hybridize with or bind to cellular mRNA and/or genomic DNA encoding a CCP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of introduction or administration of antisense nucleic acid molecules of the invention include transformation in a plant or direct injection at a tissue site in a subject. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a constitutive promoter or a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (987) *FEBS Lett.* 215:327-330).

In another embodiment, the antisense nucleic acid molecule further comprises a sense nucleic acid molecule complementary to the antisense nucleic acid molecule. Gene silencing methods based on such nucleic acid molecules are well known to the skilled artisan (e.g., Grierson et al. (1998) WO 98/53083; Waterhouse et al. (1999) WO 99/53050).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave CCP mRNA transcripts to thereby inhibit translation of CCP mRNA. A ribozyme having specificity for a CCP-encoding nucleic acid can be designed based upon the nucleotide sequence of a CCP cDNA disclosed herein (i.e., SEQ ID NO:1-66 or 228-239). For example, a derivative of a *Tetrahymena* L-19 IVS RNA can be constructed in which the nucleotide sequence of the active site is complementary to the nucleotide sequence to be cleaved in a CCP-encoding mRNA. See, e.g., Cech et al. U.S. Pat. No. 4,987,071; and Cech et al. U.S. Pat. No. 5,116,742. Alternatively, CCP mRNA can be used to select a catalytic RNA having a specific ribonuclease activity from a pool of RNA molecules. See, e.g., Bartel, D. and Szostak, J. W. (1993) *Science* 261:1411-1418.

The use of ribozymes for gene silencing in plants is known in the art (e.g., Atkins et al. (1994) WO 94/00012; Lenne et al. (1995) WO 95/03404; Lutziger et al. (2000) WO 00/00619; Prinsen et al. (1997) WO 97/13865 and Scott et al. (1997) WO/97/38116).

Alternatively, CCP gene expression can be inhibited by targeting nucleotide sequences complementary to the regulatory region of the CCP (e.g., the CCP promoter and/or enhancers) to form triple helical structures that prevent transcription of the CCP gene in target cells. See generally, Helene, C. (1991) *Anticancer Drug Des.* 6(6):569-84; Helene, C. et al. (1992) *Ann N.Y. Acad Sci.* 660:27-36; and Maher, L. J. (1992) *Bioassays* 14(12):807-15.

In yet another embodiment, the CCP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of CCP nucleic acid molecules can be used for increasing crop yield in plants or in therapeutic and diagnostic applications. For example, PNAs can be used as antisense or antigene agents for sequence-specific modulation of gene expression by, for example, inducing transcription or translation arrest or inhibiting replication. PNAs of CCP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of CCP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of CCP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using link-ers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization-triggered cross-linking agent, transport agent, or hybridization-triggered cleavage agent).

II. Isolated CCP Proteins and Anti-CCP Antibodies

One aspect of the invention pertains to isolated CCP proteins (e.g., the amino acid sequences set forth in SEQ ID NO:67-132, 205, 211, 215-216, or 220-227) and biologically active portions thereof, as well as polypeptide fragments suitable for use as immunogens to raise anti-CCP antibodies. In one embodiment, native CCP proteins can be isolated from cells or tissue sources by an appropriate purification scheme using standard protein purification techniques. In another embodiment, CCP proteins are produced by recombinant DNA techniques. Alternative to recombinant expression, a CCP protein or polypeptide can be synthesized chemically using standard peptide synthesis techniques.

An "isolated" or "purified" protein or biologically active portion thereof is substantially free of cellular material or other contaminating proteins from the cell or tissue source from which the CCP protein is derived, or substantially free from chemical precursors or other chemicals when chemically synthesized. The language "substantially free of cellular material" includes preparations of CCP protein in which the protein is separated from cellular components of the cells from which it is isolated or recombinantly produced. In one embodiment, the language "substantially free of cellular material" includes preparations of CCP protein having less than about 30% (by dry weight) of non-CCP protein (also referred to herein as a "contaminating protein"), more preferably less than about 20% of non-CCP protein, still more preferably less than about 10% of non-CCP protein, and most preferably less than about 5% non-CCP protein. When the CCP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of CCP protein in which the protein is separated from chemical precursors or other chemicals which are involved in the synthesis of the protein. In one embodiment, the language "substantially free of chemical precursors or other chemicals" includes preparations of CCP protein having less than about 30% (by dry weight) of chemical precursors or non-CCP chemicals, more preferably less than about 20% chemical precursors or non-CCP chemicals, still more preferably less than about 10% chemical precursors or non-CCP chemicals, and most preferably less than about 5% chemical precursors or non-CCP chemicals.

Biologically active portions of a CCP protein include peptides comprising amino acid sequences sufficiently homologous to or derived from the amino acid sequence of the CCP protein, which include less amino acids than the full length CCP proteins, and exhibit at least one activity of a CCP protein. Typically, biologically active portions comprise a domain or motif with at least one activity of the CCP protein. A biologically active portion of a CCP protein can be a polypeptide which is, for example, at least 10, 25, 50, 100 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NVSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of E. Meyers and W. Miller (*Comput. Appl. Biosci.*, 4:11-17 (1988)) which has been incorporated into the ALIGN program (version 2.0 or version 2.0U), using a PAM120 weight residue table, a gap length penalty of 12 and a gap penalty of 4.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to Kinase and Phosphatase nucleic acid molecules of the invention. BLAST protein searches can be performed with the XBLAST program, score=100, wordlength=3, and a Blosum62 matrix to obtain amino acid sequences homologous to Kinase and Phosphatase polypeptide molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The invention also provides CCP chimeric or fusion proteins. As used herein, a CCP "chimeric protein" or "fusion protein" comprises a CCP polypeptide operatively linked to a non-CCP polypeptide. An "CCP polypeptide" refers to a polypeptide having an amino acid sequence corresponding to CCP, whereas a "non-CCP polypeptide" refers to a polypeptide having an amino acid sequence corresponding to a protein which is not substantially homologous to the CCP protein, e.g., a protein which is different from the CCP protein and which is derived from the same or a different organism. Within a CCP fusion protein the CCP polypeptide can correspond to all or a portion of a CCP protein. In a preferred embodiment, a CCP fusion protein comprises at least one biologically active portion of a CCP protein. In another preferred embodiment, a CCP fusion protein comprises at least two biologically active portions of a CCP protein. Within the fusion protein, the term "operatively linked" is intended to indicate that the CCP polypeptide and the non-CCP polypeptide are fused in-frame to each other. The non-CCP polypeptide can be fused to the N-terminus or, C-terminus of the CCP polypeptide or can be inserted within the CCP polypeptide. The non-CCP polypeptide can, for example, be (histidine)$_6$-tag, glutathione S-transferase, protein A, maltose-binding protein, dihydrofolate reductase, Tag·100 epitope (EETARFQPGYRS; SEQ ID NO:199), c-myc epitope (EQKLISEEDL; SEQ ID NO:200), FLAG®-epitope (DYKDDDK; SEQ ID NO:201), lacZ, CMP (calmodulin-binding peptide), HA epitope (YPYDVPDYA; SEQ ID NO:202), protein C epitope (EDQVDPRUDGK; SEQ ID NO:203) or VSV epitope (YTDIEMNRLGK; SEQ ID NO:204).

For example, in one embodiment, the fusion protein is a GST-CCP fusion protein in which the CCP sequences are fused to the C-terminus of the GST sequences. Such fusion proteins can facilitate the purification of recombinant CCP.

In another embodiment, the fusion protein is a CCP protein containing a heterologous signal sequence at its N-terminus. In certain host cells (e.g., plant or mammalian host cells), expression and/or secretion of CCP can be increased through use of a heterologous signal sequence.

The CCP fusion proteins of the invention can be incorporated into pharmaceutical compositions and administered to a plant or a subject in vivo. The CCP fusion proteins can be used to affect the bioavailability of a CCP substrate. Use of CCP fusion proteins may be useful agriculturally for the increase of crop yields or therapeutically for the treatment of cellular growth related disorders, e.g., cancer. Moreover, the CCP-fusion proteins of the invention can be used as immunogens to produce anti-CCP antibodies in a subject, to purify CCP ligands and in screening assays to identify molecules which inhibit the interaction of CCP with a CCP substrate, e.g., a kinase such as CDC2b.

Preferably, a CCP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A CCP-encoding nucleic acid can be cloned into such an expression vector such that the fusion moiety is linked in-frame to the CCP protein.

The present invention also pertains to variants of the CCP proteins which function as either CCP agonists (mimetics) or as CCP antagonists. Variants of the CCP proteins can be generated by mutagenesis, e.g., discrete point mutation or truncation of a CCP protein. An agonist of the CCP proteins can retain substantially the same, or a subset, of the biological activities of the naturally occurring form of a CCP protein. An antagonist of a CCP protein can inhibit one or more of the activities of the naturally occurring form of the CCP protein by, for example, competitively modulating a cellular activity of a CCP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the CCP protein.

In one embodiment, variants of a CCP protein which function as either CCP agonists (mimetics) or as CCP antagonists can be identified by screening combinatorial libraries of mutants, e.g., truncation mutants, of a CCP protein for CCP protein agonist or antagonist activity. In one embodiment, a variegated library of CCP variants is generated by combinatorial mutagenesis at the nucleic acid level and is encoded by a variegated gene library. A variegated library of CCP variants can be produced by, for example, enzymatically ligating a mixture of synthetic oligonucleotides into gene sequences such that a degenerate set of potential CCP sequences is expressible as individual polypeptides, or alternatively, as a set of larger fusion proteins (e.g., for phage display) containing the set of CCP sequences therein. There are a variety of methods which can be used to produce libraries of potential CCP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CCP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CCP protein coding sequence can be used to generate a variegated population of CCP fragments for screening and subsequent selection of variants of a CCP protein. In one embodiment, a library of coding sequence fragments can be generated by treating a double stranded PCR fragment of a CCP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CCP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CCP proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify CCP variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated CCP library. For example, a library of expression vectors can be transfected into a cell line which ordinarily synthesizes and secretes CCP. The transfected cells are then cultured such that CCP and a particular mutant CCP are secreted and the effect of expression of the mutant on CCP activity in cell supernatants can be detected, e.g., by any of a number of enzymatic assays. Plasmid DNA can then be recovered from the cells which score for inhibition, or alternatively, potentiation of CCP activity, and the individual clones further characterized.

An isolated CCP protein, or a portion or fragment thereof, can be used as an immunogen to generate antibodies that bind CCP using standard techniques for polyclonal and monoclonal antibody preparation. A full-length CCP protein can be used or, alternatively, the invention provides antigenic peptide fragments of CCP for use as immunogens. The antigenic peptide of CCP comprises at least 8 amino acid residues and encompasses an epitope of CCP such that an antibody raised against the peptide forms a specific immune complex with CCP. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of CCP that are located on the surface of the protein, e.g., hydrophilic regions.

A CCP immunogen typically is used to prepare antibodies by immunizing a suitable subject, (e.g., rabbit, goat, mouse or other mammal) with the immunogen. An appropriate immunogenic preparation can contain, for example, recombinantly expressed CCP protein or a chemically synthesized CCP polypeptide. The preparation can further include an adjuvant, such as Freund's complete or incomplete adjuvant, or similar immunostimnulatory agent. Immunization of a suitable subject with an immunogenic CCP preparation induces a polyclonal anti-CCP antibody response.

Accordingly, another aspect of the invention pertains to anti-CCP antibodies. The term "antibody" as used herein refers to immunoglobulin molecules and immunologically active portions of immunoglobulin molecules, i.e., molecules that contain an antigen binding site which specifically binds (immunoreacts with) an antigen, such as CCP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CCP. The term "monoclonal antibody" or "monoclonal antibody composition", as used herein, refers to a population of antibody molecules that contain only one species of an antigen binding site capable of immunoreacting with a particular epitope of CCP. A monoclonal antibody composition thus typically displays a single binding affinity for a particular CCP protein with which it immunoreacts.

Polyclonal anti-CCP antibodies can be prepared as described above by immunizing a suitable subject with a CCP immunogen. The anti-CCP antibody titer in the immunized subject can be monitored over time by standard techniques, such as with an enzyme linked immunosorbent assay (ELISA) using immobilized CCP. If desired, the antibody molecules directed against CCP can be isolated from the mammal (e.g., from the blood) and further purified by well known techniques, such as protein A chromatography to obtain the IgG fraction. At an appropriate time after immunization, e.g., when the anti-CCP antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a CCP immunogen as described above, and the culture supernatants of the resulting hybridoma cells are screened to identify a hybridoma producing a monoclonal antibody that binds CCP.

Any of the many well known protocols used for fusing lymphocytes and immortalized cell lines can be applied for the purpose of generating an anti-CCP monoclonal antibody (see, e.g., G. Galfre et al. (1977) *Nature* 266:55052; Gefter et al. *Somatic Cell Genet.*, cited supra; Lerner, Yale *J. Biol. Med*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CCP, e.g., using a standard ELISA assay.

Alternative to preparing monoclonal antibody-secreting hybridomas, a monoclonal anti-CCP antibody can be identified and isolated by screening a recombinant combinatorial immunoglobulin library (e.g., an antibody phage display library) with CCP to thereby isolate immunoglobulin library members that bind CCP. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-CCP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Ada, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-CCP antibody (e.g., monoclonal antibody) can be used to isolate CCP by standard techniques, such as affinity chromatography or immunoprecipitation. An anti-CCP antibody can facilitate the purification of natural CCP from cells and of recombinantly produced CCP expressed in host cells. Moreover, an anti-CCP antibody can be used to detect CCP protein (e.g. in a cellular lysate or cell supernatant) in order to evaluate the abundance and pattern of expression of the CCP protein. These antibodies can also be used, for example, for the immunoprecipitation and immunolocalization of proteins according to the invention as well as for the monitoring of the synthesis of such proteins, for example, in recombinant organisms, and for the identification of compounds interacting with the protein according to the intention.

Anti-CCP antibodies can be Bid diagnostically to monitor protein levels in tissue as part of a clinical testing procedure e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidirn/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Computer Readable Means

The CCP nucleotide sequences of the invention (e.g., SEQ ID NO:1-66 or 228-239) or amino acid sequences of the invention (e.g., SEQ ID NO:67-132, 205, 211, 215-216, or 220-227) are also provided in a variety of mediums to facilitate use thereof. As used herein, "provided" refers to a manufacture, other than an isolated nucleic acid or amino acid molecule, which contains a nucleotide or amino acid sequences of the present invention. Such a manufacture provides the nucleotide or amino acid sequences, or a subset thereof (e.g., a subset of open reading frames (ORI's)) in a form which allows a skilled artisan to examine the manufacture using means not directly applicable to examining the nucleotide or amino acid sequences, or a subset thereof, as they exist in nature or in purified form.

In one application of this embodiment, a nucleotide or amino acid sequence of the present invention can be recorded on computer readable media. As used herein "computer readable media" includes any medium that can be read and accessed directly by a computer. Such media include, but are not limited to: magnetic storage media, such as floppy discs, hard disc storage medium, and magnetic tape; optical storage media such a CD-ROM; electrical storage media such as RAM and ROM; and hybrids of these categories such as magnetic/optical storage media. The skilled artisan win readily appreciate how any of the presently known computer readable mediums can be used to create a manufacture comprising computer readable medium having recorded thereon a nucleotide or amino acid sequence of the present invention.

As used herein "recorded" refers to a process of storing information on computer readable medium. The skilled artisan can readily adopt any of the presently known methods for recording information on a computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identity fragments or regions of the sequences of the invention which match a particular target sequence or target motif.

As used herein, a "target sequence" can be any DNA or amino acid sequence of six or more nucleotide or two or more amino acids. A skilled artisan can readily recognize that the longer a target sequence is, the less likely a target sequence will be present as a random occurrence in the database. The most preferred sequence length of a target sequence is from about 10 to 100 amino acids or form about 30 to 300 nucleotide residues. However, it is well recognized that commercially important fragments, such as sequence fragments involved in gene expression and protein processing, may be shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software of conducting search means are and can be used in the computer-based systems of the present invention. Examples of such software include, but are not limited to, MacPatter (EMBL), BLASTN and BASTX (NCBIA).

For example, software which implements the BLAST (Altschul et al. (1990) *J. Mol. Biol.* 215:403-410) and BLAZE (Brutlag et al. (1993) *Comp. Chem.* 17:203-207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzyme used in various reactions and in the production of commercially useful metabolites.

IV. Recombinant Expression Vectors and Host Cells

Another aspect of the invention pertains to vectors, preferably expression vectors, containing a nucleic acid encoding a CCP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, e.g., a plant cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., CCP proteins, mutant forms of CCP proteins, fusion proteins, and the like).

The vectors of the invention comprise a selectable and/or scorable marker. Selectable marker genes useful for the selection of transformed plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, *EMBO J.* 2 (1983), 987-995) and hygro, which confers resistance to hygromycin (Marsh, *Gene* 32 (1984), 481-485). Additional selectable genes have been described, namely trpB, which allow cells to utilize indole in place of tryptophan; hisD, which allows cells to utilize histinol in place of histidine (Hartman, *Proc. Natl. Acad. Sci. USA* 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, *Biosci. Biotechnol. Biochem.* 59 (1995), 2336-2338).

Useful scorable markers are also known to those skilled in the art and are commercially available. Advantageously, the marker is a gene encoding luciferase (Giacomin, *Pl. Sci.* 116 (1996), 59-72; Scikantha, *J. Bact.* 178 (1996), 121), green fluorescent protein (Gerdes, *FEBS Lett.* 389 (1996), 44-47) or β-glucuronidase (Jefferson, *EMBO J.* 6 (1987), 3901-3907). This embodiment is particularly useful for simple and rapid screening of cells, tissues and organisms containing a vector of the invention.

A "plant promoter" is a promoter capable of initiating transcription in plant cells. Exemplary plant promoters include, but are not limited to, those that are obtained from plants, plant viruses, and bacteria. Preferred promoters may contain additional copies of one or more specific regulatory elements, to further enhance expression and/or to alter the spatial expression and/or temporal expression of a nucleic acid molecule to which it is operably connected. For example, copper-responsive, glucocorticoid-responsive or dexamethasone-responsive regulatory elements may be placed adjacent to a heterologous promoter sequence driving expression of a nucleic acid molecule to confer copper inducible, glucocorticoid-inducible, or dexamethasone-inducible expression respectively, on said nucleic acid molecule. Examples of promoters under developmental control include promoters that preferentially initiate transcription in certain tissues, such as leaves, roots, seeds, endosperm, embryos, fibers, xylem vessels, tracheids, or sclerenchyma. Such promoters are referred to as "tissue preferred." Promoters which initiate transcription only in certain tissue are referred to as "tissue specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CCP protein can be expressed in plant cells, bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual 2nd, ed, Cold Spring Harbor Laboratory*, Cold Spring Harbor Laboratory Press, Cold Spring Harbor, N.Y., 1989), and other laboratory manuals.

Means for introducing a recombinant expression vector of this invention into plant tissue or cells include, but are not limited to; transformation using $CaCl_2$ and variations thereof, in particular the method described by Hanahan (J. Mol. Biol. 166, 557-560, 1983), direct DNA uptake into protoplasts (Krens et al, Nature 296: 72-74, 1982; Paszkowski et al, EMBO J. 3:2717-2722, 1984), PEG-mediated uptake to protoplasts (Armstrong et al, Plant Cell Reports 9: 335-339, 1990) microparticle bombardment, electroporation (Fromm et al., Proc. Natl. Acad. Sci. (USA) 82:5824-5828, 1985), microinjection of DNA (Crossway et al., Mol. Gen. Genet. 202:179-185, 1986), microparticle bombardment of tissue explants or cells (Christou et al, Plant Physiol 87: 671-674, 1988; Sanford, Particulate Science and Technology 5: 27-37, 1987), vacuum-infiltration of tissue with nucleic acid, or in the case of plants, T-DNA-mediated transfer from *Agrobacterium* to the plant tissue as described essentially by An et al. (EMBO J. 4:277-284, 1985), Herrera-Estrella et al. (Nature 303: 209-213, 1983a; EMBO J. 2: 987-995, 1983b; In: Plant Genetic Engineering, Cambridge University Press, N.Y., pp 63-93, 1985), or in planta method using *Agrobacterium tumefaciens* such as that described by Bechtold et al., (*C.R. Acad. Sci.* (*Paris, Sciences de la vie/Life Sciences*) 316: 1194-1199, 1993), Clough et al (*Plant J.* 16: 735-743, 1998), Trieu et al. (*Plant J.* 22:531-541, 2000) or Kloti (WO01/12828, 2001). Methods for transformation of monocotyledonous plants are well known in the art and include *Agrobacterium*-mediated transformation (Cheng et al. (1997) WO 97/48814; Hansen (1998) WO 98/54961; Hiei et al. (1994) WO 94/00977; Hiei et al. (1998) WO 98/17813; Rikiishi et al. (1999) WO 99/04618; Saito et al. (1995) WO 95/06722), microprojectile bombardment (Adams et al. (1999) U.S. Pat. No. 5,969,213; Bowen et al. (1998) U.S. Pat. No. 5,736,369; Chang et al. (1994) WO 94/13822; Lundquist et al. (1999) U.S. Pat. Nos. 5,874,265/5,990,390; Vasil and Vasil (1995) U.S. Pat. No. 5,405,765; Walker et al. (1999) U.S. Pat. No. 5,955,362), DNA uptake (Eval et al. (1993) WO 93/181,168), microinjection of *Agrobacterium* cells (von Holt 1994 DE 4309203), sonication (Finer et al. (1997) U.S. Pat. No. 5,693,512) and flower-dip or in planta-transformation (Kloti, WO01/12828, 2001).

The vector DNA may further comprise a selectable marker gene to facilitate the identification and/or selection of cells which are transfected or transformed with a genetic construct. Suitable selectable marker genes contemplated herein include the ampicillin resistance (Amp'), tetracycline resistance gene Tc'), bacterial kanamycin resistance gene (Kan'), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene.

For mnicroparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, includes a process by which shoots and roots are developed sequentially from meristematic centres.

The term "embryogenesis", as used herein, includes a process by which shoots and roots develop together in a concerted fashion (not sequentially), whether from somatic cells or gametes.

Preferably, the plant is produced according to the methods of the invention by transfecting or transforming the plant with a genetic sequence, or by introducing to the plant a protein, by any art-recognized means, such as microprojectile bombardment, microinjection, *Agrobacterium*-mediated transformation (including in planta transformation), protoplast fusion, or electroporation, amongst others. Most preferably the plant is produced by *Agrobacterium*-mediated transformation. *Agro-*

*bacterium*-mediated transformation or agrolistic transformation of plants, yeast, moulds or filamentous fungi is based on the transfer of part of the transformation vector sequences, called the T-DNA, to the nucleus and on integration of said T-DNA in the genome of said eukaryote.

The term "*Agrobacterium*" as used herein, includes a member of the *Agrobacteriaceae*, more preferably *Agrobacterium* or *Rhizobacterium* and most preferably *Agrobacterium tumefaciens*.

The term "T-DNA", or "transferred DNA", as used herein, includes the transformation vector flanked by T-DNA borders which is, after activation of the *Agrobacterium vir* genes, nicked at the T-DNA borders and is transferred as a single stranded DNA to the nucleus of an eukaryotic cell.

As used herein, the terms "T-DNA borders", "T-DNA border region", or "border region" include either right T-DNA borders (RB) or left T-DNA borders (LB), which comprise a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats.

As used herein, the term "T-DNA transformation vector" or "T-DNA vector" includes any vector encompassing a T-DNA sequence flanked by a right and left T-DNA border consisting of at least the right and left border core sequences, respectively, and used for transformation of any eukaryotic cell.

As used herein, the term "T-DNA vector backbone sequence" or "T-DNA vector backbone sequences" includes all DNA of a T-DNA containing vector that lies outside of the T-DNA borders and, more specifically, outside the nicking sites of the border core imperfect repeats.

The present invention includes optimized T-DNA vectors such that vector backbone integration in the genome of a eukaryotic cell is minimized or absent. The term "optimized T-DNA vector" as used herein includes a T-DNA vector designed either to decrease or abolish transfer of vector backbone sequences to the genome of a eukaryotic cell. Such T-DNA vectors are known to the one of skill in the art and include those described by Hanson et al. (1999) and by Stuiver et al. (1999—WO9901563).

The current invention clearly considers the inclusion of a DNA sequence encoding a CCP, homologue, analogue, derivative or immunologically active fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation.

As used herein, the term "binary transformation vector" includes a T-DNA transformation vector comprising: a T-DNA region comprising at least one gene of interest and/or at least one selectable marker active in the eukaryotic cell to be transformed; and a vector backbone region comprising at least origins of replication active in *E. coli* and *Agrobacterium* and markers for selection in *E. coli* and *Agrobacterium*. Alternatively, replication of the binary transformation vector in *Agrobacterium* is dependent on the presence of a separate helper plasmid. The binary vector pGreen and the helper plasmid pSoup form an example of such a system (Hellens et al. (2000), Plant Mol. Biol. 42, 819-832; http://www.pgreen-.ac.uk).

The T-DNA borders of a binary transformation vector can be derived from octopine-type or nopaline-type Ti plasmids or from both. The T-DNA of a binary vector is only transferred to a eukaryotic cell in conjunction with a helper plasmid. As used herein, the term "helper plasmid" includes a plasmid that is stably maintained in *Agrobacterium* and is at least carrying the set of vir genes necessary for enabling transfer of the T-DNA. The set of vir genes can be derived from either octopine-type or nopaline-type Ti plasmids or from both.

As used herein, the term "super-binary transformation vector" includes a binary transformation vector additionally carrying in the vector backbone region a vir region of the Ti plasmid pTiBo542 of the super-virulent *A. tumefaciens* strain A281 (EP0604662, EP0687730). Super-binary transformation vectors are used in conjunction with a helper plasmid.

As used herein, the term "co-integrate transformation vector" includes a T-DNA vector at least comprising: a T-DNA region comprising at least one gene of interest and/or at least one selectable marker active in plants; and a vector backbone region comprising at least origins of replication active in *Escherichia coli* and *Agrobacterium*, and markers for selection in *E. coli* and *Agrobacterium*, and a set of vir genes necessary for enabling transfer of the T-DNA. The T-DNA borders and the set of vir genes of the T-DNA vector can be derived from either octopine-type or nopaline-type Ti plasmids or from both.

The term "Ri-derived plant transformation vector" includes a binary transformation vector in which the T-DNA borders are derived from a Ti plasmid and the binary transformation vector being used in conjunction with a 'helper' Ri-plasmid carrying the necessary set of vir genes.

The terms "agrolistics", "agrolistic transformation" or "agrolistic transfer" include a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; Hansen and Chilton 1997—WO9712046).

A host cell of the invention, such as a prokaryotic or eukaryotic host cell in culture, can be used to produce (i.e., express) a CCP protein. Accordingly, the invention further provides methods for producing a CCP protein using the host cells of the invention. In one embodiment, the method comprises culturing the host cell of invention (into which a recombinant expression vector encoding a CCP protein has been introduced) in a suitable medium such that a CCP protein is produced. In another embodiment, the method further comprises isolating a CCP protein from the medium or the host cell.

The host cells of the invention can also be used to produce transgenic plant or non-human transgenic animals in which exogenous CCP sequences have been introduced into their genome or homologous recombinant plants or animals in which endogenous CCP sequences have been altered. Such plants and animals are useful for studying the function and/or activity of a CCP and for identifying and/or evaluating modulators of CCP activity.

Transgenic Plants

As used herein, "transgenic plant" includes a plant which comprises within its genome a heterologous polynucleotide. Generally, the heterologous polynucleotide is stably integrated within the genome such that the polynucleotide is passed on to successive generations. The heteroglogous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses as asexual propagation from the initial transgenic. The term "transgenic" as used herein does not encompass the alteration of the genome (chromosomal or extra-chromosomal) by conventional plant breeding methods or by naturally occurring event such as random cross-fertilization, non-recombinant viral infection, non-recombinant bacterial transformation, non-recombinant transposition, or spontaneous mutation.

A transgenic plant of the invention can be created by introducing a CCP-encoding nucleic acid into the plant by placing it under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. These promoters can be used to modulate (e.g. increase or decrease) CCP content and/or composition in a desired tissue. To obtain expression in all tissues of a transgenic plant, preferably constitutive promoters are used, such as the 35 S promoter of CaMV (Odell, Nature 313 (1985), 810-812) or promoters from such genes as rice actin (McElroy et al. (1990) Plant Cell 2:163-171) maize H3 histone (Lepetit et al. (1992) Mol. Gen. Genet. 231:276-285) or promoters of the polyubiquitin genes of maize (Christensen, Plant Mol. Biol. 18 (1982), 675-689). In order to achieve expression in specific tissues of a transgenic plant it is possible to use tissue specific promoters (see, e.g., Stockhaus, EMBO J. 8 (1989), 2245-2251 or Table II, below).

TABLE II

| GENE SOURCE | EXPRESSION PATTERN | REFERENCE |
|---|---|---|
| α-amylase (Amy32b) | aleurone | Lanahan, M. B., et al., Plant Cell 4: 203-211, 1992; Skriver, K., et al. Proc. Natl. Acad. Sci. (USA) 88: 7266-7270, 1991 |
| cathepsin β-like gene | aleurone | Cejudo, F. J., et al. Plant Molecular Biology 20: 849-856, 1992. |
| *Agrobacterium rhizogenes* rolB | cambium | Nilsson et al., Physiol. Plant. 100: 456-462, 1997 |
| PRP genes | cell wall | http://salus.medium.edu/mmg/tierney/html |
| barley Itr1 promoter | endosperm | |
| synthetic promoter | endosperm | Vicente-Carbajosa et al., Plant J. 13: 629-640, 1998. |
| AtPRP4 | flowers | http://salus.medium.edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |
| chitinase | fruit (berries, grapes, etc) | Thomas et al. CSIRO Plant Industry, Urrbrae, South Australia, Australia; http://winetitles.com.au/gwrdc/csh95-1.html |
| rbcs-3A | green tissue (eg leaf) | Lam, E. et al., The Plant Cell 2: 857-866, 1990.; Tucker et al., Plant Physiol. 113: 1303-1308, 1992. |
| leaf-specific genes | leaf | Baszczynski, et al., Nucl. Acid Res. 16: 4732, 1988. |
| AtPRP4 | leaf | http://salus.medium.edu/mmg/tierney/html |
| Pinus cab-6 | leaf | Yamamoto et al., Plant Cell Physiol. 35: 773-778, 1994. |
| SAM22 | senescent leaf | Crowell, et al., Plant Mol. Biol. 18: 459-466, 1992. |
| *R. japonicum* nif gene | nodule | U.S. Pat. No. 4,803,165 |
| *B. japonicum* nifH gene | nodule | U.S. Pat. No. 5,008,194 |
| GmENOD40 | nodule | Yang, et al., The Plant J. 3: 573-585. |
| PEP carboxylase (PEPC) | nodule | Pathirana, et al., Plant Mol. Biol. 20: 437-450, 1992. |
| leghaemoglobin (Lb) | nodule | Gordon, et al., J. Exp. Bot. 44: 1453-1465, 1993. |
| Tungro bacilliform virus gene | phloem | Bhattacharyya-Pakrasi, et al, The Plant J. 4: 71-79, 1992. |
| sucrose-binding protein gene | plasma membrane | Grimes, et al., The Plant Cell 4: 1561-1574, 1992. |
| pollen-specific genes | pollen; microspore | Albani, et al., Plant Mol. Biol. 15: 605, 1990; Albani, et al., Plant Mol. Biol. 16: 501, 1991) |
| Zm13 | pollen | Guerrero et al Mol. Gen. Genet. 224: 161-168 (1993) |
| apg gene | microspore | Twell et al Sex. Plant Reprod. 6: 217-224 (1993) |
| maize pollen-specific gene | pollen | Hamilton, et al., Plant Mol. Biol. 18: 211-218, 1992. |
| sunflower pollen-expressed gene | pollen | Baltz, et al., The Plant J. 2: 713-721, 1992. |
| *B. napus* pollen-specific gene | pollen; anther; tapetum | Arnoldo, et al., J. Cell. Biochem., Abstract No. Y101, 204, 1992. |
| root-expressible genes | roots | Tingey, et al., EMBO J. 6: 1, 1987. |
| tobacco auxin-inducible gene | root tip | Van der Zaal, et al., Plant Mol. Biol. 16, 983, 1991. |

TABLE II-continued

| GENE SOURCE | EXPRESSION PATTERN | REFERENCE |
|---|---|---|
| β-tubulin | root | Oppenheimer, et al., Gene 63: 87, 1988. |
| tobacco root-specific genes | root | Conkling, et al., Plant Physiol. 93: 1203, 1990. |
| *B. napus* G1-3b gene | root | U.S. Pat. No. 5,401,836 |
| SbPRP1 | roots | Suzuki et al., Plant Mol. Biol. 21: 109-119, 1993. |
| AtPRP1; AtPRP3 | roots; root hairs | http://salus.medium.edu/mmg/tierney/html |
| RD2 gene | root cortex | http://www2.cnsu.edu/ncsu/research |
| TobRB7 gene | root vasculature | http://www2.cnsu.edu/ncsu/research |
| AtPRP4 | leaves; flowers; lateral root primordia | http://salus.medium.edu/mmg/tierney/html |
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| zein | seed | Matzke et al Plant Mol Biol, 14(3): 323-32 1990 |
| napA | seed | Stalberg, et al, Planta 199: 515-519, 1996. |
| sunflower oleosin | seed (embryo and dry seed) | Cummins, et al., Plant Mol. Biol. 19: 873-876, 1992 |
| LEAFY | shoot meristem | Weigel et al., Cell 69: 843-859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah, et al., Proc. Natl. Acad. Sci. USA 85: 5551, 1988; Trick, et al., Plant Mol. Biol. 15: 203, 1990. |
| class I patatin gene | tuber | Liu et al., Plant Mol. Biol. 153: 386-395, 1991. |
| blz2 | endosperm | EP99106056.7 |
| PCNA rice | meristem | Kosugi et al, Nucleic Acids Research 19: 1571-1576, 1991; Kosugi S. and Ohashi Y, Plant Cell 9: 1607-1619, 1997. |

The promoters listed in the foregoing table are provided for the purposes of exemplification only and the present invention is not to be limited by the list provided therein. Those skilled in the art will readily be in a position to provide additional promoters that are useful in performing the present invention. The promoters listed may also be modified to provide specificity of expression as required.

Known are also promoters which are specifically active in tubers of potatoes or in seeds of different plants species, such as maize, *Vicia*, wheat, barley and the like. Inducible promoters may be used in order to be able to exactly control expression under certain environmental or developmental conditions such as pathogens, anaerobia, or light. Examples of inducible promoters include the promoters of genes encoding heat shock proteins or microspore-specific regulatory elements (WO96/16182). Furthermore, the chemically inducible Tet-system may be employed (Gatz, Mol. Gen. Genet. 227 (1991); 229-237). Further suitable promoters are known to the person skilled in the art and are described, e.g., in Ward (Plant Mol. Biol. 22 (1993), 361-366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability.

In the case that a nucleic acid molecule according to the invention is expressed in the sense orientation, the coding sequence can be modified such that the protein is located in any desired compartment of the plant cell, e.g., the nucleus, endoplasmatic reticulum, the vacuole, the mitochondria, the plastids, the apoplast, or the cytoplasm.

Methods for the introduction of foreign DNA into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment, pollen-mediated transformation, plant RNA virus-mediated transformation, liposome-mediated transformation, transformation using wounded or enzyme-degraded immature embryos, or wounded or enzyme-degraded embryogenic callus and other methods known in the art. The vectors used in the method of the invention may contain further functional elements, for example "left border"- and "right border"-sequences of the T-DNA of *Agrobacterium* which allow for stably integration into the plant genome. Furthermore, methods and vectors are known to the person skilled in the art which permit the generation of marker free transgenic plants, i.e., the selectable or scorable marker gene is lost at a certain stage of plant development or plant breeding. This can be achieved by, for example, cotransformation (Lyznik, Plant Mol. Biol. 13 (1989), 151-161; Peng, Plant Mol. Biol. 27 (1995), 91-104)

and/or by using systems which utilize enzymes capable of promoting homologous recombination in plants (see, e.g., WO97/08331; Bayley, Plant Mol. Biol. 18 (1992), 353-361; Lloyd, Mol. Gen. Genet. 242 (1994), 653-657; Maeser, Mol. Gen. Genet. 230 (1991), 170-176; Onouchi, Nucl. Acids Res. 19 (1991), 6373-6378). Methods for the preparation of appropriate vectors are described by, e.g., Sambrook (Molecular Cloning; A Laboratory Manual, 2nd Edition (1989), Cold Spring Harbor Laboratory Press, Cold Spring Harbor, N.Y.).

Suitable strains of *Agrobacterium tumefaciens* and vectors, as well as transformation of *Agrobacteria*, and appropriate growth and selection media are described in, for example, GV3101 (pM90RK), Koncz, Mol. Gen. Genet. 204 (1986), 383-396; C58C1 (pGV 3850kan), Deblaere, Nucl. Acid Res. 13 (1985), 4777; Bevan, Nucleic. Acid Res. 12 (1984), 8711; Koncz, Proc. Natl. Acad. Sci. USA 86 (1989), 8467-8471; Koncz, Plant Mol. Biol. 20 (1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1-46; An, EMBO J. 4 (1985), 277-287). Although the use of *Agrobacterium tumefaciens* is preferred in the method of the invention, other *Agrobacterium* strains, such as *Agrobacterium rhizogenes*, may be used, for example, if a phenotype conferred by said strain is desired.

Methods for the transformation using biolistic methods are known to the person skilled in the art; see, e.g., Wan, Plant Physiol. 104 (1994), 37-48; Vasil, Bio/Technology 11 (1993), 1553-1558 and Christou (1996) Trends in Plant Science 1, 423-431. Microinjection can be performed as described in Potrykus and Spangenberg (eds.), Gene Transfer To Plants. Springer Verlag, Berlin, N.Y. (1995).

The transformation of most dicotyledonous plants may be performed using the methods described above or using transformation via biolistic methods as, e.g., described above as well as protoplast transformation, electroporation of partially permeabilized cells, or introduction of DNA using glass fibers.

In general, the plants which are modified according to the invention may be derived from any desired plant species. They can be monocotyledonous plants or dicotyledonous plants, preferably they belong to plant species of interest in agriculture, wood culture or horticulture interest, such as crop plants (e.g., maize, rice, barley, wheat, rye, oats), potatoes, oil producing plants (e.g., oilseed rape, sunflower, pea nut, soy bean), cotton, sugar beet, sugar cane, leguminous plants (e.g., beans, peas), or wood producing plants, preferably trees.

The present invention also relates to a transgenic plant cell which contains (preferably stably integrated into its genome) a nucleic acid molecule of the present invention linked to regulatory elements which allow expression of the nucleic acid molecule in plant cells. The presence and expression of the nucleic acid molecule in the transgenic plant cells leads to the synthesis of a CCP protein and may lead to physiological and phenotypic changes in plants containing such cells.

Transformed plant cells which are derived by any of the above transformation techniques can be cultured to regenerate a whole plant which possesses the transformed genotype. Such regeneration techniques often rely on manipulation of certain phytohormones in a tissue culture growth medium typically relying on a biocide and/or herbicide marker which has been introduced with a polynucleotide of the present invention.

Plant cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124-176 (1983); and *Binding, Regeneration of Plants, Plant Protoplasts*, CRC Press, Boca Raton, pp. 21-73 (1985).

Transformed plant cells, calli or explant can be cultured on regeneration medium in the dark for several weeks, generally about 1 to 3 weeks to allow the somatic embryos to mature. Preferred regeneration media include media containing MS salts, such as PHI-E and PHI-F media. The plant cells, calli or explant are then typically cultured on rooting medium in a light/dark cycle until shoots and roots develop. Methods for plant regeneration are known in the art and preferred methods are provided by Kamo et al., (*Bot. Gaz.* 146(3):324-334, 1985), West et al, (*The Plant Cell* 5:1361-1369. 1993), and Duncan et al. (*Planta* 165:322-332, 1985).

Small plantlets can then be transferred to tubes containing rooting medium and allowed to grow and develop more roots for approximately another week. The plants can then be transplanted to soil mixture in pots in the greenhouse.

The regeneration of plants containing the foreign gene introduced by *Agrobacterium* from leaft explants can be achieved as described by Horsch et al., *Science,* 227:1229-1231 (1985). In this procedure, transformants are grown in the presence of a selection agent and in a medium that induces the regeneration of shoots in the plant species being transformed as described by Fraley et al., *Proc. Natl. Acad. Sci, U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.,* 38:467-486 (1987). The regeneration of plants from either single plant protoplasts or various explants is well known in the art. See, from example, *Methods for Plant Molecular Biology*, A. Weissbach and H. Weissback, eds., Academic Press, Inc., San Diego, Calif. (1988). This regeneration and growth process includes the steps of selection of transformant cells and shoots, rooting ht transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype, (e.g., altered cell cycle content or composition).

Parts obtained from the regenerated plant, such as flowers, seeds, leaves, branches, fruit and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochernist according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment of the invention is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

The present invention also relates to transgenic plants and plant tissue comprising transgenic plant cells according to the invention. Due to the (over)expression of a CCP molecule, e.g., at developmental stages and/or in plant tissue in which they do not naturally occur, these transgenic plants may show various physiological, developmental and/or morphological modifications in comparison to wild-type plants.

Therefore, part of this invention is the use of the CCP molecules to modulate the cell cycle and/or plant cell division and/or growth in plant cells, plant tissues, plant organs and/or whole plants. To the scope of the invention also belongs a method for influencing the activity of CDKs such as CDC2a, or CDC2b, CKSs, CKIs, PLPs and KLPNTs in a plant cell by transforming the plant cell with a nucleic acid molecule according to the invention and/or manipulation of the expression of the molecule.

Furthermore, the invention also relates to a transgenic plant cell which contains (preferably stably integrated into its genome) a nucleic acid molecule of the invention or part thereof, wherein the transcription and/or expression of the nucleic acid molecule or part thereof leads to reduction of the synthesis of a CCP. In a preferred embodiment, the reduction is achieved by an anti-sense, sense, ribozyme, co-suppression and/or dominant mutant effect. The reduction of the synthesis of a protein according to the invention in the transgenic plant cells can result in an alteration in, e.g., cell division. In transgenic plants comprising such cells this can lead to various physiological, developmental and/or morphological changes.

In yet another aspect, the invention relates to harvestable parts and to propagation material of the transgenic plants of the invention which either contain transgenic plant cells expressing a nucleic acid molecule according to the invention or which contain cells which show a reduced level of the described protein. Harvestable parts can be in principle any useful parts of a plant, for example, flowers, pollen, seedlings, tubers, leaves, stems, fruit, seeds, roots etc. Propagation material includes, for example, seeds, fruits, cuttings, seedlings, tubers, rootstocks, and the like.

Transgenic Animals

As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous CCP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a CCP-encoding nucleic acid into the male pronuclei of a fertilized oocyte, e.g., by microinjection, retroviral infection, and allowing the oocyte to develop in a pseudopregnant female foster animal. The CCP cDNA sequence of SEQ ID NO:1-66 or 228-239 can be introduced as a transgene into the genome of a non-human animal. Alternatively, a nonhuman homologue of a human CCP gene, such as a mouse or rat CCP gene, can be used as a transgene. Alternatively, a CCP gene homologue, such as another CCP family member, can be isolated based on hybridization to the CCP cDNA sequences of SEQ ID NO:1-66 or 228-239 (described further in subsection I above) and used as a transgene. Intronic sequences and polyadenylation signals can also be included in the transgene to increase the efficiency of expression of the transgene. A tissue-specific regulatory sequence(s) can be operably linked to a CCP transgene to direct expression of a CCP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a CCP transgene in its genome and/or expression of CCP mRNA in tissues or cells of the animals. A transgenic founder animal can then be used to breed additional animals carrying the transgene.

Moreover, transgenic animals carrying a transgene encoding a CCP protein can further be bred to other transgenic animals carrying other transgenes.

V. Agricultural, Phytopharmaceutical and Pharmaceutical Compositions

The CCP nucleic acid molecules, CCP proteins, and anti-CCP antibodies (also referred to herein as "active compounds") of the invention can be incorporated into compositions useful in agriculture and in plant cell and tissue culture. Plant protection compositions can be prepared by conventional means commonly used for the application of, for example, herbicides and pesticides. For example, certain additives known to those skilled in the art stabilizers or substances which facilitate the uptake by the plant cell, plant tissue or plant may be used.

The CCP nucleic acid molecules, CCP proteins, and anti-CCP antibodies (also referred to herein as "active compounds") of the invention can also be incorporated into pharmaceutical compositions suitable for administration into animals. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art Except insofar as any conventional media or agent is incompatible with the active compound, use thereof in the compositions is contemplated. Supplementary active compounds can also be incorporated into the compositions.

The nucleic acid molecules of the invention can be inserted into vectors and used as gene therapy vectors. Gene therapy vectors can be delivered to a plant or subject by, for example, injection, local administration (see U.S. Pat. No. 5,328,470) or by stereotactic injection (see e.g., Chen et al. (1994) *Proc. Natl. Acad. Sci. USA* 91:3054-3057). The agricultural or pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the agricultural or pharmaceutical preparation can include one or more cells which produce the gene delivery system.

The agricultural and pharmaceutical compositions can be included in a container, pack, or dispenser together with instructions for administration.

VI. Uses and Methods of the Invention

The nucleic acid molecules, proteins, protein homologues, and antibodies described herein can be used in one or more of the following methods: a) agricultural uses (e.g., to increase plant yield and to develop phytopharmaceuticals); b) screening assays; c) predictive medicine (e.g., diagnostic assays, prognostic assays, monitoring clinical trials); d) methods of treatment (e.g., phytotherapeutic, therapeutic and prophylactic); e) transcriptomics; f) proteomics; g) metabolomics; h) ligandomics; and i) pharmacogenetics or pharmacogenomics. The isolated nucleic acid molecules of the invention can be used, for example, to express CCP protein (e.g., via a recombinant expression vector in a host cell or in gene therapy applications), to detect CCP mRNA (e.g., in a biological sample) or a genetic alteration in a CCP gene, and to modulate CCP activity, as described further below. The CCP proteins can be used to treat disorders characterized by insufficient or excessive production of a CCP substrate or production of CCP inhibitors. In addition, the CCP proteins can be used to screen for naturally occurring CCP substrates, to screen for drugs or compounds which modulate CCP activity, as well as to treat disorders characterized by insufficient or excessive production of CCP protein or production of CCP protein forms which have decreased or aberrant activity compared to CCP wild type protein. Moreover, the anti-CCP antibodies of the invention can be used to detect and isolate CCP proteins, regulate the bioavailability of CCP proteins, and modulate CCP activity.

A. Agricultural Uses:

In another embodiment of the invention, a method is provided for modifying cell fate and/or plant development and/or plant morphology and/or biochemistry and/or physiology comprising the modification of expression in particular cells, tissues or organs of a plant, of a genetic sequence encoding a CCP, e.g., a CCP operably connected with a plant-operable promoter sequence.

Modulation of the expression in a plant of a CCP or a homologue, analogue or derivative thereof as defined in the present invention can produce a range of desirable phenotypes in plants, such as, for example, the modification of one or more morphological, biochemical, or physiological characteristics including: (i) modification of the length of the G1 and/or the S and/or the G2 and/or the M phase of the cell cycle of a plant; (ii) modification of the G1/S and/or S/G2 and/or G2/M and/or M/G1 phase transition of a plant cell; (iii) modification of the initiation, promotion, stimulation or enhancement of cell division; (iv) modification of the initiation, promotion, stimulation or enhancement of DNA replication; (v) modification of the initiation, promotion, stimulation or enhancement of seed set and/or seed size and/or seed development; (vi) modification of the initiation, promotion, stimulation or enhancement of tuber formation; (vii) modification of the initiation, promotion, stimulation or enhancement of fruit formation; (viii) modification of the initiation, promotion, stimulation or enhancement of leaf formation; (ix) modification of the initiation, promotion, stimulation or enhancement of shoot initiation and/or development; (x) modification of the initiation, promotion, stimulation or enhancement of root initiation and/or development; (xi) modification of the initiation, promotion, stimulation or enhancement of lateral root initiation and/or development; (xii) modification of the initiation, promotion, stimulation or enhancement of nodule formation and/or nodule function; (xiii) modification of the initiation, promotion, stimulation or enhancement of the bushiness of the plant; (xiv) modification of the initiation, promotion, stimulation or enhancement of dwarfism in the plant; (xv) modification of the initiation, promotion, stimulation or enhancement of senescence; (xvi) modification of stem thickness and/or strength characteristics and/or wind-resistance of the stem and/or stem length; (xvii) modification of tolerance and/or resistance to biotic stresses such as pathogen infection; and (xviii) modification of tolerance and/or resistance to abiotic stresses such as drought stress or salt stress.

Methods to effect expression of a CCP or a homologue, analogue or derivative thereof as defined in the present invention in a plant cell, tissue or organ, include either the introduction of the protein directly to a cell, tissue or organ such as by microinjection of ballistic means or, alternatively, introduction of an isolated nucleic acid molecule encoding the protein into the cell, tissue or organ in an expressible format. Methods to effect expression of a CCP or a homologue, analogue or derivative thereof as defined in the current invention in whole plants include regeneration of whole plants from the transformed cells in which an isolated nucleic acid molecule encoding the protein was introduced in an expressible format.

The present invention clearly extends to any plant produced by the inventive method described herein, and any and all plant parts and propagules thereof. The present invention extends further to encompass the progeny derived from a primary transformed or transfected cell, tissue, organ or whole plant that has been produced by the inventive method, the only requirement being that the progeny exhibits the same genotypic and/or phenotypic characteristic(s) as those characteristic(s) that (have) been produced in the parent by the performance of the inventive method.

By "cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein. "Cell fate" includes the cell-type or cellular characteristics of a particular cell that are produced during plant development or a cellular process therefor, in particular during the cell cycle or as a consequence of a cell cycle process.

The term "plant development" or the term "plant developmental characteristic" or similar terms shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

The term "plant morphology" or the term "plant morphological characteristic" or similar term will, when used herein, be understood by those skilled in the art to include the external appearance of a plant, including any one or more structural features or combination of structural features thereof. Such structural features include the shape, size, number, position, color, texture, arrangement, and patternation of any cell, tissue or organ or groups of cells, tissues or organs of a plant, including the root, stem, leaf, shoot, petiole, trichome, flower, petal, stigma, style, stamen, pollen; ovule, seed, embryo, endosperm, seed coat, aleurone, fibre, fruit, cambium, wood, heartwood, parenchyma, aerenchyma, sieve element, phloem or vascular tissue.

The term "plant biochemistry" or the term "plant biochemical characteristic" or similar term will, when used herein, be understood by those skilled in the art to include the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

The term "plant physiology" or the term "plant physiological characteristic" or similar term will, when used herein, be understood to include the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fibre production, secondary growth or wood production, amongst others; responses of a plant to externally-applied factors such as metals, chemicals, hormones, growth factors, environment and environmental stress factors (e.g., anoxia, hypoxia, high temperature, low temperature, dehydration, light, daylength, flooding, salt, heavy metals, amongst others), including adaptive responses of plants to said externally-applied factors.

The CCP molecules of the present invention are useful in agriculture. The nucleic acid molecules, proteins, protein homologues, and antibodies described herein can be used to modulate the protein levels or activity of a protein involved in the cell cycle, e.g., proteins involved in the G1/S and/or the G2/M transition in the cell cycle due to environmental conditions, including abiotic stress such as cold, nutrient deprivation, heat, drought, salt stress, or biotic stress such as a pathogen attack.

Thus, the CCP molecules of the present invention may be used to modulate, e.g., enhance, crop yields; modulate, e.g., attenuate, stress, e.g. heat or nutrient deprivation; modulate tolerance to pests and diseases; modulate plant architecture; modulate plant quality traits; or modulate plant reproduction and seed development.

The CCP molecules of the present invention may also be used to modulate endoreduplication in storage cells, storage tissues, and/or storage organs of plants or parts thereof. The term "endoreduplication" includes recurrent DNA replication without consequent mitosis and cytokinesis. Preferred target storage organs and parts thereof for the modulation of endoreduplication are, for example, seeds (such as from cereals, oilseed crops), roots (such as in sugar beet), tubers (such as in potatoes) and fruits (such as in vegetables and fruit species). Increased endoreduplication in storage organs, and parts thereof, correlates with enhanced storage capacity and, thus, with improved yield. In another embodiment of the invention, the endoreduplication of a whole plant is modulated.

B. Screening Assays:

The invention provides a method (also referred to herein as a "screening assay") for identifying modulators, i.e., candidate or test compounds or agents (e.g., peptides, peptidomimetics, small molecules or other drugs) which bind to CCP proteins, have a stimulatory or inhibitory effect on, for example, CCP expression or CCP activity, or have a stimulatory or inhibitory effect on, for example, the expression or activity of a CCP substrate.

In one embodiment, the invention provides assays for screening candidate or test compounds which are substrates of a CCP protein or polypeptide or biologically active portion thereof. In another embodiment, the invention provides assays for screening candidate or test compounds which bind to or modulate the activity of a CCP protein or polypeptide or biologically active portion thereof, e.g., modulate the ability of CCP to interact with its cognate ligand. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In another embodiment, an assay is a cell-based assay comprising contacting a cell expressing a CCP target molecule (e.g., a plant cyclin dependent kinase) with a test compound and determining the ability of the test compound to modulate (e.g. stimulate or inhibit) the activity of the CCP target molecule. Determining the ability of the test compound to modulate the activity of a CCP target molecule can be accomplished, for example, by determining the ability of the CCP protein to bind to or interact with the CCP target molecule, or by determining the ability of the target molecule, e.g., the plant cyclin dependent kinase, to phosphorylate a protein.

The ability of the target molecule, e.g., the plant cyclin dependent kinase, to phosphorylate a protein can be determined by, for example, an in vitro kinase assay. Briefly, a protein can be incubated with the target molecule, e.g., the plant cyclin dependent kinase, and radioactive ATP, e.g., [$\gamma$-$^{32}$P] ATP, in a buffer containing $MgCl_2$ and $MnCl_2$, e.g., 10 mM $MgCl_2$ and 5 mM $MnCl_2$. Following the incubation, the immunoprecipitated protein can be separated by SDS-polyacrylamide gel electrophoresis under reducing conditions, transferred to a membrane, e.g., a PVDF membrane, and autoradiographed. The appearance of detectable bands on the autoradiograph indicates that the protein has been phosphorylated. Phosphoaminoacid analysis of the phosphorylated substrate can also be performed in order to determine which residues on the protein are phosphorylated. Briefly, the radio-phosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards.

Determining the ability of the CCP protein to bind to or interact with a CCP target molecule can be accomplished by determining direct binding. Determining the ability of the CCP protein to bind to or interact with a CCP target molecule can be accomplished, for example, by coupling the CCP protein with a radioisotope or enzymatic label such that binding of the CCP protein to a CCP target molecule can be determined by detecting the labeled CCP protein in a complex. For example, CCP molecules, e.g., CCP proteins, can be labeled with $^{125}$I, $^{35}$S, $^{14}$C, or $^{3}$H, either directly or indirectly, and the radioisotope detected by direct counting of radioemmission or by scintillation counting. Alternatively, CCP molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between CCP and its target molecule, without the labeling of any of the interactants. For example, a microphysiometer can be used to detect the interaction of CCP with its target molecule without the labeling of either CCP or the target molecule. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the CCP protein to bind to or interact with a CCP target molecule can be accomplished by determining the activity of the target molecule. For example, the activity of the target molecule can be determined by detecting induction of a cellular second messenger of the target (e.g., intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., chloramphenicol acetyl transferase), or detecting a target-regulated cellular response.

In yet another embodiment, an assay of the present invention is a cell-free assay in which a CCP protein or biologically active portion thereof is contacted with a test compound and the ability of the test compound to bind to the CCP protein or biologically active portion thereof is determined. Binding of the test compound to the CCP protein can be determined either directly or indirectly as described above. In a preferred embodiment, the assay includes contacting the CCP protein or biologically active portion thereof with a known compound which binds CCP to form an assay mixture, contacting the assay mixture with a test compound, and determining the ability of the test compound to interact with a CCP protein, wherein determining the ability of the test compound to interact with a CCP protein comprises determining the ability of the test compound to preferentially bind to CCP or biologically active portion thereof as compared to the known compound.

In another embodiment, the assay is a cell-free assay in which a CCP protein or biologically active portion thereof is contacted with a test compound and the ability of the test compound to modulate (e.g., stimulate or inhibit) the activity of the CCP protein or biologically active portion thereof is determined. Determining the ability of the test compound to modulate the activity of a CCP protein can be accomplished, for example, by determining the ability of the CCP protein to bind to a CCP target molecule by one of the methods described above for determining direct binding. Determining the ability of the CCP protein to bind to a CCP target molecule can also be accomplished using a technology such as real-time Biomolecular Interaction Analysis (BIA). Sjolander, S, and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a CCP protein can be accomplished by determining the ability of the CCP protein to further modulate the activity of a CCP target molecule (e.g., a CCP mediated signal transduction pathway component). For example, the activity of the effector molecule on an appropriate target can be determined, or the binding of the effector to an appropriate target can be determined as previously described.

In yet another embodiment, the cell-free assay involves contacting a CCP protein or biologically active portion thereof with a known compound which binds the CCP protein to form an assay mixture, contacting the assay mixture with a test compound, and determining the ability of the test compound to interact with the CCP protein, wherein determining the ability of the test compound to interact with the CCP protein comprises determining the ability of the CCP protein to preferentially bind to or modulate the activity of a CCP target molecule.

The cell-free assays of the present invention are amenable to use of both soluble and/or membrane-bound forms of proteins (e.g., CCP proteins or biologically active portions thereof). In the case of cell-free assays in which a membrane-bound form a protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$; 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CCP or its target molecule to facilitate separation of complexed from uncomplexed forms of one or both of the proteins, as well as to accommodate automation of the assay. Binding of a test compound to a CCP protein, or interaction of a CCP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/CCP fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or CCP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CCP binding or activity determined using standard techniques.

Other techniques for immobilizing proteins on matrices can also be used in the screening assays of the invention. For example, either a CCP protein or a CCP target molecule can be immobilized utilizing conjugation of biotin and streptavidin. Biotinylated CCP protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CCP protein or target molecules but which do not interfere with binding of the CCP protein to its target molecule can be derivatized to the wells of the plate, and unbound target or CCP protein trapped in the wells by antibody conjugation. Methods for detecting such complexes, in addition to those described above for the GST-immobilized complexes, include immunodetection of complexes using antibodies reactive with the CCP protein or target molecule, as well as enzyme-linked assays which rely on detecting an enzymatic activity associated with the CCP protein or target molecule.

In another embodiment, modulators of CCP expression are identified in a method wherein a cell is contacted with a candidate compound and the expression of CCP mRNA or protein in the cell is determined. The level of expression of CCP mRNA or protein in the presence of the candidate compound is compared to the level of expression of CCP mRNA or protein in the absence of the candidate compound. The candidate compound can then be identified as a modulator of CCP expression based on this comparison. For example, when expression of CCP mRNA or protein is greater (statistically significantly greater) in the presence of the candidate compound than in its absence, the candidate compound is identified as a stimulator of CCP mRNA or protein expression. Alternatively, when expression of CCP mRNA or protein is less (statistically significantly less) in the presence of the candidate compound than in its absence, the candidate compound is identified as an inhibitor of CCP mRNA or protein expression. The level of CCP mRNA or protein expression in the cells can be determined by methods described herein for detecting CCP mRNA or protein.

In yet another aspect of the invention, the CCP proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with CCP ("CCP-binding proteins" or "CCP-bp") and are involved in CCP activity. Such CCP-binding proteins are also likely to be involved in the propagation of signals by the CCP proteins or CCP targets as, for example, downstream elements of a CCP-mediated signaling pathway. Alternatively, such CCP-binding proteins are likely to be CCP inhibitors. Alternatively, a mammalian two-hybrid system can be used which includes e.g. a chimeric green fluorescent protein encoding reporter gene (Shioda et al. 2000, Proc. Natl. Acad. Sci. USA 97, 5520-5224). Yet another alternative consists of a bacterial two-hybrid system using e.g. HIS as reporter gene (Joung et al. 2000, Proc. Natl. Acad. Sci. USA 97, 7382-7387).

The two-hybrid system is based on the modular nature of most transcription factors, which consist of separable DNA-binding and activation domains. Briefly, the assay utilizes two different DNA constructs. In one construct, the gene that codes for a CCP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a CCP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the CCP protein.

This invention further pertains to novel agents identified by the above-described screening assays. Accordingly, it is within the scope of this invention to further use an agent identified as described herein in an appropriate plant or animal model. For example, an agent identified as described herein (e.g., a CCP modulating agent, an antisense CCP nucleic acid molecule, a CCP-specific antibody, or a CCP-binding partner) can be used in a plant or animal model to determine the efficacy, toxicity, or side effects of treatment with such an agent. Alternatively, an agent identified as described herein can be used in a plant or animal model to determine the mechanism of action of such an agent. Furthermore, this invention pertains to uses of novel agents identified by the above-described screening assays for the agricultural and therapeutic uses described herein.

C. Detection Assays

Portions or fragments of the cDNA sequences identified herein (and the corresponding complete gene sequences) can be used in numerous ways as polynucleotide reagents. For example, these sequences can be used to: map their respective genes on a chromosome; and, thus, locate gene regions associated with genetic disease; identify an individual from a minute biological sample (tissue typing); and aid in forensic identification of a biological sample. Once the sequence (or a portion of the sequence) of a gene has been isolated, this sequence can be used to map the location of the gene on a chromosome. This process is called chromosome mapping. Accordingly, portions or fragments of the CCP nucleotide sequences, described herein, can be used to map the location of the CCP genes on a chromosome. The mapping of the CCP sequences to chromosomes is an important first step in correlating these sequences with genes associated with disease.

Briefly, CCP genes can be mapped to chromosomes by preparing PCR primers (preferably 15-25 bp in length) from the CCP nucleotide sequences. Computer analysis of the CCP sequences can be used to predict primers that do not span more than one exon in the genomic DNA, thus complicating the amplification process. These primers can then be used for PCR screening of cell hybrids containing individual plant or human chromosomes. Only those hybrids containing the plant or human gene corresponding to the CCP sequences will yield an amplified fragment.

Other mapping strategies which can similarly be used to map a CCP sequence to its chromosome include in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between plants affected and unaffected with a disease associated with the CCP gene, can be determined. If a mutation is observed in some or all of the affected plants but not in any unaffected plants, then the mutation is likely to be the causative agent of the particular disease. Comparison of affected and unaffected plants generally involves first looking for structural alterations in the chromosomes, such as deletions or translocations that are visible from chromosome spreads or detectable using PCR based on that DNA sequence. Ultimately, complete sequencing of genes from several plants can be performed to confirm the presence of a mutation and to distinguish mutations from polymorphisms.

D. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining CCP protein and/or nucleic acid expression as well as CCP activity, in the context of a biological sample (e.g., blood, serum, cells, tissue) to thereby determine whether an individual is afflicted with a disease or disorder, or is at risk of developing a disorder, associated with aberrant CCP expression or activity. The invention also provides for prognostic (or predictive) assays for determining whether an individual is at risk of developing a disorder associated with CCP protein, nucleic acid expression or activity. For example, mutations in a CCP gene can be assayed in a biological sample. Such assays can be used for prognostic or predictive purpose to thereby phophylactically treat an individual prior to the onset of a disorder characterized by or associated with CCP protein, nucleic acid expression or activity.

Another aspect of the invention pertains to monitoring the influence of agents (e.g., drugs, compounds) on the expression or activity of CCP in clinical trials.

E. Methods of Treatment:

The present invention provides for both prophylactic and therapeutic methods of treating a subject at risk of (or susceptible to) a disorder or having a disorder associated with aberrant CCP expression or activity. With regards to both prophylactic and therapeutic methods of treatment, such treatments may be specifically tailored or modified, based on knowledge obtained from the field of pharmacogenomics.

"Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the CCP molecules of the present invention or CCP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

This invention is further illustrated by the following examples which should not be construed as limiting. The contents of all references, patents and published patent applications cited throughout this application, as well as the Figures and the Sequence Listing are incorporated herein by reference.

EXAMPLES

Example 1

Identification of Plant Ccp Polypeptides Using the Two Hybrid System with CDC2B as a Bait A two-hybrid screening was performed using as bait a fusion between the GAL4 DNA-binding domain and one of the following: CDC2bAt.N161 (GenBank accession number D10851; residue Asp161 converted into Asn161); CKS1At (GenBank accession number AJ00016); E2Fa (=E2F5) (GenBank accession number AJ294534) dimerization domain (226-356aa; SEQ ID NO:205); CKI4 (SEQ ID NO:264); PLP1 (GenBank accession number T01601); KLPNT1 (GenBank accession number AB011479; protein ID number BAB11568) motor domain (36-508 aa); KLPNT1 (GenBank accession number AB011479; protein ID number BAB11568) stalk domain (427-867 aa); KLPNT2=TH65 (GenBank accession number AJ001729) neck domain (3-186 aa); KLPNT2=TH65 (GenBank accession number AJ001729) stalk domain (73-608 aa); E2Fb (=E2F3) (GenBank accession number AJ294533) N-terminal domain (1-385 aa; SEQ ID NO:206), respectively CDC2bAt.N161 is a dominant negative form of the CDC2bAt protein. The D161 residue in CDC2bAt is crucial for ATP binding and, thus, the mutation of this residue results in an inactive kinase. The interactions between this mutated CDK and its substrates and regulatory proteins are also more stabilised as a result of this mutation.

In yeast the PHO genes are part of a complex regulatory network linking phosphate availability with the expression of phosphatases. When phosphate levels are high the PHO80PHO85 cyclin/CDK complex phosphorylates a transcription factor. This transcription factor of phosphatase genes thereby becomes inactive. The S. cerevisiae PHO85 protein can interact with the G1 specific cyclins PCL1 and PCL2 (close homologues to the PHO80). In a yeast strain deficient for the G1 cyclins CLN1 and CLN2, PHO80 is required for G1 progression. This result suggests that PHO85 is involved in a regulatory pathway that links the nutrient status of the cell with cell division activity. The five PLP of *A. thaliana* show similarity to the yeast cyclin-like PHO80 gene.

Kinesins use the cytoskeleton to move around vesicles, organelles, chromosomes and the like in the cell. They can also be involved in spindle formation. Kinesins consist of three functional unrelated domains: the motor domain (involved in microtubule binding; contains the ATPase domain), the stalk region (involved in homo- or heterodimirisation of the kinesins), and the tail (involved in the interaction with the 'substrates' of the kinesin). Two hybrid screens were performed using different parts of two-kinesin-related proteins (KLPNT1 and KLPNT2 (being more than 80% identical to KLPNT1). Other information obtained by the two hybrid approach is the dimerization of the kinesins: the KLPNT1 and KLPNT2 interact (stalks and stalks-tail) with and between themselves.

Vectors and strains used were provided with the Matchmaker Two-Hybrid System (Clontech, Palo Alto, Calif.). The bait was constructed by inserting the CDC2bAt.N161 (GenBank accession number D10851; residue Asp161 converted into Asn161); CKS1At (GenBank accession number AJ00016); E2Fa (=E2F5) (GenBank accession number AJ294534) dimerization domain (226-356aa; SEQ ID NO:205); CKI4 (SEQ ID NO:264); PLP1 (GenBank accession number T01601); KLPNT1 (GenBank accession number AB011479; protein ID number BAB11568) motor domain (36-508 aa); KLPNT1 (GenBank accession number AB011479; protein ID number BAB11568) stalk domain (427-867 aa); KLPNT2=TH65 (GenBank accession number AJ001729) neck domain (3-186 aa); KLPNT2=TH65 (GenBank accession number AJ001729) stalk domain (73-608 aa); E2Fb (=E2F3) (GenBank accession number AJ294533) N-terminal domain (1-385 aa; SEQ ID NO:206), respectively, into the pGBT9 vector. Bait vectors where constructed by introducing the PCR fragment created from the corresponding cDNA using primers to incorporate EcoRI and BamH1 restriction enzyme sites. The PCR fragment was cut with EcoRI and BarnH1 and cloned into the EcoRI and BamH1 sites of pGBT9, resulting in the desired plasmid. The GAL4 activation domain cDNA fusion library was constructed as described in De Veylder et al 1999, 208(4) p453-62 from mRNA of *Arabidopsis thaliana* cell suspensions harvested at various growing stages: early exponential, exponential, early stationary, and stationary phase.

For the screening a 1-liter culture of the *Saccharomyces cerevisfae* strain HF7c (MATa ura3-52 his3-200 ade2-101 lys2-801 trp1-901 leu2-3, 112 gal4-542 gal80-538 LYS2:: GAL1$_{UAS}$-GAL1$_{TATA}$-HIS3 URA3::GAL4$_{17mers(3x)}$-CyCl$_{TATA}$-LacZ) was sequentially transformed with the bait plasmid and 20 μg DNA of the library using the lithium acetate method (Geitz et al. (1992) supra). To estimate the number of independent cotransformants, 1/1000 of the transformation mix was plated on Leu- and Ttp-medium. The rest of the transformation mix was plated on medium to select for histidine prototrophy (Trp-, Leu-, His-). After 5 days of growth at 30° C., the colonies larger than 2 mm were streaked on histidine-lacking medium. At total for each screening at least $10^7$ independent cotransformants were screened for there ability to grow on histidine free medium. Of the His$^+$ colonies the activation domain plasmids were isolated as described (Hoffman and Winston, 1987, Gene 57, 267-272). The hybriZAP™ inserts were PCR amplified and the PCR fragments were digested with AluI and fractionized on a 2% agarose gel. Plasmid DNA of which the inserts gave rise to different restriction patterns were electroporated into *Escherichia coli* XL1-Blue, and the DNA sequence of the inserts was determined. Extracted DNA was also used to retransform HF7c to test the specificity of the interaction.

Using the foregoing technique, 61 cDNAs were identified, their sequences were determined and found to contain open reading frames termed CCP1 through CCP61 (FIGS. 1-61).

Example 2

Extension of CCP Encoding polynucleotides To Full Length or to Recover Regulatory Elements The CCP encoding nucleic acid sequences (SEQ ID NO:1-66 or 228-239) are used to design oligonucleotide primers for extending a partial nucleotide sequence to full length or for obtaining 5' sequences from genomic or cDNA libraries. One primer is synthesized to initiate extension in the antisense direction (XLR) and the other is synthesized to extend sequence in the sense direction (XLF). Primers allow the extension of the known CCP encoding sequence "outward" generating amplicons containing new, unknown nucleotide sequence for the region of interest. The initial primers are designed from the cDNA using OLIGO® 4.06 Primer Analysis Software (National Biosciences), or another appropriate program, to be preferably 22-30 nucleotides in length, to have a GC content of preferably 50% or more, and to anneal to the target sequence at temperatures preferably about 68°-72° C. Any stretch of nucleotides which would result in hairpin structures and primer-primer dimerizations is avoided. The original, selected cDNA libraries, prepared from mRNA isolated from actively dividing cells or a plant genomic library are used to extend the sequence; the latter is most useful to obtain 5' upstream regions. If more extension is necessary or desired, additional sets of primers are designed to further extend the known region.

Sense XLF primers can also be designed based on publicly available genomic sequences. GENEMARK.hmm (hidden morkov model) version 2.2a software (default parameters) can e.g. be used to predict open reading frames. The 5' end of the predicted open reading frame is then subsequently used to design the sense XLF primer. Said XLF primer and the appropriate XLR primer are then used in an RT-PCR (reverse transcription-polymerase chain reaction) reaction to amplify the predicted cDNA. The resulting PCR product is cloned in a suitable vector and subjected to DNA sequence analysis to verify the prediction.

Primers used to amplify coding regions of the CCPs of the invention are designed such that the PCR product can be cloned in the pDONR201 vector (Gateway™ cloning system, Invitrogen). Thus, a sense primer has the attB1 site (SEQ ID NO:246) at its 5' end. For current purposes, the attB1 site is followed by a consensus Kozak sequence (SEQ ID NO:247; Kozak (1989) *J Cell Biol* 108:229-241; Lück et al. (1987) *EMBO J* 6:43-48). The 3' end of the sense primer comprises the gene-specific parts as indicated in FIGS. 1-46. An antisense primer has at the 5' end the attB2 site (SEQ ID NO:248) followed by the inverse complement of the gene/coding region of interest as indicated in FIGS. 1-46. Primers used for CCP amplification by PCR are given with their SEQ ID NOs in Table 3. The sequence of cloned CCP PCR products was or is determined using the sense primer prm1024 (SEQ ID NO:265) and the antisense primer prm1025 (SEQ ID NO:266).

TABLE III

| CCP Molecule | PCR primers sense + antisense | sense primer SEQ ID NO: | antisense primer SEQ ID NO: |
|---|---|---|---|
| CCP1 | prm0733 + prm0734 | 133 | 134 |
| CCP2 | prm0663 + prm0664 | 135 | 136 |
| CCP3 | prm0705 + prm0706 | 137 | 138 |
| CCP4 | prm0659 + prm0660 | 139 | 140 |
| CCP5 | prm0749 + prm0750 | 141 | 142 |
| CCP6 | prm0707 + prm0708 | 143 | 144 |
| CCP7/8 | prm0657 + prm0658 | 145 | 146 |
| CCP9 | prm0582 + prm0583 | 147 | 148 |
| CCP10 | prm0671 + prm0672 | 149 | 150 |
| CCP11 | prm0729 + prm0730 | 151 | 152 |
| CCP12 + CCP13 | prm1676 + prm1677 | 153 | 154 |
| CCP14 | prm0701 + prm0702 | 155 | 156 |
| CCP15 | prm0445 + prm0446 | 157 | 158 |
| CCP16 | prm0321 + prm0322 | 159 | 160 |
| CCP17 | prm0632 + prm0633 | 161 | 162 |
| CCP18 | prm0488 + prm0489 | 163 | 164 |
| CCP19 | prm0661 + prm0662 | 165 | 166 |
| CCP20 + CCP21 | prm0709 + prm0710 | 167 | 168 |
| CCP22 | prm0711 + prm0712 | 169 | 170 |
| CCP23 | prm0819 + prm0820 | 171 | 172 |
| CCP24 | prm0739 + prm0740 | 173 | 174 |
| CCP25 | prm0741 + prm0742 | 175 | 176 |
| CCP26 | prm0703 + prm0704 | 177 | 178 |
| CCP27 | prm0817 + prm0818 | 179 | 180 |
| CCP28 | prm0713 + prm0714 | 181 | 182 |
| CCP29 | / | / | / |
| CCP30 | prm0480 + prm0481 | 183 | 184 |
| CCP31 | prm0737 + prm0738 | 185 | 186 |
| CCP32 | prm1493 + prm1494 | 187 | 188 |
| CCP33 | prm0319 + prm0320 | 189 | 190 |
| CCP34 | prm1377 + prm1378 | 191 | 192 |
| CCP35 | prm1381 + prm1382 | 193 | 194 |
| CCP36 | / | / | / |
| CCP37 | prm1379 + prm1380 | 195 | 196 |
| CCP38 | prm1383 + prm1384 | 197 | 198 |

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed suing the Peltier Thermal Cycle (PTC200; MJ Research, Watertown Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4-6 for 15 additional cycles |
| Step 8 | 94° C. for 15 sec |
| Step 9 | 65° C. for 1 min |
| Step 10 | 68° C. for 7:15 min |
| Step 11 | Repeat step 8-10 for 12 cycles |
| Step 12 | 72° C. for 8 min |
| Step 13 | 4° C. (and holding) |

A 5-10 µl aliquot of the reaction mixture is analyzed by electrophoresis on a low concentration (about 0.6-0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning. After ethanol precipitation, the products are redissolved in 13 µl of ligation buffer, 1 µl T4-DNA ligase (15 units) and 1 µl T4 polynucleotide kinase are added, and the mixture is incubated at room temperature for 2-3 hours or overnight at 16° C. Competent *E. coli* cells (in 40 µl of appropriate media) are transformed with 3 µl of ligation mixture and cultured in 80 µl of SOC medium (Sambrook, supra). After incubation for one hour at 37° C., the whole transformation mixture is plated on Luria Bertani (LB)-agar (Sambrook, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array. For PCR amplification, 18 µl of concentrated PCR reaction mix (3.3×) containing 4 units of 4Tth DNA polymerase, a vector primer and both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2-4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

Example 3

Expression of Recombinant Ccp Proteins in Transgenic Plants

In this example, the CCP molecules of the present invention were expressed in a 35S expression vector in transgenic plants. The CCP molecules of this invention were cloned using standard cloning procedures between a suitable promoter, e.g. the CaMV35S promoter or any promoter from e.g. Table II, and a suitable terminator, e.g., the NOS 3' untranslated region. The resulting recombinant gene is subsequently cloned in a suitable binary vector and the resulting plant transformation vector is then transferred to *Agrobacterium tumefaciens*. *Arabidopsis thaliana* is transformed with this *Agrobacterium* applying the in planta flower-dip transformation method (Clough and Bent, *Plant J.* 16:735-743, 1998). Transgenic plant lines are selected on a growth medium containing the suitable selection agent (e.g., kanamycin or Basta) or on the basis of scoring the expression of a screenable marker (e.g., luciferase, green fluorescent protein).

For tissue-specific expression, the CCP gene can also be expressed under control of the minimal 35S promoter containing UAS elements. These UAS elements are sites for transcriptional activation by the GAL4-VP16 fusion protein. The GAL4-VP16 fusion protein in turn is expressed under control of a tissue-specific promoter. The UAS-CCP construct and the GAL4-VP16 construct are combined by co-transformation of both constructs, subsequent transformation of single constructs or by sexual cross of lines that contain the single constructs. The advantage of this two-component system is that a wide array of tissue-specific expression patterns can be generated for a specific transgene, by simply crossing selected parent lines expressing the UAS-CCP construct with various tissue-specific GAL4-VP16 lines. A tissue-specific promoter/CCP combination that gives a desired phenotype can subsequently be recloned in a single expression vector, to avoid stacking of transgene constructs in commercial lines.

Primary transformants are characterized by Northern and Western blotting using 1-4 week old plantlets. Expression levels were compared with those of non-transformed (control) plants.

Example 4

Downregulation of Target Ccp Genes in Transgenic Plants

Plant genes can be specifically downregulated by antisense and co-suppression technologies. These technologies are based on the synthesis of antisense transcripts, complementary to the mRNA of a given-CCP gene. There are several methods described in literature, that increase the efficiency of this downregulation, for example to express the sense strand with introduced inverted repeats, rather than the antisense strand. The constructs for downregulation of target genes are made similarly as those for expression of recombinant proteins, i.e., they are fused to promoter sequences and transcription termination sequences (see example 3). Promoters used for this purpose are constitutive promoters as well as tissue-specific promoters.

Example 5

*Agrobacterium*-Mediated Rice Transformation

Mature dry seeds of the rice japonica cultivars Nipponbare or Taipei 309 are dehusked, sterilised and germinated on a medium containing 2,4-D (2,4-dichlorophenoxyacetic acid). After incubation in the dark for four weeks, embryogenic, scutellum-derived calli are excised and propagated on the same medium. Selected embryogenic calluses are then co-cultivated with *Agrobacterium*. Widely used *Agrobacterium* strains such as LBA4404 or C58 harbouring binary T-DNA vectors can be used. The hpt gene in combination with hygromycin is suitable as a selectable marker system but other systems can be used. Co-cultivated callus is grown on 2,4-D-containing medium for 4 to 5 weeks in the dark in the presence of a suitable concentration of the selective agent. During this period, rapidly growing resistant callus islands develop. After transfer of this material to a medium with a reduced concentration of 2,4-D and incubation in the light, the embryogenic potential is released and shoots develop in the next four to five weeks. Shoots are excised from the callus and incubated for one week on an auxin-containing medium from which they can be transferred to the soil. Hardened shoots are grown under high humidity and short days in a phytotron. Seeds can be harvested three to five months after transplanting. The method yields single locus transformants at a rate of over 50% (Aldemita and Hodges (1996) *Planta* 199:612-617; Chan et al. (1993) *Plant Mol. Biol.* 22: 491-506; Hiei et al. (1994) *Plant J.* 6:271-282).

Example 6

Expression of Recombinant CCP Proteins in Bacterial Cells

In this example, the CCP molecules of the present invention are expressed as a recombinant glutathione-S-transferase (GST) fusion polypeptide in *E. coli* and the fusion polypeptide is isolated and characterized. Specifically, CCP molecules are fused to GST and this fusion polypeptide is expressed in *E. coli*, e.g., strain PEB199. Expression of the GST-CCP fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 7

Expression of Recombinant Ccp Proteins in COS Cells

To express the CCP gene of the present invention in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire CCP protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the CCP DNA sequence is amplified by PCR using two primers. The 5' primer contains the restriction site of interest followed by approximately twenty nucleotides of the CCP coding sequence starting from the initiation codon; the 3' end sequence contains complementary sequences to the other restriction site of interest, a translation stop codon, the HA tag or FLAG tag and the last 20 nucleotides of the CCP coding sequence. The PCR amplified fragment and the pcDNA/Amp vector are digested with the appropriate restriction enzymes and the vector is dephosphorylated using the CIAP enzyme (New England Biolabs Beverly, Mass.). Preferably the two restriction sites chosen are different so that the Kinase and/or Phosphatase gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the CCP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989. The expression of the CCP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40A 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the Kinase and/or Phosphatase coding sequence is cloned directly into the polylinker of the pcDNA/Amp vector using the appropriate restriction sites. The resulting plasmid is transfected into COS cells in the manner described above, and the expression of the CCP polypeptide is detected by radiolabelling and immunoprecipitation using a CCP specific monoclonal antibody.

Example 8

In Vitro Phosphorylation of CDC2bDN-IC26M by Plant CDKs

The CDC2bDN-IC26M coding region (SEQ ID NO:4) was amplified by PCR with Pfu polymerase (Stratagene, La Jolla, Calif.). The PCR product was subcloned into pET19b (Novagen, Madison, Wis.), to obtain CDC2bDN-IC26 MpET19b. The CDC2bDN-IC26M gene is located downstream of a T7lac promoter, in frame with a sequence encoding a 10-histidine tag followed by an enterokinase recognition site. *Escherichia coli* BL21 (DE3) cells (Novagen) containing the CDC2bDN-IC26 MpET19b plasmid were grown at 37° C. in M9 medium (Sambrook and Russel, Molecular Cloning, A Laboratory Manual, $3^{rd}$ Edition, CSHL Press, CSH New York, 2001), supplemented with 100 µg/ml of ampicillin, to obtain a cell density corresponding to an A600 of 0.6. Subsequently, expression of the CDC2bDN-IC26M gene was induced by addition of 0.4 mM isopropyl β-D-thiogalactoside, and culture was continued for 4 h at 30° C.

Cells were collected in lysis buffer containing 50 mM sodium phosphate buffer, pH 8.0, 300 mM NaCl, 0.1% Triton X-100, and 1 mM phenylmethylsulfonyl fluoride (PMSF) and were lysed on ice by sonication. The extract was clarified by centrifugation for 20 minutes at 20,000×g. The crude extract was loaded at 4° C. on a nickel-nitrilotriacetic acid-agarose affinity resin (Qiagen), and protein fractionation was performed according to the manufacturer's instructions. The fractions containing the CDC2bDN-IC26M fusion protein were pooled.

CDC2bDN-IC26M kinase assays were performed with CDK complexes purified from total plant (*Arabidopsis* seedlings) protein extracts by p13$^{suc1}$-Sepharose affinity binding according to Azzi et al. (*Eur. J. Biochem.* 203: 353-360). Briefly, p13$^{suc1}$ was purified from an overproducing *E. coli* strain by chromatography in Sephacryl S2000, and conjugated to CNBr-activated Sepharose 4B (Pharmacia) according to the manufacturer's instructions. Total plant protein extracts (300 µg) were incubated with 50 µl 50% (v/v) p13$^{suc1}$-Sepharose beads for 2 h at 4° C. The washed beads were combined with 30 µl kinase buffer containing ~1 mg/ml CDC2bDN-IC26M, 150 mM ATP and 1 µCi of [-32P]ATP (Amersham). After 20 minutes of incubation at 30° C., samples were analysed by SDS-PAGE and autoradiographed.

As shown in FIG. 48, the purified CDC2bDN-IC26M protein is phosphorylated by CDKs in vitro.

Example 9

PCR amplification of AtDPb

Based one available sequence data of putative plant DP-related partial clones from the databank (soybean DP (AI939068), tomato DP(AW217514), and cotton DP (AI731675)), three oligonucleotides, corresponding to the most conserved part of the DNA-binding and E2F heterodimerization domains (MKVCEKV, SEQ ID NO:240; LNVLMAMD, SEQ ID NO:241 and FNSTPFEL, SEQ ID NO:242), were synthesized and designated A (ATAGAAT-TCATGAAAGTTTGTGAAAAGGTG, SEQ ID NO:243), B (ATAGAATTCCTGAATGTTCTCATGGCAATGGAT, SEQ ID NO:244) and C (ATAGGATCCCAGCTCAAAAG-GAGTGCTATTGAA, SEQ ID NO:245), respectively.

PCR was performed on an *Arabidopsis*/yeast two-hybrid suspension culture cDNA library. The PCR products were purified, digested with EcoRI and BamHI, and ligated into pCR-XL-TOPO vector (Invitrogen). The cloned inserts were sequenced by double-stranded dideoxy sequencing.

Example 10

Construction of AtDP and AtE2F Mutants, In Vitro Transcription-Translation System and Immunoprecipitation Influenza hemagglutinin (HA)-tagged versions of the wild-type and mutant AtE2Fa and AtE2Fb were constructed by cloning into the pSK plasmid (Stratagene) containing the HA-tag (SEQ ID NO:202). The AtE2F mutants, namely AtE2Fa 1-420 (SEQ ID NO:217), AtE2Fa 162-485 (SEQ ID NO:218), and AtE2Fb 1-385 (SEQ ID NO:206), were obtained by PCR and cloned into the EcoRI and BamHI sites of HA-pSK. The c-myc (SEQ ID NO:200)-tagged versions of wild-type and AtDP mutants (AtDPa 1-292, SEQ ID NO:114; AtDPa 121-292, SEQ ID NO:211; AtDPa 1-142, SEQ ID NO:208; AtDPa 172-292, SEQ ID NO:213; AtDPa 121-213, SEQ ID NO:212; and AtDPb 1-385, SEQ ID NO:127; AtDPb 182-385, SEQ ID NO:216; AtDPb 1-263, SEQ ID NO:223; AtDPb 1-193, SEQ ID NO:214; and AtDPb 182-263, SEQ ID NO:215) were generated by PCR and cloned into the EcoRI and PstI sites of the pBluescript plasmid (Stratagene) containing a double c-myc tag. All cloning steps were carried out according to standard procedures, and the reading frames were verified by direct sequencing.

In vitro transcription and translation experiments were performed using the TNT T7-coupled wheat germ extract kit (Promega) primed with appropriate plasmids for 90 min at 30° C. For immunoprecipitation, 10 μl of the total in vitro translated extract (50 μl) was diluted at 1:5 in Nonidet P40 buffer (50 mM Tris, pH 7.4, 150 mM NaCl, 1% Nonidet P40, 1 mM phenylmethylsulfonyl fluoride, 10 μg/ml leupeptin/aprotinin/pepstatin) and incubated for 2 h at 4° C. with anti-c-myc (9E10; BabCo) or anti-HA (16B12; BabCo) antibodies. Protein-A-Sepharose (40 μl 25% (v/v)) was added and incubated for 1 h at 4° C., then the beads were washed four times with Nonidet P40 buffer. Immune complexes were eluted with 10 μl 2 UI sodium dodecyl sulfate (SDS) sample buffer and analyzed by 10% or 15% SDS-PAGE and by autoradiography.

An overview of the AtDP and AtE2F fragments and their SEQ ID NOs is given in Table 4.

TABLE IV

| CCP or partial CCP | SEQ ID NO amino acid sequence | SEQ ID NO DNA sequence |
|---|---|---|
| AtE2Fa 226-356 | 205 | 228 |
| AtE2Fb 1-385 | 206 | |
| AtE2Fb 1-127 | 207 | |
| AtDPa 1-142 | 208 | |
| AtDPa 42-142 | 209 | |

TABLE IV-continued

| CCP or partial CCP | SEQ ID NO amino acid sequence | SEQ ID NO DNA sequence |
|---|---|---|
| AtDPa 42-292 | 210 | |
| AtDPa 121-292 | 211 | 229 |
| AtDPa 121-213 | 212 | |
| AtDPa 172-292 | 213 | |
| AtDPb 1-193 | 214 | |
| AtDPb 182-263 | 215 | 230 |
| AtDPb 182-385 | 216 | 231 |
| AtE2Fa 1-420 | 217 | |
| AtE2Fa 162-485 | 218 | |
| AtE2Fa 1-38 | 219 | |
| AtDPa 1-214 | 220 | 239 |
| AtDPa 143-292 | 221 | 232 |
| AtDPa 143-213 | 222 | 233 |
| AtDPb 1-263 | 223 | 234 |
| AtE2Fa 232-282 | 224 | 235 |
| AtE2Fa 232-352 | 225 | 236 |
| AtE2Fb 194-243 | 226 | 237 |
| AtE2Fb 194-311 | 227 | 238 |

Example 11

Figure 50:
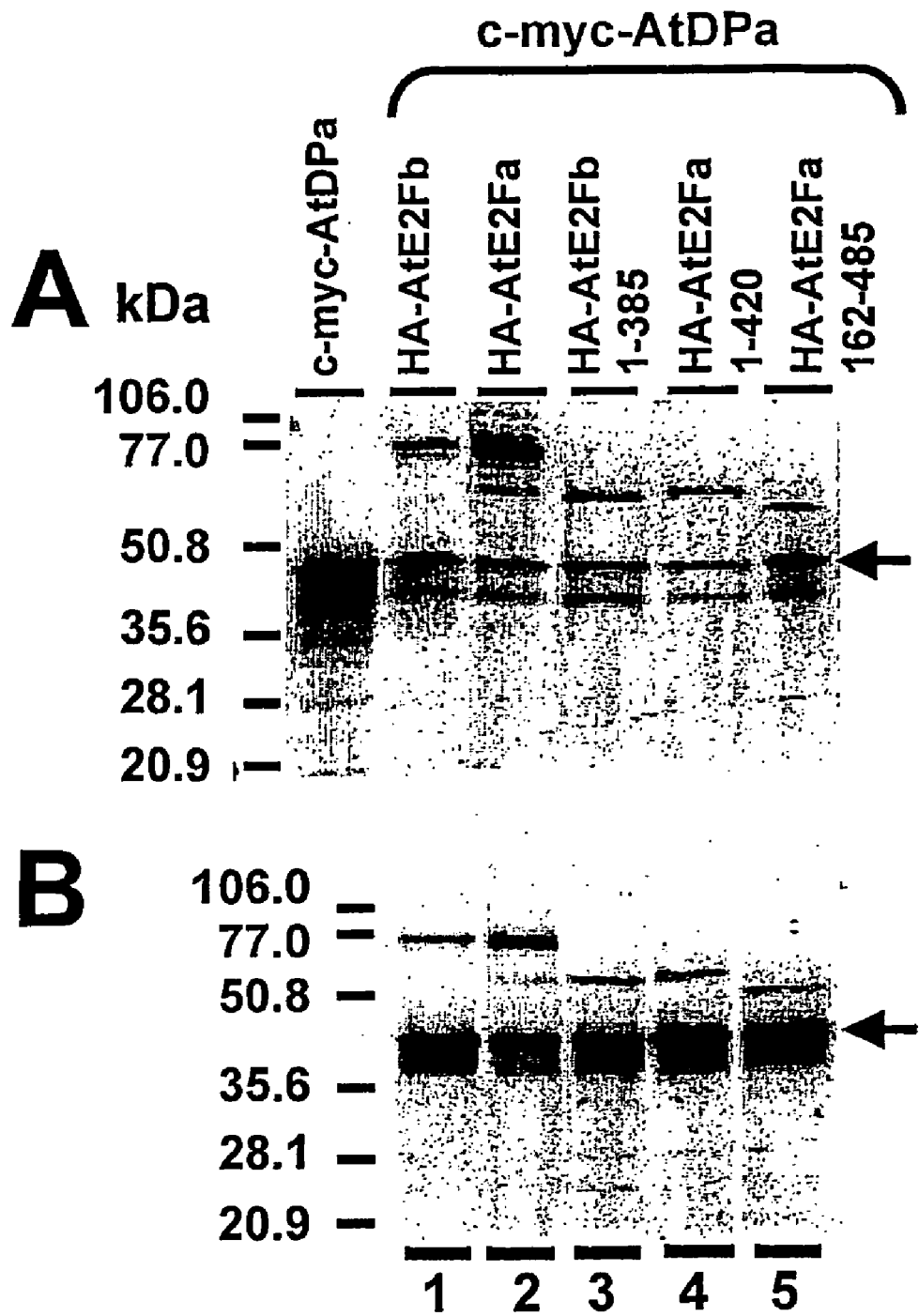
FIG. 50 depicts AtDPa in vitro interactions with AtE2Fa and AtE2Fb. The c-myc-tagged AtDPa (c-myc-AtDPa) was in vitro translated and used as control. The lower migrating proteins observed in the case of c-myc-AtDPa are most probably due to initiation of translation at internal methionine codons (panel A, unnumbered left lane). The c-myc-AtDPa was in vitro co-translated with HA-AtE2Fb (panels A and B, lane 1), HA-AtE2Fa (panels B, lane 2), the C-terminal deleted form of HA-AtE2Fb (panels A and B, lane 3), HA-AtE2Fa 1-420 (panels A and B, lane 4) and the N-terminal truncated form of HA-AtE2Fa 162-485 (panels A and B, lane 5) as indicated. Numbers in the case of the mutant AtE2Fs refer to the amino acid sequence contained in these constructs (see FIG. 49). An aliquot of each sample was analyzed directly by SDS-PAGE and autoradiographed (panel A; total IVT, total in vitro translation). Another aliquot of the same samples was subjected to immunoprecipitation with anti-c-myc monoclonal antibodies (panel B), lanes are indicated by numbering. The position of c-myc-AtDPa proteins are marked by arrows in both panels. Molecular mass markers are indicated at the left.
Figure 51:
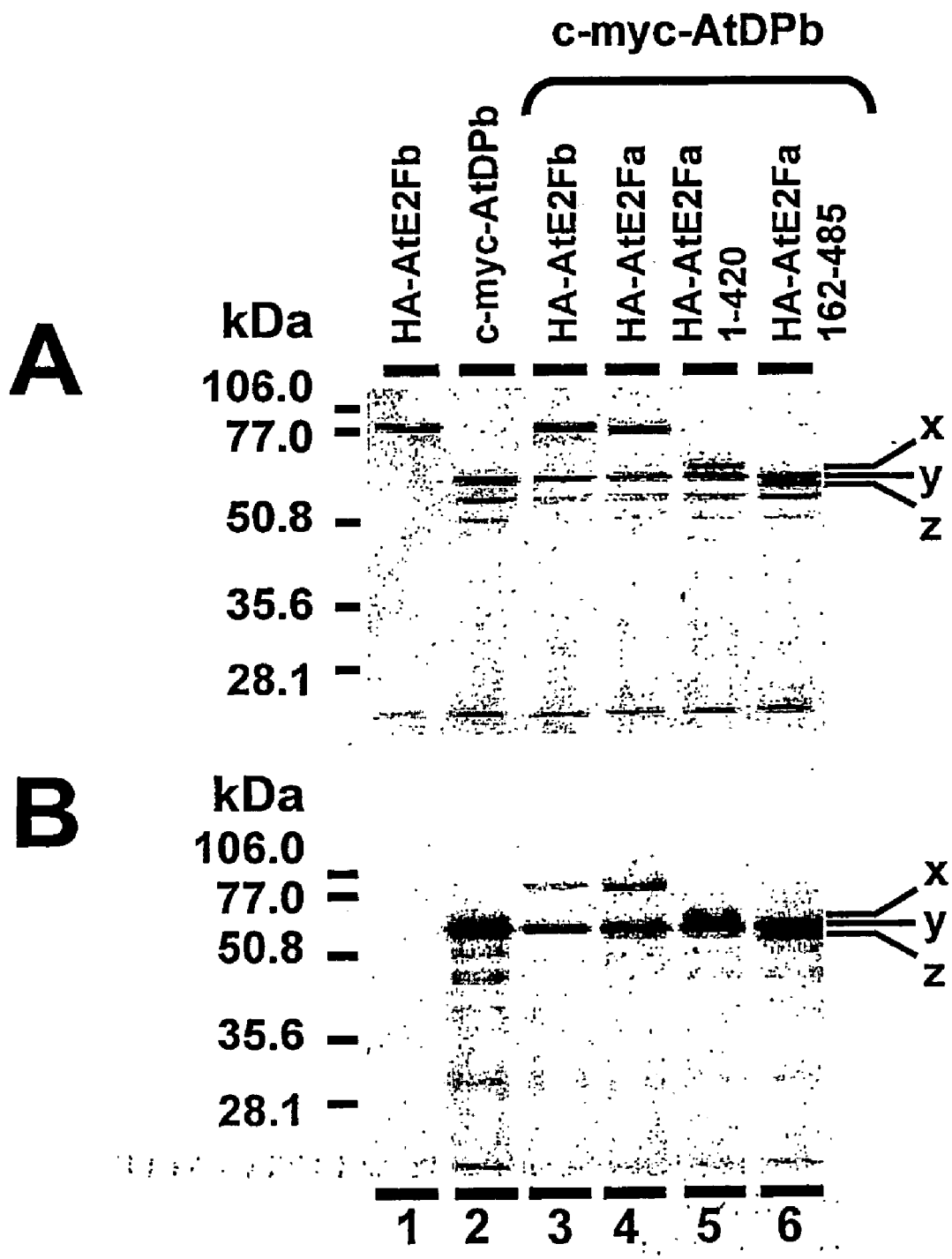
FIG. 51 shows AtDPb in vitro interactions with AtE2Fa and AtE2Fb. The c-myc-tagged AtDPb (c-myc-AtDPb, panels A and B, lane 2) and the HA-tagged AtE2Fb (HA-AtE2Fb, panels A and B, lane 1) were in vitro translated and used as controls. The lower migrating proteins observed in the case of c-myc-AtDPb are most probably due to initiation of translation at internal methionine codons (panel A, lane 2). The c-myc-AtDPb was in vitro co-translated with HA-AtE2Fb (panels A and B, lane 3), HA-AtE2Fa (panels A and B lane 4), HA-AtE2Fa 1-420 (panels A and B, lane 5) and the N-terminal truncated form of HA-AtE2Fa 162-485 (panels A and B, lane 6) as indicated. Numbers in the case of the mutant AtE2Fs refer to the amino acid sequence contained in these constructs (see FIG. 49). An aliquot of each sample was analyzed directly by SDS-PAGE and autoradiographed (panel A; total IVT, total in vitro translation). Another aliquot of the same samples was subjected to immunoprecipitation with anti-c-myc monoclonal antibodies panel B), lanes are indicated by numbering. The c-myc-AtDPb (panels A and B, lanes 2-6; indicated with 'y') co-migrated almost exactly with the mutant HA-AtE2Fa 1-420 (panels A and B, lane 5; indicated with 'x') and HA-AtE2Fa 162-485 (panels A and B, lane 6; indicated with 'z') in the gel system. These polypeptides as well as the position of c-myc-AtDPa and c-myc-AtDPb proteins are marked by arrows marked with 'y', 'x' and 'z', respectively (cfr. supra). Molecular mass markers are indicated at the left.

In Vitro Interaction Between AtDPs, AtE2Fs and Mutants Thereof Illustrated by Immunoprecipitation Experiments The AtDPa and AtDPb can efficiently interact in vitro with AtE2Fa and AtE2Fb. As a first step in comparing the biochemical properties of AtDPa and AtDPb, the ability of these molecules to heterodimerize with AtE2Fa and AtE2Fb was tested. For this purpose, the coupled in vitro transcription-translation system was used in which the c-myc-tagged AtDPa or AtDPb was co-expressed with the HA-tagged AtE2Fa or AtE2Fb. One part of each sample was resolved by SDS-PAGE (FIGS. 50 and 51, panels A), while another part was subjected to immunoprecipitation with monoclonal anti-c-myc antibodies (FIGS. 50 and 51, panels B). In the absence of DP proteins, no AtE2F2a or AtE2F2b was precipitated by the anti-c-myc antibodies (FIG. 51, panel B, lane 1). However, both HA-AtE2F proteins co-precipitated reproducibly with c-myc-tagged AtDPa (FIG. 50, panel B, lanes 1 and 2) and AtDPb (FIG. 51, panel B, lanes 3 and 4). Identical results were obtained in a reciprocal experiment with anti-HA monoclonal antibodies. These data revealed that both *Arabidopsis* DP-related proteins interacted in vitro with the different *Arabidopsis* E2F-related proteins.

Figure 52:
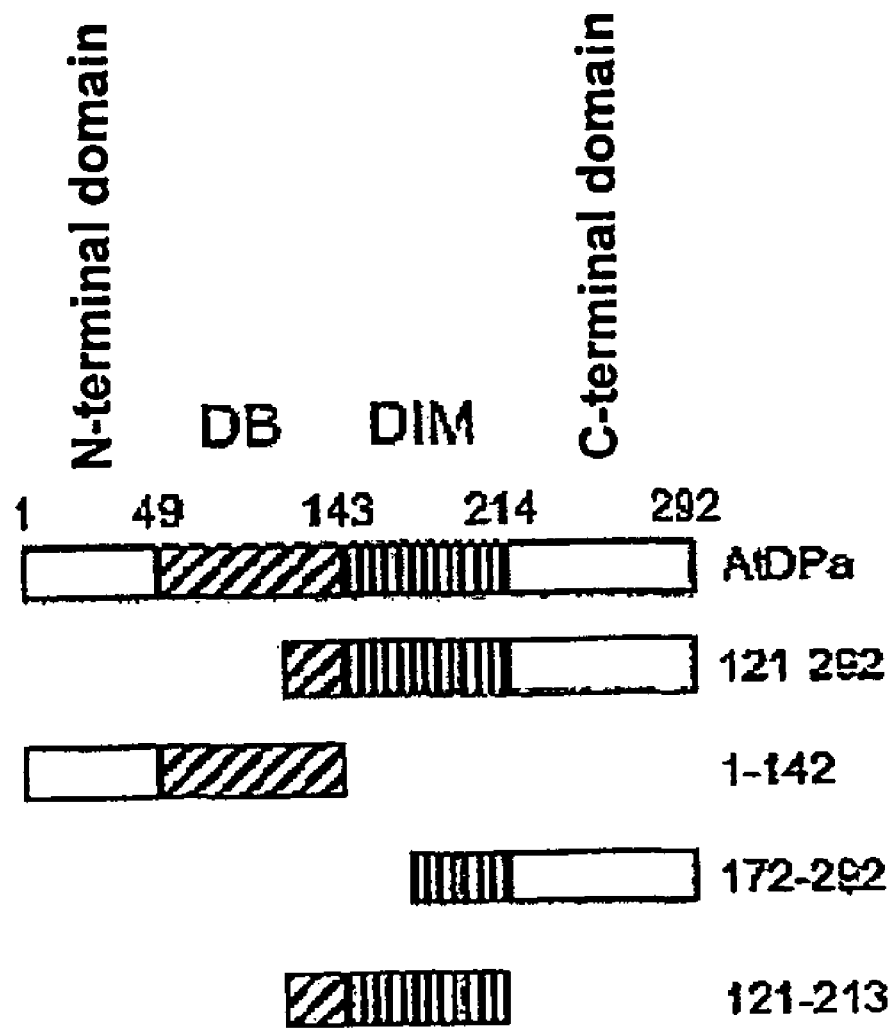
FIG. 52 schematically represents AtDPa and mutants. The DNA-binding domain (DB) and the dimerization domain (DIM) are indicated by marked boxes, N- and C-terminal regions are indicated by open boxes. Numbering on the right side refers to the amino acid sequence contained in the different AtDP constructs, which were used in the in vitro binding assays.
Figure 53:
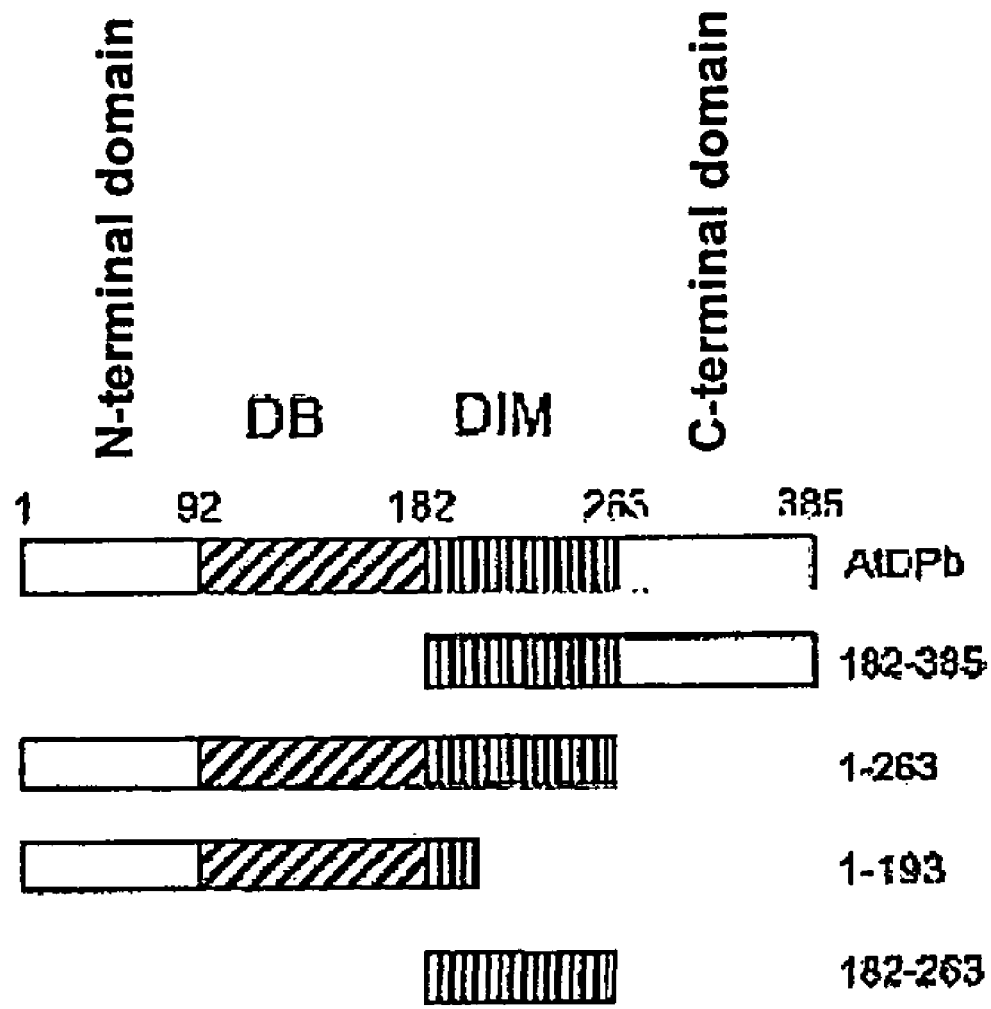
FIG. 53 schematically represents AtDPb and mutants. The DNA-binding domain (DB) and the dimerization domain (DIM) are indicated by marked boxes, N- and C-terminal regions are indicated by open boxes. Numbering on the right side refers to the amino acid sequence contained in the different AtDP constructs, which were used in the in vitro binding assays.
Figure 54:
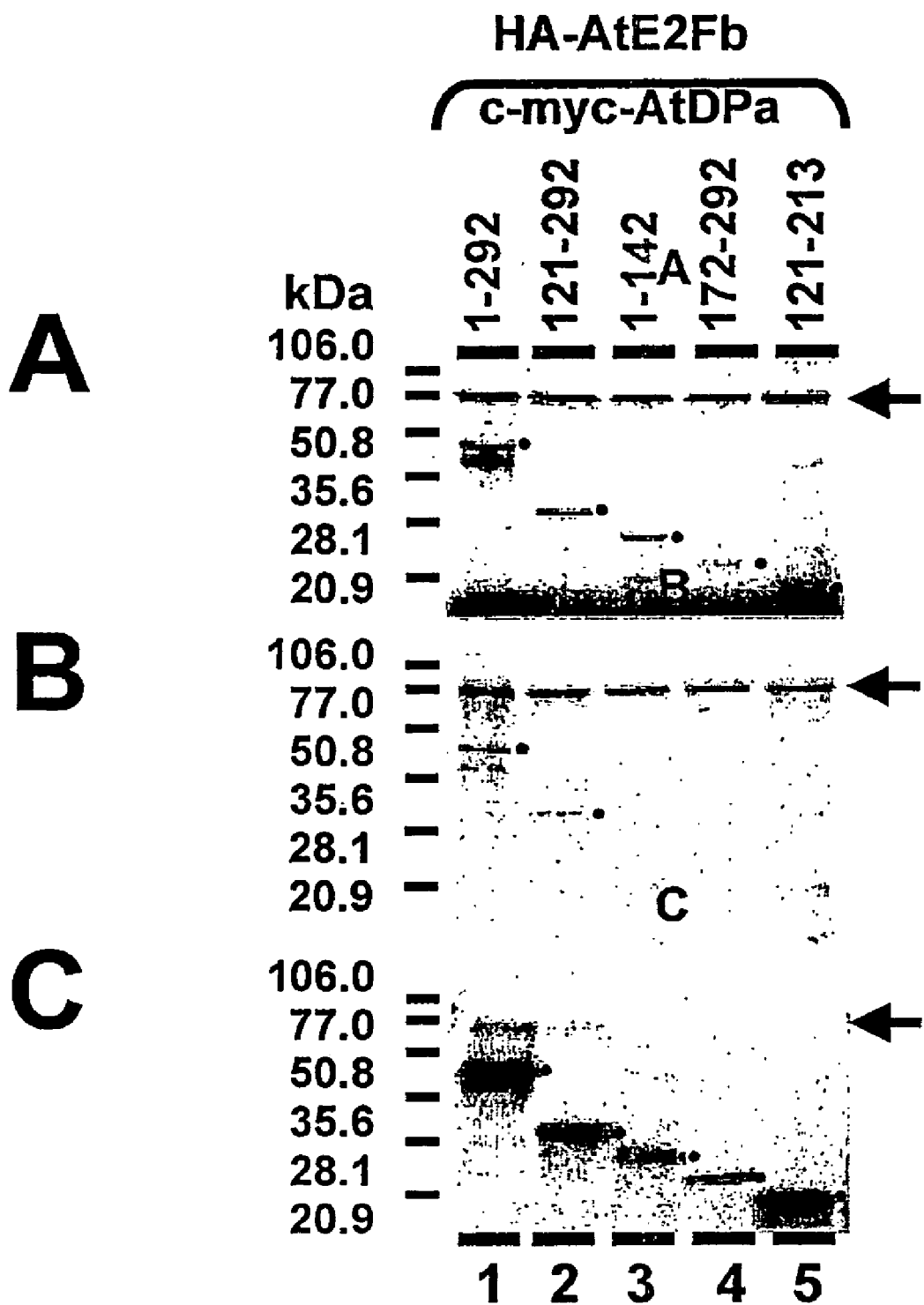
FIG. 54 shows the mapping of regions in AtDPa required for in vitro binding to AtE2Fb. HA-AtE2Fb was co-translated with series of c-myc-AtDPa mutants. An aliquot of each sample was analyzed directly by SDS-PAGE and autoradiographed (panel A). Another aliquot of the same samples was subjected to immunoprecipitation with anti-HA (panel B) or anti-c-myc (panel C) monoclonal antibodies. The c-myc-AtDPa mutants are marked by dots. Positions of the HA-AtE2Fb proteins are indicated by arrows. Molecular mass markers are indicated at the left.
Figure 55:
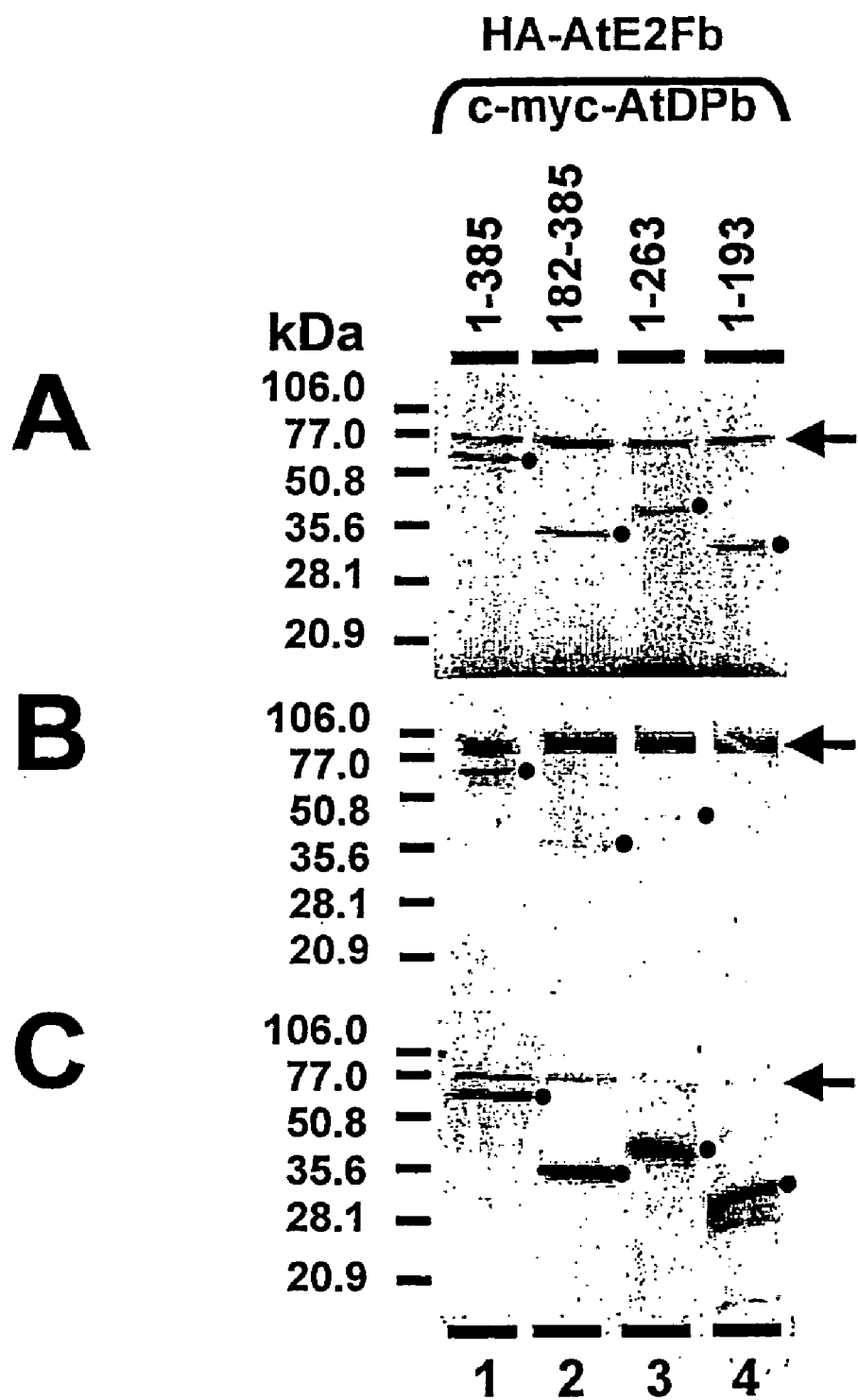
FIG. 55 shows the mapping of regions in AtDPb required for in vitro binding to AtE2Fb. HA-AtE2Fb was co-translated with series c-myc-AtDPb mutants. An aliquot of each sample was analyzed directly by SDS-PAGE and autoradiographed (panel A). Another aliquot of the same samples was subjected to immunoprecipitation with anti-HA (panel B) or anti-c-myc (panel C) monoclonal antibodies. The c-myc-AtDPb mutants are marked by dots. Positions of the LA-AtE2Fb proteins are indicated by arrows. Molecular mass markers are indicated at the left.

The conserved dimerization domain of the AtE2Fs seemed to be important for the interaction with the AtDPs, because mutational analysis showed that deletion neither of the N-terminal extension nor the C-terminal part of AtE2Fa and AtE2Fb impaired the interaction with the DPs (FIGS. 50 and 51, panels B). Similar results were obtained by two-hybrid analysis (see Table 5 of Example 12). To test whether the structural requirements for heterodimerization of the AtDPs were similar to those of their animal homologs, several deletion mutants of AtDPa and AtDPb were constructed (for a schematic illustration, see FIGS. 52 and 53), tagged with the c-myc epitope (FIGS. 54 and 55, panels A). The interactions between the mutant AtDPs and AtE2Fb were analyzed in immunoprecipitation experiments with the specific anti-HA or anti-c-myc antibodies (FIGS. A6 and A7, panels B and C, respectively). As shown in FIGS. 54 and 55, mutant AtDP proteins with deleted DNA-binding domain could bind sufficiently to the co-translated HA-AtE2Fb proteins (FIG. 54, panel C, lane 2; and FIG. 55, panel C, lane 2). No detectable interaction was found between the AtE2Fb protein and mutant DP proteins containing the complete DNA-binding domain, but lacking the putative dimerization domain (FIG. 54, panel C, lane 3; FIG. 55, panel C, lane 4). Thus, the N-terminal part of both AtDP proteins, including the conserved DNA-binding domain, was not sufficient for the in vitro interaction to occur. In contrast, a mutant form of AtDPb (amino acids 1-263; SEQ ID NO:223) could bind to AtE2Fb (FIG. 55, panel C, lane 3), indicating that the region of AtDPb between amino acids 182 and 263 was required for interaction with AtE2Fb.

Figure 56:
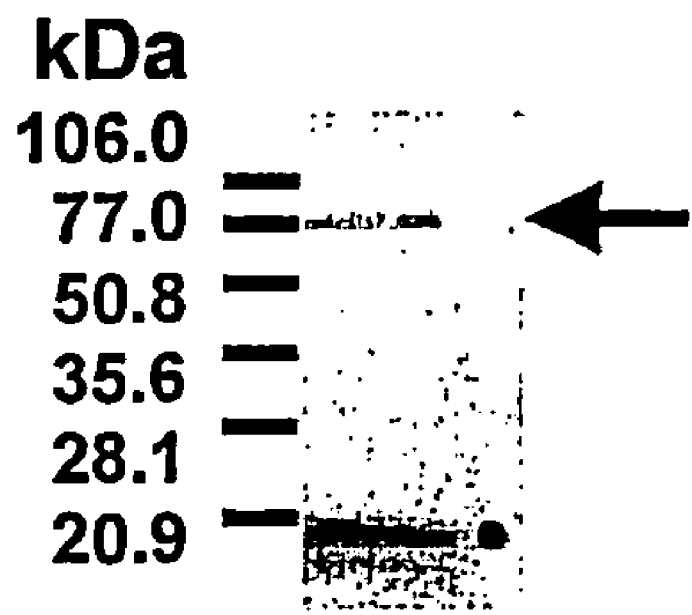
FIG. 56 shows the mapping of regions in AtDPb required for in vitro binding to AtE2Fb. HA-AtE2Fb was co-translated with c-myc-AtDPb 182-263. Because of the small size of this protein, it was hardly detectable when it was directly analyzed by SDS-PAGE (data not shown). An aliquot of this sample was subjected to immunoprecipitation with anti-c-myc monoclonal antibodies. The c-myc-AtDP mutant is marked by dots. Position of the HA-AtE2Fb protein is indicated by an arrow. Molecular mass markers are indicated at the left.

To confirm this hypothesis, a deletion mutant of AtDPb (182-263, SEQ ID NO:215) was constructed and, as expected, it could bind to AtE2Fb (FIG. 56). The requirement for the homologous dimerization domain of AtDPa for the interaction with AtE2Fb was supported by a binding assay in which the mutant AtDPa 172-292 (SEQ ID NO:213), with the N-terminal part of the dimerization domain deleted, failed to bind to AtE2Fb (FIG. 54, panels B and C, lanes 4). However, when the E2F-binding activity of the predicted dimerization domain of the AtDPa (amino acid positions 121-213, SEQ ID NO:212) was tested, no interaction could be detected between this region and the AtE2Fb protein (FIG. 54, panel B, lane 5). These data indicate that other carboxyl-terminal regions of AtDPa are required for the stable interaction with AtE2Fb.

Example 12

Yeast Two-Hybrid Experiments for Showing Interaction Between DP and E2F Mutants

For library screening, vectors and strains (HF7c) were provided with the Matchmaker two-hybrid system (Clontech). The dimerization and DNA-binding domains of the AtE2Fa (amino acids 226-356; SEQ ID NO:205) were amplified by polymerase chain reaction (PCR) and subcloned in-frame with the GAL4 DNA-binding domain of pGBT9 (Clontech) to create the bait plasmid pGBTE2Fa226-356. Screens were performed as described previously (De Veylder et al. 1999; Planta 208, 453-462). A second library screening was performed with the AtE2Fb construct (pGBTE2Fb-Rb) lacking the Rb-binding domain (amino acids 1-385; SEQ ID-NO:206). Plasmids from interacting clones were isolated and sequenced.

For the yeast two-hybrid interaction experiments, a number of yeast two-hybrid prey (in pAD-GAL424) plasmids were created by PCR amplification of fragments from the AtDPa (DPa 1-292, SEQ ID NO:114; DPa 1-142, SEQ ID NO:208; DPa 42-142, SEQ ID NO:209; DPa 42-292, SEQ ID NO:210; DPa 121-292, SEQ ID NO:211; DPa 121-213, SEQ ID NO:212; and DPa 172-292, SEQ ID NO:213) and AtDPb (DPb 1-385, SEQ ID NO:127; DPb 1-193, SEQ ID NO:214; DPb 182-263, SEQ ID NO:215; and DPb 182-385, SEQ ID NO:216) genes and confirmed by sequencing. Different combinations between bait (pGBTE2Fa226-356, pGBTE2Fb-Rb, or pGBTE2Fb 1-127, SEQ ID NO:207) and prey constructs were transformed into yeast cells and assayed for their ability to grow on His minimal media after 3 days of incubation at 30° C. Bait plasmids co-transformed with empty pAD-GAL424 and prey plasmids co-transformed with empty pGBT9 were assessed along as controls for the specificity of the interaction.

An overview of the AtDP and AtE2F fragments and their SEQ ID NOs is given in Table 4.

The results obtained were confirmed by two-hybrid interaction analysis. pGBTE2Fa226-356 and pGBTE2Fb-Rb were co-transformed in an appropriate yeast reporter stain with a plasmid producing the full-length AtDPa or AtDPb protein fused to the GAL4 transactivation domain. The specific reconstitution of GAL4-dependent gene expression measured as the ability to grow in the absence of histidine confirms the interaction between the two DP and E2F proteins (Table 5).

TABLE V

AtDPs and AtE2Fs interaction in yeast two-hybrid assays.

| Baits | Preys | | | | | | | | | | | | |
|---|---|---|---|---|---|---|---|---|---|---|---|---|---|
| | DPa 1-292 | DPa 1-142 | DPa 42-142 | DPa 42-292 | DPa 121-292 | DPa 121-213 | DPa 172-292 | DPb 1-385 | DPb 1-193 | DPb 182-263 | DPb 182-385 | E2Fa 226-356 | pAD-GAL424 |
| pGBT E2Fa 226-356 | + | − | − | + | + | − | − | + | − | + | + | − | − |
| pGBT E2Fb-Rb | + | − | − | + | + | − | − | + | − | + | + | − | − |
| pGBT E2Fb 1-127 | − | NT | NT | NT | NT | NT | NT | − | NT | NT | NT | − | − |
| pGBT DPa 1-292 | − | NT | NT | NT | NT | NT | NT | − | NT | NT | NT | + | − |
| pGBT DPb 1-385 | NT | NT | NT | NT | NT | NT | NT | − | NT | NT | NT | + | − |
| pBGT9 | − | − | − | − | − | − | − | − | − | − | − | − | − |

Different combinations between AtE2Fs bait and AtDPs prey constructs were tested for growth on His⁻ minimal media.
−, no interaction;
+, positive interaction;
NT, not tested.

Example 13

RNA Isolation and Reverse Transcription-(RT)-PCR Analysis of AtDP and AtE2F Expression

*A. thaliana* (L.) Heynh. cell suspension cultures were maintained as described previously (Glab et al. 1994, FEBS Lett. 17, 207-211). The cells were partially synchronized by the consecutive addition of aphidicolin (5 µg/ml) and propyzamide (1.54 µg/ml). The aphidicolin block was left for 24 hours. The cells were washed for 1 hour in B5 medium before the addition of propyzamide. Samples were taken at the end of the 24 hour aphidicolin block, at the end of a 1 hour washing step, and at 1, 2, 3, and 4 hours after the addition of propyzamide to the culture medium. Total RNA was isolated from the *Arabidopsis* cell suspension culture according to Magyar et al. (1997), Plant Cell 9, 223-235, and with the Triazol reagent (Gibco/BRL) from different organs. Semi-quantitative RT-PCR amplification was carried out on reverse-transcribed mRNA, ensuring that the amount of amplified product stayed in linear proportion to the initial template present in the reaction. 10 µl from the PCR was transferred onto Hybond-N/membrane, hybridized to fluorescein-labeled gene-specific probes (Gene-Images random prime labeling module; Amersham Pharmacia Bio-tech), detected with the CDP-Star detection module (Amersham), and visualized by short exposure to Kodak X-OMAT autoradiography film.

The following primer pairs (forward and reverse) were used for the amplification: 5'-ATAGAATTCATGTCCGGT-GTCGTACGA-3' (SEQ ID NO:249, EcoRI site underlined) and 5'-ATAGGATCCCACCTCCAATGTTTCTGCAGC-3' (SEQ ID NO:250, BamHI site underlined) for AtE2Fa (GenBank accession number AJ294533); 5'-ATAGAATTC-GAGAAGAAAGGGCAAT CAAGA-3' (SEQ ID NO:251, EcoRI site underlined) and 5'-ATACTGCAGAGAAATCTC-GATTCGACTAC-3' (SEQ ID NO:252, PstI site underlined) for AtDPa (GenBank accession number AJ294531); 5'-GC-CACTCTCATAGGGTTCTC CATCG-3' (SEQ ID NO:253) and 5'-GGCATGCCTCCAAGATCCTTGAAGT-3' (SEQ ID NO:254) for Arath;CDKA;1 (Genbank accession number X57839); 5'-GGGTCTTGGTCGTTTTACTGTT-3' (SEQ ID NO:255) and 5'-CCAAGACGATGACAACAGATACAGC-3' (SEQ ID NO:256) for Arath;CDKB1;1 (Genbank accession number X57840); 5'-ATAAACTAAATCTTCGCT-GAA-3' (SEQ ID NO:257) and 5'-CAAACGCGGATCTGAAAAACT-3' (SEQ ID NO:258) for histone H4 (Genbank accession number M17132); 5'-TCTCTCTTCCAAATCTCC-3' (SEQ ID NO:259) and 5'-AAGTCTCT CACTTTCTCACT-3' (SEQ ID NO:260) for ROC5 (AtCYP1, GenBank accession number U072676) (Chou and Gasser 1997, Plant Mol. Biol. 35, 873-892); 5'-CTAAGCTCTCAAGATCAAAGGCTTA-3' (SEQ ID NO:261) and 5'-TTAACATTG CAAAGAGTTTCAAGGT-3' (SEQ ID NO:262) for actin 2 gene (GenBank accession number U41998) (An et al. 1996, Plant J. 10, 107-121).

Example 14

Figure 57:
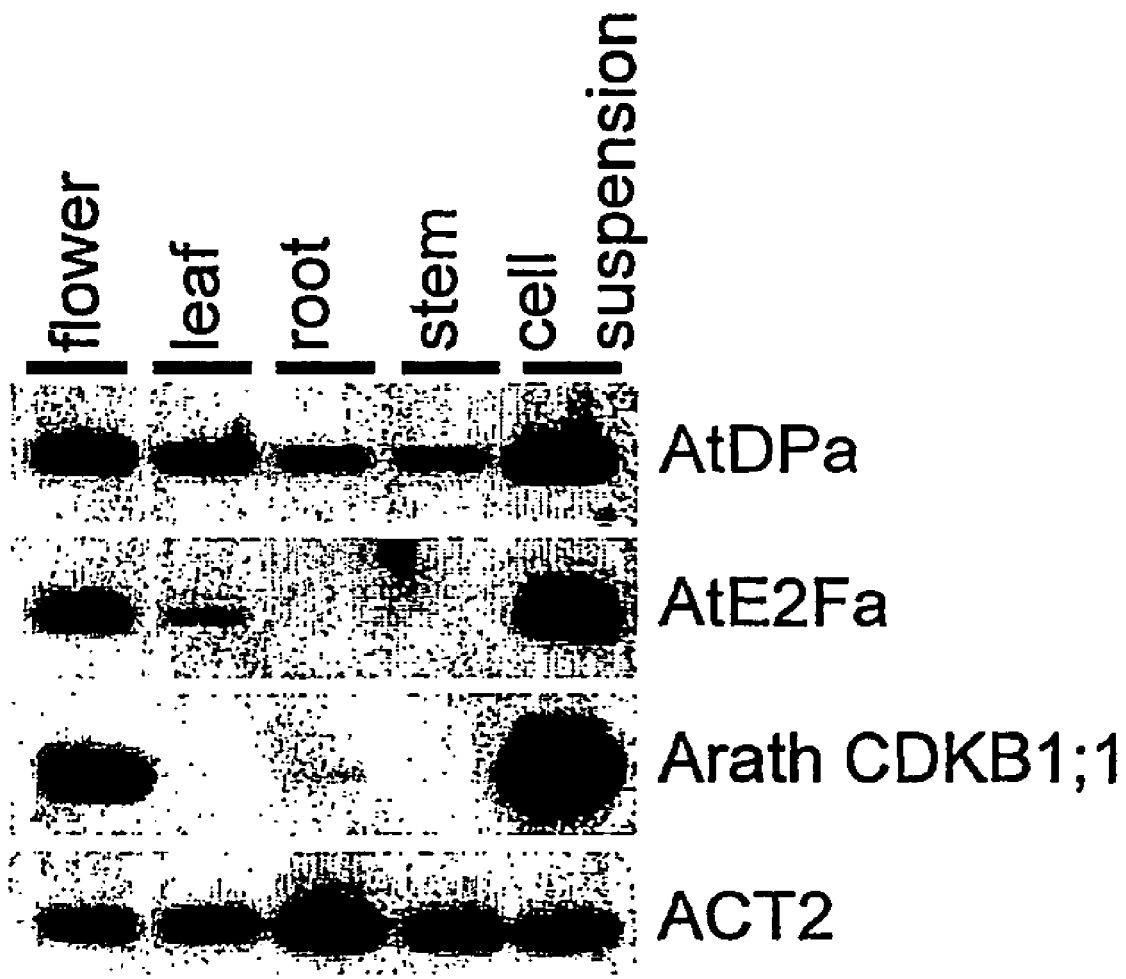
FIG. 57 shows organ- and cell cycle-specific expression of AtE2Fa and AtDPa. Tissue-specific expression of AtDPa and AtE2Fa genes. cDNA prepared from the indicated tissues was subjected to semi-quantitative RT-PCR analysis. The Arath; CDKB1;1 gene was used as a marker for highly proliferating tissues. The actin 2 gene (ACT2) was used as loading control.
Figure 58:
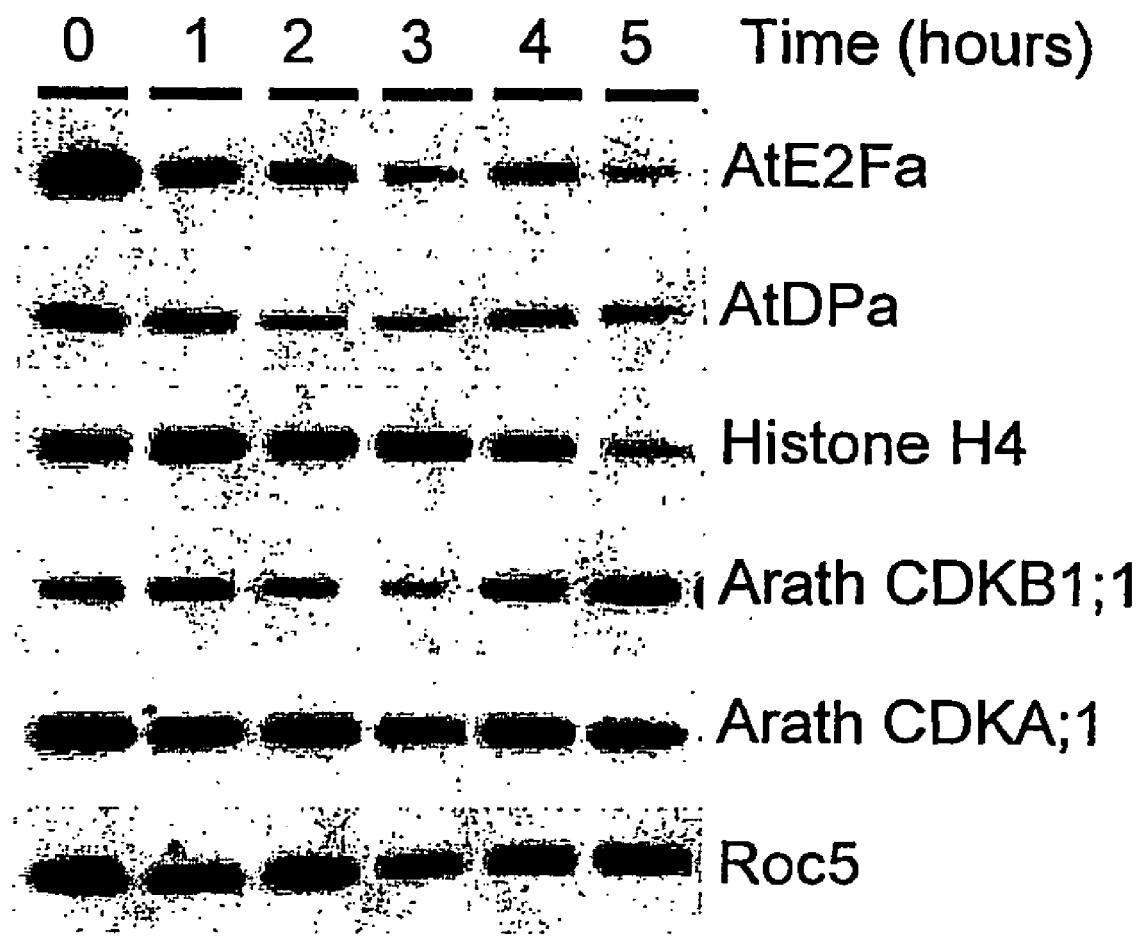
FIG. 58 shows organ- and cell cycle-specific expression of AtE2Fa and AtDPa. Co-regulated cell cycle phase-dependent transcription of AtE2Fa and AtDPa The cDNA was prepared from partially synchronized *Arabidopsis* cells harvested at the indicated time point after removal of the cell cycle blocker was subjected to semi-quantitative RT-PCR analysis. Histone H4 and Arath;CDKB1;1 were used as markers for S and G2/M phase, respectively, and ROC5 and Arath;CDKA;1 as loading controls.

The AtDPa and the AtE2Fa Genes are Co-Expressed in a Cell Cycle Phase-Dependent Manner The identification of the AtDPa in a yeast two-hybrid screen as a gene encoding an AtE2Fa-associating protein indicated that it might act cooperatively in the plant cells as a functional heterodimer. To strengthen this hypothesis, we investigated whether both genes were co-regulated at the transcriptional level. Tissue-specific expression analysis revealed that both genes were clearly up-regulated in flowers and were very strongly transcribed in actively dividing cell suspension cultures (FIG. 57). Expression in these tissues could be a sign for the correlation between the actual proliferation activity of a given tissue and the transcript accumulation, as can be seen from the Arath;CDKB1;1 gene. AtDPa transcripts were also detectable in leaf and, to a lesser extent, in root and stem tissues, whereas AtE2Fa transcripts were virtually undetectable in roots and stem with only slight levels of expression in leaf tissues. Cell cycle phase-dependent gene transcription was studied using an *Arabidopsis* cell suspension that was partially synchronized by the sequential treatment with aphidicolin and propyzamide. The *Arabidopsis* histone H4 and the Arath;CDKB1:1 gene were included to monitor the cell cycle progression (FIG. 58) (Chaubet et al. 1996, Plant J. 10, 425-435; Segers et al. 1996, Plant J. 10, 601-612). Bearing in mind the partial synchronization of the culture, it can be observed that histone H4 transcript levels peaked immediately after the removal of the inhibitor and decrease gradually thereafter (FIG. 58). The opposite expression pattern could be observed for the Arath;CDKB1;1 gene, illustrating that cells entered the G2-M phases with partial synchrony. Within this experimental setting, the AtDPa and the AtE2Fa genes show a very similar expression pattern. Both exhibit higher transcript accumulation before the peak of histone H4 gene expression and quickly decay in the following samples (FIG. 58). The similarity in the expression patterns of *Arabidopsis* AtDPa and AtE2Fa supports the possibility that they act cooperatively as a heterodimer during the S phase.

Example 15

Transformation of *Arabidopsis thaliana* with CaMV35S::DPa

Figure 59:
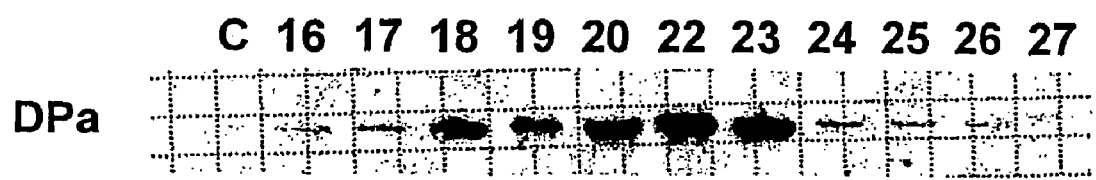
FIG. 59 is a photographic representation of Northern blotting analysis of DPa expression in independent *Arabidopsis thaliana* DPa overexpressing lines (lines 16-27 as indicated) and one untransformed control line (indicated by C).

Arabidopis plants were transformed (using the in planta flower dip method; Clough and Bent, *Plant J.* 16:735-743, 1998) with a construct containing the DPa gene under the control of the CaMV 35S promoter. The lines were molecularly analysed by northern blotting. As can be seen in FIG. 59, all lines showed increased DPa levels in comparison with the untransformed control. Generally, two classes of lines were observed: weakly expressing (e.g., 16) and strongly expressing (e.g., 23) lines (see FIG. 59). The plants are subsequently analyzed for phenotypic alterations as described herein.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for increasing yield and/or improving growth characteristics of a plant relative to a corresponding control plant, comprising introducing into a plant cell, plant or part thereof a CCP modulator nucleic acid molecule, and selecting for a plant or part thereof having increased yield and/or improved growth characteristics relative to a corresponding control plant; wherein said CCP modulator nucleic acid molecule comprises
   i) a nucleic acid molecule comprising the nucleotide sequence of SEQ ID NO: 56;
   ii) a nucleic acid molecule encoding a polypeptide comprising the amino acid sequence of SEQ ID NO: 122; or
   iii) a nucleic acid molecule encoding a polypeptide comprising an amino acid sequence having at least 95% sequence identity to the amino acid sequence of SEQ ID NO: 122 and having the activity of SEQ ID NO: 122.

2. The method of claim 1, wherein the CCP modulator comprises the nucleotide sequence of SEQ ID NO: 56 or a nucleic acid molecule encoding a polypeptide comprising the amino acid sequence of SEQ ID NO: 122.

3. The method of claim 1, wherein the plant is a monocot plant.

4. The method of claim 1, wherein the plant is a dicot plant.

5. The method of claim 1, wherein the plant is selected from the group consisting of Arabidopsis thaliana, rice, wheat, maize, tomato, alfalfa, oilseed rape, soybean, sunflower, and canola.

6. A method for modulating the growth of a plant relative to a corresponding control plant, said method comprising introducing into a plant cell, plant or part thereof a CCP modulator such that the growth of the plant or part thereof is modulated relative to a corresponding control plant, said CCP modulator comprising
   i) a nucleic acid molecule comprising the nucleotide sequence of SEQ ID NO: 56;
   ii) a nucleic acid molecule encoding a polypeptide comprising the amino acid sequence of SEQ ID NO: 122; or
   iii) a nucleic acid molecule encoding a polypeptide comprising an amino acid sequence having at least 95% sequence identity to the amino acid sequence of SEQ ID NO: 122 and having the activity of SEQ ID NO: 122.

7. The method of claim 6, wherein the CCP modulator comprises a nucleic acid molecule encoding a polypeptide comprising the amino acid sequence of SEQ ID NO: 122.

8. The method of claim 6, wherein said nucleic acid sequence comprises SEQ ID NO: 56.

9. The method of claim 6, wherein the CCP modulator comprises a nucleic acid molecule encoding a polypeptide comprising an amino acid sequence having at least 95% sequence identity to the amino acid sequence of SEQ ID NO: 122.

10. The method of claim 6, wherein said CCP modulator comprises a nucleic acid molecule encoding a polypeptide comprising an amino acid sequence having at least 98% sequence identity to the amino acid sequence of SEQ ID NO: 122.

11. The method of claim 1, further comprising obtaining a plant, part of the plant or progeny thereof having increased yield and/or improved growth characteristics relative to a corresponding control plant or part thereof.

12. The method of claim 6, further comprising obtaining a plant, part of the plant or progeny thereof having increased yield and/or improved growth characteristics relative to a corresponding control plant or part thereof.

13. A transgenic plant, part of the plant, or progeny thereof obtained by the method of claim 1, wherein the plant, part of the plant, or progeny thereof comprises the nucleic acid molecule and has increased yield and/or improved growth characteristics relative to a corresponding control plant or part thereof.

14. A transgenic plant, part of the plant or progeny thereof obtained by the method of claim 6, wherein the plant, part of the plant or progeny thereof comprises the nucleic acid molecule and has increased yield and/or improved growth characteristics relative to a corresponding control plant or part thereof.

* * * * *

SEQUENCE LISTING

<160> NUMBER OF SEQ ID NOS: 290

<210> SEQ ID NO 1
<211> LENGTH: 1255
<212> TYPE: DNA
<213> ORGANISM: Arabidopsis thaliana

<400> SEQUENCE: 1

```
ccacatatcc gtgatgagga aactaagaaa ccagactcag tttcaagtga agaaccagag      60
acgattatca ttgatgtgga tgaaagtgat aaagaaggag gtgactctaa tgagccaatg     120
tttgtacaac atactgaagc aatgctggag gagattgaac agatggagaa ggagattgaa     180
atggaagatg cagacaaaga agaagagcct gtgatcgata ttgatgcctg tgataagaat     240
aatcctttgg ctgcggttga atatatccat gatatgcata ccttctacaa gaattttgag     300
aaacttagtt gcgtgcctcc taactatatg gacaatcaac aagatcttaa tgagagaatg     360
agaggaatcc tcattgactg gttaattgag gtgcactaca agtttgaact gatgagggaa     420
actctttatc tcacaatcaa tgtcatcgac agattccttg cggttcatca aatcgtgagg     480
aaaaagcttc agcttgttgg tgttactgct ttgttgcttg catgtaaata tgaagaagtt     540
tcagttccag tggtagatga tctcatcttg atctctgaca aagcttactc tagaagagaa     600
gtgctagata tggagaagct aatggccaac accttgcaat tcaatttctc tctaccaact     660
ccatatgttt tcatgaaacg atttctcaaa gctgcccaat ctgacaagaa gcttgagatt     720
ttatcattct ttatgatcga gctttgcctt gtggagtatg agatgctaga gtatcttcca     780
tctaagctgg cggcctcagc aatctacact gctcagtgta cacttaaggg atttgaagaa     840
tggagcaaaa cctgtgagtt tcacacaggc tacaacgaaa acagctact ggcatgtgcg     900
agaaagatgg ttgctttcca tcacaaggca ggaacaggga agctcacagg agttcacaga     960
aagtacaaca catctaagtt ctgtcatgct gcaagaactg aaccagctgg gtttctgatt    1020
taatattaat aagaatctaa tatgacttaa ctcgagtttt tctttagaac aaaaagagtg    1080
tgagagaaag agatagta gagcaagttg cccaaaatgg gagaagaatg gatctttaga     1140
tatcatggca agtagcccaa aaagagtgta ttcttctctt tctaaggtct ttagatcttt    1200
cttcacttga gagagaataa aaagaatctt ctgaaaaaaa aaaaaaaaaa aaaaa         1255
```

<210> SEQ ID NO 2
<211> LENGTH: 471
<212> TYPE: DNA
<213> ORGANISM: Arabidopsis thaliana

<400> SEQUENCE: 2

```
cccgattcgg gtactgctgc tggtgggtca aactccgacc cgtttcctgc gaatcttcga      60
gttcttgtcg ttgatgatga tccaacttgt ctcatgatct tagagaggat gcttatgact     120
tgtctctaca gagtaactaa atgtaacaga gcagagagcg cattgtctct gcttcggaag     180
aacaagaatg gttttgatat tgtcattagt gatgttcata tgcctgacat ggatggtttc     240
aagctccttg aacacgttgg tttagagatg gatttacctg ttatcatgat gtctgcggat     300
gattcgaaga gcgttgtgtt gaaaggagtg actcacggtg cagttgatta cctcatcaaa     360
ccggtacgta ttgaggcttt gaagaatata tggcaacatg tggtgcggaa gaagcgtaac     420
cgagtggaat ggttctgaac attctggagg aagtattgaa gatactggcg g              471
```

<210> SEQ ID NO 3
<211> LENGTH: 1351
<212> TYPE: DNA
<213> ORGANISM: Arabidopsis thaliana

<400> SEQUENCE: 3

```
atggggaagg aaaatgctgt gtctcggcca ttcactcgtt cccttgcctc tgctttgcgc      60
gcttcagaag tgacttctac tacacagaat caacagagag taaacacaaa aagaccagcc     120
```

-continued

| | |
|---|---|
| ttggaggata caagagccac tggacccaac aagaggaaga agcgagcggt tctaggggag | 180 |
| atcacaaatg ttaactccaa tacagctata cttgaggcca aaaacagcaa gcagataaag | 240 |
| aaaggacgcg tcatggatt ggcgagtaca tcccagttgg caacttctgt tacttcagaa | 300 |
| gtcacagatc ttcagtccag gaccgatgca aaagttgaag ttgcatcaaa tacagcagga | 360 |
| aacctttctg tttctaaagg cacagataac acagctgata actgtattga gatatggaat | 420 |
| tctagattgc ctccaagacc tcttgggaga tcagcttcta cagctgagaa aagtgctgtt | 480 |
| attggtagtt caactgtacc ggatatccca aaatttgtag acatcgattc agatgacaag | 540 |
| gatcctttac tgtgctgcct ctatgcccct gaaatccact acaatttgcg tgtttcagag | 600 |
| cttaaacgca gaccacttcc ggactttatg agagaatac agaaggatgt cacccagtcc | 660 |
| atgcggggaa ttctggttga ttggcttgtg gaggtctctg aagaatacac acttgcatct | 720 |
| gacactctct acctcacagt gtatctcata gactggttcc tccatggaaa ctacgtgcaa | 780 |
| agacagcaac ttcaactgct cggcatcact gcatgctaa ttgcctcgaa gtatgaggaa | 840 |
| atctctgctc cacgcattga ggagttttgc ttcattacgg ataacaccta cacaagagat | 900 |
| caggtcctgg aaatggagaa ccaagtactt aagcatttta gctttcaaat atacactccc | 960 |
| actccaaaaa cgttccttag agatttctc agagcagctc aagcctctcg cctgagccca | 1020 |
| agccttgaag tcgagtttct agccagctat ctaacagagt tgacattaat agactaccat | 1080 |
| ttcttaaagt ttcttccttc cgttgttgct gcttcagcgg ttttctcgc caagtggaca | 1140 |
| atggaccaat caaccaccc atggaatcca acacttgagc attacacaac gtacaaagca | 1200 |
| tcggatctga aagcatctgt tcatgcctta caagatctgc agcttaacac caaaggttgc | 1260 |
| cccttgagcg ctatacgcat gaagtatagg caagagaaat acaaatctgt ggcggttctc | 1320 |
| acgtctccaa agctacttga cacgctattc t | 1351 |

<210> SEQ ID NO 4
<211> LENGTH: 672
<212> TYPE: DNA
<213> ORGANISM: Arabidopsis thaliana

<400> SEQUENCE: 4

| | |
|---|---|
| atggggaaga gtgtgatttt atgtaacggt gttgcaagaa tgtattgcga gtcagatcaa | 60 |
| gctagtttat gttgggattg cgacggtaaa gttcacggcg ctaatttctt ggtagctaaa | 120 |
| cacacgcgtt gtcttctctg tagcgcttgt cagtctctta cgccgtggaa agctactggg | 180 |
| cttcgtcttg gcccaacttt ctccgtctgc gagtcatgcg tcgctcttaa aaacgccggc | 240 |
| ggtggccgtg gaaacagagt tttatcggag aatcgtggtc aggaggaggt taatagtttc | 300 |
| gagtccgaag aagatcggat tagagaagat cacggtgacg gtgacgacgc ggagtcttac | 360 |
| gatgatgatg aggaagaaga tgaggatgaa gagtacagcg acgatgagga tgaggatgat | 420 |
| gatgaggatg tgatgatga ggaagcggag aatcaagttg tgccgtggtc tgcggcggcg | 480 |
| caagttcctc cggtgatgag ttcttcatct tctgacggag gaagcggagg ttcagtgacg | 540 |
| aagaggacga gggctagaga gaattcagat cttctctgct ccgatgatga gatcggaagc | 600 |
| tcttcagctc aagggtcaaa ctattctcgg ccgttgaagc gatcggcgtt taaatcaacg | 660 |
| gttgttgttt aa | 672 |

<210> SEQ ID NO 5
<211> LENGTH: 1287
<212> TYPE: DNA
<213> ORGANISM: Arabidopsis thaliana

<400> SEQUENCE: 5

```
atggttaact catgcgagaa caaaatcttc gttaaaccca cttcaacgac gattcttcaa    60
gatgaaacaa gaagtagaaa attcggacaa gagatgaaga gggagaagag aagagtgttg   120
cgtgtgatta accagaatct cgctggtgca agagtttatc cttgtgttgt caacaagaaa   180
ggaagcttat tgtctaataa gcaagaagaa gaagaaggat gtcaaaagaa gaagtttgat   240
tctttgcgtc cttcagttac aagatctgga gttgaggaag agactaacaa gaagctgaag   300
ccctcagttc aagtgctaac gacttcggt gattgtatat ttattgatga ggaggaagct   360
acattggacc ttccaatgcc aatgtcgctt gagaaaccat acattgaagc tgatccaatg   420
gaagaagttg agatggagga tgtaacagtg gaagaaccga tcgtggatat cgatgtctta   480
gactcgaaga actcgcttgc ggctgttgaa tatgttcaag atcttacgc atttacaga    540
acaatggaga gatttagttg tgttccagta gactatatga tgcaacaaat cgacttaaac   600
gagaagatga gagcaatact aatcgactgg ttaatcgagg tacatgacaa gtttgatctg   660
atgaacgaga cactgtttct gacagtgaat ctgatagata gattcttgtc caagcaaaat   720
gttatgagaa gaagcttca gcttgtaggg ttagtagctt tgctgttagc ttgtaagtat   780
gaggaggttt cggttcctgt tgtcgaagat ttagtactca tttcggacaa agcgtatacg   840
aggaacgatg ttctagagat ggagaaaaca atgttgagta cttttgcaatt caatatctcg   900
ttaccgacac aatacccgtt cttgaaaaga ttcctcaagg cagctcaagc agacaagaag   960
tgtgaggtct tggcgtcgtt cttgatcgag cttgcccttg tggagtacga gatgcttcgg  1020
tttccaccat cattactagc tgccacatct gtgtacactg ctcaatgtac acttgatggt  1080
tccaggaaat ggaacagtac atgtgaattc cattgtcatt actctgaaga ccagctcatg  1140
gaatgttcac ggaagctggt gagtctgcat cagagggcgg cgacaggaaa cttaacagga  1200
gtatatagga agtacagcac aagcaaattt ggttacatag caaaatgtga agctgcacac  1260
tttctagtgt ctgagtctca tcattct                                      1287
```

<210> SEQ ID NO 6
<211> LENGTH: 1078
<212> TYPE: DNA
<213> ORGANISM: Arabidopsis thaliana

<400> SEQUENCE: 6

```
actaagcagg aggccaaagc tgctttcaag tctcttttgg aatctgtaaa tgttcattcc    60
gactggacat gggaacagac attgaaagag attgttcacg ataaaagata tggtgctttg   120
aggacactcg gcgagcggaa acaagcgttt aacgagtatc ttggccaaag gaaaaaagtg   180
gaagctgaga aagacgaag gaggcagaag aaagctcggg aagaatttgt caagatgcta   240
gaggagtgtg aagaacttc atcatccctg aaatggagca aagcaatgag tttgttcgaa   300
aatgatcagc gttttaaagc tgttgaccgt cctaggatc gtgaagatct ttttgacaat   360
tacattgtgg aacttgagag gaaggaaaga gaaaaggcag cggaggaaca tcggcagtat   420
atggcagact atcggaagtt tcttgaaacc tgtgactata tcaaagctgg tacacaatgg   480
cgcaaaattc aagatagact ggaggatgat gacagatgct catgtcttga aaagatagat   540
cgtctgattg ttttgaggaa atacattctt gacctagaga aggaagaaga gagctgaag   600
agagtagaga agaacatgt aaggcgggcc gagagaaaaa accgtgatgc atttcgtaca   660
ctattggaag aacatgttgc tgcaggcatc cttacagcca agacgtactg gttggattat   720
tgcattgagt taaaagactt gccccaatac caagctgttg catctaatac atctggttca   780
```

```
actccgaaag acttgtttga agatgtcaca gaagaattag agaagcagta tcatgaggat    840
aagagctatg tgaaggatgc tatgaagtca agaaagattt ccatggtctc ctcgtggctg    900
tttgaagatt ttaaatctgc tatttcagaa gatctcagta ctcaacagat atcagacata    960
aatttaaagc ttatatatga tgacttggtt gggagagtga aggaaaaaga agaaaaagag   1020
gccagaaagc ttcagcgtct ggctgaagaa tttaccaatc tgttgcacac tttcaagg    1078
```

```
<210> SEQ ID NO 7
<211> LENGTH: 511
<212> TYPE: DNA
<213> ORGANISM: Arabidopsis thaliana

<400> SEQUENCE: 7
caagagaaac cgtgggagaa tgatcctcac tactttaaac gagtcaagat ctcagcgctc     60
gctcttctta agatggtggt tcacgctcgc tctggtggta caattgaaat aatgggtctt    120
atgcaaggta agaccgatgg tgatactatc attgttatgg atgcttttgc tttaccagtg    180
gaaggtactg agacaagggt taatgctcag gatgatgctt atgagtacat ggttgagtat    240
tcacagacca acaagctcgc ggggccggct ggagaatgtt gttggatggt atcactctca    300
ccctggatat ggatgctggc tctccggtat tgatgtttct acgcagaggc ttaaccaaca    360
gcatcaggag ccattttag ctgttgttat tgatcccaca aggactgttt cagctggtaa    420
ggttgagatt ggtgctttca gaacatactc taaaggatat aaagccctcc agatgaacct    480
gtttctgagt atcaaaacta ttcctttaaa t                                   511
```

```
<210> SEQ ID NO 8
<211> LENGTH: 1155
<212> TYPE: DNA
<213> ORGANISM: Arabidopsis thaliana

<400> SEQUENCE: 8
agtagactca cctgattcaa cctccgacaa catcttctac tacgacgata cttcacagac     60
taggttccag caagagaaac cgtgggagaa tgatcctcac tactttaaac gagtcaagat    120
ctcagcgctc gctcttctta agatggtggt tcacgctcgc tctggtggta caattgaaat    180
aatgggtctt atgcaaggta agaccgatgg tgatactatc attgttatgg atgcttttgc    240
tttaccagtg gaaggtactg agacaagggt taatgctcag gatgatgctt atgagtacat    300
ggttgagtat tcacagacca acaagctcgc ggggcggctg agaatgttg ttggatggta    360 tcactctcac cctggatatg gatgctggct ctccggtatt gatgtttcta cgcagaggct    420
taaccaacag catcaggagc cattttagc tgttgttatt gatcccacaa ggactgtttc    480
agctggtaag gttgagattg gtgctttcag aacatactct aaaggatata agcctccaga    540
tgaacctgtt tctgagtatc aaactattcc tttaaataag attgaggact tggtgttca    600 ctgcaaacag tactattcat tagatgtcac ttatttcaag tcatctcttg attctcacct    660
tctggatcta ctatggaaca gtactgggt gaacactctt tcttcttctc cactgctggg    720
taatggagac tatgttgctg acaaatatc agcttagct gagaagcttg agcaagccga    780
gagtcatctg gttcagtctc gctttggagg agttgtgcca tcatcccttc ataagaaaaa    840
agaggatgag tctcaactaa ctaagataac tcgggtagc gcaaagataa ctgtggaaca    900
ggtccatgga ctaatgtcgc aggtcataaa agatgaatta ttcaactcaa tgcgtcagtc    960
caacaacaaa tctcccactg actcgtcgga tccagaccct atgattacat attgaagttg   1020
ctcttctttt ggtttctagt tttggattga cccatcattt gttgtccttt catttatttt   1080
```

```
ctgttgtgta aagaattata atgctaatca gaataataca gaagaagatt ttggttaaaa      1140
aaaaaaaaaa aaaaa                                                        1155

<210> SEQ ID NO 9
<211> LENGTH: 1308
<212> TYPE: DNA
<213> ORGANISM: Arabidopsis thaliana

<400> SEQUENCE: 9
atgtattgct cttcttcgat gcatccaaat gcaaacaaag aaaatatctc tacttcagat        60
gtacaggaga gttttgtacg aataacgaga tcacgagcta aaaaagccat gggaagagga       120
gtatcaatac ctccaacaaa accttctttt aaacagcaaa agagacgtgc agtacttaag       180
gatgtgagta atacctctgc agatattatt tattcagaac ttcgaaaggg aggcaacatc       240
aaggcaaaca gaaaatgtct aaaagagcct aaaaagcag caaggaagg tgctaacagt        300 gccatggata ttctggtaga tatgcataca gaaaaatcaa aattagcaga agatttgtcc       360
aagatcagga tggctgaagc ccaagatgtc tctctttcaa actttaaaga tgaagaaatt       420
actgagcaac aagaagatgg atcaggtgtc atggagttac ttcaagttgt agatattgat       480
tccaacgtcg aagatccaca gtgttgcagc ttgtatgctg ctgatatata tgacaacata       540
catgttgcag agcttcaaca acgacccttg gctaattata tggagcttgt gcagcgagat       600
atcgacccag acatgagaaa gattctgatt gactggcttg tagaagtttc tgacgactac       660
aagctggttc cagatacgct ttaccttaca gtgaatctta tcgaccggtt tctgtccaac       720
agttacattg aaaggcaaag actccagctc cttggtgtct cttgcatgct tatagcttca       780
aaatatgaag agctttccgc accagggtg gaggagtttt gcttcattac ggccaacaca       840
tacacaagac gagaagtgct gagcatggag attcaaattc taaattttgt gcactttaga       900
ttatcggttc ctaccaccaa acatttctg aggcggttca ttaaagcagc tcaagcttcg       960
tacaaggtgc ctttcattga actggagtat ttagcaaact atctcgccga attgacactg      1020
gtggaatata tgtttcctaag gttcctgcca tcactaattg ctgcttcagc tgttttccta      1080
gcccgatgga cactcgacca aactgaccat ccttggaacc ctactctgca acactacacc      1140
agatatgagg tagctgagct gaagaacaca gttctcgcca tggaggactt gcagctcaac      1200
accagtggct gtactctcgc tgccacccgt gagaaataca accaaccaaa gtttaagagc      1260
gtggcaaagc tgacatctcc caaacgagtc acattactat tctcaaga                   1308

<210> SEQ ID NO 10
<211> LENGTH: 1006
<212> TYPE: DNA
<213> ORGANISM: Arabidopsis thaliana

<400> SEQUENCE: 10
agacttcaca ttttaccatt atttgctctg agctcagtag agagttcaa gaaacaatgg         60 caaagatgca attatcaatc tttatcgctg tcgttgcgct tatcgtctgc tctgcatctg       120
ctaaaaccgc aagccctcca gctccagtgc tgccaccgac accagctcca gcaccagccc       180
cggaaaatgt gaatctcacc gagcttttaa gtgtagctgg tccgttccac acattcctcg       240
actaccttct ctcgactgga gtcattgaga ctttccaaaa ccaagctaac aacactgagg       300
aaggcatcac aatctttgtc cctaaagatg atgctttcaa agctcagaag aatcctcctt       360
tgtcaaatct cacaaaggat cagcttaagc agcttgttct cttccatgct ctgcctcatt       420
actattcgct ttcggaattc aagaacttga gccaatctgg tccagtgagc acctttgctg       480
```

```
gtggtcaata ctccttgaaa ttcactgatg tttctggcac ggttaggatt gattctttat      540
ggaccaggac taaagtcagc agcagtgttt tctccactga ccctgttgcg gtttaccaag      600
tgaaccgcgt gcttctaccc gaagcaatct ttggtactga tgtccctcca atgcctgctc      660
cagctcctgc tcctatcgtt agtgctcctt cggattctcc ttcagttgct gattctgaag      720
gagcttcttc accaaagtcc tcacacaaga actccggaca aaagctgcta cttgcaccaa      780
tctccatggt tatttccggt tggtggcat tgttcttgtg atcagatggt tttgcagatt       840
gagttatgtt tttaagttac aatgtgaaag attgtattac atcatttgaa ttgtcttttt      900 gattttgaa acccattttt tattatacat ttttatcatt attattgttt gtcattacga       960
ttgttgtgaa ttgaaattgt tcctccaaaa aaaaaaaaaa aaaaaa                    1006
```

<210> SEQ ID NO 11
<211> LENGTH: 643
<212> TYPE: DNA
<213> ORGANISM: Arabidopsis thaliana

<400> SEQUENCE: 11

```
atttatcatt acagtctgat ttgagctaag ttctctcatc ataaactctc cttggagaat       60
catggctatt tcaaaagctc ttatcgcttc tcttctcata tctcttcttg ttctccaact      120
cgtccaggct gatgtcgaaa actcacagaa gaaaaatggt tacgcaaaga agatcgattg      180
tgggagtgcg tgtgtagcac ggtgcaggct ttcgaggagg ccgaggctgt gtcacagagc      240
gtgcgggact gctgctaca ggtgcaactg tgtgcctccg ggtacgtacg gaaactacga       300
caagtgccag tgctacgcta gcctcaccac ccacggtgga cgccgcaagt gcccataaga      360
agaaacaaag ctcttaattg ctgcggataa tgggacgatg tcgtttttgtt agtatttact     420 ttggcgtata tatgtggatc gaataataaa cgagaacgta cgttgtcgtt gtgagtgtga     480
gtactgtatt attaatggtt ctatttgttt ttacttgcaa gttttcttgt tttgaatttg     540 ttttttttcat atttgtatat cgattcgtgc attattgtat tatttcaatt tgtaataaga    600
ttatgttacc tttgagtggt tgtttaaaaa aaaaaaaaa aaa                         643
```

<210> SEQ ID NO 12
<211> LENGTH: 484
<212> TYPE: DNA
<213> ORGANISM: Arabidopsis thaliana

<400> SEQUENCE: 12

```
aaggaagaag caggaatgta ttggggatac aaagtacgat atgcatcaca attaagttca       60
gtattcaagg aatgcccttt cgagggtggt tacgattatt tgattggtac ctcggagcac      120
ggcctggtaa ttagttcatc tgagctgaaa ataccaacat ttaggcacct attgattgca      180
tttggtggac ttgctgggct tgaagaaagt attgaagatg ataatcagta taggggaaa      240 aacgttcgag atgtgtttaa tgtatacttg aatacttgtc cacatcaagg tagccgaacc      300
attcgagcag aggaagcgat gtttatatca cttcagtact tccaggaacc catcagcagg      360
gcagtgagaa gactttaagc ttcgataaaa agagtcaaag aagctatttt gttctctcatag    420 atctgaggtt tgtctgaaaa agagtgatgt aatgtaactg ttttagaaaa aaaaaaaaaa      480
aaaa                                                                    484
```

<210> SEQ ID NO 13
<211> LENGTH: 688
<212> TYPE: DNA
<213> ORGANISM: Arabidopsis thaliana -continued

<400> SEQUENCE: 13

```
agatggggaa gaagaacaag agaagtcaag acgagtctga gctcgaattg gagccagagc        60
taacgaaaat aatcgatgga gactctaaaa agaagaaaaa taagaataag aagaagagaa       120
gccatgaaga tacggagata gaaccggagc aaaagatgag tctcgacgga gactcgaggg       180
aggagaagat aaagaagaag aggaagaaca agaaccaaga ggaggagcca gagcttgtga       240
cggagaaaac gaaagtccaa gaggaggaaa agggaaatgt agaagagggt agagccactg       300
ttagcatagc catagctggt tcaatcatcc acaacactca atcacttgag ctcgccacac       360
gcgtaatctc tctttctctc tatctctccc ttcgtttctc tgttttttcca ttcccagata      420
atttaaagtc cccttcttcc atttctaaca tttctcagct cgccggccaa attgctcgtg       480
cagctacaat tttccgaatc gacgagatcg tagtgttcga caataagagc agctcagaaa       540
tcgaatcagc tgctacgaat gcttctgata gcaatgaaag tggtgcctcc tttctcgttc       600
gtatcttgaa gtatctagag acaccacaat atttgaggaa atctctcttc cccaagcaaa       660
atgatcttag atatgtgggt atgttgcc                                          688
```

<210> SEQ ID NO 14
<211> LENGTH: 461
<212> TYPE: DNA
<213> ORGANISM: Arabidopsis thaliana
<220> FEATURE:
<221> NAME/KEY: misc_feature
<222> LOCATION: (396)..(396)
<223> OTHER INFORMATION: n = a, c, g or t

<400> SEQUENCE: 14

```
gtcagtgctg tctggcatgg actgtatcct ggatacatta tattctttgt gcaatcagca        60
ttgatgatcg atggttcgaa agctatttac cggtggcaac aagcaatacc tccgaaaatg       120
gcaatgctga gaaatgtttt ggttctcatc aatttcctct acacagtagt ggttctcaat       180
tactcatccg tcggtttcat ggttttaagc ttgcacgaaa cactagtcgc cttcaagagt       240
gtatattaca ttggaacagt tatacctatc gctgtgcttc ttctcagcta cttagttcct       300
gtgaagcctg ttagaccaaa gaccagaaaa gaagaataat gttgtctttt taaaaaatca       360
acaacatttt ggttcttttc tttttttcca cttggnccgt tttatgtaaa acaagagaaa       420
tcaagatttg aggttttatt cttaaaaaaa aaaaaaaaa a                            461
```

<210> SEQ ID NO 15
<211> LENGTH: 862
<212> TYPE: DNA
<213> ORGANISM: Arabidopsis thaliana
<220> FEATURE:
<221> NAME/KEY: misc_feature
<222> LOCATION: (292)..(292)
<223> OTHER INFORMATION: n = a, c, g, or t
<220> FEATURE:
<221> NAME/KEY: misc_feature
<222> LOCATION: (294)..(294)
<223> OTHER INFORMATION: n = a, c, g, or t
<220> FEATURE:
<221> NAME/KEY: misc_feature
<222> LOCATION: (339)..(339)
<223> OTHER INFORMATION: n = a, c, g, or t

<400> SEQUENCE: 15

```
ggtttttgaa tacatggaca ctgatgtcaa gaaattcatc agaagtttcc gtagcactgg        60
caagaacatt ccaacccaaa ctatcaagag cttgatgtat caactatgca aggtatggc       120
attctgccat ggtcacggga tattgcacag agatctcaag cctcacaatc tcttgatgga      180
```

| | |
|---|---|
| tcccaagaca atgaggctca aaatagcaga tcttggttta gccagagcct tcactctgcc | 240 |
| aatgaagaag tatacccatg agatattaac tctttggtat agagctccag angnttcttc | 300 |
| ttggtgccac ccattactct acagctgtgg atatgtggnc tgttggctgc atatttgctg | 360 |
| aacttgtgac caaccaagca atctttcagg gagactctga gctccaacag ctcctccata | 420 |
| ttttcaagtt gttgggacac ccaatgaaga aatgtggcca ggagtgagca cactcaagaa | 480 |
| ctggcatgaa tacccacagt ggaaaccatc gactctatct ctgctgttcc aaacctcgac | 540 |
| gaggctggag ttgatcttct atctaaaatg ctgcagtacg agccagcgaa acgaatatca | 600 |
| gcaaagatgg ctatggagca tccttacttt gatgatctgc cagaaaagtc ctctctctaa | 660 |
| ggatttaaaa tcttcagtta gtatctttcc aagttttatg gttttttctag ttttgcttct | 720 |
| ttcaagcata tctctagtgt gctgcttccc cctctatgaa tcatcctttc tttagcataa | 780 |
| tatatcactt ctgattgttg tttctttcta ttcgaatatt tggattaacg gctttaatgt | 840 |
| tcttaaaaaa aaaaaaaaaa aa | 862 |

<210> SEQ ID NO 16
<211> LENGTH: 1114
<212> TYPE: DNA
<213> ORGANISM: Arabidopsis thaliana

<400> SEQUENCE: 16

| | |
|---|---|
| acccaaaaga aggatgagta tggagatgga gttgtttgtc actccagaga agcagaggca | 60 |
| acatccttca gtgagcgttg agaaaactcc agtgagaagg aaattgattg ttgatgatga | 120 |
| ttctgaaatt ggatcagaga agaaagggca atcaagaact tctggaggcg ggcttcgtca | 180 |
| attcagtgtt atggtttgtc agaagttgga agccaagaag ataactactt acaaggaggt | 240 |
| tgcagacgaa attatttcag attttgccac aattaagcaa aacgcagaga agcctttgaa | 300 |
| tgaaaatgag tacaatgaga agaacataag gcggagagtc tacgatgcgc tcaatgtgtt | 360 |
| catggcgttg gatattattg caagggataa aaaggaaatc cggtggaaag gacttcctat | 420 |
| tacctgcaaa aaggatgtgg aagaagtcaa gatggatcgt aataaagtta tgagcagtgt | 480 |
| gcaaagaag gctgcttttc ttaaagagtt gagagaaaag gtctcaagtc ttgagagtct | 540 |
| tatgtcgaga aatcaagaga tggttgtgaa gactcaaggc ccagcagaag gatttacctt | 600 |
| accattcatt ctacttgaga caaaccctca cgcagtagtc gaaatcgaga tttctgaaga | 660 |
| tatgcaactt gtacacctcg acttcaatag cacacctttc tcggtccatg atgatgctta | 720 |
| cattttgaaa ctgatgcaag aacagaagca ggaacagaac agagtatctt cttcttcatc | 780 |
| tacacatcac caatctcaac atagctccgc tcattcttca tccagttctt gcattgcttc | 840 |
| tggaacctca ggcccggttt gctggaactc gggatccatt gatactcgct gaccgagctt | 900 |
| ctattcccaa attcttcaag aagaagaagt aatgatctaa ttggtatact aaaaaattat | 960 |
| acatctggtt tagtgttcaa ttgagagaga ctgtaaaatc aattcatagg ccaacaaatg | 1020 |
| tttgtttatc caattttcct ttttattcga acttgatgcg atatttcaac ggaaacagaa | 1080 |
| actattgttt taaaccaaaa aaaaaaaaaa aaaa | 1114 |

<210> SEQ ID NO 17
<211> LENGTH: 794
<212> TYPE: DNA
<213> ORGANISM: Arabidopsis thaliana

<400> SEQUENCE: 17

| | |
|---|---|
| aagatgcaac cgacagagac gtcgcagccg gcgccgtcgg atcaaggccg ccggcttaag | 60 |

```
gatcagttat cggagagtat gagcttcagt agccaaatga agaaggaaga cgatgagttg      120
tcgatgaaag ctttgtcggc gttcaaggcc aaagaagagg agatcgagaa agaagagatg      180
gagatcagag aaagagttca agctcagctt ggtcgtgttg aagatgagtc caagcgtctc      240
gctatgattc gcgaggaact tgaaggtttt gctgatccca tgaggaagga agttactatg      300
gtgaggaaga agattgattc tctcgacaaa gaattaaagc cattggggaa tacagttcag      360
aaaaaggaaa cagagtacaa ggatgctctt gaagcattca atgaaaagaa caaggagaag      420
gtggagctga tcaccaagct acaggagttg gagggagaaa gcgagaaatt caggttcaag      480
aagctggagg agctaagcaa gaacattgat ctaaccaaac cttagtgttg gacgagcaga      540
gtcgctggga tttggctatt caagttctaa aaaagtcac tttttagagt attttcattg       600
ttcttttatg attctagtaa tatatataat ttataaaata aaaagtaaga agatatgtgt      660
ttgaactaga tgttgcaaag aaaatgtaac aaagttacga tggcactaca ttatcgacgt      720
gattggcaga attgtaatag taatgtaaag aaactatgtt tgttccggaa aaaaaaaaa      780 aaaaaaaaaa aaaa                                                       794

<210> SEQ ID NO 18
<211> LENGTH: 448
<212> TYPE: DNA
<213> ORGANISM: Arabidopsis thaliana

<400> SEQUENCE: 18
cagaaacaag ctccaggtgc aggtgatgtc ccagcaacaa tccaagaaga ggacgatgat       60
gatgatgtcc cagatcttgt agtgggagag actttcgaga cccctgctac tgaagaggct      120
cccaaagctg ctgcttctta gaggaggagg aagaagaagg agaagagctc acctgcaaaa      180
cccatcataa aaatgtttgt cgctcgacct cttctgagca ctgtcagatt cttgtttttct      240 ctaatgcttg cgaacagaaa gacttggttt tattatcact tgatgctttt tggtccgaac      300
agcaattttc cttttattaa ggttagatcg cttttttgttt accacctgtt caaatgagta      360
ctactatgtc ctgtcgcttc atacacttct tgcaacacag tcctttgttt tgagtcaaaa      420
aaaaaaaaaa aaaaaaaaa aaaaaaaa                                         448

<210> SEQ ID NO 19
<211> LENGTH: 1152
<212> TYPE: DNA
<213> ORGANISM: Arabidopsis thaliana

<400> SEQUENCE: 19
atggaggacg acgacgagat tcagtcaatt ccatctccgg agattcttc ccttcacca        60 caagctcctc cttctccgcc gattttgcca acaaacgacg tgacggtggc cgtcgtgaag      120
aaaccacaac cggggctttc ttctcaatct ccgtccatga acgctttagc gttagtggtt      180
catactcctt ctgtaaccgg tggtggtggt agcggaaaca gaaacggacg aggaggagga      240
ggaggaagcg gtggtggtgg aggaggaaga gatgattgtt ggagcgaaga agctacaaag      300
gttctaatcg aagcttgggg agatcgattc tctgaaccag gtaaggaac tttgaagcaa        360 caacattgga agaagtagc tgagattgtg aacaagagtc gtcaatgcaa ataccctaaa       420
actgatattc agtgtaagaa cagaattgat acggtgaaga agaagtataa gcaagagaaa      480
gctaagattg cttctggtga tggacctagt aaatggggttt tcttcaagaa gcttgagagt     540
ttgattggtg gtactacaac attcattgct tcttcaaaag cttcagagaa ggctcctatg      600
ggaggagctc ttgggaatag ccgttcgagt atgtttaaac ggcaaactaa aggtaatcag      660
```

| | |
|---|---|
| attgtgcagc aacaacaaga gaagagaggc tctgattcga tgcggtggca ttttaggaaa | 720 |
| cgtagtgctt ctgagactga gtctgagtct gatcctgaac ctgaggcttc tcctgaggaa | 780 |
| tctgctgaga gtctcccacc tttgcaaccg attcaaccgc tttcgtttca tatgccaaag | 840 |
| cggttgaagg tggataagag tggaggtgga gggagtggga ttggagatgt ggcgagggcg | 900 |
| atacttggat ttacggaagc ttatgagaag gcggaaactg ctaagcttaa gttaatggcg | 960 |
| gaactggaaa aggagaggat gaaatttgct aaagagatgg agttgcagag aatgcagttc | 1020 |
| ttgaaaactc aattggagat aacacagaac aatcaagaag aggaagagag gagcaggcag | 1080 |
| cgaggagaaa ggaggatcgt tgatgatgat gatgatcgca atggcaagaa taacggcaat | 1140 |
| gtaagtagct ga | 1152 |

<210> SEQ ID NO 20
<211> LENGTH: 409
<212> TYPE: DNA
<213> ORGANISM: Arabidopsis thaliana
<220> FEATURE:
<221> NAME/KEY: misc_feature
<222> LOCATION: (201)..(201)
<223> OTHER INFORMATION: n = a, c, g, or t
<220> FEATURE:
<221> NAME/KEY: misc_feature
<222> LOCATION: (344)..(344)
<223> OTHER INFORMATION: n = a, c, g, or t
<220> FEATURE:
<221> NAME/KEY: misc_feature
<222> LOCATION: (365)..(365)
<223> OTHER INFORMATION: n = a, c, g, or t
<220> FEATURE:
<221> NAME/KEY: misc_feature
<222> LOCATION: (369)..(369)
<223> OTHER INFORMATION: n = a, c, g, or t

<400> SEQUENCE: 20

| | |
|---|---|
| cctccttctc cacgcttctt cttcttcttc ctcaatctct cttacgattc cttcaaatca | 60 |
| ttcttccatg gccaccgtat cttcttcctc ctggccaaac cccaacccta atcccgattc | 120 |
| cacgtctgcc tcagattccg attctacttt tccctctcac cgcgatcgcg tagacgaacc | 180 |
| cgactctctc gattccttct nctccatgag tcttaactcc gacgaaccta atcagacttc | 240 |
| taatcaatcg cctctttctc cccctacgcc caatttaccg gtgatgcctc ctccgttcgt | 300 |
| gctttatctt tcctttaacc aagatcatgc ttgcttcgcc tgtnggcact gaccgtggct | 360 |
| ttacngatnc ttaattgcga tcccttttcgc gagattttcc ggcgggatt | 409 |

<210> SEQ ID NO 21
<211> LENGTH: 758
<212> TYPE: DNA
<213> ORGANISM: Arabidopsis thaliana

<400> SEQUENCE: 21

| | |
|---|---|
| gtcaggctca tgattccaga atagcttgct tcgctctcac gcaggatggc catttgttgg | 60 |
| ccactgctag ctctaagggt actctggttc ggatcttcaa tactgttgat ggtaccttgc | 120 |
| gtcaagaggt aaggaggggt gcggatagag cagagatcta cagtttggcc ttctcttcaa | 180 |
| atgctcagtg gttagctgtc tcaagtgaca aaggaacggt ccatgtcttt ggtctcaaag | 240 |
| tcaactccgg atctcaagtg aaagactcat cccgaattgc acctgatgct actccctcat | 300 |
| ccccatcgtc gtctctgtct ttattcaaag gagtgttacc gaggtatttc agctcggagt | 360 |
| ggtcggtggc tcagttcagg ttggttgaag gaactcagta catagccgcc tttggccatc | 420 |
| aaaagaacac cgttgttatt cttggcatgg atgggagctt ctacagatgc cagtttgatc | 480 |

| | |
|---|---|
| cggtgaacgg cggtgaaatg tctcagcttg agtaccacaa ctgtctgaaa ccgccttcag | 540 |
| ttttctaaaa gctttactac ttatactctt ttgttcctte tetetettta tatctctctg | 600 |
| caacttaagc ggtgagatat ggtgtatagt tttgtgtata taataatgat gggtcgtcct | 660 |
| ataatttgta aaacctttta tcgctacccg ggtcgactct agagccctat agtgagtcgt | 720 |
| attactgcag agatctatga atcgtagata ctgaaaaa | 758 |

<210> SEQ ID NO 22
<211> LENGTH: 624
<212> TYPE: DNA
<213> ORGANISM: Arabidopsis thaliana

<400> SEQUENCE: 22

| | |
|---|---|
| atggactttt gtgaggtatg cccggaaaag cttccaaact atgaagtgaa agtgaagagc | 60 |
| ttttcgaag aacatttaca cactgatgag gagatccgtt actgcgttgc aggaactggt | 120 |
| tactttgatg tgagagatcg taatgaagct tggattaggg tattggtaaa gaagggaggt | 180 |
| atgatagtct tacctgctgg gatctatcat cgcttcactg tggactctga caactatatc | 240 |
| aaggcaatgc ggctattcgt gggtgaaccg gtatggacac catacaatcg cccacacgac | 300 |
| catcttcctg caaggaaaga atatgtcgat aacttcatga tcaatgcctc ggcttagaga | 360 |
| gcttcctctc tctatatctg gctttctgaa acaaggatct ataaacaagg cctacaataa | 420 |
| agaaagcttt cctgtcaagt attggatatt tatatgtatt cctgtgtaga atgatggctt | 480 |
| ttggtatgct tgagttgttg taaacttagt tacactctct gatatgtctc tctttaccat | 540 |
| cttttgtcgta tcccatatac gaaaagatta cattgggatt catattgtct tacgttcgtt | 600 |
| cctatgtgca atatgttgag tttt | 624 |

<210> SEQ ID NO 23
<211> LENGTH: 495
<212> TYPE: DNA
<213> ORGANISM: Arabidopsis thaliana

<400> SEQUENCE: 23

| | |
|---|---|
| ccagtttttcc gatcactcgc aagaaaaccc taaaaatgga tggtcatgat tctgaggata | 60 |
| ctaagcagag cactgctgat atgactgctt ttgtccaaaa tcttctccag cagatgcaaa | 120 |
| ccaggttcca gacaatgtcg gactccatca tcacaaagat tgatgacatg ggaggcagaa | 180 |
| tcaatgagct ggagcaaagc atcaatgatc taagagccga gatgggagta gaaggcactc | 240 |
| ctcctccagc ctccaaatca ggcgatgaac ccaaacacc ggctagttcc tcttaaaaag | 300 |
| gaatgtggtg ttcattgaca tgtccgaagg aaaaagaaaa actatgaaat atgttaagag | 360 |
| cagtattact tttaaaattc ctgtttaaga acgagtttg ttgtttatta agttcatca | 420 |
| aatagattga tgatgtggtg cattacatta ttctccacct atgaattgca tttctatttt | 480 |
| ggtctaaaaa aaaaa | 495 |

<210> SEQ ID NO 24
<211> LENGTH: 580
<212> TYPE: DNA
<213> ORGANISM: Arabidopsis thaliana

<400> SEQUENCE: 24

| | |
|---|---|
| cgcgcaggta cgagcaaaaa tgctcaaaga agttgccacg gagaagcaaa ccgccgtgga | 60 |
| cactcatttc gcaaccgcta aaaagcttgc tcaagaagga gacgcgttgt tcgttaaaat | 120 |
| cttcgcaatc aagaaactgt tggcgaaact tgaagcagag aaagaatctg ttgatggaaa | 180 |

```
gtttaaggag actgtgaaag aactttctca tcttctggct gatgcttctg aggcttacga      240
agagtatcat ggcgcggtga ggaaggcgaa agacgagcaa gcggctgagg aatttgcgaa      300
agaggcgacg caaagtgcag agatcatttg ggttaagttt cttagttctc tttagagaac      360
aattgagatt cttggttgtg ttaagagcaa atctagagct cttgttggtt cttgttatgt      420
attttgtgat gatgttctgt ttcagagttt gtgtgttggt tgtatcagga gaaagaggct      480
gggagataga gagaaagaga gtctctgcga aaactaataa tgttttttca gatatctaaa      540
taataagctt tttacaaaaa aaaaaaaaaa aaaaaaaaa                             580
```

```
<210> SEQ ID NO 25
<211> LENGTH: 656
<212> TYPE: DNA
<213> ORGANISM: Arabidopsis thaliana

<400> SEQUENCE: 25
cggccgcgtc gacgcttgag agattcctct ggctaaaccc agatggagtt tggatctttt       60
cttgtgtcct tagggacatc ttttgttatc ttcgtcattc tcatgcttct cttcacctgg      120 cttttctcgca aatctggaaa tgctcccatt tattacccga atcggatcct taaagggctg      180
gagccatggg aaggcaccctc cttgactcga aacccttttg cttggatgcg tgaagctttg      240
acttcctctg aacaagatgt cgttaactta tccggcgtcg atactgctgt ccactttgtc      300
ttcttgagca ctgttctggg gatatttgct tgttccagtc ttcttctcct accaactcta      360
ctgcctctag ccgctacaga caacaacata aagaacacaa agaatgcgac agataccaca      420
agcaaaggaa cttttagcca acttgataat ctatcaatgg ctaacatcac aaaaaaaagt      480
tcgaggctgt gggcgttcct aggagctgtt tactggatat cttggtcac atatttcttc      540 ttgtggaaag cttataagca tgtctcttca ttgagagctc aagctctgat gtctgctgat      600
gtaaaacccg agcaattcgc tattcttgtt agggatatgc ctgcaccacc tgacgg          656
```

```
<210> SEQ ID NO 26
<211> LENGTH: 985
<212> TYPE: DNA
<213> ORGANISM: Arabidopsis thaliana

<400> SEQUENCE: 26
gttcacactc cggctggtga actgcaaaga cagattaggt catggcttgc agaaagtttt       60
gagtttctct ctgttacagc agatgatgtt tcaggagtaa ccactggcca attagagctt      120
ctttccacag caattatgga tggctggatg gctggagtag gagctccggt gcctcctcac      180
acagacgctt taggacagct tgtgtctgag tatgcaaagc gagtctacac ttctcagatg      240
cagcatctaa aggatattgc cggtactttg gcttcggaag aggcagaaga tgctggtcaa      300
gtcgcgaagc ttcgatcagc tctcgagtct gttgaccaca aaagaagaaa gattttgcaa      360
caaatgagaa gtgatgcagc tttgtttacc ttggaagaag gcagttcccc tgttcaaaat      420
ccatctacag cagccgaaga ctcgagatta gcctccctca tttctctgga tgccatactg      480
aagcaagtca aggaaataac aagacaagcc tctgtccacg ttttgagtaa agcaagaaa       540 aaggcattgc ttgagtctct tgatgaactt aacgaacgaa tgccttctct gcttgatgtt      600
gatcatccat gtgcacagag agaaattgat acggctcacc agttggtcga gacaattcca      660
gaacaagagg acaatcttca agacgaaaag agaccttcaa tagattcaat atcttcgact      720
gaaaccgatg tgtctcaatg gaatgttttg caattcaaca caggaggctc ttcagctcca      780
ttcatcataa aatgcggagc taactccaac tcagagctcg tgatcaaagc ggatgcccgt      840
```

```
attcaagaac ctaaaggagg cgaaatagtg agagttgtgc caagaccttc ggttttagaa      900
aacatgagct tagaggaaat gaaacaagtg tttggtcagt tgcccgaagc tctaagttca      960
ctggccttag ctagaacagc tgatg                                            985

<210> SEQ ID NO 27
<211> LENGTH: 527
<212> TYPE: DNA
<213> ORGANISM: Arabidopsis thaliana
<220> FEATURE:
<221> NAME/KEY: misc_feature
<222> LOCATION: (512)..(512)
<223> OTHER INFORMATION: n = a, c, g, or t

<400> SEQUENCE: 27
acttatgaga ggttaccgat tgaggaagaa caacagcaag agcagccgct tcaactagaa       60
gatgggaaga agcagaaaga agagaatgat gataacgaga gtgggaataa cggaaacgaa      120
ggatcgatgc agccgccgat gtataatatg cctcctaatt ttatcccaaa tggtcatcaa      180
atggctcaac acgacgtgta ttggggtggt cctccgcctc gtgctcctcc ttcgtattga      240
ttaagttaga taggcggtgg ttggtgcgtt ctttttactg gaatgattat attttccatt      300
aggatgggta ggcttttgtt attaaagcta tcaagtttct ttttttttac ggataattcg      360
gatgacaatt agctagtgtt tgtttgtttg ttttgtggcc ggcttttctg cttgactatt      420
ttgatcgcgg atagctttgt atgaaagtga attgattgta gaatcgtctt ttgaattttg      480
atgttggaaa aaaccaagca atggtgtgtg gnctttgcaa tggaagc                   527

<210> SEQ ID NO 28
<211> LENGTH: 610
<212> TYPE: DNA
<213> ORGANISM: Arabidopsis thaliana
<220> FEATURE:
<221> NAME/KEY: misc_feature
<222> LOCATION: (482)..(482)
<223> OTHER INFORMATION: n = a, c, g, or t
<220> FEATURE:
<221> NAME/KEY: misc_feature
<222> LOCATION: (494)..(495)
<223> OTHER INFORMATION: n = a, c, g, or t
<220> FEATURE:
<221> NAME/KEY: misc_feature
<222> LOCATION: (516)..(516)
<223> OTHER INFORMATION: n = a, c, g, or t
<220> FEATURE:
<221> NAME/KEY: misc_feature
<222> LOCATION: (560)..(560)
<223> OTHER INFORMATION: n = a, c, g, or t
<220> FEATURE:
<221> NAME/KEY: misc_feature
<222> LOCATION: (567)..(567)
<223> OTHER INFORMATION: n = a, c, g, or t
<220> FEATURE:
<221> NAME/KEY: misc_feature
<222> LOCATION: (587)..(587)
<223> OTHER INFORMATION: n = a, c, g, or t
<220> FEATURE:
<221> NAME/KEY: misc_feature
<222> LOCATION: (607)..(607)
<223> OTHER INFORMATION: n = a, c, g, or t

<400> SEQUENCE: 28
atcaaaagct agagtcttgg ccattcctga tgatctagca aatgtgtcat gcggtgtgga       60
acagattgaa gaactgaaag gattgaacct tgttgagaaa gatggtggtt catcttcttc      120
tgacggggct aggaacacta atcctgaaac tagaaggtac agtggttcct tgggtgtaga      180 ggatgggagcc tatactaatg agatgctcca gtccatagag atggttactg atgtgctgga    240
```

```
ctctcttgtg aggagggtta cagtagcaga atctgagtct gctgtcaaaa ggagagggca    300
cttttgggag aggaaagaaa tcagtaggaa agactatcca aatcgaaaat ttgtccgtga    360
agttagaaga gatggaacga tttgcttatg ggactaatag tgttctaaac gaaatgcggg    420
aaaggattga ggaattagtt gaagagcgat gaggcagagg gaaaaagctg tggaaaacga    480
anaggagttg tgtnntgtga agagagagtc gagtcnttaa aagctcctca gtactttacc    540
atgtcgagaa cactctttcn ccggagncat tcaaaccatg aggagtnttt gacggtggca    600 ctaaacnccg                                                          610
```

<210> SEQ ID NO 29
<211> LENGTH: 546
<212> TYPE: DNA
<213> ORGANISM: Arabidopsis thaliana

<400> SEQUENCE: 29

```
atgaccaata tcgccatggc tgatgctctc aaatctcttg agattgttga tggtcttgat     60
gaatacatga atcaatctga atccagtgct ccgcattctc caaccagtgt agcaaagctg    120
ccaccaagca ctgcaactag aacaactcga cggaagacca caacaaaagc tgagcctcag    180
ccatcatctc agttggtgtc ccgttcttgt cgttcgacga gcaagtctct tgctggagat    240
atggaccagg aaaacataaa caagaatgtt gctcaagaaa tgaagactag caatgtcaag    300
tttgaagcca atgtgctcaa aactccagca gcaggaagca caggaaaaac ttcagcagca    360
acttcttgca ctaagaagga tgaattggtc cagtcggtct acagcactag agatcaacc    420 aggctgttag agaaatgtat ggccgatctg agtttgaaga ctaaagaaac tgtggataat    480
aaacctgcca agaatgaaga tacagaacag aaagtatctg cacaggagaa gaatctaact    540
ggttag                                                              546
```

<210> SEQ ID NO 30
<211> LENGTH: 492
<212> TYPE: DNA
<213> ORGANISM: Arabidopsis thaliana

<400> SEQUENCE: 30

```
atgctgatgc tgtgtgggtt cacggtcttg gatatgctaa agcaccacga ccttgggaag     60
atccgagcac ccttgcatcc tctcagaaag aagatgcaga ttcagcacgc ttaccagcag    120
atacatcagg ggtcaaaact gttgaagatg gaccggatga tgttgagagg gaccaaaaga    180
aggataggcg tgaggaaagg aaacctgcaa agagagagaa ggaagaaaga catgataggc    240
gtgaaaaacg cgaaaggcat gagaagcgaa gcgctcgtga ttcagatgat agaaagaagc    300
acaagaaaga gaagaaggag aaaaaaagaa ggcatgactc tgattctgat tgaagcgaat    360
tgtcccagga tggaacattt tgctcttcag aggaagagtg gtcggctagg taccaaaatc    420
cagctaccac ttctgcaaga tttaaatctg ttgcttattt catttacgaa tcgtggagta    480
aagtgttgtt ga                                                       492
```

<210> SEQ ID NO 31
<211> LENGTH: 723
<212> TYPE: DNA
<213> ORGANISM: Arabidopsis thaliana
<220> FEATURE:
<221> NAME/KEY: misc_feature
<222> LOCATION: (559)..(559)
<223> OTHER INFORMATION: n = a, c, g, or t
<220> FEATURE:
<221> NAME/KEY: misc_feature
<222> LOCATION: (622)..(622)

```
<223> OTHER INFORMATION: n = a, c, g, or t
<220> FEATURE:
<221> NAME/KEY: misc_feature
<222> LOCATION: (677)..(677)
<223> OTHER INFORMATION: n = a, c, g, or t

<400> SEQUENCE: 31
gcaaaagaga gaaacatctg acccggaatc tgacctgaaa acccggaaga atcgaaaaat      60
ggggaaagat ggtctgagcg acgatcaggt ctcgtcgatg aaggaagcct tcatgctctt     120
cgacaccgat ggcgacggca aaatcgcacc gtcagagctc gggatcctca tgcgatctct     180
cggcggaaac ccgacccaag cccagctgaa atccataatc gcatccgaga atctctcttc     240
accgtttgat ttcaacagat tcctcgatct catggcgaaa catctgaaga cggaaccttt     300
cgatcgccag ctccgtgacg cattcaaagt gctcgataag gaaggtaccg ggttcgttgc     360
tgtggcggat ctgaggcata ttctgaccag tatcggagag aagctggagc taatgagtt      420
cgatgagtgg atcaaggagg tggatgttgg atccgatgga agatccggt atgaagattt      480
catagcaagg atggttgcta agtgagatct aatctttat gttttgaaag ttgaaatttt      540
taagaagaga ttcttttgng gttttttcac ttggttggtt tgatttcgag cgaatcctaa     600
ctaggggttg gtttatcatt gnggaatttg cttactaact ttggcttctt catggttggg     660
tttcaatttt taatggnaaa tggtggctgg gggaattcct aaaaaaaaaa aaaaaaaaa     720
aaa                                                                   723

<210> SEQ ID NO 32
<211> LENGTH: 344
<212> TYPE: DNA
<213> ORGANISM: Arabidopsis thaliana

<400> SEQUENCE: 32
cgcggagtct cctttcgatc aagagaaatg cgtccgattt ttgcaatctc tcagagaatg      60
cgttctatca aagaaagtaa agaagttctc gataccgagt caagatcacg actctgaggg     120
agcagcttca gctacaaaga gaccttcata acgttctttg ttccgatttt cttttatcgt     180
ttgagttgta atcatgtaat tgattttaat gtcatgcctt ggattcataa gctgggtcat     240
gccttgtttc ccctttgttg tcttgtatgt tgaatattgc aaactctaaa gagcatattt     300
ataagaagaa ataaaagttt ctacaaaaaa aaaaaaaaa aaaa                       344

<210> SEQ ID NO 33
<211> LENGTH: 1131
<212> TYPE: DNA
<213> ORGANISM: Arabidopsis thaliana

<400> SEQUENCE: 33
atgacaacta ctgggtctaa ttctaatcac aaccaccatg aaagcaataa taacaacaat      60
aaccctagta ctaggtcttg gggcacggcg gtttcaggtc aatctgtgtc tactagcggc     120
agtatgggct ctccgtcgag ccggagtgag caaaccatca ccgttgttac atctactagc     180
gacactactt tcaacgcct gaataatttg gacattcaag gtgatgatgc tggttctcaa      240
ggagcttctg gtgttaagaa gaagaagagg ggacagcgtg cggctggtcc agataagact     300
ggaagaggac tacgtcaatt tagtatgaaa gtttgtgaaa aggtggaaag caaggaagg     360
acaacttaca atgaggttgc agacgagctt gttgctgaat ttgcacttcc aaataacgat     420
ggaacatccc ctgatcagca acagtatgat gagaaaaaca aagacgaag agtatatgat     480
gctttaaacg tcctcatggc tatggatata atatccaagg ataaaaaaga aattcaatgg     540
```

-continued

| | |
|---|---|
| agaggtcttc ctcggacaag cttaagcgac attgaagaat taaagaacga acgactctca | 600 |
| cttaggaaca gaattgagaa gaaaactgca tattcccaag aactggaaga acaaagaaat | 660 |
| gagcacttat atagctcagg aaatgctccc agtggcggtg ttgctcttcc ttttatcctt | 720 |
| gtccagactc gtcctcacgc aacagtagaa gtggagatat cagaagatat gcagctcgtg | 780 |
| cattttgatt tcaacagcac tccatttgag ctccacgacg acaattttgt cctcaagact | 840 |
| atgaagtttt gtgatcaacc gccgcaacaa ccaaacggtc ggaacaacag ccagctggtt | 900 |
| tgtcacaatt tcacgccaga aaaccctaac aaaggcccca gcacaggtcc aacaccgcag | 960 |
| ctggatatgt acgagactca tcttcaatcg caacaacatc agcagcattc tcagctacaa | 1020 |
| atcattccta tgcctgagac taacaacgtt acttccagcg ctgatactgc tccagtgaaa | 1080 |
| tccccgtctc ttccagggat aatgaactcc agcatgaagc cggagaattg a | 1131 |

<210> SEQ ID NO 34
<211> LENGTH: 631
<212> TYPE: DNA
<213> ORGANISM: Arabidopsis thaliana

<400> SEQUENCE: 34

| | |
|---|---|
| agagtatctg aagaaagggt caccaataag cgcgctcaaa agtttcatct cgtctctctc | 60 |
| tgaacctcct caagacatca tggacgcact cttcaatgct ctctttgatg gtgtgggaaa | 120 |
| gggattcgcc aaagaagtga ctaagaagaa gaattactta gcggctgctg caacaatgca | 180 |
| agaggatgga tcacagatgc atctgctcaa ttcgattggg acattctgtg aaagaatgg | 240 |
| aaacgaagaa gctttgaaag aggtggctct ggttcttaaa gcattgtacg accaagacat | 300 |
| cattgaggaa gaggtagtgt tggattggta cgaaaagggt ctcaccggag ctgacaaaag | 360 |
| ctcgccggtt tggaagaatg ttaagccttt tgtggagtgg cttcagagcg ctgagtctga | 420 |
| gtccgaagag gaggattgag tcacttttt cttccctcct aacttttctt tgcggcattt | 480 |
| cttataatac ttcgtcagtt ttcagaattc ttaaatcttt tgctgtgtt cttataaaga | 540 |
| aacatcatct attaaagttg tcttcgtttg gatttggttt tgacgacttt gggaaatatt | 600 |
| tatgtttaag aaaaaaaaaa aaaaaaaaa a | 631 |

<210> SEQ ID NO 35
<211> LENGTH: 1333
<212> TYPE: DNA
<213> ORGANISM: Arabidopsis thaliana

<400> SEQUENCE: 35

| | |
|---|---|
| gctggaggta gagaggaatg cgtctgctgt tgctgccagt gaaacaatgg cgatgatcaa | 60 |
| taggttgcat gaggagaaag ctgcgatgca gatggaagcg ttgcagtatc agagaatgat | 120 |
| ggaggagcaa gctgagtttg atcaagaagc tttgcagttg ttgaatgagc ttatggtgaa | 180 |
| tagagagaag gagaatgctg agcttgagaa ggagctagag gtgtatagaa agagaatgga | 240 |
| ggagtatgaa gctaaagaga aaatgggat gttgaggagg agattgagag attcctctgt | 300 |
| tgattcgtat agaaataatg gcgattctga tgagaatagc aatggagagt tacagtttaa | 360 |
| gaacgttgaa ggggttacgg attggaaata tagagagaat gagatggaga atacgccggt | 420 |
| ggatgttgta cttcgtcttg atgagtgttt agatgattat gatggagaga ggctttcgat | 480 |
| tcttgggaga ttgaagtttc ttgaagagaa actcacagat cttaataacg aagaggacga | 540 |
| cgaggaggag gctaaaacgt ttgagagtaa tggtagcatc aatggaaatg agcatattca | 600 |
| tggcaaagaa acaaacggga agcacagagt tatccagtca aaaagattac ttcccctgtt | 660 |

-continued

```
tgatgcggtc gatggagaga tggaaaacgg gttaagtaac ggaaaccatc acgaaaacgg      720
gtttgatgat tcggagaagg gtgagaatgt gacgatagaa gaagagtgg atgagcttta      780 cgagaggtta aagctctag aggcagatag agagttctta agacattgtg ttggttcatt      840
gaaaaaagga gacaaaggtg tacatctcct ccatgagatt ctgcaacatc ttcgtgatct      900
aaggaatatc gatcttactc gcgtcagaga aaacggagac atgagtttat gagtttgatt      960
ttgagttttg gtttgagtc cactctttgc atagtgaccc aaagaacaag aaaaatcata     1020
caggtatgga agtgacatgt tgcttgtgag gcaaggaaca acgacaaggt ttcagatgaa     1080
gaagaaaacg ttctcagaat aaaagtattt taagtatata ctctgaggaa aagtgtcaga     1140
tcagaatgtt cgtctttctt cgttcatttt cattattata agttttgttt tttatattga     1200
agatttattt agagagaggg aagtgtcagt ataatttcac ttttatattt tatatttggg     1260
agttgtcttt atgagtggtg gtaatagaaa aaggtagaat gatgagtgaa gaaaaaaaaa     1320
aaaaaaaaaa aaa                                                        1333

<210> SEQ ID NO 36
<211> LENGTH: 2289
<212> TYPE: DNA
<213> ORGANISM: Arabidopsis thaliana

<400> SEQUENCE: 36
cttatgcaaa ctctcagcag attctgatgc caatgtccaa agtgctgctc atcttttgga      60
tcgccttgtt aaggatattg tgacggaaag tgatcagttc agtattgagg aattcatacc     120
tcttttaaaa gagcgaatga acgttctcaa cccttacgtc cggcaatttc tggttggatg     180
gatcactgtt cttgatagtg ttccagacat tgacatgctt gggtttctgc cagacttcct     240
cgatgggtta ttcaatatgt tgagcgactc tagtcatgaa atacgacagc aagctgattc     300
agctctttca gagtttcttc aagagataaa aaattcacca tctgtagatt atggtcgcat     360
ggctgaaata ctggtgcaga gggctgcttc tcctgatgaa ttcactcgat taacagccat     420
cacgtggata aacgagttcg taaaacttgg gggagaccag ctcgtgcgtt attatgctga     480
cattcttggg gctatcttgc cttgcatatc tgacaaagaa gagaaaatca gggtggttgc     540
tcgtgaaacc aatgaagaac ttcgttcaat ccatgttgaa ccctcagatg gttttgatgt     600
tggcgcaatt ctctctgttg caaggaggca gctatcaagt gagtttgagg ctactcggat     660
tgaagcattg aattggatat caacacttt aaacaagcat cgtactgagg tcttgtgctt     720
cctgaatgac atatttgaca cccttctaaa gcactatctg attcttctga tgacgtggtg     780
ctcttggttc tggaggttca tgctggtgta gcaaagatc cacaacactt tcgccagctc     840
atcgtatttc ttgtccacaa tttccgagct gataattctc ttttggaaag gcgcggtgcc     900
cttattgtcc gaagaatgtg tgtactttg gatgccgaaa gagtctaccg agagctctct     960
acaattcttg agggagaaga taatcttgac tttgcttcta ccatggttca ggcattgaat    1020
ttgattttgc ttacttcccc ggagttatcg aaactgagag aactattaaa aggttcactc    1080
gtcaatcgcg aagggaaaga acttttcgtt gccttgtata cttcatggtg ccattcaccc    1140
atgggcaatt ataagcctct gcttattagc tcaggcttac caagcatgcg agtgtcgtaa    1200
tccaatcctg ggtaaaagaa gacattaacg tccaaatttc ttaggccagc ttgataaaat    1260
tgatccggct tctggaaact ccaatcttta cttaccttag attgcagctt ctggaaccag    1320
gaaggtacac atggttgctg aaaacacttt atggtcttct tatgttactt cctcagcaaa    1380
gtgcggcgtt caagatactt aggacaagac tcaaaactgt gccaacgtac tcattcagta    1440
```

-continued

```
ctggaaacca ataggcaga gcaacttcag gagttccttt ctctcagtat aagcatcaaa    1500
acgaggacgg tgacttagaa gacgataaca tcaacagttc tcaccaagga atcaattttg   1560
ctgtgcggct acaacagttc gaaaacgtac agaatctaca tcgtggccag gcaaggacta   1620
gagtgaacta ctcatatcac tcttcctctt cttctacatc aaaggaggtg aggagatctg   1680
aagaacaaca acagcagcag cagcaacaac aacagcaaca caacaacaa caacgaccac    1740 caccttcttc gacatcatca tcagttgcag ataacaatag acctccatca gaacttcaa    1800 gaaaaggccc tggtcaatta cagctttaac ctacctggta atcataaata ataaataata   1860
ttccatcccc gacaatcatc atcttcatct tctttgtgtg acaccaccg atccctttg     1920 tctcctgtaa aattgtatat ctctcttttt tagtaactct tcaagtttcg acggaacttg   1980
tggaaaagct acggtcgtgt ccatcatctc tttctctctg tcgggttttt tttatttacg   2040
agagattctt cttcagtccc tcagtctacc tttatattgt ttttttgggg gtttctcgtt   2100
tctttgaatt tgtttcattg tttggagctt tttatatttt taccttatgt ggagatgtaa   2160 gaaaagaag tgatcatgtg gttttgtgtt gttttttat aactggaaaa ccacatgagt     2220
ttgtagaggt cacttattgg atattttatg tcaaatgatg ctccttttta caaaaaaaaa   2280
aaaaaaaaa                                                           2289
```

<210> SEQ ID NO 37
<211> LENGTH: 1094
<212> TYPE: DNA
<213> ORGANISM: Arabidopsis thaliana

<400> SEQUENCE: 37

```
cttgattgaa acttcagttg aatccaagga aacgactgaa tcagtggtta caggtgaatc     60
ggagaaagcg attgaagata tttcaaaaga agctgacaat gaggaggatg atgatgagga   120
ggaacaagaa ggagatgagg atgatgatga aaatgaagag gaagaagtgg ttgttccaga   180
aactgagaat cgagcagaag gagaagattt agtgaagaat aaggcagctg acgcgaagaa   240
gcatcttcaa atgattggag tccaactctt gaaagaatcc gatgaagcaa acagaacaaa   300
gaaacgtggg aagagggcat ctcgtatgac acttgaggat gatgcagatg aggattggtt   360
ccctgaggaa ccatttgaag cattcaaaga aatgagggaa agaaaagtgt tcgatgtggc   420
tgacatgtat acaatagcag acgtttgggg ttggacatgg gagaaggatt ttaagaacaa   480
aactccaagg aaatggtcac aagagtggga agtcgagttg gcaattgtgc tcatgacaaa   540
ggtgattgaa ttgggtggaa ttccaacgat tggtgattgt gcagtgatat tacgagctgc   600
tttaagagct cccatgcctt cagccttctt gaagatcttg cagacgacac acagtcttgg   660
ctactcattt ggcagcccgt tgtacgatga gatcatcaca ttgtgttttgg accttggaga   720 acttgatgca gccatcgcca tagttgcaga tatggaaacc acagggatca ctgtccctga   780
tcaaacccct tgacaaggtca tatctgctag acaatctaat gagagtccgc ggtctgagcc   840
tgaagagcca gcatcaacag taagctctta gttatcatat cctcttctgc ttgttgtgaa   900
gtctctataa gaaacagaaa tcggtagaag gagctgaatc tgtcttagtt atgaaagttt   960
tgttcattat aagtacaagt catgtagttc cgagtgtaga acagttttta ctagtgttgc   1020
accaggtccc tccagtctga tacttaattc tttagtgttg gatctttcta tataagaaaa   1080
aaaaaaaaaa aaaa                                                     1094
```

<210> SEQ ID NO 38
<211> LENGTH: 1204
<212> TYPE: DNA

<213> ORGANISM: Arabidopsis thaliana

<400> SEQUENCE: 38

```
aaccgattca gcctccgaca gtatattcca ctacgacgac gcttcacaag ccaaaatcca    60
gcaggagaag ccatgggcct ccgatcctaa ctacttcaag cgcgttcaca tctcagccct   120
tgctcttctc aagatggtgg ttcacgctcg ctccggtggc acaatcgaga tcatgggtct   180
tatgcagggt aaaaccgagg gtgatacaat catcgttatg gatgcttttg ctttgcctgt   240
tgaaggtact gagactaggg ttaatgctca gtctgatgcc tatgagtata tggttgaata   300
ctctcagacc agcaagctgg ctgggaggtt ggagaacgtt gttggatggt atcactctca   360
ccctgggtat ggatgttggc tctcgggtat tgatgtttcg acacagatgc ttaaccaaca   420
gtatcaggag ccattcttag ctgttgttat tgatccaaca aggactgttt cggctggtaa   480
ggttgagatt ggggcattca gaacatatcc agagggacat aagatctcgg atgatcatgt   540
ttctgagtat cagactatcc ctcttaacaa gattgaggac tttggtgtac attgcaaaca   600
gtactactca ttggacatca cttatttcaa gtcatctctc gatagtcacc ttctggatct   660
cctttggaac aagtactggg tgaacactct ttcttcttcc ccactgttgg gcaatggaga   720
ctatgttgcc gggcaaatat cagacttggc tgagaagctc gagcaagcgg agagtcagct   780
cgctaactcc cggtatggag gaattgcgcc agccggtcac caaggagga aagaggatga   840
gcctcaactc gcgaagataa ctcgggatag tgcaaagata actgtcgagc aggtccatgg   900
actaatgtca caggttatca agacatcttt gttcaattcc gctcgtcagt ccaagaagtc   960
tgctgacgac tcatcagatc cagagcccat gattacatcg tgaagttggt ctattctttt  1020
gtttttggc tgcggaaatt gactatcggt ttgacccggt ttatgaggca atgcccattg  1080
ttccctatat ctctagtgta gtatctgctt cagacaaaga tctttgggtt attaaatgac  1140
attaacataa atcgatcatt atgttttttgc gttaaaaaaa aaaaaaaaaa aaaaaaaaa   1200
aaaa                                                              1204
```

<210> SEQ ID NO 39
<211> LENGTH: 1715
<212> TYPE: DNA
<213> ORGANISM: Arabidopsis thaliana

<400> SEQUENCE: 39

```
cttttaagtt gggggatgtt tcgattttga aatttgattt cttcaagaga agagatttaa    60
tgaaaataaa taacttccgc agataacgaa gaagaagaaa atggttagat cagatgaaaa   120
tagccttgga ttaatcggat caatgagtct ccaaggtacc ctaaatcgat cgattttgtt   180
attaaaaatc aaaactttcg ttctctttga ttttcccccc aaattgattt tgaatttact   240
tgatgtaggg ggaggagtag taggaaagat caagacgacg gcaacaacag gaccgacaag   300
aagagcacta gtactatta acaagaacat cactgaagcg ccgtcttacc cttatgctgt   360
caacaagaga tcagtttctg aaagagatgg catttgtaat aaaccacctg tgcatcgacc   420
agttactagg aagtttgctg ctcagttagc agatcataag ccacatatcc gtgatgagga   480
aactaagaaa ccagactcag tttcaagtga agaaccagag acgattatca ttgatgtgga   540
tgaaagtgat aaagaaggag gtgactctaa tgagccaatg tttgtacaac atactgaagc   600
aatgctggag gagattgaac agatggagaa ggagattgaa atggaagatg cagacaaaga   660
agaagagcct gtgatcgata ttgatgcctg tgataagaat aatccctttgg ctgcggttga   720
atatatccat gatatgcata ccttctacaa gaattttgag aaacttagtt gcgtgcctcc   780
```

```
taactatatg gacaatcaac aagatcttaa tgagagaatg agaggaatcc tcattgactg      840
gttaattgag gtgcactaca agtttgaact gatggaggaa actctttatc tcacaatcaa      900
tgtcatcgac agattccttg cggttcatca atcgtgagg aaaaagcttc agcttgttgg      960
tgttactgct ttgttgcttg catgtaaata tgaagaagtt tcagttccag tggtagatga     1020
tctcatcttg atctctgaca aagcttactc tagaagagaa gtgctagata tggagaagct     1080
aatggccaac accttgcaat tcaatttctc tctaccaact ccatatgttt tcatgaaacg     1140
atttctcaaa gctgcccaat ctgacaagaa gcttgagatt ttatcattct ttatgatcga     1200
gctttgcctt gtggagtatg agatgctaga gtatcttcca tctaagctgg cggcctcagc     1260
aatctacact gctcagtgta cacttaaggg atttgaagaa tggagcaaaa cctgtgagtt     1320
tcacacaggc tacaacgaaa acagctact ggcatgtgcg agaaagatgg ttgctttcca      1380
tcacaaggca ggaacaggga agctcacagg agttcacaga aagtacaaca catctaagtt     1440
ctgtcatgct gcaagaactg aaccagctgg gtttctgatt taatattaat aagaatctaa     1500
tatgacttaa ctcgagtttt tctttagaac aaaaagagtg tgagagaaag agagatagta     1560
gagcaagttg cccaaaatgg gagaagaatg gatctttaga tatcatggca agtagcccaa     1620
aaagagtgta ttcttctctt tctaaggtct ttagatcttt cttcacttga gagagaataa     1680
aaagaatctt ctgaaaaaaa aaaaaaaaaa aaaaa                                1715

<210> SEQ ID NO 40
<211> LENGTH: 2195
<212> TYPE: DNA
<213> ORGANISM: Arabidopsis thaliana

<400> SEQUENCE: 40
aacccacgtc aattctttt caaaggcata tattctctct gtttcaaact ttgtgtctct        60
tcttctcctt ctctgatcgt tcgttttctg gacgagagag atggtaaatc cgggtcacgg      120
aagaggaccc gattcgggta ctgctgctgg tgggtcaaac tccgacccgt ttcctgcgaa      180
tcttcgagtt cttgtcgttg atgatgatcc aacttgtctc atgatcttag agaggatgct      240
tatgacttgt ctctacagag taactaaatg taacagagca gagagcgcat tgtctctgct      300
tcggaagaac aagaatggtt ttgatattgt cattagtgat gttcatatgc ctgacatgga      360
tggtttcaag ctccttgaac acgttggttt agagatggat ttacctgtta tcatgatgtc      420
tgcggatgat tcgaagagcg ttgtgttgaa aggagtgact cacggtgcag ttgattacct      480
catcaaaccg gtacgtattg aggctttgaa gaatatatgg caacatgtgg tgcggaagaa      540
gcgtaacgag tggaatgttt ctgaacattc tggaggaagt attgaagata ctggcggtga      600
cagggacagg cagcagcagc ataggaggga tgctgataac aactcgtctt cagttaatga      660
agggaacggg aggagctcga ggaagcggaa ggaagaggaa gtagatgatc aagggggatga     720 taaggaagac tcatcgagtt taagaaaacc acgcgtggtt tggtctgttg aattgcatca      780
gcagtttgtt gctgctgtga atcagctagg cgttgacaaa gctgttccta agaagatctt      840
agagatgatg aatgtacccg ggctaacgcg agaaaacgta gccagtcacc tccagaagta      900
tcggatatat ctgagacggc ttggaggagt atcgcaacac caaggaaata tgaaccattc      960
gtttatgact ggtcaagatc agagttttgg acctctttct tcgttgaatg gatttgatct     1020 tcaatctttta gctgttactg gtcagctccc tcctcagagc cttgcacagc ttcaagcagc     1080
tggtcttggc cggcctacac tcgctaaacc agggatgtcg gtttctcccc ttgtagatca     1140
gagaagcatc ttcaactttg aaaacccaaa aataagagatt ggagacggac atggtcagac     1200
```

| | |
|---|---|
| gatgaacaat ggaaatttgc ttcatggtgt cccaacgggt agtcacatgc gtctgcgtcc | 1260 |
| tggacagaat gttcagagca gcggaatgat gttgccagta gcagaccagc tacctcgagg | 1320 |
| aggaccatcg atgctaccat ccctcgggca acagccgata ttgtcaagca gcgtttcaag | 1380 |
| aagaagcgat ctcactggtg cgctggcggt tagaaacagt atccccgaga ccaacagcag | 1440 |
| agtgttacca actactcact cggtcttcaa aacttcccc gcggatctac ctcgcagcag | 1500 |
| cttcccgttg gcaagtgccc cagggatttc agttccagta tcagtttctt accaagaaga | 1560 |
| ggtcaacagc tcggatgcaa aggaggttc atcagctgct actgctggat tggtaaccc | 1620 |
| aagctacgac atatttaacg attttccgca gcaccaacag cacaacaaga acatcagcaa | 1680 |
| taaactaaac gattgggatc tgcggaatat gggattggtc ttcagttcca atcaggacgc | 1740 |
| agcaactgca accgcaaccg cagcattttc cacttcggaa gcatactctt cgtcttctac | 1800 |
| gcagagaaaa agacgggaaa cggacgcaac agttgtgggt gagcatgggc agaacctgca | 1860 |
| gtcaccgagc cggaatctgt atcatctgaa ccacgttttt atggacggtg gttcagtcag | 1920 |
| agtgaagtca gaaagagtgg cggagacagt gacttgtcct ccagcaaata cattgtttca | 1980 |
| cgagcagtat aatcaagaag atctgatgag cgcatttctc aaacaggaag gcatcccatc | 2040 |
| cgtagataac gagttcgaat ttgacggata ctccatcgat aatatccagg tctgactaca | 2100 |
| gaaactcaga ctagactgca agattctttg ttttcttct ccctccttcg aggtacaaag | 2160 |
| ctcaaaacat ggcaataacc gaagggaaag ataga | 2195 |

<210> SEQ ID NO 41
<211> LENGTH: 1413
<212> TYPE: DNA
<213> ORGANISM: Arabidopsis thaliana

<400> SEQUENCE: 41

| | |
|---|---|
| aggctgtgtt ttatcgtggg attttttaaac atggggaagg aaaatgctgt gtctcggcca | 60 |
| ttcactcgtt cccttgcctc tgctttgcgc gcttcagaag tgacttctac tacacagaat | 120 |
| caacagagag taaacacaaa aagaccagcc ttggaggata caagagccac tggacccaac | 180 |
| aagaggaaga agcgagcggt tctaggggag atcacaaatg ttaactccaa tacagctata | 240 |
| cttgaggcca aaaacagcaa gcagataaag aaaggacgcg gtcatggatt ggcgagtaca | 300 |
| tcccagttgg caacttctgt tacttcagaa gtcacagatc ttcagtccag gaccgatgca | 360 |
| aaagttgaag ttgcatcaaa tacagcagga aacctttctg tttctaaagg cacagataac | 420 |
| acagctgata actgtattga gatatggaat tctagattgc ctccaagacc tcttgggaga | 480 |
| tcagcttcta cagctgagaa aagtgctgtt attggtagtt caactgtacc ggatatccca | 540 |
| aaatttgtag acatcgattc agatgacaag gatccttac tgtgctgcct ctatgcccct | 600 |
| gaaatccact acaatttgcg tgtttcagag cttaaacgca gaccacttcc ggactttatg | 660 |
| gagagaatac agaaggatgt cacccagtcc atgcgggaa ttctggttga ttggcttgtg | 720 |
| gaggtctctg aagaatacac acttgcatct gacactctct acctcacagt gtatctcata | 780 |
| gactggttcc tccatggaaa ctacgtgcaa agacagcaac ttcaactgct cggcatcact | 840 |
| tgcatgctaa ttgcctcgaa gtatgaggaa atctctgctc cacgcattga ggagttttgc | 900 |
| ttcattacgg ataacaccta cacaagagat caggtcctgg aaatggagaa ccaagtactt | 960 |
| aagcatttta gctttcaaat atacactccc actccaaaaa cgttccttag gagatttctc | 1020 |
| agagcagctc aagcctctcg cctgagccca agccttgaag tcgagtttct agccagctat | 1080 |
| ctaacagagt tgacattaat agactaccat ttccttaaagt ttcttccttc cgttgttgct | 1140 |

```
gcttcagcgg gttttctcgc caagtggaca atggaccaat caaaccaccc atggaatcca    1200
acacttgagc attacacaac gtacaaagca tcggatctga agcatctgt tcatgcctta    1260 caagatctgc agcttaacac caaaggttgc cccttgagcg ctatacgcat gaagtatagg    1320
caagagaaat acaaatctgt ggcggttctc acgtctccaa agctacttga cacgctattc    1380
tgaaggtttc aactcctaac cgataatagt ttt                                1413
```

<210> SEQ ID NO 42
<211> LENGTH: 2766
<212> TYPE: DNA
<213> ORGANISM: Arabidopsis thaliana

<400> SEQUENCE: 42

```
atttgagagg aagctttatt ttgtgtgtag atggcgaata atcctccgca gtcttctggt      60
acccagggtc agcattttgt tcctgcagct tcacaacctt ttcaccctta tggacatgta     120
cctccaaatg ttcaaagtca gcctccacag tattctcagc cgatacagca gcagcagctc     180
tttccagtga gaccaggtca gcctgtgcat attacatcat cctcacaggc tgtatcagtt     240
ccgtatattc aaacgaacaa gattctcact tctggatcta ctcaaccaca gccaaatgca     300
cctccaatga cgggctttgc tacatctgga cctccatttt cttctccata tacttttgta     360
ccatcatctt atcctcagca acaaccaaca tccttggtcc aaccaaattc tcagatgcat     420
gtagctggcg tccctccagc agcaaacact tggcctgttc ctgttaatca agcacatca     480 cttgttcccc ctgtgcagca gactgggcaa caaacaccgg tcgcagtttc cacagaccca     540
ggaaacttga ctccgcaatc tgcatctgac tggcaggagc atacatctgc tgatgggaga     600
aaggctgatg catccactgt atggaaggaa tttacaacac tgaaggaaa gaaatattat     660 tataacaagg ttacaaagga gtctaagtgg acaattccgg aagatttaaa gttagctcgg     720
gaacaagccc aactagctag tgaaaaaacg tccctttcgg aagctggatc taccctcta     780 tcccaccatg ctgcatcctc gtctgatcta gcagttagca ctgtgacttc tgttgttccc     840
agcacatctt cagcacttac tggacattct tcaagcccta ttcaagcggg tttggctgta     900
cctgtcaccc gtcctccctc tgttgctcct gttactccaa catctggtgc aattagtgac     960
actgaggcta ctacaatgta ctattttcc ttgggaagtt ttgctgagaa taaggaaatg    1020
tctgtgaatg gaaaagccaa tttgtcacct gctggtgaca agcaaatgt cgaggaacct    1080 atggtatatg ctactaagca ggaggccaaa gctgctttca gtctcttttt ggaatctgta    1140
aatgttcatt ccgactggac atgggaacag acattgaaag agattgttca cgataaaaga    1200
tatggtgctt tgaggacact cggcgagcgg aaacaagcgt taacgagta tcttggccaa    1260 aggaaaaaag tggaagctga ggaaagacga aggaggcaga gaaagctcg ggaagaattt    1320 gtcaagatgc tagaggagtg tgaagaactt tcatcatccc tgaaatggag caaagcaatg    1380
agtttgttcg aaaatgatca gcgttttaaa gctgttgacc gtcctaggga tcgtgaagat    1440 cttttttgaca attacattgt ggaacttgag aggaaggaaa gagaaaaggc agcggaggaa    1500
catcggcagt atatgcaga ctatcggaag tttcttgaaa cctgtgacta tatcaaagct    1560
ggtacacaat ggcgcaaaat tcaagataga ctggaggatg atgacagatg ctcatgtctt    1620
gaaaagatag atcgtctgat tggttttgag gaatacattc ttgacctaga aggaagaa    1680 gaagagctga agagagtaga gaaagaacat gtaaggcggg ccgagagaaa aaaccgtgat    1740
gcatttcgta cactattgga agaacatgtt gctgcaggca tccttacagc caagacgtac    1800
tggttggatt attgcattga gttaaaagac ttgccccaat accaagctgt tgcatctaat    1860
```

```
acatctggtt caactccgaa agacttgttt gaagatgtca cagaagaatt agagaagcag    1920
tatcatgagg ataagagcta tgtgaaggat gctatgaagt caagaaaggc aaattttaaa    1980
tctgctattt cagaagatct cagtactcaa cagatatcag acataaattt aaagcttata    2040
tatgatgact tggttgggag agtgaaggaa aagaagaaa aagaggccag aaagcttcag     2100
cgtctggctg aagaatttac caatctgttg cacactttca aggaaatcac cgtagcttca    2160
aattgggaag atagcaaaca actagtagaa gaaagtcaag agtacagatc gattggagat    2220
gaaagtgtta gccaagggtt atttgaggaa tacataacga gtttacaaga aaaggcaaag    2280
gagaaggagc gtaagcgtga cgaggaaaag gttagaaaag agaaggaaag ggacgagaaa    2340
gagaaacgga agacaagga taaggagaga agggaaaagg aaagagaacg tgaaaaagag     2400
aagggaaaag agaggagtaa acgggaagaa tcagatggtg agactgctat ggatgtgagc    2460
gaaggtcata agacgagaa aagaaaggga aaagatcgtg acagaaaaca tcgaagacgg     2520
catcacaaca attctgatga agatgttagt tctgataggg atgacagaga tgagtcgaag    2580
aaatcatccc gtaaacatgg taatgatcgc aaaaaatcaa gaaagcacgc aaactcgcct    2640
gaatcggaga gtgaaaaccg gcataaaaga cagaaaaaag agagtagtcg ccgaagtggt    2700
aatgacgagc tagaggatgg agaagttggg gagtgatagt gaaattcgac attaatctga    2760
aacctt                                                               2766

<210> SEQ ID NO 43
<211> LENGTH: 1260
<212> TYPE: DNA
<213> ORGANISM: Arabidopsis thaliana

<400> SEQUENCE: 43
tgaaacctag atttctgcaa ctgaattcct aattcgaaaa agaatggagg gttcgtcgtc      60
gacgatagca aggaagacat gggaactaga gaacagcatt ctaacagtag actcacctga     120
ttcaacctcc gacaacatct tctactacga cgatacttca cagactaggt tccagcaaga     180
gaaaccgtgg gagaatgatc ctcactactt taaacgagtc aagatctcag cgctcgctct     240
tcttaagatg gtggttcacg ctcgctctgg tggtacaatt gaaataatgg gtcttatgca     300
aggtaagacc gatggtgata ctatcattgt tatggatgct tttgctttac cagtggaagg     360
tactgagaca agggttaatg ctcaggatga tgcttatgag tacatggttg agtattcaca     420
gaccaacaag ctcgcggggc ggctggagaa tgttgttgga tggtatcact ctcaccctgg     480
atatggatgc tggctctccg gtattgatgt ttctacgcag aggcttaacc aacagcatca     540
ggagccattt ttagctgttg ttattgatcc cacaaggact gtttcagctg gtaaggttga     600
gattggtgct tcagaacat actctaaagg atataagcct ccagatgaac ctgtttctga     660
gtatcaaact attcctttaa ataagattga ggactttggt gttcactgca acagtactaa    720
ttcattagat gtcacttatt tcaagtcatc tcttgattct caccttctgg atctactatg    780
gaacaagtac tgggtgaaca ctctttcttc ttctccactg ctgggtaatg gagactatgt     840
tgctggacaa atatcagact agctgagaa gcttgagcaa gccgagagtc atctggttca      900
gtctcgcttt ggaggagttg tgccatcatc ccttcataag aaaaaagagg atgagtctca    960
actaactaag ataactcggg atagcgcaaa gataactgtg gaacaggtcc atggactaat    1020
gtcgcaggtc ataaaagatg aattattcaa ctcaatgcgt cagtccaaca acaaatctcc    1080
cactgactcg tcggatccag accctatgat tacatattga agttgctctt ctttttggttt    1140 ctagttttgg attgacccat catttgttgt cctttcattt attttctgtt gtgtaaagaa    1200
```

```
ttataatgct aatcagaata atacagaaga agattttggt taaaaaaaaa aaaaaaaaaa    1260

<210> SEQ ID NO 44
<211> LENGTH: 653
<212> TYPE: DNA
<213> ORGANISM: Arabidopsis thaliana

<400> SEQUENCE: 44
cttaaactac atttatcatt acagtctgat ttgagctaag ttctctcatc ataaactctc      60
cttggagaat catggctatt tcaaaagctc ttatcgcttc tcttctcata tctcttcttg     120
ttctccaact cgtccaggct gatgtcgaaa actcacagaa gaaaaatggt tacgcaaaga     180
agatcgattg tgggagtgcg tgtgtagcac ggtgcaggct ttcgaggagg ccgaggctgt     240
gtcacagagc gtgcgggact tgctgctaca ggtgcaactg tgtgcctccg ggtacgtacg     300
gaaactacga caagtgccag tgctacgcta gcctcaccac ccacggtgga cgccgcaagt     360
gcccataaga agaaacaaag ctcttaattg ctgcggataa tgggacgatg tcgttttgtt     420
agtatttact ttggcgtata tatgtggatc gaataataaa cgagaacgta cgttgtcgtt     480
gtgagtgtga gtactgtatt attaatggtt ctatttgttt ttacttgcaa gttttcttgt     540
tttgaatttg ttttttttcat atttgtatat cgattcgtgc attattgtat tatttcaatt     600
tgtaataaga ttatgttacc tttgagtggt tgtttaaaaa aaaaaaaaaa aaa            653

<210> SEQ ID NO 45
<211> LENGTH: 1266
<212> TYPE: DNA
<213> ORGANISM: Arabidopsis thaliana
<220> FEATURE:
<221> NAME/KEY: misc_feature
<222> LOCATION: (757)..(761)
<223> OTHER INFORMATION: n = a, c, g, or t

<400> SEQUENCE: 45
agatggggaa gaagaacaag agaagtcaag acgagtctga gctcgaattg gagccagagc      60
taacgaaaat aatcgatgga gactctaaaa agaagaaaaa taagaataag aagaagagaa     120
gccatgaaga tacggagata gaaccggagc aaaagatgag tctcgacgga gactcgaggg     180
aggagaagat aaagaagaag aggaagaaca agaaccaaga ggaggagcca gagcttgtga     240
cggagaaaac gaaagtccaa gaggaggaaa agggaaatgt agaagagggt agagccactg     300
ttagcatagc catagctggt tcaatcatcc acaacactca atcacttgag ctcgccacac     360
gcgtaatctc tctttctctc tatctctccc ttcgtttctc tgtttttcca ttcccagata     420
atttaaagtc cccttcttcc atttctaaca tttctcagct cgccggccaa attgctcgtg     480
cagctacaat tttccgaatc gacgagatcg tagtgttcga caataagagc agctcagaaa     540
tcgaatcagc tgctacgaat gcttctgata gcaatgaaag tggtgcctcc tttctcgttc     600
gtatcttgaa gtatctagag acaccacaat atttgaggaa atctctcttc cccaagcaaa     660
atgatcttag atatgtgggt atgttgccgg gtatgttgcc acctcttgat gctcctcacc     720
atctgcgtaa gcacgagtgg gaacaatacc gtgaagnnnn nattgttcca ccctctaagc     780
caagggaaga agcaggaatg tattggggat acaaagtacg atatgcatca caattaagtt     840
cagtattcaa ggaatgccct ttcgagggtg gttacgatta tttgattggt acctcggagc     900
acggcctggt aattagttca tctgagctga aaataccaac atttaggcac ctattgattg     960
catttggtgg acttgctggg cttgaagaaa gtattgaaga tgataatcag tataagggga    1020
aaaacgttcg agatgtgttt aatgtatact tgaatacttg tccacatcaa ggtagccgaa    1080
```

```
ccattcgagc agaggaagcg atgtttatat cacttcagta cttccaggaa cccatcagca    1140
gggcagtgag aagactttaa gcttcgataa aaagagtcaa agaagctatt ttgttctcat    1200
agatctgagg tttgtctgaa aaagagtgat gtaatgtaac tgttttagaa aaaaaaaaa     1260 aaaaaa                                                              1266

<210> SEQ ID NO 46
<211> LENGTH: 1520
<212> TYPE: DNA
<213> ORGANISM: Arabidopsis thaliana
<220> FEATURE:
<221> NAME/KEY: misc_feature
<222> LOCATION: (1455)..(1455)
<223> OTHER INFORMATION: n = a, c, g, or t

<400> SEQUENCE: 46
atggaattgc ttgacatgaa ctcaatggct gcctcaatcg gcgtctccgt cgccgttctc      60
cgtttcctcc tctgtttcgt cgcaacgata ccaatctcat ttttatggcg attcatcccg     120
agtcgactcg gtaaacacat atactcagct gcttctggag cttttcctctc ttatctctcc    180 tttggcttct cctcaaatct tcacttcctt gtcccaatga cgattggtta cgcttcaatg     240
gcgatttatc gaccccttgtc tggattcatt acttttcttcc taggcttcgc ttatctcatt   300
ggctgtcatg tgttttatat gagtggtgat gcttggaaag aaggaggaat tgattctact     360
ggagctttga tggtattaac actgaaagtg atttcgtgtt cgataaacta caacgatgga    420
atgttgaaag aagaaggtct acgtgaggct cagaagaaga accgtttgat tcagatgcct     480
tctcttattg agtactttgg ttattgcctc tgttgtggaa gccatttcgc tggcccggtt     540
ttcgaaatga aagattatct cgaatggact gaagagaaag gaatttgggc tgtttctgaa    600
aaaggaaaga gaccatcgcc ttatggagca atgattcgag ctgtgtttca agctgcgatt     660
tgtatggctc tctatctcta tttagtacct cagtttccgt taactcggtt cactgaacca     720
gtgtaccaag aatggggatt cttgaagaga tttggttacc aatacatggc gggtttcacg     780
gctcgttgga agtattactt tatatggtct atctcagagg cttctattat tatctctggt    840
ttgggtttca gtggttggac tgatgaaact cagacaaagg ctaaatggga ccgcgctaag    900
aatgtcgata ttttgggggt tgagcttgcc aagagtgcgg ttcagattcc gcttttctgg    960
aacatacaag tcagcacatg gctccgtcac tacgtatatg agagaattgt gaagcccggg   1020
aagaaagcgg gtttcttcca attgctagct acgcaaaccg tcagtgctgt ctggcatgga   1080
ctgtatcctg gatacattat attctttgtg caatcagcat tgatgatcga tggttcgaaa   1140
gctatttacc ggtggcaaca agcaataccct ccgaaaatgg caatgctgag aaatgttttg   1200
gttctcatca atttcctcta cacagtagtg gttctcaatt actcatccgt cggtttcatg    1260
gttttaagct tgcacgaaac actagtcgcc ttcaagagtg tatattacat tggaacagtt   1320
atacctatcg ctgtgcttct tctcagctac ttagttcctg tgaagcctgt tagaccaaag   1380
accagaaaag aagaataatg ttgtcttttt aaaaaatcaa caacattttg gttcttttct    1440
ttttttccac ttggnccgtt ttatgtaaaa caagagaaat caagatttga ggttttattc   1500
ttaaaaaaaa aaaaaaaaa                                                1520

<210> SEQ ID NO 47
<211> LENGTH: 1142
<212> TYPE: DNA
<213> ORGANISM: Arabidopsis thaliana

<400> SEQUENCE: 47
```

| | |
|---|---|
| ttatataacc tatctacact ttgatctccg acaattcact ttcccaataa gaaccaactg | 60 |
| agagagagag agcgccggag aagaagaatt ttagagagcg atggacgagg gagttatagc | 120 |
| agtttccgcc atggatgctt tcgagaagct tgagaaagtt ggtgaaggga catacgggaa | 180 |
| agtttacaga gccagagaga aagctaccgg gaaaatcgtc gctctaaaga agacgcgtct | 240 |
| ccatgaggac gaagaaggcg ttccttccac cactctccgc gagatctcca ttttgcgaat | 300 |
| gctcgctcgt gatcctcacg tcgtcaggtt aatggatgtt aagcaaggac taagcaaaga | 360 |
| aggcaaaact gtactgtacc tggttttttga atacatggac actgatgtca agaaattcat | 420 |
| cagaagtttc cgtagcactg gcaagaacat tccaacccaa actatcaaga gcttgatgta | 480 |
| tcaactatgc aaaggtatgg cattctgcca tggtcacggg atattgcaca gagatctcaa | 540 |
| gcctcacaat ctcttgatgg atcccaagac aatgaggctc aaaatagcag atcttggttt | 600 |
| agccagagcc ttcactctgc caatgaagaa gtatacccat gagatattaa ctctttggta | 660 |
| tagagctcca gaggttcttc ttggtgccac ccattactct acagctgtgg atatgtggtc | 720 |
| tgttggctgc atatttgctg aacttgtgac caaccaagca atctttcagg gagactctga | 780 |
| gctccaacag ctcctccata ttttcaagtt gtttgggaca cccaatgaag aaatgtggcc | 840 |
| aggagtgagc acactcaaga actggcatga atacccacag tggaaaccat cgactctatc | 900 |
| ctctgctgtt ccaaacctcg acgaggctgg agttgatctt ctatctaaaa tgctgcagta | 960 |
| cgagccagcg aaacgaatct cagcaaagat ggctatggag catccttact ttgatgatct | 1020 |
| gccagaaaag tcctctctct aaggatttaa aatcttcagt tagtatcttt ccaagtttta | 1080 |
| tggtttttct agttttgctt ctttcaagca tatctctagt gtgctgcttc ccctctatg | 1140 |
| aa | 1142 |

<210> SEQ ID NO 48
<211> LENGTH: 1189
<212> TYPE: DNA
<213> ORGANISM: Arabidopsis thaliana

<400> SEQUENCE: 48

| | |
|---|---|
| tagtcaacga tggatttgag acatgaacaa ctaattgatt tgatttcgtg tagctaactt | 60 |
| tgttaattgg taaattgtgt agagaaggat gagtatggag atggagttgt tgtcactcc | 120 |
| agagaagcag aggcaacatc cttcagtgag cgttgagaaa actccagtga aaggaaatt | 180 |
| gattgttgat gatgattctg aaattggatc agagaagaaa gggcaatcaa gaacttctgg | 240 |
| aggcgggctt cgtcaattca gtgttatggt ttgtcagaag ttggaagcca agaagataac | 300 |
| tacttacaag gaggttgcag acgaaattat ttcagatttt gccacaatta agcaaaacgc | 360 |
| agagaagcct ttgaatgaaa atgagtacaa tgagaagaac ataaggcgga gagtctacga | 420 |
| tgcgctcaat gtgttcatgg cgttggatat tattgcaagg gataaaaagg aaatccggtg | 480 |
| gaaaggactt cctattacct gcaaaaagga tgtggaagaa gtcaagatgg atcgtaataa | 540 |
| agttatgagc agtgtgcaaa agaaggctgc ttttcttaaa gagttgagag aaaaggtctc | 600 |
| aagtcttgag agtcttatgt cgagaaatca agagatggtt gtgaagactc aaggcccagc | 660 |
| agaaggattt accttaccat tcattctact tgagacaaac cctcacgcag tagtcgaaat | 720 |
| cgagatttct gaagatatgc aacttgtaca cctcgacttc aatagcacac ctttctcggt | 780 |
| ccatgatgat gcttacattt tgaaactgat gcaagaacag aagcaagaac agaacagagt | 840 |
| atcttcttct tcatctacac atcaccaatc tcaacatagc tccgctcatt cttcatccag | 900 |
| ttcttgcatt gcttctggaa cctcaggccc ggtttgctgg aactcgggat ccattgatac | 960 |

```
tcgctgaccg agcttctatt cccaaattct tcaagaagaa gaagtaatga tctaattggt   1020
atactaaaaa attatacatc tggtttagtg ttcaattgag agagactgta aaatcaattc   1080
ataggccaac aaatgtttgt ttatccaatt ttccttttta ttcgaacttg atgcgatatt   1140
tcaacggaaa cagaaactat tgttttaaac caaaaaaaaa aaaaaaaa              1189
```

<210> SEQ ID NO 49
<211> LENGTH: 805
<212> TYPE: DNA
<213> ORGANISM: Arabidopsis thaliana

<400> SEQUENCE: 49

```
atgaataggg aaaagttgat gaagatggct aacactgtcc gcactggcgg aaaggggaca    60
gtaagaagaa agaagaaggc tgttcacaag accactacaa ccgatgacaa gaggctccag   120
agcactctta agagagttgg agtcaattcc attcccgcca ttgaagaagt taacattttt   180
aaggatgatg tagtcattca gttcattaac cctaaagttc aagcttcaat tgctgctaac   240 acatggggttg tgagtggtac accacagacg aaaaaattgc aagacattct tcctcagatt   300
atcagccaac ttggaccaga taacttggac aacctgaaga agctagcaga gcaattccag   360
aaacaagctc caggtgcagg tgatgtccca gcaacaatcc aagaagagga cgatgatgat   420
gatgtcccag atcttgtagt gggagagact ttcgagaccc ctgctactga agaggctccc   480
aaagctgctg cttcttagag gaggaggaag aagaaggaga agagctcacc tgcaaaaccc   540
atcataaaaa tgtttgtcgc tcgacctctt ctgagcactg tcagattctt gttttctcta   600
atgcttgcga acagaaagac ttggttttat tatcacttga tgcttttggg tccgaacagc   660
aattttcctt ttattaaggt tagatcgctt tttgttacc acctgttcaa atgagtacta    720
ctatgtcctg tcgcttcata cacttcttgc aacacagtcc tttgttttga gtcaaaaaaa   780 aaaaaaaaaaa aaaaaaaaaa aaaaa                                       805
```

<210> SEQ ID NO 50
<211> LENGTH: 1539
<212> TYPE: DNA
<213> ORGANISM: Arabidopsis thaliana

<400> SEQUENCE: 50

```
aagctttact acttatactc ttttgttcct atggccaccg tatcttcttc ctcctggcca    60
aaccccaacc ctaatcccga ttccacgtct gcctcagatt ccgattctac ttttccctct   120
caccgcgatc gcgtagacga acccgactct ctcgattcct tctcctccat gagtcttaac   180
tccgacgaac ctaatcagac ttctaatcaa tcgcctcttt ctcccctac gcccaattta    240 ccggtgatgc ctcctccgtc cgtgcttcat cttttcttta accaagatca tgcttgcttc   300
gctgtcggca ctgaccgtgg cttccggatc cttaattgcg atcccttcg cgagattttc    360 cggcgtgatt tcgatcgtgg cggtggtgtt gcagtcgtgg agatgctttt cagatgcaat   420
atattagccc tagttggtgg cggacctgat cctcaatatc ctcctaataa ggttatgatt   480
tgggatgatc accagggccg atgtatcgga gaactctctt tcaggtccga tgttagatcc   540
gtccggctta ggagggatcg gattattgtc gttcttgagc agaagatttt tgtctacaat   600
ttctctgacc tcaagctgat gcatcagatt gaaaccattg ccaaccctaa gggtttgtgt   660
gctgtttctc agggtgttgg ttctatggtt ttggtatgtc caggtttgca gaaaggtcaa   720
gttcggatcg agcactacgc ttctaaacgg accaaattcg tcatggctca tgattccaga   780
atagcttgct tcgctctcac gcaggatggc catttgttgg ccactgctag ctctaagggt   840
```

-continued

| | |
|---|---|
| actctggttc ggatcttcaa tactgttgat ggtaccttgc gtcaagagtc tggcacttct | 900 |
| gaggatgaaa taggtaagga gggtgcggat agagcagaga tctacagttt ggccttctct | 960 |
| tcaaatgctc agtggttagc tgtctcaagt gacaaaggaa cggtccatgt ctttggtctc | 1020 |
| aaagtcaact ccggatctca agtgaaagac tcatcccgaa ttgcacctga tgctactccc | 1080 |
| tcatccccat cgtcgtctct gtctttattc aaagtgttac cgaggtattt cagctcggag | 1140 |
| tggtcggtgg ctcagttcag gttggttgaa ggaactcagt acatagccgc ctttggccat | 1200 |
| caaaagaaca ccgttgttat tcttggcatg gatgggagct tctacagatg ccagtttgat | 1260 |
| ccggtgaacg gcggtgaaat gtctcagctt gagtaccaca actgtctgaa accgccttca | 1320 |
| gttttctaaa agctttacta cttatactct tttgttcctt ctctctcttt atatctctct | 1380 |
| gcaacttaag cggtgagata tggtgtatag ttttgtgtat ataataatga tgggtcgtcc | 1440 |
| tataatttgt aaaaccttttt atcgctaccc gggtcgactc tagagcccta tagtgagtcg | 1500 |
| tattactgca gagatctatg aatcgtagat actgaaaaa | 1539 |

<210> SEQ ID NO 51
<211> LENGTH: 1977
<212> TYPE: DNA
<213> ORGANISM: Arabidopsis thaliana

<400> SEQUENCE: 51

| | |
|---|---|
| agagcttcct ctctctatat ctggctttct atggatgtag gagttactac ggcgaagtct | 60 |
| atacttgaga agcctctgaa gcttctcact gaagaagaca tttctcagct tactcgcgaa | 120 |
| gattgccgca aattcctcaa agagaaaggt ttcttcttct ccctttctcc attttttcc | 180 |
| ggtcttattg tcttcgacga atggcggctg acacgtgtcg aaacaggaat gcgcaggcct | 240 |
| tcgtggaata aatctcaggc gatccagcaa gtttatctc ttaaagctct ctatgaacct | 300 |
| ggagatgatt ccggcgccgg aatcctccgc aagatccttg tttctcagcc gccaaatccg | 360 |
| cctcgcgtta caacaacgtt gattgagcca aggaacgagc tcgaagcttg tggaaggatt | 420 |
| cctttacagg aagatgatgg tgcgtgccat agaagggatt ctccaagatc agctgagttt | 480 |
| tctggtagtt ctggtcagtt tgttgcggat aaagatagcc acaagactgt ttctgtttcc | 540 |
| cccagaagcc cagctgaaac aaatgcggtg gttgggcaaa tgacgatatt ttatagtggc | 600 |
| aaagtgaatg tatatgatgg agtaccacct gaaaaggccc ggtctatcat gcattttgca | 660 |
| gccaatccaa ttgatttgcc tgaaaatggt attttttgctt ctagtagaat gatttcgaaa | 720 |
| cccatgagta aagagaagat ggtggagctt ccccaatatg gacttgaaaa ggcacctgct | 780 |
| tctcgtgatt ctgatgttga gggtcaggcg aacagaaaag tatcgttgca aagatatctt | 840 |
| gaaaagcgga agacagatt ttctaagacc aagaaggctc aggagttgc gtcctctagc | 900 |
| ttggagatgt ttctgaatcg tcagccacgg atgaacgctg catattcaca aaaccttagt | 960 |
| ggcacagggc attgcgagtc acctgaaaat caaacaaaaa gtcccaatat ctcagttgat | 1020 |
| ctaaacagtg atctaaacag cgaaggtgcc aaaagaactg gagatggtac tacgggtcaa | 1080 |
| aaggcgggaa gaacaatttc atgttcttat aacatgacta agacatcacg aggaacacga | 1140 |
| tgggtgaagc ggtcaagaga agaagtgatt caagcttggt atatggatga tagtgaagag | 1200 |
| gatcagagac ttcctcacca aaggatcct aaagagtttg tatcgttgga caaacttgca | 1260 |
| gagctgggag tacttagctg gagacttgat gctgataact atgaaaccga tgaggatttg | 1320 |
| aaaaagatcc gtgaatctcg tggttactct tacatggact tttgtgaggt atgcccggaa | 1380 |
| aagcttccaa actatgaagt gaaagtgaag agctttttcg aagaacattt acacactgat | 1440 |

```
gaggagatcc gttactgcgt tgcaggaact ggttactttg atgtgagaga tcgtaatgaa    1500
gcttggatta gggtattggt aaagaaggga ggtatgatag tcttacctgc tgggatctat    1560
catcgcttca ctgtggactc tgacaactat atcaaggcaa tgcggctatt cgtgggtgaa    1620
ccggtatgga caccatacaa tcgcccacac gaccatcttc ctgcaaggaa agaatatgtc    1680
gataacttca tgatcaatgc ctcggcttag agagcttcct ctctctatat ctggctttct    1740
gaaacaagga tctataaaca aggcctacaa taaagaaagc tttcctgtca agtattggat    1800
atttatatgt attcctgtgt agaatgatgg cttttggtat gcttgagttg ttgtaaactt    1860
agttacactc tctgatatgt ctctctttac catctttgtc gtatcccata tacgaaaaga    1920
ttacattggg attcatattg tcttacgttc gttcctatgt gcaatatgtt gagtttt      1977

<210> SEQ ID NO 52
<211> LENGTH: 525
<212> TYPE: DNA
<213> ORGANISM: Arabidopsis thaliana

<400> SEQUENCE: 52
catcgctttt cgctgaaatc aaaatttctc cagttttccg atcagtcgca agaaaaccct      60
aaaaatggat ggtcatgatt ctaaggatac taagcagagc actgctgata tgactgcttt     120
tgtccaaaat cttctccagc agatgcaaac caggttccag acaatgtcgg actccatcat     180
cacaaagatt gatgacatgg gaggcagaat caatgagctg agcaaagca tcaatgatct      240 aagagccgag atgggagtag aaggcactcc tcctccagcc tccaaatcag gcgatgaacc     300
caaaacaccg gctagttcct cttaaaaagg aatgtggtgt tcattgacat gtccgaagga     360
aaaagaaaaa ctatgaaata tgttaagagc agtattactt ttaaaattcc tgttttaaga    420
aacgagtttg ttgtttatta aagttcatca aatagattga tgatgtggtg cattacatta    480
ttctccacct atgaattgca tttctatttt ggtctaaaaa aaaaa                    525

<210> SEQ ID NO 53
<211> LENGTH: 2610
<212> TYPE: DNA
<213> ORGANISM: Arabidopsis thaliana

<400> SEQUENCE: 53
agaacaattg agattcttgg ttgtgttaag atggaaatct acaccatgaa aacgaatttt     60
cttgtactgg ctttgtcttt gtgtatcctt cttcaagct tccatgaggt ttcttgtcag     120
gatgatggta gtggtttgag taatttggat ctaatagaac gtgattatca agatagtgtc    180
aatgctcttc aaggcaagga cgatgaagat cagtctgcaa agatacagag tgaaaaccag    240 ataacacta cagtgactga taagaacact atttctctat ctctatcaga tgaatctgag     300
gttggatctg ttagtgatga aagcgttgga cgttcgagtc tgttggatca aatcaaactt    360
gaattcgaag ctcatcacaa tagtattaac caagctggat ctgatggtgt caaggctgaa    420
tccaaggatg atgatgaaga attatctgct catagacaga aaatgttgga agaaatcgaa    480
catgagtttg aagctgcttc agatagtctg aaacaactaa agactgatga tgtaaacgaa    540
ggaaatgatg aagaacattc tgcaaagagg caaagtttgt tggaagagat cgaacgtgag    600
tttgaagctg ctacaaaaga acttgaacaa ctaaaggtta atgacttcac cggggacaaa    660
gatgacgaag aacactctgc aaagagaaaa agtatgcttg aagctattga cgcgagtttt    720
gaagctgcta tggaaggcat tgaagcactt aaggttctg attccacagg aagcggagat      780
gatgaagaac aatctgcaaa gagactaagt atgcttgaag agatcgaacg ggaatttgaa    840
```

-continued

```
gctgcttcaa aaggtcttga caactaagg gctagcgatt caaccgcgga caataacgaa      900
gaagaacacg ctgcaaaggg acaaagtttg ttagaagaga tcgaacgaga gttcgaagct     960
gctacagaga gccttaagca acttcaagtt gatgattcta ctgaagacaa agaacactgt    1020
aaagcactct tcttcttatt atctgctatt ctttctctat ggttatctga atcaggcttt    1080
gaatgtattg tagttacagc tgcaaagagg caaagtctgc tggaagagat tgaacgtgaa    1140
tttgaagctg caacaaaaga tcttaaacaa ctaaatgatt tcactgaagg cagtgctgat    1200
gatgaacaat ctgcaaagag aaacaaaatg ttggaagata tcgaacgcga atttgaagct    1260
gctacaatag gtcttgaaca actaaaggct aatgatttct ctgaaggcaa taataatgaa    1320
gaacaatctg caaagagaaa gagtatgctt gaagagatcg aacgcgagtt cgaagctgct    1380
attggaggtc ttaaacagat caaagttgat gattccagaa atcttgaaga gaatctgct     1440
aagagaaaga taattttgga agagatggaa cgtgaatttg aagaagcaca cagtggtatt    1500
aatgcaaagg ctgacaaaga gaatctgcaa agaaacaga gtggctctgc tataccagag     1560
gttcttggac taggacagtc aggtggttgt agctgttcta acaagacga agattcctcg      1620
attgttatac caacaaaata tagcatagaa gatatcctct ctgaagaatc tgcagtccag    1680
ggaacagaga cttctagtct caccgcgtct ttgactcaac tcgttgagaa tcacaggaaa    1740
gaaaaggaat ctctactcgg acacagagtt ctcacttctc cttctatagc ttcttccaca    1800
agcgaatcat ctgctacatc agagactgta gaaaccctaa gggctaaact gaatgagctt    1860
cgcggcttaa ccgctcgtga gcttgtgaca cgtaaagatt tcggtcagat tctcattacg    1920
gctgcgagtt ttgaagagct aagttcagct ccaatcagtt acatttctag gttagctaaa    1980
tacagaaacg tcatcaaaga aggacttgaa gcttctgaga gagttcacat cgcgcaggta    2040
cgagcaaaaa tgctcaaaga agttgccacg gagaagcaaa ccgccgtgga cactcatttc    2100
gcaaccgcta aaaagcttgc tcaagaagga gacgcgttgt tcgttaaaat cttcgcaatc    2160
aagaaactgt tggcgaaact tgaagcagag aaagaatctg ttgatggaaa gtttaaggag    2220
actgtgaaag aactttctca tcttctggct gatgcttctg aggcttacga agagtatcat    2280
ggcgcggtga ggaaggcgaa agacgagcaa gcggctgagg aatttgcgaa agaggcgacg    2340
caaagtgcag agatcatttg ggttaagttt cttagttctc tttagagaac aattgagatt    2400
cttggttgtg ttaagagcaa atctagagct cttgttggtt cttgttatgt attttgtgat    2460
gatgttctgt ttcagagttt gtgtgttggt tgtatcagga gaaagaggct gggagataga    2520
gagaaagaga gtctctgcga aaactaataa tgttttttca gatatctaaa taataagctt    2580
tttacaaaaa aaaaaaaaa aaaaaaaaa                                       2610
```

<210> SEQ ID NO 54
<211> LENGTH: 2235
<212> TYPE: DNA
<213> ORGANISM: Arabidopsis thaliana

<400> SEQUENCE: 54

```
aatttgaatc caatcccaa attatctcat atggagtttg gatctttct tgtgtcctta       60
gggacatctt ttgttatctt cgtcattctc atgcttctct tcacctggct ttctcgcaaa   120
tctggaaatg ctcccattta ttacccgaat cggatcctta aagggctgga gccatgggaa    180
ggcacctcct tgactcgaaa cccttttgct tggatgcgtg aagctttgac ttcctctgaa    240
caagatgtcg ttaacttatc cggcgtcgat actgctgtcc actttgtctt cttgagcact    300
gttctgggga tatttgcttg ttccagtctt cttctcctac caactctact gcctctagcc    360
```

```
gctacagaca acaacataaa gaacacaaag aatgcgacag ataccacaag caaaggaact    420
tttagccaac ttgataatct atcaatggct aacatcacaa aaaaaagttc gaggctgtgg    480
gcgttcctag gagctgttta ctggatatct ttggtcacat atttcttctt gtggaaagct    540
tataagcatg tctcttcatt gagagctcaa gctctgatgt ctgctgatgt aaaacccgag    600
caattcgcta ttcttgttag ggatatgcct gcaccacctg acgggcagac acagaaagag    660
tttattgatt cttatttcag agaaatatac cctgagacat tctacagatc gcttgtcgca    720
acagaaaaca gcaaggttaa taaaatatgg gaaaaattgg aaggttacaa gaagaagctt    780
gcgcgagcag aagcaatatt agcagcaact aataaccgtc ccacgaacaa accggcttc    840
tgtgggctag tcggtaaaca agtagacagc attgagtatt acactgagct aatcaacgag    900
tctgtagcca aactgaaaac agagcagaaa gcggttcttg ctgagaagca gcaaaccgca    960
gcagtggttt tcttcacaac cagggttgct gctgcatcag cagctcagtc tctgcactgc   1020
cagatggttg ataaatggac tgtgaccgaa gctcctgagc cacggcagct cctatggcag   1080
aatctcaaca tcaagctctt cagcagaata atccggcaat acttcatcta cttctttgtt   1140
gcagtgacca ttctgtttta catgatacca atcgcgttcg tctctgccat caccactctt   1200
aagaatcttc agaggattat tccgttcata aagccggttg tggagataac cgccataaga   1260
accgttttgg agtctttcct tcctcagatt gcgctcattg ttttcttggc catgttgccg   1320
aagcttctct tgtttctctc caaagccgag gggattcctt cacagagcca tgccattagg   1380
gctgcttcag ggaagtactt ttacttctcg gtctttaatg tcttcattgg tgttacccctt   1440
gctgggactt tgttcaacac agtgaaggat atcgcgaaaa atcccaaact cgacatgatt   1500
attaaccttt tggctactag cctccctaag agcgcaactt tcttcctgac ctacgttgct   1560
ctcaagttct ttatcggtta tggccttgag ctgtctcgga tcatacccttt gataatcttc   1620
cacctgaaaa agaagtatct ctgcaaaacc gaagcggagg tcaaagaagc ttggtacccg   1680
ggagacttaa gctatgcgac tagggttccc ggagacatgc tcatcctcac aatcacgttc   1740
tgctattcag tcattgctcc tcttatcctc atattcggca tcacctactt tggtttaggc   1800
tggctagtcc tcaggaatca ggcgttgaaa gtgtacgttc catcatacga gagctatgga   1860
agaatgtggc cgcatattca ccagcgcata ctagcagcgt tgtttctatt ccaagtggta   1920
atgtttggct acttaggagc caagacattc ttctacacgg cccttgtgat ccctctcatt   1980
atcacctctc tcatcttcgg atatgtgtgc cgccagaaat tctacggagg gttcgaacac   2040
acagctctcg aggtagcttg ccgtgagctg aagcagagtc cagacctaga ggagattttc   2100
agagcataca ttccgcatag cttgagctct cacaaaccag aagaacacga gttcaaaggc   2160
gcaatgtctc gttatcaaga tttcaacgca atagcaggcg tttaaagctt gagagattcc   2220
tctggctaaa cccag                                                   2235

<210> SEQ ID NO 55
<211> LENGTH: 4002
<212> TYPE: DNA
<213> ORGANISM: Arabidopsis thaliana

<400> SEQUENCE: 55
aacaataaga agaaaaagtt tcattttctg atggcggagc agaagagtac caatatgtgg     60
aactgggagg tgactgggtt cgaatcgaag aagtcgcctt ctagtgagga aggcgttcat    120
cggacaccgt cttctatgct tcgacggtac tcgatcccga agaactcgct tccaccgcac    180
tcgtcggagc ttgcgtctaa ggttcagagt ttgaaggata aagttcagct tgcaaaggac    240
```

```
gattatgtgg gattgagaca ggaagctact gatcttcaag agtactccaa tgcgaagctt    300
gaaagggtta cacgttattt aggtgttctg gctgataaaa gtcgtaaact ggatcaatat    360
gcacttgaga ctgaggctag gatatctcca cttatcaatg agaagaagag actgttcaat    420
gacttactga cgaccaaagg tgcacatctt ccatttccga cgtcattctc tatccttact    480
tctattgata ttgatcacac cagaccctta tttgaagacg agggtccctc tatcattgaa    540
tttcctgata actgcactat acgcgtaaac actagtgatg atactctgtc caatcccaag    600
aaggaatttg aatttgatag agtttatggg cctcaagttg acaagcttc actgttcagt    660
gatgtccaac cttttgtgca atccgctctg gatggatcga acgtttctat atttgcgtat    720
ggccaaactc acgcggggaa gacatacacc atggttgccc ctccttttccc tttcctctct    780
gaaattagat ataggtcttg tttggattta aatatgatag gcaagttcat ggacgttcat    840
agtaagttca tggacgaagg atctaatcag gaccgtggtt tatatgctcg ttgttttgag    900
gaacttatgg acttggccaa ttctgattca acttccgcat ctcagttcag tttctctgtt    960
tcagtgtttg agctttataa cgaacaggtc agggatttac tctcggggttg tcagagcaat   1020
ttgccaaaga tcaatatggg tttacgcgaa tcggttatag aactttcaca ggaaaaagtt   1080
gataatccat cagagttcat gagagtcctg aactctgcat ttcagaatag agggaatgat   1140
aaatcaaagt ctactgtgac ccatctgatt gtctcgatac acatttgtta tagcaacaca   1200
attacgagag aaaatgtaat tagcaagctt tctttagttg acctggctgg aagtgaaggt   1260
ttaactgtgg aggatgacaa tggagatcat gtaactgatc tgctccatgt aacaaattca   1320
atttccgcgc tgggagatgt tttatcatct ttgacgtcaa aaagagatac cattccttac   1380
gagaactcat ttcttacaag aatacttgca gattcactag gagggagctc caaaacattg   1440
atgatcgtca acatttgtcc aagtgcacgg aacttgtctg aaataatgtc gtgtctcaac   1500
tatgctgcta gagctcgaaa tactgtacca agccttggga atcgagacac aattaagaaa   1560
tggagagacg tggcaaatga tgctcggaag gaggtattgg agaaagagag ggaaaatcag   1620
cgtctaaaac aagaggttac gggttttaaaa caagcactta agaagcaaa tgaccaatgt   1680
gtactgctct ataatgaagt acagagagcg tggagagttt cattcacact gcaatcagat   1740
ttaaagtcag agaatgcgat ggttgtagac aaacataaaa tagaaaagga gcagaatttt   1800
cagttaagaa atcaaatagc tcaactttta cagttagaac aggaacaaaa gctgcaggcg   1860
caacaacaag attccaccat tcaaaatctc cagtctaaag tgaaagactt agaatcacaa   1920
ctaagtaaag ctctgaagtc tgacatgaca agatcgagag atcccttgga acctcagccc   1980
agagcagctg agaacacact cgattcttct gcagttacca agaaacttga ggaagaattg   2040
aaaaaacgtg atgcactgat tgagaggttg catgaagaaa atgaaaaatt gttcgacaga   2100
ttaacagaaa agtcagtggc tagctcgact caggtatcta gcccctcatc aaaagcttca   2160
ccaacagtgc agcctgcaga tgttgacagg aaaaatagcg cgggcacttt accgtcttca   2220
gtggataaaa atgagggcac gattacatta gtaaaatcca gctctgaatt agtaaaaacc   2280
actccagctg gagaatactt aacagctgca ttgaatgatt ttgatcccga caatatgaa    2340
ggtcttgcag ccatagctga tggcgcaaac aagcttctga tgctggtctt agcagctgtc   2400
ataaaggctg gtgcttccag agagcatgaa atccttgctg agatcagaga ttctgtcttt   2460
tcatttatcc ggaaaatgga accaaggaga gtaatggata caatgcttgt ttctcgagtc   2520
aggatattgt acataaggtc cttacttgca cgatcacctg agcttcagtc gatcaaggtt   2580
tctcctgttg aacgcttttt ggagaagcca tatactggtc gaactagaag ctccagcggg   2640
```

```
agtagcagcc caggtagatc accagttcga tattatgatg agcagattta tggctttaaa    2700
gttaatttaa agccagaaaa gaaaagtaag ttggtatctg tagtttcaag aatccgtgga    2760
catgaccagg atactgggag gcagcaagtg actggaggaa agctgaggga gatacaagat    2820
gaagccaaaa gttttgccat tggaaacaaa cccttagctg ctttatttgt tcacactccg    2880
gctggtgaac tgcaaagaca gattaggtca tggcttgcag aaagttttga gtttctctct    2940
gttacagcag atgatgtttc aggagtaacc actggccaat tagagcttct ttccacagca    3000
attatggatg ctggatggc tggagtagga gctgcggtgc cacctcacac agacgcttta     3060
ggacagcttt tgtctgagta tgcaaaacga gtctacactt ctcagatgca gcatctaaag    3120
gatattgccg gtactttggc ttcggaagag gcagaagatg ctggtcaagt cgcgaagctt    3180
cgatcagctc tcgagtctgt tgaccacaaa agaagaaaga ttttgcaaca aatgagaagt    3240
gatgcagctt tgtttacctt ggaagaaggc agttcccctg ttcaaaatcc atctacagca    3300
gccgaagact cgagattagc ctccctcatt tctctggatg ccatactgaa gcaagtcaag    3360
gaaataacaa gacaagcctc tgtccacgtt ttgagtaaaa gcaagaaaaa ggcattgctt    3420
gagtctcttg atgaacttaa cgaacgaatg ccttctctgc ttgatgttga tcatccatgt    3480
gcacagagag aaattgatac ggctcaccag ttggtcgaga caattccaga acaagaggac    3540
aatcttcaag acgaaaagag accttcaata gattcaatat cttcgactga aaccgatgtg    3600
tctcaatgga atgttttgca attcaacaca ggaggctctt cagctccatt catcataaaa    3660
tgcggagcta actccaactc agagctcgtg atcaaagcgg atgcccgtat tcaagaacct    3720
aaaggaggcg aaatagtgag agttgtgcca agaccttcgg ttttagaaaa catgagctta    3780
gaggaaatga aacaagtgtt tggtcagttg cccgaagctc taagttcact ggccttagct    3840
agaacagctg atggcacacg ggctcgatac tctagactct acagaactct agccatgaag    3900
gttccctctc ttagggacct cgttggagag cttgagaaag gaggagtctt aaaagataca    3960
aaatcgacat gataggatta gggttttttc gtgaatttga aa                       4002

<210> SEQ ID NO 56
<211> LENGTH: 1251
<212> TYPE: DNA
<213> ORGANISM: Arabidopsis thaliana

<400> SEQUENCE: 56
ttagttagat aggcggtggt tggtgcgttc atggcgaatc cttggtgggt agggaatgtt      60
gcgatcggtg gagttgagag tccagtgacg tcatcagctc cttctttgca ccacagaaac     120
agtaacaaca caacccacc gactatgact cgttcggatc caagattgga ccatgacttc      180
accaccaaca acagtggaag ccctaatacc cagactcaga gccaagaaga acagaacagc     240
agagacgagc aaccagctgt tgaacccgga tccggatccg ggtctacggg tcgtcgtcct     300
agaggtagac ctcctggttc caagaacaaa ccaaagagtc cagttgttgt taccaaagaa     360
agccctaact ctctccagag ccatgttctt gagattgcta cgggagctga cgtggcggaa     420
agcttaaacg cctttgctcg tagacgcggc cggggcgttt cggtgctgag cggtagtggt     480
ttggttacta atgttactct gcgtcagcct gctgcatccg gtggagttgt tagtttacgt     540
ggtcagtttg agatcttgtc tatgtgtggg cttttcttc ctacgtctgg ctctcctgct     600
gcagccgctg gtttaaccat ttacttagct ggagctcaag gtcaagttgt gggaggtgga     660
gttgctggcc cgcttattgc ctctggaccc gttattgtga tagctgctac gttttgcaat    720
gccacttatg agaggttacc gattgaggaa gaacaacagc aagagcagcc gcttcaacta    780
```

| gaagatggga agaagcagaa agaagagaat gatgataacg agagtgggaa taacggaaac | 840 |
| gaaggatcga tgcagccgcc gatgtataat atgcctccta attttatccc aaatggtcat | 900 |
| caaatggctc aacacgacgt gtattggggt ggtcctccgc ctcgtgctcc tccttcgtat | 960 |
| tgattagtta gataggcggt ggttggtgcg ttctttttac tggaatgatt atattttcca | 1020 |
| ttaggatggt taggcttttg tttattaaag ctatcaagtt tcttttttt ttacggataa | 1080 |
| ttcggatgac aattagctag tgtttgtttg tttgttttgt ggcggctttt ctgacttgac | 1140 |
| tattttgatc gcggatagct ttgtatgaaa gtgaattgat tgtagaatcg tcttttgaat | 1200 |
| tttgatgttg gaaaaaacca agcaatggtg tgtggccttt gcaatggaag c | 1251 |

<210> SEQ ID NO 57
<211> LENGTH: 2955
<212> TYPE: DNA
<213> ORGANISM: Arabidopsis thaliana

<400> SEQUENCE: 57

| aatttgcttt atctttgcat tgttgttggc atggctctca atctccgtca gaaacagact | 60 |
| gaatgtgtaa tccggatgtt gaatctgaac caacctttga atccaagtgg aactgcgaac | 120 |
| gaagaagttt acaagatctt gatttacgat aggttttgtc agaacattct atctccattg | 180 |
| acccatgtca aggatctgcg taagcatgga gttacactct tctttctcat agacaaagat | 240 |
| cgacaacctg ttcatgatgt tcccgctgtc tactttgttc aaccaactga atccaacctc | 300 |
| cagaggatca tagccgatgc ttctagatct ctctacgata cctttcatct gaatttctcg | 360 |
| tcttcgatcc ctcgtaagtt tcttgaagag ctagcttctg ggactcttaa atctggttct | 420 |
| gttgagaaag tctcgaaagt gcatgatcag tatctggagt ttgtgacttt ggaagataac | 480 |
| ttgttctcgc tggctcagca atctacctat gttcaaatga atgacccatc agcaggggag | 540 |
| aaagagatta tgagagattat cgaaagggtc gctagtggtt tgttttgtgt gttggtaacg | 600 |
| cttggtgtgg ttcctgttat ccgatgccct agtggtggac ctgcagagat ggtggcgtct | 660 |
| ttgttggatc agaaactgag ggatcatctt ttgtccaaga acaatctgtt tactgaaggt | 720 |
| ggcggttca tgagctcgtt tcagcgtccc ctcttgtgca tatttgatag aactttgag | 780 |
| ctctcggttg ggattcagca tgatttcaga taccggcctc tcgttcacga tgttctcggg | 840 |
| ttaaagctca accaattgaa agtgcaggga gagaaaggac caccgaaatc gtttgagctg | 900 |
| gacagttcgg acccattctg gtcagcaaac agtactctgg agtttccaga tgtcgctgtg | 960 |
| gagatcgaaa cacagttgaa caagtacaag agagacgttg aagaggttaa caagaaaacc | 1020 |
| ggaggtggga gcggcgctga gtttgatggg acagatctga ttggaaacat ccacaccgag | 1080 |
| catctcatga acactgtgaa atcgctcccg gagttaactg agcgaaagaa agtgattgac | 1140 |
| aaacacacca atatcgcaac agcgctctta ggacagatca aggagagatc tattgacgct | 1200 |
| ttcactaaga aagaaagcga catgatgatg aggggcggaa tcgacagaac tgaacttatg | 1260 |
| gctgctctga aaggcaaagg gacaaagatg gacaagctcc ggtttgcaat catgtacctg | 1320 |
| atctccacag aaaccataaa ccaatcggaa gttgaagcag tggaggcagc attgaatgaa | 1380 |
| gctgaggctg atacaagtgc gtttcagtat gtaaagaaaa tcaaatcgtt aaacgcatct | 1440 |
| tttgcagcta catcagcgaa ttcagctagc agaagcaaca ttgtagactg gccgagaag | 1500 |
| ctttacggac agtctataag cgcagtgact gcaggagtca agaatctgtt atctagtgat | 1560 |
| caacaattgg cagtgactcg aacagtcgaa gctttaacag aaggaaaacc aaacccggag | 1620 |
| atcgattctt accgcttcct ggacccaaga gctccaaagt cgtctagctc cggtggtagc | 1680 |

```
catgtaaaag gaccgttcag agaagctata gtgttcatga tcggtggagg taactatgtt   1740
gagtatggaa gtttgcagga gttgactcag agacagttaa ccgttaaaaa cgttatttat   1800
ggagccactg agattcttaa cggaggtgag ttggtggagc agcttggact tttgggaaag   1860
aagatgggat taggaggtcc ggtcgcttca acgctgaaga ggctgggaat ggctggtaaa   1920
gaggagactg atgtatctgc acaagggtct ttaaccaggg aggccactga gatatggagg   1980
agtgagttgg aatctcgccg gtttcaggta gatagtttag aagctgaact tgtggatgtc   2040
aaggcttacc ttgagtttgg ctcagaagaa gatgccagaa aggagttagg agttctttcg   2100
ggtagggtca gatcgactgc aactatgttg cgttatttga gatcaaaagc tagagtcttg   2160
gccattcctg atgatctagc aaatgtgtca tgcggtgtgg aacagattga agaactgaaa   2220
ggattgaacc ttgttgagaa agatggtggt tcatcttctt ctgacgggc taggaacact    2280 aatcctgaaa ctagaaggta cagtggttcc ttgggtgtag aggatggagc ctatactaat   2340
gagatgctcc agtccataga gatggttact gatgtgctgg actctcttgt gaggagggtt   2400
acagtagcag aatctgagtc tgctgttcaa aaggagaggg cacttttggg agaggaagaa   2460
atcagtagga agactatcca aatcgaaaat ttgtccgtga agttagaaga gatggaacga   2520
tttgcttatg ggactaatag tgttctaaac gaaatgcggg aaaggattga ggaattagtt   2580
gaagagacga tgaggcagag ggaaaaagct gtggaaaacg aagaggagtt gtgtcgtgtg   2640
aagagagagt tcgagtcgct taaaagctac gtcagtactt ttaccaatgt tcgagaaaca   2700
cttctttcgt ccgagagaca attcaaaacc attgaggagc tctttgaacg gttggtcact   2760
aagacgacac aattagaagg ggagaaggca caaaaggagg ttgaagtaca gaaactgatg   2820
gaggagaatg tgaaattgac agcacttctc gacaagaaag aggctcagct tctagctttg   2880
aatgaacaat gcaaagttat ggctttgagt gcatcaaaca tatgactctc taatccaacc   2940
gaatctcaag cttcc                                                   2955

<210> SEQ ID NO 58
<211> LENGTH: 865
<212> TYPE: DNA
<213> ORGANISM: Arabidopsis thaliana

<400> SEQUENCE: 58
ggctgataaa tatagggaga actatttggg tcacagtatc aaagcccctg ttggaagatg    60
gcaaaaaggt aaagatcttc attggtatgc tagagataaa aagcaaaagg gttccgagat   120
ggatgctatg aaagaagaga ttcaaagagt taaggaacaa gaggagcagg ccatgaggga   180
ggctcttggc ttggcaccaa agtcctctac aaggccacaa ggaaatcgcc ttgataagca   240
agagtttact gaacttgtga gaggggttc gacagcagag gacttaggtg cagggaatgc   300
tgatgctgtg tgggttcacg gtcttggata tgctaaagca ccacgacctt gggaagatcc   360
gagcaccctt gcatcctctc agaaagaaga tgcagattca gcacgcttac cagcagatac   420 atcagggtc aaaactgttg aagatggacc ggatgatgtt gagagggacc aaagaaggat   480
aggcgtgagg aaaggaaacc tgcaaagaga gagaaggaag aaagacatga taggcgtgaa   540
aaacgcgaaa ggcatgagaa gcgaagcgct cgtgattcag atgatagaaa gaagcacaag   600
aaagagaaga aggagaaaaa aagaaggcat gactctgatt ctgattgaag cgaattgtcc   660
caggatggaa cattttgctc ttcagaggaa gagtggtcgg ctaggtacca aaatccagct   720
accacttctg caagatttaa atctgttgct tatttcattt acgaatcgtg gagtaaagtg   780
ttgttgaaca ttgttgaaaa tgtttgttaa aacacatgaa aaatgtggtt tgatattata   840
```

```
acaaaccgag acgctcgttt tagct                                         865

<210> SEQ ID NO 59
<211> LENGTH: 723
<212> TYPE: DNA
<213> ORGANISM: Arabidopsis thaliana
<220> FEATURE:
<221> NAME/KEY: misc_feature
<222> LOCATION: (559)..(559)
<223> OTHER INFORMATION: n= a, c, g, t
<220> FEATURE:
<221> NAME/KEY: misc_feature
<222> LOCATION: (622)..(622)
<223> OTHER INFORMATION: n= a, c, g, t
<220> FEATURE:
<221> NAME/KEY: misc_feature
<222> LOCATION: (677)..(677)
<223> OTHER INFORMATION: n= a, c, g, t

<400> SEQUENCE: 59
gcaaaagaga gaaacatctg acccggaatc tgacctgaaa acccggaaga atcgaaaaat    60
ggggaaagat ggtctgagcg acgatcaggt ctcgtcgatg aaggaagcct tcatgctctt   120
cgacaccgat ggcgacggca aaatcgcacc gtcagagctc gggatcctca tgcgatctct   180
cggcggaaac ccgacccaag cccagctgaa atccataatc gcatccgaga atctctcttc   240
accgtttgat ttcaacagat tcctcgatct catggcgaaa catctgaaga cggaaccttt   300
cgatcgccag ctccgtgacg cattcaaagt gctcgataag gaaggtaccg ggttcgttgc   360
tgtggcggat ctgaggcata ttctgaccag tatcggagag aagctggagc ctaatgagtt   420
cgatgagtgg atcaaggagg tggatgttgg atccgatgga aagatccggt atgaagattt   480
catagcaagg atggttgcta agtgagatct aatcttttat gttttgaaag ttgaaatttt   540
taagaagaga ttcttttgng gttttttcac ttggttggtt tgatttcgag cgaatcctaa   600
ctaggggttg gttatcatt gnggaatttg cttactaact ttggcttctt catggttggg    660
tttcaatttt taatggnaaa tggtggctgg gggaattcct aaaaaaaaaa aaaaaaaaa    720
aaa                                                                 723

<210> SEQ ID NO 60
<211> LENGTH: 426
<212> TYPE: DNA
<213> ORGANISM: Arabidopsis thaliana

<400> SEQUENCE: 60 caaaaaaga gatcgcttca atggagaaac agagtactca accaatttgc ggccaagagg    60
ctctccaact tctcaattgc gtcgcggagt ctcctttcga tcaagagaaa tgcgtccgat   120
ttttgcaatc tctcagagaa tgcgttctat caaagaaagt aaagaagttc tcgataccga   180
gtcaagatca cgactctgag ggagcagctt cagctacaaa gagaccttca taacgttctt   240
tgttccgatt tcttttatc gtttgagttg taatcatgta attgatttta atgtcatgcc    300
ttggattcat aagctgggtc atgccttgtt tccccttgt tgtcttgtat gttgaatatt    360
gcaaactcta agagcatat ttataagaag aaataaagt ttctacaaaa aaaaaaaaa     420
aaaaaa                                                              426

<210> SEQ ID NO 61
<211> LENGTH: 1442
<212> TYPE: DNA
<213> ORGANISM: Arabidopsis thaliana

<400> SEQUENCE: 61
```

-continued

| | |
|---|---|
| tcaaaatcag aaactttcct tgacaaattt taacaaatct ctttctcgtt ttctattgaa | 60 |
| ttctccagta gcgcggtagt tagttttagg tggaagaaga atgacaacta ctgggtctaa | 120 |
| ttctaatcac aaccaccatg aaagcaataa taacaacaat aaccctagta ctaggtcttg | 180 |
| gggcacggcg gtttcaggtc aatctgtgtc tactagcggc agtatgggct ctccgtcgag | 240 |
| ccggagtgag caaaccatca ccgttgttac atctactagc gacactactt ttcaacgcct | 300 |
| gaataatttg gacattcaag gtgatgatgc tggttctcaa ggagcttctg gtgttaagaa | 360 |
| gaagaagagg ggacagcgtg cggctggtcc agataagact ggaagaggac tacgtcaatt | 420 |
| tagtatgaaa ggtcttatct ctttctctgc ccctattatg ctttcatcta aatgcctttc | 480 |
| aatttgtgaa aaggtggaaa gcaaaggaag gacaacttac aatgaggttg cagacgagct | 540 |
| tgttgctgaa tttgcacttc caaataacga tggaacatcc cctgatcagc aacagtatga | 600 |
| tgagaaaaac ataagacgaa gagtatatga tgctttaaac gtcctcatgg ctatggatat | 660 |
| aatatccaag gataaaaaag aaattcaatg gagaggtctt cctcggacaa gcttaagcga | 720 |
| cattgaagaa ttaagaacg aacgactctc acttaggaac agaattgaga gaaaaactgc | 780 |
| atattcccaa gaactggaag aacaagtaat gaacatcatc gatactctcg gcttatctgc | 840 |
| ttcctgcctt cagaatctga tacagagaaa tgagcactta tatagctcag gaaatgctcc | 900 |
| cagtggcggt gttgctcttc cttttatcct tgtccagact cgtcctcacg caacagtaga | 960 |
| agtggagata tcagaagata tgcagctcgt gcattttgat ttcaacagca ctccatttga | 1020 |
| gctccacgac gacaattttg tcctcaagac tatgaagttt tgtgatcaac cgccgcaaca | 1080 |
| accaaacggt cggaacaaca gccagctggt ttgtcacaat ttcacgccag aaaaccctaa | 1140 |
| caaaggcccc agcacaggtc caacaccgca gctggatatg tacgagactc atcttcaatc | 1200 |
| gcaacaacat cagcagcatt ctcagctaca aatcattcct atgcctgaga ctaacaacgt | 1260 |
| tacttccagc gctgatactg ctccagtgaa atccccgtct cttccaggga taatgaactc | 1320 |
| cagcatgaag ccggagaatt gaaacacgta tgaaggcccc ttgtacaatt tctgtaaaac | 1380 |
| tgtaaagtag ctcttgaaaa actttacctg gttttttgac gaatagtctg tttagcggta | 1440 |
| aa | 1442 |

<210> SEQ ID NO 62
<211> LENGTH: 1506
<212> TYPE: DNA
<213> ORGANISM: Arabidopsis thaliana

<400> SEQUENCE: 62

| | |
|---|---|
| atggcgctgc agaacattgg tgcttccaac cgtaacgatg ccttctacag gtacaagatg | 60 |
| cctaagatgg ttaccaaaac cgaaggcaaa ggtaatggca ttaagaccaa cattatcaac | 120 |
| aatgttgaga ttgccaaagc cttggctaga ccgccttctt atacgaccaa gtactttggt | 180 |
| tgtgagcttg gagcgcagtc taagtttgat gagaagactg gacgtcgct tgtgaatgga | 240 |
| gctcacaaca cgtctaagct tgctgggctt ttggagaatt ttattaagaa gtttgttcag | 300 |
| tgttatggat gtggtaaccc ggagactgag attattatta cgaagacgca gatggtgaat | 360 |
| ctcaagtgtg ctgcttgtgg gtttatctct gaggtcgaca tgagggataa gttgactaat | 420 |
| ttcattctca agaacccacc tgagcagaag aaggtgtcaa aggataagaa agcaatgagg | 480 |
| aaagctgaga ggagaggct taagaaggc gagctagctg atgaggagca gagaaagctg | 540 |
| aaagctaaga agaaagcatt gtctaacgga aaggattcta agacgtctaa gaaccattct | 600 |
| tctgatgagg atataagccc gaagcatgat gagaatgctc tagaggtgga tgaggatgaa | 660 |

```
gatgatgatg atggtgtcga gtggcaaact gatacttccc gagaagctgc tgagaaaaga    720
atgatggaac agttgagtgc taaaactgcc gaaatggtga tgctctctgc aatgaaagta    780
gaagagaaaa aggcgcccaa aagcaaatct aacgggaacg ttgtgaaaac tgagaatcct    840
cctccgcaag agaagaatct cgtgcaggat atgaaagagt atctgaagaa agggtcacca    900
ataagcgcgc tcaaaagttt catctcgtct ctctctgaac ctcctcaaga catcatggac    960
gcactcttca atgctctctt tgatggtgtg ggaaagggat cgccaaaga agtgactaag   1020 aagaagaatt acttagcggc tgctgcaaca atgcaagagg atggatcaca gatgcatctg   1080
ctcaattcga ttgggacatt ctgtggaaag aatggaaacg aagaagcttt gaaagaggtg   1140
gctctggttc ttaaagcatt gtacgaccaa gacatcattg aggaagaggt agtgttggat   1200
tggtacgaaa agggtctcac cggagctgac aaaagctcgc cggtttggaa gaatgttaag   1260
ccttttgtgg agtggcttca gagcgctgag tctgagtccg aagaggagga ttgagtcact   1320 ttttcttcc ctcctaactt ttcttgcgg catttcttat aatacttcgt cagttttcag   1380
aattcttaaa tcttttgct gtgttcttat aaagaaacat catctattaa agttgtcttc   1440
gtttggattt ggttttgacg actttgggaa atatttatgt ttaagaaaaa aaaaaaaaa   1500 aaaaaa                                                              1506

<210> SEQ ID NO 63
<211> LENGTH: 2631
<212> TYPE: DNA
<213> ORGANISM: Arabidopsis thaliana

<400> SEQUENCE: 63
atggcggcta acaaattcgc gactctgatt catcggaaaa caaaccgaat cactttaatc     60
ctcgtatacg cttttctcga atggtcactc attttcttca ttttgctcaa ctctctcttt    120
tcttatttca tactcagatt cgctgattat ttcggtctta aacgtccttg tctcttctgc    180
tctagactcg atcgtttctt cgatgcttct ggtaaatctc cttctcatcg agatcttctc    240
tgcgatgatc atgctctcca attacattca aaacctgttg aagaatctaa ttgtggtttc    300
ggagaatttc acaatgattt ggttcatcgt ggttgttgcg tagagaagat aagttcgtca    360
ctatgtgctc cgattgagtc tgactttggg aatttagatt atccaattgg agatgaaggt    420
cagatttaca atggtcttaa gtttcctcga tcgatcttcg tctttgaaga agagaaagta    480
ggatctgtaa atttgaatga ttctcaggaa gaaacagagg agaagaaagt tccccaatct    540
catgagaaac ttgaagatga tgatgttgat gaggagtttt catgctatgt atcaagcttc    600
gattgtaaga caaagaaaat tgcaacagag aaggaagaag aaaacagagt ggatctacct    660
ataggagtgg aaactgcaga atcagctccg aaaaacctcg agttctatat tgatgaagaa    720
gactgtcatt tgattccagt tgaattctat aaaccgagtg aagaagttcg agagatttcc    780
gacattaacg gagattttat cctcgatttc ggcgttgagc atgatttcac ggcggcggcg    840
gagacggagg aaatctccga ctttgcttcg ccgggtgaat cgaaaccgga ggatgcagag    900
acgaatctag ttgcttcgga aatggaaaac gacgacgaag aaacagacgc agaggtttct    960
ataggtacag agattcctga tcatgagcaa atcggagata ttccttctca ccagctcatt   1020
cctcaccacg atgacgatga tcatgaggag gaaacgttgg agttcaaaac agtaacgatt   1080
gaaaccaaga tgccagtctt aaacatcaac gaagagcgga ttttagaagc tcaaggctcg   1140
atggaaagct cgcatagtag tctacataac gctatgtttc acttagagca aagagtatct   1200
gttgatggta ttgaatgtcc tgaaggagta ctcactgttg ataagttgaa gtttgagtta   1260
```

```
caagaagaga gaaaagcact tcacgcgtta tacgaggagc tggaggtaga gaggaatgcg    1320
tctgctgttg ctgccagtga aacaatggcg atgatcaata ggttgcatga ggagaaagct    1380
gcgatgcaga tggaagcgtt gcagtatcag agaatgatgg aggagcaagc tgagtttgat    1440
caagaagctt tgcagttgtt gaatgagctt atggtgaata gagagaagga gaatgctgag    1500
cttgagaagg agctagaggt gtatagaaag agaatggagg agtatgaagc taaagagaaa    1560
atggggatgt tgaggaggag attgagagat tcctctgttg attcgtatag aaataatggc    1620
gattctgatg agaatagcaa tggagagtta cagtttaaga acgttgaagg ggttacggat    1680
tggaaatata gagagaatga gatggagaat acgccggtgg atgttgtact tcgtcttgat    1740
gagtgtttag atgattatga tggagagagg ctttcgattc ttgggagatt gaagtttctt    1800
gaagagaaac tcacagatct taataacgaa gaggacgacg aggaggaggc taaaacgttt    1860
gagagtaatg gtagcatcaa tggaaatgag catattcatg gcaaagaaac aaacgggaag    1920
cacagagtta tcaagtcaaa gagattactt cccctgtttg atgcggtcga tggagagatg    1980
gaaaacgggt taagtaacgg aaaccatcac gaaaacgggt tgatgattc ggagaagggt     2040 gagaatgtga cgatagaaga agaagtggat gagctttacg agaggttaga agctctagag    2100
gcagatagag agttcttaag acattgtgtt ggttcattga aaaaggaga caaggtgta     2160 catctcctcc atgagattct gcaacatctt cgtgatctaa ggaatatcga tcttactcgc    2220
gtcagagaaa acggagacat gagtttatga gtttgatttt gagttttggg tttgagtcca    2280
ctctttgcat agtgacccaa agaacaagaa aaatcataca ggtatggaag tgacatgttg    2340
cttgtgaggc aaggaacaac gacaaggttt cagatgaaga agaaaacgtt ctcagaataa    2400 aagtattta agtatatact ctgaggaaaa gtgtcagatc agaatgttcg tctttcttcg    2460
ttcattttca ttattataag ttttgttttt tatattgaag atttatttag agagagggaa    2520
gtgtcagtat aatttcactt ttatattta tatttgggag ttgtctttat gagtggtggt    2580
aatagaaaaa ggtagaatga tgagtgaaga aaaaaaaaaa aaaaaaaaaa a            2631
```

<210> SEQ ID NO 64
<211> LENGTH: 2743
<212> TYPE: DNA
<213> ORGANISM: Arabidopsis thaliana

<400> SEQUENCE: 64

```
atgtcagacg ctctttctgc gattccggcc gcagttcatc gcaatctctc cgataaactc     60
tatgagaagc gcaaaaatgc tgcgcttgag cttgagaata ttgtgaagaa tctaacttct    120
tcgggtgatc atgacaagat ctcgaaagtc attgagatgt tgattaagga atttgccaaa    180
tctcctcaag ctaatcatcg gaagggtggt ctaattggct tagctgctgt aactgttggt    240
ttgtctacag aagctgctca atatcttgag caaatagtgc cacctgtgat taattccttt    300
tctgatcaag atagccgagt tcggtactat gcatgtgaag ctctctataa cattgcaaag    360
gttgtgcgag gcgatttcat tattttcttc aataagatat ttgatgcctt atgcaaactc    420
tcagcagatt ctgatgccaa tgtccaaagt gctgctcatc ttttggatcg ccttgttaag    480
gatattgtga cggaaagtga tcagttcagt attgaggaat catacctct tttaaaagag     540 cgaatgaacg ttctcaaccc ttacgtccgg caatttctgg ttggatggat cactgttctt    600
gatagtgttc cagacattga catgcttggg tttctgccag actttctcga tgggttattc    660
aatatgttga gcgactctag tcatgaaata cgacagcaag ctgattcagc tctttcagag    720
tttcttcaag agataaaaaa ttcaccatct gtagattatg gtcgcatggc tgaaatactg    780
```

```
gtgcagaggg ctgcttctcc tgatgaattc actcgattaa cagccatcac gtggataaac    840
gagttcgtaa aacttggggg agaccagctc gtgcgttatt atgctgacat tcttggggct    900
atcttgcctt gcatatctga caaagaagag aaaatcaggg tggttgctcg tgaaaccaat    960
gaagaacttc gttcaatcca tgttgaaccc tcagatggtt ttgatgttgg cgcaattctc   1020
tctgttgcaa ggaggcagct atcaagtgag tttgaggcta ctcggattga agcattgaat   1080
tggatatcaa cacttttaaa caagcatcgt actgaggtct tgtgcttcct gaatgacata   1140
tttgacaccc ttctaaaagc actatctgat tcttctgatg acgtggtgct cttggttctg   1200
gaggttcatg ctggtgtagc aaaagatcca caacactttc gccagctcat cgtatttctt   1260
gtccacaatt ccgagctga taattctctt ttggaaaggt atctggaaag aacatattat   1320
ttagttggtc aaaacatatc tcgttatagg cgcggtgccc ttattgtccg aagaatgtgt   1380
gtacttttgg atgccgaaag agtctaccga gagctctcta caattcttga gggagaagat   1440
aatcttgact tgcttctac catggttcag gcattgaatt tgattttgct tacttccccg    1500
gagttatcga aactgagaga actattaaaa ggttcactcg tcaatcgcga agggaaagaa   1560
cttttcgttg ccttgtatac ttcatggtgc cattcaccca tggcaattat aagcctctgc   1620
ttattagctc aggcttacca gcatgcgagt gtcgtgattc aatcattggt agaagaagac   1680
attaacgtca aatttctagt acagcttgat aaattgatcc ggcttctgga aactccaatc   1740
tttacttacc ttagattgca gcttctggaa ccaggaaggt acacatggtt gctgaaaaca   1800
ctttatggtc ttcttatgtt acttcctcag caaagtgcgg cgttcaagat acttaggaca   1860
agactcaaaa ctgtgccaac gtactcattc agtactggaa accaaatagg cagagcaact   1920
tcaggagttc cttctctca gtataagcat caaaacgagg acggtgactt agaagacgat    1980
aacatcaaca gttctcacca aggaatcaat tttgctgtgc ggctacaaca gttcgaaaac   2040
gtacagaatc tacatcgtgg ccaggcaagg actagagtga actactcata tcactcttcc   2100
tcttcttcta catcaaagga ggtgaggaga tctgaagaac aacaacagca gcagcagcaa   2160
caacaacagc aacaacaaca caacaacga ccaccaccctt cttcgacatc atcatcagtt    2220
gcagataaca atagacctcc atcaagaact tcaagaaaag gccctggtca attacagctt   2280
taacctacct ggtaatcata ataataaat atattccat ccccgacaat catcatcttc      2340
atcttctttg tgtggacacc accgatccct tttgtctcct gtaaaattgt atatctctct    2400
tttttagtaa ctcttcaagt ttcgacggaa cttgtggaaa agctacggtc gtgtccatca   2460
tctctttctc tctgtcgggt tttttttatt tacgagagat tcttcttcag tccctcagtc   2520
tacctttata ttgtttttt gggggtttct cgtttctttg aatttgtttc attgtttgga     2580 gcttttata ttttaccttt atgtggagat gtaagaaaaa gaagtgatca tgtggttttg     2640
tgttgttttt ttataactgg aaaccacat gagtttgtag aggtcactta ttggatattt     2700
tatgtcaaat gatgctcctt tttacaaaaa aaaaaaaaaa aaa                      2743

<210> SEQ ID NO 65
<211> LENGTH: 2959
<212> TYPE: DNA
<213> ORGANISM: Arabidopsis thaliana

<400> SEQUENCE: 65
atgtcactct tgttcctcaa tcctccgttt ccctccaatt caatccaccc aattcctcgt      60
cgtgccgccg gaatatcctc cattcgatgc tcaattctg caccggagaa gaaaccgagg      120
aggaggagga agcagaagcg cggcgacgga gctgagaatg acgactcttt gtcttccgga    180
```

| | |
|---|---|
| agtggtgaag ctgtctccgc tctggagagg agtctccgcc tcactttat ggacgagctt | 240 |
| atggaacgag ctagaaatcg agatacttca ggtgtttctg aggttatcta tgacatgatt | 300 |
| gctgctgggc ttagccctgg acctcgttct ttccatggtt tggttgtagc tcacgcgctt | 360 |
| aacggcgacg aacaaggcgc gatgcactcg ctgagaaagg agctaggtgc aggccaacgt | 420 |
| ccgcttcctg agactatgat tgctttggtt cgtctctctg gttcgaaagg gaatgctacg | 480 |
| agaggcctag aaatcctcgc cgctatggaa aagcttaagt atgacattcg tcaagcttgg | 540 |
| ctcattcttg ttgaggagct catgaggatc aatcacttgg aagatgcgaa taaagttttc | 600 |
| ttgaagggtg caagaggtgg gatgagagca acagatcagc tttatgattt gatgattgaa | 660 |
| gaagattgca aagctggaga tcattctaat gccttagaca tctcttacga aatggaggca | 720 |
| gctggtagaa tggccacaac atttcatttc aactgtcttc ttagtgtgca ggctacatgt | 780 |
| gggattcccg aggtagctta tgctacattc gaaaatatgg agtacggtga aggtttattt | 840 |
| atgaagcctg acactgagac atataactgg gtgattcaag cctacactag agccgagtca | 900 |
| tatgataggg ttcaggatgt tgctgaatta cttggaatga tggttgagga ccacaaacgt | 960 |
| gtgcagccaa atgtgaagac ttatgcgctc ttagttgagt gcttcaccaa atattgtgtc | 1020 |
| gtgaaggaag cgattagaca ttttcgtgct cttaaaaact ttgaaggagg aacagtaatt | 1080 |
| ttacacaatg cagggaattt tgaggatcct ctctctttgt atctcagggc tttgtgtcga | 1140 |
| gaaggaagaa ttgttgagct tattgatgct ttagatgcaa tgcgcaaaga taaccaacct | 1200 |
| atacctccaa gagccatgat tatgagcaga aagtatcgaa cactagtcag ctcatggatt | 1260 |
| gaaccattgc aagaagaagc tgaacttggc tatgagattg attatttagc gaggtacata | 1320 |
| gaggaagggg gacttactgg tgaacgcaag cgttgggtac ctcgaagagg gaaaactcct | 1380 |
| ttagatcccg atgcttctgg ttttatatac tcaaacccta ttgaaacatc ctttaaacag | 1440 |
| agatgccttg aagattggaa agttcaccat aggaagctct tgagaacctt acagagtgaa | 1500 |
| ggtcttccag ttctaggaga tgcatcagaa tctgattaca tgagagtggt ggagagatta | 1560 |
| cggaacataa taaaaggtcc tgcactgaat cttttgaagc cgaaagcagc aagcaagatg | 1620 |
| gttgtatcag agttaaagga gaactcgaa gctcagggtt tgccaattga tggaacaaga | 1680 |
| aatgtgcttt accagcgtgt ccaaaaagca aggagaataa acaaatctcg aggtcgacct | 1740 |
| cttttgggttc ctccaattga agaagaagag gaggaggtcg atgaagaagt agacgattta | 1800 |
| atatgtcgaa tcaagctaca tgaaggagac acagagttct ggaaacgtcg gtttcttgga | 1860 |
| gaaggcttga ttgaaacttc agttgaatcc aaggaaacga ctgaatcagt ggttacaggt | 1920 |
| gaatcggaga aagcgattga agatatttca aaagaagctg acaatgagga ggatgatgat | 1980 |
| gaggaggaac aagaaggaga tgaggatgat gatgaaaatg aagaggaaga agtggttgtt | 2040 |
| ccagaaactg agaatcgagc agaaggagaa gatttagtga agaataaggc agctgacgcg | 2100 |
| aagaagcatc ttcaaatgat tggagtccaa ctccttgaaag aatccgatga agcaaacaga | 2160 |
| acaaagaaac gtgggaagag ggcatctcgt atgacacttg aggatgatgc agatgaggat | 2220 |
| tggttccctg aggaaccatt tgaagcattc aaagaaatga gggaaagaaa agtgttcgat | 2280 |
| gtggctgaca tgtatacaat agcagacgtt tggggttgga catgggagaa ggattttaag | 2340 |
| aacaaaactc caaggaaatg gtcacaagag tgggaagtcg agttggcaat tgtgctcatg | 2400 |
| acaaaggtga ttgaattggg tggaattcca acgattggtg attgtgcagt gatattacga | 2460 |
| gctgctttaa gagctcccat gccttcagcc ttcttgaaga tcttgcagac gacacacagt | 2520 |
| cttggctact catttggcag cccgttgtac gatgagatca tcacattgtg tttggacctt | 2580 |

```
ggagaacttg atgcagccat cgccatagtt gcagatatgg aaaccacagg gatcactgtc    2640
cctgatcaaa cccttgacaa ggtcatatct gctagacaat ctaatgagag tccgcggtct    2700
gagcctgaag agccagcatc aacagtaagc tcttagttat catatcctct tctgcttgtt    2760
gtgaagtctc tataagaaac agaaatcggt agaaggagct gaatctgtct tagttatgaa    2820
agttttgttc attataagta caagtcatgt agttccgagt gtagaacagt ttttactagt    2880
gttgcaccag gtccctccag tctgatactt aattctttag tgttggatct ttctatataa    2940
gaaaaaaaaa aaaaaaaa                                                  2959

<210> SEQ ID NO 66
<211> LENGTH: 1295
<212> TYPE: DNA
<213> ORGANISM: Arabidopsis thaliana

<400> SEQUENCE: 66
aagcttcgaa gtcgatttca atggaaggtt cctcgtcagc catcgcgagg aagacatggg      60
agctagagaa caacattctc ccagtggaac caaccgattc agcctccgac agtatattcc     120
actacgacga cgcttcacaa gccaaaatcc agcaggagaa gccatgggcc tccgatccta     180
actacttcaa gcgcgttcac atctcagccc ttgctcttct caagatggtg gttcacgctc     240
gctccggtgg cacaatcgag atcatgggtc ttatgcaggg taaaaccgag ggtgatacaa     300
tcatcgttat ggatgctttt gctttgcctg ttgaaggtac tgagactagg gttaatgctc     360
agtctgatgc ctatgagtat atggttgaat actctcagac cagcaagctg gctgggaggt     420
tggagaacgt tgttggatgg tatcactctc accctgggta tggatgttgg ctctcgggta     480
ttgatgtttc gacacagatg cttaaccaac agtatcagga gccattctta gctgttgtta     540
ttgatccaac aaggactgtt tcggctggta aggttgagat tggggcattc agaacatatc     600
cagagggaca taagatctcg gatgatcatg tttctgagta tcagactatc cctcttaaca     660
agattgagga ctttggtgta cattgcaaac agtactactc attggacatc acttatttca     720
agtcatctct cgatagtcac cttctggatc tcctttggaa caagtactgg gtgaacactc     780
tttcttcttc cccactgttg ggcaatggag actatgttgc cgggcaaata tcagacttgg     840
ctgagaagct cgagcaagcg gagagtcagc tcgctaactc ccggtatgga ggaattgcgc     900
cagccggtca ccaaaggagg aaagaggatg agcctcaact cgcgaagata actcgggata     960
gtgcaaagat aactgtcgag caggtccatg gactaatgtc acaggttatc aaagacatct    1020
tgttcaattc cgctcgtcag tccaagaagt ctgctgacga ctcatcagat ccagagccca    1080
tgattacatc gtgaagttgg tctattcttt tgttttttgg ctgcggaaat tgactatcgg    1140
tttgacccgg tttatgaggc aatgcccatt gttccctata tctctagtgt agtatctgct    1200
tcagacaaag atctttgggt tattaaatga cattaacata aatcgatcat tatgttttg     1260 cgttaaaaaa aaaaaaaaaa aaaaaaaaaa aaaaa                               1295

<210> SEQ ID NO 67
<211> LENGTH: 340
<212> TYPE: PRT
<213> ORGANISM: Arabidopsis thaliana

<400> SEQUENCE: 67

Pro His Ile Arg Asp Glu Glu Thr Lys Lys Pro Asp Ser Val Ser Ser
 1               5                  10                  15

Glu Glu Pro Glu Thr Ile Ile Ile Asp Val Asp Glu Ser Asp Lys Glu
            20                  25                  30
```

```
Gly Gly Asp Ser Asn Glu Pro Met Phe Val Gln His Thr Glu Ala Met
            35                  40                  45
Leu Glu Glu Ile Glu Gln Met Glu Lys Glu Ile Glu Met Glu Asp Ala
 50                  55                  60
Asp Lys Glu Glu Glu Pro Val Ile Asp Ile Asp Ala Cys Asp Lys Asn
 65                  70                  75                  80
Asn Pro Leu Ala Ala Val Glu Tyr Ile His Asp Met His Thr Phe Tyr
                85                  90                  95
Lys Asn Phe Glu Lys Leu Ser Cys Val Pro Pro Asn Tyr Met Asp Asn
                100                 105                 110
Gln Gln Asp Leu Asn Glu Arg Met Arg Gly Ile Leu Ile Asp Trp Leu
            115                 120                 125
Ile Glu Val His Tyr Lys Phe Glu Leu Met Glu Glu Thr Leu Tyr Leu
130                 135                 140
Thr Ile Asn Val Ile Asp Arg Phe Leu Ala Val His Gln Ile Val Arg
145                 150                 155                 160
Lys Lys Leu Gln Leu Val Gly Val Thr Ala Leu Leu Leu Ala Cys Lys
                165                 170                 175
Tyr Glu Glu Val Ser Val Pro Val Val Asp Asp Leu Ile Leu Ile Ser
            180                 185                 190
Asp Lys Ala Tyr Ser Arg Arg Glu Val Leu Asp Met Glu Lys Leu Met
            195                 200                 205
Ala Asn Thr Leu Gln Phe Asn Phe Ser Leu Pro Thr Pro Tyr Val Phe
210                 215                 220
Met Lys Arg Phe Leu Lys Ala Ala Gln Ser Asp Lys Lys Leu Glu Ile
225                 230                 235                 240
Leu Ser Phe Phe Met Ile Glu Leu Cys Leu Val Glu Tyr Glu Met Leu
                245                 250                 255
Glu Tyr Leu Pro Ser Lys Leu Ala Ala Ser Ala Ile Tyr Thr Ala Gln
            260                 265                 270
Cys Thr Leu Lys Gly Phe Glu Glu Trp Ser Lys Thr Cys Glu Phe His
            275                 280                 285
Thr Gly Tyr Asn Glu Lys Gln Leu Leu Ala Cys Ala Arg Lys Met Val
        290                 295                 300
Ala Phe His His Lys Ala Gly Thr Gly Lys Leu Thr Gly Val His Arg
305                 310                 315                 320
Lys Tyr Asn Thr Ser Lys Phe Cys His Ala Ala Arg Thr Glu Pro Ala
                325                 330                 335
Gly Phe Leu Ile
            340

<210> SEQ ID NO 68
<211> LENGTH: 145
<212> TYPE: PRT
<213> ORGANISM: Arabidopsis thaliana

<400> SEQUENCE: 68

Pro Asp Ser Gly Thr Ala Ala Gly Gly Ser Asn Ser Asp Pro Phe Pro
 1               5                   10                  15
Ala Asn Leu Arg Val Leu Val Val Asp Asp Asp Pro Thr Cys Leu Met
                20                  25                  30
Ile Leu Glu Arg Met Leu Met Thr Cys Leu Tyr Arg Val Thr Lys Cys
            35                  40                  45
Asn Arg Ala Glu Ser Ala Leu Ser Leu Leu Arg Lys Asn Lys Asn Gly
 50                  55                  60
```

-continued

Phe Asp Ile Val Ile Ser Asp Val His Met Pro Asp Met Asp Gly Phe
65                  70                  75                  80

Lys Leu Leu Glu His Val Gly Leu Glu Met Asp Leu Pro Val Ile Met
                85                  90                  95

Met Ser Ala Asp Asp Ser Lys Ser Val Val Leu Lys Gly Val Thr His
            100                 105                 110

Gly Ala Val Asp Tyr Leu Ile Lys Pro Val Arg Ile Glu Ala Leu Lys
        115                 120                 125

Asn Ile Trp Gln His Val Val Arg Lys Lys Arg Asn Arg Val Glu Trp
    130                 135                 140

Phe
145

<210> SEQ ID NO 69
<211> LENGTH: 450
<212> TYPE: PRT
<213> ORGANISM: Arabidopsis thaliana

<400> SEQUENCE: 69

Met Gly Lys Glu Asn Ala Val Ser Arg Pro Phe Thr Arg Ser Leu Ala
1               5                   10                  15

Ser Ala Leu Arg Ala Ser Glu Val Thr Ser Thr Thr Gln Asn Gln Gln
            20                  25                  30

Arg Val Asn Thr Lys Arg Pro Ala Leu Glu Asp Thr Arg Ala Thr Gly
        35                  40                  45

Pro Asn Lys Arg Lys Lys Arg Ala Val Leu Gly Glu Ile Thr Asn Val
    50                  55                  60

Asn Ser Asn Thr Ala Ile Leu Glu Ala Lys Asn Ser Lys Gln Ile Lys
65                  70                  75                  80

Lys Gly Arg Gly His Gly Leu Ala Ser Thr Ser Gln Leu Ala Thr Ser
                85                  90                  95

Val Thr Ser Glu Val Thr Asp Leu Gln Ser Arg Thr Asp Ala Lys Val
            100                 105                 110

Glu Val Ala Ser Asn Thr Ala Gly Asn Leu Ser Val Ser Lys Gly Thr
        115                 120                 125

Asp Asn Thr Ala Asp Asn Cys Ile Glu Ile Trp Asn Ser Arg Leu Pro
    130                 135                 140

Pro Arg Pro Leu Gly Arg Ser Ala Ser Thr Ala Glu Lys Ser Ala Val
145                 150                 155                 160

Ile Gly Ser Ser Thr Val Pro Asp Ile Pro Lys Phe Val Asp Ile Asp
                165                 170                 175

Ser Asp Asp Lys Asp Pro Leu Leu Cys Cys Leu Tyr Ala Pro Glu Ile
            180                 185                 190

His Tyr Asn Leu Arg Val Ser Glu Leu Lys Arg Arg Pro Leu Pro Asp
        195                 200                 205

Phe Met Glu Arg Ile Gln Lys Asp Val Thr Gln Ser Met Arg Gly Ile
    210                 215                 220

Leu Val Asp Trp Leu Val Glu Val Ser Glu Glu Tyr Thr Leu Ala Ser
225                 230                 235                 240

Asp Thr Leu Tyr Leu Thr Val Tyr Leu Ile Asp Trp Phe Leu His Gly
                245                 250                 255

Asn Tyr Val Gln Arg Gln Leu Gln Leu Leu Gly Ile Thr Cys Met
            260                 265                 270

Leu Ile Ala Ser Lys Tyr Glu Glu Ile Ser Ala Pro Arg Ile Glu Glu
        275                 280                 285

```
Phe Cys Phe Ile Thr Asp Asn Thr Tyr Thr Arg Asp Gln Val Leu Glu
            290                 295                 300

Met Glu Asn Gln Val Leu Lys His Phe Ser Phe Gln Ile Tyr Thr Pro
305                 310                 315                 320

Thr Pro Lys Thr Phe Leu Arg Arg Phe Leu Arg Ala Ala Gln Ala Ser
                    325                 330                 335

Arg Leu Ser Pro Ser Leu Glu Val Glu Phe Leu Ala Ser Tyr Leu Thr
            340                 345                 350

Glu Leu Thr Leu Ile Asp Tyr His Phe Leu Lys Phe Leu Pro Ser Val
            355                 360                 365

Val Ala Ala Ser Ala Gly Phe Leu Ala Lys Trp Thr Met Asp Gln Ser
370                 375                 380

Asn His Pro Trp Asn Pro Thr Leu Glu His Tyr Thr Thr Tyr Lys Ala
385                 390                 395                 400

Ser Asp Leu Lys Ala Ser Val His Ala Leu Gln Asp Leu Gln Leu Asn
                    405                 410                 415

Thr Lys Gly Cys Pro Leu Ser Ala Ile Arg Met Lys Tyr Arg Gln Glu
            420                 425                 430

Lys Tyr Lys Ser Val Ala Val Leu Thr Ser Pro Lys Leu Leu Asp Thr
            435                 440                 445

Leu Phe
    450

<210> SEQ ID NO 70
<211> LENGTH: 223
<212> TYPE: PRT
<213> ORGANISM: Arabidopsis thaliana

<400> SEQUENCE: 70

Met Gly Lys Lys Cys Asp Leu Cys Asn Gly Val Ala Arg Met Tyr Cys
1               5                   10                  15

Glu Ser Asp Gln Ala Ser Leu Cys Trp Asp Cys Asp Gly Lys Val His
            20                  25                  30

Gly Ala Asn Phe Leu Val Ala Lys His Thr Arg Cys Leu Leu Cys Ser
        35                  40                  45

Ala Cys Gln Ser Leu Thr Pro Trp Lys Ala Thr Gly Leu Arg Leu Gly
    50                  55                  60

Pro Thr Phe Ser Val Cys Glu Ser Cys Val Ala Leu Lys Asn Ala Gly
65                  70                  75                  80

Gly Gly Arg Gly Asn Arg Val Leu Ser Glu Asn Arg Gly Gln Glu Glu
                85                  90                  95

Val Asn Ser Phe Glu Ser Glu Glu Asp Arg Ile Arg Glu Asp His Gly
            100                 105                 110

Asp Gly Asp Asp Ala Glu Ser Tyr Asp Asp Asp Glu Glu Glu Asp Glu
        115                 120                 125

Asp Glu Glu Tyr Ser Asp Asp Asp Asp Asp Glu Asp Gly
    130                 135                 140

Asp Asp Glu Glu Ala Glu Asn Gln Val Val Pro Trp Ser Ala Ala
145                 150                 155                 160

Gln Val Pro Pro Val Met Ser Ser Ser Ser Asp Gly Ser Gly
                165                 170                 175

Gly Ser Val Thr Lys Arg Thr Arg Ala Arg Glu Asn Ser Asp Leu Leu
            180                 185                 190

Cys Ser Asp Asp Glu Ile Gly Ser Ser Ala Gln Gly Ser Asn Tyr
        195                 200                 205
```

Ser Arg Pro Leu Lys Arg Ser Ala Phe Lys Ser Thr Val Val Val
210                215                 220

<210> SEQ ID NO 71
<211> LENGTH: 429
<212> TYPE: PRT
<213> ORGANISM: Arabidopsis thaliana

<400> SEQUENCE: 71

Met Val Asn Ser Cys Glu Asn Lys Ile Phe Val Lys Pro Thr Ser Thr
1               5                   10                  15

Thr Ile Leu Gln Asp Glu Thr Arg Ser Arg Lys Phe Gly Gln Glu Met
            20                  25                  30

Lys Arg Glu Lys Arg Arg Val Leu Arg Val Ile Asn Gln Asn Leu Ala
        35                  40                  45

Gly Ala Arg Val Tyr Pro Cys Val Val Asn Lys Lys Gly Ser Leu Leu
    50                  55                  60

Ser Asn Lys Gln Glu Glu Glu Gly Cys Gln Lys Lys Lys Phe Asp
65                  70                  75                  80

Ser Leu Arg Pro Ser Val Thr Arg Ser Gly Val Glu Glu Thr Asn
                85                  90                  95

Lys Lys Leu Lys Pro Ser Val Pro Ser Ala Asn Asp Phe Gly Asp Cys
            100                 105                 110

Ile Phe Ile Asp Glu Glu Glu Ala Thr Leu Asp Leu Pro Met Pro Met
        115                 120                 125

Ser Leu Glu Lys Pro Tyr Ile Glu Ala Asp Pro Met Glu Val Glu
    130                 135                 140

Met Glu Asp Val Thr Val Glu Glu Pro Ile Val Asp Ile Asp Val Leu
145                 150                 155                 160

Asp Ser Lys Asn Ser Leu Ala Ala Val Glu Tyr Val Gln Asp Leu Tyr
                165                 170                 175

Ala Phe Tyr Arg Thr Met Glu Arg Phe Ser Cys Val Pro Val Asp Tyr
            180                 185                 190

Met Met Gln Gln Ile Asp Leu Asn Glu Lys Met Arg Ala Ile Leu Ile
        195                 200                 205

Asp Trp Leu Ile Glu Val His Asp Lys Phe Asp Leu Met Asn Glu Thr
    210                 215                 220

Leu Phe Leu Thr Val Asn Leu Ile Asp Arg Phe Leu Ser Lys Gln Asn
225                 230                 235                 240

Val Met Arg Lys Lys Leu Gln Leu Val Gly Leu Val Ala Leu Leu Leu
                245                 250                 255

Ala Cys Lys Tyr Glu Glu Val Ser Val Pro Val Val Glu Asp Leu Val
            260                 265                 270

Leu Ile Ser Asp Lys Ala Tyr Thr Arg Asn Asp Val Leu Glu Met Glu
        275                 280                 285

Lys Thr Met Leu Ser Thr Leu Gln Phe Asn Ile Ser Leu Pro Thr Gln
    290                 295                 300

Tyr Pro Phe Leu Lys Arg Phe Leu Lys Ala Ala Gln Ala Asp Lys Lys
305                 310                 315                 320

Cys Glu Val Leu Ala Ser Phe Leu Ile Glu Leu Ala Leu Val Glu Tyr
                325                 330                 335

Glu Met Leu Arg Phe Pro Pro Ser Leu Leu Ala Ala Thr Ser Val Tyr
            340                 345                 350

Thr Ala Gln Cys Thr Leu Asp Gly Ser Arg Lys Trp Asn Ser Thr Cys
        355                 360                 365

```
Glu Phe His Cys His Tyr Ser Glu Asp Gln Leu Met Glu Cys Ser Arg
            370                 375                 380

Lys Leu Val Ser Leu His Gln Arg Ala Ala Thr Gly Asn Leu Thr Gly
385                 390                 395                 400

Val Tyr Arg Lys Tyr Ser Thr Ser Lys Phe Gly Tyr Ile Ala Lys Cys
                405                 410                 415

Glu Ala Ala His Phe Leu Val Ser Glu Ser His His Ser
            420                 425

<210> SEQ ID NO 72
<211> LENGTH: 359
<212> TYPE: PRT
<213> ORGANISM: Arabidopsis thaliana

<400> SEQUENCE: 72

Thr Lys Gln Glu Ala Lys Ala Ala Phe Lys Ser Leu Leu Glu Ser Val
1               5                   10                  15

Asn Val His Ser Asp Trp Thr Trp Glu Gln Thr Leu Lys Glu Ile Val
            20                  25                  30

His Asp Lys Arg Tyr Gly Ala Leu Arg Thr Leu Gly Glu Arg Lys Gln
        35                  40                  45

Ala Phe Asn Glu Tyr Leu Gly Gln Arg Lys Lys Val Glu Ala Glu Glu
    50                  55                  60

Arg Arg Arg Arg Gln Lys Lys Ala Arg Glu Glu Phe Val Lys Met Leu
65                  70                  75                  80

Glu Glu Cys Glu Glu Leu Ser Ser Ser Leu Lys Trp Ser Lys Ala Met
                85                  90                  95

Ser Leu Phe Glu Asn Asp Gln Arg Phe Lys Ala Val Asp Arg Pro Arg
            100                 105                 110

Asp Arg Glu Asp Leu Phe Asp Asn Tyr Ile Val Glu Leu Glu Arg Lys
        115                 120                 125

Glu Arg Glu Lys Ala Ala Glu Glu His Arg Gln Tyr Met Ala Asp Tyr
    130                 135                 140

Arg Lys Phe Leu Glu Thr Cys Asp Tyr Ile Lys Ala Gly Thr Gln Trp
145                 150                 155                 160

Arg Lys Ile Gln Asp Arg Leu Glu Asp Asp Arg Cys Ser Cys Leu
                165                 170                 175

Glu Lys Ile Asp Arg Leu Ile Gly Phe Glu Glu Tyr Ile Leu Asp Leu
            180                 185                 190

Glu Lys Glu Glu Glu Glu Leu Lys Arg Val Lys Glu His Val Arg
        195                 200                 205

Arg Ala Glu Arg Lys Asn Arg Asp Ala Phe Arg Thr Leu Leu Glu Glu
    210                 215                 220

His Val Ala Ala Gly Ile Leu Thr Ala Lys Thr Tyr Trp Leu Asp Tyr
225                 230                 235                 240

Cys Ile Glu Leu Lys Asp Leu Pro Gln Tyr Gln Ala Val Ala Ser Asn
                245                 250                 255

Thr Ser Gly Ser Thr Pro Lys Asp Leu Phe Glu Asp Val Thr Glu Glu
            260                 265                 270

Leu Glu Lys Gln Tyr His Glu Asp Lys Ser Tyr Val Lys Asp Ala Met
        275                 280                 285

Lys Ser Arg Lys Ile Ser Met Val Ser Ser Trp Leu Phe Glu Asp Phe
    290                 295                 300

Lys Ser Ala Ile Ser Glu Asp Leu Ser Thr Gln Gln Ile Ser Asp Ile
305                 310                 315                 320
```

Asn Leu Lys Leu Ile Tyr Asp Asp Leu Val Gly Arg Val Lys Glu Lys
            325                 330                 335

Glu Glu Lys Glu Ala Arg Lys Leu Gln Arg Leu Ala Glu Glu Phe Thr
        340                 345                 350

Asn Leu Leu His Thr Phe Lys
        355

<210> SEQ ID NO 73
<211> LENGTH: 110
<212> TYPE: PRT
<213> ORGANISM: Arabidopsis thaliana

<400> SEQUENCE: 73

Gln Glu Lys Pro Trp Glu Asn Asp Pro His Tyr Phe Lys Arg Val Lys
1               5                   10                  15

Ile Ser Ala Leu Ala Leu Leu Lys Met Val Val His Ala Arg Ser Gly
            20                  25                  30

Gly Thr Ile Glu Ile Met Gly Leu Met Gln Gly Lys Thr Asp Gly Asp
        35                  40                  45

Thr Ile Ile Val Met Asp Ala Phe Ala Leu Pro Val Glu Gly Thr Glu
    50                  55                  60

Thr Arg Val Asn Ala Gln Asp Asp Ala Tyr Glu Tyr Met Val Glu Tyr
65                  70                  75                  80

Ser Gln Thr Asn Lys Leu Ala Gly Pro Ala Gly Glu Cys Cys Trp Met
                85                  90                  95

Val Ser Leu Ser Pro Trp Ile Trp Met Leu Ala Leu Arg Tyr
            100                 105                 110

<210> SEQ ID NO 74
<211> LENGTH: 337
<212> TYPE: PRT
<213> ORGANISM: Arabidopsis thaliana

<400> SEQUENCE: 74

Val Asp Ser Pro Asp Ser Thr Ser Asp Asn Ile Phe Tyr Tyr Asp Asp
1               5                   10                  15

Thr Ser Gln Thr Arg Phe Gln Gln Glu Lys Pro Trp Glu Asn Asp Pro
            20                  25                  30

His Tyr Phe Lys Arg Val Lys Ile Ser Ala Leu Ala Leu Leu Lys Met
        35                  40                  45

Val Val His Ala Arg Ser Gly Gly Thr Ile Glu Ile Met Gly Leu Met
    50                  55                  60

Gln Gly Lys Thr Asp Gly Asp Thr Ile Ile Val Met Asp Ala Phe Ala
65                  70                  75                  80

Leu Pro Val Glu Gly Thr Glu Thr Arg Val Asn Ala Gln Asp Asp Ala
                85                  90                  95

Tyr Glu Tyr Met Val Glu Tyr Ser Gln Thr Asn Lys Leu Ala Gly Arg
            100                 105                 110

Leu Glu Asn Val Val Gly Trp Tyr His Ser His Pro Gly Tyr Gly Cys
        115                 120                 125

Trp Leu Ser Gly Ile Asp Val Ser Thr Gln Arg Leu Asn Gln Gln His
    130                 135                 140

Gln Glu Pro Phe Leu Ala Val Ile Asp Pro Thr Arg Thr Val Ser
145                 150                 155                 160

Ala Gly Lys Val Glu Ile Gly Ala Phe Arg Thr Tyr Ser Lys Gly Tyr
                165                 170                 175

Lys Pro Pro Asp Glu Pro Val Ser Glu Tyr Gln Thr Ile Pro Leu Asn

-continued

```
            180                 185                 190
Lys Ile Glu Asp Phe Gly Val His Cys Lys Gln Tyr Tyr Ser Leu Asp
        195                 200                 205
Val Thr Tyr Phe Lys Ser Ser Leu Asp Ser His Leu Leu Asp Leu Leu
        210                 215                 220
Trp Asn Lys Tyr Trp Val Asn Thr Leu Ser Ser Ser Pro Leu Leu Gly
225                 230                 235                 240
Asn Gly Asp Tyr Val Ala Gly Gln Ile Ser Asp Leu Ala Glu Lys Leu
                245                 250                 255
Glu Gln Ala Glu Ser His Leu Val Gln Ser Arg Phe Gly Gly Val Val
            260                 265                 270
Pro Ser Ser Leu His Lys Lys Lys Glu Asp Glu Ser Gln Leu Thr Lys
        275                 280                 285
Ile Thr Arg Asp Ser Ala Lys Ile Thr Val Glu Gln Val His Gly Leu
        290                 295                 300
Met Ser Gln Val Ile Lys Asp Glu Leu Phe Asn Ser Met Arg Gln Ser
305                 310                 315                 320
Asn Asn Lys Ser Pro Thr Asp Ser Ser Asp Pro Asp Pro Met Ile Thr
                325                 330                 335
Tyr

<210> SEQ ID NO 75
<211> LENGTH: 436
<212> TYPE: PRT
<213> ORGANISM: Arabidopsis thaliana

<400> SEQUENCE: 75

Met Tyr Cys Ser Ser Ser Met His Pro Asn Ala Asn Lys Glu Asn Ile
1               5                   10                  15
Ser Thr Ser Asp Val Gln Glu Ser Phe Val Arg Ile Thr Arg Ser Arg
                20                  25                  30
Ala Lys Lys Ala Met Gly Arg Gly Val Ser Ile Pro Pro Thr Lys Pro
            35                  40                  45
Ser Phe Lys Gln Gln Lys Arg Arg Ala Val Leu Lys Asp Val Ser Asn
        50                  55                  60
Thr Ser Ala Asp Ile Ile Tyr Ser Glu Leu Arg Lys Gly Gly Asn Ile
65                  70                  75                  80
Lys Ala Asn Arg Lys Cys Leu Lys Glu Pro Lys Lys Ala Ala Lys Glu
                85                  90                  95
Gly Ala Asn Ser Ala Met Asp Ile Leu Val Asp Met His Thr Glu Lys
            100                 105                 110
Ser Lys Leu Ala Glu Asp Leu Ser Lys Ile Arg Met Ala Glu Ala Gln
        115                 120                 125
Asp Val Ser Leu Ser Asn Phe Lys Asp Glu Glu Ile Thr Glu Gln Gln
        130                 135                 140
Glu Asp Gly Ser Gly Val Met Glu Leu Leu Gln Val Val Asp Ile Asp
145                 150                 155                 160
Ser Asn Val Glu Asp Pro Gln Cys Cys Ser Leu Tyr Ala Ala Asp Ile
                165                 170                 175
Tyr Asp Asn Ile His Val Ala Glu Leu Gln Gln Arg Pro Leu Ala Asn
            180                 185                 190
Tyr Met Glu Leu Val Gln Arg Asp Ile Asp Pro Asp Met Arg Lys Ile
        195                 200                 205
Leu Ile Asp Trp Leu Val Glu Val Ser Asp Asp Tyr Lys Leu Val Pro
        210                 215                 220
```

```
Asp Thr Leu Tyr Leu Thr Val Asn Leu Ile Asp Arg Phe Leu Ser Asn
225                 230                 235                 240

Ser Tyr Ile Glu Arg Gln Arg Leu Gln Leu Leu Gly Val Ser Cys Met
            245                 250                 255

Leu Ile Ala Ser Lys Tyr Glu Glu Leu Ser Ala Pro Gly Val Glu Glu
        260                 265                 270

Phe Cys Phe Ile Thr Ala Asn Thr Tyr Thr Arg Arg Glu Val Leu Ser
    275                 280                 285

Met Glu Ile Gln Ile Leu Asn Phe Val His Phe Arg Leu Ser Val Pro
290                 295                 300

Thr Thr Lys Thr Phe Leu Arg Arg Phe Ile Lys Ala Ala Gln Ala Ser
305                 310                 315                 320

Tyr Lys Val Pro Phe Ile Glu Leu Glu Tyr Leu Ala Asn Tyr Leu Ala
            325                 330                 335

Glu Leu Thr Leu Val Glu Tyr Ser Phe Leu Arg Phe Leu Pro Ser Leu
        340                 345                 350

Ile Ala Ala Ser Ala Val Phe Leu Ala Arg Trp Thr Leu Asp Gln Thr
    355                 360                 365

Asp His Pro Trp Asn Pro Thr Leu Gln His Tyr Thr Arg Tyr Glu Val
370                 375                 380

Ala Glu Leu Lys Asn Thr Val Leu Ala Met Glu Asp Leu Gln Leu Asn
385                 390                 395                 400

Thr Ser Gly Cys Thr Leu Ala Ala Thr Arg Glu Lys Tyr Asn Gln Pro
            405                 410                 415

Lys Phe Lys Ser Val Ala Lys Leu Thr Ser Pro Lys Arg Val Thr Leu
        420                 425                 430

Leu Phe Ser Arg
        435

<210> SEQ ID NO 76
<211> LENGTH: 254
<212> TYPE: PRT
<213> ORGANISM: Arabidopsis thaliana

<400> SEQUENCE: 76

Met Ala Lys Met Gln Leu Ser Ile Phe Ile Ala Val Val Ala Leu Ile
1               5                   10                  15

Val Cys Ser Ala Ser Ala Lys Thr Ala Ser Pro Ala Pro Val Leu
            20                  25                  30

Pro Pro Thr Pro Ala Pro Ala Pro Glu Asn Val Asn Leu Thr
        35                  40                  45

Glu Leu Leu Ser Val Ala Gly Pro Phe His Thr Phe Leu Asp Tyr Leu
    50                  55                  60

Leu Ser Thr Gly Val Ile Glu Thr Phe Gln Asn Gln Ala Asn Asn Thr
65                  70                  75                  80

Glu Glu Gly Ile Thr Ile Phe Val Pro Lys Asp Asp Ala Phe Lys Ala
                85                  90                  95

Gln Lys Asn Pro Pro Leu Ser Asn Leu Thr Lys Asp Gln Leu Lys Gln
            100                 105                 110

Leu Val Leu Phe His Ala Leu Pro His Tyr Tyr Ser Leu Ser Glu Phe
        115                 120                 125

Lys Asn Leu Ser Gln Ser Gly Pro Val Ser Thr Phe Ala Gly Gly Gln
    130                 135                 140

Tyr Ser Leu Lys Phe Thr Asp Val Ser Gly Thr Val Arg Ile Asp Ser
145                 150                 155                 160
```

```
Leu Trp Thr Arg Thr Lys Val Ser Ser Val Phe Ser Thr Asp Pro
                165                 170                 175

Val Ala Val Tyr Gln Val Asn Arg Val Leu Leu Pro Glu Ala Ile Phe
            180                 185                 190

Gly Thr Asp Val Pro Pro Met Pro Ala Pro Ala Pro Ala Pro Ile Val
            195                 200                 205

Ser Ala Pro Ser Asp Ser Pro Ser Val Ala Asp Ser Glu Gly Ala Ser
        210                 215                 220

Ser Pro Lys Ser His Lys Asn Ser Gly Gln Lys Leu Leu Leu Ala
225                 230                 235                 240

Pro Ile Ser Met Val Ile Ser Gly Leu Val Ala Leu Phe Leu
                245                 250

<210> SEQ ID NO 77
<211> LENGTH: 86
<212> TYPE: PRT
<213> ORGANISM: Arabidopsis thaliana

<400> SEQUENCE: 77

Met Ala Ile Ser Lys Ala Leu Ile Ala Ser Phe Leu Ile Ser Leu Leu
 1               5                  10                  15

Val Leu Gln Leu Val Gln Ala Asp Val Glu Asn Ser Gln Lys Lys Asn
            20                  25                  30

Gly Tyr Ala Lys Lys Ile Asp Cys Gly Ser Ala Cys Val Ala Arg Leu
        35                  40                  45

Gln Ala Phe Glu Glu Ala Glu Ala Val Ser Gln Ser Val Arg Asp Leu
    50                  55                  60

Leu Leu Gln Val Gln Leu Cys Ala Ser Gly Tyr Val Arg Lys Leu Arg
65                  70                  75                  80

Gln Val Pro Val Leu Arg
                85

<210> SEQ ID NO 78
<211> LENGTH: 125
<212> TYPE: PRT
<213> ORGANISM: Arabidopsis thaliana

<400> SEQUENCE: 78

Lys Glu Glu Ala Gly Met Tyr Trp Gly Tyr Lys Val Arg Tyr Ala Ser
 1               5                  10                  15

Gln Leu Ser Ser Val Phe Lys Glu Cys Pro Phe Glu Gly Gly Tyr Asp
            20                  25                  30

Tyr Leu Ile Gly Thr Ser Glu His Gly Leu Val Ile Ser Ser Ser Glu
        35                  40                  45

Leu Lys Ile Pro Thr Phe Arg His Leu Leu Ile Ala Phe Gly Gly Leu
    50                  55                  60

Ala Gly Leu Glu Glu Ser Ile Glu Asp Asp Asn Gln Tyr Lys Gly Lys
65                  70                  75                  80

Asn Val Arg Asp Val Phe Asn Val Tyr Leu Asn Thr Cys Pro His Gln
                85                  90                  95

Gly Ser Arg Thr Ile Arg Ala Glu Glu Ala Met Phe Ile Ser Leu Gln
            100                 105                 110

Tyr Phe Gln Glu Pro Ile Ser Arg Ala Val Arg Arg Leu
        115                 120                 125

<210> SEQ ID NO 79
<211> LENGTH: 231
```

```
<212> TYPE: PRT
<213> ORGANISM: Arabidopsis thaliana

<400> SEQUENCE: 79

Ala Arg Glu Met Gly Lys Lys Asn Lys Arg Ser Gln Asp Glu Ser Glu
 1               5                  10                  15

Leu Glu Leu Glu Pro Glu Leu Thr Lys Ile Ile Asp Gly Asp Ser Lys
             20                  25                  30

Lys Lys Lys Asn Lys Asn Lys Lys Arg Ser His Glu Asp Thr Glu
         35                  40                  45

Ile Glu Pro Glu Gln Lys Met Ser Leu Asp Gly Asp Ser Arg Glu Glu
 50                  55                  60

Lys Ile Lys Lys Lys Arg Lys Asn Lys Asn Gln Glu Glu Pro Glu
 65                  70                  75                  80

Leu Val Thr Glu Lys Thr Lys Val Gln Glu Glu Lys Gly Asn Val
             85                  90                  95

Glu Glu Gly Arg Ala Thr Val Ser Ile Ala Ile Ala Gly Ser Ile Ile
             100                 105                 110

His Asn Thr Gln Ser Leu Glu Leu Ala Thr Arg Val Ile Ser Leu Ser
         115                 120                 125

Leu Tyr Leu Ser Leu Arg Phe Ser Val Phe Pro Phe Pro Asp Asn Leu
 130                 135                 140

Lys Ser Pro Ser Ser Ile Ser Asn Ile Ser Gln Leu Ala Gly Gln Ile
145                 150                 155                 160

Ala Arg Ala Ala Thr Ile Phe Arg Ile Asp Glu Ile Val Val Phe Asp
                 165                 170                 175

Asn Lys Ser Ser Ser Glu Ile Glu Ser Ala Ala Thr Asn Ala Ser Asp
             180                 185                 190

Ser Asn Glu Ser Gly Ala Ser Phe Leu Val Arg Ile Leu Lys Tyr Leu
         195                 200                 205

Glu Thr Pro Gln Tyr Leu Arg Lys Ser Leu Phe Pro Lys Gln Asn Asp
 210                 215                 220

Leu Arg Tyr Val Gly Met Leu
225                 230

<210> SEQ ID NO 80
<211> LENGTH: 112
<212> TYPE: PRT
<213> ORGANISM: Arabidopsis thaliana

<400> SEQUENCE: 80

Val Ser Ala Val Trp His Gly Leu Tyr Pro Gly Tyr Ile Ile Phe Phe
 1               5                  10                  15

Val Gln Ser Ala Leu Met Ile Asp Gly Ser Lys Ala Ile Tyr Arg Trp
             20                  25                  30

Gln Gln Ala Ile Pro Pro Lys Met Ala Met Leu Arg Asn Val Leu Val
         35                  40                  45

Leu Ile Asn Phe Leu Tyr Thr Val Val Leu Asn Tyr Ser Ser Val
 50                  55                  60

Gly Phe Met Val Leu Ser Leu His Glu Thr Leu Val Ala Phe Lys Ser
 65                  70                  75                  80

Val Tyr Tyr Ile Gly Thr Val Ile Pro Ile Ala Val Leu Leu Leu Ser
                 85                  90                  95

Tyr Leu Val Pro Val Lys Pro Val Arg Pro Lys Thr Arg Lys Glu Glu
                 100                 105                 110
```

```
<210> SEQ ID NO 81
<211> LENGTH: 119
<212> TYPE: PRT
<213> ORGANISM: Arabidopsis thaliana
<220> FEATURE:
<221> NAME/KEY: MISC_FEATURE
<222> LOCATION: (97)..(98)
<223> OTHER INFORMATION: Xaa = any amino acid
<220> FEATURE:
<221> NAME/KEY: MISC_FEATURE
<222> LOCATION: (113)..(113)
<223> OTHER INFORMATION: Xaa = any amino acid

<400> SEQUENCE: 81

Val Phe Glu Tyr Met Asp Thr Asp Val Lys Phe Ile Arg Ser Phe
 1               5                  10                  15

Arg Ser Thr Gly Lys Asn Ile Pro Thr Gln Thr Ile Lys Ser Leu Met
             20                  25                  30

Tyr Gln Leu Cys Lys Gly Met Ala Phe Cys His Gly His Gly Ile Leu
         35                  40                  45

His Arg Asp Leu Lys Pro His Asn Leu Leu Met Asp Pro Lys Thr Met
     50                  55                  60

Arg Leu Lys Ile Ala Asp Leu Gly Leu Ala Arg Ala Phe Thr Leu Pro
 65                  70                  75                  80

Met Lys Lys Tyr Thr His Glu Ile Leu Thr Leu Trp Tyr Arg Ala Pro
                 85                  90                  95

Xaa Xaa Ser Ser Trp Cys His Pro Leu Leu Tyr Ser Cys Gly Tyr Val
            100                 105                 110

Xaa Cys Trp Leu His Ile Cys
            115

<210> SEQ ID NO 82
<211> LENGTH: 296
<212> TYPE: PRT
<213> ORGANISM: Arabidopsis thaliana

<400> SEQUENCE: 82

Pro Lys Arg Arg Met Ser Met Glu Met Glu Leu Phe Val Thr Pro Glu
 1               5                  10                  15

Lys Gln Arg Gln His Pro Ser Val Ser Val Glu Lys Thr Pro Val Arg
             20                  25                  30

Arg Lys Leu Ile Val Asp Asp Ser Glu Ile Gly Ser Glu Lys Lys
         35                  40                  45

Gly Gln Ser Arg Thr Ser Gly Gly Leu Arg Gln Phe Ser Val Met
     50                  55                  60

Val Cys Gln Lys Leu Glu Ala Lys Lys Ile Thr Thr Tyr Lys Glu Val
 65                  70                  75                  80

Ala Asp Glu Ile Ile Ser Asp Phe Ala Thr Ile Lys Gln Asn Ala Glu
                 85                  90                  95

Lys Pro Leu Asn Glu Asn Glu Tyr Asn Glu Lys Asn Ile Arg Arg Arg
            100                 105                 110

Val Tyr Asp Ala Leu Asn Val Phe Met Ala Leu Asp Ile Ile Ala Arg
            115                 120                 125

Asp Lys Lys Glu Ile Arg Trp Lys Gly Leu Pro Ile Thr Cys Lys Lys
        130                 135                 140

Asp Val Glu Glu Val Lys Met Asp Arg Asn Lys Val Met Ser Ser Val
145                 150                 155                 160

Gln Lys Lys Ala Ala Phe Leu Lys Glu Leu Arg Glu Lys Val Ser Ser
                165                 170                 175
```

```
Leu Glu Ser Leu Met Ser Arg Asn Gln Glu Met Val Val Lys Thr Gln
            180                 185                 190

Gly Pro Ala Glu Gly Phe Thr Leu Pro Phe Ile Leu Leu Glu Thr Asn
            195                 200                 205

Pro His Ala Val Val Glu Ile Glu Ile Ser Glu Asp Met Gln Leu Val
            210                 215                 220

His Leu Asp Phe Asn Ser Thr Pro Phe Ser Val His Asp Asp Ala Tyr
225                 230                 235                 240

Ile Leu Lys Leu Met Gln Glu Lys Gln Glu Gln Asn Arg Val Ser
            245                 250                 255

Ser Ser Ser Thr His His Gln Ser Gln His Ser Ser Ala His Ser
            260                 265                 270

Ser Ser Ser Ser Cys Ile Ala Ser Gly Thr Ser Gly Pro Val Cys Trp
            275                 280                 285

Asn Ser Gly Ser Ile Asp Thr Arg
            290                 295

<210> SEQ ID NO 83
<211> LENGTH: 173
<212> TYPE: PRT
<213> ORGANISM: Arabidopsis thaliana

<400> SEQUENCE: 83

Met Gln Pro Thr Glu Thr Ser Gln Pro Ala Pro Ser Asp Gln Gly Arg
1               5                   10                  15

Arg Leu Lys Asp Gln Leu Ser Glu Ser Met Ser Phe Ser Ser Gln Met
            20                  25                  30

Lys Lys Glu Asp Asp Glu Leu Ser Met Lys Ala Leu Ser Ala Phe Lys
        35                  40                  45

Ala Lys Glu Glu Glu Ile Glu Lys Lys Met Glu Ile Arg Glu Arg
    50                  55                  60

Val Gln Ala Gln Leu Gly Arg Val Glu Asp Glu Ser Lys Arg Leu Ala
65                  70                  75                  80

Met Ile Arg Glu Glu Leu Glu Gly Phe Ala Asp Pro Met Arg Lys Glu
                85                  90                  95

Val Thr Met Val Arg Lys Lys Ile Asp Ser Leu Asp Lys Glu Leu Lys
            100                 105                 110

Pro Leu Gly Asn Thr Val Gln Lys Glu Thr Glu Tyr Lys Asp Ala
            115                 120                 125

Leu Glu Ala Phe Asn Glu Lys Asn Lys Glu Lys Val Glu Leu Ile Thr
    130                 135                 140

Lys Leu Gln Glu Leu Glu Gly Glu Ser Glu Lys Phe Arg Phe Lys Lys
145                 150                 155                 160

Leu Glu Glu Leu Ser Lys Asn Ile Asp Leu Thr Lys Pro
                165                 170

<210> SEQ ID NO 84
<211> LENGTH: 46
<212> TYPE: PRT
<213> ORGANISM: Arabidopsis thaliana

<400> SEQUENCE: 84

Gln Lys Gln Ala Pro Gly Ala Gly Asp Val Pro Ala Thr Ile Gln Glu
1               5                   10                  15

Glu Asp Asp Asp Asp Val Pro Asp Leu Val Val Gly Glu Thr Phe
            20                  25                  30

Glu Thr Pro Ala Thr Glu Glu Ala Pro Lys Ala Ala Ala Ser
```

35                  40                  45

<210> SEQ ID NO 85
<211> LENGTH: 383
<212> TYPE: PRT
<213> ORGANISM: Arabidopsis thaliana

<400> SEQUENCE: 85

Met Glu Asp Asp Glu Ile Gln Ser Ile Pro Ser Pro Gly Asp Ser
 1               5                  10                  15

Ser Leu Ser Pro Gln Ala Pro Pro Ser Pro Ile Leu Pro Thr Asn
                20                  25                  30

Asp Val Thr Val Ala Val Val Lys Pro Gln Pro Gly Leu Ser Ser
                35                  40                  45

Gln Ser Pro Ser Met Asn Ala Leu Ala Leu Val Val His Thr Pro Ser
 50                  55                  60

Val Thr Gly Gly Gly Ser Gly Asn Arg Asn Gly Arg Gly Gly
 65              70                  75                  80

Gly Gly Ser Gly Gly Gly Gly Gly Arg Asp Asp Cys Trp Ser Glu
                85                  90                  95

Glu Ala Thr Lys Val Leu Ile Glu Ala Trp Gly Asp Arg Phe Ser Glu
                100                 105                 110

Pro Gly Lys Gly Thr Leu Lys Gln Gln His Trp Lys Glu Val Ala Glu
                115                 120                 125

Ile Val Asn Lys Ser Arg Gln Cys Lys Tyr Pro Lys Thr Asp Ile Gln
                130                 135                 140

Cys Lys Asn Arg Ile Asp Thr Val Lys Lys Lys Tyr Lys Gln Glu Lys
145                 150                 155                 160

Ala Lys Ile Ala Ser Gly Asp Gly Pro Ser Lys Trp Val Phe Phe Lys
                165                 170                 175

Lys Leu Glu Ser Leu Ile Gly Gly Thr Thr Thr Phe Ile Ala Ser Ser
                180                 185                 190

Lys Ala Ser Glu Lys Ala Pro Met Gly Gly Ala Leu Gly Asn Ser Arg
                195                 200                 205

Ser Ser Met Phe Lys Arg Gln Thr Lys Gly Asn Gln Ile Val Gln Gln
                210                 215                 220

Gln Gln Glu Lys Arg Gly Ser Asp Ser Met Arg Trp His Phe Arg Lys
225                 230                 235                 240

Arg Ser Ala Ser Glu Thr Glu Ser Glu Ser Asp Pro Glu Pro Glu Ala
                245                 250                 255

Ser Pro Glu Glu Ser Ala Glu Ser Leu Pro Pro Leu Gln Pro Ile Gln
                260                 265                 270

Pro Leu Ser Phe His Met Pro Lys Arg Leu Lys Val Asp Lys Ser Gly
                275                 280                 285

Gly Gly Gly Ser Gly Val Gly Asp Val Ala Arg Ala Ile Leu Gly Phe
                290                 295                 300

Thr Glu Ala Tyr Glu Lys Ala Glu Thr Ala Lys Leu Lys Leu Met Ala
305                 310                 315                 320

Glu Leu Glu Lys Glu Arg Met Lys Phe Ala Lys Glu Met Glu Leu Gln
                325                 330                 335

Arg Met Gln Phe Leu Lys Thr Gln Leu Glu Ile Thr Gln Asn Asn Gln
                340                 345                 350

Glu Glu Glu Glu Arg Ser Arg Gln Arg Gly Glu Arg Arg Ile Val Asp
                355                 360                 365

Asp Asp Asp Asp Arg Asn Gly Lys Asn Asn Gly Asn Val Ser Ser

<210> SEQ ID NO 86
<211> LENGTH: 131
<212> TYPE: PRT
<213> ORGANISM: Arabidopsis thaliana
<220> FEATURE:
<221> NAME/KEY: MISC_FEATURE
<222> LOCATION: (70)..(70)
<223> OTHER INFORMATION: Xaa = any amino acid
<220> FEATURE:
<221> NAME/KEY: MISC_FEATURE
<222> LOCATION: (118)..(118)
<223> OTHER INFORMATION: Xaa = any amino acid

<400> SEQUENCE: 86

```
Gly Thr Ser Leu Leu His Ala Ser Ser Ser Ser Ser Ile Ser
  1               5                  10                  15

Leu Thr Ile Pro Ser Asn His Ser Ser Met Ala Thr Val Ser Ser
             20                  25                  30

Ser Trp Pro Asn Pro Asn Pro Asp Ser Thr Ser Ala Ser Asp
         35                  40                  45

Ser Asp Ser Thr Phe Pro Ser His Arg Asp Arg Val Asp Glu Pro Asp
 50                  55                  60

Ser Leu Asp Ser Phe Xaa Ser Met Ser Leu Asn Ser Asp Glu Pro Asn
 65                  70                  75                  80

Gln Thr Ser Asn Gln Ser Pro Leu Ser Pro Pro Thr Pro Asn Leu Pro
                 85                  90                  95

Val Met Pro Pro Pro Phe Val Leu Tyr Leu Ser Phe Asn Gln Asp His
                100                 105                 110

Ala Cys Phe Ala Cys Xaa His Phe Val Pro Ser Leu Ser Leu Tyr Leu
            115                 120                 125

Ser Ala Thr
    130
```

<210> SEQ ID NO 87
<211> LENGTH: 181
<212> TYPE: PRT
<213> ORGANISM: Arabidopsis thaliana

<400> SEQUENCE: 87

```
Gln Ala His Asp Ser Arg Ile Ala Cys Phe Ala Leu Thr Gln Asp Gly
  1               5                  10                  15

His Leu Leu Ala Thr Ala Ser Lys Gly Thr Leu Val Arg Ile Phe
             20                  25                  30

Asn Thr Val Asp Gly Thr Leu Arg Gln Glu Val Arg Arg Gly Ala Asp
         35                  40                  45

Arg Ala Glu Ile Tyr Ser Leu Ala Phe Ser Ser Asn Ala Gln Trp Leu
 50                  55                  60

Ala Val Ser Ser Asp Lys Gly Thr Val His Val Phe Gly Leu Lys Val
 65                  70                  75                  80

Asn Ser Gly Ser Gln Val Lys Asp Ser Ser Arg Ile Ala Pro Asp Ala
                 85                  90                  95

Thr Pro Ser Ser Pro Ser Ser Ser Leu Ser Leu Phe Lys Gly Val Leu
                100                 105                 110

Pro Arg Tyr Phe Ser Ser Glu Trp Ser Val Ala Gln Phe Arg Leu Val
            115                 120                 125

Glu Gly Thr Gln Tyr Ile Ala Ala Phe Gly His Gln Lys Asn Thr Val
        130                 135                 140
```

```
Val Ile Leu Gly Met Asp Gly Ser Phe Tyr Arg Cys Gln Phe Asp Pro
145                 150                 155                 160

Val Asn Gly Gly Glu Met Ser Gln Leu Glu Tyr His Asn Cys Leu Lys
            165                 170                 175

Pro Pro Ser Val Phe
            180

<210> SEQ ID NO 88
<211> LENGTH: 175
<212> TYPE: PRT
<213> ORGANISM: Arabidopsis thaliana

<400> SEQUENCE: 88

Met Asp Asp Ser Glu Glu Asp Gln Arg Leu Pro His His Lys Asp Pro
1               5                   10                  15

Lys Glu Phe Val Ser Leu Asp Lys Leu Ala Glu Leu Gly Val Leu Ser
                20                  25                  30

Trp Arg Leu Asp Ala Asp Asn Tyr Glu Thr Asp Glu Asp Leu Lys Lys
            35                  40                  45

Ile Arg Glu Ser Arg Gly Tyr Ser Tyr Met Asp Phe Cys Glu Val Cys
    50                  55                  60

Pro Glu Lys Leu Pro Asn Tyr Glu Val Lys Val Lys Ser Phe Phe Glu
65                  70                  75                  80

Glu His Leu His Thr Asp Glu Glu Ile Arg Tyr Cys Val Ala Gly Thr
                85                  90                  95

Gly Tyr Phe Asp Val Arg Asp Arg Asn Glu Ala Trp Ile Arg Val Leu
            100                 105                 110

Val Lys Lys Gly Gly Met Ile Val Leu Pro Ala Gly Ile Tyr His Arg
        115                 120                 125

Phe Thr Val Asp Ser Asp Asn Tyr Ile Lys Ala Met Arg Leu Phe Val
130                 135                 140

Gly Glu Pro Val Trp Thr Pro Tyr Asn Arg Pro His Asp His Leu Pro
145                 150                 155                 160

Ala Arg Lys Glu Tyr Val Asp Asn Phe Met Ile Asn Ala Ser Ala
                165                 170                 175

<210> SEQ ID NO 89
<211> LENGTH: 98
<212> TYPE: PRT
<213> ORGANISM: Arabidopsis thaliana

<400> SEQUENCE: 89

Thr Ser Phe Pro Ile Thr Arg Lys Lys Thr Leu Lys Met Asp Gly His
1               5                   10                  15

Asp Ser Glu Asp Thr Lys Gln Ser Thr Ala Asp Met Thr Ala Phe Val
                20                  25                  30

Gln Asn Leu Leu Gln Gln Met Gln Thr Arg Phe Gln Thr Met Ser Asp
            35                  40                  45

Ser Ile Ile Thr Lys Ile Asp Asp Met Gly Gly Arg Ile Asn Glu Leu
    50                  55                  60

Glu Gln Ser Ile Asn Asp Leu Arg Ala Glu Met Gly Val Glu Gly Thr
65                  70                  75                  80

Pro Pro Pro Ala Ser Lys Ser Gly Asp Glu Pro Lys Thr Pro Ala Ser
                85                  90                  95

Ser Ser

<210> SEQ ID NO 90
```

```
<211> LENGTH: 117
<212> TYPE: PRT
<213> ORGANISM: Arabidopsis thaliana

<400> SEQUENCE: 90

Ala Gln Val Arg Ala Lys Met Leu Lys Glu Val Ala Thr Glu Lys Gln
  1               5                  10                  15

Thr Ala Val Asp Thr His Phe Ala Thr Ala Lys Lys Leu Ala Gln Glu
                 20                  25                  30

Gly Asp Ala Leu Phe Val Lys Ile Phe Ala Ile Lys Lys Leu Leu Ala
             35                  40                  45

Lys Leu Glu Ala Glu Lys Glu Ser Val Asp Gly Lys Phe Lys Glu Thr
 50                  55                  60

Val Lys Glu Leu Ser His Leu Leu Ala Asp Ala Ser Glu Ala Tyr Glu
 65                  70                  75                  80

Glu Tyr His Gly Ala Val Arg Lys Ala Lys Asp Gln Ala Ala Glu
                 85                  90                  95

Glu Phe Ala Lys Glu Ala Thr Gln Ser Ala Glu Ile Ile Trp Val Lys
                100                 105                 110

Phe Leu Ser Ser Leu
            115

<210> SEQ ID NO 91
<211> LENGTH: 216
<212> TYPE: PRT
<213> ORGANISM: Arabidopsis thaliana

<400> SEQUENCE: 91

Met Glu Phe Gly Ser Phe Leu Val Ser Leu Gly Thr Ser Phe Val Ile
  1               5                  10                  15

Phe Val Ile Leu Met Leu Leu Phe Thr Trp Leu Ser Arg Lys Ser Gly
                 20                  25                  30

Asn Ala Pro Ile Tyr Tyr Pro Asn Arg Ile Leu Lys Gly Leu Glu Pro
             35                  40                  45

Trp Glu Gly Thr Ser Leu Thr Arg Asn Pro Phe Ala Trp Met Arg Glu
 50                  55                  60

Ala Leu Thr Ser Ser Glu Gln Asp Val Val Asn Leu Ser Gly Val Asp
 65                  70                  75                  80

Thr Ala Val His Phe Val Phe Leu Ser Thr Val Leu Gly Ile Phe Ala
                 85                  90                  95

Cys Ser Ser Leu Leu Leu Leu Pro Thr Leu Leu Pro Leu Ala Ala Thr
                100                 105                 110

Asp Asn Asn Ile Lys Asn Thr Lys Asn Ala Thr Asp Thr Thr Ser Lys
            115                 120                 125

Gly Thr Phe Ser Gln Leu Asp Asn Leu Ser Met Ala Asn Ile Thr Lys
130                 135                 140

Lys Ser Ser Arg Leu Trp Ala Phe Leu Gly Ala Val Tyr Trp Ile Ser
145                 150                 155                 160

Leu Val Thr Tyr Phe Phe Leu Trp Lys Ala Tyr Lys His Val Ser Ser
                165                 170                 175

Leu Arg Ala Gln Ala Leu Met Ser Ala Asp Val Lys Pro Glu Gln Phe
            180                 185                 190

Ala Ile Leu Val Arg Asp Met Pro Ala Pro Asp Gly Arg Arg Gly
        195                 200                 205

Arg Glu Phe Gln Ile Tyr Glu Ser
    210                 215
```

<210> SEQ ID NO 92
<211> LENGTH: 328
<212> TYPE: PRT
<213> ORGANISM: Arabidopsis thaliana

<400> SEQUENCE: 92

Val His Thr Pro Ala Gly Glu Leu Gln Arg Gln Ile Arg Ser Trp Leu
1               5                   10                  15

Ala Glu Ser Phe Glu Phe Leu Ser Val Thr Ala Asp Asp Val Ser Gly
            20                  25                  30

Val Thr Thr Gly Gln Leu Glu Leu Leu Ser Thr Ala Ile Met Asp Gly
        35                  40                  45

Trp Met Ala Gly Val Gly Ala Pro Val Pro Pro His Thr Asp Ala Leu
    50                  55                  60

Gly Gln Leu Val Ser Glu Tyr Ala Lys Arg Val Tyr Thr Ser Gln Met
65                  70                  75                  80

Gln His Leu Lys Asp Ile Ala Gly Thr Leu Ala Ser Glu Glu Ala Glu
                85                  90                  95

Asp Ala Gly Gln Val Ala Lys Leu Arg Ser Ala Leu Glu Ser Val Asp
            100                 105                 110

His Lys Arg Arg Lys Ile Leu Gln Gln Met Arg Ser Asp Ala Ala Leu
        115                 120                 125

Phe Thr Leu Glu Glu Gly Ser Ser Pro Val Gln Asn Pro Ser Thr Ala
    130                 135                 140

Ala Glu Asp Ser Arg Leu Ala Ser Leu Ile Ser Leu Asp Ala Ile Leu
145                 150                 155                 160

Lys Gln Val Lys Glu Ile Thr Arg Gln Ala Ser Val His Val Leu Ser
                165                 170                 175

Lys Ser Lys Lys Lys Ala Leu Leu Glu Ser Leu Asp Glu Leu Asn Glu
            180                 185                 190

Arg Met Pro Ser Leu Leu Asp Val Asp His Pro Cys Ala Gln Arg Glu
        195                 200                 205

Ile Asp Thr Ala His Gln Leu Val Glu Thr Ile Pro Glu Gln Glu Asp
    210                 215                 220

Asn Leu Gln Asp Glu Lys Arg Pro Ser Ile Asp Ser Ile Ser Ser Thr
225                 230                 235                 240

Glu Thr Asp Val Ser Gln Trp Asn Val Leu Gln Phe Asn Thr Gly Gly
                245                 250                 255

Ser Ser Ala Pro Phe Ile Ile Lys Cys Gly Ala Asn Ser Asn Ser Glu
            260                 265                 270

Leu Val Ile Lys Ala Asp Ala Arg Ile Gln Glu Pro Lys Gly Gly Glu
        275                 280                 285

Ile Val Arg Val Val Pro Arg Pro Ser Val Leu Glu Asn Met Ser Leu
    290                 295                 300

Glu Glu Met Lys Gln Val Phe Gly Gln Leu Pro Glu Ala Leu Ser Ser
305                 310                 315                 320

Leu Ala Leu Ala Arg Thr Ala Asp
                325

<210> SEQ ID NO 93
<211> LENGTH: 79
<212> TYPE: PRT
<213> ORGANISM: Arabidopsis thaliana

<400> SEQUENCE: 93

Thr Tyr Glu Arg Leu Pro Ile Glu Glu Glu Gln Gln Gln Glu Gln Pro

```
               1               5                  10                 15
Leu Gln Leu Glu Asp Gly Lys Lys Gln Lys Glu Glu Asn Asp Asp Asn
                    20                  25                  30

Glu Ser Gly Asn Asn Gly Asn Glu Gly Ser Met Gln Pro Pro Met Tyr
            35                  40                  45

Asn Met Pro Pro Asn Phe Ile Pro Asn Gly His Gln Met Ala Gln His
        50                  55                  60

Asp Val Tyr Trp Gly Gly Pro Pro Arg Ala Pro Pro Ser Tyr
65                  70                  75

<210> SEQ ID NO 94
<211> LENGTH: 150
<212> TYPE: PRT
<213> ORGANISM: Arabidopsis thaliana

<400> SEQUENCE: 94

Ser Lys Ala Arg Val Leu Ala Ile Pro Asp Asp Leu Ala Asn Val Ser
1               5                   10                  15

Cys Gly Val Glu Gln Ile Glu Glu Leu Lys Gly Leu Asn Leu Val Glu
            20                  25                  30

Lys Asp Gly Gly Ser Ser Ser Asp Gly Ala Arg Asn Thr Asn Pro
        35                  40                  45

Glu Thr Arg Arg Tyr Ser Gly Ser Leu Gly Val Glu Asp Gly Ala Tyr
    50                  55                  60

Thr Asn Glu Met Leu Gln Ser Ile Glu Met Val Thr Asp Val Leu Asp
65                  70                  75                  80

Ser Leu Val Arg Arg Val Thr Val Ala Glu Ser Ser Ala Val Gln
                85                  90                  95

Lys Glu Arg Ala Leu Leu Gly Glu Glu Glu Ile Ser Arg Lys Thr Ile
            100                 105                 110

Gln Ile Glu Asn Leu Ser Val Lys Leu Glu Glu Met Glu Arg Phe Ala
        115                 120                 125

Tyr Gly Thr Asn Ser Val Leu Asn Glu Met Arg Glu Arg Ile Glu Glu
    130                 135                 140

Leu Val Glu Glu Thr Met
145                 150

<210> SEQ ID NO 95
<211> LENGTH: 181
<212> TYPE: PRT
<213> ORGANISM: Arabidopsis thaliana

<400> SEQUENCE: 95

Met Thr Asn Ile Ala Met Ala Asp Ala Leu Lys Ser Leu Glu Ile Val
1               5                   10                  15

Asp Gly Leu Asp Glu Tyr Met Asn Gln Ser Glu Ser Ser Ala Pro His
            20                  25                  30

Ser Pro Thr Ser Val Ala Lys Leu Pro Pro Ser Thr Ala Thr Arg Thr
        35                  40                  45

Thr Arg Arg Lys Thr Thr Thr Lys Ala Glu Pro Gln Pro Ser Ser Gln
    50                  55                  60

Leu Val Ser Arg Ser Cys Arg Ser Thr Ser Lys Ser Leu Ala Gly Asp
65                  70                  75                  80

Met Asp Gln Glu Asn Ile Asn Lys Asn Val Ala Gln Glu Met Lys Thr
                85                  90                  95

Ser Asn Val Lys Phe Glu Ala Asn Val Leu Lys Thr Pro Ala Ala Gly
            100                 105                 110
```

```
Ser Thr Arg Lys Thr Ser Ala Ala Thr Ser Cys Thr Lys Lys Asp Glu
            115                 120                 125

Leu Val Gln Ser Val Tyr Ser Thr Arg Arg Ser Thr Arg Leu Leu Glu
        130                 135                 140

Lys Cys Met Ala Asp Leu Ser Leu Lys Thr Lys Glu Thr Val Asp Asn
145                 150                 155                 160

Lys Pro Ala Lys Asn Glu Asp Thr Glu Gln Lys Val Ser Ala Gln Glu
                165                 170                 175

Lys Asn Leu Thr Gly
            180

<210> SEQ ID NO 96
<211> LENGTH: 163
<212> TYPE: PRT
<213> ORGANISM: Arabidopsis thaliana

<400> SEQUENCE: 96

Met Leu Met Leu Cys Gly Phe Thr Val Leu Asp Met Leu Lys His His
1               5                   10                  15

Asp Leu Gly Lys Ile Arg Ala Pro Leu His Pro Leu Arg Lys Lys Met
            20                  25                  30

Gln Ile Gln His Ala Tyr Gln Gln Ile His Gln Gly Ser Lys Leu Leu
        35                  40                  45

Lys Met Asp Arg Met Met Leu Arg Gly Thr Lys Arg Arg Ile Gly Val
    50                  55                  60

Arg Lys Gly Asn Leu Gln Arg Glu Arg Arg Lys Lys Asp Met Ile Gly
65                  70                  75                  80

Val Lys Asn Ala Lys Gly Met Arg Ser Glu Ala Leu Val Ile Gln Met
                85                  90                  95

Ile Glu Arg Ser Thr Arg Lys Arg Arg Arg Lys Lys Glu Gly Met
            100                 105                 110

Thr Leu Ile Leu Ile Glu Ala Asn Cys Pro Arg Met Glu His Phe Ala
        115                 120                 125

Leu Gln Arg Lys Ser Gly Arg Leu Gly Thr Lys Ile Gln Leu Pro Leu
    130                 135                 140

Leu Gln Asp Leu Asn Leu Leu Ile Ser Phe Thr Asn Arg Gly Val
145                 150                 155                 160

Lys Cys Cys

<210> SEQ ID NO 97
<211> LENGTH: 170
<212> TYPE: PRT
<213> ORGANISM: Arabidopsis thaliana

<400> SEQUENCE: 97

Gly Thr Arg Gln Lys Arg Glu Thr Ser Asp Pro Glu Ser Asp Leu Lys
1               5                   10                  15

Thr Arg Lys Asn Arg Lys Met Gly Lys Asp Gly Leu Ser Asp Asp Gln
            20                  25                  30

Val Ser Ser Met Lys Glu Ala Phe Met Leu Phe Asp Thr Asp Gly Asp
        35                  40                  45

Gly Lys Ile Ala Pro Ser Glu Leu Gly Ile Leu Met Arg Ser Leu Gly
    50                  55                  60

Gly Asn Pro Thr Gln Ala Gln Leu Lys Ser Ile Ile Ala Ser Glu Asn
65                  70                  75                  80

Leu Ser Ser Pro Phe Asp Phe Asn Arg Phe Leu Asp Leu Met Ala Lys
```

```
                     85                  90                  95
His Leu Lys Thr Glu Pro Phe Asp Arg Gln Leu Arg Asp Ala Phe Lys
            100                 105                 110

Val Leu Asp Lys Glu Gly Thr Gly Phe Val Ala Val Ala Asp Leu Arg
            115                 120                 125

His Ile Leu Thr Ser Ile Gly Glu Lys Leu Glu Pro Asn Glu Phe Asp
            130                 135                 140

Glu Trp Ile Lys Glu Val Asp Val Gly Ser Asp Gly Lys Ile Arg Tyr
145                 150                 155                 160

Glu Asp Phe Ile Ala Arg Met Val Ala Lys
                165                 170

<210> SEQ ID NO 98
<211> LENGTH: 38
<212> TYPE: PRT
<213> ORGANISM: Arabidopsis thaliana

<400> SEQUENCE: 98

Arg Gly Val Ser Phe Arg Ser Arg Glu Met Arg Pro Ile Phe Ala Ile
1               5                   10                  15

Ser Gln Arg Met Arg Ser Ile Lys Glu Ser Lys Glu Val Leu Asp Thr
            20                  25                  30

Glu Ser Arg Ser Arg Leu
        35

<210> SEQ ID NO 99
<211> LENGTH: 376
<212> TYPE: PRT
<213> ORGANISM: Arabidopsis thaliana

<400> SEQUENCE: 99

Met Thr Thr Thr Gly Ser Asn Ser Asn His Asn His His Glu Ser Asn
1               5                   10                  15

Asn Asn Asn Asn Asn Pro Ser Thr Arg Ser Trp Gly Thr Ala Val Ser
            20                  25                  30

Gly Gln Ser Val Ser Thr Ser Gly Ser Met Gly Ser Pro Ser Ser Arg
            35                  40                  45

Ser Glu Gln Thr Ile Thr Val Val Thr Ser Thr Ser Asp Thr Thr Phe
        50                  55                  60

Gln Arg Leu Asn Asn Leu Asp Ile Gln Gly Asp Asp Ala Gly Ser Gln
65                  70                  75                  80

Gly Ala Ser Gly Val Lys Lys Lys Arg Gly Gln Arg Ala Ala Gly
            85                  90                  95

Pro Asp Lys Thr Gly Arg Gly Leu Arg Gln Phe Ser Met Lys Val Cys
            100                 105                 110

Glu Lys Val Glu Ser Lys Gly Arg Thr Thr Tyr Asn Glu Val Ala Asp
            115                 120                 125

Glu Leu Val Ala Glu Phe Ala Leu Pro Asn Asn Asp Gly Thr Ser Pro
            130                 135                 140

Asp Gln Gln Gln Tyr Asp Glu Lys Asn Ile Arg Arg Arg Val Tyr Asp
145                 150                 155                 160

Ala Leu Asn Val Leu Met Ala Met Asp Ile Ile Ser Lys Asp Lys Lys
                165                 170                 175

Glu Ile Gln Trp Arg Gly Leu Pro Arg Thr Ser Leu Ser Asp Ile Glu
            180                 185                 190

Glu Leu Lys Asn Glu Arg Leu Ser Leu Arg Asn Arg Ile Glu Lys Lys
            195                 200                 205
```

Thr Ala Tyr Ser Gln Glu Leu Glu Glu Gln Arg Asn Glu His Leu Tyr
    210                 215                 220

Ser Ser Gly Asn Ala Pro Ser Gly Gly Val Ala Leu Pro Phe Ile Leu
225                 230                 235                 240

Val Gln Thr Arg Pro His Ala Thr Val Val Glu Ile Ser Glu Asp
                245                 250                 255

Met Gln Leu Val His Phe Asp Phe Asn Ser Thr Pro Phe Glu Leu His
                260                 265                 270

Asp Asp Asn Phe Val Leu Lys Thr Met Lys Phe Cys Asp Gln Pro Pro
                275                 280                 285

Gln Gln Pro Asn Gly Arg Asn Asn Ser Gln Leu Val Cys His Asn Phe
            290                 295                 300

Thr Pro Glu Asn Pro Asn Lys Gly Pro Ser Thr Gly Pro Thr Pro Gln
305                 310                 315                 320

Leu Asp Met Tyr Glu Thr His Leu Gln Ser Gln Gln His Gln Gln His
                325                 330                 335

Ser Gln Leu Gln Ile Ile Pro Met Pro Glu Thr Asn Asn Val Thr Ser
            340                 345                 350

Ser Ala Asp Thr Ala Pro Val Lys Ser Pro Ser Leu Pro Gly Ile Met
        355                 360                 365

Asn Ser Ser Met Lys Pro Glu Asn
        370                 375

<210> SEQ ID NO 100
<211> LENGTH: 145
<212> TYPE: PRT
<213> ORGANISM: Arabidopsis thaliana

<400> SEQUENCE: 100

Glu Tyr Leu Lys Lys Gly Ser Pro Ile Ser Ala Leu Lys Ser Phe Ile
1               5                   10                  15

Ser Ser Leu Ser Glu Pro Pro Gln Asp Ile Met Asp Ala Leu Phe Asn
                20                  25                  30

Ala Leu Phe Asp Gly Val Gly Lys Gly Phe Ala Lys Glu Val Thr Lys
            35                  40                  45

Lys Lys Asn Tyr Leu Ala Ala Ala Thr Met Gln Glu Asp Gly Ser
    50                  55                  60

Gln Met His Leu Leu Asn Ser Ile Gly Thr Phe Cys Gly Lys Asn Gly
65                  70                  75                  80

Asn Glu Glu Ala Leu Lys Glu Val Ala Val Leu Lys Ala Leu Tyr
                85                  90                  95

Asp Gln Asp Ile Ile Glu Glu Val Val Leu Asp Trp Tyr Glu Lys
            100                 105                 110

Gly Leu Thr Gly Ala Asp Lys Ser Ser Pro Val Trp Lys Asn Val Lys
        115                 120                 125

Pro Phe Val Glu Trp Leu Gln Ser Ala Glu Ser Glu Ser Glu Glu
    130                 135                 140

Asp
145

<210> SEQ ID NO 101
<211> LENGTH: 316
<212> TYPE: PRT
<213> ORGANISM: Arabidopsis thaliana

<400> SEQUENCE: 101

```
Leu Glu Val Glu Arg Asn Ala Ser Ala Ala Ser Glu Thr Met
 1               5                  10                  15

Ala Met Ile Asn Arg Leu His Glu Glu Lys Ala Ala Met Gln Met Glu
             20                  25                  30

Ala Leu Gln Tyr Gln Arg Met Met Glu Glu Gln Ala Glu Phe Asp Gln
         35                  40                  45

Glu Ala Leu Gln Leu Leu Asn Glu Leu Met Val Asn Arg Lys Glu
     50                  55                  60

Asn Ala Glu Leu Glu Lys Glu Leu Glu Val Tyr Arg Lys Arg Met Glu
 65                  70                  75                  80

Glu Tyr Glu Ala Lys Lys Met Gly Met Leu Arg Arg Leu Arg
             85                  90                  95

Asp Ser Ser Val Asp Ser Tyr Arg Asn Asn Gly Asp Ser Asp Glu Asn
                100                 105                 110

Ser Asn Gly Glu Leu Gln Phe Lys Asn Val Glu Gly Val Thr Asp Trp
            115                 120                 125

Lys Tyr Arg Glu Asn Glu Met Glu Asn Thr Pro Val Asp Val Val Leu
            130                 135                 140

Arg Leu Asp Glu Cys Leu Asp Asp Tyr Asp Gly Glu Arg Leu Ser Ile
145                 150                 155                 160

Leu Gly Arg Leu Lys Phe Leu Glu Glu Lys Leu Thr Asp Leu Asn Asn
                165                 170                 175

Glu Glu Asp Asp Glu Glu Glu Ala Lys Thr Phe Glu Ser Asn Gly Ser
            180                 185                 190

Ile Asn Gly Asn Glu His Ile His Gly Lys Glu Thr Asn Gly Lys His
            195                 200                 205

Arg Val Ile Gln Ser Lys Arg Leu Leu Pro Leu Phe Asp Ala Val Asp
210                 215                 220

Gly Glu Met Glu Asn Gly Leu Ser Asn Gly Asn His His Glu Asn Gly
225                 230                 235                 240

Phe Asp Asp Ser Glu Lys Gly Glu Asn Val Thr Ile Glu Glu Glu Val
                245                 250                 255

Asp Glu Leu Tyr Glu Arg Leu Glu Ala Leu Glu Ala Arg Glu Phe
            260                 265                 270

Leu Arg His Cys Val Gly Ser Leu Lys Lys Gly Asp Lys Gly Val His
            275                 280                 285

Leu Leu His Glu Ile Leu Gln His Leu Arg Asp Leu Arg Asn Ile Asp
            290                 295                 300

Leu Thr Arg Val Arg Glu Asn Gly Asp Met Ser Leu
305                 310                 315

<210> SEQ ID NO 102
<211> LENGTH: 194
<212> TYPE: PRT
<213> ORGANISM: Arabidopsis thaliana

<400> SEQUENCE: 102

Ala Ser Leu Ile Lys Leu Ile Arg Leu Leu Glu Thr Pro Ile Phe Thr
 1               5                  10                  15

Tyr Leu Arg Leu Gln Leu Leu Glu Pro Gly Arg Tyr Thr Trp Leu Leu
             20                  25                  30

Lys Thr Leu Tyr Gly Leu Leu Met Leu Leu Pro Gln Gln Ser Ala Ala
         35                  40                  45

Phe Lys Ile Leu Arg Thr Arg Leu Lys Thr Val Pro Thr Tyr Ser Phe
     50                  55                  60
```

```
Ser Thr Gly Asn Gln Ile Gly Arg Ala Thr Ser Val Pro Phe Ser
 65                  70                  75                  80

Gln Tyr Lys His Gln Asn Glu Asp Gly Leu Glu Asp Asp Asn Ile
                 85                  90                  95

Asn Ser Ser His Gln Gly Ile Asn Phe Ala Val Arg Leu Gln Gln Phe
            100                 105                 110

Glu Asn Val Gln Asn Leu His Arg Gly Gln Ala Arg Thr Arg Val Asn
        115                 120                 125

Tyr Ser Tyr His Ser Ser Ser Ser Thr Ser Lys Glu Val Arg Arg
130                 135                 140

Ser Glu Glu Gln Gln Gln Gln Gln Gln Gln Gln Gln Gln Gln Gln
145                 150                 155                 160

Gln Gln Gln Arg Pro Pro Ser Ser Thr Ser Ser Val Ala Asp
                165                 170                 175

Asn Asn Arg Pro Pro Ser Arg Thr Ser Arg Lys Gly Pro Gly Gln Leu
                180                 185                 190

Gln Leu

<210> SEQ ID NO 103
<211> LENGTH: 289
<212> TYPE: PRT
<213> ORGANISM: Arabidopsis thaliana

<400> SEQUENCE: 103

Leu Ile Glu Thr Ser Val Glu Ser Lys Glu Thr Thr Glu Ser Val Val
  1               5                  10                  15

Thr Gly Glu Ser Glu Lys Ala Ile Glu Asp Ile Ser Lys Glu Ala Asp
                 20                  25                  30

Asn Glu Glu Asp Asp Asp Glu Glu Gln Gly Asp Glu Asp Asp
             35                  40                  45

Asp Glu Asn Glu Glu Glu Val Val Pro Glu Thr Glu Asn Arg
         50                  55                  60

Ala Glu Gly Glu Asp Leu Val Lys Asn Lys Ala Ala Asp Ala Lys Lys
 65                  70                  75                  80

His Leu Gln Met Ile Gly Val Gln Leu Leu Lys Glu Ser Asp Glu Ala
                 85                  90                  95

Asn Arg Thr Lys Lys Arg Gly Lys Arg Ala Ser Arg Met Thr Leu Glu
            100                 105                 110

Asp Asp Ala Asp Glu Asp Trp Phe Pro Glu Glu Pro Phe Glu Ala Phe
        115                 120                 125

Lys Glu Met Arg Glu Arg Lys Val Phe Asp Val Ala Asp Met Tyr Thr
130                 135                 140

Ile Ala Asp Val Trp Gly Trp Thr Trp Glu Lys Asp Phe Lys Asn Lys
145                 150                 155                 160

Thr Pro Arg Lys Trp Ser Gln Glu Trp Glu Val Glu Leu Ala Ile Val
                165                 170                 175

Leu Met Thr Lys Val Ile Glu Leu Gly Gly Ile Pro Thr Ile Gly Asp
            180                 185                 190

Cys Ala Val Ile Leu Arg Ala Ala Leu Arg Ala Pro Met Pro Ser Ala
        195                 200                 205

Phe Leu Lys Ile Leu Gln Thr Thr His Ser Leu Gly Tyr Ser Phe Gly
    210                 215                 220

Ser Pro Leu Tyr Asp Glu Ile Ile Thr Leu Cys Leu Asp Leu Gly Glu
225                 230                 235                 240

Leu Asp Ala Ala Ile Ala Ile Val Ala Asp Met Glu Thr Thr Gly Ile
```

```
                         245                 250                 255
Thr Val Pro Asp Gln Thr Leu Asp Lys Val Ile Ser Ala Arg Gln Ser
            260                 265                 270
Asn Glu Ser Pro Arg Ser Glu Pro Glu Pro Ala Ser Thr Val Ser
            275                 280                 285
Ser

<210> SEQ ID NO 104
<211> LENGTH: 333
<212> TYPE: PRT
<213> ORGANISM: Arabidopsis thaliana

<400> SEQUENCE: 104

Thr Asp Ser Ala Ser Asp Ser Ile Phe His Tyr Asp Ala Ser Gln
  1               5                  10                  15

Ala Lys Ile Gln Gln Glu Lys Pro Trp Ala Ser Asp Pro Asn Tyr Phe
                 20                  25                  30

Lys Arg Val His Ile Ser Ala Leu Ala Leu Lys Met Val Val His
             35                  40                  45

Ala Arg Ser Gly Gly Thr Ile Glu Ile Met Gly Leu Met Gln Gly Lys
         50                  55                  60

Thr Glu Gly Asp Thr Ile Ile Val Met Asp Ala Phe Ala Leu Pro Val
 65                  70                  75                  80

Glu Gly Thr Glu Thr Arg Val Asn Ala Gln Ser Asp Ala Tyr Glu Tyr
                 85                  90                  95

Met Val Glu Tyr Ser Gln Thr Ser Lys Leu Ala Gly Arg Leu Glu Asn
            100                 105                 110

Val Val Gly Trp Tyr His Ser His Pro Gly Tyr Gly Cys Trp Leu Ser
            115                 120                 125

Gly Ile Asp Val Ser Thr Gln Met Leu Asn Gln Gln Tyr Gln Glu Pro
        130                 135                 140

Phe Leu Ala Val Val Ile Asp Pro Thr Arg Thr Val Ser Ala Gly Lys
145                 150                 155                 160

Val Glu Ile Gly Ala Phe Arg Thr Tyr Pro Glu Gly His Lys Ile Ser
                165                 170                 175

Asp Asp His Val Ser Glu Tyr Gln Thr Ile Pro Leu Asn Lys Ile Glu
            180                 185                 190

Asp Phe Gly Val His Cys Lys Gln Tyr Tyr Ser Leu Asp Ile Thr Tyr
        195                 200                 205

Phe Lys Ser Ser Leu Asp Ser His Leu Leu Asp Leu Leu Trp Asn Lys
    210                 215                 220

Tyr Trp Val Asn Thr Leu Ser Ser Ser Pro Leu Leu Gly Asn Gly Asp
225                 230                 235                 240

Tyr Val Ala Gly Gln Ile Ser Asp Leu Ala Glu Lys Leu Glu Gln Ala
                245                 250                 255

Glu Ser Gln Leu Ala Asn Ser Arg Tyr Gly Gly Ile Ala Pro Ala Gly
            260                 265                 270

His Gln Arg Arg Lys Glu Asp Glu Pro Gln Leu Ala Lys Ile Thr Arg
        275                 280                 285

Asp Ser Ala Lys Ile Thr Val Glu Gln Val His Gly Leu Met Ser Gln
    290                 295                 300

Val Ile Lys Asp Ile Leu Phe Asn Ser Ala Arg Gln Ser Lys Lys Ser
305                 310                 315                 320

Ala Asp Asp Ser Ser Asp Pro Glu Pro Met Ile Thr Ser
                325                 330
```

<210> SEQ ID NO 105
<211> LENGTH: 460
<212> TYPE: PRT
<213> ORGANISM: Arabidopsis thaliana

<400> SEQUENCE: 105

```
Met Val Arg Ser Asp Glu Asn Ser Leu Gly Leu Ile Gly Ser Met Ser
1               5                   10                  15

Leu Gln Gly Thr Leu Asn Arg Ser Ile Leu Leu Lys Ile Lys Thr
            20                  25                  30

Phe Val Leu Phe Asp Phe Ser Pro Lys Leu Ile Leu Asn Leu Leu Asp
        35                  40                  45

Val Gly Gly Gly Val Val Gly Lys Ile Lys Thr Thr Ala Thr Thr Gly
    50                  55                  60

Pro Thr Arg Arg Ala Leu Ser Thr Ile Asn Lys Asn Ile Thr Glu Ala
65                  70                  75                  80

Pro Ser Tyr Pro Tyr Ala Val Asn Lys Arg Ser Val Ser Glu Arg Asp
                85                  90                  95

Gly Ile Cys Asn Lys Pro Pro Val His Arg Pro Val Thr Arg Lys Phe
            100                 105                 110

Ala Ala Gln Leu Ala Asp His Lys Pro His Ile Arg Asp Glu Glu Thr
        115                 120                 125

Lys Lys Pro Asp Ser Val Ser Ser Glu Glu Pro Glu Thr Ile Ile Ile
    130                 135                 140

Asp Val Asp Glu Ser Asp Lys Glu Gly Gly Asp Ser Asn Glu Pro Met
145                 150                 155                 160

Phe Val Gln His Thr Glu Ala Met Leu Glu Glu Ile Glu Gln Met Glu
                165                 170                 175

Lys Glu Ile Glu Met Glu Asp Ala Asp Lys Glu Glu Pro Val Ile
            180                 185                 190

Asp Ile Asp Ala Cys Asp Lys Asn Asn Pro Leu Ala Ala Val Glu Tyr
        195                 200                 205

Ile His Asp Met His Thr Phe Tyr Lys Asn Phe Glu Lys Leu Ser Cys
    210                 215                 220

Val Pro Pro Asn Tyr Met Asp Asn Gln Gln Asp Leu Asn Glu Arg Met
225                 230                 235                 240

Arg Gly Ile Leu Ile Asp Trp Leu Ile Glu Val His Tyr Lys Phe Glu
                245                 250                 255

Leu Met Glu Glu Thr Leu Tyr Leu Thr Ile Asn Val Ile Asp Arg Phe
            260                 265                 270

Leu Ala Val His Gln Ile Val Arg Lys Lys Leu Gln Leu Val Gly Val
        275                 280                 285

Thr Ala Leu Leu Leu Ala Cys Lys Tyr Glu Glu Val Ser Val Pro Val
    290                 295                 300

Val Asp Asp Leu Ile Leu Ile Ser Asp Lys Ala Tyr Ser Arg Arg Glu
305                 310                 315                 320

Val Leu Asp Met Glu Lys Leu Met Ala Asn Thr Leu Gln Phe Asn Phe
                325                 330                 335

Ser Leu Pro Thr Pro Tyr Val Phe Met Lys Arg Phe Leu Lys Ala Ala
            340                 345                 350

Gln Ser Asp Lys Lys Leu Glu Ile Leu Ser Phe Phe Met Ile Glu Leu
        355                 360                 365

Cys Leu Val Glu Tyr Glu Met Leu Glu Tyr Leu Pro Ser Lys Leu Ala
    370                 375                 380
```

```
Ala Ser Ala Ile Tyr Thr Ala Gln Cys Thr Leu Lys Gly Phe Glu Glu
385                 390                 395                 400

Trp Ser Lys Thr Cys Glu Phe His Thr Gly Tyr Asn Glu Lys Gln Leu
            405                 410                 415

Leu Ala Cys Ala Arg Lys Met Val Ala Phe His His Lys Ala Gly Thr
        420                 425                 430

Gly Lys Leu Thr Gly Val His Arg Lys Tyr Asn Thr Ser Lys Phe Cys
    435                 440                 445

His Ala Ala Arg Thr Glu Pro Ala Gly Phe Leu Ile
450                 455                 460

<210> SEQ ID NO 106
<211> LENGTH: 664
<212> TYPE: PRT
<213> ORGANISM: Arabidopsis thaliana

<400> SEQUENCE: 106

Met Val Asn Pro Gly His Gly Arg Gly Pro Asp Ser Gly Thr Ala Ala
1               5                   10                  15

Gly Gly Ser Asn Ser Asp Pro Phe Pro Ala Asn Leu Arg Val Leu Val
            20                  25                  30

Val Asp Asp Asp Pro Thr Cys Leu Met Ile Leu Glu Arg Met Leu Met
        35                  40                  45

Thr Cys Leu Tyr Arg Val Thr Lys Cys Asn Arg Ala Glu Ser Ala Leu
    50                  55                  60

Ser Leu Leu Arg Lys Asn Lys Asn Gly Phe Asp Ile Val Ile Ser Asp
65                  70                  75                  80

Val His Met Pro Asp Met Asp Gly Phe Lys Leu Leu Glu His Val Gly
                85                  90                  95

Leu Glu Met Asp Leu Pro Val Ile Met Met Ser Ala Asp Asp Ser Lys
            100                 105                 110

Ser Val Val Leu Lys Gly Val Thr His Gly Ala Val Asp Tyr Leu Ile
        115                 120                 125

Lys Pro Val Arg Ile Glu Ala Leu Lys Asn Ile Trp Gln His Val Val
    130                 135                 140

Arg Lys Lys Arg Asn Glu Trp Asn Val Ser Glu His Ser Gly Gly Ser
145                 150                 155                 160

Ile Glu Asp Thr Gly Gly Asp Arg Asp Arg Gln Gln His Arg Glu
                165                 170                 175

Asp Ala Asp Asn Asn Ser Ser Val Asn Glu Gly Asn Gly Arg Ser
            180                 185                 190

Ser Arg Lys Arg Lys Glu Glu Glu Val Asp Asp Gln Gly Asp Asp Lys
        195                 200                 205

Glu Asp Ser Ser Ser Leu Lys Lys Pro Arg Val Val Trp Ser Val Glu
    210                 215                 220

Leu His Gln Gln Phe Val Ala Ala Val Asn Gln Leu Gly Val Asp Lys
225                 230                 235                 240

Ala Val Pro Lys Lys Ile Leu Glu Met Met Asn Val Pro Gly Leu Thr
                245                 250                 255

Arg Glu Asn Val Ala Ser His Leu Gln Lys Tyr Arg Ile Tyr Leu Arg
            260                 265                 270

Arg Leu Gly Gly Val Ser Gln His Gln Gly Asn Met Asn His Ser Phe
        275                 280                 285

Met Thr Gly Gln Asp Gln Ser Phe Gly Pro Leu Ser Ser Leu Asn Gly
    290                 295                 300
```

```
Phe Asp Leu Gln Ser Leu Ala Val Thr Gly Gln Pro Pro Gln Ser
305                 310                 315                 320

Leu Ala Gln Leu Gln Ala Ala Gly Leu Gly Arg Pro Thr Leu Ala Lys
            325                 330                 335

Pro Gly Met Ser Val Ser Pro Leu Val Asp Gln Arg Ser Ile Phe Asn
        340                 345                 350

Phe Glu Asn Pro Lys Ile Arg Phe Gly Asp Gly His Gly Gln Thr Met
    355                 360                 365

Asn Asn Gly Asn Leu Leu His Gly Val Pro Thr Gly Ser His Met Arg
370                 375                 380

Leu Arg Pro Gly Gln Asn Val Gln Ser Ser Gly Met Met Leu Pro Val
385                 390                 395                 400

Ala Asp Gln Leu Pro Arg Gly Gly Pro Ser Met Leu Pro Ser Leu Gly
            405                 410                 415

Gln Gln Pro Ile Leu Ser Ser Val Ser Arg Arg Ser Asp Leu Thr
        420                 425                 430

Gly Ala Leu Ala Val Arg Asn Ser Ile Pro Glu Thr Asn Ser Arg Val
    435                 440                 445

Leu Pro Thr Thr His Ser Val Phe Asn Asn Phe Pro Ala Asp Leu Pro
450                 455                 460

Arg Ser Ser Phe Pro Leu Ala Ser Ala Pro Gly Ile Ser Val Pro Val
465                 470                 475                 480

Ser Val Ser Tyr Gln Glu Glu Val Asn Ser Ser Asp Ala Lys Gly Gly
            485                 490                 495

Ser Ser Ala Ala Thr Ala Gly Phe Gly Asn Pro Ser Tyr Asp Ile Phe
        500                 505                 510

Asn Asp Phe Pro Gln His Gln Gln His Asn Lys Asn Ile Ser Asn Lys
    515                 520                 525

Leu Asn Asp Trp Asp Leu Arg Asn Met Gly Leu Val Phe Ser Ser Asn
530                 535                 540

Gln Asp Ala Ala Thr Ala Thr Ala Thr Ala Ala Phe Ser Thr Ser Glu
545                 550                 555                 560

Ala Tyr Ser Ser Ser Ser Thr Gln Arg Lys Arg Arg Glu Thr Asp Ala
            565                 570                 575

Thr Val Val Gly Glu His Gly Asn Leu Gln Ser Pro Ser Arg Asn
        580                 585                 590

Leu Tyr His Leu Asn His Val Phe Met Asp Gly Gly Ser Val Arg Val
    595                 600                 605

Lys Ser Glu Arg Val Ala Glu Thr Val Thr Cys Pro Pro Ala Asn Thr
610                 615                 620

Leu Phe His Glu Gln Tyr Asn Gln Glu Asp Leu Met Ser Ala Phe Leu
625                 630                 635                 640

Lys Gln Glu Gly Ile Pro Ser Val Asp Asn Glu Phe Glu Phe Asp Gly
            645                 650                 655

Tyr Ser Ile Asp Asn Ile Gln Val
        660

<210> SEQ ID NO 107
<211> LENGTH: 450
<212> TYPE: PRT
<213> ORGANISM: Arabidopsis thaliana

<400> SEQUENCE: 107

Met Gly Lys Glu Asn Ala Val Ser Arg Pro Phe Thr Arg Ser Leu Ala
1               5                   10                  15
```

```
Ser Ala Leu Arg Ala Ser Glu Val Thr Ser Thr Thr Gln Asn Gln Gln
            20                  25                  30
Arg Val Asn Thr Lys Arg Pro Ala Leu Glu Asp Thr Arg Ala Thr Gly
                35                  40                  45
Pro Asn Lys Arg Lys Arg Ala Val Leu Gly Glu Ile Thr Asn Val
 50                  55                  60
Asn Ser Asn Thr Ala Ile Leu Glu Ala Lys Asn Ser Lys Gln Ile Lys
 65                  70                  75                  80
Lys Gly Arg Gly His Gly Leu Ala Ser Thr Ser Gln Leu Ala Thr Ser
                85                  90                  95
Val Thr Ser Glu Val Thr Asp Leu Gln Ser Arg Thr Asp Ala Lys Val
                100                 105                 110
Glu Val Ala Ser Asn Thr Ala Gly Asn Leu Ser Val Ser Lys Gly Thr
                115                 120                 125
Asp Asn Thr Ala Asp Asn Cys Ile Glu Ile Trp Asn Ser Arg Leu Pro
                130                 135                 140
Pro Arg Pro Leu Gly Arg Ser Ala Ser Thr Ala Glu Lys Ser Ala Val
145                 150                 155                 160
Ile Gly Ser Ser Thr Val Pro Asp Ile Pro Lys Phe Val Asp Ile Asp
                165                 170                 175
Ser Asp Asp Lys Asp Pro Leu Leu Cys Cys Leu Tyr Ala Pro Glu Ile
                180                 185                 190
His Tyr Asn Leu Arg Val Ser Glu Leu Lys Arg Arg Pro Leu Pro Asp
                195                 200                 205
Phe Met Glu Arg Ile Gln Lys Asp Val Thr Gln Ser Met Arg Gly Ile
                210                 215                 220
Leu Val Asp Trp Leu Val Glu Val Ser Glu Glu Tyr Thr Leu Ala Ser
225                 230                 235                 240
Asp Thr Leu Tyr Leu Thr Val Tyr Leu Ile Asp Trp Phe Leu His Gly
                245                 250                 255
Asn Tyr Val Gln Arg Gln Gln Leu Gln Leu Leu Gly Ile Thr Cys Met
                260                 265                 270
Leu Ile Ala Ser Lys Tyr Glu Glu Ile Ser Ala Pro Arg Ile Glu Glu
                275                 280                 285
Phe Cys Phe Ile Thr Asp Asn Thr Tyr Thr Arg Asp Gln Val Leu Glu
                290                 295                 300
Met Glu Asn Gln Val Leu Lys His Phe Ser Phe Gln Ile Tyr Thr Pro
305                 310                 315                 320
Thr Pro Lys Thr Phe Leu Arg Arg Phe Leu Arg Ala Ala Gln Ala Ser
                325                 330                 335
Arg Leu Ser Pro Ser Leu Glu Val Glu Phe Leu Ala Ser Tyr Leu Thr
                340                 345                 350
Glu Leu Thr Leu Ile Asp Tyr His Phe Leu Lys Phe Leu Pro Ser Val
                355                 360                 365
Val Ala Ala Ser Ala Val Phe Leu Ala Lys Trp Thr Met Asp Gln Ser
                370                 375                 380
Asn His Pro Trp Asn Pro Thr Leu Glu His Tyr Thr Thr Tyr Lys Ala
385                 390                 395                 400
Ser Asp Leu Lys Ala Ser Val His Ala Leu Gln Asp Leu Gln Leu Asn
                405                 410                 415
Thr Lys Gly Cys Pro Leu Ser Ala Ile Arg Met Lys Tyr Arg Gln Glu
                420                 425                 430
Lys Tyr Lys Ser Val Ala Val Leu Thr Ser Pro Lys Leu Leu Asp Thr
```

```
                  435                 440                 445

Leu Phe
    450

<210> SEQ ID NO 108
<211> LENGTH: 901
<212> TYPE: PRT
<213> ORGANISM: Arabidopsis thaliana

<400> SEQUENCE: 108

Met Ala Asn Asn Pro Pro Gln Ser Ser Gly Thr Gln Gly Gln His Phe
1               5                   10                  15

Val Pro Ala Ala Ser Gln Pro Phe His Pro Tyr Gly His Val Pro Pro
            20                  25                  30

Asn Val Gln Ser Gln Pro Pro Gln Tyr Ser Gln Pro Ile Gln Gln Gln
        35                  40                  45

Gln Leu Phe Pro Val Arg Pro Gly Gln Pro Val His Ile Thr Ser Ser
    50                  55                  60

Ser Gln Ala Val Ser Val Pro Tyr Ile Gln Thr Asn Lys Ile Leu Thr
65                  70                  75                  80

Ser Gly Ser Thr Gln Pro Gln Pro Asn Ala Pro Pro Met Thr Gly Phe
                85                  90                  95

Ala Thr Ser Gly Pro Pro Phe Ser Ser Pro Tyr Thr Phe Val Pro Ser
            100                 105                 110

Ser Tyr Pro Gln Gln Gln Pro Thr Ser Leu Val Gln Pro Asn Ser Gln
        115                 120                 125

Met His Val Ala Gly Val Pro Pro Ala Ala Asn Thr Trp Pro Val Pro
    130                 135                 140

Val Asn Gln Ser Thr Ser Leu Val Ser Pro Val Gln Gln Thr Gly Gln
145                 150                 155                 160

Gln Thr Pro Val Ala Val Ser Thr Asp Pro Gly Asn Leu Thr Pro Gln
                165                 170                 175

Ser Ala Ser Asp Trp Gln Glu His Thr Ser Ala Asp Gly Arg Lys Ala
            180                 185                 190

Asp Ala Ser Thr Val Trp Lys Glu Phe Thr Thr Pro Glu Gly Lys Lys
        195                 200                 205

Tyr Tyr Tyr Asn Lys Val Thr Lys Glu Ser Lys Trp Thr Ile Pro Glu
    210                 215                 220

Asp Leu Lys Leu Ala Arg Glu Gln Ala Gln Leu Ala Ser Glu Lys Thr
225                 230                 235                 240

Ser Leu Ser Glu Ala Gly Ser Thr Pro Leu Ser His His Ala Ala Ser
                245                 250                 255

Ser Ser Asp Leu Ala Val Ser Thr Val Thr Ser Val Val Pro Ser Thr
            260                 265                 270

Ser Ser Ala Leu Thr Gly His Ser Ser Ser Pro Ile Gln Ala Gly Leu
        275                 280                 285

Ala Val Pro Val Thr Arg Pro Pro Ser Val Ala Pro Val Thr Pro Thr
    290                 295                 300

Ser Gly Ala Ile Ser Asp Thr Glu Ala Thr Thr Met Tyr Tyr Phe Ser
305                 310                 315                 320

Leu Gly Ser Phe Ala Glu Asn Lys Glu Met Ser Val Asn Gly Lys Ala
                325                 330                 335

Asn Leu Ser Pro Ala Gly Asp Lys Ala Asn Val Glu Glu Pro Met Val
            340                 345                 350

Tyr Ala Thr Lys Gln Glu Ala Lys Ala Ala Phe Lys Ser Leu Leu Glu
```

```
                355                 360                 365
Ser Val Asn Val His Ser Asp Trp Thr Trp Glu Gln Thr Leu Lys Glu
            370                 375                 380
Ile Val His Asp Lys Arg Tyr Gly Ala Leu Arg Thr Leu Gly Glu Arg
385                 390                 395                 400
Lys Gln Ala Phe Asn Glu Tyr Leu Gly Gln Arg Lys Lys Val Glu Ala
                405                 410                 415
Glu Glu Arg Arg Arg Gln Lys Lys Ala Arg Glu Glu Phe Val Lys
            420                 425                 430
Met Leu Glu Glu Cys Glu Glu Leu Ser Ser Leu Lys Trp Ser Lys
            435                 440                 445
Ala Met Ser Leu Phe Glu Asn Asp Gln Arg Phe Lys Ala Val Asp Arg
            450                 455                 460
Pro Arg Asp Arg Glu Asp Leu Phe Asp Asn Tyr Ile Val Glu Leu Glu
465                 470                 475                 480
Arg Lys Glu Arg Glu Lys Ala Ala Glu Glu His Arg Gln Tyr Met Ala
                485                 490                 495
Asp Tyr Arg Lys Phe Leu Glu Thr Cys Asp Tyr Ile Lys Ala Gly Thr
            500                 505                 510
Gln Trp Arg Lys Ile Gln Asp Arg Leu Glu Asp Asp Arg Cys Ser
            515                 520                 525
Cys Leu Glu Lys Ile Asp Arg Leu Ile Gly Phe Glu Tyr Ile Leu
            530                 535                 540
Asp Leu Glu Lys Glu Glu Glu Leu Lys Arg Val Glu Lys Glu His
545                 550                 555                 560
Val Arg Arg Ala Glu Arg Lys Asn Arg Asp Ala Phe Arg Thr Leu Leu
                565                 570                 575
Glu Glu His Val Ala Ala Gly Ile Leu Thr Ala Lys Thr Tyr Trp Leu
            580                 585                 590
Asp Tyr Cys Ile Glu Leu Lys Asp Leu Pro Gln Tyr Gln Ala Val Ala
            595                 600                 605
Ser Asn Thr Ser Gly Ser Thr Pro Lys Asp Leu Phe Glu Asp Val Thr
            610                 615                 620
Glu Glu Leu Glu Lys Gln Tyr His Glu Asp Lys Ser Tyr Val Lys Asp
625                 630                 635                 640
Ala Met Lys Ser Arg Lys Ala Asn Phe Lys Ser Ala Ile Ser Glu Asp
                645                 650                 655
Leu Ser Thr Gln Gln Ile Ser Asp Ile Asn Leu Lys Leu Ile Tyr Asp
            660                 665                 670
Asp Leu Val Gly Arg Val Lys Glu Lys Glu Glu Lys Glu Ala Arg Lys
            675                 680                 685
Leu Gln Arg Leu Ala Glu Glu Phe Thr Asn Leu Leu His Thr Phe Lys
            690                 695                 700
Glu Ile Thr Val Ala Ser Asn Trp Glu Asp Ser Lys Gln Leu Val Glu
705                 710                 715                 720
Glu Ser Gln Glu Tyr Arg Ser Ile Gly Asp Glu Ser Val Ser Gln Gly
                725                 730                 735
Leu Phe Glu Glu Tyr Ile Thr Ser Leu Gln Glu Lys Ala Lys Glu Lys
            740                 745                 750
Glu Arg Lys Arg Asp Glu Glu Lys Val Arg Lys Glu Lys Glu Arg Asp
            755                 760                 765
Glu Lys Glu Lys Arg Lys Asp Lys Asp Lys Glu Arg Arg Glu Lys Glu
            770                 775                 780
```

```
Arg Glu Arg Glu Lys Glu Lys Gly Lys Glu Arg Ser Lys Arg Glu Glu
785                 790                 795                 800

Ser Asp Gly Glu Thr Ala Met Asp Val Ser Gly His Lys Asp Glu
            805                 810                 815

Lys Arg Lys Gly Lys Asp Arg Asp Arg Lys His Arg Arg His His
        820                 825                 830

Asn Asn Ser Asp Glu Asp Val Ser Ser Asp Arg Asp Arg Asp Glu
        835                 840                 845

Ser Lys Lys Ser Ser Arg Lys His Gly Asn Asp Arg Lys Lys Ser Arg
850                 855                 860

Lys His Ala Asn Ser Pro Glu Ser Glu Ser Glu Asn Arg His Lys Arg
865                 870                 875                 880

Gln Lys Lys Glu Ser Ser Arg Arg Ser Gly Asn Asp Glu Leu Glu Asp
            885                 890                 895

Gly Glu Val Gly Glu
            900

<210> SEQ ID NO 109
<211> LENGTH: 358
<212> TYPE: PRT
<213> ORGANISM: Arabidopsis thaliana

<400> SEQUENCE: 109

Met Glu Gly Ser Ser Ser Thr Ile Ala Arg Lys Thr Trp Glu Leu Glu
1               5                   10                  15

Asn Ser Ile Leu Thr Val Asp Ser Pro Asp Ser Thr Ser Asp Asn Ile
            20                  25                  30

Phe Tyr Tyr Asp Asp Thr Ser Gln Thr Arg Phe Gln Gln Glu Lys Pro
        35                  40                  45

Trp Glu Asn Asp Pro His Tyr Phe Lys Arg Val Lys Ile Ser Ala Leu
    50                  55                  60

Ala Leu Leu Lys Met Val Val His Ala Arg Ser Gly Gly Thr Ile Glu
65                  70                  75                  80

Ile Met Gly Leu Met Gln Gly Lys Thr Asp Gly Asp Thr Ile Ile Val
            85                  90                  95

Met Asp Ala Phe Ala Leu Pro Val Glu Gly Thr Glu Thr Arg Val Asn
            100                 105                 110

Ala Gln Asp Asp Ala Tyr Glu Tyr Met Val Glu Tyr Ser Gln Thr Asn
        115                 120                 125

Lys Leu Ala Gly Arg Leu Glu Asn Val Val Gly Trp Tyr His Ser His
    130                 135                 140

Pro Gly Tyr Gly Cys Trp Leu Ser Gly Ile Asp Val Ser Thr Gln Arg
145                 150                 155                 160

Leu Asn Gln Gln His Gln Glu Pro Phe Leu Ala Val Ile Asp Pro
            165                 170                 175

Thr Arg Thr Val Ser Ala Gly Lys Val Glu Ile Gly Ala Phe Arg Thr
            180                 185                 190

Tyr Ser Lys Gly Tyr Lys Pro Pro Asp Glu Pro Val Ser Glu Tyr Gln
        195                 200                 205

Thr Ile Pro Leu Asn Lys Ile Glu Asp Phe Gly Val His Cys Lys Gln
    210                 215                 220

Tyr Tyr Ser Leu Asp Val Thr Tyr Phe Lys Ser Ser Leu Asp Ser His
225                 230                 235                 240

Leu Leu Asp Leu Leu Trp Asn Lys Tyr Trp Val Asn Thr Leu Ser Ser
            245                 250                 255
```

```
Ser Pro Leu Leu Gly Asn Gly Asp Tyr Val Ala Gly Gln Ile Ser Asp
            260                 265                 270

Leu Ala Glu Lys Leu Glu Gln Ala Glu Ser His Leu Val Gln Ser Arg
            275                 280                 285

Phe Gly Gly Val Val Pro Ser Ser Leu His Lys Lys Lys Glu Asp Glu
290                 295                 300

Ser Gln Leu Thr Lys Ile Thr Arg Asp Ser Ala Lys Ile Thr Val Glu
305                 310                 315                 320

Gln Val His Gly Leu Met Ser Gln Val Ile Lys Asp Glu Leu Phe Asn
                325                 330                 335

Ser Met Arg Gln Ser Asn Asn Lys Ser Pro Thr Asp Ser Asp Pro
            340                 345                 350

Asp Pro Met Ile Thr Tyr
            355

<210> SEQ ID NO 110
<211> LENGTH: 98
<212> TYPE: PRT
<213> ORGANISM: Arabidopsis thaliana

<400> SEQUENCE: 110

Met Ala Ile Ser Lys Ala Leu Ile Ala Ser Leu Leu Ile Ser Leu Leu
1               5                   10                  15

Val Leu Gln Leu Val Gln Ala Asp Val Glu Asn Ser Gln Lys Lys Asn
            20                  25                  30

Gly Tyr Ala Lys Lys Ile Asp Cys Gly Ser Ala Cys Val Ala Arg Cys
        35                  40                  45

Arg Leu Ser Arg Arg Pro Arg Leu Cys His Arg Ala Cys Gly Thr Cys
    50                  55                  60

Cys Tyr Arg Cys Asn Cys Val Pro Pro Gly Thr Tyr Gly Asn Tyr Asp
65                  70                  75                  80

Lys Cys Gln Cys Tyr Ala Ser Leu Thr Thr His Gly Gly Arg Arg Lys
                85                  90                  95

Cys Pro

<210> SEQ ID NO 111
<211> LENGTH: 385
<212> TYPE: PRT
<213> ORGANISM: Arabidopsis thaliana
<220> FEATURE:
<221> NAME/KEY: MISC_FEATURE
<222> LOCATION: (252)..(253)
<223> OTHER INFORMATION: Xaa = any amino acid

<400> SEQUENCE: 111

Met Gly Lys Lys Asn Lys Arg Ser Gln Asp Glu Ser Glu Leu Glu Leu
1               5                   10                  15

Glu Pro Glu Leu Thr Lys Ile Ile Asp Gly Asp Ser Lys Lys Lys Lys
            20                  25                  30

Asn Lys Asn Lys Lys Lys Arg Ser His Glu Asp Thr Glu Ile Glu Pro
        35                  40                  45

Glu Gln Lys Met Ser Leu Asp Gly Asp Ser Arg Glu Glu Lys Ile Lys
    50                  55                  60

Lys Lys Arg Lys Asn Lys Asn Gln Glu Glu Pro Glu Leu Val Thr
65                  70                  75                  80

Glu Lys Thr Lys Val Gln Glu Glu Lys Gly Asn Val Glu Glu Gly
                85                  90                  95

Arg Ala Thr Val Ser Ile Ala Ile Ala Gly Ser Ile Ile His Asn Thr
```

```
                100             105                 110
    Gln Ser Leu Glu Leu Ala Thr Arg Val Ile Ser Leu Ser Leu Tyr Leu
            115                 120                 125

Ser Leu Arg Phe Ser Val Phe Pro Phe Pro Asp Asn Leu Lys Ser Pro
        130                 135                 140

Ser Ser Ile Ser Asn Ile Ser Gln Leu Ala Gly Gln Ile Ala Arg Ala
145                 150                 155                 160

Ala Thr Ile Phe Arg Ile Asp Glu Ile Val Val Phe Asp Asn Lys Ser
                    165                 170                 175

Ser Ser Glu Ile Glu Ser Ala Ala Thr Asn Ala Ser Asp Ser Asn Glu
                180                 185                 190

Ser Gly Ala Ser Phe Leu Val Arg Ile Leu Lys Tyr Leu Glu Thr Pro
                195                 200                 205

Gln Tyr Leu Arg Lys Ser Leu Phe Pro Lys Gln Asn Asp Leu Arg Tyr
            210                 215                 220

Val Gly Met Leu Pro Gly Met Leu Pro Leu Asp Ala Pro His His
225                 230                 235                 240

Leu Arg Lys His Glu Trp Glu Gln Tyr Arg Glu Xaa Xaa Ile Val Pro
                    245                 250                 255

Pro Ser Lys Pro Arg Glu Glu Ala Gly Met Tyr Trp Gly Tyr Lys Val
                260                 265                 270

Arg Tyr Ala Ser Gln Leu Ser Ser Val Phe Lys Glu Cys Pro Phe Glu
                275                 280                 285

Gly Gly Tyr Asp Tyr Leu Ile Gly Thr Ser Glu His Gly Leu Val Ile
            290                 295                 300

Ser Ser Ser Glu Leu Lys Ile Pro Thr Phe Arg His Leu Leu Ile Ala
305                 310                 315                 320

Phe Gly Gly Leu Ala Gly Leu Glu Glu Ser Ile Glu Asp Asp Asn Gln
                    325                 330                 335

Tyr Lys Gly Lys Asn Val Arg Asp Val Phe Asn Val Tyr Leu Asn Thr
                340                 345                 350

Cys Pro His Gln Gly Ser Arg Thr Ile Arg Ala Glu Glu Ala Met Phe
                355                 360                 365

Ile Ser Leu Gln Tyr Phe Gln Glu Pro Ile Ser Arg Ala Val Arg Arg
            370                 375                 380

Leu
385

<210> SEQ ID NO 112
<211> LENGTH: 465
<212> TYPE: PRT
<213> ORGANISM: Arabidopsis thaliana

<400> SEQUENCE: 112

Met Glu Leu Leu Asp Met Asn Ser Met Ala Ala Ser Ile Gly Val Ser
1                   5                   10                  15

Val Ala Val Leu Arg Phe Leu Leu Cys Phe Val Ala Thr Ile Pro Ile
                    20                  25                  30

Ser Phe Leu Trp Arg Phe Ile Pro Ser Arg Leu Gly Lys His Ile Tyr
                35                  40                  45

Ser Ala Ala Ser Gly Ala Phe Leu Ser Tyr Leu Ser Phe Gly Phe Ser
            50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
```

|   |   |   | 85 |   |   |   |   | 90 |   |   |   |   | 95 |   |   |
|---|---|---|---|---|---|---|---|---|---|---|---|---|---|---|---|
| Ala | Tyr | Leu | Ile | Gly | Cys | His | Val | Phe | Tyr | Met | Ser | Gly | Asp | Ala | Trp |
|   |   |   | 100 |   |   |   |   | 105 |   |   |   |   | 110 |   |   |
| Lys | Glu | Gly | Gly | Ile | Asp | Ser | Thr | Gly | Ala | Leu | Met | Val | Leu | Thr | Leu |
|   |   |   | 115 |   |   |   |   | 120 |   |   |   |   | 125 |   |   |
| Lys | Val | Ile | Ser | Cys | Ser | Ile | Asn | Tyr | Asn | Asp | Gly | Met | Leu | Lys | Glu |
|   |   |   | 130 |   |   |   |   | 135 |   |   |   |   | 140 |   |   |
| Glu | Gly | Leu | Arg | Glu | Ala | Gln | Lys | Lys | Asn | Arg | Leu | Ile | Gln | Met | Pro |
| 145 |   |   |   |   | 150 |   |   |   |   | 155 |   |   |   |   | 160 |
| Ser | Leu | Ile | Glu | Tyr | Phe | Gly | Tyr | Cys | Leu | Cys | Cys | Gly | Ser | His | Phe |
|   |   |   |   | 165 |   |   |   |   | 170 |   |   |   |   | 175 |   |
| Ala | Gly | Pro | Val | Phe | Glu | Met | Lys | Asp | Tyr | Leu | Glu | Trp | Thr | Glu | Glu |
|   |   |   | 180 |   |   |   |   | 185 |   |   |   |   | 190 |   |   |
| Lys | Gly | Ile | Trp | Ala | Val | Ser | Glu | Lys | Gly | Lys | Arg | Pro | Ser | Pro | Tyr |
|   |   |   | 195 |   |   |   |   | 200 |   |   |   |   | 205 |   |   |
| Gly | Ala | Met | Ile | Arg | Ala | Val | Phe | Gln | Ala | Ala | Ile | Cys | Met | Ala | Leu |
|   |   |   | 210 |   |   |   |   | 215 |   |   |   |   | 220 |   |   |
| Tyr | Leu | Tyr | Leu | Val | Pro | Gln | Phe | Pro | Leu | Thr | Arg | Phe | Thr | Glu | Pro |
| 225 |   |   |   |   | 230 |   |   |   |   | 235 |   |   |   |   | 240 |
| Val | Tyr | Gln | Glu | Trp | Gly | Phe | Leu | Lys | Arg | Phe | Gly | Tyr | Gln | Tyr | Met |
|   |   |   |   | 245 |   |   |   |   | 250 |   |   |   |   | 255 |   |
| Ala | Gly | Phe | Thr | Ala | Arg | Trp | Lys | Tyr | Phe | Ile | Trp | Ser | Ile | Ser |   |
|   |   |   | 260 |   |   |   |   | 265 |   |   |   |   | 270 |   |   |
| Glu | Ala | Ser | Ile | Ile | Ile | Ser | Gly | Leu | Gly | Phe | Ser | Gly | Trp | Thr | Asp |
|   |   |   | 275 |   |   |   |   | 280 |   |   |   |   | 285 |   |   |
| Glu | Thr | Gln | Thr | Lys | Ala | Lys | Trp | Asp | Arg | Ala | Lys | Asn | Val | Asp | Ile |
|   |   |   | 290 |   |   |   |   | 295 |   |   |   |   | 300 |   |   |
| Leu | Gly | Val | Glu | Leu | Ala | Lys | Ser | Ala | Val | Gln | Ile | Pro | Leu | Phe | Trp |
| 305 |   |   |   |   | 310 |   |   |   |   | 315 |   |   |   |   | 320 |
| Asn | Ile | Gln | Val | Ser | Thr | Trp | Leu | Arg | His | Tyr | Val | Tyr | Glu | Arg | Ile |
|   |   |   |   | 325 |   |   |   |   | 330 |   |   |   |   | 335 |   |
| Val | Lys | Pro | Gly | Lys | Lys | Ala | Gly | Phe | Phe | Gln | Leu | Leu | Ala | Thr | Gln |
|   |   |   | 340 |   |   |   |   | 345 |   |   |   |   | 350 |   |   |
| Thr | Val | Ser | Ala | Val | Trp | His | Gly | Leu | Tyr | Pro | Gly | Tyr | Ile | Ile | Phe |
|   |   |   | 355 |   |   |   |   | 360 |   |   |   |   | 365 |   |   |
| Phe | Val | Gln | Ser | Ala | Leu | Met | Ile | Asp | Gly | Ser | Lys | Ala | Ile | Tyr | Arg |
|   |   |   | 370 |   |   |   |   | 375 |   |   |   |   | 380 |   |   |
| Trp | Gln | Gln | Ala | Ile | Pro | Pro | Lys | Met | Ala | Met | Leu | Arg | Asn | Val | Leu |
| 385 |   |   |   |   | 390 |   |   |   |   | 395 |   |   |   |   | 400 |
| Val | Leu | Ile | Asn | Phe | Leu | Tyr | Thr | Val | Val | Leu | Asn | Tyr | Ser | Ser |   |
|   |   |   |   | 405 |   |   |   |   | 410 |   |   |   |   | 415 |   |
| Val | Gly | Phe | Met | Val | Leu | Ser | Leu | His | Glu | Thr | Leu | Val | Ala | Phe | Lys |
|   |   |   | 420 |   |   |   |   | 425 |   |   |   |   | 430 |   |   |
| Ser | Val | Tyr | Tyr | Ile | Gly | Thr | Val | Ile | Pro | Ile | Ala | Val | Leu | Leu | Leu |
|   |   |   | 435 |   |   |   |   | 440 |   |   |   |   | 445 |   |   |
| Ser | Tyr | Leu | Val | Pro | Val | Lys | Pro | Val | Arg | Pro | Lys | Thr | Arg | Lys | Glu |
| 450 |   |   |   |   | 455 |   |   |   |   | 460 |   |   |   |   |   |
| Glu |   |   |   |   |   |   |   |   |   |   |   |   |   |   |   |
| 465 |   |   |   |   |   |   |   |   |   |   |   |   |   |   |   |

```
<210> SEQ ID NO 113
<211> LENGTH: 313
<212> TYPE: PRT
<213> ORGANISM: Arabidopsis thaliana
```

<400> SEQUENCE: 113

```
Met Asp Glu Gly Val Ile Ala Val Ser Ala Met Asp Ala Phe Glu Lys
1               5                   10                  15

Leu Glu Lys Val Gly Glu Gly Thr Tyr Gly Lys Val Tyr Arg Ala Arg
            20                  25                  30

Glu Lys Ala Thr Gly Lys Ile Val Ala Leu Lys Lys Thr Arg Leu His
        35                  40                  45

Glu Asp Glu Glu Gly Val Pro Ser Thr Thr Leu Arg Glu Ile Ser Ile
    50                  55                  60

Leu Arg Met Leu Ala Arg Asp Pro His Val Val Arg Leu Met Asp Val
65                  70                  75                  80

Lys Gln Gly Leu Ser Lys Glu Gly Lys Thr Val Leu Tyr Leu Val Phe
                85                  90                  95

Glu Tyr Met Asp Thr Asp Val Lys Lys Phe Ile Arg Ser Phe Arg Ser
            100                 105                 110

Thr Gly Lys Asn Ile Pro Thr Gln Thr Ile Lys Ser Leu Met Tyr Gln
        115                 120                 125

Leu Cys Lys Gly Met Ala Phe Cys His Gly His Gly Ile Leu His Arg
    130                 135                 140

Asp Leu Lys Pro His Asn Leu Leu Met Asp Pro Lys Thr Met Arg Leu
145                 150                 155                 160

Lys Ile Ala Asp Leu Gly Leu Ala Arg Ala Phe Thr Leu Pro Met Lys
                165                 170                 175

Lys Tyr Thr His Glu Ile Leu Thr Leu Trp Tyr Arg Ala Pro Glu Val
            180                 185                 190

Leu Leu Gly Ala Thr His Tyr Ser Thr Ala Val Asp Met Trp Ser Val
        195                 200                 205

Gly Cys Ile Phe Ala Glu Leu Val Thr Asn Gln Ala Ile Phe Gln Gly
    210                 215                 220

Asp Ser Glu Leu Gln Gln Leu His Ile Phe Lys Leu Phe Gly Thr
225                 230                 235                 240

Pro Asn Glu Glu Met Trp Pro Gly Val Ser Thr Leu Lys Asn Trp His
                245                 250                 255

Glu Tyr Pro Gln Trp Lys Pro Ser Thr Leu Ser Ser Ala Val Pro Asn
            260                 265                 270

Leu Asp Glu Ala Gly Val Asp Leu Leu Ser Lys Met Leu Gln Tyr Glu
        275                 280                 285

Pro Ala Lys Arg Ile Ser Ala Lys Met Ala Met Glu His Pro Tyr Phe
    290                 295                 300

Asp Asp Leu Pro Glu Lys Ser Ser Leu
305                 310
```

<210> SEQ ID NO 114
<211> LENGTH: 292
<212> TYPE: PRT
<213> ORGANISM: Arabidopsis thaliana

<400> SEQUENCE: 114

```
Met Ser Met Glu Met Glu Leu Phe Val Thr Pro Glu Lys Gln Arg Gln
1               5                   10                  15

His Pro Ser Val Ser Val Glu Lys Thr Pro Val Arg Arg Lys Leu Ile
            20                  25                  30

Val Asp Asp Asp Ser Glu Ile Gly Ser Glu Lys Lys Gly Gln Ser Arg
        35                  40                  45

Thr Ser Gly Gly Gly Leu Arg Gln Phe Ser Val Met Val Cys Gln Lys
```

```
              50                  55                  60
Leu Glu Ala Lys Lys Ile Thr Thr Tyr Lys Glu Val Ala Asp Glu Ile
 65                  70                  75                  80

Ile Ser Asp Phe Ala Thr Ile Lys Gln Asn Ala Glu Lys Pro Leu Asn
                 85                  90                  95

Glu Asn Glu Tyr Asn Glu Lys Asn Ile Arg Arg Val Tyr Asp Ala
                100                 105                 110

Leu Asn Val Phe Met Ala Leu Asp Ile Ile Ala Arg Asp Lys Lys Glu
                115                 120                 125

Ile Arg Trp Lys Gly Leu Pro Ile Thr Cys Lys Asp Val Glu Glu
130                 135                 140

Val Lys Met Asp Arg Asn Lys Val Met Ser Ser Val Gln Lys Lys Ala
145                 150                 155                 160

Ala Phe Leu Lys Glu Leu Arg Glu Lys Val Ser Ser Leu Glu Ser Leu
                165                 170                 175

Met Ser Arg Asn Gln Glu Met Val Val Lys Thr Gln Gly Pro Ala Glu
                180                 185                 190

Gly Phe Thr Leu Pro Phe Ile Leu Leu Glu Thr Asn Pro His Ala Val
                195                 200                 205

Val Glu Ile Glu Ile Ser Glu Asp Met Gln Leu Val His Leu Asp Phe
210                 215                 220

Asn Ser Thr Pro Phe Ser Val His Asp Asp Ala Tyr Ile Leu Lys Leu
225                 230                 235                 240

Met Gln Glu Gln Lys Gln Glu Gln Asn Arg Val Ser Ser Ser Ser
                245                 250                 255

Thr His His Gln Ser Gln His Ser Ser Ala His Ser Ser Ser Ser
                260                 265                 270

Cys Ile Ala Ser Gly Thr Ser Gly Pro Val Cys Trp Asn Ser Gly Ser
275                 280                 285

Ile Asp Thr Arg
    290

<210> SEQ ID NO 115
<211> LENGTH: 165
<212> TYPE: PRT
<213> ORGANISM: Arabidopsis thaliana

<400> SEQUENCE: 115

Met Asn Arg Glu Lys Leu Met Lys Met Ala Asn Thr Val Arg Thr Gly
  1               5                  10                  15

Gly Lys Gly Thr Val Arg Arg Lys Lys Ala Val His Lys Thr Thr
                 20                  25                  30

Thr Thr Asp Asp Lys Arg Leu Gln Ser Thr Leu Lys Arg Val Gly Val
                 35                  40                  45

Asn Ser Ile Pro Ala Ile Glu Glu Val Asn Ile Phe Lys Asp Asp Val
 50                  55                  60

Val Ile Gln Phe Ile Asn Pro Lys Val Gln Ala Ser Ile Ala Ala Asn
 65                  70                  75                  80

Thr Trp Val Val Ser Gly Thr Pro Gln Thr Lys Lys Leu Gln Asp Ile
                 85                  90                  95

Leu Pro Gln Ile Ile Ser Gln Leu Gly Pro Asp Asn Leu Asp Asn Leu
                100                 105                 110

Lys Lys Leu Ala Glu Gln Phe Gln Lys Gln Ala Pro Gly Ala Gly Asp
                115                 120                 125

Val Pro Ala Thr Ile Gln Glu Glu Asp Asp Asp Asp Val Pro Asp
```

```
                    130                 135                 140
Leu Val Val Gly Glu Thr Phe Glu Thr Pro Ala Thr Glu Ala Pro
145                 150                 155                 160

Lys Ala Ala Ala Ser
                165

<210> SEQ ID NO 116
<211> LENGTH: 432
<212> TYPE: PRT
<213> ORGANISM: Arabidopsis thaliana

<400> SEQUENCE: 116

Met Ala Thr Val Ser Ser Ser Trp Pro Asn Pro Asn Pro Asn Pro
1               5                   10                  15

Asp Ser Thr Ser Ala Ser Asp Ser Asp Ser Thr Phe Pro Ser His Arg
            20                  25                  30

Asp Arg Val Asp Glu Pro Asp Ser Leu Asp Ser Phe Ser Ser Met Ser
            35                  40                  45

Leu Asn Ser Asp Glu Pro Asn Gln Thr Ser Asn Gln Ser Pro Leu Ser
        50                  55                  60

Pro Pro Thr Pro Asn Leu Pro Val Met Pro Pro Ser Val Leu His
65                  70                  75                  80

Leu Ser Phe Asn Gln Asp His Ala Cys Phe Ala Val Gly Thr Asp Arg
                85                  90                  95

Gly Phe Arg Ile Leu Asn Cys Asp Pro Phe Arg Glu Ile Phe Arg Arg
                100                 105                 110

Asp Phe Asp Arg Gly Gly Gly Val Ala Val Val Glu Met Leu Phe Arg
            115                 120                 125

Cys Asn Ile Leu Ala Leu Val Gly Gly Pro Asp Pro Gln Tyr Pro
130                 135                 140

Pro Asn Lys Val Met Ile Trp Asp Asp His Gln Gly Arg Cys Ile Gly
145                 150                 155                 160

Glu Leu Ser Phe Arg Ser Asp Val Arg Ser Val Arg Leu Arg Arg Asp
                165                 170                 175

Arg Ile Ile Val Val Leu Glu Gln Lys Ile Phe Val Tyr Asn Phe Ser
            180                 185                 190

Asp Leu Lys Leu Met His Gln Ile Glu Thr Ile Ala Asn Pro Lys Gly
        195                 200                 205

Leu Cys Ala Val Ser Gln Gly Val Gly Ser Met Val Leu Val Cys Pro
210                 215                 220

Gly Leu Gln Lys Gly Gln Val Arg Ile Glu His Tyr Ala Ser Lys Arg
225                 230                 235                 240

Thr Lys Phe Val Met Ala His Asp Ser Arg Ile Ala Cys Phe Ala Leu
                245                 250                 255

Thr Gln Asp Gly His Leu Leu Ala Thr Ala Ser Ser Lys Gly Thr Leu
            260                 265                 270

Val Arg Ile Phe Asn Thr Val Asp Gly Thr Leu Arg Gln Glu Ser Gly
        275                 280                 285

Thr Ser Glu Asp Glu Ile Gly Lys Glu Gly Ala Asp Arg Ala Glu Ile
290                 295                 300

Tyr Ser Leu Ala Phe Ser Ser Asn Ala Gln Trp Leu Ala Val Ser Ser
305                 310                 315                 320

Asp Lys Gly Thr Val His Val Phe Gly Leu Lys Val Asn Ser Gly Ser
                325                 330                 335

Gln Val Lys Asp Ser Ser Arg Ile Ala Pro Asp Ala Thr Pro Ser Ser
```

```
                     340             345             350
Pro Ser Ser Ser Leu Ser Leu Phe Lys Val Leu Pro Arg Tyr Phe Ser
                355                 360                 365

Ser Glu Trp Ser Val Ala Gln Phe Arg Leu Val Glu Gly Thr Gln Tyr
        370                 375                 380

Ile Ala Ala Phe Gly His Gln Lys Asn Thr Val Val Ile Leu Gly Met
385                 390                 395                 400

Asp Gly Ser Phe Tyr Arg Cys Gln Phe Asp Pro Val Asn Gly Gly Glu
                405                 410                 415

Met Ser Gln Leu Glu Tyr His Asn Cys Leu Lys Pro Pro Ser Val Phe
                420                 425                 430

<210> SEQ ID NO 117
<211> LENGTH: 559
<212> TYPE: PRT
<213> ORGANISM: Arabidopsis thaliana

<400> SEQUENCE: 117

Met Asp Val Gly Val Thr Thr Ala Lys Ser Ile Leu Glu Lys Pro Leu
1               5                   10                  15

Lys Leu Leu Thr Glu Glu Asp Ile Ser Gln Leu Thr Arg Glu Asp Cys
                20                  25                  30

Arg Lys Phe Leu Lys Glu Lys Gly Phe Phe Phe Leu Ser Pro Phe
            35                  40                  45

Phe Ser Gly Leu Ile Val Phe Asp Glu Trp Arg Leu Thr Arg Val Glu
        50                  55                  60

Thr Gly Met Arg Arg Pro Ser Trp Asn Lys Ser Gln Ala Ile Gln Gln
65                  70                  75                  80

Val Leu Ser Leu Lys Ala Leu Tyr Glu Pro Gly Asp Asp Ser Gly Ala
                85                  90                  95

Gly Ile Leu Arg Lys Ile Leu Val Ser Gln Pro Pro Asn Pro Pro Arg
            100                 105                 110

Val Thr Thr Thr Leu Ile Glu Pro Arg Asn Glu Leu Glu Ala Cys Gly
        115                 120                 125

Arg Ile Pro Leu Gln Glu Asp Asp Gly Ala Cys His Arg Arg Asp Ser
    130                 135                 140

Pro Arg Ser Ala Glu Phe Ser Gly Ser Ser Gly Gln Phe Val Ala Asp
145                 150                 155                 160

Lys Asp Ser His Lys Thr Val Ser Val Ser Pro Arg Ser Pro Ala Glu
                165                 170                 175

Thr Asn Ala Val Val Gly Gln Met Thr Ile Phe Tyr Ser Gly Lys Val
            180                 185                 190

Asn Val Tyr Asp Gly Val Pro Pro Glu Lys Ala Arg Ser Ile Met His
        195                 200                 205

Phe Ala Ala Asn Pro Ile Asp Leu Pro Glu Asn Gly Ile Phe Ala Ser
    210                 215                 220

Ser Arg Met Ile Ser Lys Pro Met Ser Lys Glu Lys Met Val Glu Leu
225                 230                 235                 240

Pro Gln Tyr Gly Leu Glu Lys Ala Pro Ala Ser Arg Asp Ser Asp Val
                245                 250                 255

Glu Gly Gln Ala Asn Arg Lys Val Ser Leu Gln Arg Tyr Leu Glu Lys
            260                 265                 270

Arg Lys Asp Arg Phe Ser Lys Thr Lys Lys Ala Pro Gly Val Ala Ser
        275                 280                 285

Ser Ser Leu Glu Met Phe Leu Asn Arg Gln Pro Arg Met Asn Ala Ala
```

```
                290                 295                 300
Tyr Ser Gln Asn Leu Ser Gly Thr Gly His Cys Glu Ser Pro Glu Asn
305                 310                 315                 320

Gln Thr Lys Ser Pro Asn Ile Ser Val Asp Leu Asn Ser Asp Leu Asn
                325                 330                 335

Ser Glu Gly Ala Lys Arg Thr Gly Asp Gly Thr Gly Gln Lys Ala
            340                 345                 350

Gly Arg Thr Ile Ser Cys Ser Tyr Asn Met Thr Lys Thr Ser Arg Gly
        355                 360                 365

Thr Arg Trp Val Lys Arg Ser Arg Glu Glu Val Ile Gln Ala Trp Tyr
    370                 375                 380

Met Asp Asp Ser Glu Glu Asp Gln Arg Leu Pro His His Lys Asp Pro
385                 390                 395                 400

Lys Glu Phe Val Ser Leu Asp Lys Leu Ala Glu Leu Gly Val Leu Ser
                405                 410                 415

Trp Arg Leu Asp Ala Asp Asn Tyr Glu Thr Asp Glu Asp Leu Lys Lys
            420                 425                 430

Ile Arg Glu Ser Arg Gly Tyr Ser Tyr Met Asp Phe Cys Glu Val Cys
        435                 440                 445

Pro Glu Lys Leu Pro Asn Tyr Glu Val Lys Val Lys Ser Phe Phe Glu
    450                 455                 460

Glu His Leu His Thr Asp Glu Glu Ile Arg Tyr Cys Val Ala Gly Thr
465                 470                 475                 480

Gly Tyr Phe Asp Val Arg Asp Arg Asn Glu Ala Trp Ile Arg Val Leu
                485                 490                 495

Val Lys Lys Gly Gly Met Ile Val Leu Pro Ala Gly Ile Tyr His Arg
            500                 505                 510

Phe Thr Val Asp Ser Asp Asn Tyr Ile Lys Ala Met Arg Leu Phe Val
        515                 520                 525

Gly Glu Pro Val Trp Thr Pro Tyr Asn Arg Pro His Asp His Leu Pro
    530                 535                 540

Ala Arg Lys Glu Tyr Val Asp Asn Phe Met Ile Asn Ala Ser Ala
545                 550                 555

<210> SEQ ID NO 118
<211> LENGTH: 86
<212> TYPE: PRT
<213> ORGANISM: Arabidopsis thaliana

<400> SEQUENCE: 118

Met Asp Gly His Asp Ser Lys Asp Thr Lys Gln Ser Thr Ala Asp Met
1               5                   10                  15

Thr Ala Phe Val Gln Asn Leu Leu Gln Gln Met Gln Thr Arg Phe Gln
            20                  25                  30

Thr Met Ser Asp Ser Ile Ile Thr Lys Ile Asp Asp Met Gly Gly Arg
        35                  40                  45

Ile Asn Glu Leu Glu Gln Ser Ile Asn Asp Leu Arg Ala Glu Met Gly
    50                  55                  60

Val Glu Gly Thr Pro Pro Ala Ser Lys Ser Gly Asp Glu Pro Lys
65                  70                  75                  80

Thr Pro Ala Ser Ser Ser
            85

<210> SEQ ID NO 119
<211> LENGTH: 784
<212> TYPE: PRT
```

<213> ORGANISM: Arabidopsis thaliana

<400> SEQUENCE: 119

| | | | | | | | | | | | | | | | |
|---|---|---|---|---|---|---|---|---|---|---|---|---|---|---|---|

Met Glu Ile Tyr Thr Met Lys Thr Asn Phe Leu Val Leu Ala Leu Ser
1               5                   10                  15

Leu Cys Ile Leu Leu Ser Ser Phe His Glu Val Ser Cys Gln Asp Asp
            20                  25                  30

Gly Ser Gly Leu Ser Asn Leu Asp Leu Ile Glu Arg Asp Tyr Gln Asp
        35                  40                  45

Ser Val Asn Ala Leu Gln Gly Lys Asp Asp Glu Asp Gln Ser Ala Lys
    50                  55                  60

Ile Gln Ser Glu Asn Gln Asn Asn Thr Thr Val Thr Asp Lys Asn Thr
65                  70                  75                  80

Ile Ser Leu Ser Leu Ser Asp Glu Ser Glu Val Gly Ser Val Ser Asp
                85                  90                  95

Glu Ser Val Gly Arg Ser Ser Leu Leu Asp Gln Ile Lys Leu Glu Phe
            100                 105                 110

Glu Ala His His Asn Ser Ile Asn Gln Ala Gly Ser Asp Gly Val Lys
        115                 120                 125

Ala Glu Ser Lys Asp Asp Glu Glu Leu Ser Ala His Arg Gln Lys
    130                 135                 140

Met Leu Glu Glu Ile Glu His Glu Phe Glu Ala Ala Ser Asp Ser Leu
145                 150                 155                 160

Lys Gln Leu Lys Thr Asp Asp Val Asn Glu Gly Asn Asp Glu His
                165                 170                 175

Ser Ala Lys Arg Gln Ser Leu Leu Glu Glu Ile Glu Arg Glu Phe Glu
            180                 185                 190

Ala Ala Thr Lys Glu Leu Glu Gln Leu Lys Val Asn Asp Phe Thr Gly
        195                 200                 205

Asp Lys Asp Asp Glu Glu His Ser Ala Lys Arg Lys Ser Met Leu Glu
    210                 215                 220

Ala Ile Glu Arg Glu Phe Glu Ala Ala Met Glu Gly Ile Glu Ala Leu
225                 230                 235                 240

Lys Val Ser Asp Ser Thr Gly Ser Gly Asp Asp Glu Glu Gln Ser Ala
                245                 250                 255

Lys Arg Leu Ser Met Leu Glu Glu Ile Glu Arg Glu Phe Glu Ala Ala
            260                 265                 270

Ser Lys Gly Leu Glu Gln Leu Arg Ala Ser Asp Ser Thr Ala Asp Asn
        275                 280                 285

Asn Glu Glu Glu His Ala Ala Lys Gly Gln Ser Leu Leu Glu Glu Ile
    290                 295                 300

Glu Arg Glu Phe Glu Ala Ala Thr Glu Ser Leu Lys Gln Leu Gln Val
305                 310                 315                 320

Asp Asp Ser Thr Glu Asp Lys Glu His Cys Lys Ala Leu Phe Phe Leu
                325                 330                 335

Leu Ser Ala Ile Leu Ser Leu Trp Leu Ser Glu Ser Gly Phe Glu Cys
            340                 345                 350

Ile Val Val Thr Ala Ala Lys Arg Gln Ser Leu Leu Glu Glu Ile Glu
        355                 360                 365

Arg Glu Phe Glu Ala Ala Thr Lys Asp Leu Lys Gln Leu Asn Asp Phe
    370                 375                 380

Thr Glu Gly Ser Ala Asp Asp Glu Gln Ser Ala Lys Arg Asn Lys Met
385                 390                 395                 400

Leu Glu Asp Ile Glu Arg Glu Phe Glu Ala Ala Thr Ile Gly Leu Glu

```
            405                 410                 415
Gln Leu Lys Ala Asn Asp Phe Ser Glu Gly Asn Asn Glu Glu Gln
            420                 425                 430

Ser Ala Lys Arg Lys Ser Met Leu Glu Glu Ile Glu Arg Glu Phe Glu
            435                 440                 445

Ala Ala Ile Gly Gly Leu Lys Gln Ile Lys Val Asp Asp Ser Arg Asn
            450                 455                 460

Leu Glu Glu Glu Ser Ala Lys Arg Lys Ile Ile Leu Glu Glu Met Glu
465                 470                 475                 480

Arg Glu Phe Glu Glu Ala His Ser Gly Ile Asn Ala Lys Ala Asp Lys
                485                 490                 495

Glu Glu Ser Ala Lys Lys Gln Ser Gly Ser Ala Ile Pro Glu Val Leu
                500                 505                 510

Gly Leu Gly Gln Ser Gly Gly Cys Ser Cys Ser Lys Gln Asp Glu Asp
                515                 520                 525

Ser Ser Ile Val Ile Pro Thr Lys Tyr Ser Ile Glu Asp Ile Leu Ser
                530                 535                 540

Glu Glu Ser Ala Val Gln Gly Thr Glu Thr Ser Ser Leu Thr Ala Ser
545                 550                 555                 560

Leu Thr Gln Leu Val Glu Asn His Arg Lys Glu Lys Glu Ser Leu Leu
                565                 570                 575

Gly His Arg Val Leu Thr Ser Pro Ser Ile Ala Ser Ser Thr Ser Glu
                580                 585                 590

Ser Ser Ala Thr Ser Glu Thr Val Glu Thr Leu Arg Ala Lys Leu Asn
                595                 600                 605

Glu Leu Arg Gly Leu Thr Ala Arg Glu Leu Val Thr Arg Lys Asp Phe
                610                 615                 620

Gly Gln Ile Leu Ile Thr Ala Ala Ser Phe Glu Glu Leu Ser Ser Ala
625                 630                 635                 640

Pro Ile Ser Tyr Ile Ser Arg Leu Ala Lys Tyr Arg Asn Val Ile Lys
                645                 650                 655

Glu Gly Leu Glu Ala Ser Glu Arg Val His Ile Ala Gln Val Arg Ala
                660                 665                 670

Lys Met Leu Lys Glu Val Ala Thr Glu Lys Gln Thr Ala Val Asp Thr
                675                 680                 685

His Phe Ala Thr Ala Lys Lys Leu Ala Gln Glu Gly Asp Ala Leu Phe
                690                 695                 700

Val Lys Ile Phe Ala Ile Lys Lys Leu Leu Ala Lys Leu Glu Ala Glu
705                 710                 715                 720

Lys Glu Ser Val Asp Gly Lys Phe Lys Glu Thr Val Lys Glu Leu Ser
                725                 730                 735

His Leu Leu Ala Asp Ala Ser Glu Ala Tyr Glu Glu Tyr His Gly Ala
                740                 745                 750

Val Arg Lys Ala Lys Asp Glu Gln Ala Ala Glu Glu Phe Ala Lys Glu
                755                 760                 765

Ala Thr Gln Ser Ala Glu Ile Ile Trp Val Lys Phe Leu Ser Ser Leu
770                 775                 780

<210> SEQ ID NO 120
<211> LENGTH: 724
<212> TYPE: PRT
<213> ORGANISM: Arabidopsis thaliana

<400> SEQUENCE: 120

Met Glu Phe Gly Ser Phe Leu Val Ser Leu Gly Thr Ser Phe Val Ile
```

-continued

```
          1               5                  10                 15
Phe Val Ile Leu Met Leu Leu Phe Thr Trp Leu Ser Arg Lys Ser Gly
                    20                  25                  30

Asn Ala Pro Ile Tyr Tyr Pro Asn Arg Ile Leu Lys Gly Leu Glu Pro
                35                  40                  45

Trp Glu Gly Thr Ser Leu Thr Arg Asn Pro Phe Ala Trp Met Arg Glu
            50                  55                  60

Ala Leu Thr Ser Ser Glu Gln Asp Val Val Asn Leu Ser Gly Val Asp
 65                 70                  75                  80

Thr Ala Val His Phe Val Phe Leu Ser Thr Val Leu Gly Ile Phe Ala
                    85                  90                  95

Cys Ser Ser Leu Leu Leu Leu Pro Thr Leu Leu Pro Leu Ala Ala Thr
                100                 105                 110

Asp Asn Asn Ile Lys Asn Thr Lys Asn Ala Thr Asp Thr Thr Ser Lys
                115                 120                 125

Gly Thr Phe Ser Gln Leu Asp Asn Leu Ser Met Ala Asn Ile Thr Lys
        130                 135                 140

Lys Ser Ser Arg Leu Trp Ala Phe Leu Gly Ala Val Tyr Trp Ile Ser
145                 150                 155                 160

Leu Val Thr Tyr Phe Phe Leu Trp Lys Ala Tyr Lys His Val Ser Ser
                    165                 170                 175

Leu Arg Ala Gln Ala Leu Met Ser Ala Asp Val Lys Pro Glu Gln Phe
                180                 185                 190

Ala Ile Leu Val Arg Asp Met Pro Ala Pro Pro Asp Gly Gln Thr Gln
                195                 200                 205

Lys Glu Phe Ile Asp Ser Tyr Phe Arg Glu Ile Tyr Pro Glu Thr Phe
        210                 215                 220

Tyr Arg Ser Leu Val Ala Thr Glu Asn Ser Lys Val Asn Lys Ile Trp
225                 230                 235                 240

Glu Lys Leu Glu Gly Tyr Lys Lys Lys Leu Ala Arg Ala Glu Ala Ile
                    245                 250                 255

Leu Ala Ala Thr Asn Asn Arg Pro Thr Asn Lys Thr Gly Phe Cys Gly
                260                 265                 270

Leu Val Gly Lys Gln Val Asp Ser Ile Glu Tyr Tyr Thr Glu Leu Ile
                275                 280                 285

Asn Glu Ser Val Ala Lys Leu Glu Thr Glu Gln Lys Ala Val Leu Ala
        290                 295                 300

Glu Lys Gln Gln Thr Ala Ala Val Val Phe Thr Thr Arg Val Ala
305                 310                 315                 320

Ala Ala Ser Ala Ala Gln Ser Leu His Cys Gln Met Val Asp Lys Trp
                    325                 330                 335

Thr Val Thr Glu Ala Pro Glu Pro Arg Gln Leu Leu Trp Gln Asn Leu
                340                 345                 350

Asn Ile Lys Leu Phe Ser Arg Ile Ile Arg Gln Tyr Phe Ile Tyr Phe
                355                 360                 365

Phe Val Ala Val Thr Ile Leu Phe Tyr Met Ile Pro Ile Ala Phe Val
        370                 375                 380

Ser Ala Ile Thr Thr Leu Lys Asn Leu Gln Arg Ile Pro Phe Ile
385                 390                 395                 400

Lys Pro Val Val Glu Ile Thr Ala Ile Arg Thr Val Leu Glu Ser Phe
                    405                 410                 415

Leu Pro Gln Ile Ala Leu Ile Val Phe Leu Ala Met Leu Pro Lys Leu
                420                 425                 430
```

```
Leu Leu Phe Leu Ser Lys Ala Glu Gly Ile Pro Ser Gln Ser His Ala
            435                 440                 445

Ile Arg Ala Ala Ser Gly Lys Tyr Phe Tyr Phe Ser Val Phe Asn Val
        450                 455                 460

Phe Ile Gly Val Thr Leu Ala Gly Thr Leu Phe Asn Thr Val Lys Asp
465                 470                 475                 480

Ile Ala Lys Asn Pro Lys Leu Asp Met Ile Ile Asn Leu Leu Ala Thr
                485                 490                 495

Ser Leu Pro Lys Ser Ala Thr Phe Phe Leu Thr Tyr Val Ala Leu Lys
            500                 505                 510

Phe Phe Ile Gly Tyr Gly Leu Glu Leu Ser Arg Ile Ile Pro Leu Ile
        515                 520                 525

Ile Phe His Leu Lys Lys Lys Tyr Leu Cys Lys Thr Glu Ala Glu Val
        530                 535                 540

Lys Glu Ala Trp Tyr Pro Gly Asp Leu Ser Tyr Ala Thr Arg Val Pro
545                 550                 555                 560

Gly Asp Met Leu Ile Leu Thr Ile Thr Phe Cys Tyr Ser Val Ile Ala
                565                 570                 575

Pro Leu Ile Leu Ile Phe Gly Ile Thr Tyr Phe Gly Leu Gly Trp Leu
            580                 585                 590

Val Leu Arg Asn Gln Ala Leu Lys Val Tyr Val Pro Ser Tyr Glu Ser
        595                 600                 605

Tyr Gly Arg Met Trp Pro His Ile His Gln Arg Ile Leu Ala Ala Leu
        610                 615                 620

Phe Leu Phe Gln Val Val Met Phe Gly Tyr Leu Gly Ala Lys Thr Phe
625                 630                 635                 640

Phe Tyr Thr Ala Leu Val Ile Pro Leu Ile Ile Thr Ser Leu Ile Phe
                645                 650                 655

Gly Tyr Val Cys Arg Gln Lys Phe Tyr Gly Gly Phe Glu His Thr Ala
            660                 665                 670

Leu Glu Val Ala Cys Arg Glu Leu Lys Gln Ser Pro Asp Leu Glu Glu
        675                 680                 685

Ile Phe Arg Ala Tyr Ile Pro His Ser Leu Ser Ser His Lys Pro Glu
        690                 695                 700

Glu His Glu Phe Lys Gly Ala Met Ser Arg Tyr Gln Asp Phe Asn Ala
705                 710                 715                 720

Ile Ala Gly Val

<210> SEQ ID NO 121
<211> LENGTH: 1313
<212> TYPE: PRT
<213> ORGANISM: Arabidopsis thaliana

<400> SEQUENCE: 121

Met Ala Glu Gln Lys Ser Thr Asn Met Trp Asn Trp Glu Val Thr Gly
1               5                   10                  15

Phe Glu Ser Lys Lys Ser Pro Ser Ser Glu Glu Gly Val His Arg Thr
            20                  25                  30

Pro Ser Ser Met Leu Arg Arg Tyr Ser Ile Pro Lys Asn Ser Leu Pro
        35                  40                  45

Pro His Ser Ser Glu Leu Ala Ser Lys Val Gln Ser Leu Lys Asp Lys
    50                  55                  60

Val Gln Leu Ala Lys Asp Asp Tyr Val Gly Leu Arg Gln Glu Ala Thr
65                  70                  75                  80

Asp Leu Gln Glu Tyr Ser Asn Ala Lys Leu Glu Arg Val Thr Arg Tyr
```

-continued

```
                    85                  90                  95
Leu Gly Val Leu Ala Asp Lys Ser Arg Lys Leu Asp Gln Tyr Ala Leu
                100                 105                 110

Glu Thr Glu Ala Arg Ile Ser Pro Leu Ile Asn Glu Lys Lys Arg Leu
                115                 120                 125

Phe Asn Asp Leu Leu Thr Thr Lys Gly Ala His Leu Pro Phe Pro Thr
130                 135                 140

Ser Phe Ser Ile Leu Thr Ser Ile Asp Ile Asp His Thr Arg Pro Leu
145                 150                 155                 160

Phe Glu Asp Glu Gly Pro Ser Ile Ile Glu Phe Pro Asp Asn Cys Thr
                165                 170                 175

Ile Arg Val Asn Thr Ser Asp Asp Thr Leu Ser Asn Pro Lys Lys Glu
                180                 185                 190

Phe Glu Phe Asp Arg Val Tyr Gly Pro Gln Val Gly Gln Ala Ser Leu
                195                 200                 205

Phe Ser Asp Val Gln Pro Phe Val Gln Ser Ala Leu Asp Gly Ser Asn
                210                 215                 220

Val Ser Ile Phe Ala Tyr Gly Gln Thr His Ala Gly Lys Thr Tyr Thr
225                 230                 235                 240

Met Val Ala Pro Pro Phe Pro Phe Leu Ser Glu Ile Arg Tyr Arg Ser
                245                 250                 255

Cys Leu Asp Leu Asn Met Ile Gly Lys Phe Met Asp Val His Ser Lys
                260                 265                 270

Phe Met Asp Glu Gly Ser Asn Gln Asp Arg Gly Leu Tyr Ala Arg Cys
                275                 280                 285

Phe Glu Glu Leu Met Asp Leu Ala Asn Ser Asp Ser Thr Ser Ala Ser
                290                 295                 300

Gln Phe Ser Phe Ser Val Ser Val Phe Glu Leu Tyr Asn Glu Gln Val
305                 310                 315                 320

Arg Asp Leu Leu Ser Gly Cys Gln Ser Asn Leu Pro Lys Ile Asn Met
                325                 330                 335

Gly Leu Arg Glu Ser Val Ile Glu Leu Ser Gln Glu Lys Val Asp Asn
                340                 345                 350

Pro Ser Glu Phe Met Arg Val Leu Asn Ser Ala Phe Gln Asn Arg Gly
                355                 360                 365

Asn Asp Lys Ser Lys Ser Thr Val Thr His Leu Ile Val Ser Ile His
                370                 375                 380

Ile Cys Tyr Ser Asn Thr Ile Thr Arg Glu Asn Val Ile Ser Lys Leu
385                 390                 395                 400

Ser Leu Val Asp Leu Ala Gly Ser Glu Gly Leu Thr Val Glu Asp Asp
                405                 410                 415

Asn Gly Asp His Val Thr Asp Leu Leu His Val Thr Asn Ser Ile Ser
                420                 425                 430

Ala Leu Gly Asp Val Leu Ser Ser Leu Thr Ser Lys Arg Asp Thr Ile
                435                 440                 445

Pro Tyr Glu Asn Ser Phe Leu Thr Arg Ile Leu Ala Asp Ser Leu Gly
                450                 455                 460

Gly Ser Ser Lys Thr Leu Met Ile Val Asn Ile Cys Pro Ser Ala Arg
465                 470                 475                 480

Asn Leu Ser Glu Ile Met Ser Cys Leu Asn Tyr Ala Ala Arg Ala Arg
                485                 490                 495

Asn Thr Val Pro Ser Leu Gly Asn Arg Asp Thr Ile Lys Lys Trp Arg
                500                 505                 510
```

```
Asp Val Ala Asn Asp Ala Arg Lys Glu Val Leu Glu Lys Glu Arg Glu
            515                 520                 525

Asn Gln Arg Leu Lys Gln Glu Val Thr Gly Leu Lys Gln Ala Leu Lys
530                 535                 540

Glu Ala Asn Asp Gln Cys Val Leu Leu Tyr Asn Glu Val Gln Arg Ala
545                 550                 555                 560

Trp Arg Val Ser Phe Thr Leu Gln Ser Asp Leu Lys Ser Glu Asn Ala
            565                 570                 575

Met Val Val Asp Lys His Lys Ile Glu Lys Glu Gln Asn Phe Gln Leu
            580                 585                 590

Arg Asn Gln Ile Ala Gln Leu Leu Gln Leu Glu Gln Glu Gln Lys Leu
            595                 600                 605

Gln Ala Gln Gln Gln Asp Ser Thr Ile Gln Asn Leu Gln Ser Lys Val
610                 615                 620

Lys Asp Leu Glu Ser Gln Leu Ser Lys Ala Leu Lys Ser Asp Met Thr
625                 630                 635                 640

Arg Ser Arg Asp Pro Leu Glu Pro Gln Pro Arg Ala Ala Glu Asn Thr
            645                 650                 655

Leu Asp Ser Ser Ala Val Thr Lys Lys Leu Glu Glu Glu Leu Lys Lys
            660                 665                 670

Arg Asp Ala Leu Ile Glu Arg Leu His Glu Glu Asn Glu Lys Leu Phe
            675                 680                 685

Asp Arg Leu Thr Glu Lys Ser Val Ala Ser Ser Thr Gln Val Ser Ser
690                 695                 700

Pro Ser Ser Lys Ala Ser Pro Thr Val Gln Pro Ala Asp Val Asp Arg
705                 710                 715                 720

Lys Asn Ser Ala Gly Thr Leu Pro Ser Ser Val Asp Lys Asn Glu Gly
            725                 730                 735

Thr Ile Thr Leu Val Lys Ser Ser Glu Leu Val Lys Thr Thr Pro
            740                 745                 750

Ala Gly Glu Tyr Leu Thr Ala Ala Leu Asn Asp Phe Asp Pro Glu Gln
            755                 760                 765

Tyr Glu Gly Leu Ala Ala Ile Ala Asp Gly Ala Asn Lys Leu Leu Met
770                 775                 780

Leu Val Leu Ala Ala Val Ile Lys Ala Gly Ala Ser Arg Glu His Glu
785                 790                 795                 800

Ile Leu Ala Glu Ile Arg Asp Ser Val Phe Ser Phe Ile Arg Lys Met
            805                 810                 815

Glu Pro Arg Arg Val Met Asp Thr Met Leu Val Ser Arg Val Arg Ile
            820                 825                 830

Leu Tyr Ile Arg Ser Leu Leu Ala Arg Ser Pro Glu Leu Gln Ser Ile
            835                 840                 845

Lys Val Ser Pro Val Glu Arg Phe Leu Glu Lys Pro Tyr Thr Gly Arg
850                 855                 860

Thr Arg Ser Ser Ser Gly Ser Ser Pro Gly Arg Ser Pro Val Arg
865                 870                 875                 880

Tyr Tyr Asp Glu Gln Ile Tyr Gly Phe Lys Val Asn Leu Lys Pro Glu
            885                 890                 895

Lys Lys Ser Lys Leu Val Ser Val Val Ser Arg Ile Arg Gly His Asp
            900                 905                 910

Gln Asp Thr Gly Arg Gln Val Thr Gly Gly Lys Leu Arg Glu Ile
            915                 920                 925

Gln Asp Glu Ala Lys Ser Phe Ala Ile Gly Asn Lys Pro Leu Ala Ala
930                 935                 940
```

```
Leu Phe Val His Thr Pro Ala Gly Glu Leu Gln Arg Gln Ile Arg Ser
945                 950                 955                 960

Trp Leu Ala Glu Ser Phe Glu Phe Leu Ser Val Thr Ala Asp Asp Val
                965                 970                 975

Ser Gly Val Thr Thr Gly Gln Leu Glu Leu Leu Ser Thr Ala Ile Met
            980                 985                 990

Asp Gly Trp Met Ala Gly Val Gly Ala Ala Val Pro Pro His Thr Asp
        995                 1000                1005

Ala Leu Gly Gln Leu Leu Ser Glu Tyr Ala Lys Arg Val Tyr Thr
    1010                1015                1020

Ser Gln Met Gln His Leu Lys Asp Ile Ala Gly Thr Leu Ala Ser
    1025                1030                1035

Glu Glu Ala Glu Asp Ala Gly Gln Val Ala Lys Leu Arg Ser Ala
    1040                1045                1050

Leu Glu Ser Val Asp His Lys Arg Arg Lys Ile Leu Gln Gln Met
    1055                1060                1065

Arg Ser Asp Ala Ala Leu Phe Thr Leu Glu Glu Gly Ser Ser Pro
    1070                1075                1080

Val Gln Asn Pro Ser Thr Ala Ala Glu Asp Ser Arg Leu Ala Ser
    1085                1090                1095

Leu Ile Ser Leu Asp Ala Ile Leu Lys Gln Val Lys Glu Ile Thr
    1100                1105                1110

Arg Gln Ala Ser Val His Val Leu Ser Lys Ser Lys Lys Lys Ala
    1115                1120                1125

Leu Leu Glu Ser Leu Asp Glu Leu Asn Glu Arg Met Pro Ser Leu
    1130                1135                1140

Leu Asp Val Asp His Pro Cys Ala Gln Arg Glu Ile Asp Thr Ala
    1145                1150                1155

His Gln Leu Val Glu Thr Ile Pro Glu Gln Glu Asp Asn Leu Gln
    1160                1165                1170

Asp Glu Lys Arg Pro Ser Ile Asp Ser Ile Ser Ser Thr Glu Thr
    1175                1180                1185

Asp Val Ser Gln Trp Asn Val Leu Gln Phe Asn Thr Gly Gly Ser
    1190                1195                1200

Ser Ala Pro Phe Ile Ile Lys Cys Gly Ala Asn Ser Asn Ser Glu
    1205                1210                1215

Leu Val Ile Lys Ala Asp Arg Ile Gln Glu Pro Lys Gly Gly
    1220                1225                1230

Glu Ile Val Arg Val Pro Arg Pro Ser Val Leu Glu Asn Met
    1235                1240                1245

Ser Leu Glu Glu Met Lys Gln Val Phe Gly Gln Leu Pro Glu Ala
    1250                1255                1260

Leu Ser Ser Leu Ala Leu Ala Arg Thr Ala Asp Gly Thr Arg Ala
    1265                1270                1275

Arg Tyr Ser Arg Leu Tyr Arg Thr Leu Ala Met Lys Val Pro Ser
    1280                1285                1290

Leu Arg Asp Leu Val Gly Glu Leu Glu Lys Gly Gly Val Leu Lys
    1295                1300                1305

Asp Thr Lys Ser Thr
    1310

<210> SEQ ID NO 122
<211> LENGTH: 310
<212> TYPE: PRT
```

<213> ORGANISM: Arabidopsis thaliana

<400> SEQUENCE: 122

Met Ala Asn Pro Trp Trp Val Gly Asn Val Ala Ile Gly Gly Val Glu
1               5                   10                  15

Ser Pro Val Thr Ser Ser Ala Pro Ser Leu His His Arg Asn Ser Asn
            20                  25                  30

Asn Asn Asn Pro Pro Thr Met Thr Arg Ser Asp Pro Arg Leu Asp His
        35                  40                  45

Asp Phe Thr Thr Asn Asn Ser Gly Ser Pro Asn Thr Gln Thr Gln Ser
    50                  55                  60

Gln Glu Glu Gln Asn Ser Arg Asp Glu Gln Pro Ala Val Glu Pro Gly
65                  70                  75                  80

Ser Gly Ser Gly Ser Thr Gly Arg Arg Pro Arg Gly Arg Pro Pro Gly
                85                  90                  95

Ser Lys Asn Lys Pro Lys Ser Pro Val Val Val Thr Lys Glu Ser Pro
            100                 105                 110

Asn Ser Leu Gln Ser His Val Leu Glu Ile Ala Thr Gly Ala Asp Val
        115                 120                 125

Ala Glu Ser Leu Asn Ala Phe Ala Arg Arg Arg Gly Arg Gly Val Ser
    130                 135                 140

Val Leu Ser Gly Ser Gly Leu Val Thr Asn Val Thr Leu Arg Gln Pro
145                 150                 155                 160

Ala Ala Ser Gly Gly Val Val Ser Leu Arg Gly Gln Phe Glu Ile Leu
                165                 170                 175

Ser Met Cys Gly Ala Phe Leu Pro Thr Ser Gly Ser Pro Ala Ala Ala
            180                 185                 190

Ala Gly Leu Thr Ile Tyr Leu Ala Gly Ala Gln Gly Gln Val Val Gly
        195                 200                 205

Gly Gly Val Ala Gly Pro Leu Ile Ala Ser Gly Pro Val Ile Val Ile
    210                 215                 220

Ala Ala Thr Phe Cys Asn Ala Thr Tyr Glu Arg Leu Pro Ile Glu Glu
225                 230                 235                 240

Glu Gln Gln Gln Glu Gln Pro Leu Gln Leu Glu Asp Gly Lys Lys Gln
                245                 250                 255

Lys Glu Glu Asn Asp Asp Asn Glu Ser Gly Asn Asn Gly Asn Glu Gly
            260                 265                 270

Ser Met Gln Pro Pro Met Tyr Asn Met Pro Pro Asn Phe Ile Pro Asn
        275                 280                 285

Gly His Gln Met Ala Gln His Asp Val Tyr Trp Gly Gly Pro Pro Pro
    290                 295                 300

Arg Ala Pro Pro Ser Tyr
305                 310

<210> SEQ ID NO 123
<211> LENGTH: 964
<212> TYPE: PRT
<213> ORGANISM: Arabidopsis thaliana

<400> SEQUENCE: 123

Met Ala Leu Asn Leu Arg Gln Lys Gln Thr Glu Cys Val Ile Arg Met
1               5                   10                  15

Leu Asn Leu Asn Gln Pro Leu Asn Pro Ser Gly Thr Ala Asn Glu Glu
            20                  25                  30

Val Tyr Lys Ile Leu Ile Tyr Asp Arg Phe Cys Gln Asn Ile Leu Ser
        35                  40                  45

-continued

Pro Leu Thr His Val Lys Asp Leu Arg Lys His Gly Val Thr Leu Phe
            50                  55                  60

Phe Leu Ile Asp Lys Asp Arg Gln Pro Val His Asp Val Pro Ala Val
 65                  70                  75                  80

Tyr Phe Val Gln Pro Thr Glu Ser Asn Leu Gln Arg Ile Ile Ala Asp
                85                  90                  95

Ala Ser Arg Ser Leu Tyr Asp Thr Phe His Leu Asn Phe Ser Ser Ser
            100                 105                 110

Ile Pro Arg Lys Phe Leu Glu Glu Leu Ala Ser Gly Thr Leu Lys Ser
            115                 120                 125

Gly Ser Val Glu Lys Val Ser Lys Val His Asp Gln Tyr Leu Glu Phe
            130                 135                 140

Val Thr Leu Glu Asp Asn Leu Phe Ser Leu Ala Gln Gln Ser Thr Tyr
145                 150                 155                 160

Val Gln Met Asn Asp Pro Ser Ala Gly Glu Lys Glu Ile Asn Glu Ile
                165                 170                 175

Ile Glu Arg Val Ala Ser Gly Leu Phe Cys Val Leu Val Thr Leu Gly
            180                 185                 190

Val Val Pro Val Ile Arg Cys Pro Ser Gly Gly Pro Ala Glu Met Val
            195                 200                 205

Ala Ser Leu Leu Asp Gln Lys Leu Arg Asp His Leu Leu Ser Lys Asn
210                 215                 220

Asn Leu Phe Thr Glu Gly Gly Phe Met Ser Ser Phe Gln Arg Pro
225                 230                 235                 240

Leu Leu Cys Ile Phe Asp Arg Asn Phe Glu Leu Ser Val Gly Ile Gln
                245                 250                 255

His Asp Phe Arg Tyr Arg Pro Leu Val His Asp Val Leu Gly Leu Lys
            260                 265                 270

Leu Asn Gln Leu Lys Val Gln Gly Glu Lys Gly Pro Pro Lys Ser Phe
            275                 280                 285

Glu Leu Asp Ser Ser Asp Pro Phe Trp Ser Ala Asn Ser Thr Leu Glu
290                 295                 300

Phe Pro Asp Val Ala Val Glu Ile Glu Thr Gln Leu Asn Lys Tyr Lys
305                 310                 315                 320

Arg Asp Val Glu Glu Val Asn Lys Lys Thr Gly Gly Ser Gly Ala
                325                 330                 335

Glu Phe Asp Gly Thr Asp Leu Ile Gly Asn Ile His Thr Glu His Leu
            340                 345                 350

Met Asn Thr Val Lys Ser Leu Pro Glu Leu Thr Glu Arg Lys Lys Val
            355                 360                 365

Ile Asp Lys His Thr Asn Ile Ala Thr Ala Leu Leu Gly Gln Ile Lys
            370                 375                 380

Glu Arg Ser Ile Asp Ala Phe Thr Lys Lys Glu Ser Asp Met Met Met
385                 390                 395                 400

Arg Gly Gly Ile Asp Arg Thr Glu Leu Met Ala Ala Leu Lys Gly Lys
                405                 410                 415

Gly Thr Lys Met Asp Lys Leu Arg Phe Ala Ile Met Tyr Leu Ile Ser
            420                 425                 430

Thr Glu Thr Ile Asn Gln Ser Glu Val Glu Ala Val Glu Ala Ala Leu
            435                 440                 445

Asn Glu Ala Glu Ala Asp Thr Ser Ala Phe Gln Tyr Val Lys Lys Ile
450                 455                 460

Lys Ser Leu Asn Ala Ser Phe Ala Ala Thr Ser Ala Asn Ser Ala Ser

-continued

```
            465                 470                 475                 480
        Arg Ser Asn Ile Val Asp Trp Ala Glu Lys Leu Tyr Gly Gln Ser Ile
                        485                 490                 495
        Ser Ala Val Thr Ala Gly Val Lys Asn Leu Leu Ser Ser Asp Gln Gln
                        500                 505                 510
        Leu Ala Val Thr Arg Thr Val Glu Ala Leu Thr Glu Gly Lys Pro Asn
                        515                 520                 525
        Pro Glu Ile Asp Ser Tyr Arg Phe Leu Asp Pro Arg Ala Pro Lys Ser
                        530                 535                 540
        Ser Ser Ser Gly Gly Ser His Val Lys Gly Pro Phe Arg Glu Ala Ile
        545                 550                 555                 560
        Val Phe Met Ile Gly Gly Gly Asn Tyr Val Glu Tyr Gly Ser Leu Gln
                        565                 570                 575
        Glu Leu Thr Gln Arg Gln Leu Thr Val Lys Asn Val Ile Tyr Gly Ala
                        580                 585                 590
        Thr Glu Ile Leu Asn Gly Gly Glu Leu Val Gln Leu Gly Leu Leu
                        595                 600                 605
        Gly Lys Lys Met Gly Leu Gly Gly Pro Val Ala Ser Thr Leu Lys Arg
                        610                 615                 620
        Leu Gly Met Ala Gly Lys Glu Glu Thr Asp Val Ser Ala Gln Gly Ser
        625                 630                 635                 640
        Leu Thr Arg Glu Ala Thr Glu Ile Trp Arg Ser Glu Leu Glu Ser Arg
                        645                 650                 655
        Arg Phe Gln Val Asp Ser Leu Glu Ala Glu Leu Val Asp Val Lys Ala
                        660                 665                 670
        Tyr Leu Glu Phe Gly Ser Glu Asp Ala Arg Lys Glu Leu Gly Val
                        675                 680                 685
        Leu Ser Gly Arg Val Arg Ser Thr Ala Thr Met Leu Arg Tyr Leu Arg
                        690                 695                 700
        Ser Lys Ala Arg Val Leu Ala Ile Pro Asp Asp Leu Ala Asn Val Ser
        705                 710                 715                 720
        Cys Gly Val Glu Gln Ile Glu Glu Leu Lys Gly Leu Asn Leu Val Glu
                        725                 730                 735
        Lys Asp Gly Gly Ser Ser Ser Asp Gly Ala Arg Asn Thr Asn Pro
                        740                 745                 750
        Glu Thr Arg Arg Tyr Ser Gly Ser Leu Gly Val Glu Asp Gly Ala Tyr
                        755                 760                 765
        Thr Asn Glu Met Leu Gln Ser Ile Glu Met Val Thr Asp Val Leu Asp
                        770                 775                 780
        Ser Leu Val Arg Arg Val Thr Val Ala Glu Ser Glu Ser Ala Val Gln
        785                 790                 795                 800
        Lys Glu Arg Ala Leu Leu Gly Glu Glu Ile Ser Arg Lys Thr Ile
                        805                 810                 815
        Gln Ile Glu Asn Leu Ser Val Lys Leu Glu Glu Met Glu Arg Phe Ala
                        820                 825                 830
        Tyr Gly Thr Asn Ser Val Leu Asn Glu Met Arg Glu Arg Ile Glu Glu
                        835                 840                 845
        Leu Val Glu Glu Thr Met Arg Gln Arg Glu Lys Ala Val Glu Asn Glu
                        850                 855                 860
        Glu Glu Leu Cys Arg Val Lys Arg Glu Phe Glu Ser Leu Lys Ser Tyr
        865                 870                 875                 880
        Val Ser Thr Phe Thr Asn Val Arg Glu Thr Leu Leu Ser Glu Arg
                        885                 890                 895
```

```
Gln Phe Lys Thr Ile Glu Glu Leu Phe Glu Arg Leu Val Thr Lys Thr
                900                 905                 910

Thr Gln Leu Glu Gly Glu Lys Ala Gln Lys Glu Val Glu Val Gln Lys
            915                 920                 925

Leu Met Glu Glu Asn Val Lys Leu Thr Ala Leu Leu Asp Lys Lys Glu
        930                 935                 940

Ala Gln Leu Leu Ala Leu Asn Glu Gln Cys Lys Val Met Ala Leu Ser
945                 950                 955                 960

Ala Ser Asn Ile

<210> SEQ ID NO 124
<211> LENGTH: 222
<212> TYPE: PRT
<213> ORGANISM: Arabidopsis thaliana

<400> SEQUENCE: 124

Met Asp Ala Met Lys Glu Glu Ile Gln Arg Val Lys Glu Gln Glu Glu
  1               5                  10                  15

Gln Ala Met Arg Glu Ala Leu Gly Leu Ala Pro Lys Ser Ser Thr Arg
             20                  25                  30

Pro Gln Gly Asn Arg Leu Asp Lys Gln Glu Phe Thr Glu Leu Val Lys
         35                  40                  45

Arg Gly Ser Thr Ala Glu Asp Leu Gly Ala Gly Asn Ala Asp Ala Val
     50                  55                  60

Trp Val His Gly Leu Gly Tyr Ala Lys Ala Pro Arg Pro Trp Glu Asp
 65                  70                  75                  80

Pro Ser Thr Leu Ala Ser Ser Gln Lys Glu Asp Ala Asp Ser Ala Arg
                 85                  90                  95

Leu Pro Ala Asp Thr Ser Gly Val Lys Thr Val Glu Asp Gly Pro Asp
            100                 105                 110

Asp Val Glu Arg Asp Gln Arg Arg Ile Gly Val Arg Lys Gly Asn Leu
        115                 120                 125

Gln Arg Glu Arg Arg Lys Lys Asp Met Ile Gly Val Lys Asn Ala Lys
    130                 135                 140

Gly Met Arg Ser Glu Ala Leu Val Ile Gln Met Ile Glu Arg Ser Thr
145                 150                 155                 160

Arg Lys Arg Arg Arg Lys Lys Glu Gly Met Thr Leu Ile Leu Ile
                165                 170                 175

Glu Ala Asn Cys Pro Arg Met Glu His Phe Ala Leu Gln Arg Lys Ser
            180                 185                 190

Gly Arg Leu Gly Thr Lys Ile Gln Leu Pro Leu Leu Gln Asp Leu Asn
        195                 200                 205

Leu Leu Leu Ile Ser Phe Thr Asn Arg Gly Val Lys Cys Cys
    210                 215                 220

<210> SEQ ID NO 125
<211> LENGTH: 148
<212> TYPE: PRT
<213> ORGANISM: Arabidopsis thaliana

<400> SEQUENCE: 125

Met Gly Lys Asp Gly Leu Ser Asp Asp Gln Val Ser Ser Met Lys Glu
  1               5                  10                  15

Ala Phe Met Leu Phe Asp Thr Asp Gly Asp Gly Lys Ile Ala Pro Ser
             20                  25                  30

Glu Leu Gly Ile Leu Met Arg Ser Leu Gly Gly Asn Pro Thr Gln Ala
         35                  40                  45
```

```
Gln Leu Lys Ser Ile Ile Ala Ser Glu Asn Leu Ser Ser Pro Phe Asp
         50                  55                  60

Phe Asn Arg Phe Leu Asp Leu Met Ala Lys His Leu Lys Thr Glu Pro
 65                  70                  75                  80

Phe Asp Arg Gln Leu Arg Asp Ala Phe Lys Val Leu Asp Lys Glu Gly
                 85                  90                  95

Thr Gly Phe Val Ala Val Ala Asp Leu Arg His Ile Leu Thr Ser Ile
            100                 105                 110

Gly Glu Lys Leu Glu Pro Asn Glu Phe Asp Glu Trp Ile Lys Glu Val
        115                 120                 125

Asp Val Gly Ser Asp Gly Lys Ile Arg Tyr Glu Asp Phe Ile Ala Arg
130                 135                 140

Met Val Ala Lys
145

<210> SEQ ID NO 126
<211> LENGTH: 70
<212> TYPE: PRT
<213> ORGANISM: Arabidopsis thaliana

<400> SEQUENCE: 126

Met Glu Lys Gln Ser Thr Gln Pro Ile Cys Gly Gln Glu Ala Leu Gln
 1               5                  10                  15

Leu Leu Asn Cys Val Ala Glu Ser Pro Phe Asp Gln Glu Lys Cys Val
                20                  25                  30

Arg Phe Leu Gln Ser Leu Arg Glu Cys Val Leu Ser Lys Lys Val Lys
             35                  40                  45

Lys Phe Ser Ile Pro Ser Gln Asp His Asp Ser Glu Gly Ala Ala Ser
         50                  55                  60

Ala Thr Lys Arg Pro Ser
 65                  70

<210> SEQ ID NO 127
<211> LENGTH: 385
<212> TYPE: PRT
<213> ORGANISM: Arabidopsis thaliana

<400> SEQUENCE: 127

Met Thr Thr Thr Gly Ser Asn Ser Asn His Asn His His Glu Ser Asn
 1               5                  10                  15

Asn Asn Asn Asn Asn Pro Ser Thr Arg Ser Trp Gly Thr Ala Val Ser
                20                  25                  30

Gly Gln Ser Val Ser Thr Ser Gly Ser Met Gly Ser Pro Ser Ser Arg
             35                  40                  45

Ser Glu Gln Thr Ile Thr Val Val Thr Ser Thr Ser Asp Thr Thr Phe
         50                  55                  60

Gln Arg Leu Asn Asn Leu Asp Ile Gln Gly Asp Ala Gly Ser Gln
 65                  70                  75                  80

Gly Ala Ser Gly Val Lys Lys Lys Arg Gly Gln Arg Ala Ala Gly
                 85                  90                  95

Pro Asp Lys Thr Gly Arg Gly Leu Arg Gln Phe Ser Met Lys Val Cys
            100                 105                 110

Glu Lys Val Glu Ser Lys Gly Arg Thr Thr Tyr Asn Glu Val Ala Asp
        115                 120                 125

Glu Leu Val Ala Glu Phe Ala Leu Pro Asn Asn Asp Gly Thr Ser Pro
130                 135                 140
```

```
Asp Gln Gln Gln Tyr Asp Glu Lys Asn Ile Arg Arg Val Tyr Asp
145                 150                 155                 160

Ala Leu Asn Val Leu Met Ala Met Asp Ile Ile Ser Lys Asp Lys Lys
            165                 170                 175

Glu Ile Gln Trp Arg Gly Leu Pro Arg Thr Ser Leu Ser Asp Ile Glu
        180                 185                 190

Glu Leu Lys Asn Glu Arg Leu Ser Leu Arg Asn Arg Ile Glu Lys Lys
    195                 200                 205

Thr Ala Tyr Ser Gln Glu Leu Glu Glu Gln Tyr Val Gly Leu Gln Asn
210                 215                 220

Leu Ile Gln Arg Asn Glu His Leu Tyr Ser Ser Gly Asn Ala Pro Ser
225                 230                 235                 240

Gly Gly Val Ala Leu Pro Phe Ile Leu Val Gln Thr Arg Pro His Ala
            245                 250                 255

Thr Val Glu Val Glu Ile Ser Glu Asp Met Gln Leu Val His Phe Asp
        260                 265                 270

Phe Asn Ser Thr Pro Phe Glu Leu His Asp Asp Asn Phe Val Leu Lys
    275                 280                 285

Thr Met Lys Phe Cys Asp Gln Pro Gln Gln Pro Asn Gly Arg Asn
290                 295                 300

Asn Ser Gln Leu Val Cys His Asn Phe Thr Pro Glu Asn Pro Asn Lys
305                 310                 315                 320

Gly Pro Ser Thr Gly Pro Thr Pro Gln Leu Asp Met Tyr Glu Thr His
            325                 330                 335

Leu Gln Ser Gln Gln His Gln Gln His Ser Gln Leu Gln Ile Ile Pro
        340                 345                 350

Met Pro Glu Thr Asn Asn Val Thr Ser Ser Ala Asp Thr Ala Pro Val
    355                 360                 365

Lys Ser Pro Ser Leu Pro Gly Ile Met Asn Ser Ser Met Lys Pro Glu
370                 375                 380

Asn
385

<210> SEQ ID NO 128
<211> LENGTH: 437
<212> TYPE: PRT
<213> ORGANISM: Arabidopsis thaliana

<400> SEQUENCE: 128

Met Ala Leu Gln Asn Ile Gly Ala Ser Asn Arg Asn Asp Ala Phe Tyr
1               5                   10                  15

Arg Tyr Lys Met Pro Lys Met Val Thr Lys Thr Glu Gly Lys Gly Asn
            20                  25                  30

Gly Ile Lys Thr Asn Ile Ile Asn Asn Val Glu Ile Ala Lys Ala Leu
        35                  40                  45

Ala Arg Pro Pro Ser Tyr Thr Thr Lys Tyr Phe Gly Cys Glu Leu Gly
    50                  55                  60

Ala Gln Ser Lys Phe Asp Glu Lys Thr Gly Thr Ser Leu Val Asn Gly
65                  70                  75                  80

Ala His Asn Thr Ser Lys Leu Ala Gly Leu Leu Glu Asn Phe Ile Lys
            85                  90                  95

Lys Phe Val Gln Cys Tyr Gly Cys Gly Asn Pro Glu Thr Glu Ile Ile
        100                 105                 110

Ile Thr Lys Thr Gln Met Val Asn Leu Lys Cys Ala Ala Cys Gly Phe
    115                 120                 125
```

```
Ile Ser Glu Val Asp Met Arg Asp Lys Leu Thr Asn Phe Ile Leu Lys
    130                 135                 140

Asn Pro Pro Glu Gln Lys Lys Val Ser Lys Asp Lys Lys Ala Met Arg
145                 150                 155                 160

Lys Ala Glu Lys Glu Arg Leu Lys Glu Gly Glu Leu Ala Asp Glu Glu
                165                 170                 175

Gln Arg Lys Leu Lys Ala Lys Lys Ala Leu Ser Asn Gly Lys Asp
        180                 185                 190

Ser Lys Thr Ser Lys Asn His Ser Ser Asp Glu Asp Ile Ser Pro Lys
        195                 200                 205

His Asp Glu Asn Ala Leu Glu Val Asp Glu Asp Glu Asp Asp Asp
    210                 215                 220

Gly Val Glu Trp Gln Thr Asp Thr Ser Arg Glu Ala Ala Glu Lys Arg
225                 230                 235                 240

Met Met Glu Gln Leu Ser Ala Lys Thr Ala Glu Met Val Met Leu Ser
                245                 250                 255

Ala Met Glu Val Glu Lys Lys Ala Pro Lys Ser Lys Ser Asn Gly
        260                 265                 270

Asn Val Val Lys Thr Glu Asn Pro Pro Gln Glu Lys Asn Leu Val
        275                 280                 285

Gln Asp Met Lys Glu Tyr Leu Lys Lys Gly Ser Pro Ile Ser Ala Leu
    290                 295                 300

Lys Ser Phe Ile Ser Ser Leu Ser Glu Pro Pro Gln Asp Ile Met Asp
305                 310                 315                 320

Ala Leu Phe Asn Ala Leu Phe Asp Gly Val Gly Lys Gly Phe Ala Lys
                325                 330                 335

Glu Val Thr Lys Lys Lys Asn Tyr Leu Ala Ala Ala Thr Met Gln
        340                 345                 350

Glu Asp Gly Ser Gln Met His Leu Leu Asn Ser Ile Gly Thr Phe Cys
    355                 360                 365

Gly Lys Asn Gly Asn Glu Glu Ala Leu Lys Glu Val Ala Leu Val Leu
    370                 375                 380

Lys Ala Leu Tyr Asp Gln Asp Ile Ile Glu Glu Glu Val Val Leu Asp
385                 390                 395                 400

Trp Tyr Glu Lys Gly Leu Thr Gly Ala Asp Lys Ser Ser Pro Val Trp
                405                 410                 415

Lys Asn Val Lys Pro Phe Val Glu Trp Leu Gln Ser Ala Glu Ser Glu
        420                 425                 430

Ser Glu Glu Glu Asp
        435

<210> SEQ ID NO 129
<211> LENGTH: 749
<212> TYPE: PRT
<213> ORGANISM: Arabidopsis thaliana

<400> SEQUENCE: 129

Met Ala Ala Asn Lys Phe Ala Thr Leu Ile His Arg Lys Thr Asn Arg
1               5                   10                  15

Ile Thr Leu Ile Leu Val Tyr Ala Phe Leu Glu Trp Ser Leu Ile Phe
            20                  25                  30

Phe Ile Leu Leu Asn Ser Leu Phe Ser Tyr Phe Ile Leu Arg Phe Ala
        35                  40                  45

Asp Tyr Phe Gly Leu Lys Arg Pro Cys Leu Phe Cys Ser Arg Leu Asp
    50                  55                  60
```

```
Arg Phe Phe Asp Ala Ser Gly Lys Ser Pro Ser His Arg Asp Leu Leu
 65                  70                  75                  80

Cys Asp Asp His Ala Leu Gln Leu His Ser Lys Pro Val Glu Glu Ser
                 85                  90                  95

Asn Cys Gly Phe Gly Glu Phe His Asn Asp Leu Val His Arg Gly Cys
                100                 105                 110

Cys Val Glu Lys Ile Ser Ser Ser Leu Cys Ala Pro Ile Glu Ser Asp
            115                 120                 125

Phe Gly Asn Leu Asp Tyr Pro Ile Gly Asp Glu Gly Gln Ile Tyr Asn
            130                 135                 140

Gly Leu Lys Phe Pro Arg Ser Ile Phe Val Phe Glu Glu Glu Lys Val
145                 150                 155                 160

Gly Ser Val Asn Leu Asn Asp Ser Gln Glu Glu Thr Glu Glu Lys Lys
                165                 170                 175

Val Pro Gln Ser His Glu Lys Leu Glu Asp Asp Val Asp Glu Glu
                180                 185                 190

Phe Ser Cys Tyr Val Ser Ser Phe Asp Cys Lys Asn Lys Glu Ile Ala
            195                 200                 205

Thr Glu Lys Glu Glu Asn Arg Val Asp Leu Pro Ile Glu Val Glu
            210                 215                 220

Thr Ala Glu Ser Ala Pro Lys Asn Leu Glu Phe Tyr Ile Asp Glu Glu
225                 230                 235                 240

Asp Cys His Leu Ile Pro Val Glu Phe Tyr Lys Pro Ser Glu Glu Val
                245                 250                 255

Arg Glu Ile Ser Asp Ile Asn Gly Asp Phe Ile Leu Asp Phe Gly Val
            260                 265                 270

Glu His Asp Phe Thr Ala Ala Ala Glu Thr Glu Glu Ile Ser Asp Phe
            275                 280                 285

Ala Ser Pro Gly Glu Ser Lys Pro Glu Asp Ala Glu Thr Asn Leu Val
290                 295                 300

Ala Ser Glu Met Glu Asn Asp Asp Glu Glu Thr Asp Ala Glu Val Ser
305                 310                 315                 320

Ile Gly Thr Glu Ile Pro Asp His Glu Gln Ile Gly Asp Ile Pro Ser
                325                 330                 335

His Gln Leu Ile Pro His His Asp Asp Asp Asp His Glu Glu Glu Thr
                340                 345                 350

Leu Glu Phe Lys Thr Val Thr Ile Glu Thr Lys Met Pro Val Leu Asn
                355                 360                 365

Ile Asn Glu Glu Arg Ile Leu Glu Ala Gln Gly Ser Met Glu Ser Ser
                370                 375                 380

His Ser Ser Leu His Asn Ala Met Phe His Leu Glu Gln Arg Val Ser
385                 390                 395                 400

Val Asp Gly Ile Glu Cys Pro Glu Gly Val Leu Thr Val Asp Lys Leu
                405                 410                 415

Lys Phe Glu Leu Gln Glu Glu Arg Lys Ala Leu His Ala Leu Tyr Glu
                420                 425                 430

Glu Leu Glu Val Glu Arg Asn Ala Ser Ala Val Ala Ala Ser Glu Thr
                435                 440                 445

Met Ala Met Ile Asn Arg Leu His Glu Glu Lys Ala Ala Met Gln Met
450                 455                 460

Glu Ala Leu Gln Tyr Gln Arg Met Met Glu Glu Gln Ala Glu Phe Asp
465                 470                 475                 480

Gln Glu Ala Leu Gln Leu Leu Asn Glu Leu Met Val Asn Arg Glu Lys
                485                 490                 495
```

-continued

```
Glu Asn Ala Glu Leu Glu Lys Glu Leu Glu Val Tyr Arg Lys Arg Met
                500                 505                 510

Glu Glu Tyr Glu Ala Lys Glu Lys Met Gly Met Leu Arg Arg Arg Leu
            515                 520                 525

Arg Asp Ser Ser Val Asp Ser Tyr Arg Asn Asn Gly Asp Ser Asp Glu
        530                 535                 540

Asn Ser Asn Gly Glu Leu Gln Phe Lys Asn Val Glu Gly Val Thr Asp
545                 550                 555                 560

Trp Lys Tyr Arg Glu Asn Glu Met Glu Asn Thr Pro Val Asp Val Val
                565                 570                 575

Leu Arg Leu Asp Glu Cys Leu Asp Asp Tyr Asp Gly Glu Arg Leu Ser
            580                 585                 590

Ile Leu Gly Arg Leu Lys Phe Leu Glu Glu Lys Leu Thr Asp Leu Asn
        595                 600                 605

Asn Glu Glu Asp Asp Glu Glu Ala Lys Thr Phe Glu Ser Asn Gly
610                 615                 620

Ser Ile Asn Gly Asn Glu His Ile His Gly Lys Glu Thr Asn Gly Lys
625                 630                 635                 640

His Arg Val Ile Lys Ser Lys Arg Leu Leu Pro Leu Phe Asp Ala Val
                645                 650                 655

Asp Gly Glu Met Glu Asn Gly Leu Ser Asn Gly Asn His His Glu Asn
            660                 665                 670

Gly Phe Asp Asp Ser Glu Lys Gly Glu Asn Val Thr Ile Glu Glu Glu
        675                 680                 685

Val Asp Glu Leu Tyr Glu Arg Leu Glu Ala Leu Glu Ala Asp Arg Glu
690                 695                 700

Phe Leu Arg His Cys Val Gly Ser Leu Lys Lys Gly Asp Lys Gly Val
705                 710                 715                 720

His Leu Leu His Glu Ile Leu Gln His Leu Arg Asp Leu Arg Asn Ile
                725                 730                 735

Asp Leu Thr Arg Val Arg Glu Asn Gly Asp Met Ser Leu
            740                 745

<210> SEQ ID NO 130
<211> LENGTH: 742
<212> TYPE: PRT
<213> ORGANISM: Arabidopsis thaliana

<400> SEQUENCE: 130

Met Ser Asp Ala Leu Ser Ala Ile Pro Ala Ala Val His Arg Asn Leu
1               5                   10                  15

Ser Asp Lys Leu Tyr Glu Lys Arg Lys Asn Ala Ala Leu Glu Leu Glu
                20                  25                  30

Asn Ile Val Lys Asn Leu Thr Ser Ser Gly Asp His Asp Lys Ile Ser
            35                  40                  45

Lys Val Ile Glu Met Leu Ile Lys Glu Phe Ala Lys Ser Pro Gln Ala
        50                  55                  60

Asn His Arg Lys Gly Gly Leu Ile Gly Leu Ala Ala Val Thr Val Gly
65                  70                  75                  80

Leu Ser Thr Glu Ala Ala Gln Tyr Leu Glu Gln Ile Val Pro Pro Val
                85                  90                  95

Ile Asn Ser Phe Ser Asp Gln Asp Ser Arg Val Arg Tyr Tyr Ala Cys
            100                 105                 110

Glu Ala Leu Tyr Asn Ile Ala Lys Val Val Arg Gly Asp Phe Ile Ile
        115                 120                 125
```

```
Phe Phe Asn Lys Ile Phe Asp Ala Leu Cys Lys Leu Ser Ala Asp Ser
    130                 135                 140

Asp Ala Asn Val Gln Ser Ala Ala His Leu Leu Asp Arg Leu Val Lys
145                 150                 155                 160

Asp Ile Val Thr Glu Ser Asp Gln Phe Ser Ile Glu Glu Phe Ile Pro
                165                 170                 175

Leu Leu Lys Glu Arg Met Asn Val Leu Asn Pro Tyr Val Arg Gln Phe
            180                 185                 190

Leu Val Gly Trp Ile Thr Val Leu Asp Ser Val Pro Asp Ile Asp Met
        195                 200                 205

Leu Gly Phe Leu Pro Asp Phe Leu Asp Gly Leu Phe Asn Met Leu Ser
    210                 215                 220

Asp Ser Ser His Glu Ile Arg Gln Gln Ala Asp Ser Ala Leu Ser Glu
225                 230                 235                 240

Phe Leu Gln Glu Ile Lys Asn Ser Pro Ser Val Asp Tyr Gly Arg Met
                245                 250                 255

Ala Glu Ile Leu Val Gln Arg Ala Ala Ser Pro Asp Glu Phe Thr Arg
            260                 265                 270

Leu Thr Ala Ile Thr Trp Ile Asn Glu Phe Val Lys Leu Gly Gly Asp
        275                 280                 285

Gln Leu Val Arg Tyr Tyr Ala Asp Ile Leu Gly Ala Ile Leu Pro Cys
    290                 295                 300

Ile Ser Asp Lys Glu Glu Lys Ile Arg Val Val Ala Arg Glu Thr Asn
305                 310                 315                 320

Glu Glu Leu Arg Ser Ile His Val Glu Pro Ser Asp Gly Phe Asp Val
                325                 330                 335

Gly Ala Ile Leu Ser Val Ala Arg Arg Gln Leu Ser Ser Glu Phe Glu
            340                 345                 350

Ala Thr Arg Ile Glu Ala Leu Asn Trp Ile Ser Thr Leu Leu Asn Lys
        355                 360                 365

His Arg Thr Glu Val Leu Cys Phe Leu Asn Asp Ile Phe Asp Thr Leu
    370                 375                 380

Leu Lys Ala Leu Ser Asp Ser Ser Asp Asp Val Val Leu Leu Val Leu
385                 390                 395                 400

Glu Val His Ala Gly Val Ala Lys Asp Pro Gln His Phe Arg Gln Leu
                405                 410                 415

Ile Val Phe Leu Val His Asn Phe Arg Ala Asp Asn Ser Leu Leu Glu
            420                 425                 430

Arg Gly Ala Leu Ile Val Arg Arg Met Cys Val Leu Leu Asp Ala Glu
        435                 440                 445

Arg Val Tyr Arg Glu Leu Ser Thr Ile Leu Glu Gly Glu Asp Asn Leu
    450                 455                 460

Asp Phe Ala Ser Thr Met Val Gln Ala Leu Asn Leu Ile Leu Leu Thr
465                 470                 475                 480

Ser Pro Glu Leu Ser Lys Leu Arg Glu Leu Lys Gly Ser Leu Val
                485                 490                 495

Asn Arg Glu Gly Lys Glu Leu Phe Val Ala Leu Tyr Thr Ser Trp Cys
            500                 505                 510

His Ser Pro Met Ala Ile Ser Leu Cys Leu Leu Ala Gln Ala Tyr
        515                 520                 525

Gln His Ala Ser Val Val Ile Gln Ser Leu Val Glu Glu Asp Ile Asn
    530                 535                 540

Val Lys Phe Leu Val Gln Leu Asp Lys Leu Ile Arg Leu Leu Glu Thr
```

```
                545                 550                 555                 560
Pro Ile Phe Thr Tyr Leu Arg Leu Gln Leu Leu Glu Pro Gly Arg Tyr
                    565                 570                 575
Thr Trp Leu Leu Lys Thr Leu Tyr Gly Leu Leu Met Leu Leu Pro Gln
                580                 585                 590
Gln Ser Ala Ala Phe Lys Ile Leu Arg Thr Arg Leu Lys Thr Val Pro
                    595                 600                 605
Thr Tyr Ser Phe Ser Thr Gly Asn Gln Ile Gly Arg Ala Thr Ser Gly
                610                 615                 620
Val Pro Phe Ser Gln Tyr Lys His Gln Asn Glu Asp Gly Asp Leu Glu
625                 630                 635                 640
Asp Asp Asn Ile Asn Ser Ser His Gln Gly Ile Asn Phe Ala Val Arg
                    645                 650                 655
Leu Gln Gln Phe Glu Asn Val Gln Asn Leu His Arg Gly Gln Ala Arg
                660                 665                 670
Thr Arg Val Asn Tyr Ser Tyr His Ser Ser Ser Ser Thr Ser Lys
                    675                 680                 685
Glu Val Arg Arg Ser Glu Glu Gln Gln Gln Gln Gln Gln Gln Gln
            690                 695                 700
Gln Gln Gln Gln Gln Gln Arg Pro Pro Ser Ser Thr Ser Ser
705                 710                 715                 720
Ser Val Ala Asp Asn Asn Arg Pro Pro Ser Arg Thr Ser Arg Lys Gly
                    725                 730                 735
Pro Gly Gln Leu Gln Leu
            740

<210> SEQ ID NO 131
<211> LENGTH: 911
<212> TYPE: PRT
<213> ORGANISM: Arabidopsis thaliana

<400> SEQUENCE: 131

Met Ser Leu Leu Phe Leu Asn Pro Pro Phe Pro Ser Asn Ser Ile His
1               5                   10                  15
Pro Ile Pro Arg Arg Ala Ala Gly Ile Ser Ser Ile Arg Cys Ser Ile
                20                  25                  30
Ser Ala Pro Glu Lys Lys Pro Arg Arg Arg Lys Gln Lys Arg Gly
            35                  40                  45
Asp Gly Ala Glu Asn Asp Asp Ser Leu Ser Phe Gly Ser Gly Glu Ala
    50                  55                  60
Val Ser Ala Leu Glu Arg Ser Leu Arg Leu Thr Phe Met Asp Glu Leu
65                  70                  75                  80
Met Glu Arg Ala Arg Asn Arg Asp Thr Ser Gly Val Ser Glu Val Ile
                85                  90                  95
Tyr Asp Met Ile Ala Ala Gly Leu Ser Pro Gly Pro Arg Ser Phe His
                100                 105                 110
Gly Leu Val Val Ala His Ala Leu Asn Gly Asp Glu Gln Gly Ala Met
            115                 120                 125
His Ser Leu Arg Lys Glu Leu Gly Ala Gly Gln Arg Pro Leu Pro Glu
    130                 135                 140
Thr Met Ile Ala Leu Val Arg Leu Ser Gly Ser Lys Gly Asn Ala Thr
145                 150                 155                 160
Arg Gly Leu Glu Ile Leu Ala Ala Met Glu Lys Leu Lys Tyr Asp Ile
                165                 170                 175
Arg Gln Ala Trp Leu Ile Leu Val Glu Glu Leu Met Arg Ile Asn His
```

```
                    180                 185                 190
Leu Glu Asp Ala Asn Lys Val Phe Leu Lys Gly Ala Arg Gly Gly Met
            195                 200                 205
Arg Ala Thr Asp Gln Leu Tyr Asp Leu Met Ile Glu Glu Asp Cys Lys
            210                 215                 220
Ala Gly Asp His Ser Asn Ala Leu Asp Ile Ser Tyr Glu Met Glu Ala
225                 230                 235                 240
Ala Gly Arg Met Ala Thr Thr Phe His Phe Asn Cys Leu Leu Ser Val
            245                 250                 255
Gln Ala Thr Cys Gly Ile Pro Glu Val Ala Tyr Ala Thr Phe Glu Asn
            260                 265                 270
Met Glu Tyr Gly Glu Gly Leu Phe Met Lys Pro Asp Thr Glu Thr Tyr
            275                 280                 285
Asn Trp Val Ile Gln Ala Tyr Thr Arg Ala Glu Ser Tyr Asp Arg Val
            290                 295                 300
Gln Asp Val Ala Glu Leu Leu Gly Met Met Val Glu Asp His Lys Arg
305                 310                 315                 320
Val Gln Pro Asn Val Lys Thr Tyr Ala Leu Leu Val Glu Cys Phe Thr
            325                 330                 335
Lys Tyr Cys Val Val Lys Glu Ala Ile Arg His Phe Arg Ala Leu Lys
            340                 345                 350
Asn Phe Glu Gly Gly Thr Val Ile Leu His Asn Ala Gly Asn Phe Glu
            355                 360                 365
Asp Pro Leu Ser Leu Tyr Leu Arg Ala Leu Cys Arg Glu Gly Arg Ile
            370                 375                 380
Val Glu Leu Ile Asp Ala Leu Asp Ala Met Arg Lys Asp Asn Gln Pro
385                 390                 395                 400
Ile Pro Pro Arg Ala Met Ile Met Ser Arg Lys Tyr Arg Thr Leu Val
            405                 410                 415
Ser Ser Trp Ile Glu Pro Leu Gln Glu Glu Ala Glu Leu Gly Tyr Glu
            420                 425                 430
Ile Asp Tyr Leu Ala Arg Tyr Ile Glu Glu Gly Gly Leu Thr Gly Glu
            435                 440                 445
Arg Lys Arg Trp Val Pro Arg Arg Gly Lys Thr Pro Leu Asp Pro Asp
450                 455                 460
Ala Ser Gly Phe Ile Tyr Ser Asn Pro Ile Glu Thr Ser Phe Lys Gln
465                 470                 475                 480
Arg Cys Leu Glu Asp Trp Lys Val His His Arg Lys Leu Leu Arg Thr
            485                 490                 495
Leu Gln Ser Glu Gly Leu Pro Val Leu Gly Asp Ala Ser Glu Ser Asp
            500                 505                 510
Tyr Met Arg Val Val Glu Arg Leu Arg Asn Ile Ile Lys Gly Pro Ala
            515                 520                 525
Leu Asn Leu Leu Lys Pro Lys Ala Ala Ser Lys Met Val Val Ser Glu
            530                 535                 540
Leu Lys Glu Glu Leu Glu Ala Gln Gly Leu Pro Ile Asp Gly Thr Arg
545                 550                 555                 560
Asn Val Leu Tyr Gln Arg Val Gln Lys Ala Arg Arg Ile Asn Lys Ser
            565                 570                 575
Arg Gly Arg Pro Leu Trp Val Pro Pro Ile Glu Glu Glu Glu Glu Glu
            580                 585                 590
Val Asp Glu Glu Val Asp Asp Leu Ile Cys Arg Ile Lys Leu His Glu
            595                 600                 605
```

```
Gly Asp Thr Glu Phe Trp Lys Arg Arg Phe Leu Gly Glu Gly Leu Ile
            610                 615                 620

Glu Thr Ser Val Glu Ser Lys Glu Thr Thr Glu Ser Val Val Thr Gly
625                 630                 635                 640

Glu Ser Glu Lys Ala Ile Glu Asp Ile Ser Lys Glu Ala Asp Asn Glu
            645                 650                 655

Glu Asp Asp Glu Glu Gln Gly Asp Glu Asp Asp Glu
            660                 665                 670

Asn Glu Glu Glu Val Val Pro Glu Thr Glu Asn Arg Ala Glu
            675                 680                 685

Gly Glu Asp Leu Val Lys Asn Lys Ala Ala Asp Ala Lys Lys His Leu
            690                 695                 700

Gln Met Ile Gly Val Gln Leu Leu Lys Glu Ser Asp Glu Ala Asn Arg
705                 710                 715                 720

Thr Lys Lys Arg Gly Lys Arg Ala Ser Arg Met Thr Leu Glu Asp Asp
            725                 730                 735

Ala Asp Glu Asp Trp Phe Pro Glu Glu Pro Phe Glu Ala Phe Lys Glu
            740                 745                 750

Met Arg Glu Arg Lys Val Phe Asp Val Ala Asp Met Tyr Thr Ile Ala
            755                 760                 765

Asp Val Trp Gly Trp Thr Trp Glu Lys Asp Phe Lys Asn Lys Thr Pro
            770                 775                 780

Arg Lys Trp Ser Gln Glu Trp Glu Val Glu Leu Ala Ile Val Leu Met
785                 790                 795                 800

Thr Lys Val Ile Glu Leu Gly Gly Ile Pro Thr Ile Gly Asp Cys Ala
            805                 810                 815

Val Ile Leu Arg Ala Ala Leu Arg Ala Pro Met Pro Ser Ala Phe Leu
            820                 825                 830

Lys Ile Leu Gln Thr Thr His Ser Leu Gly Tyr Ser Phe Gly Ser Pro
            835                 840                 845

Leu Tyr Asp Glu Ile Ile Thr Leu Cys Leu Asp Leu Gly Glu Leu Asp
            850                 855                 860

Ala Ala Ile Ala Ile Val Ala Asp Met Glu Thr Thr Gly Ile Thr Val
865                 870                 875                 880

Pro Asp Gln Thr Leu Asp Lys Val Ile Ser Ala Arg Gln Ser Asn Glu
            885                 890                 895

Ser Pro Arg Ser Glu Pro Glu Pro Ala Ser Thr Val Ser Ser
            900                 905                 910

<210> SEQ ID NO 132
<211> LENGTH: 357
<212> TYPE: PRT
<213> ORGANISM: Arabidopsis thaliana

<400> SEQUENCE: 132

Met Glu Gly Ser Ser Ser Ala Ile Ala Arg Lys Thr Trp Glu Leu Glu
1               5                   10                  15

Asn Asn Ile Leu Pro Val Glu Pro Thr Asp Ser Ala Ser Asp Ser Ile
            20                  25                  30

Phe His Tyr Asp Asp Ala Ser Gln Ala Lys Ile Gln Gln Glu Lys Pro
        35                  40                  45

Trp Ala Ser Asp Pro Asn Tyr Phe Lys Arg Val His Ile Ser Ala Leu
    50                  55                  60

Ala Leu Leu Lys Met Val Val His Ala Arg Ser Gly Gly Thr Ile Glu
65                  70                  75                  80
```

```
Ile Met Gly Leu Met Gln Gly Lys Thr Glu Gly Asp Thr Ile Ile Val
                85                  90                  95

Met Asp Ala Phe Ala Leu Pro Val Glu Gly Thr Glu Thr Arg Val Asn
            100                 105                 110

Ala Gln Ser Asp Ala Tyr Glu Tyr Met Val Glu Tyr Ser Gln Thr Ser
        115                 120                 125

Lys Leu Ala Gly Arg Leu Glu Asn Val Val Gly Trp Tyr His Ser His
    130                 135                 140

Pro Gly Tyr Gly Cys Trp Leu Ser Gly Ile Asp Val Ser Thr Gln Met
145                 150                 155                 160

Leu Asn Gln Gln Tyr Gln Glu Pro Phe Leu Ala Val Val Ile Asp Pro
                165                 170                 175

Thr Arg Thr Val Ser Ala Gly Lys Val Glu Ile Gly Ala Phe Arg Thr
            180                 185                 190

Tyr Pro Glu Gly His Lys Ile Ser Asp Asp His Val Ser Glu Tyr Gln
        195                 200                 205

Thr Ile Pro Leu Asn Lys Ile Glu Asp Phe Gly Val His Cys Lys Gln
    210                 215                 220

Tyr Tyr Ser Leu Asp Ile Thr Tyr Phe Lys Ser Ser Leu Asp Ser His
225                 230                 235                 240

Leu Leu Asp Leu Leu Trp Asn Lys Tyr Trp Val Asn Thr Leu Ser Ser
                245                 250                 255

Ser Pro Leu Leu Gly Asn Gly Asp Tyr Val Ala Gly Gln Ile Ser Asp
            260                 265                 270

Leu Ala Glu Lys Leu Glu Gln Ala Glu Ser Gln Leu Ala Asn Ser Arg
        275                 280                 285

Tyr Gly Gly Ile Ala Pro Ala Gly His Gln Arg Arg Lys Glu Asp Glu
    290                 295                 300

Pro Gln Leu Ala Lys Ile Thr Arg Asp Ser Ala Lys Ile Thr Val Glu
305                 310                 315                 320

Gln Val His Gly Leu Met Ser Gln Val Ile Lys Asp Ile Leu Phe Asn
                325                 330                 335

Ser Ala Arg Gln Ser Lys Lys Ser Ala Asp Asp Ser Ser Asp Pro Glu
            340                 345                 350

Pro Met Ile Thr Ser
        355

<210> SEQ ID NO 133
<211> LENGTH: 57
<212> TYPE: DNA
<213> ORGANISM: artificial sequence
<220> FEATURE:
<223> OTHER INFORMATION: primer

<400> SEQUENCE: 133
ggggacaagt ttgtacaaaa aagcaggctt cacaatggtt agatcagatg aaaatag      57

<210> SEQ ID NO 134
<211> LENGTH: 54
<212> TYPE: DNA
<213> ORGANISM: artificial sequence
<220> FEATURE:
<223> OTHER INFORMATION: primer

<400> SEQUENCE: 134
ggggaccact ttgtacaaga aagctgggtt cttattaata ttaaatcaga aacc      54

<210> SEQ ID NO 135
```

```
<211> LENGTH: 52
<212> TYPE: DNA
<213> ORGANISM: artificial sequence
<220> FEATURE:
<223> OTHER INFORMATION: primer

<400> SEQUENCE: 135 gggacaagt ttgtacaaaa aagcaggctt cacaatggta aatccgggtc ac        52

<210> SEQ ID NO 136
<211> LENGTH: 51
<212> TYPE: DNA
<213> ORGANISM: artificial sequence
<220> FEATURE:
<223> OTHER INFORMATION: primer

<400> SEQUENCE: 136
ggggaccact ttgtacaaga aagctgggtt ttctgtagtc agacctggat a         51

<210> SEQ ID NO 137
<211> LENGTH: 55
<212> TYPE: DNA
<213> ORGANISM: artificial sequence
<220> FEATURE:
<223> OTHER INFORMATION: primer

<400> SEQUENCE: 137
ggggacaagt ttgtacaaaa aagcaggctt cacaatgggg aaggaaaatg ctgtg     55

<210> SEQ ID NO 138
<211> LENGTH: 54
<212> TYPE: DNA
<213> ORGANISM: artificial sequence
<220> FEATURE:
<223> OTHER INFORMATION: primer

<400> SEQUENCE: 138
ggggaccact ttgtacaaga aagctgggtc cttcagaata gcgtgtcaag tagc      54

<210> SEQ ID NO 139
<211> LENGTH: 54
<212> TYPE: DNA
<213> ORGANISM: artificial sequence
<220> FEATURE:
<223> OTHER INFORMATION: primer

<400> SEQUENCE: 139
ggggacaagt ttgtacaaaa aagcaggctt cacaatgggg aagaagtgtg attt      54

<210> SEQ ID NO 140
<211> LENGTH: 50
<212> TYPE: DNA
<213> ORGANISM: artificial sequence
<220> FEATURE:
<223> OTHER INFORMATION: primer

<400> SEQUENCE: 140
ggggaccact ttgtacaaga aagctgggtt gtgagttaaa caacaaccgt           50

<210> SEQ ID NO 141
<211> LENGTH: 55
<212> TYPE: DNA
<213> ORGANISM: artificial sequence
<220> FEATURE:
<223> OTHER INFORMATION: primer

<400> SEQUENCE: 141
```

```
ggggacaagt tgtacaaaa aagcaggctt cacaatggtt aactcatgcg agaac          55
```

<210> SEQ ID NO 142
<211> LENGTH: 52
<212> TYPE: DNA
<213> ORGANISM: artificial sequence
<220> FEATURE:
<223> OTHER INFORMATION: primer

<400> SEQUENCE: 142

```
ggggaccact ttgtacaaga aagctgggtt ggattaagaa tgatgagact ca           52
```

<210> SEQ ID NO 143
<211> LENGTH: 52
<212> TYPE: DNA
<213> ORGANISM: artificial sequence
<220> FEATURE:
<223> OTHER INFORMATION: primer

<400> SEQUENCE: 143

```
ggggacaagt tgtacaaaa aagcaggctt cacaatggcg aataatcctc cg            52
```

<210> SEQ ID NO 144
<211> LENGTH: 51
<212> TYPE: DNA
<213> ORGANISM: artificial sequence
<220> FEATURE:
<223> OTHER INFORMATION: primer

<400> SEQUENCE: 144

```
ggggaccact ttgtacaaga aagctgggtc actatcactc cccaacttct c            51
```

<210> SEQ ID NO 145
<211> LENGTH: 51
<212> TYPE: DNA
<213> ORGANISM: artificial sequence
<220> FEATURE:
<223> OTHER INFORMATION: primer

<400> SEQUENCE: 145

```
ggggacaagt tgtacaaaa aagcaggctt cacaatggag ggttcgtcgt c             51
```

<210> SEQ ID NO 146
<211> LENGTH: 49
<212> TYPE: DNA
<213> ORGANISM: artificial sequence
<220> FEATURE:
<223> OTHER INFORMATION: primer

<400> SEQUENCE: 146

```
ggggaccact ttgtacaaga aagctgggtc caaaagaaga gcaacttca              49
```

<210> SEQ ID NO 147
<211> LENGTH: 56
<212> TYPE: DNA
<213> ORGANISM: artificial sequence
<220> FEATURE:
<223> OTHER INFORMATION: primer

<400> SEQUENCE: 147

```
ggggacaagt tgtacaaaa aagcaggctt cacaatgtat tgctcttctt cgatgc        56
```

<210> SEQ ID NO 148
<211> LENGTH: 52
<212> TYPE: DNA
<213> ORGANISM: artificial sequence
<220> FEATURE:

<223> OTHER INFORMATION: primer

<400> SEQUENCE: 148
ggggaccact ttgtacaaga aagctgggtg cttggtgtca tcttgagaat ag                52

<210> SEQ ID NO 149
<211> LENGTH: 54
<212> TYPE: DNA
<213> ORGANISM: artificial sequence
<220> FEATURE:
<223> OTHER INFORMATION: primer

<400> SEQUENCE: 149
ggggacaagt tgtacaaaa aagcaggctt cacaatggca aagatgcaat tatc              54

<210> SEQ ID NO 150
<211> LENGTH: 50
<212> TYPE: DNA
<213> ORGANISM: artificial sequence
<220> FEATURE:
<223> OTHER INFORMATION: primer

<400> SEQUENCE: 150
ggggaccact ttgtacaaga aagctgggta accatctgat cacaagaaca                    50

<210> SEQ ID NO 151
<211> LENGTH: 58
<212> TYPE: DNA
<213> ORGANISM: artificial sequence
<220> FEATURE:
<223> OTHER INFORMATION: primer

<400> SEQUENCE: 151
ggggacaagt tgtacaaaa aagcaggctt cacaatggct atttcaaaag ctcttatc            58

<210> SEQ ID NO 152
<211> LENGTH: 48
<212> TYPE: DNA
<213> ORGANISM: artificial sequence
<220> FEATURE:
<223> OTHER INFORMATION: primer

<400> SEQUENCE: 152
ggggaccact ttgtacaaga aagctgggtg aggctagcgt agcactgg                     48

<210> SEQ ID NO 153
<211> LENGTH: 54
<212> TYPE: DNA
<213> ORGANISM: artificial sequence
<220> FEATURE:
<223> OTHER INFORMATION: primer

<400> SEQUENCE: 153
ggggacaagt tgtacaaaa aagcaggctt cacaatgggg aagaagaaca agag              54

<210> SEQ ID NO 154
<211> LENGTH: 51
<212> TYPE: DNA
<213> ORGANISM: artificial sequence
<220> FEATURE:
<223> OTHER INFORMATION: primer

<400> SEQUENCE: 154
ggggaccact ttgtacaaga aagctgggtg cttctttgac tcttttatc g                  51

<210> SEQ ID NO 155

```
<211> LENGTH: 55
<212> TYPE: DNA
<213> ORGANISM: artificial sequence
<220> FEATURE:
<223> OTHER INFORMATION: primer

<400> SEQUENCE: 155
ggggacaagt ttgtacaaaa aagcaggctt cacaatggaa ttgcttgaca tgaac         55

<210> SEQ ID NO 156
<211> LENGTH: 53
<212> TYPE: DNA
<213> ORGANISM: artificial sequence
<220> FEATURE:
<223> OTHER INFORMATION: primer

<400> SEQUENCE: 156
ggggaccact ttgtacaaga aagctgggtc aacattattc ttcttttctg gtc           53

<210> SEQ ID NO 157
<211> LENGTH: 54
<212> TYPE: DNA
<213> ORGANISM: artificial sequence
<220> FEATURE:
<223> OTHER INFORMATION: primer

<400> SEQUENCE: 157
ggggacaagt ttgtacaaaa aagcaggctt cacaatggac gagggagtta tagc          54

<210> SEQ ID NO 158
<211> LENGTH: 50
<212> TYPE: DNA
<213> ORGANISM: artificial sequence
<220> FEATURE:
<223> OTHER INFORMATION: primer

<400> SEQUENCE: 158
ggggaccact ttgtacaaga aagctgggtc cttagagaga ggacttttct               50

<210> SEQ ID NO 159
<211> LENGTH: 55
<212> TYPE: DNA
<213> ORGANISM: artificial sequence
<220> FEATURE:
<223> OTHER INFORMATION: primer

<400> SEQUENCE: 159
ggggacaagt ttgtacaaaa aagcaggctt cacaatggag ttgtttgtca ctcca         55

<210> SEQ ID NO 160
<211> LENGTH: 49
<212> TYPE: DNA
<213> ORGANISM: artificial sequence
<220> FEATURE:
<223> OTHER INFORMATION: primer

<400> SEQUENCE: 160
ggggaccact ttgtacaaga aagctgggtt cagcgagtat caatggatc                49

<210> SEQ ID NO 161
<211> LENGTH: 52
<212> TYPE: DNA
<213> ORGANISM: artificial sequence
<220> FEATURE:
<223> OTHER INFORMATION: primer

<400> SEQUENCE: 161
```

```
ggggacaagt tgtacaaaa aagcaggctt cacaatgcaa ccgacagaga cg          52

<210> SEQ ID NO 162
<211> LENGTH: 49
<212> TYPE: DNA
<213> ORGANISM: artificial sequence
<220> FEATURE:
<223> OTHER INFORMATION: primer

<400> SEQUENCE: 162
ggggaccact ttgtacaaga aagctgggtg ctcgtccaac actaaggtt             49

<210> SEQ ID NO 163
<211> LENGTH: 55
<212> TYPE: DNA
<213> ORGANISM: artificial sequence
<220> FEATURE:
<223> OTHER INFORMATION: primer

<400> SEQUENCE: 163
ggggacaagt ttgtacaaaa aagcaggctt cacaatgaat agggaaaagt tgatg      55

<210> SEQ ID NO 164
<211> LENGTH: 47
<212> TYPE: DNA
<213> ORGANISM: artificial sequence
<220> FEATURE:
<223> OTHER INFORMATION: primer

<400> SEQUENCE: 164
ggggaccact ttgtacaaga aagctgggtc ctctaagaag cagcagc               47

<210> SEQ ID NO 165
<211> LENGTH: 52
<212> TYPE: DNA
<213> ORGANISM: artificial sequence
<220> FEATURE:
<223> OTHER INFORMATION: primer

<400> SEQUENCE: 165
ggggacaagt ttgtacaaaa aagcaggctt cacaatggag gacgacgacg ag         52

<210> SEQ ID NO 166
<211> LENGTH: 50
<212> TYPE: DNA
<213> ORGANISM: artificial sequence
<220> FEATURE:
<223> OTHER INFORMATION: primer

<400> SEQUENCE: 166
ggggaccact ttgtacaaga aagctgggtt gtcagctact tacattgccg            50

<210> SEQ ID NO 167
<211> LENGTH: 51
<212> TYPE: DNA
<213> ORGANISM: artificial sequence
<220> FEATURE:
<223> OTHER INFORMATION: primer

<400> SEQUENCE: 167
ggggacaagt ttgtacaaaa aagcaggctt cacaatggcc accgtatctt c          51

<210> SEQ ID NO 168
<211> LENGTH: 48
<212> TYPE: DNA
<213> ORGANISM: artificial sequence
<220> FEATURE:
```

```
<223> OTHER INFORMATION: primer

<400> SEQUENCE: 168 gggggaccact ttgtacaaga aagctgggtg attagaaaac tgaaggcg            48

<210> SEQ ID NO 169
<211> LENGTH: 56
<212> TYPE: DNA
<213> ORGANISM: artificial sequence
<220> FEATURE:
<223> OTHER INFORMATION: primer

<400> SEQUENCE: 169
ggggacaagt ttgtacaaaa aagcaggctt cacaatggat gtaggagtta ctacgg      56

<210> SEQ ID NO 170
<211> LENGTH: 47
<212> TYPE: DNA
<213> ORGANISM: artificial sequence
<220> FEATURE:
<223> OTHER INFORMATION: primer

<400> SEQUENCE: 170
ggggaccact ttgtacaaga aagctgggtc taagccgagg cattgat                47

<210> SEQ ID NO 171
<211> LENGTH: 56
<212> TYPE: DNA
<213> ORGANISM: artificial sequence
<220> FEATURE:
<223> OTHER INFORMATION: primer

<400> SEQUENCE: 171
ggggacaagt ttgtacaaaa aagcaggctt cacaatggat ggtcatgatt ctaagg      56

<210> SEQ ID NO 172
<211> LENGTH: 49
<212> TYPE: DNA
<213> ORGANISM: artificial sequence
<220> FEATURE:
<223> OTHER INFORMATION: primer

<400> SEQUENCE: 172
ggggaccact ttgtacaaga aagctgggtt taagaggaac tagccggtg              49

<210> SEQ ID NO 173
<211> LENGTH: 52
<212> TYPE: DNA
<213> ORGANISM: artificial sequence
<220> FEATURE:
<223> OTHER INFORMATION: primer

<400> SEQUENCE: 173
ggggacaagt ttgtacaaaa aagcaggctt cacaatggaa atctacacca tg          52

<210> SEQ ID NO 174
<211> LENGTH: 51
<212> TYPE: DNA
<213> ORGANISM: artificial sequence
<220> FEATURE:
<223> OTHER INFORMATION: primer

<400> SEQUENCE: 174
ggggaccact ttgtacaaga aagctgggta actaaagaga actaagaaac t           51

<210> SEQ ID NO 175
```

```
<211> LENGTH: 53
<212> TYPE: DNA
<213> ORGANISM: artificial sequence
<220> FEATURE:
<223> OTHER INFORMATION: primer

<400> SEQUENCE: 175
ggggacaagt ttgtacaaaa aagcaggctt cacaatggag tttggatctt ttc        53

<210> SEQ ID NO 176
<211> LENGTH: 47
<212> TYPE: DNA
<213> ORGANISM: artificial sequence
<220> FEATURE:
<223> OTHER INFORMATION: primer

<400> SEQUENCE: 176
ggggaccact ttgtacaaga aagctgggtc tctcaagctt taaacgc                47

<210> SEQ ID NO 177
<211> LENGTH: 54
<212> TYPE: DNA
<213> ORGANISM: artificial sequence
<220> FEATURE:
<223> OTHER INFORMATION: primer

<400> SEQUENCE: 177
ggggacaagt ttgtacaaaa aagcaggctt cacaatggcg gagcagaaga gtac       54

<210> SEQ ID NO 178
<211> LENGTH: 54
<212> TYPE: DNA
<213> ORGANISM: artificial sequence
<220> FEATURE:
<223> OTHER INFORMATION: primer

<400> SEQUENCE: 178
ggggaccact ttgtacaaga aagctgggtc ctatcatgtc gattttgtat cttt       54

<210> SEQ ID NO 179
<211> LENGTH: 51
<212> TYPE: DNA
<213> ORGANISM: artificial sequence
<220> FEATURE:
<223> OTHER INFORMATION: primer

<400> SEQUENCE: 179
ggggacaagt ttgtacaaaa aagcaggctt cacaatggcg aatccttggt g          51

<210> SEQ ID NO 180
<211> LENGTH: 48
<212> TYPE: DNA
<213> ORGANISM: artificial sequence
<220> FEATURE:
<223> OTHER INFORMATION: primer

<400> SEQUENCE: 180
ggggaccact ttgtacaaga aagctgggtt caatacgaag gaggagca              48

<210> SEQ ID NO 181
<211> LENGTH: 53
<212> TYPE: DNA
<213> ORGANISM: artificial sequence
<220> FEATURE:
<223> OTHER INFORMATION: primer

<400> SEQUENCE: 181
```

```
gggacaagt ttgtacaaaa aagcaggctt cacaatggct ctcaatctcc gtc        53
```

<210> SEQ ID NO 182
<211> LENGTH: 54
<212> TYPE: DNA
<213> ORGANISM: artificial sequence
<220> FEATURE:
<223> OTHER INFORMATION: primer

<400> SEQUENCE: 182

```
ggggaccact ttgtacaaga aagctgggtg gattagagag tcatatgttt gatg       54
```

<210> SEQ ID NO 183
<211> LENGTH: 52
<212> TYPE: DNA
<213> ORGANISM: artificial sequence
<220> FEATURE:
<223> OTHER INFORMATION: primer

<400> SEQUENCE: 183

```
ggggacaagt ttgtacaaaa aagcaggctt cacaatgctg atgctgtgtg gg         52
```

<210> SEQ ID NO 184
<211> LENGTH: 52
<212> TYPE: DNA
<213> ORGANISM: artificial sequence
<220> FEATURE:
<223> OTHER INFORMATION: primer

<400> SEQUENCE: 184

```
ggggaccact ttgtacaaga aagctgggtt ttcaacaatg ttcaacaaca ct         52
```

<210> SEQ ID NO 185
<211> LENGTH: 54
<212> TYPE: DNA
<213> ORGANISM: artificial sequence
<220> FEATURE:
<223> OTHER INFORMATION: primer

<400> SEQUENCE: 185

```
ggggacaagt ttgtacaaaa aagcaggctt cacaatggtg aagttgatga tacg       54
```

<210> SEQ ID NO 186
<211> LENGTH: 49
<212> TYPE: DNA
<213> ORGANISM: artificial sequence
<220> FEATURE:
<223> OTHER INFORMATION: primer

<400> SEQUENCE: 186

```
ggggaccact ttgtacaaga aagctgggtt ttagtgcaac caaagagtc             49
```

<210> SEQ ID NO 187
<211> LENGTH: 56
<212> TYPE: DNA
<213> ORGANISM: artificial sequence
<220> FEATURE:
<223> OTHER INFORMATION: primer

<400> SEQUENCE: 187

```
ggggacaagt ttgtacaaaa aagcaggctt cacaatggag aaacagagta ctcaac     56
```

<210> SEQ ID NO 188
<211> LENGTH: 51
<212> TYPE: DNA
<213> ORGANISM: artificial sequence
<220> FEATURE:

```
<223> OTHER INFORMATION: primer

<400> SEQUENCE: 188
ggggaccact ttgtacaaga aagctgggtt tatgaaggtc tctttgtagc t                51

<210> SEQ ID NO 189
<211> LENGTH: 58
<212> TYPE: DNA
<213> ORGANISM: artificial sequence
<220> FEATURE:
<223> OTHER INFORMATION: primer

<400> SEQUENCE: 189
ggggacaagt ttgtacaaaa aagcaggctt cacaatgaca actactgggt ctaattct       58

<210> SEQ ID NO 190
<211> LENGTH: 47
<212> TYPE: DNA
<213> ORGANISM: artificial sequence
<220> FEATURE:
<223> OTHER INFORMATION: primer

<400> SEQUENCE: 190
ggggaccact ttgtacaaga aagctgggtt caattctccg gcttcat                    47

<210> SEQ ID NO 191
<211> LENGTH: 52
<212> TYPE: DNA
<213> ORGANISM: artificial sequence
<220> FEATURE:
<223> OTHER INFORMATION: primer

<400> SEQUENCE: 191
ggggacaagt ttgtacaaaa aagcaggctt cacaatggcg ctgcagaaca tt              52

<210> SEQ ID NO 192
<211> LENGTH: 51
<212> TYPE: DNA
<213> ORGANISM: artificial sequence
<220> FEATURE:
<223> OTHER INFORMATION: primer

<400> SEQUENCE: 192
ggggaccact ttgtacaaga aagctgggtg caaagaaaag ttaggaggga a                51

<210> SEQ ID NO 193
<211> LENGTH: 53
<212> TYPE: DNA
<213> ORGANISM: artificial sequence
<220> FEATURE:
<223> OTHER INFORMATION: primer

<400> SEQUENCE: 193
ggggacaagt ttgtacaaaa aagcaggctt cacaatggcg gctaacaaat tcg             53

<210> SEQ ID NO 194
<211> LENGTH: 49
<212> TYPE: DNA
<213> ORGANISM: artificial sequence
<220> FEATURE:
<223> OTHER INFORMATION: primer

<400> SEQUENCE: 194
ggggaccact ttgtacaaga aagctgggtg tcgttgttcc ttgcctcac                  49

<210> SEQ ID NO 195
```

```
<211> LENGTH: 57
<212> TYPE: DNA
<213> ORGANISM: artificial sequence
<220> FEATURE:
<223> OTHER INFORMATION: primer

<400> SEQUENCE: 195 gggacaagt tgtacaaaa aagcaggctt cacaatgtca ctcttgttcc tcaatcc        57

<210> SEQ ID NO 196
<211> LENGTH: 54
<212> TYPE: DNA
<213> ORGANISM: artificial sequence
<220> FEATURE:
<223> OTHER INFORMATION: primer

<400> SEQUENCE: 196
ggggaccact ttgtacaaga aagctgggtc cttctaccga tttctgtttc ttat          54

<210> SEQ ID NO 197
<211> LENGTH: 53
<212> TYPE: DNA
<213> ORGANISM: artificial sequence
<220> FEATURE:
<223> OTHER INFORMATION: primer

<400> SEQUENCE: 197 gggacaagt tgtacaaaa aagcaggctt cacaatggaa ggttcctcgt cag             53

<210> SEQ ID NO 198
<211> LENGTH: 48
<212> TYPE: DNA
<213> ORGANISM: artificial sequence
<220> FEATURE:
<223> OTHER INFORMATION: primer

<400> SEQUENCE: 198
ggggaccact ttgtacaaga aagctgggtt cacgatgtaa tcatgggc                 48

<210> SEQ ID NO 199
<211> LENGTH: 12
<212> TYPE: PRT
<213> ORGANISM: artificial sequence
<220> FEATURE:
<223> OTHER INFORMATION: motif

<400> SEQUENCE: 199

Glu Glu Thr Ala Arg Phe Gln Pro Gly Tyr Arg Ser
 1               5                  10

<210> SEQ ID NO 200
<211> LENGTH: 10
<212> TYPE: PRT
<213> ORGANISM: artificial sequence
<220> FEATURE:
<223> OTHER INFORMATION: motif

<400> SEQUENCE: 200

Glu Gln Lys Leu Ile Ser Glu Glu Asp Leu
 1               5                  10

<210> SEQ ID NO 201
<211> LENGTH: 7
<212> TYPE: PRT
<213> ORGANISM: artificial sequence
<220> FEATURE:
<223> OTHER INFORMATION: motif
```

```
<400> SEQUENCE: 201

Asp Tyr Lys Asp Asp Lys
 1               5

<210> SEQ ID NO 202
<211> LENGTH: 9
<212> TYPE: PRT
<213> ORGANISM: artificial sequence
<220> FEATURE:
<223> OTHER INFORMATION: motif

<400> SEQUENCE: 202

Tyr Pro Tyr Asp Val Pro Asp Tyr Ala
 1               5

<210> SEQ ID NO 203
<211> LENGTH: 12
<212> TYPE: PRT
<213> ORGANISM: artificial sequence
<220> FEATURE:
<223> OTHER INFORMATION: motif

<400> SEQUENCE: 203

Glu Asp Gln Val Asp Pro Arg Leu Ile Asp Gly Lys
 1               5                  10

<210> SEQ ID NO 204
<211> LENGTH: 11
<212> TYPE: PRT
<213> ORGANISM: artificial sequence
<220> FEATURE:
<223> OTHER INFORMATION: motif

<400> SEQUENCE: 204

Tyr Thr Asp Ile Glu Met Asn Arg Leu Gly Lys
 1               5                  10

<210> SEQ ID NO 205
<211> LENGTH: 131
<212> TYPE: PRT
<213> ORGANISM: Arabidopsis thaliana

<400> SEQUENCE: 205

Asn Arg Ile Leu Trp Lys Gly Val Asp Ala Cys Pro Gly Asp Glu Asp
 1               5                  10                  15

Ala Asp Val Ser Val Leu Gln Leu Gln Ala Glu Ile Glu Asn Leu Ala
                 20                  25                  30

Leu Glu Glu Gln Ala Leu Asp Asn Gln Ile Arg Gln Thr Glu Glu Arg
             35                  40                  45

Leu Arg Asp Leu Ser Glu Asn Glu Lys Asn Gln Lys Trp Leu Phe Val
         50                  55                  60

Thr Glu Glu Asp Ile Lys Ser Leu Pro Gly Phe Gln Asn Gln Thr Leu
 65                  70                  75                  80

Ile Ala Val Lys Ala Pro His Gly Thr Thr Leu Glu Val Pro Asp Pro
                 85                  90                  95

Asp Glu Ala Ala Asp His Pro Gln Arg Arg Tyr Arg Ile Ile Leu Arg
                100                 105                 110

Ser Thr Met Gly Pro Ile Asp Val Tyr Leu Val Ser Glu Phe Glu Gly
            115                 120                 125

Lys Phe Glu
        130
```

```
<210> SEQ ID NO 206
<211> LENGTH: 385
<212> TYPE: PRT
<213> ORGANISM: Arabidopsis thaliana

<400> SEQUENCE: 206

Met Ser Glu Glu Val Pro Gln Gln Phe Pro Ser Ser Lys Arg Gln Leu
 1               5                  10                  15

His Pro Ser Leu Ser Ser Met Lys Pro Pro Leu Val Ala Pro Gly Glu
            20                  25                  30

Tyr His Arg Phe Asp Ala Ala Glu Thr Arg Gly Gly Gly Ala Val Ala
        35                  40                  45

Asp Gln Val Val Ser Asp Ala Ile Val Ile Lys Ser Thr Leu Lys Arg
    50                  55                  60

Lys Thr Asp Leu Val Asn Gln Ile Val Glu Val Asn Glu Leu Asn Thr
65                  70                  75                  80

Gly Val Leu Gln Thr Pro Val Ser Gly Lys Gly Gly Lys Ala Lys Lys
                85                  90                  95

Thr Ser Arg Ser Ala Lys Ser Asn Lys Ser Gly Thr Leu Ala Ser Gly
            100                 105                 110

Ser Asn Ala Gly Ser Pro Gly Asn Asn Phe Ala Gln Ala Gly Thr Cys
        115                 120                 125

Arg Tyr Asp Ser Ser Leu Gly Leu Leu Thr Lys Lys Phe Ile Asn Leu
    130                 135                 140

Ile Lys Gln Ala Glu Asp Gly Ile Leu Asp Leu Asn Lys Ala Ala Asp
145                 150                 155                 160

Thr Leu Glu Val Gln Lys Arg Arg Ile Tyr Asp Ile Thr Asn Val Leu
                165                 170                 175

Glu Gly Ile Gly Leu Ile Glu Lys Thr Leu Lys Asn Arg Ile Gln Trp
            180                 185                 190

Lys Gly Leu Asp Val Ser Lys Pro Gly Glu Thr Ile Glu Ser Ile Ala
        195                 200                 205

Asn Leu Gln Asp Glu Val Gln Asn Leu Ala Ala Glu Ala Arg Leu
    210                 215                 220

Asp Asp Gln Ile Arg Glu Ser Gln Glu Arg Leu Thr Ser Leu Ser Glu
225                 230                 235                 240

Asp Glu Asn Asn Lys Arg Leu Leu Phe Val Thr Glu Asn Asp Ile Lys
                245                 250                 255

Asn Leu Pro Cys Phe Gln Asn Lys Thr Leu Ile Ala Val Lys Ala Pro
            260                 265                 270

His Gly Thr Thr Leu Glu Val Pro Asp Pro Asp Glu Ala Gly Gly Tyr
        275                 280                 285

Gln Arg Arg Tyr Arg Ile Ile Leu Arg Ser Thr Met Gly Pro Ile Asp
    290                 295                 300

Val Tyr Leu Val Ser Gln Phe Glu Glu Ser Phe Glu Asp Ile Pro Gln
305                 310                 315                 320

Ala Asp Glu Pro Ser Asn Val Pro Asp Glu Pro Ser Asn Val Pro Asp
                325                 330                 335

Glu Pro Ser Asn Leu Pro Ser Thr Ser Gly Leu Pro Glu Asn His Asp
            340                 345                 350

Val Ser Met Pro Met Lys Glu Glu Ser Thr Glu Arg Asn Met Glu Thr
        355                 360                 365

Gln Glu Val Asp Asp Thr Gln Arg Val Tyr Ser Asp Ile Glu Ser His
    370                 375                 380

Asp
```

<210> SEQ ID NO 207
<211> LENGTH: 127
<212> TYPE: PRT
<213> ORGANISM: Arabidopsis thaliana

<400> SEQUENCE: 207

Met Ser Glu Glu Val Pro Gln Gln Phe Pro Ser Ser Lys Arg Gln Leu
1               5                   10                  15

His Pro Ser Leu Ser Ser Met Lys Pro Pro Leu Val Ala Pro Gly Glu
            20                  25                  30

Tyr His Arg Phe Asp Ala Ala Glu Thr Arg Gly Gly Gly Ala Val Ala
        35                  40                  45

Asp Gln Val Val Ser Asp Ala Ile Val Ile Lys Ser Thr Leu Lys Arg
    50                  55                  60

Lys Thr Asp Leu Val Asn Gln Ile Val Glu Val Asn Glu Leu Asn Thr
65                  70                  75                  80

Gly Val Leu Gln Thr Pro Val Ser Gly Lys Gly Lys Ala Lys Lys
                85                  90                  95

Thr Ser Arg Ser Ala Lys Ser Asn Lys Ser Gly Thr Leu Ala Ser Gly
            100                 105                 110

Ser Asn Ala Gly Ser Pro Gly Asn Asn Phe Ala Gln Ala Gly Thr
        115                 120                 125

<210> SEQ ID NO 208
<211> LENGTH: 142
<212> TYPE: PRT
<213> ORGANISM: Arabidopsis thaliana

<400> SEQUENCE: 208

Met Ser Met Glu Met Glu Leu Phe Val Thr Pro Glu Lys Gln Arg Gln
1               5                   10                  15

His Pro Ser Val Ser Val Glu Lys Thr Pro Val Arg Arg Lys Leu Ile
            20                  25                  30

Val Asp Asp Ser Glu Ile Gly Ser Glu Lys Lys Gly Gln Ser Arg
        35                  40                  45

Thr Ser Gly Gly Gly Leu Arg Gln Phe Ser Val Met Val Cys Gln Lys
    50                  55                  60

Leu Glu Ala Lys Lys Ile Thr Thr Tyr Lys Glu Val Ala Asp Glu Ile
65                  70                  75                  80

Ile Ser Asp Phe Ala Thr Ile Lys Gln Asn Ala Glu Lys Pro Leu Asn
                85                  90                  95

Glu Asn Glu Tyr Asn Glu Lys Asn Ile Arg Arg Arg Val Tyr Asp Ala
            100                 105                 110

Leu Asn Val Phe Met Ala Leu Asp Ile Ile Ala Arg Asp Lys Lys Glu
        115                 120                 125

Ile Arg Trp Lys Gly Leu Pro Ile Thr Cys Lys Lys Asp Val
    130                 135                 140

<210> SEQ ID NO 209
<211> LENGTH: 101
<212> TYPE: PRT
<213> ORGANISM: Arabidopsis thaliana

<400> SEQUENCE: 209

Glu Lys Lys Gly Gln Ser Arg Thr Ser Gly Gly Gly Leu Arg Gln Phe
1               5                   10                  15

```
Ser Val Met Val Cys Gln Lys Leu Glu Ala Lys Lys Ile Thr Thr Tyr
            20                  25                  30

Lys Glu Val Ala Asp Glu Ile Ile Ser Asp Phe Ala Thr Ile Lys Gln
            35                  40                  45

Asn Ala Glu Lys Pro Leu Asn Glu Asn Glu Tyr Asn Glu Lys Asn Ile
        50                  55                  60

Arg Arg Arg Val Tyr Asp Ala Leu Asn Val Phe Met Ala Leu Asp Ile
65                  70                  75                  80

Ile Ala Arg Asp Lys Lys Glu Ile Arg Trp Lys Gly Leu Pro Ile Thr
                85                  90                  95

Cys Lys Lys Asp Val
            100

<210> SEQ ID NO 210
<211> LENGTH: 251
<212> TYPE: PRT
<213> ORGANISM: Arabidopsis thaliana

<400> SEQUENCE: 210

Glu Lys Lys Gly Gln Ser Arg Thr Ser Gly Gly Leu Arg Gln Phe
1               5                   10                  15

Ser Val Met Val Cys Gln Lys Leu Glu Ala Lys Lys Ile Thr Thr Tyr
            20                  25                  30

Lys Glu Val Ala Asp Glu Ile Ile Ser Asp Phe Ala Thr Ile Lys Gln
            35                  40                  45

Asn Ala Glu Lys Pro Leu Asn Glu Asn Glu Tyr Asn Glu Lys Asn Ile
        50                  55                  60

Arg Arg Arg Val Tyr Asp Ala Leu Asn Val Phe Met Ala Leu Asp Ile
65                  70                  75                  80

Ile Ala Arg Asp Lys Lys Glu Ile Arg Trp Lys Gly Leu Pro Ile Thr
                85                  90                  95

Cys Lys Lys Asp Val Glu Glu Val Lys Met Asp Arg Asn Lys Val Met
            100                 105                 110

Ser Ser Val Gln Lys Lys Ala Ala Phe Leu Lys Glu Leu Arg Glu Lys
            115                 120                 125

Val Ser Ser Leu Glu Ser Leu Met Ser Arg Asn Gln Glu Met Val Val
        130                 135                 140

Lys Thr Gln Gly Pro Ala Gly Glu Gly Phe Thr Leu Pro Phe Ile Leu Leu
145                 150                 155                 160

Glu Thr Asn Pro His Ala Val Val Glu Ile Glu Ile Ser Glu Asp Met
                165                 170                 175

Gln Leu Val His Leu Asp Phe Asn Ser Thr Pro Phe Ser Val His Asp
            180                 185                 190

Asp Ala Tyr Ile Leu Lys Leu Met Gln Glu Gln Lys Gln Glu Gln Asn
            195                 200                 205

Arg Val Ser Ser Ser Ser Thr His His Gln Ser Gln His Ser Ser
        210                 215                 220

Ala His Ser Ser Ser Ser Cys Ile Ala Ser Gly Thr Ser Gly Pro
225                 230                 235                 240

Val Cys Trp Asn Ser Gly Ser Ile Asp Thr Arg
                245                 250

<210> SEQ ID NO 211
<211> LENGTH: 172
<212> TYPE: PRT
<213> ORGANISM: Arabidopsis thaliana
```

-continued

```
<400> SEQUENCE: 211

Ile Ile Ala Arg Asp Lys Lys Glu Ile Arg Trp Lys Gly Leu Pro Ile
1               5                   10                  15

Thr Cys Lys Lys Asp Val Glu Glu Val Lys Met Asp Arg Asn Lys Val
                20                  25                  30

Met Ser Ser Val Gln Lys Lys Ala Ala Phe Leu Lys Glu Leu Arg Glu
            35                  40                  45

Lys Val Ser Ser Leu Glu Ser Leu Met Ser Arg Asn Gln Glu Met Val
        50                  55                  60

Val Lys Thr Gln Gly Pro Ala Glu Gly Phe Thr Leu Pro Phe Ile Leu
65                  70                  75                  80

Leu Glu Thr Asn Pro His Ala Val Val Glu Ile Glu Ile Ser Glu Asp
                85                  90                  95

Met Gln Leu Val His Leu Asp Phe Asn Ser Thr Pro Phe Ser Val His
                100                 105                 110

Asp Asp Ala Tyr Ile Leu Lys Leu Met Gln Gln Lys Gln Glu Gln
            115                 120                 125

Asn Arg Val Ser Ser Ser Ser Thr His His Gln Ser Gln His Ser
130                 135                 140

Ser Ala His Ser Ser Ser Ser Cys Ile Ala Ser Gly Thr Ser Gly
145                 150                 155                 160

Pro Val Cys Trp Asn Ser Gly Ser Ile Asp Thr Arg
                165                 170

<210> SEQ ID NO 212
<211> LENGTH: 93
<212> TYPE: PRT
<213> ORGANISM: Arabidopsis thaliana

<400> SEQUENCE: 212

Ile Ile Ala Arg Asp Lys Lys Glu Ile Arg Trp Lys Gly Leu Pro Ile
1               5                   10                  15

Thr Cys Lys Lys Asp Val Glu Glu Val Lys Met Asp Arg Asn Lys Val
                20                  25                  30

Met Ser Ser Val Gln Lys Lys Ala Ala Phe Leu Lys Glu Leu Arg Glu
            35                  40                  45

Lys Val Ser Ser Leu Glu Ser Leu Met Ser Arg Asn Gln Glu Met Val
        50                  55                  60

Val Lys Thr Gln Gly Pro Ala Glu Gly Phe Thr Leu Pro Phe Ile Leu
65                  70                  75                  80

Leu Glu Thr Asn Pro His Ala Val Val Glu Ile Glu Ile
                85                  90

<210> SEQ ID NO 213
<211> LENGTH: 121
<212> TYPE: PRT
<213> ORGANISM: Arabidopsis thaliana

<400> SEQUENCE: 213

Ser Leu Glu Ser Leu Met Ser Arg Asn Gln Glu Met Val Val Lys Thr
1               5                   10                  15

Gln Gly Pro Ala Glu Gly Phe Thr Leu Pro Phe Ile Leu Leu Glu Thr
                20                  25                  30

Asn Pro His Ala Val Val Glu Ile Glu Ile Ser Glu Asp Met Gln Leu
            35                  40                  45

Val His Leu Asp Phe Asn Ser Thr Pro Phe Ser Val His Asp Asp Ala
        50                  55                  60
```

```
Tyr Ile Leu Lys Leu Met Gln Glu Gln Lys Gln Glu Gln Asn Arg Val
 65                  70                  75                  80

Ser Ser Ser Ser Ser Thr His His Gln Ser Gln His Ser Ser Ala His
                 85                  90                  95

Ser Ser Ser Ser Ser Cys Ile Ala Ser Gly Thr Ser Gly Pro Val Cys
                100                 105                 110

Trp Asn Ser Gly Ser Ile Asp Thr Arg
            115                 120

<210> SEQ ID NO 214
<211> LENGTH: 193
<212> TYPE: PRT
<213> ORGANISM: Arabidopsis thaliana

<400> SEQUENCE: 214

Met Thr Thr Thr Gly Ser Asn Ser Asn His Asn His His Glu Ser Asn
  1               5                  10                  15

Asn Asn Asn Asn Pro Ser Thr Arg Ser Trp Gly Thr Ala Val Ser
                 20                  25                  30

Gly Gln Ser Val Ser Thr Ser Gly Ser Met Gly Ser Pro Ser Ser Arg
                 35                  40                  45

Ser Glu Gln Thr Ile Thr Val Val Thr Ser Thr Ser Asp Thr Thr Phe
     50                  55                  60

Gln Arg Leu Asn Asn Leu Asp Ile Gln Gly Asp Asp Ala Gly Ser Gln
 65                  70                  75                  80

Gly Ala Ser Gly Val Lys Lys Lys Arg Gly Gln Arg Ala Ala Gly
                 85                  90                  95

Pro Asp Lys Thr Gly Arg Gly Leu Arg Gln Phe Ser Met Lys Val Cys
                100                 105                 110

Glu Lys Val Glu Ser Lys Gly Arg Thr Thr Tyr Asn Glu Val Ala Asp
                115                 120                 125

Glu Leu Val Ala Glu Phe Ala Leu Pro Asn Asn Asp Gly Thr Ser Pro
            130                 135                 140

Asp Gln Gln Gln Tyr Asp Glu Lys Asn Ile Arg Arg Arg Val Tyr Asp
145                 150                 155                 160

Ala Leu Asn Val Leu Met Ala Met Asp Ile Ile Ser Lys Asp Lys Lys
                165                 170                 175

Glu Ile Gln Trp Arg Gly Leu Pro Arg Thr Ser Leu Ser Asp Ile Glu
                180                 185                 190

Glu

<210> SEQ ID NO 215
<211> LENGTH: 81
<212> TYPE: PRT
<213> ORGANISM: Arabidopsis thaliana

<400> SEQUENCE: 215

Gly Leu Pro Arg Thr Ser Leu Ser Asp Ile Glu Glu Leu Lys Asn Glu
  1               5                  10                  15

Arg Leu Ser Leu Arg Asn Arg Ile Glu Lys Lys Thr Ala Tyr Ser Gln
                 20                  25                  30

Glu Leu Glu Glu Gln Tyr Val Gly Leu Gln Asn Leu Ile Gln Arg Asn
             35                  40                  45

Glu His Leu Tyr Ser Ser Gly Asn Ala Pro Ser Gly Gly Val Ala Leu
     50                  55                  60

Pro Phe Ile Leu Val Gln Thr Arg Pro His Ala Thr Val Glu Val Glu
```

```
                65                  70                  75                  80
Ile

<210> SEQ ID NO 216
<211> LENGTH: 204
<212> TYPE: PRT
<213> ORGANISM: Arabidopsis thaliana

<400> SEQUENCE: 216

Gly Leu Pro Arg Thr Ser Leu Ser Asp Ile Glu Glu Leu Lys Asn Glu
  1               5                  10                  15

Arg Leu Ser Leu Arg Asn Arg Ile Glu Lys Thr Ala Tyr Ser Gln
             20                  25                  30

Glu Leu Glu Glu Gln Tyr Val Gly Leu Gln Asn Leu Ile Gln Arg Asn
         35                  40                  45

Glu His Leu Tyr Ser Ser Gly Asn Ala Pro Ser Gly Gly Val Ala Leu
     50                  55                  60

Pro Phe Ile Leu Val Gln Thr Arg Pro His Ala Thr Val Glu Val Glu
 65                  70                  75                  80

Ile Ser Glu Asp Met Gln Leu Val His Phe Asp Phe Asn Ser Thr Pro
                 85                  90                  95

Phe Glu Leu His Asp Asp Asn Phe Val Leu Lys Thr Met Lys Phe Cys
            100                 105                 110

Asp Gln Pro Pro Gln Gln Pro Asn Gly Arg Asn Asn Ser Gln Leu Val
        115                 120                 125

Cys His Asn Phe Thr Pro Glu Asn Pro Asn Lys Gly Pro Ser Thr Gly
    130                 135                 140

Pro Thr Pro Gln Leu Asp Met Tyr Glu Thr His Leu Gln Ser Gln Gln
145                 150                 155                 160

His Gln Gln His Ser Gln Leu Gln Ile Ile Pro Met Pro Glu Thr Asn
                165                 170                 175

Asn Val Thr Ser Ser Ala Asp Thr Ala Pro Val Lys Ser Pro Ser Leu
            180                 185                 190

Pro Gly Ile Met Asn Ser Ser Met Lys Pro Glu Asn
        195                 200

<210> SEQ ID NO 217
<211> LENGTH: 420
<212> TYPE: PRT
<213> ORGANISM: Arabidopsis thaliana

<400> SEQUENCE: 217

Met Ser Gly Val Val Arg Ser Ser Pro Gly Ser Ser Gln Pro Pro Pro
  1               5                  10                  15

Pro Pro Pro His His Pro Pro Ser Ser Pro Val Pro Val Thr Ser Thr
             20                  25                  30

Pro Val Ile Pro Pro Ile Arg Arg His Leu Ala Phe Ala Ser Thr Lys
         35                  40                  45

Pro Pro Phe His Pro Ser Asp Asp Tyr His Arg Phe Asn Pro Ser Ser
     50                  55                  60

Leu Ser Asn Asn Asn Asp Arg Ser Phe Val His Gly Cys Gly Val Val
 65                  70                  75                  80

Asp Arg Glu Glu Asp Ala Val Val Arg Ser Pro Ser Arg Lys Arg
                 85                  90                  95

Lys Ala Thr Met Asp Met Val Val Ala Pro Ser Asn Asn Gly Phe Thr
            100                 105                 110
```

Ser Ser Gly Phe Thr Asn Ile Pro Ser Ser Pro Cys Gln Thr Pro Arg
            115                 120                 125

Lys Gly Gly Arg Val Asn Ile Lys Ser Lys Ala Lys Gly Asn Lys Ser
    130                 135                 140

Thr Pro Gln Thr Pro Ile Ser Thr Asn Ala Gly Ser Pro Ile Thr Leu
145                 150                 155                 160

Thr Pro Ser Gly Ser Cys Arg Tyr Asp Ser Ser Leu Gly Leu Leu Thr
                165                 170                 175

Lys Lys Phe Val Asn Leu Ile Lys Gln Ala Lys Asp Gly Met Leu Asp
                180                 185                 190

Leu Asn Lys Ala Ala Glu Thr Leu Glu Val Gln Lys Arg Arg Ile Tyr
                195                 200                 205

Asp Ile Thr Asn Val Leu Glu Gly Ile Asp Leu Ile Glu Lys Pro Phe
                210                 215                 220

Lys Asn Arg Ile Leu Trp Lys Gly Val Asp Ala Cys Pro Gly Asp Glu
225                 230                 235                 240

Asp Ala Asp Val Ser Val Leu Gln Leu Gln Ala Glu Ile Glu Asn Leu
                245                 250                 255

Ala Leu Glu Glu Gln Ala Leu Asp Asn Gln Ile Arg Gln Thr Glu Glu
                260                 265                 270

Arg Leu Arg Asp Leu Ser Glu Asn Glu Lys Asn Gln Lys Trp Leu Phe
                275                 280                 285

Val Thr Glu Glu Asp Ile Lys Ser Leu Pro Gly Phe Gln Asn Gln Thr
                290                 295                 300

Leu Ile Ala Val Lys Ala Pro His Gly Thr Thr Leu Glu Val Pro Asp
305                 310                 315                 320

Pro Asp Glu Ala Ala Asp His Pro Gln Arg Arg Tyr Arg Ile Ile Leu
                325                 330                 335

Arg Ser Thr Met Gly Pro Ile Asp Val Tyr Leu Val Ser Glu Phe Glu
                340                 345                 350

Gly Lys Phe Glu Asp Thr Asn Gly Ser Gly Ala Ala Pro Pro Ala Cys
                355                 360                 365

Leu Pro Ile Ala Ser Ser Ser Gly Ser Thr Gly His His Asp Ile Glu
                370                 375                 380

Ala Leu Thr Val Asp Asn Pro Glu Thr Ala Ile Val Ser His Asp His
385                 390                 395                 400

Pro His Pro Gln Pro Gly Asp Thr Ser Asp Leu Asn Tyr Leu Gln Glu
                405                 410                 415

Gln Val Gly Gly
            420

<210> SEQ ID NO 218
<211> LENGTH: 324
<212> TYPE: PRT
<213> ORGANISM: Arabidopsis thaliana

<400> SEQUENCE: 218

Pro Ser Gly Ser Cys Arg Tyr Asp Ser Ser Leu Gly Leu Leu Thr Lys
1               5                   10                  15

Lys Phe Val Asn Leu Ile Lys Gln Ala Lys Asp Gly Met Leu Asp Leu
                20                  25                  30

Asn Lys Ala Ala Glu Thr Leu Glu Val Gln Lys Arg Arg Ile Tyr Asp
                35                  40                  45

Ile Thr Asn Val Leu Glu Gly Ile Asp Leu Ile Glu Lys Pro Phe Lys
            50                  55                  60

```
Asn Arg Ile Leu Trp Lys Gly Val Asp Ala Cys Pro Gly Asp Glu Asp
 65                  70                  75                  80

Ala Asp Val Ser Val Leu Gln Leu Gln Ala Glu Ile Glu Asn Leu Ala
                 85                  90                  95

Leu Glu Glu Gln Ala Leu Asp Asn Gln Ile Arg Gln Thr Glu Arg
            100                 105                 110

Leu Arg Asp Leu Ser Glu Asn Glu Lys Asn Gln Lys Trp Leu Phe Val
            115                 120                 125

Thr Glu Glu Asp Ile Lys Ser Leu Pro Gly Phe Gln Asn Gln Thr Leu
    130                 135                 140

Ile Ala Val Lys Ala Pro His Gly Thr Thr Leu Glu Val Pro Asp Pro
145                 150                 155                 160

Asp Glu Ala Ala Asp His Pro Gln Arg Arg Tyr Arg Ile Ile Leu Arg
                165                 170                 175

Ser Thr Met Gly Pro Ile Asp Val Tyr Leu Val Ser Glu Phe Glu Gly
                180                 185                 190

Lys Phe Glu Asp Thr Asn Gly Ser Gly Ala Ala Pro Pro Ala Cys Leu
            195                 200                 205

Pro Ile Ala Ser Ser Ser Gly Ser Thr Gly His His Asp Ile Glu Ala
210                 215                 220

Leu Thr Val Asp Asn Pro Glu Thr Ala Ile Val Ser His Asp His Pro
225                 230                 235                 240

His Pro Gln Pro Gly Asp Thr Ser Asp Leu Asn Tyr Leu Gln Glu Gln
                245                 250                 255

Val Gly Gly Met Leu Lys Ile Thr Pro Ser Asp Val Glu Asn Asp Glu
            260                 265                 270

Ser Asp Tyr Trp Leu Leu Ser Asn Ala Glu Ile Ser Met Thr Asp Ile
            275                 280                 285

Trp Lys Thr Asp Ser Gly Ile Asp Trp Asp Tyr Gly Ile Ala Asp Val
    290                 295                 300

Ser Thr Pro Pro Pro Gly Met Gly Glu Ile Ala Pro Thr Ala Val Asp
305                 310                 315                 320

Ser Thr Pro Arg

<210> SEQ ID NO 219
<211> LENGTH: 38
<212> TYPE: PRT
<213> ORGANISM: Arabidopsis thaliana

<400> SEQUENCE: 219

Met Ser Gly Val Val Arg Ser Ser Pro Gly Ser Ser Gln Pro Pro Pro
 1               5                  10                  15

Pro Pro Pro His His Pro Ser Ser Pro Val Pro Val Thr Ser Thr
                20                  25                  30

Pro Val Ile Pro Pro Ile
        35

<210> SEQ ID NO 220
<211> LENGTH: 142
<212> TYPE: PRT
<213> ORGANISM: Arabidopsis thaliana

<400> SEQUENCE: 220

Met Ser Met Glu Met Glu Leu Phe Val Thr Pro Glu Lys Gln Arg Gln
 1               5                  10                  15

His Pro Ser Val Ser Val Glu Lys Thr Pro Val Arg Arg Lys Leu Ile
                20                  25                  30
```

```
Val Asp Asp Asp Ser Glu Ile Gly Ser Glu Lys Lys Gly Gln Ser Arg
        35                  40                  45

Thr Ser Gly Gly Gly Leu Arg Gln Phe Ser Val Met Val Cys Gln Lys
 50                  55                  60

Leu Glu Ala Lys Lys Ile Thr Thr Tyr Lys Glu Val Ala Asp Glu Ile
 65                  70                  75                  80

Ile Ser Asp Phe Ala Thr Ile Lys Gln Asn Ala Glu Lys Pro Leu Asn
                 85                  90                  95

Glu Asn Glu Tyr Asn Glu Lys Asn Ile Arg Arg Val Tyr Asp Ala
                100                 105                 110

Leu Asn Val Phe Met Ala Leu Asp Ile Ile Ala Arg Asp Lys Lys Glu
                115                 120                 125

Ile Arg Trp Lys Gly Leu Pro Ile Thr Cys Lys Lys Asp Val
130                 135                 140
```

<210> SEQ ID NO 221
<211> LENGTH: 150
<212> TYPE: PRT
<213> ORGANISM: Arabidopsis thaliana

<400> SEQUENCE: 221

```
Glu Glu Val Lys Met Asp Arg Asn Lys Val Met Ser Ser Val Gln Lys
 1                   5                  10                  15

Lys Ala Ala Phe Leu Lys Glu Leu Arg Glu Lys Val Ser Ser Leu Glu
                 20                  25                  30

Ser Leu Met Ser Arg Asn Gln Glu Met Val Val Lys Thr Gln Gly Pro
                 35                  40                  45

Ala Glu Gly Phe Thr Leu Pro Phe Ile Leu Leu Glu Thr Asn Pro His
 50                  55                  60

Ala Val Val Glu Ile Glu Ile Ser Glu Asp Met Gln Leu Val His Leu
 65                  70                  75                  80

Asp Phe Asn Ser Thr Pro Phe Ser Val His Asp Asp Ala Tyr Ile Leu
                 85                  90                  95

Lys Leu Met Gln Glu Gln Lys Gln Glu Gln Asn Arg Val Ser Ser Ser
                100                 105                 110

Ser Ser Thr His His Gln Ser Gln His Ser Ser Ala His Ser Ser Ser
                115                 120                 125

Ser Ser Cys Ile Ala Ser Gly Thr Ser Gly Pro Val Cys Trp Asn Ser
                130                 135                 140

Gly Ser Ile Asp Thr Arg
145                 150
```

<210> SEQ ID NO 222
<211> LENGTH: 71
<212> TYPE: PRT
<213> ORGANISM: Arabidopsis thaliana

<400> SEQUENCE: 222

```
Glu Glu Val Lys Met Asp Arg Asn Lys Val Met Ser Ser Val Gln Lys
 1                   5                  10                  15

Lys Ala Ala Phe Leu Lys Glu Leu Arg Glu Lys Val Ser Ser Leu Glu
                 20                  25                  30

Ser Leu Met Ser Arg Asn Gln Glu Met Val Val Lys Thr Gln Gly Pro
                 35                  40                  45

Ala Glu Gly Phe Thr Leu Pro Phe Ile Leu Leu Glu Thr Asn Pro His
 50                  55                  60
```

```
Ala Val Val Glu Ile Glu Ile
 65                  70
```

<210> SEQ ID NO 223
<211> LENGTH: 262
<212> TYPE: PRT
<213> ORGANISM: Arabidopsis thaliana

<400> SEQUENCE: 223

```
Met Thr Thr Thr Gly Ser Asn Ser Asn His Asn His His Glu Ser Asn
  1               5                  10                  15

Asn Asn Asn Asn Asn Pro Ser Thr Arg Ser Trp Gly Thr Ala Val Ser
             20                  25                  30

Gly Gln Ser Val Ser Thr Ser Gly Ser Met Gly Ser Pro Ser Ser Arg
         35                  40                  45

Ser Glu Gln Thr Ile Thr Val Val Thr Ser Ser Asp Thr Thr Phe
 50                  55                  60

Gln Arg Leu Asn Asn Leu Asp Ile Gln Gly Asp Asp Ala Gly Ser Gln
 65                  70                  75                  80

Gly Ala Ser Gly Val Lys Lys Lys Arg Gly Gln Arg Ala Ala Gly
                 85                  90                  95

Pro Asp Lys Thr Gly Arg Gly Leu Arg Gln Phe Ser Met Lys Val Cys
            100                 105                 110

Glu Lys Val Glu Ser Lys Gly Arg Thr Thr Tyr Asn Glu Val Ala Asp
        115                 120                 125

Glu Leu Val Ala Glu Phe Ala Leu Pro Asn Asn Asp Gly Thr Ser Pro
130                 135                 140

Asp Gln Gln Gln Tyr Asp Glu Lys Asn Ile Arg Arg Arg Val Tyr Asp
145                 150                 155                 160

Ala Leu Asn Val Leu Met Ala Met Asp Ile Ile Ser Lys Asp Lys Lys
                165                 170                 175

Glu Ile Gln Trp Arg Gly Leu Pro Arg Thr Ser Leu Ser Asp Ile Glu
            180                 185                 190

Glu Leu Lys Asn Glu Arg Leu Ser Leu Arg Asn Arg Ile Glu Lys Lys
        195                 200                 205

Thr Ala Tyr Ser Gln Glu Leu Glu Glu Gln Tyr Val Gly Leu Gln Asn
    210                 215                 220

Leu Ile Gln Arg Asn Glu His Leu Tyr Ser Ser Gly Asn Ala Pro Ser
225                 230                 235                 240

Gly Gly Val Ala Leu Pro Phe Ile Leu Val Gln Thr Arg Pro His Ala
                245                 250                 255

Thr Val Glu Val Glu Ile
            260
```

<210> SEQ ID NO 224
<211> LENGTH: 51
<212> TYPE: PRT
<213> ORGANISM: Arabidopsis thaliana

<400> SEQUENCE: 224

```
Gly Val Asp Ala Cys Pro Gly Asp Glu Asp Ala Asp Val Ser Val Leu
  1               5                  10                  15

Gln Leu Gln Ala Glu Ile Glu Asn Leu Ala Leu Glu Glu Gln Ala Leu
             20                  25                  30

Asp Asn Gln Ile Arg Gln Thr Glu Glu Arg Leu Arg Asp Leu Ser Glu
         35                  40                  45

Asn Glu Lys
```

-continued

<210> SEQ ID NO 225
<211> LENGTH: 121
<212> TYPE: PRT
<213> ORGANISM: Arabidopsis thaliana

<400> SEQUENCE: 225

Gly Val Asp Ala Cys Pro Gly Asp Glu Asp Ala Asp Val Ser Val Leu
1               5                   10                  15

Gln Leu Gln Ala Glu Ile Glu Asn Leu Ala Leu Glu Glu Gln Ala Leu
            20                  25                  30

Asp Asn Gln Ile Arg Gln Thr Glu Glu Arg Leu Arg Asp Leu Ser Glu
        35                  40                  45

Asn Glu Lys Asn Gln Lys Trp Leu Phe Val Thr Glu Glu Asp Ile Lys
    50                  55                  60

Ser Leu Pro Gly Phe Gln Asn Gln Thr Leu Ile Ala Val Lys Ala Pro
65                  70                  75                  80

His Gly Thr Thr Leu Glu Val Pro Asp Pro Asp Glu Ala Ala Asp His
                85                  90                  95

Pro Gln Arg Arg Tyr Arg Ile Ile Leu Arg Ser Thr Met Gly Pro Ile
            100                 105                 110

Asp Val Tyr Leu Val Ser Glu Phe Glu
        115                 120

<210> SEQ ID NO 226
<211> LENGTH: 50
<212> TYPE: PRT
<213> ORGANISM: Arabidopsis thaliana

<400> SEQUENCE: 226

Gly Leu Asp Val Ser Lys Pro Gly Glu Thr Ile Glu Ser Ile Ala Asn
1               5                   10                  15

Leu Gln Asp Glu Val Gln Asn Leu Ala Ala Glu Ala Arg Leu Asp
            20                  25                  30

Asp Gln Ile Arg Glu Ser Gln Glu Arg Leu Thr Ser Leu Ser Glu Asp
        35                  40                  45

Glu Asn
    50

<210> SEQ ID NO 227
<211> LENGTH: 118
<212> TYPE: PRT
<213> ORGANISM: Arabidopsis thaliana

<400> SEQUENCE: 227

Gly Leu Asp Val Ser Lys Pro Gly Glu Thr Ile Glu Ser Ile Ala Asn
1               5                   10                  15

Leu Gln Asp Glu Val Gln Asn Leu Ala Ala Glu Ala Arg Leu Asp
            20                  25                  30

Asp Gln Ile Arg Glu Ser Gln Glu Arg Leu Thr Ser Leu Ser Glu Asp
        35                  40                  45

Glu Asn Asn Lys Arg Leu Leu Phe Val Thr Glu Asn Asp Ile Lys Asn
    50                  55                  60

Leu Pro Cys Phe Gln Asn Lys Thr Leu Ile Ala Val Lys Ala Pro His
65                  70                  75                  80

Gly Thr Thr Leu Glu Val Pro Asp Pro Asp Glu Ala Gly Gly Tyr Gln
                85                  90                  95

Arg Arg Tyr Arg Ile Ile Leu Arg Ser Thr Met Gly Pro Ile Asp Val
        100                 105                 110

Tyr Leu Val Ser Gln Phe
      115

<210> SEQ ID NO 228
<211> LENGTH: 393
<212> TYPE: DNA
<213> ORGANISM: Arabidopsis thaliana

<400> SEQUENCE: 228

| | | | | | |
|---|---|---|---|---|---|
| aatcgaatac | tttggaaggg | agttgatgcg | tgtcctggcg | atgaggatgc | tgacgtatct | 60 |
| gtattacagc | tgcaggcaga | aattgaaaac | ctcgccctcg | aagagcaagc | attagacaac | 120 |
| caaatcagac | aaacagagga | aagattaaga | gacctgagcg | aaaatgaaaa | gaatcagaaa | 180 |
| tggcttttg | taactgaaga | ggatatcaag | agtttaccag | gtttccagaa | ccagactctg | 240 |
| atagccgtca | aagctcctca | tggcacaact | ttggaagtgc | ctgatccaga | tgaagcggct | 300 |
| gaccacccac | aaaggagata | caggatcatt | cttagaagta | caatgggacc | tattgacgta | 360 |
| tacctcgtca | gcgaatttga | agggaaattc | gaa | | | 393 |

<210> SEQ ID NO 229
<211> LENGTH: 516
<212> TYPE: DNA
<213> ORGANISM: Arabidopsis thaliana

<400> SEQUENCE: 229

| | | | | | |
|---|---|---|---|---|---|
| attattgcaa | gggataaaaa | ggaaatccgg | tggaaaggac | ttcctattac | ctgcaaaaag | 60 |
| gatgtggaag | aagtcaagat | ggatcgtaat | aaagttatga | gcagtgtgca | aaagaaggct | 120 |
| gcttttctta | aagagttgag | agaaaaggtc | tcaagtcttg | agagtcttat | gtcgagaaat | 180 |
| caagagatgg | ttgtgaagac | tcaaggccca | gcagaaggat | ttaccttacc | attcattcta | 240 |
| cttgagacaa | accctcacgc | agtagtcgaa | atcgagattt | ctgaagatat | gcaacttgta | 300 |
| cacctcgact | tcaatagcac | acctttctcg | gtccatgatg | atgcttacat | tttgaaactg | 360 |
| atgcaagaac | agaagcaaga | acagaacaga | gtatcttctt | cttcatctac | acatcaccaa | 420 |
| tctcaacata | gctccgctca | ttcttcatcc | agttcttgca | ttgcttctgg | aacctcaggc | 480 |
| ccggtttgct | ggaactcggg | atccattgat | actcgc | | | 516 |

<210> SEQ ID NO 230
<211> LENGTH: 276
<212> TYPE: DNA
<213> ORGANISM: Arabidopsis thaliana

<400> SEQUENCE: 230

| | | | | | |
|---|---|---|---|---|---|
| ggtcttcctc | ggacaagctt | aagcgacatt | gaagaattaa | agaacgaacg | actctcactt | 60 |
| aggaacagaa | ttgagaagaa | aactgcatat | tcccaagaac | tggaagaaca | agtaatgaac | 120 |
| atcatcgata | ctctcggctt | atctgcttcc | tgccttcaga | atctgataca | gagaaatgag | 180 |
| cacttatata | gctcaggaaa | tgctcccagt | ggcggtgttg | ctcttccttt | tatccttgtc | 240 |
| cagactcgtc | ctcacgcaac | agtagaagtg | gagata | | | 276 |

<210> SEQ ID NO 231
<211> LENGTH: 645
<212> TYPE: DNA
<213> ORGANISM: Arabidopsis thaliana

<400> SEQUENCE: 231

```
ggtcttcctc ggacaagctt aagcgacatt gaagaattaa agaacgaacg actctcactt      60
aggaacagaa ttgagaagaa aactgcatat tcccaagaac tggaagaaca agtaatgaac     120
atcatcgata ctctcggctt atctgcttcc tgccttcaga atctgataca gagaaatgag     180
cacttatata gctcaggaaa tgctcccagt ggcggtgttg ctcttccttt tatccttgtc     240
cagactcgtc ctcacgcaac agtagaagtg gagatatcag aagatatgca gctcgtgcat     300
tttgatttca acagcactcc atttgagctc cacgacgaca attttgtcct caagactatg     360
aagttttgtg atcaaccgcc gcaacaacca aacggtcgga acaacagcca gctggtttgt     420
cacaatttca cgccagaaaa ccctaacaaa ggccccagca caggtccaac accgcagctg     480
gatatgtacg agactcatct tcaatcgcaa caacatcagc agcattctca gctacaaatc     540
attcctatgc ctgagactaa caacgttact tccagcgctg atactgctcc agtgaaatcc     600
ccgtctcttc cagggataat gaactccagc atgaagccgg agaat                     645

<210> SEQ ID NO 232
<211> LENGTH: 450
<212> TYPE: DNA
<213> ORGANISM: Arabidopsis thaliana

<400> SEQUENCE: 232
gaagaagtca agatggatcg taataaagtt atgagcagtg tgcaaaagaa ggctgctttt      60
cttaaagagt tgagagaaaa ggtctcaagt cttgagagtc ttatgtcgag aaatcaagag     120
atggttgtga agactcaagg cccagcagaa ggatttacct taccattcat tctacttgag     180
acaaaccctc acgcagtagt cgaaatcgag atttctgaag atatgcaact tgtacacctc     240
gacttcaata gcacaccttt ctcggtccat gatgatgctt acattttgaa actgatgcaa     300
gaacagaagc aagaacagaa cagagtatct tcttcttcat ctacacatca ccaatctcaa     360
catagctccg ctcattcttc atccagttct tgcattgctt ctggaaccct caggcccggtt     420 tgctggaact cgggatccat tgatactcgc                                      450

<210> SEQ ID NO 233
<211> LENGTH: 213
<212> TYPE: DNA
<213> ORGANISM: Arabidopsis thaliana

<400> SEQUENCE: 233
gaagaagtca agatggatcg taataaagtt atgagcagtg tgcaaaagaa ggctgctttt      60
cttaaagagt tgagagaaaa ggtctcaagt cttgagagtc ttatgtcgag aaatcaagag     120
atggttgtga agactcaagg cccagcagaa ggatttacct taccattcat tctacttgag     180
acaaaccctc acgcagtagt cgaaatcgag att                                   213

<210> SEQ ID NO 234
<211> LENGTH: 870
<212> TYPE: DNA
<213> ORGANISM: Arabidopsis thaliana

<400> SEQUENCE: 234
atgacaacta ctgggtctaa ttctaatcac aaccaccatg aaagcaataa taacaacaat      60
aaccctagta ctaggtcttg ggcacggcg gtttcaggtc aatctgtgtc tactagcggc     120
agtatgggct ctccgtcgag ccggagtgag caaaccatca ccgttgttac atctactagc     180
gacactactt ttcaacgcct gaataatttg acattcaag gtgatgatgc tggttctcaa     240
ggagcttctg gtgttaagaa gaagaagagg ggacagcgtg cggctggtcc agataagact     300
```

```
ggaagaggac tacgtcaatt tagtatgaaa ggtcttatct ctttctctgc ccctattatg    360
ctttcatcta aatgcctttc aatttgtgaa aaggtggaaa gcaaaggaag gacaacttac    420
aatgaggttg cagacgagct tgttgctgaa tttgcacttc caaataacga tggaacatcc    480
cctgatcagc aacagtatga tgagaaaaac ataagacgaa gagtatatga tgctttaaac    540
gtcctcatgg ctatggatat aatatccaag gataaaaaag aaattcaatg gagaggtctt    600
cctcggacaa gcttaagcga cattgaagaa ttaaagaacg aacgactctc acttaggaac    660
agaattgaga agaaaactgc atattcccaa gaactggaag aacaagtaat gaacatcatc    720
gatactctcg gctatctgc ttcctgcctt cagaatctga tacagagaaa tgagcactta    780
tatagctcag gaaatgctcc cagtggcggt gttgctcttc cttttatcct tgtccagact    840
cgtcctcacg caacagtaga agtggagata                                     870

<210> SEQ ID NO 235
<211> LENGTH: 153
<212> TYPE: DNA
<213> ORGANISM: Arabidopsis thaliana

<400> SEQUENCE: 235
ggagttgatg cgtgtcctgg cgatgaggat gctgacgtat ctgtattaca gctgcaggca     60
gaaattgaaa acctcgccct cgaagagcaa gcattagaca accaaatcag acaaacagag    120
gaaagattaa gagacctgag cgaaaatgaa aag                                 153

<210> SEQ ID NO 236
<211> LENGTH: 363
<212> TYPE: DNA
<213> ORGANISM: Arabidopsis thaliana

<400> SEQUENCE: 236
ggagttgatg cgtgtcctgg cgatgaggat gctgacgtat ctgtattaca gctgcaggca     60
gaaattgaaa acctcgccct cgaagagcaa gcattagaca accaaatcag acaaacagag    120
gaaagattaa gagacctgag cgaaaatgaa agaatcaga aatggctttt tgtaactgaa    180
gaggatatca agagtttacc aggtttccag aaccagactc tgatagccgt caaagctcct    240
catggcacaa cttttggaagt gcctgatcca gatgaagcgg ctgaccaccc acaaaggaga    300
tacaggatca ttcttagaag tacaatggga cctattgacg tatacctcgt cagcgaattt    360
gaa                                                                 363

<210> SEQ ID NO 237
<211> LENGTH: 150
<212> TYPE: DNA
<213> ORGANISM: Arabidopsis thaliana

<400> SEQUENCE: 237
ggtctcgatg tctcaaaacc aggagaaaca atcgaaagca tagctaacct acaggatgaa     60
gtacaaaacc tcgcagctga ggaggcaaga ttagatgacc aaatcagaga atcacaagaa    120
agattaacaa gcttgagtga ggatgaaaac                                    150

<210> SEQ ID NO 238
<211> LENGTH: 354
<212> TYPE: DNA
<213> ORGANISM: Arabidopsis thaliana

<400> SEQUENCE: 238
ggtctcgatg tctcaaaacc aggagaaaca atcgaaagca tagctaacct acaggatgaa     60
```

```
gtacaaaacc tcgcagctga ggaggcaaga ttagatgacc aaatcagaga atcacaagaa    120
agattaacaa gcttgagtga ggatgaaaac aacaaaaggt tactgttcgt cactgaaaac    180
gacattaaga acctaccatg cttccagaat aagacgctga tagctgtaaa ggcaccgcat    240
ggaacaactc ttgaggttcc agatcctgat gaggctggtg ttatcagag gaggtacaga    300 atcattctga gaagcacaat gggaccaata gacgtgtacc tagtcagtca attc          354

<210> SEQ ID NO 239
<211> LENGTH: 426
<212> TYPE: DNA
<213> ORGANISM: Arabidopsis thaliana

<400> SEQUENCE: 239
atgagtatgg agatggagtt gtttgtcact ccagagaagc agaggcaaca tccttcagtg     60
agcgttgaga aaactccagt gagaaggaaa ttgattgttg atgatgattc tgaaattgga    120
tcagagaaga aagggcaatc aagaacttct ggaggcgggc ttcgtcaatt cagtgttatg    180
gtttgtcaga gttggaagc caagaagata actacttaca aggaggttgc agacgaaatt    240
atttcagatt ttgccacaat taagcaaaac gcagagaagc ctttgaatga aaatgagtac    300
aatgagaaga acataaggcg gagagtctac gatgcgctca atgtgttcat ggcgttggat    360
attattgcaa gggataaaaa ggaaatccgg tggaaaggac ttcctattac ctgcaaaaag    420
gatgtg                                                              426

<210> SEQ ID NO 240
<211> LENGTH: 7
<212> TYPE: PRT
<213> ORGANISM: artificial sequence
<220> FEATURE:
<223> OTHER INFORMATION: motif

<400> SEQUENCE: 240

Met Lys Val Cys Glu Lys Val
 1               5

<210> SEQ ID NO 241
<211> LENGTH: 8
<212> TYPE: PRT
<213> ORGANISM: artificial sequence
<220> FEATURE:
<223> OTHER INFORMATION: motif

<400> SEQUENCE: 241

Leu Asn Val Leu Met Ala Met Asp
 1               5

<210> SEQ ID NO 242
<211> LENGTH: 8
<212> TYPE: PRT
<213> ORGANISM: artificial sequence
<220> FEATURE:
<223> OTHER INFORMATION: motif

<400> SEQUENCE: 242

Phe Asn Ser Thr Pro Phe Glu Leu
 1               5

<210> SEQ ID NO 243
<211> LENGTH: 30
<212> TYPE: DNA
<213> ORGANISM: artificial sequence
<220> FEATURE:
<223> OTHER INFORMATION: primer
```

```
<400> SEQUENCE: 243
atagaattca tgaaagtttg tgaaaaggtg                                    30

<210> SEQ ID NO 244
<211> LENGTH: 33
<212> TYPE: DNA
<213> ORGANISM: artificial sequence
<220> FEATURE:
<223> OTHER INFORMATION: primer

<400> SEQUENCE: 244
atagaattcc tgaatgttct catggcaatg gat                                33

<210> SEQ ID NO 245
<211> LENGTH: 33
<212> TYPE: DNA
<213> ORGANISM: artificial sequence
<220> FEATURE:
<223> OTHER INFORMATION: primer

<400> SEQUENCE: 245
ataggatccc agctcaaaag gagtgctatt gaa                                33

<210> SEQ ID NO 246
<211> LENGTH: 29
<212> TYPE: DNA
<213> ORGANISM: artificial sequence
<220> FEATURE:
<223> OTHER INFORMATION: motif

<400> SEQUENCE: 246
ggggacaagt ttgtacaaaa aagcaggct                                     29

<210> SEQ ID NO 247
<211> LENGTH: 5
<212> TYPE: DNA
<213> ORGANISM: artificial sequence
<220> FEATURE:
<223> OTHER INFORMATION: motif

<400> SEQUENCE: 247 tcaca                                                                5

<210> SEQ ID NO 248
<211> LENGTH: 29
<212> TYPE: DNA
<213> ORGANISM: artificial sequence
<220> FEATURE:
<223> OTHER INFORMATION: motif

<400> SEQUENCE: 248
ggggaccact ttgtacaaga aagctgggt                                     29

<210> SEQ ID NO 249
<211> LENGTH: 27
<212> TYPE: DNA
<213> ORGANISM: artificial sequence
<220> FEATURE:
<223> OTHER INFORMATION: primer

<400> SEQUENCE: 249
atagaattca tgtccggtgt cgtacga                                       27

<210> SEQ ID NO 250
<211> LENGTH: 30
```

```
<212> TYPE: DNA
<213> ORGANISM: artificial sequence
<220> FEATURE:
<223> OTHER INFORMATION: primer

<400> SEQUENCE: 250
ataggatccc acctccaatg tttctgcagc                              30

<210> SEQ ID NO 251
<211> LENGTH: 30
<212> TYPE: DNA
<213> ORGANISM: artificial sequence
<220> FEATURE:
<223> OTHER INFORMATION: primer

<400> SEQUENCE: 251
atagaattcg agaagaaagg gcaatcaaga                              30

<210> SEQ ID NO 252
<211> LENGTH: 30
<212> TYPE: DNA
<213> ORGANISM: artificial sequence
<220> FEATURE:
<223> OTHER INFORMATION: primer

<400> SEQUENCE: 252
atactgcaga gaaatctcga tttcgactac                              30

<210> SEQ ID NO 253
<211> LENGTH: 25
<212> TYPE: DNA
<213> ORGANISM: artificial sequence
<220> FEATURE:
<223> OTHER INFORMATION: primer

<400> SEQUENCE: 253
gccactctca tagggttctc catcg                                   25

<210> SEQ ID NO 254
<211> LENGTH: 25
<212> TYPE: DNA
<213> ORGANISM: artificial sequence
<220> FEATURE:
<223> OTHER INFORMATION: primer

<400> SEQUENCE: 254
ggcatgcctc caagatcctt gaagt                                   25

<210> SEQ ID NO 255
<211> LENGTH: 22
<212> TYPE: DNA
<213> ORGANISM: artificial sequence
<220> FEATURE:
<223> OTHER INFORMATION: primer

<400> SEQUENCE: 255
gggtcttggt cgttttactg tt                                      22

<210> SEQ ID NO 256
<211> LENGTH: 25
<212> TYPE: DNA
<213> ORGANISM: artificial sequence
<220> FEATURE:
<223> OTHER INFORMATION: primer

<400> SEQUENCE: 256
ccaagacgat gacaacagat acagc                                   25
```

<210> SEQ ID NO 257
<211> LENGTH: 21
<212> TYPE: DNA
<213> ORGANISM: artificial sequence
<220> FEATURE:
<223> OTHER INFORMATION: primer

<400> SEQUENCE: 257
ataaactaaa tcttcgctga a                                              21

<210> SEQ ID NO 258
<211> LENGTH: 21
<212> TYPE: DNA
<213> ORGANISM: artificial sequence
<220> FEATURE:
<223> OTHER INFORMATION: primer

<400> SEQUENCE: 258
caaacgcgga tctgaaaaac t                                              21

<210> SEQ ID NO 259
<211> LENGTH: 18
<212> TYPE: DNA
<213> ORGANISM: artificial sequence
<220> FEATURE:
<223> OTHER INFORMATION: primer

<400> SEQUENCE: 259
tctctcttcc aaatctcc                                                  18

<210> SEQ ID NO 260
<211> LENGTH: 20
<212> TYPE: DNA
<213> ORGANISM: artificial sequence
<220> FEATURE:
<223> OTHER INFORMATION: primer

<400> SEQUENCE: 260
aagtctctca ctttctcact                                                20

<210> SEQ ID NO 261
<211> LENGTH: 25
<212> TYPE: DNA
<213> ORGANISM: artificial sequence
<220> FEATURE:
<223> OTHER INFORMATION: primer

<400> SEQUENCE: 261
ctaagctctc aagatcaaag gctta                                          25

<210> SEQ ID NO 262
<211> LENGTH: 25
<212> TYPE: DNA
<213> ORGANISM: artificial sequence
<220> FEATURE:
<223> OTHER INFORMATION: primer

<400> SEQUENCE: 262
ttaacattgc aaagagtttc aaggt                                          25

<210> SEQ ID NO 263
<211> LENGTH: 4
<212> TYPE: PRT
<213> ORGANISM: artificial sequence
<220> FEATURE:
<223> OTHER INFORMATION: motif

<400> SEQUENCE: 263

Thr Pro Trp Lys
 1

<210> SEQ ID NO 264
<211> LENGTH: 289
<212> TYPE: PRT
<213> ORGANISM: Arabidopsis thaliana

<400> SEQUENCE: 264

Met Gly Lys Tyr Ile Arg Lys Ser Lys Ile Asp Gly Ala Gly Ala Gly
 1               5                  10                  15

Ala Gly Gly Gly Gly Gly Gly Gly Gly Glu Ser Ser Ile Ala
             20                  25                  30

Leu Met Asp Val Val Ser Pro Ser Ser Ser Ser Leu Gly Val Leu
             35                  40                  45

Thr Arg Ala Lys Ser Leu Ala Leu Gln Gln Gln Gln Arg Cys Leu
 50                  55                  60

Leu Gln Lys Pro Ser Ser Pro Ser Ser Leu Pro Pro Thr Ser Ala Ser
 65                  70                  75                  80

Pro Asn Pro Pro Ser Lys Gln Lys Met Lys Lys Gln Gln Gln Met
                 85                  90                  95

Asn Asp Cys Gly Ser Tyr Leu Gln Leu Arg Ser Arg Leu Gln Lys
                100                 105                 110

Lys Pro Pro Ile Val Val Ile Arg Ser Thr Lys Arg Lys Gln Gln
             115                 120                 125

Arg Arg Asn Glu Thr Cys Gly Arg Asn Pro Asn Pro Arg Ser Asn Leu
130                 135                 140

Asp Ser Ile Arg Gly Asp Gly Ser Arg Ser Asp Ser Val Ser Glu Ser
145                 150                 155                 160

Val Val Phe Gly Lys Asp Lys Asp Leu Ile Ser Glu Ile Asn Lys Asp
                165                 170                 175

Pro Thr Phe Gly Gln Asn Phe Phe Asp Leu Glu Glu Glu His Thr Gln
            180                 185                 190

Ser Phe Asn Arg Thr Thr Arg Glu Ser Thr Pro Cys Ser Leu Ile Arg
        195                 200                 205

Arg Pro Glu Ile Met Thr Thr Pro Gly Ser Ser Thr Lys Leu Asn Ile
    210                 215                 220

Cys Val Ser Glu Ser Asn Gln Arg Glu Asp Ser Leu Ser Arg Ser His
225                 230                 235                 240

Arg Arg Arg Pro Thr Thr Pro Glu Met Asp Glu Phe Ser Gly Ala
                245                 250                 255

Glu Glu Glu Gln Gln Lys Gln Phe Ile Glu Lys Tyr Asn Phe Asp Pro
                260                 265                 270

Val Asn Glu Gln Pro Leu Pro Gly Arg Phe Glu Trp Thr Lys Val Asp
            275                 280                 285

Asp

<210> SEQ ID NO 265
<211> LENGTH: 20
<212> TYPE: DNA
<213> ORGANISM: artificial sequence
<220> FEATURE:
<223> OTHER INFORMATION: primer

<400> SEQUENCE: 265

```
cggggccccaa ataatgattt                                              20

<210> SEQ ID NO 266
<211> LENGTH: 18
<212> TYPE: DNA
<213> ORGANISM: artificial sequence
<220> FEATURE:
<223> OTHER INFORMATION: primer

<400> SEQUENCE: 266
gacacgggcc agagctgc                                                 18

<210> SEQ ID NO 267
<211> LENGTH: 10
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (5)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Ile or Val
<220> FEATURE:
<221> NAME/KEY: MISC_FEATURE
<222> LOCATION: (8)..(9)
<223> OTHER INFORMATION: Xaa = any amino acid and may be present or
      absent.

<400> SEQUENCE: 267

Arg Xaa Xaa Leu Xaa Xaa Xaa Xaa Xaa Asn
 1               5                  10

<210> SEQ ID NO 268
<211> LENGTH: 8
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: Xaa =any amino acid
<220> FEATURE:
<221> NAME/KEY: MISC_FEATURE
<222> LOCATION: (6)..(6)
<223> OTHER INFORMATION: Xaa = Ile or Val

<400> SEQUENCE: 268

Met Arg Xaa Ile Leu Xaa Asp Trp
 1               5

<210> SEQ ID NO 269
<211> LENGTH: 8
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (5)..(7)
<223> OTHER INFORMATION: Xaa = any amino acid

<400> SEQUENCE: 269

Lys Tyr Glu Glu Xaa Xaa Xaa Pro
```

```
<210> SEQ ID NO 270
<211> LENGTH: 9
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = any amino acid

<400> SEQUENCE: 270

Gly Xaa Gly Xaa Xaa Gly Xaa Val Tyr
1               5

<210> SEQ ID NO 271
<211> LENGTH: 10
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(7)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = any amino acid

<400> SEQUENCE: 271

His Arg Asp Xaa Lys Xaa Xaa Asn Xaa Leu
1               5                   10

<210> SEQ ID NO 272
<211> LENGTH: 12
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(3)
<223> OTHER INFORMATION: Xaa = any amino acid and may be present or
      absent
<220> FEATURE:
<221> NAME/KEY: MISC_FEATURE
<222> LOCATION: (4)..(4)
<223> OTHER INFORMATION: Xaa = Trp or Tyr
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (8)..(11)
<223> OTHER INFORMATION: Xaa = any amino acid

<400> SEQUENCE: 272

Asp Xaa Xaa Xaa Ser Xaa Gly Xaa Xaa Xaa Xaa Glu
```

```
<210> SEQ ID NO 273
<211> LENGTH: 5
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(4)
<223> OTHER INFORMATION: Xaa = any amino acid and may be present or
      absent
<220> FEATURE:
<221> NAME/KEY: MISC_FEATURE
<222> LOCATION: (5)..(5)
<223> OTHER INFORMATION: Xaa = Arg or Lys

<400> SEQUENCE: 273

Thr Pro Xaa Xaa Xaa
  1               5

<210> SEQ ID NO 274
<211> LENGTH: 4
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Arg or Lys

<400> SEQUENCE: 274

Ser Pro Xaa Xaa
  1

<210> SEQ ID NO 275
<211> LENGTH: 4
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Ile, Leu, Val or Met

<400> SEQUENCE: 275

Ser Pro Xaa Xaa
  1

<210> SEQ ID NO 276
<211> LENGTH: 4
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(3)
<223> OTHER INFORMATION: Xaa = Ile, Leu, Val or Met
<220> FEATURE:
<221> NAME/KEY: MISC_FEATURE
<222> LOCATION: (4)..(4)
```

<223> OTHER INFORMATION: Xaa = any amino acid

<400> SEQUENCE: 276

Ser Pro Xaa Xaa
1

<210> SEQ ID NO 277
<211> LENGTH: 7
<212> TYPE: PRT
<213> ORGANISM: artificial sequence
<220> FEATURE:
<223> OTHER INFORMATION: motif

<400> SEQUENCE: 277

Pro Lys Lys Lys Arg Lys Val
1               5

<210> SEQ ID NO 278
<211> LENGTH: 16
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(12)
<223> OTHER INFORMATION: Xaa = any amino acid

<400> SEQUENCE: 278

Lys Arg Xaa Xaa Xaa Xaa Xaa Xaa Xaa Xaa Xaa Xaa Lys Lys Lys Lys
1               5                   10                  15

<210> SEQ ID NO 279
<211> LENGTH: 5
<212> TYPE: PRT
<213> ORGANISM: artificial sequence
<220> FEATURE:
<223> OTHER INFORMATION: motif

<400> SEQUENCE: 279

Lys Arg Pro Arg Pro
1               5

<210> SEQ ID NO 280
<211> LENGTH: 9
<212> TYPE: PRT
<213> ORGANISM: artificial sequence
<220> FEATURE:
<223> OTHER INFORMATION: motif

<400> SEQUENCE: 280

Pro Ala Ala Lys Arg Val Lys Leu Asp
1               5

<210> SEQ ID NO 281
<211> LENGTH: 4
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(3)
<223> OTHER INFORMATION: Xaa = any amino acid

<400> SEQUENCE: 281

Arg Xaa Xaa Phe
1

```
<210> SEQ ID NO 282
<211> LENGTH: 5
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 282

Leu Xaa Cys Xaa Glu
 1               5

<210> SEQ ID NO 283
<211> LENGTH: 5
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid

<400> SEQUENCE: 283

Leu Xaa Ser Xaa Glu
 1               5

<210> SEQ ID NO 284
<211> LENGTH: 17
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(9)
<223> OTHER INFORMATION: Xaa = any amino acid
<220> FEATURE:
<221> NAME/KEY: MISC_FEATURE
<222> LOCATION: (11)..(13)
<223> OTHER INFORMATION: Xaa = any amino acid

<400> SEQUENCE: 284

Asp Tyr Xaa Xaa Xaa Xaa Xaa Xaa Xaa Glu Xaa Xaa Xaa Asp Leu Phe
 1               5                  10                  15

Asp

<210> SEQ ID NO 285
<211> LENGTH: 17
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (3)..(8)
<223> OTHER INFORMATION: Xaa = any amino acid
<220> FEATURE:
<221> NAME/KEY: MISC_FEATURE
<222> LOCATION: (10)..(13)
<223> OTHER INFORMATION: Xaa = any amino acid
```

<400> SEQUENCE: 285

Asp Tyr Xaa Xaa Xaa Xaa Xaa Asp Xaa Xaa Xaa Xaa Asp Met Trp
1               5                   10                  15

Glu

<210> SEQ ID NO 286
<211> LENGTH: 35
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = Asp or Asn and may be present or absent
<220> FEATURE:
<221> NAME/KEY: MISC_FEATURE
<222> LOCATION: (2)..(2)
<223> OTHER INFORMATION: Xaa = Gln or Glu
<220> FEATURE:
<221> NAME/KEY: MISC_FEATURE
<222> LOCATION: (7)..(7)
<223> OTHER INFORMATION: Xaa = Arg or Gly
<220> FEATURE:
<221> NAME/KEY: MISC_FEATURE
<222> LOCATION: (10)..(10)
<223> OTHER INFORMATION: Xaa = Tyr or Asp
<220> FEATURE:
<221> NAME/KEY: MISC_FEATURE
<222> LOCATION: (16)..(16)
<223> OTHER INFORMATION: Xaa = Leu or Phe
<220> FEATURE:
<221> NAME/KEY: MISC_FEATURE
<222> LOCATION: (19)..(19)
<223> OTHER INFORMATION: Xaa = Met, Ile or Leu any may be present or
      absent
<220> FEATURE:
<221> NAME/KEY: MISC_FEATURE
<222> LOCATION: (20)..(20)
<223> OTHER INFORMATION: Xaa = Asp or Asn
<220> FEATURE:
<221> NAME/KEY: MISC_FEATURE
<222> LOCATION: (21)..(21)
<223> OTHER INFORMATION: Xaa = Val or Ile
<220> FEATURE:
<221> NAME/KEY: MISC_FEATURE
<222> LOCATION: (23)..(23)
<223> OTHER INFORMATION: Xaa = Ser or Ala
<220> FEATURE:
<221> NAME/KEY: MISC_FEATURE
<222> LOCATION: (24)..(24)
<223> OTHER INFORMATION: Xaa = Lys or Arg
<220> FEATURE:
<221> NAME/KEY: MISC_FEATURE
<222> LOCATION: (25)..(25)
<223> OTHER INFORMATION: Xaa = Asp or Glu
<220> FEATURE:
<221> NAME/KEY: MISC_FEATURE
<222> LOCATION: (30)..(30)
<223> OTHER INFORMATION: Xaa = Lys, Gln or Arg and may be present or
      absent
<220> FEATURE:
<221> NAME/KEY: MISC_FEATURE
<222> LOCATION: (32)..(32)
<223> OTHER INFORMATION: Xaa = Arg, Lys or Ile

<400> SEQUENCE: 286

Xaa Xaa Lys Asn Ile Arg Xaa Arg Val Xaa Asp Ala Leu Asn Val Xaa
1               5                   10                  15

Met Ala Xaa Xaa Xaa Ile Xaa Xaa Xaa Lys Lys Glu Ile Xaa Trp Xaa
            20                  25                  30

Gly Leu Pro
        35

```
<210> SEQ ID NO 287
<211> LENGTH: 53
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = Gly or Asn
<220> FEATURE:
<221> NAME/KEY: MISC_FEATURE
<222> LOCATION: (2)..(2)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = His or Gln
<220> FEATURE:
<221> NAME/KEY: MISC_FEATURE
<222> LOCATION: (9)..(9)
<223> OTHER INFORMATION: Xaa = Met or Val
<220> FEATURE:
<221> NAME/KEY: MISC_FEATURE
<222> LOCATION: (10)..(10)
<223> OTHER INFORMATION: Xaa = Lys or Met
<220> FEATURE:
<221> NAME/KEY: MISC_FEATURE
<222> LOCATION: (11)..(11)
<223> OTHER INFORMATION: Xaa = Ile or Val
<220> FEATURE:
<221> NAME/KEY: MISC_FEATURE
<222> LOCATION: (12)..(28)
<223> OTHER INFORMATION: Xaa = any amino acid and may be present or
      absent
<220> FEATURE:
<221> NAME/KEY: MISC_FEATURE
<222> LOCATION: (30)..(30)
<223> OTHER INFORMATION: Xaa = Glu or Gln
<220> FEATURE:
<221> NAME/KEY: MISC_FEATURE
<222> LOCATION: (32)..(32)
<223> OTHER INFORMATION: Xaa = Val or Leu
<220> FEATURE:
<221> NAME/KEY: MISC_FEATURE
<222> LOCATION: (33)..(33)
<223> OTHER INFORMATION: Xaa = Gln or Glu and may be present or absent
<220> FEATURE:
<221> NAME/KEY: MISC_FEATURE
<222> LOCATION: (34)..(34)
<223> OTHER INFORMATION: Xaa = Ser and may be present or absent
<220> FEATURE:
<221> NAME/KEY: MISC_FEATURE
<222> LOCATION: (35)..(35)
<223> OTHER INFORMATION: Xaa = any amino acid
<220> FEATURE:
<221> NAME/KEY: MISC_FEATURE
<222> LOCATION: (37)..(37)
<223> OTHER INFORMATION: Xaa = Gly or Lys
<220> FEATURE:
<221> NAME/KEY: MISC_FEATURE
<222> LOCATION: (38)..(38)
<223> OTHER INFORMATION: Xaa = Arg or Ile and may be present or absent
<220> FEATURE:
<221> NAME/KEY: MISC_FEATURE
<222> LOCATION: (41)..(41)
<223> OTHER INFORMATION: Xaa = Ser and may be present or absent
<220> FEATURE:
<221> NAME/KEY: MISC_FEATURE
<222> LOCATION: (43)..(43)
<223> OTHER INFORMATION: Xaa = Asn or Lys
<220> FEATURE:
<221> NAME/KEY: MISC_FEATURE
<222> LOCATION: (49)..(49)
<223> OTHER INFORMATION: Xaa = Leu or Ile
<220> FEATURE:
<221> NAME/KEY: MISC_FEATURE
<222> LOCATION: (50)..(50)
```

```
<223> OTHER INFORMATION: Xaa = Val or Ile
<220> FEATURE:
<221> NAME/KEY: MISC_FEATURE
<222> LOCATION: (51)..(51)
<223> OTHER INFORMATION: Xaa = Ala or Ser
<220> FEATURE:
<221> NAME/KEY: MISC_FEATURE
<222> LOCATION: (52)..(52)
<223> OTHER INFORMATION: Xaa = Glu or Gln

<400> SEQUENCE: 287

Xaa Xaa Gly Leu Arg Xaa Phe Ser Xaa Xaa Xaa Xaa Xaa Xaa Xaa
 1               5                  10                  15

Xaa Xaa Xaa Xaa Xaa Xaa Xaa Xaa Xaa Xaa Xaa Cys Xaa Lys Xaa
             20                  25                  30

Xaa Xaa Xaa Lys Xaa Xaa Thr Thr Xaa Tyr Xaa Glu Val Ala Asp Glu
         35                  40                  45

Xaa Xaa Xaa Xaa Phe
     50

<210> SEQ ID NO 288
<211> LENGTH: 9
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = Arg or Ser
<220> FEATURE:
<221> NAME/KEY: MISC_FEATURE
<222> LOCATION: (2)..(2)
<223> OTHER INFORMATION: Xaa = Ile or Val
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Gln or Lys
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Leu or Ser
<220> FEATURE:
<221> NAME/KEY: MISC_FEATURE
<222> LOCATION: (8)..(8)
<223> OTHER INFORMATION: Xaa = any amino acid

<400> SEQUENCE: 288

Xaa Xaa Xaa Xaa Lys Xaa Xaa Xaa Glu
 1               5

<210> SEQ ID NO 289
<211> LENGTH: 27
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = Arg or Ser
<220> FEATURE:
<221> NAME/KEY: MISC_FEATURE
<222> LOCATION: (2)..(2)
<223> OTHER INFORMATION: Xaa = Ile or Val
```

```
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Gln or Lys
<220> FEATURE:
<221> NAME/KEY: MISC_FEATURE
<222> LOCATION: (6)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = Leu or Ser
<220> FEATURE:
<221> NAME/KEY: MISC_FEATURE
<222> LOCATION: (10)..(10)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = Leu or Met
<220> FEATURE:
<221> NAME/KEY: MISC_FEATURE
<222> LOCATION: (13)..(15)
<223> OTHER INFORMATION: Xaa = any amino acid and may be present or
      absent
<220> FEATURE:
<221> NAME/KEY: MISC_FEATURE
<222> LOCATION: (16)..(16)
<223> OTHER INFORMATION: Xaa = Gln or His
<220> FEATURE:
<221> NAME/KEY: MISC_FEATURE
<222> LOCATION: (17)..(21)
<223> OTHER INFORMATION: Xaa = any amino acid and may be present or
      absent
<220> FEATURE:
<221> NAME/KEY: MISC_FEATURE
<222> LOCATION: (24)..(24)
<223> OTHER INFORMATION: Xaa = Val, Ile or Met
<220> FEATURE:
<221> NAME/KEY: MISC_FEATURE
<222> LOCATION: (25)..(25)
<223> OTHER INFORMATION: Xaa = Gln or Glu

<400> SEQUENCE: 289

Xaa Xaa Xaa Xaa Lys Xaa Xaa Xaa Xaa Xaa Glu Xaa Xaa Xaa Xaa Xaa
1               5                   10                  15

Xaa Xaa Xaa Xaa Xaa Asn Leu Xaa Xaa Arg Asn
            20                  25

<210> SEQ ID NO 290
<211> LENGTH: 46
<212> TYPE: PRT
<213> ORGANISM: artificial sequence
<220> FEATURE:
<223> OTHER INFORMATION: motif
<220> FEATURE:
<221> NAME/KEY: MISC_FEATURE
<222> LOCATION: (1)..(1)
<223> OTHER INFORMATION: Xaa = Leu or Ile
<220> FEATURE:
<221> NAME/KEY: MISC_FEATURE
<222> LOCATION: (5)..(5)
<223> OTHER INFORMATION: Xaa = Leu or Ile
<220> FEATURE:
<221> NAME/KEY: MISC_FEATURE
<222> LOCATION: (6)..(6)
<223> OTHER INFORMATION: Xaa = Val or Leu
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
```

```
<222> LOCATION: (9)..(12)
<223> OTHER INFORMATION: Xaa = any amino acid and may be present or
      absent
<220> FEATURE:
<221> NAME/KEY: MISC_FEATURE
<222> LOCATION: (13)..(13)
<223> OTHER INFORMATION: Xaa = thr or Val
<220> FEATURE:
<221> NAME/KEY: MISC_FEATURE
<222> LOCATION: (15)..(28)
<223> OTHER INFORMATION: Xaa = any amino acid and may be present or
      absent
<220> FEATURE:
<221> NAME/KEY: MISC_FEATURE
<222> LOCATION: (30)..(33)
<223> OTHER INFORMATION: Xaa = any amino acid and may be present or
      absent
<220> FEATURE:
<221> NAME/KEY: MISC_FEATURE
<222> LOCATION: (35)..(35)
<223> OTHER INFORMATION: Xaa = Glu or Ser
<220> FEATURE:
<221> NAME/KEY: MISC_FEATURE
<222> LOCATION: (36)..(36)
<223> OTHER INFORMATION: Xaa = Met, Ile, Val or Leu
<220> FEATURE:
<221> NAME/KEY: MISC_FEATURE
<222> LOCATION: (40)..(41)
<223> OTHER INFORMATION: Xaa = any amino acid
<220> FEATURE:
<221> NAME/KEY: MISC_FEATURE
<222> LOCATION: (42)..(42)
<223> OTHER INFORMATION: Xaa = Val or Ile
<220> FEATURE:
<221> NAME/KEY: MISC_FEATURE
<222> LOCATION: (44)..(44)
<223> OTHER INFORMATION: Xaa = Arg or Lys
<220> FEATURE:
<221> NAME/KEY: MISC_FEATURE
<222> LOCATION: (45)..(45)
<223> OTHER INFORMATION: Xaa = any amino acid

<400> SEQUENCE: 290

Xaa Pro Phe Ile Xaa Xaa Xaa Thr Xaa Xaa Xaa Xaa Xaa Val Xaa Xaa
 1               5                  10                  15

Xaa Xaa Xaa Xaa Xaa Xaa Xaa Xaa Xaa Xaa Xaa Xaa Phe Xaa Xaa Xaa
             20                  25                  30

Xaa Phe Xaa Xaa His Asp Asp Xaa Xaa Xaa Leu Xaa Xaa Met
         35                  40                  45
```